US007915250B2

(12) United States Patent
Aay et al.

(10) Patent No.: US 7,915,250 B2
(45) Date of Patent: Mar. 29, 2011

(54) AZETIDINES AS MEK INHIBITORS FOR THE TREATMENT OF PROLIFERATIVE DISEASES

(75) Inventors: Naing Aay, San Mateo, CA (US); Neel Kumar Anand, Burlingame, CA (US); Charles M. Blazey, San Francisco, CA (US); Owen Joseph Bowles, Pacifica, CA (US); Joerg Bussenius, Foster City, CA (US); Simona Costanzo, Los Altos, CA (US); Jeffry Kimo Curtis, San Anselmo, CA (US); Steven Charles DeFina, Burlingame, CA (US); Larisa Dubenko, San Francisco, CA (US); Anagha Abhijit Joshi, Fremont, CA (US); Abigail R. Kennedy, Oakland, CA (US); Angie Inyoung Kim, San Mateo, CA (US); Elena S. Koltun, Foster City, CA (US); Jean-Claire Limun Manalo, Daly City, CA (US); Csaba J. Peto, Alameda, CA (US); Kenneth D. Rice, San Rafael, CA (US); Tsze H. Tsang, El Cerrito, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 12/774,544

(22) Filed: May 5, 2010

(65) Prior Publication Data

US 2010/0249096 A1  Sep. 30, 2010

Related U.S. Application Data

(62) Division of application No. 11/995,928, filed as application No. PCT/US2006/039126 on Oct. 5, 2006, now Pat. No. 7,803,839.

(60) Provisional application No. 60/724,578, filed on Oct. 7, 2005, provisional application No. 60/802,840, filed on May 23, 2006.

(51) Int. Cl.
*A61K 31/397* (2006.01)
*A61K 31/50* (2006.01)
*A61K 31/505* (2006.01)
*A61K 31/4523* (2006.01)
*A61K 31/4178* (2006.01)

(52) U.S. Cl. ............ 514/210.18; 514/248; 514/252.03; 514/252.05; 514/256; 514/318; 514/403; 544/235; 544/242; 544/333; 544/405; 546/208; 546/210; 546/268.1; 546/268.4; 546/275.4

(58) Field of Classification Search ............ 514/210.18, 514/248, 252.03, 252.05, 256, 318, 403; 544/235, 242, 333, 405; 546/208, 210, 268.1, 546/268.4, 275.4
See application file for complete search history.

(56) References Cited

U.S. PATENT DOCUMENTS

| 4,510,139 | A | 4/1985 | Bailey |
| 6,048,885 | A | 4/2000 | Takase et al. |
| 6,960,614 | B2 | 11/2005 | Barrett et al. |
| 6,974,878 | B2 | 12/2005 | Guram et al. |
| 7,141,312 | B2 | 11/2006 | Richter et al. |
| 7,371,751 | B2 | 5/2008 | Nettekoven et al. |
| 2004/0116710 | A1 | 6/2004 | Wallace et al. |
| 2004/0192653 | A1 | 9/2004 | Munson et al. |
| 2005/0049276 | A1 | 3/2005 | Kaufman |
| 2005/0049419 | A1 | 3/2005 | Wallace et al. |
| 2005/0054701 | A1 | 3/2005 | Wallace et al. |
| 2005/0153962 | A1 | 7/2005 | Nettekoven et al. |
| 2005/0256123 | A1 | 11/2005 | Marlow et al. |
| 2006/0030610 | A1 | 2/2006 | Koch et al. |
| 2007/0105859 | A1 | 5/2007 | Isshiki et al. |

FOREIGN PATENT DOCUMENTS

| EP | 1 262 176 A1 | 12/2002 |
| EP | 1 780 197 A1 | 5/2007 |
| JP | 2003-192592 A | 7/2003 |
| JP | 2005-162727 A | 6/2005 |
| WO | 89/03818 A1 | 5/1989 |
| WO | 97/12613 A1 | 4/1997 |
| WO | 98/37881 A1 | 9/1998 |
| WO | 99/01421 A | 1/1999 |
| WO | 99/01426 A1 | 1/1999 |
| WO | 00/35435 A1 | 6/2000 |
| WO | 00/35436 A2 | 6/2000 |
| WO | 00/37141 A1 | 6/2000 |
| WO | 00/40235 A2 | 7/2000 |
| WO | 00/40237 A1 | 7/2000 |
| WO | 00/41505 A | 7/2000 |
| WO | 00/41994 A1 | 7/2000 |
| WO | 00/42003 A1 | 7/2000 |
| WO | 00/42022 A | 7/2000 |

(Continued)

OTHER PUBLICATIONS

Shpiro, N. et al., "Improved Experimental Procedure for the Synthesis of the Potent MEK Inhibitor PD184352", Synthetic Communications, vol. 35, 2005-2265-2269.

*Primary Examiner* — Rebecca L Anderson
*Assistant Examiner* — Samantha L Shterengarts
(74) *Attorney, Agent, or Firm* — McDonnell Boehnen Hulbert & Berghoff LLP

(57) ABSTRACT

Disclosed are compounds of Formula (I) and pharmaceutically acceptable salts and solvates thereof. Such compounds are MEK inhibitors and are useful in the treatment of proliferative diseases, such as cancer. Also disclosed are pharmaceutical compositions containing such compounds as well as methods of using the compounds and compositions of the invention in the treatment of cancer.

26 Claims, No Drawings

FOREIGN PATENT DOCUMENTS

| | | |
|---|---|---|
| WO | 00/42029 A1 | 7/2000 |
| WO | 01/05390 A2 | 1/2001 |
| WO | 01/05391 A2 | 1/2001 |
| WO | 01/05392 A2 | 1/2001 |
| WO | 01/05393 A2 | 1/2001 |
| WO | 01/19788 A2 | 3/2001 |
| WO | 01/68619 A1 | 9/2001 |
| WO | 01/77101 A1 | 10/2001 |
| WO | 02/06213 A2 | 1/2002 |
| WO | 03/037329 A1 | 5/2003 |
| WO | 03/062189 A1 | 7/2003 |
| WO | 03/062191 A1 | 7/2003 |
| WO | 03/077855 A2 | 9/2003 |
| WO | 03/077914 A1 | 9/2003 |
| WO | 03/103590 A2 | 12/2003 |
| WO | 2004/056789 A1 | 7/2004 |
| WO | 2004/083167 A1 | 9/2004 |
| WO | 2004/089876 A | 10/2004 |
| WO | 2004/113347 A | 12/2004 |
| WO | 2005/000818 A1 | 1/2005 |
| WO | 2005/007616 A1 | 1/2005 |
| WO | 2005/009975 A2 | 2/2005 |
| WO | 2005/023251 A1 | 3/2005 |
| WO | 2005/023759 A | 3/2005 |
| WO | 2005/051300 A2 | 6/2005 |
| WO | 2005/051301 A | 6/2005 |
| WO | 2005/051302 A2 | 6/2005 |
| WO | 2006/010594 A1 | 2/2006 |
| WO | 2006/045514 A | 5/2006 |

AZETIDINES AS MEK INHIBITORS FOR THE TREATMENT OF PROLIFERATIVE DISEASES

CROSS REFERENCE TO RELATED APPLICATIONS

This application is a divisional of U.S. patent application Ser. No. 11/995,928 filed on Jan. 16, 2008, which is a U.S. national phase of International Application No. PCT/US2006/039126 filed on Oct. 5, 2006, claiming priority to U.S. Provisional Application No. 60/724,578 filed on Oct. 7, 2005 and U.S. Provisional Application No. 60/802,840 filed on May 23, 2006, the disclosures of which are incorporated herein by reference in its entirety.

BACKGROUND OF THE INVENTION

1. Field of the Invention

This invention relates to certain inhibitors of MEK which are useful in the treatment of hyperproliferative diseases, such as cancer, in mammals. This invention also relates to a method of using such compounds in the treatment of hyperproliferative diseases in mammals, especially humans, and to pharmaceutical compositions containing such compounds.

2. State of the Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity are staggering; cell differentiation and proliferation; i.e., virtually all aspects of cell life in one-way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular. They are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-kit and FLK-II. In addition, there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., *DN&P* 7(6): 334-339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lek, Blk, Hck, Fgr, and Yrk. The Src subfamily of enzymes has been linked to oncogenesis. For a more detailed discussion of the non-receptor type of tyrosine kinases, see Bolen, *Oncogene,* 8:2025-2031 (1993), which is hereby incorporated by reference.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers. Gleevec is a selective Abl kinase inhibitor.

Modulation (particularly inhibition) of cell proliferation and angiogenesis, two key cellular processes needed for tumor growth and survival (Matter A. *Drug Disc Technol* 2001 6, 1005-1024), is an attractive goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. As well, cell antiproliferative agents are desirable to slow or stop the growth of tumors.

One particularly attractive target for small-molecule modulation, with respect to antiangiogenic and antiproliferative activity is MEK. Inhibition of MEK1 (MAPK/ERK Kinase) is a promising strategy to control the growth of tumors that are dependent on aberrant ERK/MAPK pathway signaling (Solit et al., 2006; Wellbrock et al., 2004). The MEK-ERK signal transduction cascade is a conserved pathway which regulates cell growth, proliferation, differentiation, and apoptosis in response to growth factors, cytokines, and hormones. This pathway operates downstream of Ras which is often upregulated or mutated in human tumors. It has been demonstrated that MEK is a critical effector of Ras function. The ERK/MAPK pathway is upregulated in 30% of all tumors and oncogenic activating mutations in K-Ras and B-Raf have been identified in 22% and 18% of all cancers respectively (Allen et al., 2003; Bamford S, 2004; Davies et al., 2002; Malumbres and Barbacid, 2003). A large portion of human cancers, including 66% (B-Raf) of malignant melanomas, 60% (K-Ras) and 4% (B-Raf) of pancreatic cancers, 50% of colorectal cancers (colon, in particular, K-Ras: 30%, B-Raf: 15%), 20% (K-Ras) of lung cancers, 27% (B-Raf) papillary and anaplastic thyroid cancer, and 10-20% (B-Raf) of endometriod ovarian cancers, harbor activating Ras and Raf mutations. It has been shown that inhibition of the ERK pathway, and in particular inhibition of MEK kinase activity, results in anti-metastatic and anti-angiogenic effects largely

3 due to a reduction of cell-cell contact and motility as well as downregulation of vascular endothelial growth factor (VEGF) expression. Furthermore, expression of dominant negative MEK, or ERK reduced the transforming ability of mutant Ras as seen in cell culture and in primary and metastatic growth of human tumor xenografts in vivo. Therefore, the MEK-ERK signal transduction pathway is an appropriate pathway to target for therapeutic intervention.

Accordingly, the identification of small-molecule compounds that specifically inhibit, regulate and/or modulate the signal transduction of kinases, particularly MEK, is desirable as a means to treat or prevent disease states associated with cancer and is an object of this invention.

SUMMARY OF THE INVENTION

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

This invention provides compounds that inhibit, regulate and/or modulate the signal transduction of kinases, particularly MEK. The compounds of the invention are certain azetidin-1-yl(2-(2-fluorophenylamino)cyclic)methanones derivatives that are useful in the treatment of hyperproliferative diseases, such as cancer, in humans. This invention also provides methods of making the compound, methods of using such compounds in the treatment of hyperproliferative diseases in humans and to pharmaceutical compositions containing such compounds.

In one aspect, the invention provides a compound of Formula I:

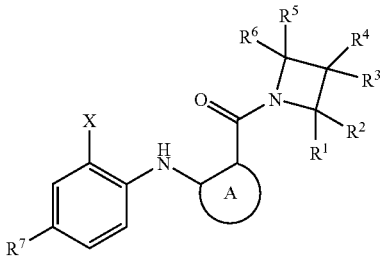

I or a pharmaceutically acceptable salt or solvate, thereof, wherein A, X, $R^1$, $R^2$, $R^3$, $R^4$, $R^5$, $R^6$, and $R^7$ are as defined in Group A, Group B, Group C, or Group D:

Group A:

A is arylene optionally substituted with one, two, three or four groups selected from $R^{10}$, $R^{12}$, $R^{14}$, and $R^{16}$ where $R^{10}$, $R^{12}$, $R^{14}$ and $R^{16}$ are independently hydrogen, alkyl, alkenyl, alkynyl, halo, haloalkoxy, hydroxy, alkoxy, amino, alkylamino, dialkylamino, haloalkyl, —NHS(O)$_2$R$^8$, —CN, —C(O)R$^8$, —C(O)OR$^8$, —C(O)NR$^8$R$^{8'}$ and —NR$^8$C(O)R$^{8'}$;

X is alkyl, halo, haloalkyl, or haloalkoxy;

$R^1$, $R^2$, $R^3$, $R^4$, $R^5$ and $R^6$ are independently hydrogen, halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)NR$^8$R$^{8'}$, —NR$^8$C(O)OR$^{8'}$, —NR$^8$C(O)NR$^8$R$^{8''}$, —NR$^8$C(O)OR$^{8'}$, —NR$^8$C(O)R$^{8'}$, —CH$_2$N(R$^{25}$)(NR$^{25a}$R$^{25b}$),

4

—CH$_2$NR$^{25}$C(=NH)(NR$^{25a}$R$^{25b}$), —CH$_2$NR$^{25}$C(=NH)(N(R$^{25a}$)(NO$_2$)), —CH$_2$NR$^{25}$C(=NH)(N(R$^{25a}$)(CN)), —CH$_2$NR$^{25}$C(=NH)(R$^{25}$), —CH$_2$NR$^{25}$C(NR$^{25a}$R$^{25b}$)=CH(NO$_2$), alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —OR$^8$, —NR$^8$R$^{8'}$, —NR$^8$S(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^8$R$^{8''}$, —NR$^8$C(O)OR$^{8'}$ and —NR$^8$C(O)R$^{8'}$; or one of R$^1$ and R$^2$ together with the carbon to which they are attached, R$^3$ and R$^4$ together with the carbon to which they are attached, and R$^5$ and R$^6$ together with the carbon to which they are attached form C(O) or C(=NOH);

m is 0, 1, or 2;

$R^7$ is hydrogen, halo or alkyl;

$R^8$, $R^{8'}$ and $R^{8''}$ are independently selected from hydrogen, hydroxy, optionally substituted alkoxy, alkyl, alkenyl, alkynyl, aryl, cycloalkyl, heteroaryl, and heterocycloalkyl; where the alkyl, alkenyl, alkynyl, aryl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, alkoxycarbonyl, alkenyloxycarbonyl, optionally substituted cycloalkyl, optionally substituted cycloalkyloxycarbonyl, optionally substituted aryl, optionally substituted aryloxy, optionally substituted aryloxycarbonyl, optionally substituted arylalkyl, optionally substituted arylalkyloxy, optionally substituted arylalkyloxycarbonyl, nitro, cyano, optionally substituted heterocycloalkyl, optionally substituted heteroaryl, —S(O)$_n$R$^{31}$ (where n is 0, 1, or 2 and R$^{31}$ is optionally substituted alkyl, optionally substituted aryl, optionally substituted heterocycloalkyl, or optionally substituted heteroaryl), —NR$^{34}$SO$_2$R$^{34a}$ (where R$^{34}$ is hydrogen or alkyl and R$^{34a}$ is alkyl, alkenyl, cycloalkyl, aryl, heteroaryl, or heterocycloalkyl), —SO$_2$NR$^{35}$R$^{35a}$ (where R$^{35}$ is hydrogen or alkyl and R$^{35a}$ is alkyl, alkenyl, cycloalkyl, aryl, heteroaryl, or heterocycloalkyl), —NR$^{32}$C(O)R$^{32a}$ (where R$^{32}$ is hydrogen or alkyl and R$^{32a}$ is alkyl, alkenyl, alkoxy, or cycloalkyl), —NR$^{30}$R$^{30'}$ (where R$^{30}$ and R$^{30'}$ are independently hydrogen, alkyl, or hydroxyalkyl), and —C(O)NR$^{33}$R$^{33a}$ (where R$^{33}$ is hydrogen or alkyl and R$^{33a}$ is alkyl, alkenyl, alkynyl, or cycloalkyl);

$R^9$ is alkyl, alkenyl, alkynyl, aryl, cycloalkyl, heteroaryl, and heterocycloalkyl; where the alkyl, alkenyl, alkynyl, aryl, cycloalkyl, heteroaryl, and heterocycloalkyl are independently optionally susbstituted with one, two, three, four, or five groups selected from halo, hydroxy, alkyl, haloalkyl, haloalkoxy, amino, alkylamino, and dialkylamino;

$R^{25}$ and $R^{25b}$ are independently hydrogen, alkyl, alkenyl, optionally substituted cycloalkyl, or optionally substituted aryl; and $R^{25a}$ is hydrogen, alkyl, or alkenyl;

Group B:

A is heteroarylene optionally substituted with one, two, three, or four groups selected from $R^{10}$, $R^{12}$, $R^{14}$, $R^{16}$ and $R^{19}$ where $R^{10}$, $R^{12}$, $R^{14}$ and $R^{16}$ are independently hydrogen, alkyl, alkenyl, alkynyl, halo, haloalkoxy, hydroxy, alkoxy, cyano, amino, alkylamino, dialkylamino, haloalkyl, alkylsulfonylamino, alkylcarbonyl, alkenylcarbonyl, alkoxycarbonyl, alkenyloxycarbonyl, aminocarbonyl, alkylaminocarbonyl, dialkylaminocarbonyl, or alkylcarbonylamino; where $R^{19}$ is hydrogen, alkyl, or alkenyl; and where each alkyl and alkenyl, either alone or as part of another group within $R^{10}$, $R^{12}$, $R^{14}$, $R^{16}$, and $R^{19}$ is independently optionally substituted with halo, hydroxy, or alkoxy;

X is alkyl, halo, haloalkyl, or haloalkoxy;

$R^1$, $R^2$, $R^3$, $R^4$, $R^5$ and $R^6$ are independently hydrogen, halo, nitro, —$NR^8R^{8'}$, —$OR^8$, —$NHS(O)_2R^8$, —CN, —$S(O)_m R^8$, —$S(O)_2NR^8R^{8'}$, —$C(O)R^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^8R^{8''}$, —$NR^8C(O)OR^{8'}$, and —$NR^8C(O)R^{8'}$; or one of $R^1$ and $R^2$ together with the carbon to which they are attached, $R^3$ and $R^4$ together with the carbon to which they are attached, and $R^5$ and $R^6$ together with the carbon to which they are attached form C(O) or C(=NOH);

m is 1 or 2;

$R^7$ is hydrogen, halo or alkyl; and $R^8$, $R^{8'}$ and $R^{8''}$ are independently selected from hydrogen, hydroxy, optionally substituted alkoxy, alkyl, haloalkyl, alkenyl, alkynyl, aryl, cycloalkyl, heteroaryl, and heterocycloalkyl, where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, carboxy ester, nitro, cyano, —$S(O)_nR^{31}$ (where n is 0, 1, or 2 and $R^{31}$ is optionally substituted alkyl, optionally substituted aryl, optionally substituted cycloalkyl, optionally substituted heterocycloalkyl, or optionally substituted heteroaryl), —$NR^{36}S(O)_2R^{36a}$ (where $R^{36}$ is hydrogen, alkyl, or alkenyl and $R^{36a}$ is alkyl, alkenyl, optionally substituted aryl, optionally substituted cycloalkyl, optionally substituted heterocycloalkyl, or optionally substituted heteroaryl), —$S(O)_2NR^{37}R^{37a}$ (where $R^{37}$ is hydrogen, alkyl, or alkenyl and $R^{37a}$ is alkyl, alkenyl, optionally substituted aryl, optionally substituted cycloalkyl, optionally substituted heterocycloalkyl, or optionally substituted heteroaryl), optionally substituted cycloalkyl, optionally substituted heterocycloalkyl, optionally substituted aryl, optionally substituted arylalkyl, optionally substituted aryloxy, optionally substituted arylalkyloxy, optionally substituted heteroaryl, —$NHC(O)R^{32}$ (where $R^{32}$ is alkyl, alkenyl, alkoxy, or cycloalkyl) and —$NR^{30}R^{30'}$ (where $R^{30}$ and $R^{30'}$ are independently hydrogen, alkyl, or hydroxyalkyl), and —$C(O)NHR^{33}$ (where $R^{33}$ is alkyl, alkenyl, alkynyl, or cycloalkyl);

Group C:

A is

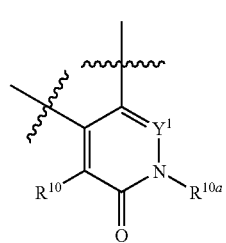

(a)

where $R^{10}$ is hydrogen, alkyl, alkenyl, alkynyl, halo, haloalkoxy, hydroxy, alkoxy, amino, alkylamino, dialkylamino, haloalkyl, —$NHS(O)_2R^8$, —CN, —$C(O)R^8$, —$C(O)OR^8$, —$C(O)NR^8R^{8'}$ and —$NR^8C(O)R^{8'}$;

$R^{10a}$ is hydrogen, alkyl, or alkenyl;

$Y^1$ is =CH— or =N—;

X is alkyl, halo, haloalkyl, or haloalkoxy;

$R^1$, $R^2$, $R^3$, $R^4$, $R^5$ and $R^6$ are independently hydrogen, halo, nitro, —$NR^8R^{8'}$, —$OR^8$, —$NHS(O)_2R^8$, —CN, —$S(O)_m R^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^8R^{8''}$, —$NR^8C(O)OR^{8'}$ and —$NR^8C(O)R^{8'}$; or one of $R^1$ and $R^2$ together with the carbon to which they are attached, $R^3$ and $R^4$ together with the carbon to which they are attached, and $R^5$ and $R^6$ together with the carbon to which they are attached form C(O) or C(=NOH);

m is 1 or 2;

$R^7$ is hydrogen, halo or alkyl; and $R^8$, $R^{8'}$ and $R_{8''}$ are independently selected from hydrogen, hydroxy, optionally substituted alkoxy, alkyl, haloalkyl, alkenyl, alkynyl, aryl, cycloalkyl, heteroaryl, and heterocycloalkyl, where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, carboxy ester, nitro, cyano, —$S(O)_nR^{31}$ (where n is 0, 1, or 2 and $R^{31}$ is optionally substituted alkyl, optionally substituted aryl, optionally substituted cycloalkyl, optionally substituted heterocycloalkyl, or optionally substituted heteroaryl), —$NR^{36}S(O)_2R^{36a}$ (where $R^{36}$ is hydrogen, alkyl, or alkenyl and $R^{36a}$ is alkyl, alkenyl, optionally substituted aryl, optionally substituted cycloalkyl, optionally substituted heterocycloalkyl, or optionally substituted heteroaryl), —$S(O)_2NR^{37}R^{37a}$ (where $R^{37}$ is hydrogen, alkyl, or alkenyl and $R^{37a}$ is alkyl, alkenyl, optionally substituted aryl, optionally substituted cycloalkyl, optionally substituted heterocycloalkyl, or optionally substituted heteroaryl), optionally substituted cycloalkyl, optionally substituted heterocycloalkyl, optionally substituted aryl, optionally substituted arylalkyl, optionally substituted aryloxy, optionally substituted arylalkyloxy, optionally substituted heteroaryl, —NHC(O)R$^{32}$ (where R$^{32}$ is alkyl, alkenyl, alkoxy, or cycloalkyl) and ≧NR$^{30}$R$^{30'}$ (where R$^{30}$ and R$^{30'}$ are independently hydrogen, alkyl, or hydroxyalkyl), and —C(O)NHR$^{33}$ (where R$^{33}$ is alkyl, alkenyl, alkynyl, or cycloalkyl); or Group D:

A is

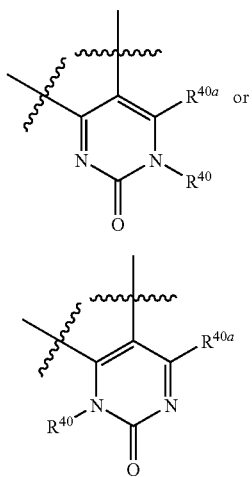

R$^{40}$ and R$^{40a}$ are independently hydrogen or alkyl;

X is alkyl, halo, haloalkyl, or haloalkoxy;

R$^1$, R$^2$, R$^3$, R$^4$, R$^5$ and R$^6$ are independently hydrogen, halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)OR$^8$, —C(O)NR$^8$R$^{8'}$, —NR$^8$C(O)OR$^{8'}$, —NR$^8$C(O)NR$^{8'}$R$^{8''}$, —NR$^8$C(O)OR$^{8'}$, —NR$^8$C(O)R$^{8'}$, —CH$_2$N(R$^{25}$)(NR$^{25a}$R$^{25b}$), —CH$_2$NR$^{25}$C(=NH)(NR$^{25a}$R$^{25b}$), —CH$_2$NR$^{25}$C(=NH)(N(R$^{25a}$)(NO$_2$)), —CH$_2$NR$^{25}$C(=NH)(N(R$^{25a}$)(CN)), —CH$_2$NR$^{25}$C(=NH)(R$^{25}$), —CH$_2$NR$^{25}$C(NR$^{25a}$R$^{25b}$)=CH(NO$_2$), alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —OR$^8$, —NR$^8$R$^{8'}$, —NR$^8$S(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^8$R$^{8''}$, —NR$^8$C(O)OR$^{8'}$ and —NR$^8$C(O)R$^{8'}$; or one of R$^1$ and R$^2$ together with the carbon to which they are attached, R$^3$ and R$^4$ together with the carbon to which they are attached, and R$^5$ and R$^6$ together with the carbon to which they are attached form C(O) or C(=NOH);

m is 1 or 2;

R$^7$ is hydrogen, halo or alkyl; and

R$^8$, R$^{8'}$ and R$_{8''}$ are independently selected from hydrogen, hydroxy, optionally substituted alkoxy, alkyl, haloalkyl, alkenyl, alkynyl, aryl, cycloalkyl, heteroaryl, and heterocycloalkyl, where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, carboxy ester, nitro, cyano, —S(O)$_n$R$^{31}$ (where n is 0, 1, or 2 and R$^{31}$ is optionally substituted alkyl, optionally substituted aryl, optionally substituted cycloalkyl, optionally substituted heterocycloalkyl, or optionally substituted heteroaryl), —NR$^{36}$S(O)$_2$R$^{36a}$ (where R$^{36}$ is hydrogen, alkyl, or alkenyl and R$^{36a}$ is alkyl, alkenyl, optionally substituted aryl, optionally substituted cycloalkyl, optionally substituted heterocycloalkyl, or optionally substituted heteroaryl), —S(O)$_2$NR$^{37}$R$^{37a}$ (where R$^{37}$ is hydrogen, alkyl, or alkenyl and R$^{37a}$ is alkyl, alkenyl, optionally substituted aryl, optionally substituted cycloalkyl, optionally substituted heterocycloalkyl, or optionally substituted heteroaryl), optionally substituted cycloalkyl, optionally substituted heterocycloalkyl, optionally substituted aryl, optionally substituted arylalkyl, optionally substituted aryloxy, optionally substituted arylalkyloxy, optionally substituted heteroaryl, —NHC(O)R$^{32}$ (where R$^{32}$ is alkyl, alkenyl, alkoxy, or cycloalkyl) and —NR$^{30}$R$^{30'}$ (where R$^{30}$ and R$^{30'}$ are independently hydrogen, alkyl, or hydroxyalkyl), and —C(O)NHR$^{33}$ (where R$^{33}$ is alkyl, alkenyl, alkynyl, or cycloalkyl).

A second aspect of the Invention provides a pharmaceutical composition which comprises a compound of Formula I, or a pharmaceutically acceptable salt or solvate therof, and a pharmaceutically acceptable carrier, excipient, or diluent.

In a third aspect, the invention is directed to a method of inhibiting MEK comprising administering to a patient a therapeutically effective amount of a compound of Formula I, or a pharmaceutically acceptable salt or solvate thereof, and optionally a pharmaceutically acceptable carrier, excipient, or diluent.

In a fourth aspect, the invention comprises a method of inhibiting MEK in a cell, comprising contacting a cell with a compound of Formula I or a pharmaceutically acceptable salt or solvate therof, or with a pharmaceutical composition comprising a therapeutically effective amount of a compound of Formula I and a pharmaceutically acceptable carrier, excipient, or diluent.

A fifth aspect of the Invention provides a method for treating a disease, disorder, or syndrome which method comprises administering to a patient a compound of Formula I or a pharmaceutically acceptable salt or solvate thereof, or a pharmaceutical composition comprising a therapeutically effective amount of a compound of Formula I and a pharmaceutically acceptable carrier, excipient, or diluent.

A sixth aspect of the invention is directed to a process of preparing a compound of Formula I, comprising:

(a) reacting an intermediate of formula 19:

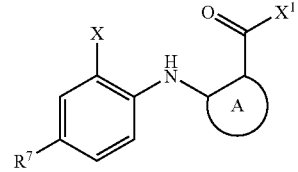

where X$^1$ is OH or halo, specifically chloro or fluoro, and all other groups are as defined in the Summary of the Invention for a compound selected from Group A, Group B, Group C, and Group D; with an intermediate of formula 17:

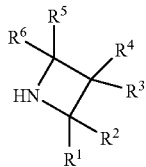

where $R^1$, $R^2$, $R^3$, $R^4$, $R^5$, and $R^6$ are as defined in the Summary of the Invention for a compound selected from Group A, Group B, Group C, and Group D; and (b) optionally separating individual isomers; and
(c) optionally modifying any of the $R^1$, $R^2$, $R^3$, $R^4$, $R^5$, and $R^6$ groups.

A seventh aspect of the invention is directed to a process of preparing intermediates of formula 3, 4, 5, 6, 10, and 13, comprising:

(a) reacting an intermediate of formula 2(a):

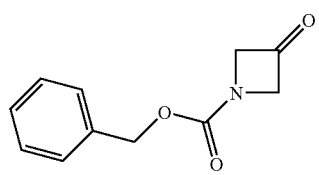

with $R^4M$ (where $R^4M$ is a Grignard reagent or organometallic species and $R^4$ is as defined in the Summary of the Invention for a compound of Group A, Group B, Group C, or Group D); with $R^{4"}CH_2NO_2$ (where $R^{4"}$ is hydrogen or alkyl optionally substituted as described for $R^4$ in the Summary of the Invention for a compound of Group A, Group B, Group C, or Group D); with $R^{4"}R^{4"'}C(O)$ ($R^{4"}$ is alkyl optionally substituted as described for $R^4$ in the Summary of the Invention for a compound of Group A, Group B, Group C, or Group D and $R^{4"'}$ is hydrogen or $R^{4"}$); with $R'R"CHP(Ph)_3$ (where $R'$ and $R"$ are independently hydrogen, alkyl, alkenyl, aryl, or heteroaryl and the alkyl, alkenyl, aryl, and heteroaryl are optionally substituted as described for $R^4$ in the Summary of the Invention for a compound of Group A, Group B, Group C, or Group D); with a chiral oxazolidinone auxiliary and subsequent treatment with a base, such as lithium hydroxide, in aqueous hydrogen peroxide; or with a N-protected heterocycloalkyl group where $P^1$ is Boc and $P^2$ is CBz or $P^1$ is CBz and $P^2$ is Boc; to yield the intermediates of formula 3, 4, 5, 6, 12, and 13, respectively:

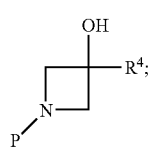

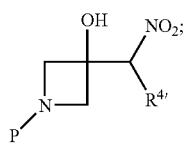

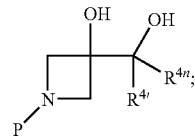

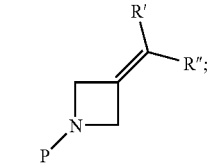

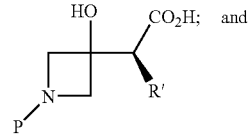

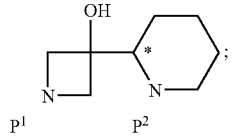

(b) optionally further reacting 6 with m-CPBA to form an epoxide and further opening the epoxide with an amine of formula $NHR^8R^{8'}$ to yield an intermediate of formula 8:

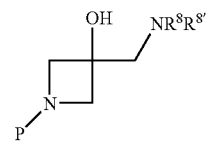

where P is a N-protecting group and $R^8$ and $R^{8'}$ are as defined in the Summary of the Invention for a compound of Group A, Group B, Group C, or Group D;

(c) optionally further subjecting 10 to a Curtius rearrangement and subsequent treatment to yield an intermediate of formula 12:

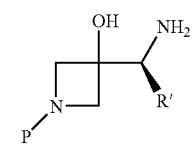

where P is a N-protecting group and R' is an alkyl group such as methyl or ethyl;
(d) optionally further resolving individual isomers; and
(e) optionally modifying any of the $R^1$, $R^2$, $R^3$, $R^4$, $R^5$, and $R^6$ groups.

DETAILED DESCRIPTION OF THE INVENTION

Abbreviations and Definitions

The following abbreviations and terms have the indicated meanings throughout:

| Abbreviation | Meaning |
| --- | --- |
| Ac | acetyl |
| br | broad |
| °C. | degrees Celsius |
| CBZ | CarboBenZoxy = benzyloxycarbonyl |
| d | doublet |
| dd | doublet of doublet |
| dt | doublet of triplet |
| DAST | (diethylamino)sulfur trifluoride |
| DCM | dichloromethane |
| DIPEA | N,N-diisopropylethylamine |
| DMAP | 4-dimethylaminopyridine |
| DMF | N,N-dimethylformamide |
| DMSO | dimethyl sulfoxide |
| DPPA | diphenylphosphoryl azide |
| EDCI | 1-(3-dimethylaminopropyl)-3-ethylcarbodiimide |
| EI | Electron Impact ionization |
| Et | ethyl |
| g | gram(s) |
| GC | gas chromatography |
| h or hr | hour(s) |
| HBTU | 2-(1H-benzotriazole-1-yl)-1,1,3,3-tetramethyluronium hexafluorophosphate |
| HOAc | acetic acid |
| HOBt | hydroxybenzotriazole |
| HPLC | high pressure liquid chromatography |
| L | liter(s) |
| LDA | lithium diiosopropylamide |
| LHMDS | lithium hexamethyldisilazide |
| M | molar or molarity |
| m | multiplet |
| MCPBA | meta-chloroperbenzoic acid |
| Me | methyl |
| mg | milligram(s) |
| MHz | megahertz (frequency) |
| min | minute(s) |
| mL | milliliter(s) |
| mM | millimolar |
| mmol | millimole(s) |
| mol | mole(s) |
| MS | mass spectral analysis |
| N | normal or normality |
| nM | nanomolar |
| NMM | N-methylmorpholine |
| NMR | nuclear magnetic resonance spectroscopy |
| PyBOP | benzotriazole-1-yl-oxy-tris-pyrrolidino-phosphonium hexafluorophosphate |
| q | quartet |
| RT | room temperature |
| s | singlet |
| s- | secondary |
| t- | tertiary |
| t or tr | triplet |
| THF | tetrahydrofuran |
| μL | microliter(s) |
| μM | micromole(s) or micromolar |

The symbol "–" means a single bond, "=" means a double bond, "≡" means a triple bond, and "⁼" means a single bond and optionally a double bond. When chemical structures are depicted or described, unless explicitly stated otherwise, all carbons are assumed to have hydrogen substitution to conform to a valence of four.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH₂CH₂—. It is understood by one of ordinary skill in the art that the aforementioned descriptive techniques are common in the chemical arts to provide brevity and simplicity to description of otherwise complex structures.

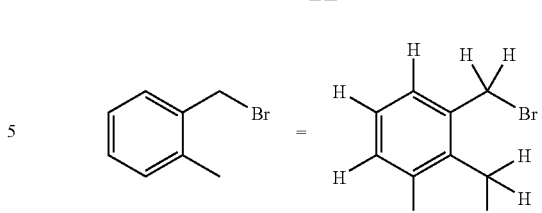

If a group "R" is depicted as "floating" on a ring system, as for example in the formula:

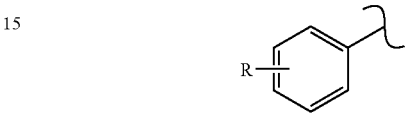

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

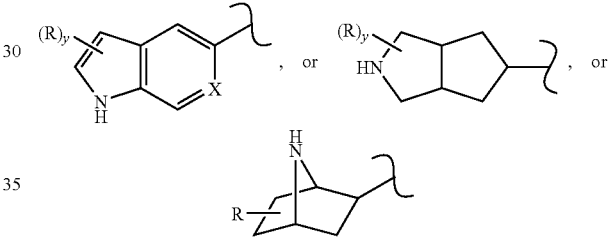

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

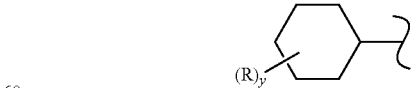

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a germinal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

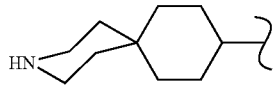

"Acyl" means a —C(O)R radical where R is optionally substituted alkyl, optionally substituted alkenyl, haloalkyl, cycloalkyl, cycloalkylalkyl, aryl, aralkyl, heteroaryl, heteroaralkyl, heterocycloalkyl, or heterocycloalkylalkyl, as defined herein, e.g., acetyl, benzoyl, trifluoromethylcarbonyl, or 2-methoxyethylcarbonyl, and the like.

"Acylamino" means a —NRR' group where R is acyl, as defined herein, and R' is hydrogen or alkyl.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

"Alkenyl" means a means a linear monovalent hydrocarbon radical of one to six carbon atoms or a branched monovalent hydrocarbon radical of three to 6 carbon atoms which radical contains at least one double bond, e.g., ethenyl, propenyl, 1-but-3-enyl, 1-pent-3-enyl, 1-hex-5-enyl and the like.

"Alkenylcarbonyl" means a —C(O)R group where R is alkenyl, as defined herein.

"Alkenyloxycarbonyl" means a —C(O)OR group where R is alkenyl, as defined herein.

"Alkoxy" means an —OR group where R is alkyl group as defined herein. Examples include methoxy, ethoxy, propoxy, isopropoxy, and the like. Lower-alkoxy refers to groups containing one to six carbons.

"Alkoxyalkyl" means an alkyl group, as defined herein, substituted with at least one, preferably one, two, or three, alkoxy groups as defined herein. Representative examples include methoxymethyl and the like.

"Alkoxycarbonyl" means a —C(O)OR group where R is alkyl as defined herein.

"Alkoxycarbonylamino" means a —NR'R" group where R' is hydrogen, alkyl, hydroxy, or alkoxy and R" is alkoxycarbonyl, as defined herein.

"Alkyl" means a linear saturated monovalent hydrocarbon radical of one to eight carbon atoms or a branched saturated monovalent hydrocarbon radical of three to eight carbon atoms, e.g., methyl, ethyl, propyl, 2-propyl, butyl (including all isomeric forms), or pentyl (including all isomeric forms), and the like.

"Alkylamino" means a —NHR radical where R is alkyl as defined herein, or an N-oxide derivative, or a protected derivative thereof, e.g., methylamino, ethylamino, n-propylamino, iso-propylamino, n-butylamino, iso-butylamino, tert-butylamino, or methylamino-N-oxide, and the like.

"Alkylaminoalkyl" means an alkyl group substituted with one or two alkylamino groups, as defined herein.

"Alkylaminocarbonyl" means a —C(O)R group where R is alkylamino, as defined herein.

"Alkylcarbonyl" means a —C(O)R group where R is alkyl, as defined herein.

"Alkylcarbonylamino" means a —NRR' group where R is hydrogen or alkyl as defined herein and R' is alkylcarbonyl, as defined herein.

"Alkylcarbonyloxy" means an —OC(O)R group where R is alkyl, as defined herein.

"Alkylsulfonylamino" means a —NRS(O)$_2$R' group where R is hydrogen or alkyl as defined herein, and R' is alkyl, as defined herein.

"Alkynyl" means a straight or branched hydrocarbon radical having from 2 to 8 carbon atoms and at least one triple bond and includes ethynyl, propynyl, butynyl, pentyn-2-yl and the like.

"Aminoalkyl" means an alkyl group substituted with at least one, specifically one, two or three, amino groups.

"Aminocarbonyl" means a —C(O)NH$_2$ group.

"Aryl" means a monovalent six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Representative examples include phenyl, naphthyl, and indanyl, and the like.

"Arylene" means a divalent six- to fourteen-membered, mono- or bi-carbocyclic ring, wherein the monocyclic ring is aromatic and at least one of the rings in the bicyclic ring is aromatic. Representative examples include phenylene, naphthylene, and indanylene, and the like.

"Arylalkyl" means an alkyl group, as defined herein, substituted with one or two aryl groups, as defined herein. Examples include benzyl, phenethyl, and the like.

"Carboxy ester" means a —C(O)OR group where R is lower alkyl, lower alkenyl, lower alkynyl, cycloalkyl, aryl or arylalkyl, each of which is defined herein. Representative examples include methoxycarbonyl, ethoxycarbonyl, and benzyloxycarbonyl, and the like.

"Cycloalkyl" means a monocyclic or fused bicyclic, saturated or partially unsaturated (but not aromatic), monovalent hydrocarbon radical of three to ten carbon ring atoms. Fused bicyclic hydrocarbon radical includes bridged ring systems. Unless stated otherwise, the valency of the group may be located on any atom of any ring within the radical, valency rules permitting. One or two ring carbon atoms may be replaced by a —C(O)—, —C(S)—, or —C(=NH)— group. More specifically, the term cycloalkyl includes, but is not limited to, cyclopropyl, cyclobutyl, cyclopentyl, cyclohexyl, cyclohexyl, or cyclohex-3-enyl, and the like.

"Dialkylamino" means a —NRR' radical where R and R' are alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with one or two dialkylamino groups, as defined herein.

"Dialkylaminocarbonyl" means a —C(O)R group where R is dialkylamino, as defined herein.

"Fused-polycyclic" or "fused ring system" means a polycyclic ring system that contains fused rings and, unless otherwise indicated, can contain bridged rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A Spiro ring system is not a fused-polycyclic by this definition, but fused polycyclic ring systems of the invention may themselves have Spiro rings attached Thereto via a single ring atom of the fused-polycyclic. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Haloalkoxy" means an —OR' group where R' is haloalkyl as defined herein, e.g., trifluoromethoxy or 2,2,2-trifluoroethoxy, and the like.

"Halogen" or "halo" means fluoro, chloro, bromo and iodo.

"Haloalkyl" means an alkyl group, as defined herein, that is substituted with one or more halogens, preferably one to five halo atoms. Representative examples include trifluoromethyl, difluoromethyl, 1-chloro-2-fluoro-ethyl, and the like.

"Heteroaryl" means a monocyclic, fused bicyclic, or fused tricyclic, monovalent radical of 5 to 14 ring atoms containing one or more, preferably one, two, three, or four ring heteroatoms independently selected from —O—, —S(O)$_n$— (n is 0, 1, or 2), —N—, —N(R$^x$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^x$ is hydrogen, alkyl, hydroxy, alkoxy, acyl, or alkylsulfonyl. Unless stated otherwise, the valency may be located on any atom of any ring of the heteroaryl group, valency rules permitting. In particular, when the point of valency is located on the nitrogen, is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, or N-oxide or a protected derivative thereof.

"Heteroarylene" means a monocyclic, fused bicyclic, or fused tricyclic, divalent radical of 5 to 14 ring atoms containing one or more, preferably one, two, three, or four ring heteroatoms independently selected from —O—, —S(O)$_n$— (n is 0, 1, or 2), —N—, —N(R$^{19}$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R$^{19}$ is hydrogen, alkyl, or alkenyl. Unless stated otherwise, the valencies may be located on any atom of any ring of the heteroarylene group, valency rules permitting. In particular, when the point of valency is located on the nitrogen, R$^x$ is absent. More specifically, the term heteroaryl includes, but is not limited to, thien-diyl, benzo[d]isoxazol-diyl, benzo[a] isothiazol-diyl, 1H-indazol-diyl (optionally substituted at the N1 position with R$^{19}$), benzo[d]oxazol-diyl, benzo[d]thiazol-diyl, 1H-benzo[d]imidazol-diyl (optionally substituted at the N1 position with R$^{19}$), 1H-benzo[d][1,2,3]triazol-diyl (optionally substituted at the N1 position with R$^{19}$), imidazo[1,2-a]pyridin-diyl, cinnolin-diyl, quinolin-diyl, pyridin-diyl, 1-oxido-pyridin-diyl, [1,2,4]triazolo[4,3-a]pyridin-diyl, and 2,3-dihydroimidazo[1,2-a]pyridin-diyl, and the like.

"Heterocycloalkyl" means a saturated or partially unsaturated (but not aromatic) monovalent monocyclic group of 3 to 8 ring atoms or a saturated or partially unsaturated (but not aromatic) monovalent fused bicyclic group of 5 to 12 ring atoms in which one or more, specifically one, two, three, or four ring heteroatoms independently selected from O, S(O)$_n$ (n is 0, 1, or 2), N, N(R$^y$) (where R$^y$ is hydrogen, alkyl, hydroxy, alkoxy, acyl, or alkylsulfonyl), the remaining ring atoms being carbon. One or two ring carbon atoms may be replaced by a —C(O)—, —C(S)—, or —C(=NH)— group. Fused bicyclic radical includes bridged ring systems. Unless otherwise stated, the valency of the group may be located on any atom of any ring within the radical, valency rules permitting. When the point of valency is located on a nitrogen atom, R$^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and the derivatives thereof and N-oxide or a protected derivative thereof.

"Hydroxyalkyl" means an alkyl, as defined herein, substituted with at least one, preferably one, two, or three, hydroxy group(s), provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl, and the like.

"Hydroxyamino" means a —NH(OH) group.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted arylC$_{1-8}$ alkyl," both the "C$_{1-8}$ alkyl" portion and the "aryl" portion of the molecule may or may not be substituted. A list of exemplary optional substitutions is presented below in the definition of "substituted."

"Optionally substituted alkoxy" means an —OR radical where R is optionally substituted alkyl as defined herein. Representative examples include —OCH$_2$CH$_2$OCH$_3$, —OCH$_2$CH$_2$OH, —OCH$_2$CH(NH$_2$)CH$_3$, and the like.

"Optionally substituted alkyl" means an alkyl radical, as defined herein, optionally substituted with one or more group(s), specifically one, two, three, four, or five groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, halo, hydroxy, hydroxyalkoxy, carboxy, alkylcarbonylamino, alkylcarbonyloxy, —S(O)$_{0-2}$-alkyl, —S(O)$_{0-2}$-alkenyl, aminosulfonyl, alkylaminosulfonyl, dialkylaminosulfonyl, —NR$^c$S(O)$_2$-alkyl (where R$^c$ is hydrogen, alkyl, optionally substituted alkenyl, optionally substituted alkynyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —C(O)NR$^a$R$^b$ (where R$^a$ and R$^b$ are independently hydrogen, alkyl, optionally substituted alkenyl, optionally substituted alkynyl, hydroxy, alkoxy, alkenyloxy, or cyanoalkyl).

"Optionally substituted aryl" means an aryl group, as defined herein, which is optionally substituted with one, two, three, four, of five groups selected from halo, haloalkyl, haloalkoxy, hydroxy, alkyl, alkenyl, alkynyl, alkoxy, carboxy, carboxy ester, amino, alkylamino, dialkylamino, optionally substituted cycloalkyl, optionally substituted heterocycloalkyl, optionally substituted heteroaryl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —NHS(O)$_2$R' (where R' is alkyl, aryl, or heteroaryl).

"Optionally substituted arylalkyl means an alkyl group substituted with one or two optionally substituted aryl group(s) as defined herein.

"Optionally substituted arylalkyloxy" means an —OR group where R is optionally substituted arylalkyl, as defined herein.

"Optionally substituted arylalkyloxycarbonyl" means a —C(O)R group where R is optionally substituted arylalkyloxy, as defined herein.

"Optionally substituted aryloxy" means an —OR group where R is optionally substituted aryl, as defined herein.

"Optionally substituted aryloxycarbonyl" means a —C(O)R group where R is optionally substituted aryloxy as defined herein.

"Optionally substituted cycloalkyl" means a cycloalkyl radical, as defined herein, that is optionally substituted with one, two, three, or four groups independently selected from alkyl, alkenyl, alkynyl, alkoxy, halo, haloalkyl, haloalkoxy, oxo, hydroxy, cyano, nitro, amino, mono(C$_1$-C$_6$)alkylamino, dialkylamino, haloalkyl, haloalkoxy, aminoalkyl, alkylaminoalkyl dialkylaminoalkyl, carboxy, carboxy ester, cycloalkyl, hydroxyalkyl, —C(O)NR'R" (where R' is hydrogen, alkyl, hydroxy, or alkoxy and R" is hydrogen, alkyl, aryl, heteroaryl, or heterocycloalkyl), optionally substituted heterocycloalkyl, optionally substituted heteroaryl, —NR'C(O)R" (where R' is hydrogen or alkyl and R" is alkyl, aryl, heteroaryl, or heterocycloalkyl), and —NHS(O)$_2$R' (where R' is alkyl, aryl, or hetercyclyl).

"Optionally substituted cycloalkyloxycarbonyl" means a —C(O)OR group where R is optionally substituted cycloalkyl as defined herein.

"Optionally substituted heteroaryl" means a heteroaryl group, as defined herein, optionally substituted with one, two, three, four, or five groups selected from halo, haloalkyl, haloalkoxy, alkyl, alkenyl, alkynyl, alkoxy, hydroxy, oxo (valency rules permitting), carboxy, carboxy ester, amino, alkylamino, dialkylamino, optionally substituted cycloalkyl, optionally substituted heterocycloalkyl, heteroaryl, optionally substituted aryl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —NHS(O)$_2$R' (where R' is alkyl, aryl, or heteroaryl).

"Optionally substituted heterocycloalkyl" means a heterocycloalkyl ring, as defined herein, optionally substituted with one, two, three, four, or five groups selected from halo, haloalkyl, haloalkoxy, hydroxy, oxo, alkyl, alkenyl, alkynyl, alkoxy, optionally substituted cycloalkyl, heterocycloalkyl, optionally substituted aryl, optionally substituted heteroaryl, alkylaminoalkyl, dialkylaminoalkyl, carboxy, alkoxycarbonyl, aryloxycarbonyl, arylalkyloxycarbonyl, cycloalkyloxycarbonyl, cycloalkylalkyloxycarbonyl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), amino, alkylamino, dialkylamino, and —NHS(O)$_2$R' (where R' is alkyl, aryl, or heteroaryl).

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spiro", "Spirocyclyl" or "Spiro ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto.

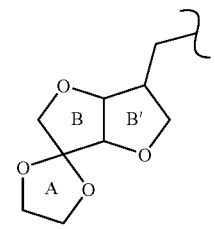

"Yield" for each of the reactions described herein is expressed as a percentage of the theoretical yield.

"Patient" for the purposes of the present invention includes humans and other animals, particularly mammals, and other organisms. Thus the methods are applicable to both human therapy and veterinary applications. In a specific embodiment the patient is a mammal, and in a more specific embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal Glands: neuroblastoma. Thus, the term "cancerous cell" as provided herein, includes a cell afflicted by any one of the above-identified conditions.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

EMBODIMENTS OF THE INVENTION

In one embodiment of the Invention, $R^7$ is halo and all other groups are as defined in the Summary of the Invention for Group A, Group B, Group C, or Group D. In a more specific embodiment, $R^7$ is iodo or bromo. In an even more specific embodiment, $R^7$ is iodo. Yet even more specifically, the compound is that where $R^7$ is iodo or bromo and all other groups are as defined in the Summary of the Invention for Group A.

In another embodiment of the Invention, X is halo and all other groups are as defined in the Summary of the Invention for Group A, Group B, Group C, or Group D. In a more specific embodiment, X is fluoro or chloro. In an even more specific embodiment, X is fluoro. Yet even more specifically, the compound is that where X is fluoro or chloro and all other groups are as defined in the Summary of the Invention for Group A.

In another embodiment of the Invention, $R^7$ and X are halo and all other groups are as defined in the Summary of the Invention for Group A, Group B, Group C, or Group D. More specifcally, $R^7$ is iodo and X is fluoro. Even more specifically, the compound is that where $R^7$ is iodo and X is fluoro and all other groups are as defined in the Summary of the Invention for Group A.

In another embodiment of the Invention, $R^1$, $R^2$, $R^5$, and $R^6$ are hydrogen and all other groups are as defined in the Summary of the Invention for Group A, Group B, Group C, or Group D. More specifically, $R^1$, $R^2$, $R^5$, and $R^6$ are hydrogen and all other groups are as defined in the Summary of the Invention for Group A.

In another embodiment of the Invention, the compound of Formula I is selected from Group A where all groups are as defined in the Summary of the Invention.

In another embodiment of the invention (A1), X and $R^7$ are halo and all other groups are as defined in the Summary of the Invention for a compound of Group A.

In another embodiment (A2), the compound of Formula I is selected from Group A where $R^{10}$ and $R^{12}$ are independently hydrogen or halo. In a more specific embodiment, $R^{10}$ and $R^{12}$ are independently hydrogen or fluoro. More specifically, $R^{10}$ is 3-fluoro and $R^{12}$ is hydrogen. In another more specific embodiment, $R^{10}$ and $R^{12}$ are fluoro, more specifically, 3-fluoro and 4-fluoro, 4-fluoro and 5-fluoro, or 4-fluoro and 6-fluoro.

In another embodiment of the invention (A3), the compound is that where $R^1$, $R^2$, $R^5$ and $R^6$ are hydrogen and all other groups are as defined in the Summary of the Invention for Group A.

In another embodiment (A4), the compound of Formula I is selected from Group A where X, $R^7$, and A are as defined in the Summary of the Invention; and one of $R^1$, $R^2$, $R^3$, $R^4$, $R^5$, and $R^6$ is halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)NR^8R^{8'}$, —$NR^8C(O)OR^{8'}$, —$NR^8C(O)R^{8'}$, —$CH_2N(R^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^8R^{8'}$, —$NR^8C(O)OR^{8'}$ and —$NR^8C(O)R^{8'}$; and the others of $R^1$, $R^2$, $R^3$, $R^4$, $R^5$, and $R^6$ are as defined in the Summary of the Invention; or one of $R^1$ and $R^2$ together with the carbon to which they are attached, $R^3$ and $R^4$ together with the carbon to which they are attached, and $R^5$ and $R^6$ together with the carbon to which they are attached forms C(O) or C(=NOH); and the others of $R^1$, $R^2$, $R^3$, $R^4$, $R^5$, and $R^6$ are as defined in the Summary of the invention.

In a more another embodiment of the Invention (A5), the compound of Formula I is selected from Group A where X, $R^7$, and A are as defined in the Summary of the Invention; and $R^3$ is halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —$OR^8$, —$NR^8R^{8'}$, —$NR^8S(O)_2R^9$, —CN, —$S(O)_mR^9$, —$C(O)R^8$, —$C(O)OR^8R^{8'}$, —$NR^8C(O)NR^8R^{8''}$, —$NR^8C(O)OR^{8'}$ and —$NR^8C(O)R^{8'}$; and $R^4$ is as defined in the Summary of the Invention; or $R^3$ and $R^4$ together with the carbon to which they are attached form C(O) or C(=NOH); and $R^1$, $R^2$, $R^5$ and $R^6$ are as defined in the Summary of the Invention.

A more specific embodiment of embodiment A5 is that where $R^1$, $R^2$, $R^5$ and $R^6$ are hydrogen.

In another embodiment of the Invention (A6), the compound of Formula I is selected from Group A where X, $R^7$, and A are as defined in the Summary of the Invention; and $R^3$ and $R^4$ are independently halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)NR^8R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^8R^{8''}$, —$NR^8C(O)OR^{8'}$ and —$NR^8C(O)R^{8'}$; or $R^3$ and $R^4$ together with the carbon to which they are attached form C(O) or C(=NOH);

$R^1$, $R^2$, $R^5$ and $R^6$ are as defined in the Summary of the Invention.

A more specific embodiment of embodiment A6 is that where $R^1$, $R^2$, $R^5$ and $R^6$ are hydrogen.

In another embodiment of the Invention (A7), the compound of Formula I is selected from Group A where X and $R^7$ are halo; A is phenylene optionally substituted with $R^{10}$ and $R^{12}$ where $R^{10}$ and $R^{12}$ are independently hydrogen or halo; $R^1$, $R^2$, $R^5$ and $R^6$ are hydrogen;

$R^3$ is hydrogen and $R^4$ is —$NR^8R^{8'}$ (where $R^8$ is hydrogen, hydroxy, alkyl, alkoxy, aryl, cycloalkyl, heteroaryl, or heterocycloalkyl and $R^{8'}$ is hydroxy, alkoxy, aryl, cycloalkyl, heteroaryl, or heterocycloalkyl), —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^{8'}$, alkenyl, and alkynyl; where the alkenyl and alkynyl are optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^8R^{8''}$, —$NR^8C(O)R^{8'}$; or $R^3$ and $R^4$ together with the carbon to which they are attached form C(O) or C(=NOH);

m, $R^{8''}$, and $R^9$ are as defined in the Summary of the Invention for a compound of Group A; and unless otherwise specified in this embodiment, $R^8$ and $R^{8'}$ are as defined in the Summary of the Invention for a compound of Group A.

In another embodiment of the Invention (A8), the compound of Formula I is selected from Group A where $R^3$ is hydrogen, halo, hydroxy, alkoxy, or amino. More specifically, $R^3$ is hydrogen, fluoro, hydroxy, methoxy, or amino. Even more specifically, $R^3$ is hydrogen or hydroxy. Yet even more specifically, $R^3$ is hydroxy.

In a more specific embodiment of embodiment A8, X and $R^7$ are halo; A is phenylene optionally substituted with $R^{10}$ and $R^{12}$ where $R^{10}$ and $R^{12}$ are independently hydrogen or halo; $R^1$, $R^2$, $R^5$ and $R^6$ are hydrogen; and $R^4$, is as defined in the Summary of the Invention for a compound of Group A.

Another specific embodiment of the Invention (A9) is that where the compound of Formula I is selected from Group A where $R^1$, $R^2$, $R^5$ and $R^6$ are hydrogen; $R^3$ is hydrogen, halo, hydroxy, alkoxy, or amino; and $R^4$ is heterocycloalkyl, heteroaryl, or alkyl substituted with —$NR^8R^{8'}$ where $R^8$ and $R^{8'}$ and all other groups are as defined in the Summary of the Invention for a compound of Group A.

Another specific embodiment of embodiment A9 is that where $R^4$ is alkyl substituted with —$NR^8R^{8'}$ where $R^8$ and $R^{8'}$ and all other groups are as defined in the Summary of the Invention for a compound of Group A. Specifically, the compound is of Formula I(a) or I(b):

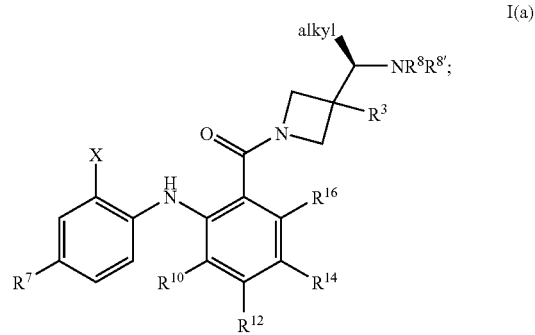

-continued

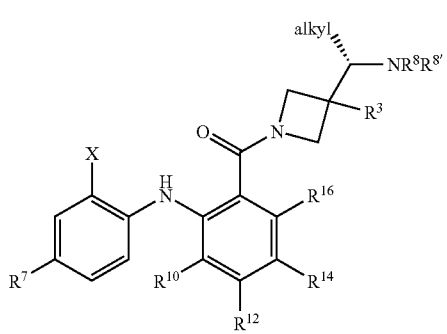

I(b)

where $R^3$ is as defined in A9; X, $R^7$, $R^8$, $R^{8'}$, $R^{10}$, $R^{12}$, $R^{14}$, $R^{16}$ are as defined in the Summary of the Invention for a compound of Group A.

Another specific embodiment of embodiment A9 is that where $R^4$ is heterocycloalkyl.

In a specific embodiment of embodiment A9, the compound is that where X and $R^7$ are halo; A is phenylene optionally substituted with $R^{10}$ and $R^{12}$ where $R^{10}$ and $R^{12}$ are independently hydrogen or halo; $R^3$ is hydroxy; and $R^4$ is alkyl substituted with —$NR^8R^{8'}$ or $R^4$ is heterocycloalkyl optionally substituted with one, two, or three groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^8R^{8''}$, —$NR^8C(O)OR^{8'}$ and —$NR^8C(O)R^{8'}$; and where m, $R^3$, $R^8$, $R^{8'}$, $R^{8''}$, and $R^9$ are as defined in the Summary of the Invention for a compound of Group A.

In another embodiment of the Invention (A10), the compound of Formula I is selected from Group A where $R^4$ is
a) hydrogen;
b) —$CH_2N(R^{25})(NR^{25a}R^{25b})$;
c) —$CH_2NR^{25}C(=NH)(NR^{25a}R^{25b})$;
d) —$CH_2NR^{25}C(=NH)(N(R^{25a})(NO_2))$;
e) —$CH_2NR^{25}C(=NH)(N(R^{25a})(CN))$;
f) —$CH_2NR^{25}C(=NH)(R^{25})$;
g) —$CH_2NR^{25}C(NR^{25a}R^{25b})=CH(NO_2)$;
h) alkyl;
i) alkyl substituted with one or two —$OR^8$ where $R^8$ is hydrogen, aryl, or alkyl where the alkyl is substituted with one or two hydroxy;
j) alkyl substituted with one, two, or three halo;
k) alkyl substituted with nitro;
l) alkyl substituted with —$S(O)_mR^9$ (where m is 0 and $R^9$ is aryl);
m) alkyl substituted with optionally substituted heterocycloalkyl;
n) alkenyl;
o) —$NR^8R^{8'}$ (where $R^8$ and $R^{8'}$ are independently hydrogen; alkyl; alkenyl; alkyl substituted with one or two hydroxy; alkyl substituted with one or two —$NR^{30}R^{30'}$ where $R^{30}$ and $R^{30'}$ are independently hydrogen, alkyl, or hydroxyalkyl; alkyl substituted with optionally substituted heteroaryl; or alkyl substituted with optionally substituted cycloalkyl);
p) —$C(O)NR^8R^{8'}$ (where $R^8$ is hydrogen, alkyl, or alkenyl; and $R^{8'}$ is hydrogen; hydroxy; alkyl; alkenyl; alkyl substituted with one or two hydroxy; alkyl substituted with optionally substituted heterocycloalkyl; alkyl substituted with —$NR^{30}R^{30'}$ where $R^{30}$ and $R^{30'}$ are independently hydrogen, alkyl, or hydroxyalkyl; or optionally substituted alkoxy);
q) —$NR^8C(O)OR^{8'}$ (where $R^8$ and $R^{8'}$ are independently hydrogen, alkyl, or alkenyl);
r) alkyl substituted with —$NR^8R^{8'}$ (where $R^8$ is hydrogen, alkyl, alkenyl, alkynyl, or alkyl substituted with one or two hydroxy; and $R^{8'}$ is hydrogen; hydroxy; alkoxy; alkyl; alkenyl; alkynyl; optionally substituted alkoxy; alkyl substituted with one or two hydroxy; alkyl substituted with one or two alkoxy; alkyl substituted with —$NR^{30}R^{30'}$ where $R^{30}$ and $R^{30'}$ are independently hydrogen, alkyl, or hydroxyalkyl; alkyl substituted with one or two hydroxy and one or two —$NR^{30}R^{30'}$ where $R^{30}$ and $R^{30'}$ are independently hydrogen, alkyl, or hydroxyalkyl; alkyl substituted with one, two, three, four, or five halo; alkyl substituted with optionally substituted cycloalkyl; alkyl substituted with optionally substituted aryl; alkyl substituted with one or two hydroxy and one optionally substituted aryl; alkyl substituted with optionally substituted heterocycloalkyl; alkyl substituted with optionally substituted heteroaryl; aryl; aryl substituted with one or two hydroxy; aryl substituted with one or two alkoxy; aryl substituted with one or two halo; aryl substituted with one or two —$NR^{32}C(O)R^{32a}$ where $R^{32}$ is hydrogen or alkyl and $R^{32a}$ is alkyl, alkenyl, alkoxy, or cycloalkyl; aryl substituted with —$NR^{34}SO_2R^{34a}$ where $R^{34}$ is hydrogen or alkyl and $R^{34a}$ is alkyl, alkenyl, cycloalkyl, aryl, heteroaryl, or heterocycloalkyl; cycloalkyl; cycloalkyl substituted with one or two hydroxy; cycloalkyl substituted with one or two hydroxy and one or two hydroxyalkyl; cycloalkyl substituted with one or two alkoxy; cycloalkyl substituted with carboxy; cycloalkyl substituted with —$C(O)NR^{33}R^{33a}$ where $R^{33}$ is hydrogen or alkyl and $R^{33a}$ is alkyl, alkenyl, alkynyl, or cycloalkyl; alkyl substituted with —$C(O)NR^{33}R^{33a}$ where $R^{33}$ is hydrogen or alkyl and $R^{33a}$ is alkyl, alkenyl, alkynyl, or cycloalkyl; cycloalkyl substituted with optionally substituted cycloalkyl; heterocycloalkyl; heterocycloalkyl substituted with alkyl; heterocycloalkyl substituted with alkoxycarbonyl; heterocycloalkyl substituted with optionally substituted arylalkyl; heterocycloalkyl substituted with one or two hydroxy; heterocycloalkyl substituted with one or two alkoxy; heterocycloalkyl substituted with one or two hydroxyalkyl; heterocycloalkyl substituted with one or two hydroxy, one or two alkoxy, and one or two hydroxyalkyl; alkyl substituted with optionally substituted aryloxy; alkyl substituted with —$S(O)_nR^{31}$ where n is 0 and $R^{31}$ is alkyl; alkyl substituted with carboxy; alkyl substituted with alkoxycarbonyl; or alkyl substituted with —$NR^{32}C(O)R^{32a}$ where $R^{32}$ is hydrogen or alkyl and $R^{32a}$ is alkyl, alkenyl, alkoxy, or cycloalkyl);
s) —$NR^8C(O)R^{8'}$ (where $R^8$ is hydrogen, alkyl, or alkenyl; and $R^{8'}$ is hydrogen; alkyl; alkyl substituted with one or two hydroxy; alkyl substituted with optionally substituted heterocycloalkyl; alkyl substituted with —$NR^{30}R^{30'}$ where $R^{30}$ and $R^{30'}$ are independently hydrogen, alkyl, hydroxyalkyl, or alkenyl);
t) cycloalkyl;
u) cycloalkyl substituted with —$NR^8R^{8'}$ where $R^8$ and $R^{8'}$ are independently hydrogen, alkyl, or alkenyl;
v) heterocycloalkyl;
w) heterocycloalkyl substituted with —$NR^8R^{8'}$ where $R^8$ and $R^{8'}$ are independently hydrogen, alkyl, or alkenyl;

x) heterocycloalkyl substituted with one or two alkyl;
y) heterocylcloalkyl substituted with —C(O)OR$^8$ where R$^8$ is alkyl or alkenyl;
z) alkyl substituted with —NR$^8$C(O)R$^{8'}$ (where R$^8$ is hydrogen, alkyl, or alkenyl and R$^{8'}$ is alkyl; alkenyl; or alkyl substituted with alkoxy, aryl, and one, two, or three halo);
aa) heteroaryl;
bb) heteroaryl substituted with —NR$^8$R$^{8'}$ where R$^8$ and R$^{8'}$ are independently hydrogen, alkyl, or alkenyl; alkyl substituted with optionally substituted heteroaryl;
cc) alkyl substituted with —NR$^8$S(O)$_2$R$^9$ where R$^8$ is hydrogen, alkyl, or alkenyl and R$^9$ is alkyl or alkenyl;
dd) alkyl substituted with —NR$^8$C(O)OR$^{8'}$ where R$^8$ and R$^{8'}$ are independently hydrogen, alkyl, or alkenyl;
ee) alkyl substituted with one aryl and one —NR$^8$R$^{8'}$ where R$^8$ and R$^{8'}$ are independently hydrogen, alkyl, or alkenyl; or
ff) alkyl substituted with one or two —OR$^8$ (where R$^8$ is hydrogen) and one or two —NR$^8$R$^{8'}$ where R$^8$ and R$^{8'}$ are independently hydrogen, alkyl, or alkenyl.

Even more specifically, R$^4$ is hydrogen, —CH$_2$N(H)(NHCH$_3$), —CH$_2$NHC(=NH)(NH$_2$), —CH$_2$NHC(=NH)(NHNO$_2$), —CH$_2$NHC(=NH)(NHCN), —CH$_2$NHC(=NH)(phenyl), —CH$_2$NHC(NH$_2$)=CH(NO$_2$), methyl, ethyl, hydroxymethyl, 2,3-dihydroxypropyl, 3-hydroxy-2-methyl-prop-2-yl, N-(1-methoxy-prop-2-yl)-aminomethyl, N-(ethoxypropyl)-aminomethyl, N-(ethoxyethyl)-aminomethyl, N-(2,2-dimethoxyethyl)-aminomethyl, N-(methoxyethyl)-aminomethyl, N-(isopropxyethyl)-aminomethyl, trifluoromethyl, 1-nitro-ethyl, 1-methyl-1-nitro-ethyl, 1-nitropropyl, 3-methyl-1-nitro-butyl, phenylthiomethyl, allyl, ethenyl, 2-methylthio-ethylaminomethyl, 3-methylthio-propylaminomethyl, N-(tert-butoxycarbonylaminopropyl)-aminomethyl, N-(1-carboxyethyl)-aminomethyl, N-(1R-carboxyethyl)-aminomethyl, N-(1S-carboxyethyl)-aminomethyl, N-(1-methoxycarbonylethyl)-aminomethyl, —NH$_2$, —NH(CH$_2$)$_3$CH$_3$, —NHCH$_3$, —NH(CH$_2$CH$_3$), —NHCH$_2$CH(CH$_3$)$_2$, —NHCH$_2$CH$_2$OH, —NHCH$_2$CH$_2$CH$_2$NH$_2$, —N(CH$_3$)CH$_2$CH$_2$(heteroaryl), —NHCH$_2$(cycloalkyl), —C(O)NH$_2$, —C(O)NHOH, —C(O)NH(OCH$_2$CH(OH)CH$_2$OH), —C(O)NH(CH$_2$)$_3$CH$_3$, —C(O)NHCH$_2$CH=CH$_2$, —C(O)NHCH$_2$CH$_3$, —C(O)NHCH$_2$CH$_2$OH, —C(O)NHCH$_2$CH(OH)CH$_2$OH, —C(O)NHCH$_2$CH$_2$CH(OH)CH$_2$OH, —C(O)NH CH$_2$CH$_2$(piperidin-1-yl), —C(O)NH(phenyl), —C(O)NHCH$_2$CH$_2$N(CH$_2$CH$_3$)$_2$, —NHC(O)OC(CH$_3$)$_3$, —NHC(O)OCH$_3$, azetidinylmethyl, pyrrolidinylmethyl, 3-hydroxy-pyrrolidinylmethyl, 2-(methoxymethyl)-pyrrolidinylmethyl, 2S-(methoxymethyl)-pyrrolidinylmethyl, 2R-(methoxymethyl)-pyrrolidinylmethyl, morpholinylmethyl, hydroxypiperidinylmethyl, 4-alkyl-piperazinylmethyl, 4-alkyl-homopiperazinylmethyl, 4-(heterocycloalkyl)-piperidinylmethyl, 4-(dialkylaminoalkyl)-piperazinylmethyl, N-hydroxyaminomethyl, N-methoxyaminomethyl, N-ethoxyaminomethyl, N-ethylaminomethyl, 1-(N-ethyl-amino)-ethyl, N,N-diethylaminomethyl, N,N-dimethylaminomethyl, aminomethyl, 1-amino-ethyl, 1R-amino-ethyl, 1S-amino-ethyl, 1_(methylamino)-ethyl, 1-(N,N-dimethylamino)-ethyl, 1-amino-1-methyl-ethyl, 1-aminopropyl, 1S-aminopropyl, 1R-aminopropyl, N-(n-propyl)-aminomethyl, N-(isopropyl)-aminomethyl, 2-(N-isopropylamino)-ethyl, 3-(N-isopropylamino)-2-methyl-prop-2-yl, 1-(N-ethyl-amino)-propyl, 1-(N,N-diethyl-amino)-propyl, 1-aminobutyl, 1-amino-isobutyl, N-(2-aminoethyl)-aminomethyl, N-(n-butyl)-aminomethyl, N-isobutylaminomethyl, tert-butylaminomethyl, 1-(tert-butylamino)-ethyl, sec-butylaminomethyl, N-(2-methyl-but-3-yl)-aminomethyl, N-(3,3-dimethyl-butyl)-aminomethyl, N-(3-methylbut-3-yl)-aminomethyl, N-(2-methylbutyl)-aminomethyl, N-(pent-3-yl)-aminomethyl, n-pentylaminomethyl, isopentylaminomethyl, sec-pentylaminomethyl, neopentylaminomethyl, N-(2,2,4-trimethyl-pent-4-yl)-aminomethyl, N-(2-ethyl-butyl)-aminomethyl, N-allyl-aminomethyl, 3-methyl-but-1-yn-3-ylaminomethyl, N-(2,3-dihydroxypropyloxy)-aminomethyl, N-cyclopropylaminomethyl, N-cyclobutylaminomethyl, N-cyclopentylaminomethyl, N-cyclopenten-4-ylaminomethyl, N-(1(R,S)-hydroxy-cyclopent-2-yl)-aminomethyl, N-(1S-hydroxy-cyclopent-2-yl)-aminomethyl, N-(1R-hydroxy-cyclopent-2-yl)-aminomethyl, N-(1(R,S)-hydroxy-1-methyl-cyclopent-2-yl)-aminomethyl, N-(1S-hydroxy-1-methyl-cyclopent-2-yl)-aminomethyl, N-(1R-hydroxy-1-methyl-cyclopent-2-yl)-aminomethyl, N-(3,4-dihydroxy-cyclopentyl)-aminomethyl, N-(1-hydroxymethyl-cyclopent-1-yl)-aminomethyl, N-(2,3-dihydroxy-4-hydroxymethyl-cyclopentyl)-aminomethyl, N-(1(R,S)-methoxy-cyclopent-2-yl)-aminomethyl, N-(1S-methoxy-cyclopent-2-yl)-aminomethyl, N-(1R-methoxy-cyclopent-2-yl)-aminomethyl, N-(1-carboxy-cyclopentyl)-aminomethyl, N-cyclohexylaminomethyl, N-(1(R,S)-hydroxy-cyclohex-2-yl)-aminomethyl, N-(cis-4-hydroxy-cyclohexyl)-aminomethyl, N-(trans-4-hydroxy-cyclohexyl)-aminomethyl, 1-[N-(cis-4-hydroxy-cyclohexyl)-amino]-ethyl, 1-[N-(trans-4-hydroxy-cyclohexyl)-amino]-ethyl, N-(1(R)-hydroxy-cyclohex-2-yl)-aminomethyl, N-(1(S)-hydroxy-cyclohex-2-yl)-aminomethyl, N-(1-hydroxymethyl-cyclohexyl)-aminomethyl, N-(2-cyclohexyl-cyclohexyl)-aminomethyl, N-{(2R,3S,4R,6R)-2-(hydroxymethyl)-3,4-dihydroxy-6-methoxy-tetrahydro-2H-pyran-5-yl}-aminomethyl, N-(cycloheptyl)-aminomethyl, N-(cyclooctyl)-aminomethyl, [(1r,3r,5R,7R)-tricyclo[3.3.1.1~3,7~]dec-2-ylamino]methyl, N-[1-(cyclopropylaminocarbonyl)-cyclopentyl]-aminomethyl, —CH$_2$NHC(CH$_3$)$_2$C(O)NH(cyclohexyl), —CH$_2$NHC(CH$_3$)$_2$C(O)NH(CH$_2$CH$_3$), N-(1-benzyloxy-cyclopent-2-yl)-aminomethyl, N-(cyclopropylmethyl)-aminomethyl, N-(cyclohexylmethyl)-aminomethyl, N-(1-cyclohexyl-ethyl)-aminomethyl, N-(imidazolyl)-aminomethyl, N-(1,3,5-triazinyl)-aminomethyl, N-(5-hydroxy-pyrazol-3-yl)-aminomethyl, N-(5-methyl-pyrazol-3-yl)-aminomethyl, N-(benzimidazolyl)-aminomethyl, N-(pyrimidin-2-yl)-aminomethyl, N-(pyridin-2-yl)-aminomethyl, N-(pyridin-3-yl)-aminomethyl, N-(pyridin-4-yl)-aminomethyl, N-indan-1-yl-aminomethyl, N-indan-2-yl-aminomethyl, phenylaminomethyl, N-(2-hydroxyphenyl)-aminomethyl, N-(3-hydroxyphenyl)-aminomethyl, N-(4-hydroxyphenyl)-aminomethyl, N-(2-methoxyphenyl)-aminomethyl, N-(3-methoxyphenyl)-aminomethyl, N-(4-methoxyphenyl)-aminomethyl, N-(2-fluorophenyl)-aminomethyl, N-(3-fluorophenyl)-aminomethyl, N-(4-fluorophenyl)-aminomethyl, N-(2-chlorophenyl)-aminomethyl, N-(3-chlorophenyl)-aminomethyl, N-(4-chlorophenyl)-aminomethyl, N-(3-methylcarbonylamino-phenyl)-aminomethyl, N-(4-methylcarbonylamino-phenyl)-aminomethyl, N-(2-aminophenyl)-aminomethyl, N-(3-aminophenyl)-aminomethyl, N-(4-aminophenyl)-aminomethyl, N-(2-methylsulfonylaminophenyl)-aminomethyl, N-(3-methylsulfonylaminophenyl)-aminomethyl, N-(4-methylsulfonylaminophenyl)-aminomethyl, N-(2-fluoro-4-hydroxy-phenyl)-aminomethyl, N-(3-fluoro-4-hydroxy-phenyl)-aminomethyl, N-(benzyl)-aminomethyl, N-(2-hydroxyphenylmethyl)-aminomethyl, N-(3-hydroxyphenylmethyl)-aminomethyl, N-(4- hydroxyphenylmethyl)-aminomethyl, N-(2-(N-methylpiperazin-1-yl)-phenylmethyl)-aminomethyl, N-(4-alkyl-phenethyl)-aminomethyl, N-(1-hydroxy-3-phenyl-prop-2-yl)-aminomethyl, N-(pyrrolidin-2-ylmethyl)-aminomethyl, N-(N-alkyl-pyrrolidinylmethyl)-aminomethyl, N-(N-alkyl-pyrrolidinylethyl)-aminomethyl, N-(pyrrolidinylpropyl)-aminomethyl, N-(1,1-dimethyl-2-pyrrolidin-1-yl-ethyl)-aminomethyl, N-(tetrahydrofuranyl-methyl)-aminomethyl, N-(tetrahydro-2H-pyran-4-ylm-ethyl)-aminomethyl, N-(tetrahydro-2H-pyranylethyl)-aminomethyl, N-(piperidin-4-ylmethyl)-aminomethyl, N-(N-methylpiperidin-4-ylmethyl)-aminomethyl, N-(N-tert-butoxycarbonylpiperidin-4-ylmethyl)-aminomethyl, N-(N-methylimidazol-4-ylmethyl)-aminomethyl, N-(N-meth-ylimidazol-5-ylmethyl)-aminomethyl, N-[2-(imidazol-4-yl)-ethyl]-aminomethyl, N-[3-(imidazolyl)-propyl]-aminomethyl, N-(pyridin-3-ylethyl)-aminomethyl, N-(pyridin-4-ylethyl)-aminomethyl, N-(thien-2-ylethyl)-aminomethyl, N-(furan-2-ylethyl)-aminomethyl, N-(5-me-thyl-1,3,4-oxadiazol-2-ylmethyl)-aminomethyl, N-(2-indo-lin-3-ylethyl)-aminomethyl, 2-(N,N-dimethylamino)-ethylaminomethyl, 2-(N,N-dimethylamino)-1-methyl-ethylaminomethyl, 3-aminopropylaminomethyl, 3-(N,N-dimethylamino)-propylaminomethyl, 3-(N,N-diethylamino)-propylaminomethyl, N-(N,N-diisopropylaminoethyl)-aminomethyl, N-(N,N-dimethylaminobutyl)-aminomethyl, N-(3-hydroxypropyl)-aminomethyl, N-(2-hydroxypropyl)-aminomethyl, N-(1,2-dihydroxypropyl)-aminomethyl, N-(1-amino-2-hydroxy-prop-3-yl)-aminomethyl, N-(N-ethoxycarbonyl-piperidin-4-yl)-aminomethyl, N-(N-benzylpiperidin-4-yl)-aminomethyl, N-(homopiperidin-3-yl)-aminomethyl, N-(N-benzylpyrroli-din-3-yl)-aminomethyl, N-(N-ethylpiperidin-3-yl)aminom-ethyl, 2,2,2-trifluoroethylaminomethyl, 3,3,3-trifluoropropy-laminomethyl, 2,2,3,3,3-pentafluoropropylaminomethyl, —CH$_2$N(CH$_2$CH$_2$OH)$_2$, —CH$_2$N(CH$_3$)(CH$_2$CH$_2$OH), —CH$_2$NH(CH$_2$CH$_2$OH), —CH$_2$NH(CH$_2$CH$_2$CH$_2$CH$_2$OH), —CH$_2$N(CH$_3$)(N-methyl-pyrrolidin-3-yl), —CH$_2$NH(C(CH$_3$)$_2$CH$_2$OH), —NHC(O)CH(CH$_3$)$_2$, —NHC(O)CH$_2$N(CH$_2$CH$_3$)$_2$, —NHC(O)CH$_2$NH(CH$_3$), —NHC(O)H, —NHC(O)CH$_2$CH(OH)CH$_2$OH, —NHC(O)CH$_2$NH$_2$, —NHC(O)CH$_2$N(CH$_2$CH$_2$OH)$_2$, —NHC(O)CH$_2$CH$_2$N(CH$_2$CH$_2$OH)$_2$, —NHC(O)CH$_2$(4-alkyl-piperazinyl), —NHC(O)CH$_2$(piperidinyl), N-(phenyloxyethyl)-aminom-ethyl, cyclopentyl, 1-amino-cyclopentyl, (cis,trans)-2-amino-cyclopentyl, (cis,trans)-2-amino-cyclopentyl, cis-2-amino-cyclopentyl, trans-2-amino-cyclopentyl, (cis,trans)-2-hydroxy-cyclohexyl, cis-2-hydroxy-cyclohexyl, trans-2-hydroxy-cyclohexyl, (cis,trans)-2-amino-cyclohexyl, cis-2-amino-cyclohexyl, trans-2-amino-cyclohexyl, azetidin-3-yl, pyrrolidinyl, N-alkyl-pyrrolidinyl, 3-(dialkylamino)-pyrro-lidinyl, piperidinyl, 2-methyl-piperidin-6-yl, N-tert-butoxy-carbonylpiperidin-2-yl, piperazinyl, —CH$_2$NHC(O)CH$_3$, —CH(CH$_3$)NHC(O)CH$_3$, —CH(CH$_3$)NHC(O)C(OCH$_3$)(CF$_3$)phenyl, pyrrol-1-yl, pyrrol-2-yl, pyrrol-3-yl, imidazol-1-yl, imidazol-2-yl, imidazol-4-yl, imidazol-5-yl, N-methyl-imidazol-2-yl, 5-methyl-imidazol-2-yl, 1,2,4-triazol-3-yl, thiazol-2-yl, 2-aminopyrimidin-3-yl, pyridinyl, benzimida-zolyl, imidazol-1-ylmethyl, imidazol-2-ylmethyl, triazolyl-methyl, (5-amino-3-methylpyrazol-1-yl)-methyl, phe-noxymethyl, methylsulfonylaminomethyl, 1-(methoxycarbonylamino)-ethyl, 1-amino-1-phenyl-me-thyl, or 1-amino-3-hydroxy-propyl.

A more specific embodiment of embodiment A10 is that wherein X and R$^7$ are halo; A is phenylene optionally substi-tuted with R$^{10}$ and R$^{12}$ where R$^{10}$ and R$^{12}$ are independently hydrogen or halo; R$^1$, R$^2$, R$^5$ and R$^6$ are hydrogen; and R$^3$ is hydrogen, halo, hydroxy, alkoxy, or amino.

A more specific embodiment of embodiment A10 is that where R$^3$ is hydrogen and R$^4$ is
a) hydrogen;
b) —NR$^8$R$^{8'}$ (where R$^8$ and R$^{8'}$ are independently hydrogen; alkyl; alkenyl; alkyl substituted with one or two hydroxy; alkyl substituted with one or two —NR$^{30}$R$^{30'}$ where R$^{30}$ and R$^{30'}$ are independently hydrogen, alkyl, or hydroxyalkyl; alkyl substituted with optionally substituted heteroaryl; or alkyl substituted with optionally substituted cycloalkyl);
c) —C(O)NR$^8$R$^{8'}$ (where R$^8$ is hydrogen, alkyl, or alkenyl; and R$^{8'}$ is hydrogen; hydroxy; alkyl; alkenyl; alkyl substituted with one or two hydroxy; alkyl substituted with heterocycloalkyl; alkyl substituted with —NR$^{30}$R$^{30'}$ where R$^{30}$ and R$^{30'}$ are independently hydrogen, alkyl, or hydroxyalkyl; or optionally substituted alkoxy);
d) —NR$^8$C(O)OR$^{8'}$ (where R$^8$ and R$^{8'}$ are independently hydrogen, alkyl, or alkenyl);
e) —NR$^8$C(O)R$^{8'}$ (where R$^8$ is hydrogen, alkyl, or, alkenyl; and R$^{8'}$ is hydrogen; alkyl; alkyl substituted with one or two hydroxy; alkyl substituted with optionally substituted heterocycloalkyl; alkyl substituted with —NR$^{30}$R$^{30'}$ where R$^{30}$ and R$^{30'}$ are independently hydrogen, alkyl, hydroxyalkyl, or alkenyl);
f) alkyl;
g) alkyl substituted with one or two —OR$^8$ (where R$^8$ is hydrogen);
h) alkyl substituted with —NR$^8$R$^{8'}$ (where R$^8$ is hydrogen, alkyl, alkenyl, alkynyl, or alkyl substituted with one or two hydroxy; and R$^{8'}$ is hydrogen; alkyl; alkenyl; alkynyl; alkyl substituted with one or two hydroxy; heterocycloalkyl substituted with alkyl; or alkyl substituted with —NR$^{30}$R$^{30'}$ where R$^{30}$ and R$^{30'}$ are independently hydrogen, alkyl, or hydroxyalkyl);
i) heterocycloalkyl; or
j) heterocycloalkyl substituted with —NR$^8$R$^{8'}$ (where R$^8$ and R$^{8'}$ are independently hydrogen, alkyl, or alkenyl).

Even more specifically, R$^3$ is hydrogen and R$^4$ is hydrogen, hydroxymethyl, —NH$_2$, —NH(CH$_2$)$_3$CH$_3$, —NHCH$_3$, —NH(CH$_2$CH$_3$), —NHCH$_2$CH(CH$_3$)$_2$, —NHCH$_2$CH$_2$OH, —NHCH$_2$CH$_2$CH$_2$NH$_2$, —N(CH$_3$)CH$_2$CH$_2$(pyridin-2-yl), —NHCH$_2$(cyclopropyl), —NHCH$_2$(cyclopentyl), —NHCH$_2$(cyclohexyl), —C(O)NHOH, —C(O)NH(OCH$_2$CH(OH)CH$_2$OH), —C(O)NH(CH$_2$)$_3$CH$_3$, —C(O)NHCH$_2$CH=CH$_2$, —C(O)NHCH$_2$CH$_3$, —C(O)NHCH$_2$CH$_2$OH, —C(O)NHCH$_2$CH(OH)CH$_2$OH, —C(O)NHCH$_2$CH$_2$CH(OH)CH$_2$OH, —C(O)NHCH$_2$CH$_2$(piperidin-1-yl), —C(O)NH(phenyl), —C(O)NHCH$_2$CH$_2$N(CH$_2$CH$_3$)$_2$, N-(isopropyl)-aminomethyl, N,N-dimethylaminomethyl, N-(2-aminoethyl)-aminomethyl, —NHC(O)OC(CH$_3$)$_3$, —NHC(O)OCH$_3$, —NHC(O)CH(CH$_3$)$_2$, —NHC(O)CH$_2$NH$_2$, —NHC(O)CH$_2$N(CH$_2$CH$_3$)$_2$, —NHC(O)CH$_2$NH(CH$_3$), —NHC(O)H, —NHC(O)CH$_2$CH(OH)CH$_2$OH, —NHC(O)CH$_2$N(CH$_2$CH$_2$OH)$_2$, —NHC(O)CH$_2$CH$_2$N(CH$_2$CH$_2$OH)$_2$, —NHC(O)CH$_2$(4-alkyl-piperazinyl), —NHC(O)CH$_2$(piperidinyl), pyrrolidinyl, 3-(dialkylamino)-pyrrolidinyl, piperidinyl, 2-methyl-piperidin-6-yl, N-methylpiperidin-2-yl, or piperazin-2-yl.

A more specific embodiment of embodiment A10 is that where R$^3$ is alkoxy and R$^4$ is alkyl substituted with —NR$^8$R$^{8'}$ (where R$^8$ and R$^{8'}$ are independently hydrogen, alkyl, or alkenyl). More specifically, R$^3$ is methoxy and R$^4$ is alkyl substituted with —NR$^8$R$^{8'}$ (where R$^8$ and R$^{8'}$ are independently hydrogen, alkyl, or alkenyl).

A more specific embodiment of embodiment A10 is that where $R^3$ is halo and $R^4$ is alkyl substituted with —$NR^8R^{8'}$ (where $R^8$ and $R^{8'}$ are independently hydrogen, alkyl, or alkenyl). More specifically, $R^3$ is fluoro and $R^4$ is alkyl substituted with —$NR^8R^{8'}$ (where $R^8$ and $R^{8'}$ are independently hydrogen, alkyl, or alkenyl).

A more specific embodiment of embodiment A10 is that where $R^3$ is amino and $R^4$ is alkyl substituted with —$NR^8R^{8'}$ (where $R^8$ and $R^{8'}$ are independently hydrogen, alkyl, or alkenyl).

A more specific embodiment of embodiment A10 is that where $R^3$ is hydroxy and $R^4$ is
a) hydrogen;
b) —$CH_2N(R^{25})(NR^{25a}R^{25b})$;
c) —$CH_2NR^{25}C(=NH)(NR^{25a}R^{25b})$;
d) —$CH_2NR^{25}C(=NH)(N(R^{25a})(NO_2))$;
e) —$CH_2NR^{25}C(=NH)(N(R^{25a})(CN))$;
f) —$CH_2NR^{25}C(=NH)(R^{25})$;
g) —$CH_2NR^{25}C(NR^{25a}R^{25b})=CH(NO_2)$;
h) alkyl;
i) alkenyl;
j) alkyl substituted with one or two —$OR^8$ where $R^8$ is hydrogen, aryl, or alkyl where the alkyl is substituted with one or two hydroxy;
k) alkyl substituted with one, two, or three halo;
l) alkyl substituted with nitro;
m) alkyl substituted with —$S(O)_mR^9$ (where m is 0 and $R^9$ is aryl);
n) alkyl substituted with optionally substituted heterocycloalkyl;
o) alkyl substituted with —$NR^8R^{8'}$ (where $R^8$ is hydrogen, alkyl, alkenyl, alkynyl, or alkyl substituted with one or two hydroxy; and $R^{8'}$ is hydrogen; hydroxy; alkoxy; alkyl; alkenyl; alkynyl; optionally substituted alkoxy; alkyl substituted with one or two hydroxy; alkyl substituted with —$NR^{30}R^{30'}$ where $R^{30}$ and $R^{30'}$ are independently hydrogen, alkyl, or hydroxyalkyl; alkyl substituted with one or two hydroxy and one or two —$NR^{30}R^{30'}$ where $R^{30}$ and $R^{30'}$ are independently hydrogen, alkyl, or hydroxyalkyl; heterocycloalkyl substituted with alkyl, alkoxycarbonyl, or optionally substituted arylalkyl; alkyl substituted with one, two, three, four, or five halo; alkyl substituted with optionally substituted cycloalkyl; alkyl substituted with optionally substituted aryl; alkyl substituted with one or two hydroxy and one optionally substituted awl; alkyl substituted with optionally substituted heterocycloalkyl; alkyl substituted with optionally substituted heteroaryl; heteroaryl; aryl; aryl substituted with one or two hydroxy; aryl substituted with one or two alkoxy; aryl substituted with one or two halo; aryl substituted with one or two —$NR^{32}C(O)R^{32a}$ where $R^{32}$ is hydrogen or alkyl and $R^{32a}$ is alkyl, alkenyl, alkoxy, or cycloalkyl; aryl substituted with —$NR^{34}SO_2R^{34a}$ where $R^{34}$ is hydrogen or alkyl and $R^{34a}$ is alkyl, alkenyl, cycloalkyl, aryl, heteroaryl, or heterocycloalkyl; cycloalkyl; cycloalkyl substituted with one or two hydroxy; cycloalkyl substituted with one or two hydroxy and one or two hydroxyalkyl; cycloalkyl substituted with one or two alkoxy; cycloalkyl substituted with carboxy; cycloalkyl substituted with —$C(O)NR^{33}R^{33a}$ where $R^{33}$ is hydrogen or alkyl and $R^{33a}$ is alkyl, alkenyl, alkynyl, or cycloalkyl; cycloalkyl substituted with optionally substituted cycloalkyl; heterocycloalkyl; heterocycloalkyl substituted with one or two hydroxy; heterocycloalkyl substituted with one or two alkoxy; heterocycloalkyl substituted with one or two hydroxyalkyl; heterocycloalkyl substituted with one or two hydroxy, one or two alkoxy, and one or two hydroxyalkyl; alkyl substituted with $\cong C(O)NR^{33}R^{33a}$ where $R^{33}$ is hydrogen or alkyl and $R^{33a}$ is alkyl, alkenyl, alkynyl, or cycloalkyl; alkyl substituted with optionally substituted aryloxy; alkyl substituted with —$S(O)_nR^{31}$ where n is 0 and $R^{31}$ is alkyl; alkyl substituted with carboxy; alkyl substituted with alkoxycarbonyl; or alkyl substituted with —$NR^{32}C(O)R^{32a}$ where $R^{32}$ is hydrogen or alkyl and $R^{32a}$ is alkyl, alkenyl, alkoxy, or cycloalkyl);
p) heterocycloalkyl;
q) —$C(O)NR^8R^{8'}$ (where $R^8$ is hydrogen, alkyl, or alkenyl; and $R^{8'}$ is hydrogen; alkyl; alkyl; alkenyl; or substituted with one or two hydroxy;);
r) alkyl substituted with —$NR^8C(O)R^{8'}$ (where $R^8$ is hydrogen, alkyl, or alkenyl and $R^{8'}$ is alkyl; alkenyl; or alkyl substituted with alkoxy, aryl, and one, two, or three halo);
s) cycloalkyl;
t) cycloalkyl substituted with —$NR^8R^{8'}$ where $R^8$ and $R^{8'}$ are independently hydrogen, alkyl, or alkenyl;
u) cycloalkyl substituted with —$C(O)NR^{33}R^{33a}$ where $R^{33}$ is hydrogen or alkyl and $R^{33a}$ is alkyl, alkenyl, alkynyl, or cycloalkyl;
v) heterocycloalkyl;
w) heterocycloalkyl substituted with one or two alkyl;
x) heterocylcoalkyl substituted with —$C(O)OR^8$ where $R^8$ is alkyl or alkenyl;
y) heteroaryl;
z) heteroaryl optionally substituted with —$NR^8R^{8'}$ where $R^8$ and $R^{8'}$ are independently hydrogen, alkyl, or alkenyl;
aa) alkyl substituted with optionally substituted heteroaryl;
bb) alkyl substituted with —$NR^8S(O)_2R^9$ where $R^8$ is hydrogen, alkyl, or alkenyl and $R^9$ is alkyl or alkenyl;
cc) alkyl substituted with —$NR^8C(O)OR^{8'}$ where $R^8$ and $R^{8'}$ are independently hydrogen, alkyl, or alkenyl;
dd) alkyl substituted with one aryl and one —$NR^8R^{8'}$ where $R^8$ and $R^{8'}$ are independently hydrogen, alkyl, or alkenyl; or
ee) alkyl substituted with one or two —$OR^8$ (where $R^8$ is hydrogen) and one or two —$NR^8R^{8'}$ where $R^8$ and $R^{8'}$ are independently hydrogen, alkyl, or alkenyl.

Even more specifically, $R^3$ is hydroxy and $R^4$ is hydrogen, —$CH_2N(H)(NHCH_3)$, —$CH_2NHC(=NH)(NH_2)$, —$CH_2NHC(=NH)(NHNO_2)$, —$CH_2NHC(=NH)(NHCN)$, —$CH_2NHC(=NH)(phenyl)$, —$CH_2NHC(NH_2)=CH(NO_2)$, methyl, ethyl, hydroxymethyl, 2,3-dihydroxypropyl, 3-hydroxy-2-methyl-prop-2-yl, N-(1-methoxyprop-2-yl)-aminomethyl, N-(ethoxypropyl)-aminomethyl, N-(ethoxyethyl)-aminomethyl, N-(2,2-dimethoxyethyl)-aminomethyl, N-(methoxyethyl)-aminomethyl, N-(isopropxyethyl)-aminomethyl, trifluoromethyl, 1-nitro-ethyl, 1-methyl-1-nitro-ethyl, 1-nitro-propyl, 3-methyl-1-nitro-butyl, phenylthiomethyl, allyl, ethenyl, 2-methylthio-ethylaminomethyl, 3-methylthio-propylaminomethyl, N-(tert-butoxyearbonylaminopropyl)-aminomethyl, N-(1-carboxyethyl)-aminomethyl, N-(1R-carboxyethyl)-aminomethyl, N-(1S-carboxyethyl)-aminomethyl, N-(1-methoxycarbonylethyl)-aminomethyl, azetidinylmethyl, pyrrolidinylmethyl, 3-hydroxy-pyrrolidinylmethyl, 2-(methoxymethyl)-pyrrolidinylmethyl, 2S-(methoxymethyl)-pyrrolidinylmethyl, 2R-(methoxymethyl)-pyrrolidinylmethyl, morpholinylmethyl, 4-hydroxypiperidinylmethyl, 4-methyl-piperazinylmethyl, 4-methyl-homopiperazinylmethyl, 4-(piperidinyl)-piperidinylmethyl, 4-[2-(N,N-diethylamino)-ethyl]-piperazinylmethyl, N-hydroxyaminomethyl, N-methoxyaminomethyl, N-ethoxyaminomethyl, N-ethylaminomethyl, 1-(N-ethylamino)-ethyl, N,N-diethylaminomethyl, N,N-dimethylaminomethyl, aminomethyl, 1-amino-ethyl, 1R-amino-ethyl, 1S-amino-ethyl, 1-(methylamino)-ethyl, 1-(N,N-dimethylamino)-ethyl, 1-amino-1-methyl-ethyl, 1-aminopropyl, 1S-aminopropyl, 1R-aminopropyl, N-(n-propyl)-aminomethyl, N-(isopropyl)-aminomethyl, 2-(N-isopropylamino)-ethyl, 3-(N-isopropylamino)-2-methyl-prop-2-yl, 1-(N-ethyl-amino)-propyl, 1-(N,N-diethyl-amino)-propyl, 1-aminobutyl, 1-amino-isobutyl, N-(n-butyl)-aminomethyl, N-isobutylaminomethyl, tert-butylaminomethyl, 1-(tert-butylamino)-ethyl, sec-butylaminomethyl, N-(2-methyl-but-3-yl)-aminomethyl, N-(3,3-dimethyl-butyl)-aminomethyl, N-(3-methylbut-3-yl)-aminomethyl, N-(2-methylbutyl)-aminomethyl, N-(pent-3-yl)-aminomethyl, n-pentylaminomethyl, isopentylaminomethyl, sec-pentylaminomethyl, neopentylaminomethyl, N-(2,2,4-trimethyl-pent-4-yl)-aminomethyl, N-(2-ethyl-butyl)-aminomethyl, N-allyl-aminomethyl, 3-methyl-but-1-yn-3-ylaminomethyl, N-(2,3-dihydroxypropyloxy)-aminomethyl, N-cyclopropylaminomethyl, N-cyclopentylaminomethyl, N-cyclopenten-4-ylaminomethyl, N-(1(R,S)-hydroxy-cyclopent-2-yl)-aminomethyl, N-(1S-hydroxy-cyclopent-2-yl)-aminomethyl, N-(1R-hydroxy-cyclopent-2-yl)-aminomethyl, N-(1(R,S)-hydroxy-1-methyl-cyclopent-2-yl)-aminomethyl, N-(1S-hydroxy-1-methyl-cyclopent-2-yl)-aminomethyl, N-(1R-hydroxy-1-methyl-cyclopent-2-yl)-aminomethyl, N-(3,4-dihydroxy-cyclopentyl)-aminomethyl, N-(1-hydroxymethyl-cyclopent-1-yl)-aminomethyl, N-(2,3-dihydroxy-4-hydroxymethyl-cyclopentyl)-aminomethyl, N-(1(R,S)-methoxy-cyclopent-2-yl)-aminomethyl, N-(1S-methoxy-cyclopent-2-yl)-aminomethyl, N-(1R-methoxy-cyclopent-2-yl)-aminomethyl, N-(1-carboxy-cyclopentyl)-aminomethyl, N-cyclohexylaminomethyl, N-(1(R,S)-hydroxy-cyclohex-2-yl)-aminomethyl, N-(1(R)-hydroxycyclohex-2-yl)-aminomethyl, N-(1(S)-hydroxy-cyclohex-2-yl)-aminomethyl, N-(cis-4-hydroxy-cyclohexyl)-aminomethyl, N-(trans-4-hydroxy-cyclohexyl)-aminomethyl, 1-[N-(cis-4-hydroxy-cyclohexyl)-amino]-ethyl, 1-[N-(trans-4-hydroxy-cyclohexyl)-amino]-ethyl, N-(1-hydroxymethyl-cyclohexyl)-aminomethyl, N-(2-cyclohexyl-cyclohexyl)-aminomethyl, N-{(2R,3S,4R,6R)-2-(hydroxymethyl)-3,4-dihydroxy-6-methoxy-tetrahydro-2H-pyran-5-yl}-aminomethyl, N-(cycloheptyl)-aminomethyl, N-(cyclooctyl)-aminomethyl, [(1r,3r,5R,7R)-tricyclo[3.3.1.1~3,7~]dec-2-ylamino]methyl, N-(1-benzyloxy-cyclopent-2-yl)-aminomethyl, N-[1-(cyclopropylaminocarbonyl)-cyclopentyl]-aminomethyl, —CH$_2$NHC(CH$_3$)$_2$C(O)NH(cyclohexyl), —CH$_2$NHC(CH$_3$)$_2$C(O)NH(CH$_2$CH$_3$), N-(cyclopropylmethyl)-aminomethyl, N-(cyclohexylmethyl)-aminomethyl, N-(1-cyclohexylethyl)-aminomethyl, N-(imidazolyl)-aminomethyl, N-(1,3,5-triazinyl)-aminomethyl, N-(5-hydroxy-pyrazol-3-yl)-aminomethyl, N-(5-methyl-pyrazol-3-yl)-aminomethyl, N-(benzimidazolyl)-aminomethyl, N-(pyrimidin-2-yl)-aminomethyl, N-(pyridin-2-yl)-aminomethyl, N-(pyridin-3-yl)-aminomethyl, N-(pyridin-4-yl)-aminomethyl, N-indan-1-yl-aminomethyl, N-indan-2-yl-aminomethyl, phenylaminomethyl, N-(2-hydroxyphenyl)-aminomethyl, N-(3-hydroxyphenyl)-aminomethyl, N-(4-hydroxyphenyl)-aminomethyl, N-(2-methoxyphenyl)-aminomethyl, N-(3-methoxyphenyl)-aminomethyl, N-(4-methoxyphenyl)-aminomethyl, N-(2-fluorophenyl)-aminomethyl, N-(3-fluorophenyl)-aminomethyl, N-(4-fluorophenyl)-aminomethyl, N-(2-chlorophenyl)-aminomethyl, N-(3-chlorophenyl)-aminomethyl, N-(4-chlorophenyl)-aminomethyl, N-(3-methylcarbonylamino-phenyl)-aminomethyl, N-(4-methylcarbonylamino-phenyl)-aminomethyl, N-(2-aminophenyl)-aminomethyl, N-(3-aminophenyl)-aminomethyl, N-(4-aminophenyl)-aminomethyl, N-(2-methylsulfonylaminophenyl)-aminomethyl, N-(3-methylsulfonylaminophenyl)-aminomethyl, N-(4-methylsulfonylaminophenyl)-aminomethyl, N-(2-fluoro-4-hydroxy-phenyl)-aminomethyl, N-(3-fluoro-4-hydroxy-phenyl)-aminomethyl, N-(benzyl)-aminomethyl, N-(2-hydroxyphenylmethyl)-aminomethyl, N-(3-hydroxyphenylmethyl)-aminomethyl, N-(4-hydroxyphenylmethyl)-aminomethyl, N-(2-(N-methylpiperazin-1-yl)-phenylmethyl)-aminomethyl, N-(4-methyl-phenethyl)-aminomethyl, N-(1-hydroxy-3-phenyl-prop-2-yl)-aminomethyl, N-(pyrrolidin-2-ylmethyl)-aminomethyl, N-(N-ethyl-pyrrolidinylmethyl)-aminomethyl, N-(N-methyl-pyrrolidin-2-ylethyl)-aminomethyl, N-(pyrrolidinylpropyl)-aminomethyl, N-(1,1-dimethyl-2-pyrrolidin-1-ylethyl)-aminomethyl, N-(tetrahydrofuranylmethyl)-aminomethyl, N-(tetrahydro-2H-pyran-4-ylmethyl)-aminomethyl, N-(tetrahydro-2H-pyranylethyl)-aminomethyl, N-(piperidin-4-ylmethyl)-aminomethyl, N-(N-methylpiperidin-4-ylmethyl)-aminomethyl, N-(N-tert-butoxycarbonylpiperidin-4-ylmethyl)-aminomethyl, N-(N-methylimidazol-5-ylmethyl)-aminomethyl, N-(N-methylimidazol-4-ylmethyl)-aminomethyl, N-[2-(imidazol-4-yl)-ethyl]-aminomethyl, N-[3-(imidazolyl)-propyl]-aminomethyl, N-(pyridin-3-ylethyl)-aminomethyl, N-(pyridin-4-ylethyl)-aminomethyl, N-(thien-2-ylethyl)-aminomethyl, N-(furan-2-ylethyl)-aminomethyl, N-(5-methyl-1,3,4-oxadiazol-2-ylmethyl)-aminomethyl, N-(2-indolin-3-ylethyl)-aminomethyl, 2-(N,N-dimethylamino)-ethylaminomethyl, 2-(N,N-dimethylamino)-1-methyl-ethylaminomethyl, 3-aminopropylaminomethyl, 3-(N,N-dimethylamino)-propylaminomethyl, 3-(N,N-diethylamino)-propylaminomethyl, N-(N,N-diisopropylaminoethyl)-aminomethyl, N-(N,N-dimethylaminobutyl)-aminomethyl, 3-hydroxypropylaminomethyl, N-(1,2-dihydroxypropyl)-aminomethyl, N-(1-amino-2-hydroxy-prop-3-yl)-aminomethyl, N-(N-ethoxycarbonyl-piperidin-4-yl)-aminomethyl, N-(N-benzylpiperidin-4-yl)-aminomethyl, N-(homopiperidin-3-yl)-aminomethyl, N-(N-benzylpyrrolidin-3-yl)-aminomethyl, N-(N-ethylpiperidin-3-yl)aminomethyl, 2,2,2-trifluoroethylaminomethyl, 3,3,3-trifluoropropylaminomethyl, 2,2,3,3,3-pentafluoropropylaminomethyl, —CH$_2$N(CH$_2$CH$_2$OH)$_2$, —CH$_2$N(CH$_3$)(CH$_2$CH$_2$OH), —CH$_2$NH(CH$_2$CH$_2$OH), —CH$_2$NH(CH$_2$CH$_2$CH$_2$OH), —CH$_2$NH(C(CH$_3$)$_2$CH$_2$OH), —CH$_2$N(CH$_3$)(N-methyl-pyrrolidin-3-yl), —C(O)NH$_2$, —C(O)NHCH$_2$CH═CH$_2$, —C(O)NHCH$_2$CH(OH)CH$_2$OH, N-(phenyloxyethyl)-aminomethyl, —CH$_2$NHC(O)CH$_3$, —CH(CH$_3$)NHC(O)CH$_3$, —CH(CH$_3$)NHC(O)C(OCH$_3$)(CF$_3$)phenyl, cyclopentyl, 1-amino-cyclopentyl, (cis,trans)-2-amino-cyclopentyl, (cis,trans)-2-amino-cyclopentyl, cis-2-amino-cyclopentyl, trans-2-amino-cyclopentyl, (cis,trans)-2-hydroxy-cyclohexyl, cis-2-hydroxy-cyclohexyl, trans-2-hydroxy-cyclohexyl, (cis,trans)-2-amino-cyclohexyl, cis-2-amino-cyclohexyl, trans-2-amino-cyclohexyl, azetidin-3-yl, pyrrolidinyl, N-methyl-pyrrolidin-2-yl, N-ethyl-pyrrolidin-2-yl, 3-(dimethylamino)-pyrrolidinyl, piperidinyl, 2-methyl-piperidin-6-yl, N-methylpiperidin-2-yl, N-tert-butoxycarbonylpiperidin-2-yl, piperazin-2-yl, pyrrol-1-yl, pyrrol-2-yl, pyrrol-3-yl, imidazol-1-yl, imidazol-2-yl, imidazol-4-yl, imidazol-5-yl, N-methyl-imidazol-2-yl, 5-methyl-imidazol-2-yl, 1,2,4-triazol-3-yl, thiazol-2-yl, 2-aminopyrimidin-3-yl, pyridin-2-yl, pyridin-3-yl, pyridin-4-yl, benzimidazolyl, imidazol-1-ylmethyl, imidazol-2-ylmethyl, triazol-1-ylmethyl, (5-amino-3-methyl-pyrazol-3-yl)-methyl, phenoxymethyl, 2-hydroxyethyloxymethyl, methylsulfonylaminomethyl, 1-(methoxycarbonylamino)-ethyl, 1-amino-1-phenyl-methyl, or 1-amino-3-hydroxy-propyl.

Another specific embodiment of the Invention (A11) is that where the compound of Formula I is selected from Group A where $R^3$ and $R^4$ together with the carbon to which they are attached form C(O) or C(=NOH). More specifically, X and $R^7$ are halo; A is phenylene optionally substituted with $R^{10}$ and $R^{12}$ where $R^{10}$ and $R^{12}$ are independently hydrogen or halo; $R^1$, $R^2$, $R^5$ and $R^6$ are hydrogen; and $R^3$ and $R^4$ together with the carbon to which they are attached form C(O) or C(=NOH).

Another specific embodiment of the Invention (A12) is that where the compound of Formula I is selected from Group A where X and $R^7$ are halo; A is phenylene optionally substituted with $R^{10}$ and $R^{12}$ where $R^{10}$ and $R^{12}$ are independently hydrogen or halo; and $R^1$, $R^2$, $R^4$, $R^5$ and $R^6$ are hydrogen.

Another specific embodiment of the Invention (A13) is that where the compound of Formula I is selected from Group A where A is phenylene.

Another specific embodiment of the Invention (A14) is that where the compound of Formula I is selected from Group A where $R^1$ is hydrogen and $R^2$ is alkyl substituted with —$NR^8R^{8'}$ where $R^8$ and $R^{8'}$ and all other groups are as defined in the Summary of the Invention for a compound of Group A.

Another specific embodiment of the Invention (A15) is that where the compound of Formula I is selected from Group A where A is phenylene; $R^7$ is iodo or bromo; X is fluoro or chloro; and $R^1$, $R^2$, $R^5$, and $R^6$ are hydrogen; and $R^{10}$, $R^{12}$, $R^{14}$, and $R^{16}$ are independently hydrogen or fluoro. More specifically, $R^{10}$ is 3-fluoro and $R^{12}$, $R^{14}$, and $R^{16}$ are hydrogen or halo; $R^{10}$ is 3-fluoro, $R^{12}$ is 4-fluoro, and $R^{14}$ and $R^{16}$ are hydrogen; $R^{10}$ is 4-fluoro, $R^{12}$ is 5-fluoro, and $R^{14}$ and $R^{16}$ are hydrogen; $R^{10}$ is 4-fluoro, $R^{12}$ is 6-fluoro, and $R^{14}$ and $R^{16}$ are hydrogen; or $R^{12}$ is 4-fluoro and $R^{10}$, $R^{14}$, and $R^{16}$ are hydrogen.

In another embodiment of the invention is a compound of Formula selected form Group A where $R^3$ is hydroxy and $R^4$ is heterocycloalkyl, alkyl, or heteroaryl, where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with groups independently selected from hydroxy and alkyl) and the heteroaryl is optionally substituted with alkyl. Specifically, $R^3$ is hydroxy and $R^4$ is heterocycloalkyl or alkyl, where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with groups independently selected from hydroxy and alkyl).

In another embodiment of the Invention (B1) the compound of Formula I is selected from Group B where all groups are as defined in the Summary of the Invention.

In another embodiment of the invention (B2), X and $R^7$ are halo; and all other groups are as defined in the Summary of the Invention for a compound of Group B. Specifically, X is fluoro or chloro and $R^7$ is iodo or bromo.

In another embodiment of the invention (B3), the compound is selected from Group B where $R^3$ is halo, nitro, —$NR^8R^{8'}$, —$OR^8$, —$NHS(O)_2R^8$, —CN, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^{8'}R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^{8'}R^{8''}$, —$NR^8C(O)OR^{8'}$ and —$NR^8C(O)R^{8'}$ and $R^4$ is as defined in the Summary of the Invention; or $R^3$ and $R^4$ together with the carbon to which they are attached form C(O) or C(=NOH); and all other groups are as defined in the Summary of the Invention for a compound of Group B. More specifically, $R^1$, $R^2$, $R^5$ and $R^6$ are hydrogen; and X and $R^7$ are halo.

In another embodiment of the invention (B4), the compound is selected from Group B where $R^3$ and $R^4$ are independently halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)NR^8R^{8'}$, —$C(O)NR^8R^{8'}$, —$NR^8C(O)OR^{8'}$, —$NR^8C(O)NR^{8'}R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)N(R^{25a})(NO_2))$, —$CH_2NR^{25}C(=NH)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^{8'}R^{8''}$, —$NR^8C(O)OR^{8'}$ and —$NR^8C(O)R^{8'}$; or $R^3$ and $R^4$ together with the carbon to which they are attached form C(O) or C(=NOH); and all other groups are as defined in the Summary of the Invention for a compound of Group B. More specifically, $R^1$, $R^2$, $R^5$ and $R^6$ are hydrogen; and X and $R^7$ are halo.

In another embodiment of the invention (B5), A is heteroarylene selected from thien-diyl, benzo[d]isoxazol-diyl, benzo[d]isothiazol-diyl, 1H-indazol-diyl (optionally substituted at the N1 position with $R^{19}$ where $R^{19}$ is as defined in the Summary of the Invention for a compound of Group B), benzo[d]oxazol-diyl, benzo[d]thiazol-diyl, 1H-benzo[d]imidazol-diyl (optionally substituted at the N1 position with $R^{19}$ where $R^{19}$ is as defined in the Summary of the Invention for a compound of Group B), 1H-benzo[d][1,2,3]triazol-diyl (optionally substituted at the N1 position with $R^{19}$ where $R^{19}$ is as defined in the Summary of the Invention for a compound of Group B), imidazo[1,2-a]pyridin-diyl, cinnolin-diyl, quinolin-diyl, pyridin-diyl, 1-oxido-pyridin-diyl, [1,2,4]triazolo[4,3-a]pyridin-diyl, and 2,3-dihydroimidazo[1,2-a]pyridin-diyl; and A is further optionally substituted with one, two, three, or four groups selected from $R^{10}$, $R^{12}$, $R^{14}$, and $R^{16}$ where $R^{10}$, $R^{12}$, $R^{14}$, and $R^{16}$ and all other groups are as defined in the Summary of the Invention for a compound of Group B. More specifically A is selected from thien-3,4-diyl, benzo[d]isoxazol-5,6-diyl, benzo[d]isothiazol-5,6-diyl, 1H-indazol-5,6-diyl (optionally substituted at the N1 position with $R^{19}$ where $R^{19}$ is alkyl or alkenyl), benzo[d]oxazol-5,6-diyl, benzo[d]thiazol-5,6-diyl, 1H-benzo[d]imidazol-5,6-diyl (optionally substituted at the N1 position with $R^{19}$ where $R^{19}$ is alkyl or alkenyl), 1H-benzo[d][1,2,3]triazol-5,6-diyl (optionally substituted at the N1 position with $R^{19}$ where $R^{19}$ is alkyl or alkenyl), imidazo[1,2-a]pyridin-5,6-diyl, cinnolin-6,7-diyl, quinolin-6,7-diyl, pyridin-3,4-diyl, 1-oxido-pyridin-3,4-diyl, [1,2,4]triazolo[4,3-a]pyridin-6,7-diyl, and 2,3-dihydroimidazo[1,2-a]pyridin-6,7-diyl.

In another embodiment of the Invention (B6), the compound of Formula I is selected from Group B where A is thien-diyl and X, $R^1$, $R^2$, $R^3$, $R^4$, $R^5$, $R^6$, $R^7$, $R^{10}$, and $R^{12}$ are as defined in the Summary of the Invention for a compound of Group B. More specifically A is thien-3,4-diyl; $R^{10}$ and $R^{12}$ are hydrogen; X and $R^7$ are halo; and $R^1$, $R^2$, $R^5$, and $R^6$ are hydrogen. Even more specifically, X is fluoro or chloro; $R^7$ is iodo or bromo; $R^3$ is hydrogen or hydroxy; and $R^4$ is —$NR^8R^{8'}$ (where $R^8$ and $R^{8'}$ are independently hydrogen or alkyl), heterocycloalkyl, heteroaryl (optionally substituted with alkyl), or alkyl where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with one or two groups independently selected from hydroxy and alkyl).

In another embodiment (B7), the compound is of Formula I(c) or I(d)

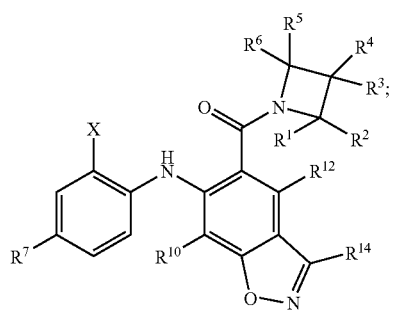

I(c)

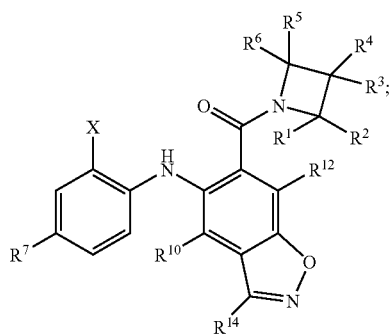

I(d)

where X, $R^1$, $R^2$, $R^3$, $R^4$, $R^5$, $R^6$, $R^7$, $R^{10}$, $R^{12}$ and $R^{14}$ are as defined in the Summary of the are as defined in the Summary of the Invention for a compound of Group B. More specifically, $R^1$, $R^2$, $R^5$, and $R^6$ are hydrogen; X and $R^7$ are halo; $R^3$ and $R^4$ are as defined in the Summary of the Invention for Group B; and $R^{10}$, $R^{12}$, and $R^{14}$ are independently hydrogen, halo, or alkyl. Even more specifically, X is fluoro or chloro and $R^7$ is iodo or bromo; $R^{10}$ is hydrogen or halo, more specifically hydrogen or fluoro; $R^{12}$ is hydrogen; $R^{14}$ is hydrogen or alkyl; and $R^3$ is hydroxy. Yet even more specifically, $R^4$ is heterocycloalkyl, alkyl, or heteroaryl, where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with groups independently selected from hydroxy and alkyl) and the heteroaryl is optionally substituted with alkyl. Yet even more specifically, $R^4$ is piperidinyl, pyrrolidinyl, 1(R,S)-amino-ethyl, 1(R)-amino-ethyl, 1(S)-amino-ethyl, 1(R,S)-(methylamino)-ethyl, 1(R)-(methylamino)-ethyl, 1(S)-(methylamino)-ethyl, 1(R,S)-(dimethylamino)-ethyl, 1(R)-(dimethylamino)-ethyl, 1(S)-(dimethylamino)-ethyl, 1(R,S)-(3,4-cis-dihydroxy-cyclopentylamino)-ethyl, 1(R)-(3,4-cis-dihydroxy-cyclopentylamino)-ethyl, or 1(S)-(3,4-cis-dihydroxy-cyclopentylamino)-ethyl.

In another embodiment of the Invention (B8), the compound is of Formula I(e) or I(f):

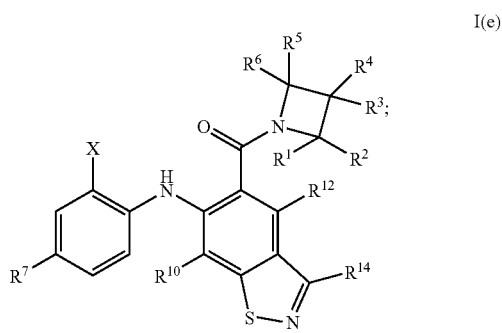

I(e)

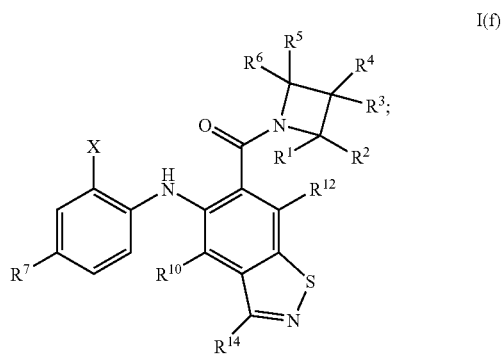

I(f)

where X, $R^1$, $R^2$, $R^3$, $R^4$, $R^5$, $R^6$, $R^7$, $R^{10}$, $R^{12}$ and $R^{14}$ are as defined in the Summary of the Invention for a compound of Group B. More specifically, $R^1$, $R^2$, $R^5$, and $R^6$ are hydrogen; X and $R^7$ are halo; $R^3$ and $R^4$ are as defined in the Summary of the Invention for Group B; and $R^{10}$, $R^{12}$, and $R^{14}$ are independently hydrogen, halo, or alkyl. Even more specifically, X is fluoro or chloro and $R^7$ is iodo or bromo; $R^{10}$ is hydrogen or halo, more specifically hydrogen or fluoro; $R^{12}$ and $R^{14}$ are hydrogen; $R^3$ is hydroxy; and $R^4$ is heterocycloalkyl, alkyl, or heteroaryl, where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with one or two groups independently selected from hydroxy and alkyl) and the heteroaryl is optionally substituted with alkyl.

In another embodiment of the Invention (B9), the compound is of Formula I(g) or I(h):

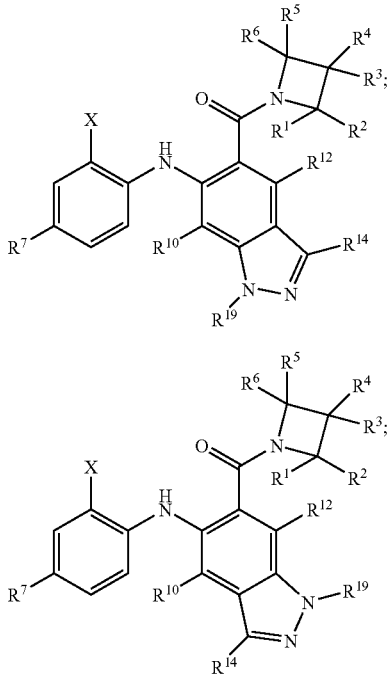

where X, $R^1$, $R^2$, $R^3$, $R^4$, $R^5$, $R^6$, $R^7$, $R^{10}$, $R^{12}$, $R^{14}$, and $R^{19}$ are as defined in the Summary of the Invention for a compound of Group B.

In a more specific embodiment of embodiment B9, the compound is of formula I(g) or I(h) where
$R^3$ is halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)N(R^{25a})(CN))$, —$CH_2NR^{25}C(=NH)(R^{25})$, —$CH_2NR^{25}C(NR^{25a}R^{25b})=CH(NO_2)$, cycloalkyl, heteroaryl, or heterocycloalkyl; where the cycloalkyl, heteroaryl, and heterocycloalkyl are optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^8R^{8''}$, —$NR^8C(O)OR^{8'}$ and —$NR^8C(O)R^{8'}$; and $R^4$ is as defined in the Summary of the Invention; or $R^3$ and $R^4$ together with the carbon to which they are attached form C(O) or C(=NOH); and
all other groups are as defined in the Summary of the Invention for a compound of Group B.

In a more specific embodiment of embodiment B9, the compound is of formula I(g) or I(h) where $R^3$ is hydroxy and all other groups are as defined in the Summary of the Invention for a compound of Group B.

In a more specific embodiment of embodiment B9, the compound is of formula I(g) or I(h) where $R^1$, $R^2$, $R^5$, and $R^6$ are hydrogen; X and $R^7$ are halo; $R^3$ and $R^4$ are as defined in the Summary of the Invention for Group B; $R^{10}$, $R^{12}$, and $R^{14}$ are independently hydrogen, halo, or alkyl; and $R^{19}$ is hydrogen or methyl. Even more specifically, X is fluoro or chloro and $R^7$ is iodo or bromo; $R^{10}$ is hydrogen or halo, more specifically hydrogen or fluoro; $R^{12}$ and $R^{14}$ are hydrogen; $R^3$ is hydroxy; and $R^4$ is heterocycloalkyl, alkyl, or heteroaryl, where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with one or two groups independently selected from hydroxy and alkyl) and the heteroaryl is optionally substituted with alkyl.

In another embodiment of the Invention (B10), the compound is of Formula I(i) or I(j):

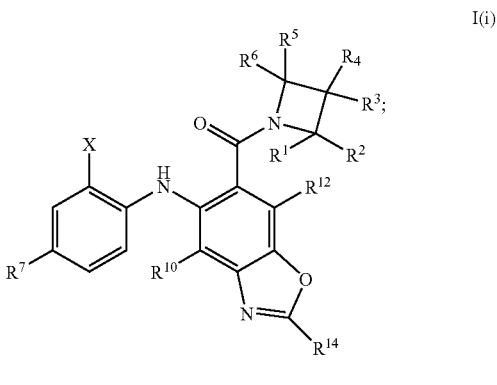

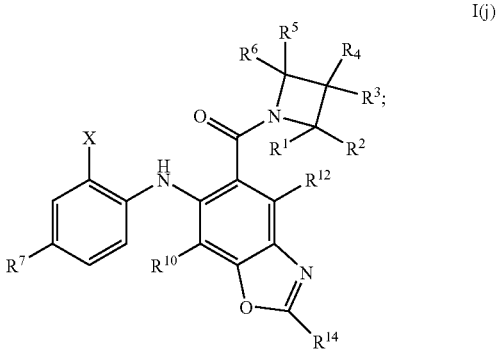

where X, $R^1$, $R^2$, $R^3$, $R^4$, $R^5$, $R^6$, $R^7$, $R^{10}$, $R^{12}$ and $R^{14}$ are as defined in the Summary of the Invention for a compound of Group B. More specifically, $R^1$, $R^2$, $R^5$, and $R^6$ are hydrogen; X and $R^7$ are halo; $R^3$ and $R^4$ are as defined in the Summary of the Invention for Group B; and $R^{10}$, $R^{12}$, and $R^{14}$ are independently hydrogen, halo, or alkyl. Even more specifically, X is fluoro or chloro and $R^7$ is iodo or bromo; $R^{10}$ is hydrogen or halo, more specifically hydrogen or fluoro; $R^{12}$ and $R^{14}$ are hydrogen; $R^3$ is hydroxy; and $R^4$ is heterocycloalkyl, alkyl, or heteroaryl, where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with one or two groups independently selected from hydroxy and alkyl) and the heteroaryl is optionally substituted with alkyl.

In another embodiment of the Invention (B11), the compound is of Formula I(k) or I(m):

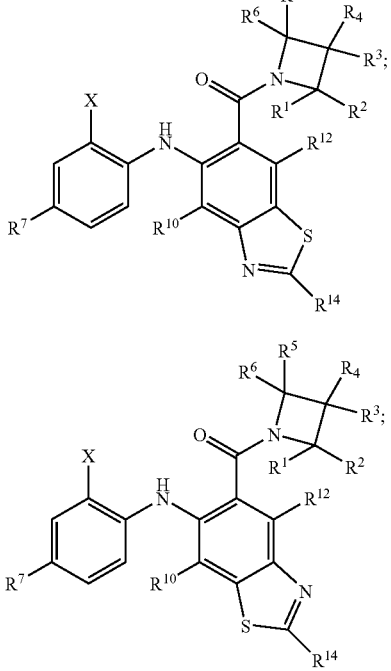

where X, R$^1$, R$^2$, R$^3$, R$^4$, R$^5$, R$^6$, R$^7$, R$^{10}$, R$^{12}$ and R$^{14}$ are as defined in the Summary of the Invention for a compound of Group B. More specifically, R$^1$, R$^2$, R$^5$, and R$^6$ are hydrogen; X and R$^7$ are halo; R$^3$ and R$^4$ are as defined in the Summary of the Invention for Group B; and R$^{10}$, R$^{12}$, and R$^{14}$ are independently hydrogen, halo, or alkyl. Even more specifically, X is fluoro or chloro and R$^7$ is iodo or bromo; R$^{10}$ is hydrogen or halo, more specifically hydrogen or fluoro; R$^{12}$ and R$^{14}$ are hydrogen; R$^3$ is hydroxy; and R$^4$ is heterocycloalkyl, alkyl, or heteroaryl, where the alkyl is optionally substituted with —NR$^8$R$^{8'}$ (where R$^8$ is hydrogen or alkyl and R$^{8'}$ is hydrogen, alkyl, or cycloalkyl where the cycloalkyl is optionally substituted with one or two groups independently selected from hydroxy and alkyl) and the heteroaryl is optionally substituted with alkyl.

In another embodiment of the Invention (B12), the compound is of Formula I(n) or I(o):

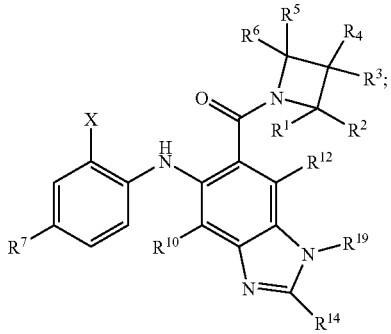

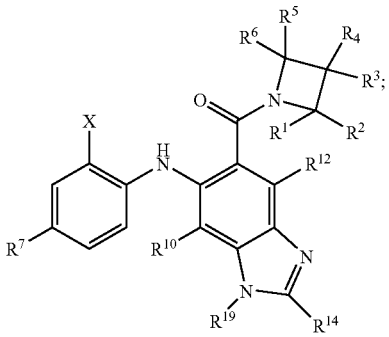

where X, R$^1$, R$^2$, R$^3$, R$^4$, R$^5$, R$^6$, R$^7$, R$^{10}$, R$^{12}$, R$^{14}$, and R$^{19}$ are as defined in the Summary of the Invention for a compound of Group B.

In a more specific embodiment of embodiment B12, the compound is of formula I(n) or I(o) where R$^7$ is halo or alkyl; and all other groups are as defined in the Summary of the Invention for a compound of Group B. More specifically, R$^7$ is iodo or bromo.

In a more specific embodiment of embodiment B12, the compound is of formula I(n) or I(o) where X is halo, haloalkyl, or haloalkoxy; and all other groups are as defined in the Summary of the Invention for a compound of Group B. More specifically, X is halo. Even more specifically X is fluoro or chloro.

In a more specific embodiment of embodiment B12, the compound is of formula I(n) or I(o) where
R$^3$ is halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)OR$^8$, —C(O)NR$^8$R$^{8'}$, —NR$^8$C(O)OR$^{8'}$, —NR$^8$C(O)NR$^8$R$^{8''}$, —NR$^8$C(O)OR$^{8'}$, —NR$^8$C(O)R$^{8'}$, —CH$_2$N(R$^{25}$)(NR$^{25a}$R$^{25b}$), —CH$_2$NR$^{25}$C(=NH)(NR$^{25a}$R$^{25b}$), —CH$_2$NR$^{25}$C(=NH)(N(R$^{25a}$)(NO$_2$)), —CH$_2$NR$^{25}$C(=NH)(N(R$^{25a}$)(CN)), —CH$_2$NR$^{25}$C(=NH)(R$^{25}$), —CH$_2$NR$^{25}$C(NR$^{25a}$R$^{25b}$)=CH(NO$_2$), alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —OR$^8$, —NR$^8$R$^{8'}$, —NR$^8$S(O)$_2$R$^9$, —CN, —S(O)$_m$R$^9$, —C(O)R$^8$, —C(O)OR$^8$R$^{8'}$, —NR$^8$C(O)NR$^8$R$^{8''}$, —NR$^8$C(O)OR$^{8'}$ and —NR$^8$C(O)R$^{8'}$; and R$^4$ is as defined in the Summary of the Invention; or
R$^3$ and R$^4$ together with the carbon to which they are attached form C(O) or C(=NOH); and
unless otherwise indicated, R$^8$ and R$^{8'}$ are as defined in the Summary of the Invention; and all other groups are as defined in the Summary of the Invention for a compound of Group B.

In a more specific embodiment of embodiment B12, the compound is of formula I(n) or I(o) where R$^{19}$ is alkyl; R$^1$, R$^2$, R$^5$, and R$^6$ are hydrogen; X and R$^7$ are halo; R$^3$ and R$^4$ are as defined in the Summary of the Invention for Group B; and R$^{10}$, R$^{12}$, and R$^{14}$ are independently hydrogen or halo. Even more specifically, R$^{19}$ is methyl; X is fluoro or chloro and R$^7$ is iodo or bromo; R$^{10}$ is hydrogen or fluoro; R$^{12}$ and R$^{14}$ are hydrogen; and R$^3$ is hydroxy. Yet even more specifically, R$^4$ is heterocycloalkyl, alkyl, or heteroaryl, where the alkyl is optionally substituted with —NR$^8$R$^{8'}$ (where R$^8$ is hydrogen or alkyl and R$^{8'}$ is hydrogen, alkyl, or cycloalkyl where the cycloalkyl is optionally substituted with one or two groups independently selected from hydroxy and alkyl) and the heteroaryl is optionally substituted with alkyl. Yet even more specifically, R⁴ is piperidinyl, pyrrolidinyl, 1(R,S)-amino-ethyl, 1(R)-amino-ethyl, 1(S)-amino-ethyl, 1(R,S)-(methylamino)-ethyl, 1(R)-(methylamino)-ethyl, 1(S)-(methylamino)-ethyl, 1(R,S)-(dimethylamino)-ethyl, 1(R)-(dimethylamino)-ethyl, 1(S)-(dimethylamino)-ethyl, 1(R,S)-(3,4-cis-dihydroxy-cyclopentylamino)-ethyl, 1(R)-(3,4-cis-dihydroxy-cyclopentylamino)-ethyl, or 1(S)-(3,4-cis-dihydroxy-cyclopentylamino)-ethyl.

In another embodiment of the Invention (B13), the compound is of Formula I(p):

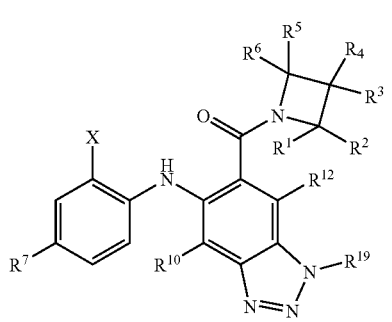

I(p)

where X, R¹, R², R³, R⁴, R⁵, R⁶, R⁷, R¹⁰, R¹², and R¹⁹ are as defined in the Summary of the Invention for a compound of Group B. More specifically, R¹, R², R⁵, and R⁶ are hydrogen; X and R⁷ are halo; R³ and R⁴ are as defined in the Summary of the Invention for Group B; and R¹⁰ and R¹² are independently hydrogen, halo, or alkyl. Even more specifically, X is fluoro or chloro; R⁷ is iodo or bromo; R¹⁰ is hydrogen or halo, more specifically hydrogen or fluoro; R¹² is hydrogen; R¹⁹ is hydrogen or alkyl, more specifically hydrogen or methyl; R³ is hydroxy. Even more specifically, R⁴ is heterocycloalkyl, alkyl, or heteroaryl, where the alkyl is optionally substituted with —NR⁸R⁸' (where R⁸ is hydrogen or alkyl and R⁸' is hydrogen, alkyl, or cycloalkyl where the cycloalkyl is optionally substituted with one or two groups independently selected from hydroxy and alkyl) and the heteroaryl is optionally substituted with alkyl. Yet even more specifically, R⁴ is piperidinyl, pyrrolidinyl, 1(R,S)-amino-ethyl, 1(R)-amino-ethyl, 1(S)-amino-ethyl, 1(R,S)-(methylamino)-ethyl, 1(R)-(methylamino)-ethyl, 1(S)-(methylamino)-ethyl, 1(R,S)-(dimethylamino)-ethyl, 1(R)-(dimethylamino)-ethyl, 1(S)-(dimethylamino)-ethyl, 1(R,S)-(3,4-cis-dihydroxy-cyclopentylamino)-ethyl, 1(R)-(3,4-cis-dihydroxy-cyclopentylamino)-ethyl, or 1(S)-(3,4-cis-dihydroxy-cyclopentylamino)-ethyl.

In another embodiment of the Invention (B14), the compound is of Formula I(q):

I(q)

where X, R¹, R², R³, R⁴, R⁵, R⁶, R⁷, R¹⁰, R¹² R¹⁴, and R¹⁶ are as defined in the Summary of the Invention for a compound of Group B.

In a more specific embodiment of embodiment B14, the compound is of formula I(q) where R³ is halo, nitro, —NR⁸R⁸', —OR⁸, —NHS(O)₂R⁸, —CN, —S(O)ₘR⁸, —S(O)₂NR⁸R⁸', —C(O)R⁸, —C(O)OR⁸, —C(O)NR⁸R⁸', —NR⁸C(O)OR⁸', —NR⁸C(O)NR⁸R⁸'', —NR⁸C(O)OR⁸', —NR⁸C(O)R⁸', —CH₂N(R²⁵)(NR²⁵ᵃR²⁵ᵇ), —CH₂NR²⁵C(=NH)(NR²⁵ᵃR²⁵ᵇ), —CH₂NR²⁵C(=NH)(N(R²⁵ᵃ)(NO₂)), —CH₂NR²⁵C(=NH)(N(R²⁵ᵃ)(CN)), —CH₂NR²⁵C(=NH)(R²⁵), —CH₂NR²⁵C(NR²⁵ᵃR²⁵ᵇ)=CH(NO₂), alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —OR⁸, —NR⁸R⁸', —NR⁸S(O)₂R⁹, —CN, —S(O)ₘR⁹, —C(O)R⁸, —C(O)OR⁸, —C(O)NR⁸R⁸', —NR⁸C(O)NR⁸R⁸'', —NR⁸C(O)OR⁸' and —NR⁸C(O)R⁸'; and R⁴ is as defined in the Summary of the Invention; or R³ and R⁴ together with the carbon to which they are attached form C(O) or C(=NOH); and all other groups are as defined in the Summary of the Invention for a compound of Group B.

In a more specific embodiment of embodiment B14, the compound is of formula I(q) where R¹, R², R⁵, and R⁶ are hydrogen; X and R⁷ are halo; R³ and R⁴ are as defined in the Summary of the Invention for Group B; and R¹⁰, R¹², R¹⁴, and R¹⁶ are independently hydrogen or halo. Even more specifically, R¹⁰ is halo and R¹², R¹⁴, and R¹⁶ are hydrogen. Even more specifically, X is fluoro or chloro; R⁷ is iodo or bromo; R¹⁰ is chloro; and R³ is hydroxy. Even more specifically, R⁴ is heterocycloalkyl, alkyl, or heteroaryl, where the alkyl is optionally substituted with —NR⁸R⁸' (where R⁸ is hydrogen or alkyl and R⁸' is hydrogen, alkyl, or cycloalkyl where the cycloalkyl is optionally substituted with one or two groups independently selected from hydroxy and alkyl) and the heteroaryl is optionally substituted with alkyl. Yet even more specifically, R⁴ is piperidinyl, pyrrolidinyl, benzimidazolyl, 1(R,S)-amino-ethyl, 1(R)-amino-ethyl, 1(S)-amino-ethyl, 1(R,S)-(methylamino)-ethyl, 1(R)-(methylamino)-ethyl, 1(S)-(methylamino)-ethyl, 1(R,S)-(3,4-cis-dihydroxy-cyclopentylamino)-ethyl, 1(R)-(3,4-cis-dihydroxy-cyclopentylamino)-ethyl, or 1(S)-(3,4-cis-dihydroxy-cyclopentylamino)-ethyl.

In another embodiment of the Invention (B15), the compound is of Formula I(r):

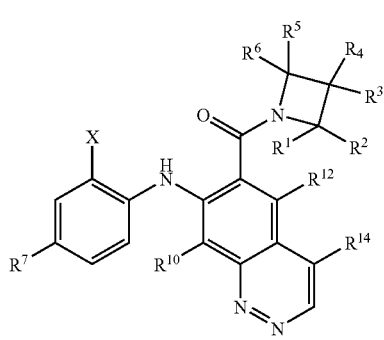

I(r)

where X, $R^1$, $R^2$, $R^3$, $R^4$, $R^5$, $R^6$, $R^7$, $R^{10}$, $R^{12}$ and $R^{14}$ are as defined in the Summary of the Invention for a compound of Group B. More specifically, $R^1$, $R^2$, $R^5$, and $R^6$ are hydrogen; X and $R^7$ are halo; $R^3$ and $R^4$ are as defined in the Summary of the Invention for Group B; $R^{10}$ and $R^{12}$ are independently hydrogen, halo, or alkyl; and $R^{14}$ is hydrogen, halo, alkyl, or amino. Even more specifically, X is fluoro or chloro; $R^7$ is iodo or bromo; $R^{10}$ is hydrogen or halo, more specifically hydrogen or fluoro; $R^{12}$ is hydrogen; $R^{14}$ is hydrogen, alkyl, or amino, more specifically hydrogen, methyl, or amino; $R^3$ is hydroxy. Even more specifically, $R^4$ is heterocycloalkyl, alkyl, or heteroaryl, where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with one or two groups independently selected from hydroxy and alkyl) and the heteroaryl is optionally substituted with alkyl. Yet even more specifically, $R^4$ is piperidinyl, pyrrolidinyl, 1(R,S)-amino-ethyl, 1(R)-amino-ethyl, 1(S)-amino-ethyl, 1(R,S)-(methylamino)-ethyl, 1(R)-(methylamino)-ethyl, 1(S)-(methylamino)-ethyl, 1(R,S)-(3,4-cis-dihydroxy-cyclopentylamino)-ethyl, 1(R)-(3,4-cis-dihydroxy-cyclopentylamino)-ethyl, or 1(S)-(3,4-cis-dihydroxy-cyclopentylamino)-ethyl.

In another embodiment of the Invention (B16), the compound is of Formula I(s):

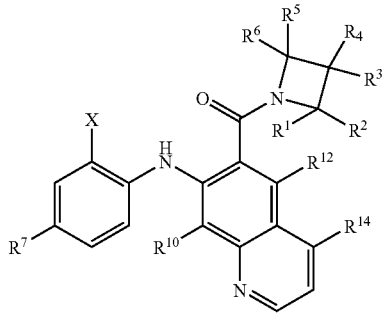

I(s)

where X, $R^1$, $R^2$, $R^3$, $R^4$, $R^5$, $R^6$, $R^7$, $R^{10}$, $R^{12}$ and $R^{14}$ are as defined in the Summary of the Invention for a compound of Group B. More specifically, $R^1$, $R^2$, $R^5$, and $R^6$ are hydrogen; X and $R^7$ are halo; $R^3$ and $R^4$ are as defined in the Summary of the Invention for Group B; and $R^{10}$ and $R^{12}$ are independently hydrogen, halo, or alkyl; and $R^{14}$ is hydrogen, halo, alkyl, or amino. Even more specifically, X is fluoro or chloro and $R^7$ is iodo or bromo; $R^{10}$ is hydrogen or halo, more specifically hydrogen or fluoro; $R^{12}$ is hydrogen; $R^{14}$ is hydrogen, methyl, or amino; $R^3$ is hydroxy; and $R^4$ is heterocycloalkyl, alkyl, or heteroaryl, where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with one or two groups independently selected from hydroxy and alkyl) and the heteroaryl is optionally substituted with alkyl.

In another embodiment of the Invention (B18), the compound is of Formula I(u), I(v), I(w), or I(x):

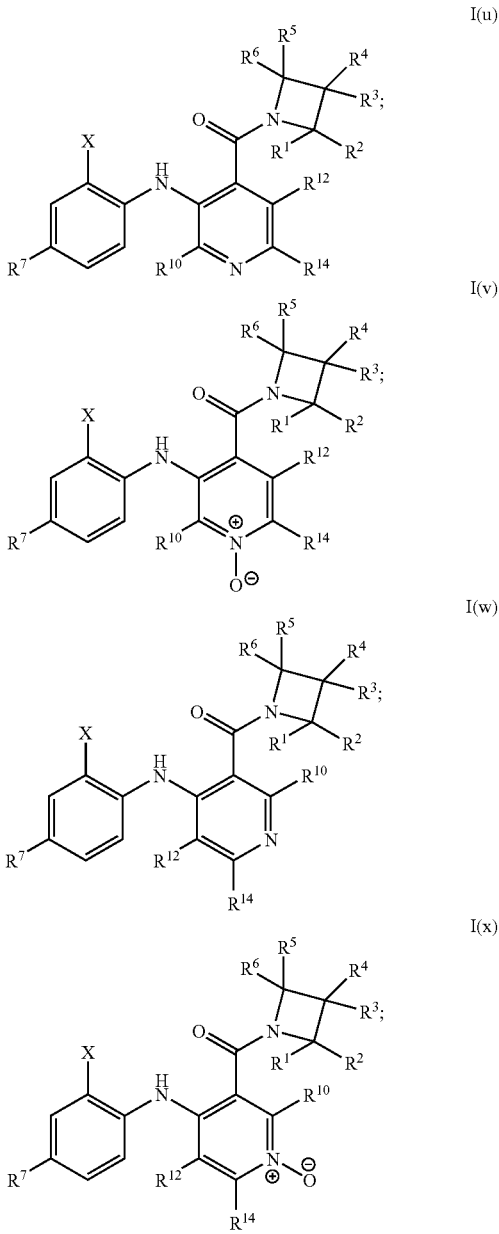

where X, $R^1$, $R^2$, $R^3$, $R^4$, $R^5$, $R^6$, $R^7$, $R^{10}$, $R^{12}$ and $R^{14}$ are as defined in the Summary of the Invention for a compound of Group B.

In a more specific embodiment of embodiment B18, the compound is of formula I(u), I(v), I(w), or I(x) where $R^3$ is halo, nitro, —$NR^8R^{8'}$, —$OR^8$, —$NHS(O)_2R^8$, —CN, —S(O)$_m$R$^8$, —S(O)$_2$NR$^8$R$^{8'}$, —C(O)R$^8$, —C(O)OR$^8$, —C(O)NR$^8$R$^{8'}$, —NR$^8$C(O)OR$^{8'}$, —NR$^8$C(O)NR$^8$R$^{8''}$, —NR$^8$C(O)OR$^{8'}$, —NR$^8$C(O)R$^{8'}$, —CH$_2$N(R$^{25}$)(NR$^{25a}$R$^{25b}$), —CH$_2$NR$^{25}$C(=NH)(NR$^{25a}$R$^{25b}$), —CH$_2$NR$^{25}$C(=NH)(N(R$^{25a}$)(NO$_2$)), —CH$_2$NR$^{25}$C(=NH)(N(R$^{25a}$)(CN)), —CH$_2$NR$^{25}$C(=NH)(R$^{25}$), —CH$_2$NR$^{25}$C(NR$^{25a}$R$^{25b}$)=CH(NO$_2$), alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —OR$^8$, —NR$^8$R$^{8'}$, —NR$^8$S(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^{8'}$R$^{8''}$, —NR$^8$C(O)OR$^{8'}$ and —NR$^8$C(O)R$^{8'}$; and R$^4$ is as defined in the Summary of the Invention for a compound of Group B; or R$^3$ and R$^4$ together with the carbon to which they are attached form C(O) or C(=NOH); and all other groups are as defined in the Summary of the Invention for a compound of Group B.

In a more specific embodiment of embodiment B18, the compound is of formula I(t), I(u), I(v), or I(w) where R$^3$ and R$^4$ are independently halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)NR$^8$R$^{8'}$, —NR$^8$C(O)OR$^{8'}$, —NR$^8$C(O)NR$^8$R$^{8''}$, —NR$^8$C(O)OR$^{8'}$, —NR$^8$C(O)R$^{8'}$, —CH$_2$N(R$^{25}$)(NR$^{25a}$R$^{25b}$), —CH$_2$NR$^{25}$C(=NH)(NR$^{25a}$R$^{25b}$), —CH$_2$NR$^{25}$C(=NH)(N(R$^{25a}$)(NO$_2$)), —CH$_2$NR$^{25}$C(=NH)(N(R$^{25a}$)(CN)), —CH$_2$NR$^{25}$C(=NH)(R$^{25}$), —CH$_2$NR$^{25}$C(NR$^{25a}$R$^{25b}$)=CH(NO$_2$), alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —OR$^8$, —NR$^8$R$^{8'}$, —NR$^8$S(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^{8'}$R$^{8''}$, —NR$^8$C(O)OR$^{8'}$ and —NR$^8$C(O)R$^{8'}$; or R$^3$ and R$^4$ together with the carbon to which they are attached form C(O) or C(=NOH); and all other groups are as defined in the Summary of the Invention for a compound of Group B.

In a more specific embodiment of embodiment B18, the compound is of formula I(u), I(v), I(w), or I(x) where R$^4$ is heterocycloalkyl, heteroaryl (optionally substituted with alkyl), or alkyl where the alkyl is optionally substituted with —NR$^8$R$^{8'}$ (where R$^8$ is hydrogen or alkyl and R$^{8'}$ is hydrogen, alkyl, or cycloalkyl where the cycloalkyl is optionally substituted with one or two groups independently selected from hydroxy and alkyl). More specifically, R$^4$ is piperidinyl, pyrrolidinyl, 1(R,S)-amino-propyl, 1(R)-amino-propyl, 1(S)-amino-propyl, 1(R,S)-(methylamino)-propyl, 1(R)-(methylamino)-propyl, 1(S)-(methylamino)-propyl, 1(R,S)-(3,4-cis-dihydroxy-cyclopentylamino)-propyl, 1(R)-(3,4-cis-dihydroxy-cyclopentylamino)-propyl, or 1(S)-(3,4-cis-dihydroxy-cyclopentylamino)-propyl.

In a more specific embodiment of embodiment B18, the compound is of formula I(u), I(v), I(w), or I(x) where R$^1$, R$^2$, R$^5$, and R$^6$ are hydrogen; X and R$^7$ are halo; R$^3$ and R$^4$ are as defined in the Summary of the Invention for Group B; and R$^{10}$, R$^{12}$, and R$^{14}$ are independently hydrogen, halo, or alkyl. Even more specifically, X is fluoro or chloro; R$^7$ is iodo or bromo; R$^{10}$ is hydrogen or halo, more specifically hydrogen or fluoro; R$^{12}$ and R$^{14}$ are hydrogen; and R$^3$ is hydroxy. Even more specifically R$^4$ is heterocycloalkyl, alkyl, or heteroaryl, where the alkyl is optionally substituted with —NR$^8$R$^{8'}$ (where R$^8$ is hydrogen or alkyl and R$^{8'}$ is hydrogen, alkyl, or cycloalkyl where the cycloalkyl is optionally substituted with one or two groups independently selected from hydroxy and alkyl) and the heteroaryl is optionally substituted with alkyl.

In another embodiment of the Invention (B19), the compound is of Formula I(cc)

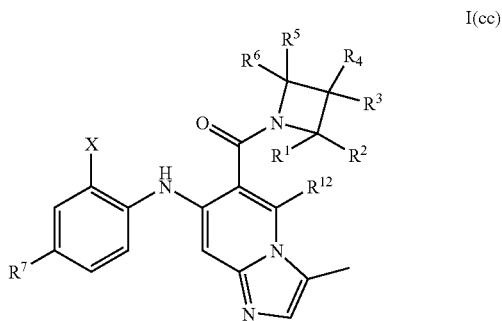

I(cc)

where X, R$^1$, R$^2$, R$^3$, R$^4$, R$^5$, R$^6$, and R$^7$ are as defined in the Summary of the Invention for a compound of Group B. Specifically, R$^1$, R$^2$, R$^5$, and R$^6$ are hydrogen; and X and R$^7$ are halo. More specifically, X is fluoro or chloro; and R$^3$ is hydrogen or hydroxy; R$^7$ is iodo or bromo. Even more specifically, R$^4$ is heterocycloalkyl, alkyl, or heteroaryl, where the alkyl is optionally substituted with —NR$^8$R$^{8'}$ (where R$^8$ is hydrogen or alkyl and R$^{8'}$ is hydrogen, alkyl, or cycloalkyl where the cycloalkyl is optionally substituted with one or two groups independently selected from hydroxy and alkyl) and the heteroaryl is optionally substituted with alkyl. Yet even more specifically, R$^4$ is piperidinyl, pyrrolidinyl, benzimidazolyl, N-methyl-benzimidazolyl, methylaminomethyl, 1(R,S)-amino-ethyl, 1(R)-amino-ethyl, 1(S)-amino-ethyl, 1(R,S)-(methylamino)-ethyl, 1(R)-(methylamino)-ethyl, 1(S)-(methylamino)-ethyl, 1(R,S)-(dimethylamino)-ethyl, 1(R)-(dimethylamino)-ethyl, 1(S)-(dimethylamino)-ethyl, 1(R,S)-amino-propyl, 1(R)-amino-propyl, 1(S)-amino-propyl, 1(R,S)-(methylamino)-propyl, 1(R)-(methylamino)-propyl, 1(S)-(methylamino)-propyl, 1(R,S)-(dimethylamino)-propyl, 1(R)-(dimethylamino)-propyl, 1(S)-(dimethylamino)-propyl, 1(R,S)-(3,4-cis-dihydroxy-cyclopentylamino)-ethyl, 1(R)-(3,4-cis-dihydroxy-cyclopentylamino)-ethyl, or 1(S)-(3,4-cis-dihydroxy-cyclopentylamino)-ethyl.

In a specific embodiment (B19a) of embodiment B19 is that where R$^4$ is heterocycloalkyl or alkyl where the alkyl is optionally substituted with —NR$^8$R$^{8'}$ (where R$^8$ is hydrogen or alkyl and R$^{8'}$ is hydrogen, alkyl, or cycloalkyl where the cycloalkyl is optionally substituted with one or two groups independently selected from hydroxy and alkyl). Specifically, R$^4$ is piperidinyl, pyrrolidinyl, methylaminomethyl, 1(R,S)-amino-ethyl, 1(R)-amino-ethyl, 1(S)-amino-ethyl, 1(R,S)-(methylamino)-ethyl, 1(R)-(methylamino)-ethyl, 1(S)-(methylamino)-ethyl, 1(R,S)-(dimethylamino)-ethyl, 1(R)-(dimethylamino)-ethyl, 1(S)-(dimethylamino)-ethyl, 1(R,S)-amino-propyl, 1(R)-amino-propyl, 1(S)-amino-propyl, 1(R,S)-(methylamino)-propyl, 1(R)-(methylamino)-propyl, 1(S)-(methylamino)-propyl, 1(R,S)-(dimethylamino)-propyl, 1(R)-(dimethylamino)-propyl, 1(S)-(dimethylamino)-propyl, 1(R,S)-(3,4-cis-dihydroxy-cyclopentylamino)-ethyl, 1(R)-(3,4-cis-dihydroxy-cyclopentylamino)-ethyl, or 1(S)-(3,4-cis-dihydroxy-cyclopentylamino)-ethyl.

In another embodiment of the Invention (B20), the compound is of Formula I(dd)

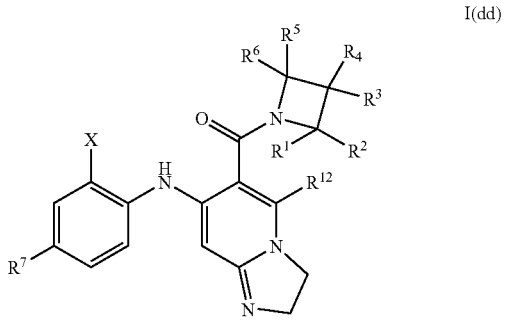

where X, $R^1$, $R^2$, $R^3$, $R^4$, $R^5$, $R^6$, and $R^7$ are as defined in the Summary of the Invention for a compound of Group B. Specifically, $R^1$, $R^2$, $R^5$, and $R^6$ are hydrogen; and X and $R^7$ are halo. More specifically, X is fluoro or chloro; and $R^3$ is hydrogen or hydroxy; $R^7$ is iodo or bromo. Even more specifically, $R^4$ is heterocycloalkyl, alkyl, or heteroaryl, where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with one or two groups independently selected from hydroxy and alkyl) and the heteroaryl is optionally substituted with alkyl. Yet even more specifically, $R^4$ is piperidinyl, pyrrolidinyl, benzimidazolyl, N-methyl-benzimidazolyl, methylaminomethyl, 1(R,S)-amino-ethyl, 1(R)-amino-ethyl, 1(S)-amino-ethyl, 1(R,S)-(methylamino)-ethyl, 1(R)-(methylamino)-ethyl, 1(S)-(methylamino)-ethyl, 1(R,S)-(dimethylamino)-ethyl, 1(R)-(dimethylamino)-ethyl, 1(S)-(dimethylamino)-ethyl, 1(R,S)-amino-propyl, 1(R)-amino-propyl, 1(S)-amino-propyl, 1(R,S)-(methylamino)-propyl, 1(R)-(methylamino)-propyl, 1(S)-(methylamino)-propyl, 1(R,S)-(dimethylamino)-propyl, 1(R)-(dimethylamino)-propyl, 1(S)-(dimethylamino)-propyl, 1(R,S)-(3,4-cis-dihydroxy-cyclopentylamino)-ethyl, 1(R)-(3,4-cis-dihydroxy-cyclopentylamino)-ethyl, or 1(S)-(3,4-cis-dihydroxy-cyclopentylamino)-ethyl.

In a specific embodiment (B20a) of embodiment B20 is that where $R^4$ is heterocycloalkyl or alkyl where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with one or two groups independently selected from hydroxy and alkyl). Specifically, $R^4$ is piperidinyl, pyrrolidinyl, methylaminomethyl, 1(R,S)-amino-ethyl, 1(R)-amino-ethyl, 1(S)-amino-ethyl, 1(R,S)-(methylamino)-ethyl, 1(R)-(methylamino)-ethyl, 1(S)-(methylamino)-ethyl, 1(R,S)-(dimethylamino)-ethyl, 1(R)-(dimethylamino)-ethyl, 1(S)-(dimethylamino)-ethyl, 1(R,S)-amino-propyl, 1(R)-amino-propyl, 1(S)-amino-propyl, 1(R,S)-(methylamino)-propyl, 1(R)-(methylamino)-propyl, 1(S)-(methylamino)-propyl, 1(R,S)-(dimethylamino)-propyl, 1(R)-(dimethylamino)-propyl, 1(S)-(dimethylamino)-propyl, 1(R,S)-(3,4-cis-dihydroxy-cyclopentylamino)-ethyl, 1(R)-(3,4-cis-dihydroxy-cyclopentylamino)-ethyl, or 1(S)-(3,4-cis-dihydroxy-cyclopentylamino)-ethyl.

In one embodiment of the Invention (C1), the compound of Formula I is selected from Group C where all groups are as defined in the Summary of the Invention.

In another embodiment of the invention (C2), X and $R^7$ are halo; and all other groups are as defined for a compound selected from Group C.

In another embodiment of the invention (C3), the compound is selected from Group C where $R^3$ is halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}CH(=NH)(N(R^{25a})(NO_2))$, —$CH_2NR^{25}C(=NH(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^8R^{8''}$, —$NR^8C(O)OR^{8'}$ and —$NR^8C(O)R^{8'}$; and $R^4$ is as defined in the Summary of the Invention; or $R^3$ and $R^4$ together with the carbon to which they are attached form C(O) or C(=NOH); and all other groups are as defined in the Summary of the Invention for a compound of Group C. More specifically, $R^1$, $R^2$, $R^5$ and $R^6$ are hydrogen; and X and $R^7$ are halo.

In another embodiment of the invention (C4), the compound is selected from Group C where $R^3$ and $R^4$ are independently halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —$OR^8$, —$NR^8R^{8'}$, —$NR^8S(O)_2R^9$, —CN, —$S(O)_mR^9$, —$C(O)R^8$, —$(O)OR^8$, —$C(O)NR^8R^{8'}$, —$NR^8C(O)NR^8R^{8''}$, —$NR^8C(O)OR^{8'}$ and —$NR^8C(O)R^{8'}$; or $R^3$ and $R^4$ together with the carbon to which they are attached form C(O) or C(=NOH); and all other groups are as defined in the Summary of the Invention for a compound of Group C. More specifically, $R^1$, $R^2$, $R^5$ and $R^6$ are hydrogen; and X and $R^7$ are halo.

In another embodiment of the invention (C5), A is

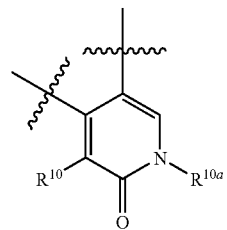

and X, $R^1$, $R^2$, $R^3$, $R^4$, $R^5$, $R^6$, $R^7$, $R^{10}$, and $R^{10a}$ are as defined in the Summary of the invention for a compound of Group C.

More specifically, $R^1$, $R^2$, $R^5$, and $R^6$ are hydrogen; X and $R^7$ are halo; $R^{10}$ is hydrogen or halo; and $R^{10a}$ is alkyl. Even more specifically, X is fluoro or chloro; $R^3$ is hydroxy; $R^7$ is iodo or bromo; $R^{10}$ is hydrogen or fluoro; and $R^{10a}$ is methyl. Even more specifically, $R^4$ is heterocycloalkyl, alkyl, or heteroaryl, where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with one or two groups independently selected from hydroxy and alkyl) and the heteroaryl is optionally substituted with alkyl. Yet even more specifically, $R^4$ is piperidinyl, pyrrolidinyl, benzimidazolyl, N-methyl-benzimidazolyl, methylaminomethyl, 1(R,S)-amino-ethyl, 1(R)-amino-ethyl, 1(S)-amino-ethyl, 1(R,S)-(methylamino)-ethyl, 1(R)-(methylamino)-ethyl, 1(S)-(methylamino)-ethyl, 1(R,S)-(dimethylamino)-ethyl, 1(R)-(dimethylamino)-ethyl, 1(S)-(dimethylamino)-ethyl, 1(R,S)-amino-propyl, 1(R)-amino-propyl, 1(S)-amino-propyl, 1(R,S)-(methylamino)-propyl, 1(R)-(methylamino)-propyl, 1(S)-(methylamino)-propyl, 1(R,S)-(dimethylamino)-propyl, 1(R)-(dimethylamino)-propyl, 1(S)-(dimethylamino)-propyl, 1(R,S)-(3,4-cis-dihydroxy-cyclopentylamino)-ethyl, 1(R)-(3,4-cis-dihydroxy-cyclopentylamino)-ethyl, or 1(S)-(3,4-cis-dihydroxy-cyclopentylamino)-ethyl.

In another embodiment of the invention (C6), A is

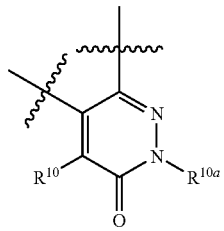

and X, $R^1$, $R^2$, $R^3$, $R^4$, $R^5$, $R^6$, $R^7$, $R^{10}$, and $R^{10a}$ are as defined in the Summary of the invention for a compound of Group C. More specifically, $R^1$, $R^2$, $R^5$, and $R^6$ are hydrogen; X and $R^7$ are halo; $R^{10}$ is hydrogen or halo; and $R^{10a}$ is alkyl. Even more specifically, X is fluoro or chloro; $R^3$ is hydroxy; $R^7$ is iodo or bromo; $R^{10}$ is hydrogen or fluoro; and $R^{10a}$ is methyl. Even more specifically, $R^4$ is heterocycloalkyl, alkyl, or heteroaryl, where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with one or two groups independently selected from hydroxy and alkyl) and the heteroaryl is optionally substituted with alkyl. Yet even more specifically, $R^4$ is piperidinyl, pyrrolidinyl, benzimidazolyl, N-methylbenzimidazolyl, 1(R,S)-amino-ethyl, 1(R)-amino-ethyl, 1(S)-amino-ethyl, 1(R,S)-amino-propyl, 1(R)-amino-propyl, 1(S)-amino-propyl, 1(R,S)-(methylamino)-propyl, 1(R)-(methylamino)-propyl, 1(S)-(methylamino)-propyl, 1(R,S)-(3,4-cis-dihydroxy-cyclopentylamino)-propyl, 1(R)-(3,4-cis-dihydroxy-cyclopentylamino)-propyl, 1(S)-(3,4-cis-dihydroxy-cyclopentylamino)-propyl, 1(R,S)-(3,4-cis-dihydroxy-cyclopentylamino)-ethyl, 1(R)-(3,4-cis-dihydroxy-cyclopentylamino)-ethyl, or 1(S)-(3,4-cis-dihydroxy-cyclopentylamino)-ethyl.

In another embodiment of the Invention (C7), the compound is of Formula I(y) or I(z):

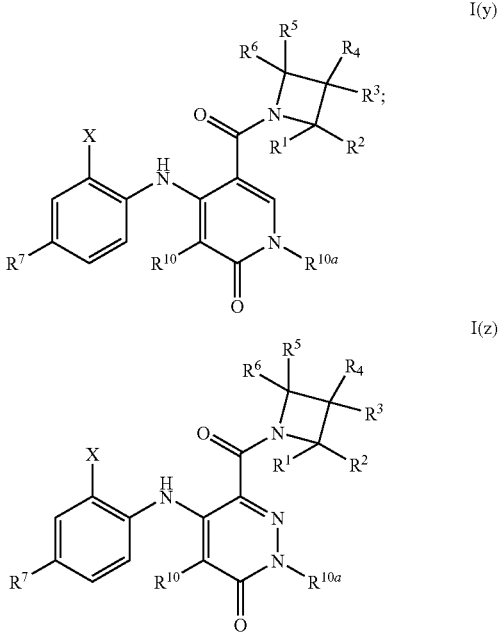

where $R^1$, $R^2$, $R^5$, and $R^6$ are hydrogen; X and $R^7$ are halo; $R^3$, $R^4$, $R^{10}$, $R^{10a}$, and $Y^1$ are as defined in the Summary of the Invention for a compound of Group C. In a more specific embodiment, X is fluoro or chloro; $R^7$ is iodo or bromo; $R^{10}$ is hydrogen, halo, or alkyl, more specifically hydrogen or halo; and $R^{10a}$ is alkyl, more specifically methyl. Even more specifically $R^{10}$ is hydrogen or fluoro; $R^3$ is hydroxy; and $R^4$ is heterocycloalkyl, alkyl, or heteroaryl, where the alkyl is optionally substituted with —$NR^8R^{8'}$ (where $R^8$ is hydrogen or alkyl and $R^{8'}$ is hydrogen, alkyl, or cycloalkyl where the cycloalkyl is optionally substituted with one or two groups independently selected from hydroxy and alkyl) and the heteroaryl is optionally substituted with alkyl.

In one embodiment of the Invention (D), the compound of Formula I is selected from Group D where all groups are as defined in the Summary of the Invention.

In another embodiment of the invention (D1), X and $R^7$ are halo; and all other groups are as defined for a compound selected from Group D.

In another embodiment of the invention (D2), the compound is selected from Group D where $R^3$ is halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —$OR^8$, —$NR^8R^{8'}$, —$NR^8S(O)_2R^9$, —CN, —S(O)$_m$R$^9$, —C(O)R$^8$, —C(O)OR$^8$, —C(O)NR$^8$R$^{8'}$, —NR$^8$C(O)NR$^8$R$^{8''}$, —NR$^8$C(O)OR$^{8'}$ and —NR$^8$C(O)R$^{8'}$; and R$^4$ is as defined in the Summary of the Invention; or R$^3$ and R$^4$ together with the carbon to which they are attached form C(O) or C(=NOH); and all other groups are as defined in the Summary of the Invention for a compound of Group C. More specifically, R$^1$, R$^2$, R$^5$ and R$^6$ are hydrogen; and X and R$^7$ are halo.

In another embodiment of the invention (D3), the compound is selected from Group D where R$^3$ and R$^4$ are independently halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)OR$^8$, —C(O)NR$^8$R$^{8'}$, —NR$^8$C(O)OR$^{8'}$, —NR$^8$C(O)NR$^8$R$^{8''}$, —NR$^8$C(O)OR$^{8'}$, —NR$^8$C(O)R$^{8'}$, —CH$_2$N(R$^{25}$)(NR$^{25a}$R$^{25b}$), —CH$_2$NR$^{25}$C(=NH)(NR$^{25a}$R$^{25b}$), —CH$_2$NR$^{25}$C(=NH)(N(R$^{25a}$)(NO$_2$)), —CH$_2$NR$^{25}$C(=NH)(N(R$^{25a}$)(CN)), —CH$_2$NR$^{25}$C(=NH)(R$^{25}$), —CH$_2$NR$^{25}$C(NR$^{25a}$R$^{25b}$)=CH(NO$_2$), alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —OR$^8$, —NR$^8$R$^{8'}$, —NR$^8$S(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^8$R$^{8''}$, —NR$^8$C(O)OR$^{8'}$ and —NR$^8$C(O)R$^{8'}$; or R$^3$ and R$^4$ together with the carbon to which they are attached form C(O) or C(=NOH); and all other groups are as defined in the Summary of the Invention for a compound of Group C. More specifically, R$^1$, R$^2$, R$^5$ and R$^6$ are hydrogen; and X and R$^7$ are halo.

In another embodiment of the invention (D4), A is

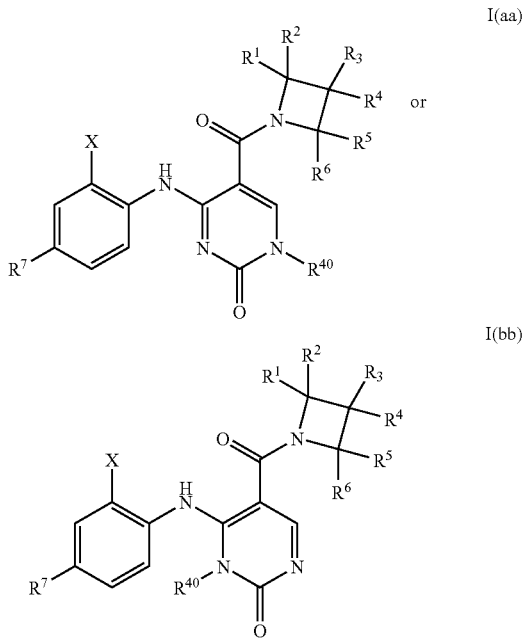

I(aa)

I(bb)

where R$^{40}$ is hydrogen or methyl (specifically, R$^{40}$ is hydrogen) and all other groups are as defined in the Summary of the Invention. Specifically, R$^1$, R$^2$, R$^5$, and R$^6$ are hydrogen; X and R$^7$ are halo; and R$^{40}$ is hydrogen or methyl. More specifically, X is fluoro or chloro; and R$^3$ is hydrogen or hydroxy; R$^7$ is iodo or bromo. Even more specifically, R$^4$ is heterocycloalkyl, alkyl, or heteroaryl, where the alkyl is optionally substituted with —NR$^8$R$^{8'}$ (where R$^8$ is hydrogen or alkyl and R$^{8'}$ is hydrogen, alkyl, or cycloalkyl where the cycloalkyl is optionally substituted with one or two groups independently selected from hydroxy and alkyl) and the heteroaryl is optionally substituted with alkyl. Yet even more specifically, R$^4$ is piperidinyl, pyrrolidinyl, benzimidazolyl, N-methyl-benzimidazolyl, methylaminomethyl, 1(R, 5)-amino-ethyl, 1(R)-amino-ethyl, 1(S)-amino-ethyl, 1(R,S)-(methylamino)-ethyl, 1(R)-(methylamino)-ethyl, 1(S)-(methylamino)-ethyl, 1(R, S)-(dimethylamino)-ethyl, 1(R)-(dimethylamino)-ethyl, 1(S)-(dimethylamino)-ethyl, 1(R,S)-amino-propyl, 1(R)-amino-propyl, 1(S)-amino-propyl, 1(R,S)-(methylamino)-propyl, 1(R)-(methylamino)-propyl, 1(S)-(methylamino)-propyl, 1(R,S)-(dimethylamino)-propyl, 1(R)-(dimethylamino)-propyl, 1(S)-(dimethylamino)-propyl, 1(R, S)-(3,4-cis-dihydroxy-cyclopentylamino)-ethyl 1(R)-(3,4-cis-dihydroxy-cyclopentylamino)-ethyl, or 1(S)-(3,4-cis-dihydroxy-cyclopentylamino)-ethyl.

In a specific embodiment (D4a) of the invention of D4 is that where R$^4$ is heterocycloalkyl or alkyl where the alkyl is optionally substituted with —NR$^8$R$^{8'}$ (where R$^8$ is hydrogen or alkyl and R$^{8'}$ is hydrogen, alkyl, or cycloalkyl where the cycloalkyl is optionally substituted with one or two groups independently selected from hydroxy and alkyl). Specifically, R$^4$ is piperidinyl, pyrrolidinyl, methylaminomethyl, 1(R,S)-amino-ethyl, 1(R)-amino-ethyl, 1(S)-amino-ethyl, 1(R,S)-(methylamino)-ethyl, 1(R)-(methylamino)-ethyl, 1(S)-(methylamino)-ethyl, 1(R,S)-(dimethylamino)-ethyl, 1(R)-(dimethylamino)-ethyl, 1(S)-(dimethylamino)-ethyl, 1(R,S)-amino-propyl, 1(R)-amino-propyl, 1(S)-amino-propyl, 1(R, S)-(methylamino)-propyl, 1(R)-(methylamino)-propyl, 1(S)-(methylamino)-propyl, 1(R,S)-(dimethylamino)-propyl, 1(R)-(dimethylamino)-propyl, 1(S)-(dimethylamino)-propyl, 1(R,S)-(3,4-cis-dihydroxy-cyclopentylamino)-ethyl, 1(R)-(3,4-cis-dihydroxy-cyclopentylamino)-ethyl, or 1(S)-(3,4-cis-dihydroxy-cyclopentylamino)-ethyl.

Another embodiment of the Invention (E) is directed to a Compound selected from Group A, Group B, and Group C where
Group A
A is phenylene optionally substituted with one or two groups selected from R$^{10}$, R$^{12}$, R$^{14}$, and R$^{16}$ where R$^{10}$, R$^{12}$, R$^{14}$ and R$^{16}$ are independently hydrogen or halo;
X is halo;
R$^1$, R$^2$, R$^5$ and R$^6$ are hydrogen;
R$^3$ is hydrogen, halo, hydroxy, alkoxy, or amino;
R$^4$ is hydrogen, —NR$^8$R$^{8'}$, —C(O)NR$^8$R$^{8'}$, —NR$^8$C(O)OR$^{8'}$, —NR$^8$C(O)R$^{8'}$, —CH$_2$N(R$^{25}$)(NR$^{25a}$R$^{25b}$), —CH$_2$NR$^{25}$C(=NH)(NR$^{25a}$R$^{25b}$), —CH$_2$NR$^{25}$C(=NH)(N(R$^{25a}$)(NO$_2$)), —CH$_2$NR$^{25}$C(=NH)(N(R$^{25a}$)(CN)), —CH$_2$NR$^{25}$C(=NH)(R$^{25}$), —CH$_2$NR$^{25}$C(NR$^{25a}$R$^{25b}$)=CH(NO$_2$), alkyl, alkenyl, cycloalkyl, heterocycloalkyl, or heteroaryl; where the R$^4$ alkyl is optionally substituted with one, two, or three groups independently selected from —OR$^8$, halo, nitro, —S(O)$_m$R$^9$, optionally substituted heterocycloalkyl, —NR$^8$R$^{8'}$, —NR$^8$C(O)R$^{8'}$, —NR$^8$S(O)$_2$R$^9$, —NR$^8$C(O)OR$^{8'}$, and aryl; where the R$^4$ cycloalkyl is optionally substituted with one or two groups selected from —OR$^8$ and —NR$^8$R$^{8'}$; where the R$^4$ heterocycloalkyl is optionally substituted with one or two groups independently selected from alkyl and —C(O)OR$^8$; and where the R$^4$ heteroaryl is optionally substituted with —NR$^8$R$^{8'}$; or R³ and R⁴ together with the carbon to which they are attached form C(O) or C(=NOH);
m is 0;
R⁷ is halo;
R⁸ and R⁸' are independently selected from hydrogen, hydroxy, alkyl, alkenyl, alkynyl, aryl, heterocycloalkyl, heteroaryl, and cycloalkyl;
where the R⁸ and R⁸' alkyl are independently optionally substituted with one, two, or three groups indendently selected from hydroxy, —NR³⁰R³⁰' (where R³⁰ and R³⁰' are independently hydrogen, alkyl, or hydroxyalkyl), optionally substituted heteroaryl, optionally substituted cycloalkyl), optionally substituted alkoxy, optionally substituted cycloalkyl, optionally substituted aryl, optionally substituted heterocycloalkyl, optionally substituted heteroaryl, —C(O)NR³³R³³ᵃ (where R³³ is hydrogen or alkyl and R³³ᵃ is alkyl, alkenyl, alkynyl, or cycloalkyl), optionally substituted aryloxy, —S(O)ₙR³¹ (where n is 0 and R³¹ is alkyl), carboxy, alkoxycarbonyl, and —NR³²C(C)R³²ᵃ (where R³² is hydrogen or alkyl and R³²ᵃ is alkyl, alkenyl, alkoxy, or cycloalkyl); or where the alkyl is optionally substituted with one, two, three, four, or five halo;
where the R⁸ and R⁸' heteroaryl are independently optionally substituted with one or two groups indendently selected from amino and alkyl;
where the R⁸ and R⁸' heterocycloalkyl are independently optionally substituted with one, two, or three groups indendently selected from alkyl, alkoxycarbonyl, optionally substituted arylalkyl, hydroxy, alkoxy, and hydroxyalkyl;
where the R⁸ and R⁸' aryl are independently optionally substituted with one or two groups indendently selected from hydroxy, alkoxy, halo, —NR³²C(O)R³²ᵃ (where R³² is hydrogen or alkyl and R³²ᵃ is alkyl, alkenyl, alkoxy, or cycloalkyl), and —NR³⁴SO₂R³⁴ᵃ (where R³⁴ is hydrogen or alkyl and R³⁴ᵃ is alkyl, alkenyl, cycloalkyl, aryl, heteroaryl, or heterocycloalkyl); and
where the R⁸ and R⁸' cycloalkyl are independently optionally substituted with one, two, or three groups indendently selected from hydroxy, hydroxyalkyl, alkoxy, carboxy, —C(O)NR³³R³³ᵃ (where R³³ is hydrogen or alkyl and R³³ᵃ is alkyl, alkenyl, alkynyl, or cycloalkyl), and optionally substituted cycloalkyl; and
R⁹ is alkyl or aryl;

Group B
A is thien-3,4-diyl, benzo[d]isoxazol-5,6-diyl, 1H-indazol-5,6-diyl (optionally substituted at the N1 position with R¹⁹ where R¹⁹ is alkyl or alkenyl), benzo[d]oxazol-5,6-diyl, benzo[d]thiazol-5,6-diyl, 1H-benzo[d]imidazol-5,6-diyl (optionally substituted at the N1 position with R¹⁹ where R¹⁹ is alkyl or alkenyl), 1H-benzo[d][1,2,3]triazol-5,6-diyl (optionally substituted at the N1 position with R¹⁹ where R¹⁹ is alkyl or alkenyl), imidazo[1,2-a]pyridin-6,7-diyl, cinnolin-6,7-diyl, quinolin-6,7-diyl, pyridin-3,4-diyl, or 1-oxido-pyridin-3,4-diyl; where A is optionally substituted with one, two, or three groups independently selected from R¹⁰, R¹², R¹⁴, R¹⁶ and R¹⁹ where R¹⁰, R¹², R¹⁴ and R¹⁶ are independently hydrogen, alkyl, halo, or amino; and R¹⁹ is hydrogen or alkyl;
X is halo;
R¹, R², R⁵ and R⁶ are hydrogen;
R³ is hydrogen or hydroxy;
R⁴ is —NR⁸R⁸', heterocycloalkyl, heteroaryl, or alkyl; where the alkyl is optionally substituted with —NR⁸R⁸' and where the heteroaryl is optionaly substituted with alkyl;
R⁷ is halo;
R⁸ is hydrogen or alkyl; and
R⁸' is hydrogen, alkyl, or cycloalkyl; where the cycloalkyl is optionally substituted with one or two groups independently selected from hydroxy and alkyl;

Group C
A is (a)

where R¹⁰ is hydrogen or halo;
R¹⁰ᵃ is hydrogen or alkyl;
Y¹ is =CH— or
X is halo;
R¹, R², R⁵ and R⁶ are hydrogen;
R³ is hydrogen or hydroxy;
R⁴ is —NR⁸R⁸', heterocycloalkyl, heteroaryl, or alkyl; where the alkyl is optionally substituted with —NR⁸R⁸' and where the heteroaryl is optionaly substituted with alkyl;
R⁷ is halo;
R⁸ is hydrogen or alkyl; and
R⁸' is hydrogen, alkyl, or cycloalkyl; where the cycloalkyl is optionally substituted with one or two groups independently selected from hydroxy and alkyl.

One embodiment of the invention provides a pharmaceutical composition which comprises a compound of Formula I selected from Group A, or a pharmaceutically acceptable salt or solvate therof and a pharmaceutically acceptable carrier, excipient, or diluent.

Another embodiment of the invention provides a pharmaceutical composition which comprises a compound of Formula I selected from Group B, or a pharmaceutically acceptable salt or solvate therof and a pharmaceutically acceptable carrier, excipient, or diluent. Specifically, the compound is of Formula I(c), I(d), I(e), I(f), I(g), I(h), I(i), I(j), I(k), I(m), I(n), I(o), I(p), I(q), I(r), I(s), I(t), I(u), I(v), I(w), I(x), I(cc), or I(dd).

Another embodiment of the invention provides a pharmaceutical composition which comprises a compound of Formula I selected from Group C, or a pharmaceutically acceptable salt or solvate therof and a pharmaceutically acceptable carrier, excipient, or diluent.

Another embodiment of the invention provides a pharmaceutical composition which comprises a compound of Formula I selected from Group D, or a pharmaceutically acceptable salt or solvate therof and a pharmaceutically acceptable carrier, excipient, or diluent.

In another embodiment, the invention comprises a method of inhibiting MEK in a cell, comprising contacting a cell with a compound of Formula I selected from Group A or a pharmaceutically acceptable salt or solvate therof, or with a pharmaceutical composition comprising a therapeutically effective amount of a compound of Formula I selected from Group A and a pharmaceutically acceptable carrier, excipient, or diluent.

In another embodiment, the invention comprises a method of inhibiting MEK in a cell, comprising contacting a cell with a compound of Formula I selected from Group B or a pharmaceutically acceptable salt or solvate therof, or with a pharmaceutical composition comprising a therapeutically effective amount of a compound of Formula I selected from Group B and a pharmaceutically acceptable carrier, excipient, or diluent.

In another embodiment, the invention comprises a method of inhibiting MEK in a cell, comprising contacting a cell with a compound of Formula I selected from Group C or a pharmaceutically acceptable salt or solvate therof, or with a pharmaceutical composition comprising a therapeutically effective amount of a compound of Formula I selected from Group C and a pharmaceutically acceptable carrier, excipient, or diluent.

In another embodiment, the invention comprises a method of inhibiting MEK in a cell, comprising contacting a cell with a compound of Formula I selected from Group D or a pharmaceutically acceptable salt or solvate therof, or with a pharmaceutical composition comprising a therapeutically effective amount of a compound of Formula I selected from Group D and a pharmaceutically acceptable carrier, excipient, or diluent.

Another embodiment of the Invention provides a method for treating a proliferative disease which method comprises administering to a patient a compound of Formula I or a pharmaceutically acceptable salt or solvate therof, or administering a pharmaceutical composition comprising a therapeutically effective amount of a compound of Formula I and a pharmaceutically acceptable carrier, excipient, or diluent. In a specific embodiment, the disease is cancer. More specifically, the cancer is selected from malignant melanoma, colorectal cancer, pancreatic cancer, breast cancer, non-small cell lung cancer, small cell lung cancer, papillary and anaplastic thyroid cancer, and endometriod ovarian cancers.

One of ordinary skill in the art would understand that certain crystallized, protein-ligand complexes and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

Representative Compounds

Representative compounds of Formula I are depicted below. The examples are merely illustrative and do not limit the scope of the invention in any way. Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Names were generated using ACD/Labs naming software 8.00 release, product version 8.08.

TABLE 1

| Cmpd No. | Structure | Name |
| --- | --- | --- |
| 1 | 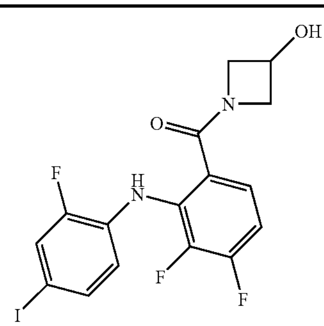 | 1-({3,4-difluoro-2-[(2-fluoro-4-iodophenyl)amino]phenyl}-carbonyl)azetidin-3-ol |

TABLE 1-continued

| Cmpd No. | Structure | Name |
|---|---|---|
| 2 | 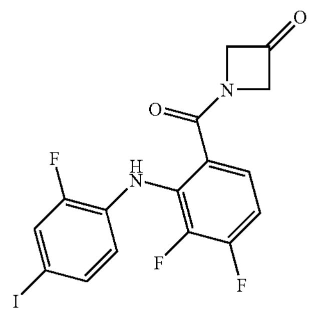 | 1-({3,4-difluoro-2-((2-fluoro-4-iodophenyl)amino]phenyl}carbonyl)azetidin-3-one |
| 3 | 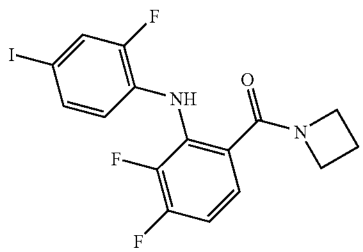 | 6-(azetidin-1-ylcarbonyl)-2,3-difluoro-N-(2-fluoro-4-iodophenyl)aniline |
| 4 | 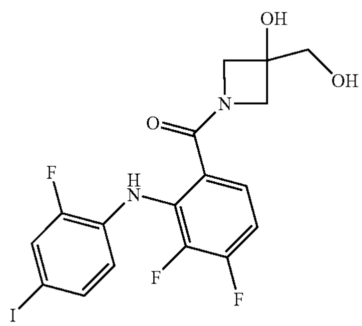 | 1-({3,4-difluoro-2-[(2-fluoro-4-iodophenyl)amino]phenyl}carbonyl)-3-(hydroxymethyl)azetidin-3-ol |
| 5 | 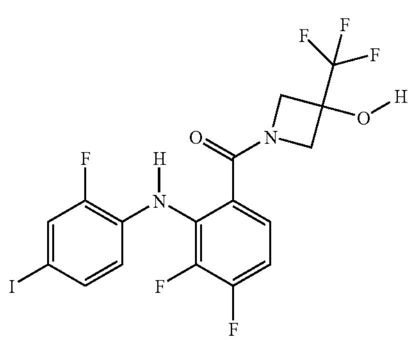 | 1-({3,4-difluoro-2-[(2-fluoro-4-iodophenyl)amino]phenyl}carbonyl)-3-(trifluoromethyl)azetidin-3-ol |
| 6 | 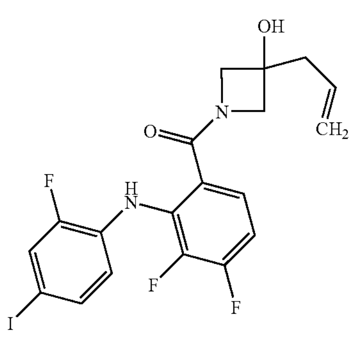 | 1-({3,4-difluoro-2-[(2-fluoro-4-iodoplienyl)amino]phenyl}carbonyl)-3-prop-2-en-1-ylazetidin-3-ol |

TABLE 1-continued

| Cmpd No. | Structure | Name |
|---|---|---|
| 7 | 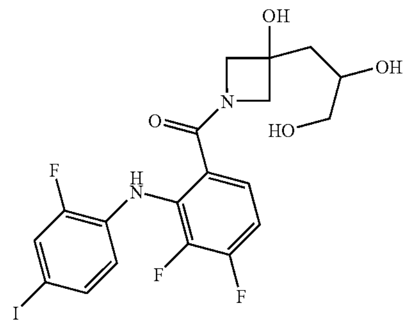 | 3-[1-({3,4-difluoro-2-[(2-fluoro-4-iodophenyl)amino]phenyl}carbonyl)-3-hydroxyazetidin-3-yl]propane-1,2-diol |
| 8 | 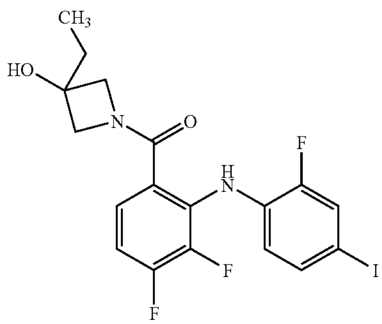 | 1-({3,4-difluoro-2-[(2-fluoro-4-iodophenyl)amino]phenyl}carbonyl)-3-ethylazetidin-3-ol |
| 9 | 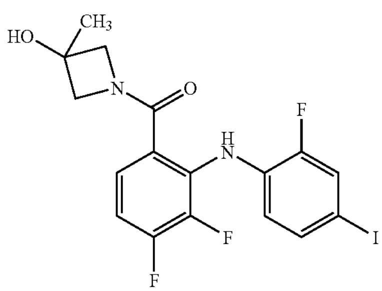 | 1-({3,4-difluoro-2-[(2-fluoro-4-iodophenyl)amino]phenyl}carbonyl)-3-methylazetidin-3-ol |
| 10 | 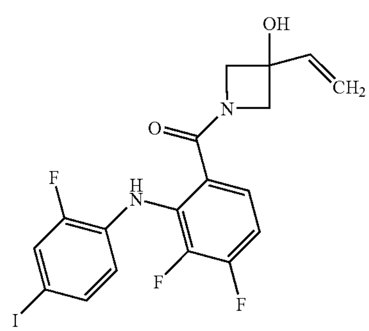 | 1-({3,4-difluoro-2-[(2-fluoro-4-iodophenyl)amino]phenyl}carbonyl)-3-ethenylazetidin-3-ol |
| 11 | 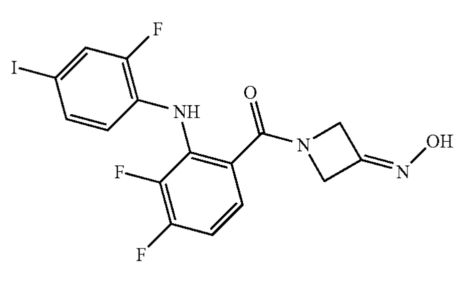 | 1-({3,4-difluoro-2-[(2-fluoro-4-iodophenyl)amino]phenyl}carbonyl)azetidin-3-one oxime |

TABLE 1-continued

| Cmpd No. | Structure | Name |
|---|---|---|
| 12 | 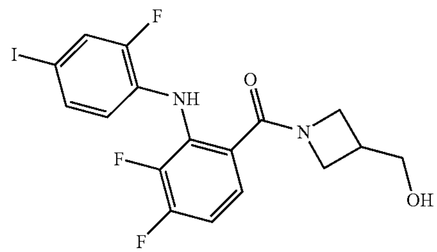 | [1-({3,4-difluoro-2-{(2-fluoro-4-iodophenyl)amino]phenyl}carbonyl)azetidin-3-yl]methanol |
| 13 | 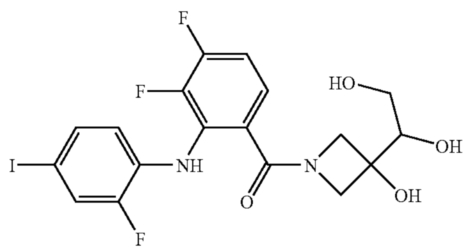 | 1-[1-({3,4-difluoro-2-[(2-fluoro-4-iodophenyl)amino]phenyl}carbonyl)-3-hydroxyazetidin-3-yl]ethane-1,2-diol |
| 14 | 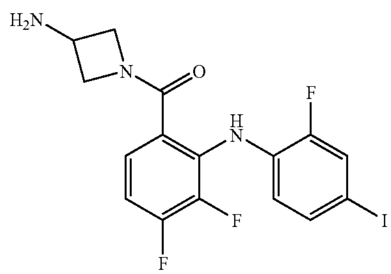 | 1-({3,4-difluoro-2-[(2-fluoro-4-iodophenyl)amino]phenyl}carbonyl)azetidin-3-amine |
| 15 | 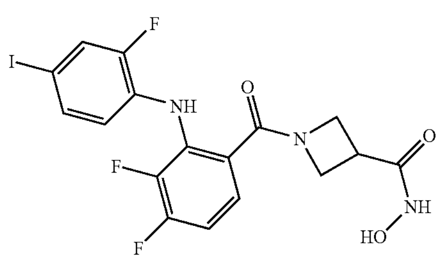 | 1-({3,4-difluoro-2-[(2-fluoro-4-iodophenyl)amino]phenyl}carbonyl)-N-hydroxyazetidine-3-carboxamide |
| 16 | 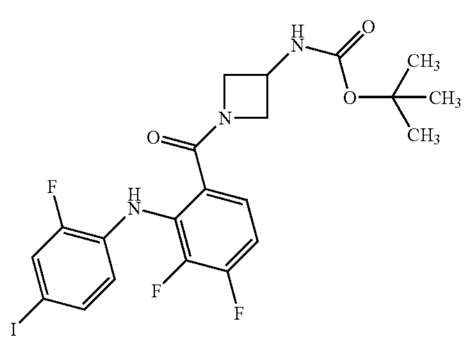 | 1,1-dimethylethyl [1-({3,4-difluoro-2-[(2-fluoro-4-iodophenyl)amino]phenyl}carbonyl)azetidin-3-yl]carbamate |

TABLE 1-continued

| Cmpd No. | Structure | Name |
|---|---|---|
| 17 | 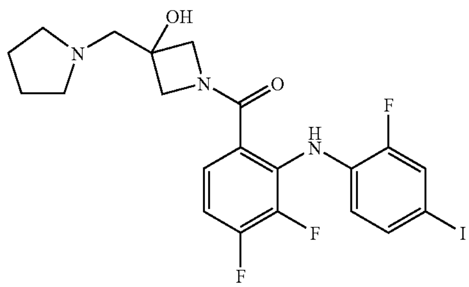 | 1-({3,4-difluoro-2-[(2-fluoro-4-iodophenyl)amino]phenyl}carbonyl)-3-(pyrrolidin-1-ylmethyl)azetidin-3-ol |
| 18 | 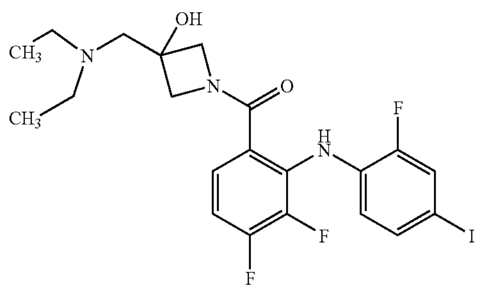 | 3-[(diethylamino)methyl]-1-({3,4-difluoro-2-[(2-fluoro-4-iodophenyl)amino]phenyl}carbonyl)azetidin-3-ol |
| 19 | 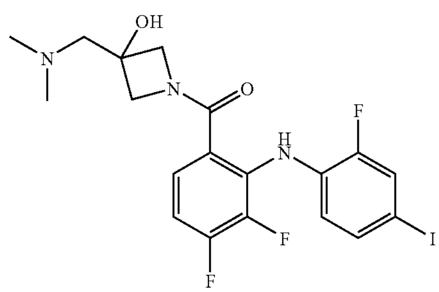 | 1-({3,4-difluoro-2-[(2-fluoro-4-iodophenyl)amino]phenyl}carbonyl)-3-[(dimethylamino)methyl]azetidin-3-ol |
| 20 | 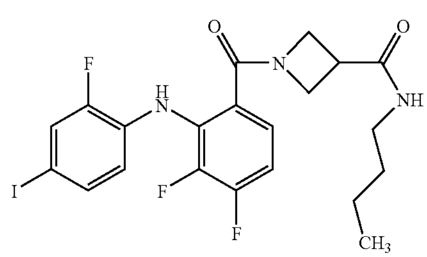 | N-butyl-1-({3,4-difluoro-2-[(2-fluoro-4-iodophenyl)amino]phenyl}carbonyl)azetidine-3-carboxamide |
| 21 | 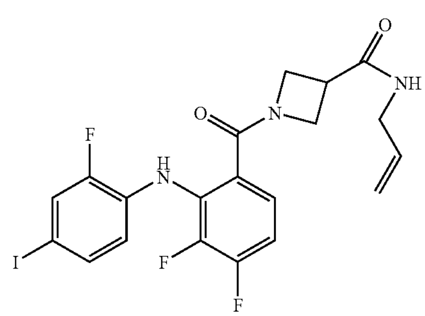 | 1-({3,4-difluoro-2-[(2-fluoro-4-iodophenyl)amino]phenyl}carbonyl)-N-prop-2-en-1-ylazetidine-3-carboxamide |

TABLE 1-continued

| Cmpd No. | Structure | Name |
|---|---|---|
| 22 | 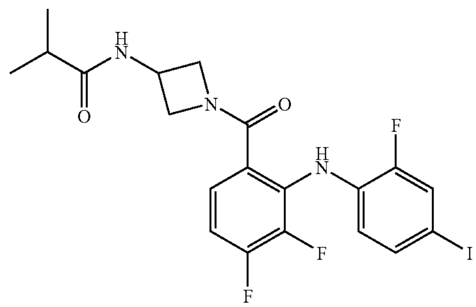 | N-[1-({3,4-difluoro-2-[(2-fluoro-4-iodophenyl)amino]phenyl}carbonyl)-azetidin-3-yl]-2-methylpropanamide |
| 23 | 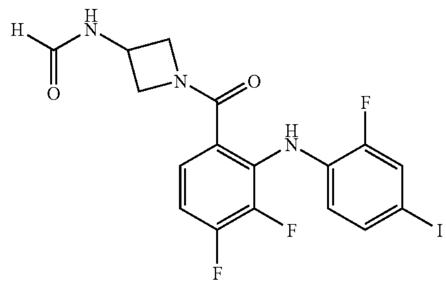 | N-[1-({3,4-difluoro-2-[(2-fluoro-4-iodophenyl)amino]phenyl}carbonyl)azetidin-3-yl]formamide |
| 24 | 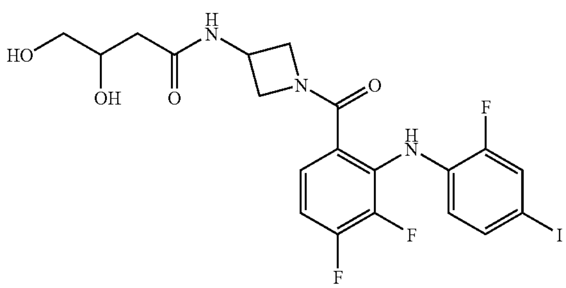 | N-[1-({3,4-difluoro-2-[(2-fluoro-4-iodophenyl)amino]phenyl}carbonyl)azetidin-3-yl]-3,4-dihydroxybutanamide |
| 25 | 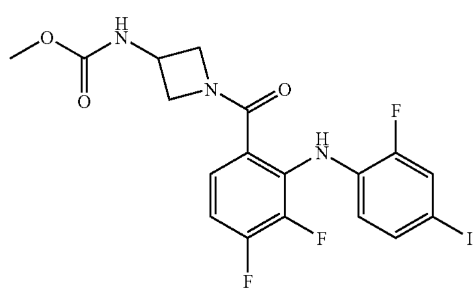 | methyl [1-({3,4-difluoro-2-[(2-fluoro-4-iodophenyl)amino]phenyl}carbonyl)azetidin-3-yl]carbamate |
| 26 | 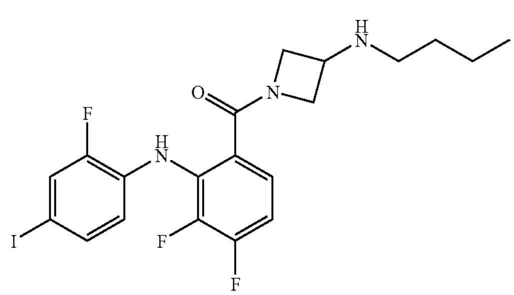 | N-butyl-1-({3,4-difluoro-2-[(2-fluoro-4-iodophenyl)amino]phenyl}carbonyl)azetidin-3-amine |

TABLE 1-continued

| Cmpd No. | Structure | Name |
|---|---|---|
| 27 | 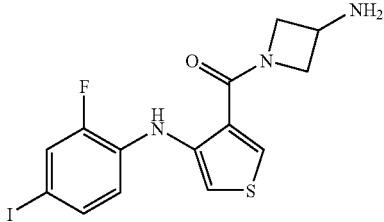 | 1-({4-[(2-fluoro-4-iodophenyl)amino]3-thienyl}carbonyl)azetidin-3-amine |
| 28 | 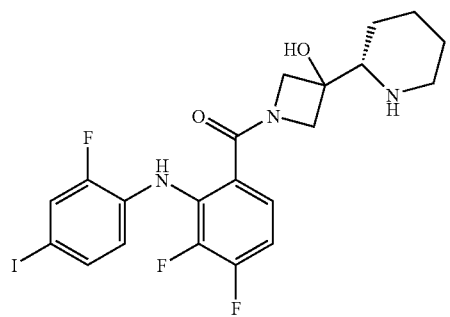 | 1-({3,4-difluoro-2-[(2-fluoro-4-iodophenyl)amino]phenyl}carbonyl)-3-[(2S)-piperidin-2-yl]azetidin-3-ol |
| 29 | 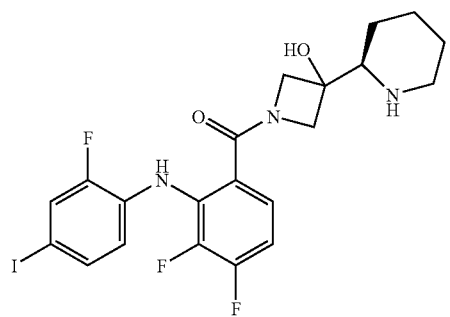 | 1-({3,4-difluoro-2-[(2-fluoro-4-iodophenyl)amino]phenyl}carbonyl)-3-[(2R)-piperidin-2-yl]azetidin-3-ol |
| 30 | 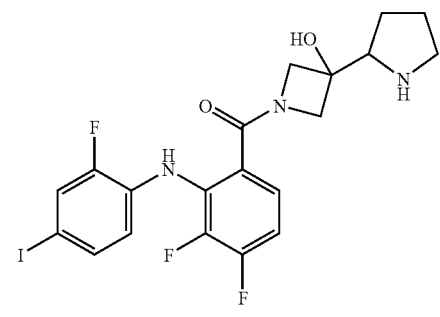 | 1-({3,4-difluoro-2-[(2-fluoro-4-iodophenyl)amino]phenyl}carbonyl)-3-pyrrolidin-2-ylazetidin-3-ol |
| 31 | 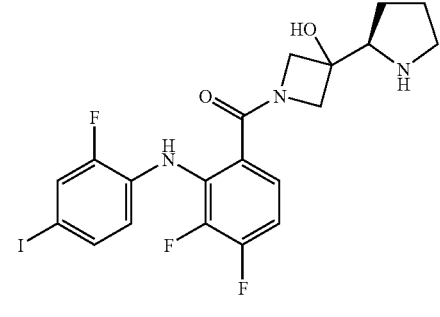 | (R)-1-({3,4-difluoro-2-[(2-fluoro-4-iodophenyl)amino]phenyl}carbonyl)-3-pyrrolidin-2-ylazetidin-3-ol |

TABLE 1-continued

| Cmpd No. | Structure | Name |
|---|---|---|
| 32 | 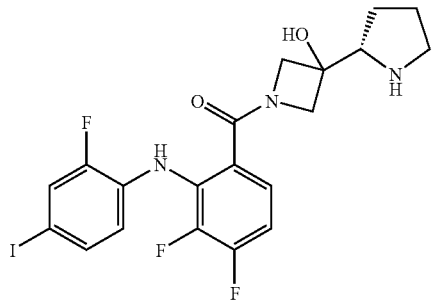 | (S)-1-({3,4-difluoro-2-[(2-fluoro-4-iodophenyl)amino]phenyl}carbonyl)-3-pyrrolidin-2-ylazetidin-3-ol |
| 33 | 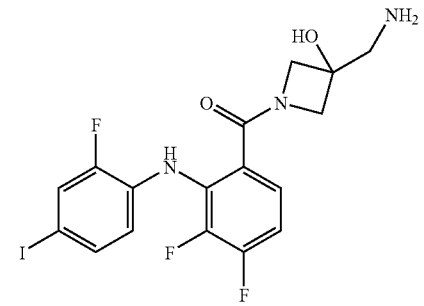 | 3-(aminomethyl)-1-({3,4-difluoro-2-[(2-fluoro-4-iodophenyl)amino]phenyl}carbonyl)azetidin-3-ol |
| 34 | 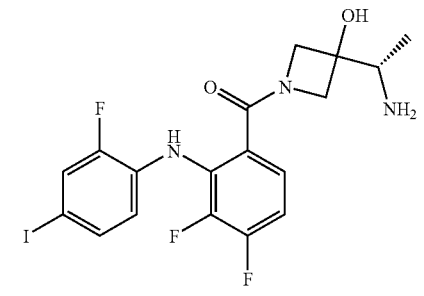 | 3-[(1S)-1-aminoethyl]-1-({3,4-difluoro-2-[(2-fluoro-4-iodophenyl)amino]phenyl}carbonyl)azetidin-3-ol |
| 35 | 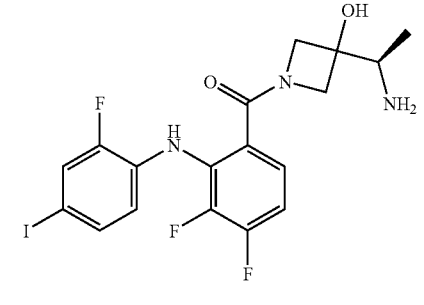 | 3-[(1R)-1-aminoethyl]-1-({3,4-difluoro-2-[(2-fluoro-4-iodophenyl)amino]phenyl}carbonyl)azetidin-3-ol |
| 36 | 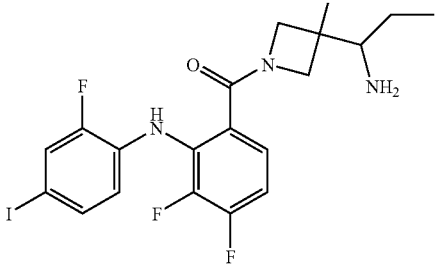 | (3-(1-aminopropyl)-3-hydroxyazetidin-1-yl)(3,4-difluoro-2-(2-fluoro-4-iodophenylamino)phenyl)methanone |

TABLE 1-continued

| Cmpd No. | Structure | Name |
|---|---|---|
| 37 | 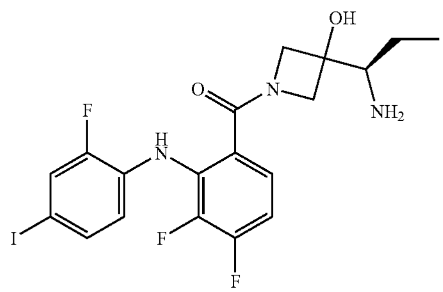 | (R)-(3-(1-aminopropyl)-3-hydroxyazetidin-1-yl)(3,4-difluoro-2-(2-fluoro-4-iodophenylamino)phenyl)methanone |
| 38 | 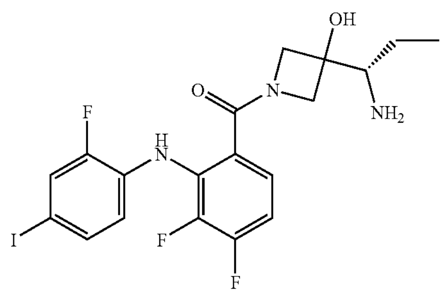 | (S)-(3-(1-aminopropyl)-3-hydroxyazetidin-1-yl)(3,4-difluoro-2-(2-fluoro-4-iodophenylamino)phenyl)methanone |
| 39 | 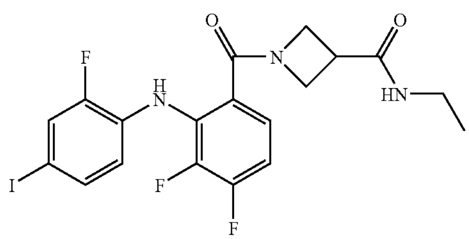 | 1-({3,4-difluoro-2-[(2-fluoro-4-iodophenyl)amino]phenyl}carbonyl)-N-ethylazetidine-3-carboxamide |
| 40 | 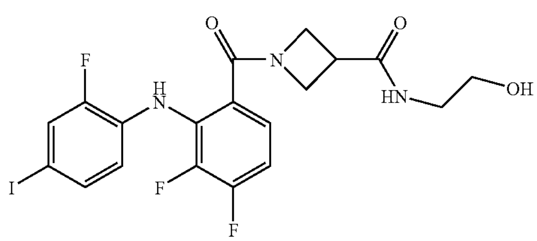 | 1-({3,4-difluoro-2-[(2-fluoro-4-iodophenyl)amino]phenyl}carbonyl)-N-(2-hydroxyethyl)azetidine-3-carboxamide |
| 41 | 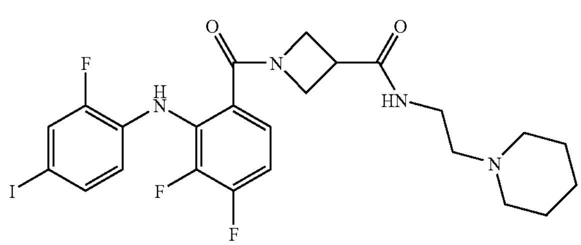 | 1-({3,4-difluoro-2-[(2-fluoro-4-iodophenyl)amino]phenyl}carbonyl)-N-(2-piperidin-1-ylethyl)azetidine-3-carboxamide |

TABLE 1-continued

| Cmpd No. | Structure | Name |
|---|---|---|
| 42 | 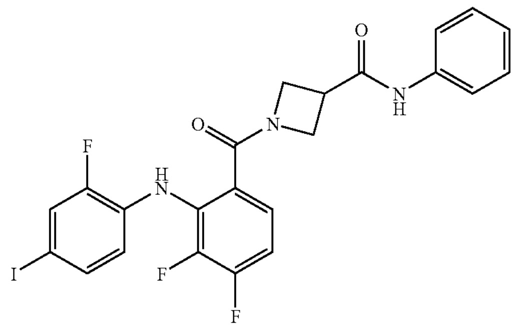 | 1-({3,4-difluoro-2-{(2-fluoro-4-iodophenyl)amino]phenyl}carbonyl)-N-phenylazetidine-3-carboxamide |
| 43 | 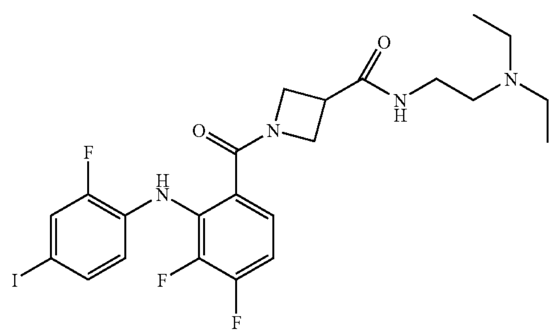 | N-[2-(diethylamino)ethyl]-1-({3,4-difluoro-2-[(2-fluoro-4-iodophenyl)amino]phenyl}carbonyl)azetidine-3-carboxamide |
| 44 | 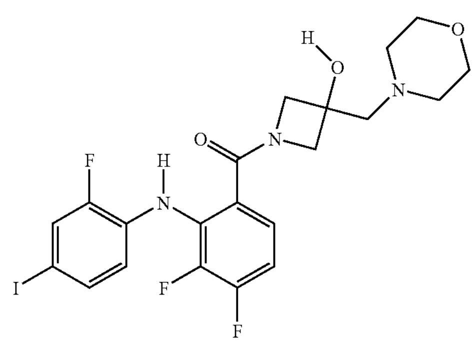 | 1-({3,4-difluoro-2-[(2-fluoro-4-iodophenyl)amino]phenyl}carbonyl)-3-(morpholin-4-ylmethyl)azetidin-3-ol |
| 45 | 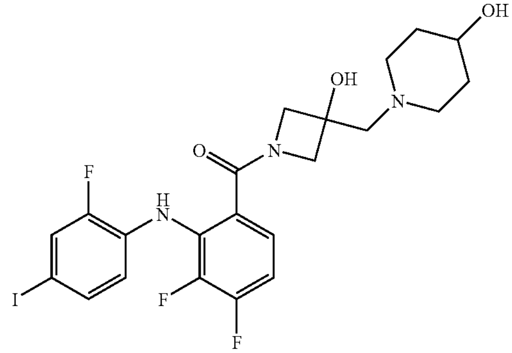 | 1-{[1-({3,4-difluoro-2-[(2-fluoro-4-iodophenyl)amino]phenyl}carbonyl)-3-hydroxyazetidin-3-yl]methyl}piperidin-4-ol |

TABLE 1-continued

| Cmpd No. | Structure | Name |
|---|---|---|
| 46 | 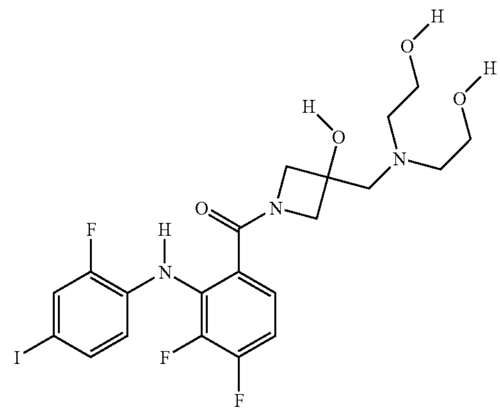 | 3-{[bis(2-hydroxyethyl)amino]methyl}-1-({3,4-difluoro-2-[(2-fluoro-4-iodophenyl)amino]phenyl}carbonyl)azetidin-3-ol |
| 47 | 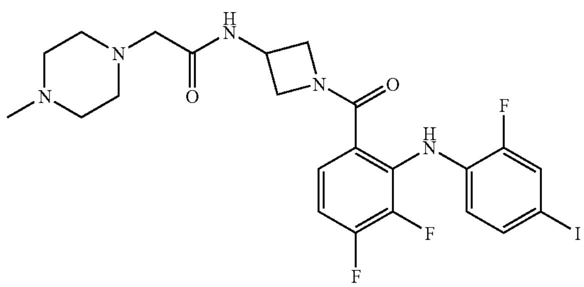 | N-[1-({3,4-difluoro-2-[(2-fluoro-4-iodophenyl)amino]phenyl}carbonyl)azetidin-3-yl]-2-(4-methylpiperazin-1-yl)acetamide |
| 48 | 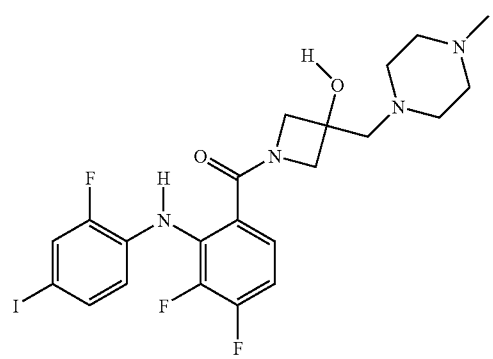 | 1-({3,4-difluoro-2-[(2-fluoro-4-iodophenyl)amino]phenyl}carbonyl)-3-[(4-methylpiperazin-1-yl)methyl]azetidin-3-ol |
| 49 | 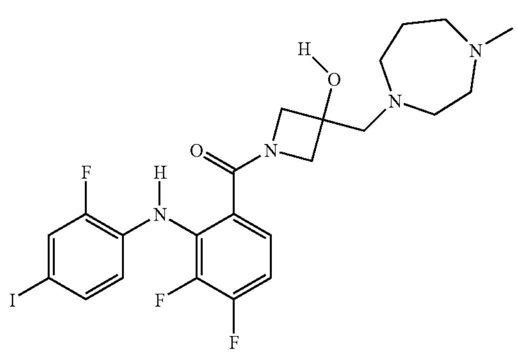 | 1-({3,4-difluoro-2-[(2-fluoro-4-iodophenyl)amino]phenyl}carbonyl)-3-[(4-methyl-1,4-diazepan-1-yl)methyl]azetidin-3-ol |

| Cmpd No. | Structure | Name |
|---|---|---|
| 50 | 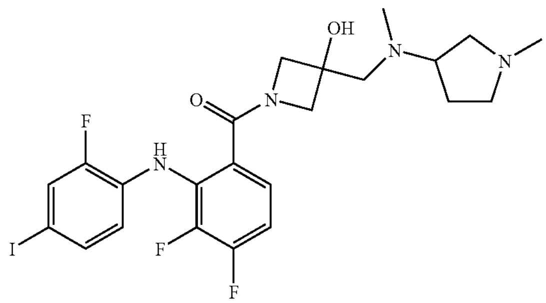 | 1-({3,4-difluoro-2-[(2-fluoro-4-iodophenyl)amino]phenyl}carbonyl)-3-{[methyl(1-methylpyrrolidin-3-yl)amino]methyl}azetidin-3-ol |
| 51 | 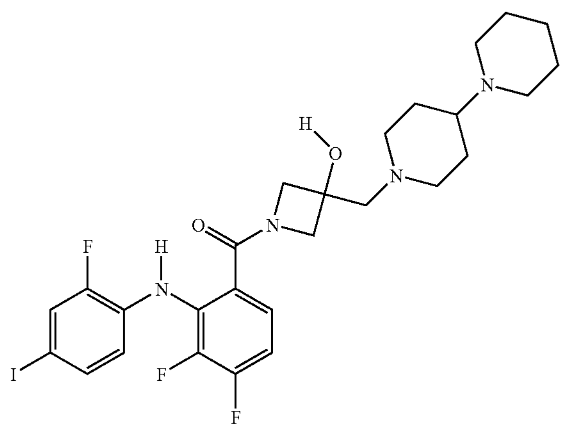 | 3-(1,4'-bipiperidin-1'-ylmethyl)-1-({3,4-difluoro-2-[(2-fluoro-4-iodophenyl)amino]phenyl}carbonyl)azetidin-3-ol |
| 52 | 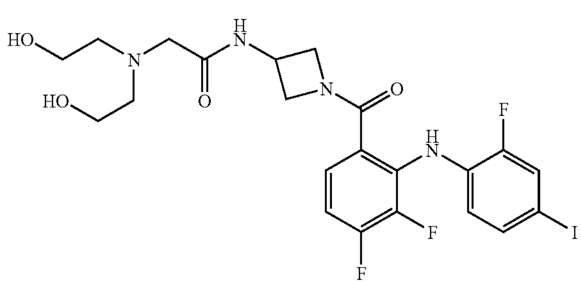 | N-[1-({3,4-difluoro-2-[(2-fluoro-4-iodophenyl)amino]phenyl}carbonyl)azetidin-3-yl]-N,N-bis(2-hydroxyethyl)glycinamide |
| 53 | 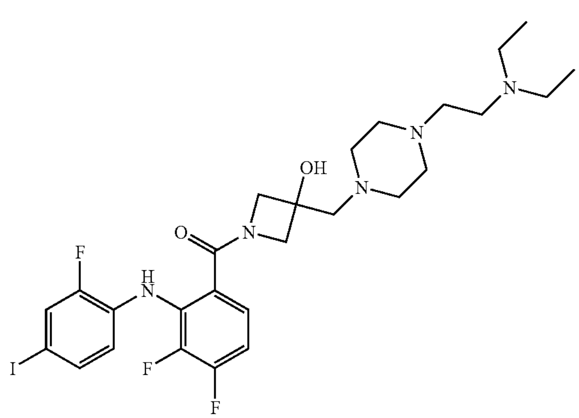 | 3-({4-[2-(diethylamino)ethyl]-piperazin-1-yl}methyl)-1-({3,4-difluoro-2-[(2-fluoro-4-iodophenyl)amino]phenyl}carbonyl)azetidin-3-ol |

TABLE 1-continued

| Cmpd No. | Structure | Name |
| --- | --- | --- |
| 54 | 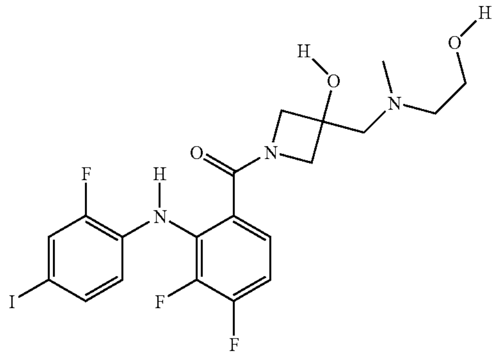 | 1-({3,4-difluoro-2-[(2-fluoro-4-iodophenyl)amino]phenyl}carbonyl)-3-{[(2-hydroxyethyl)(methyl)amino]methyl}azetidin-3-ol |
| 55 | 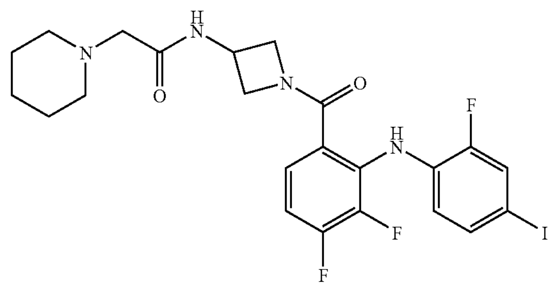 | N-[1-({3,4-difluoro-2-[(2-fluoro-4-iodophenyl)amino]phenyl}carbonyl)azetidin-3-yl]-2-piperidin-1-ylacetamide |
| 56 | 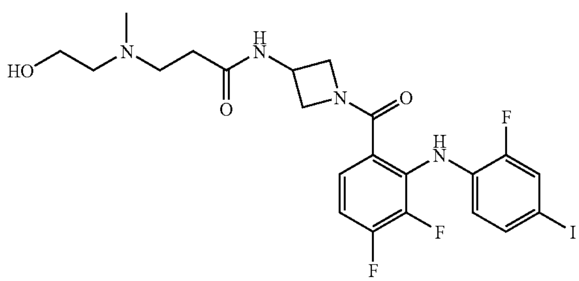 | N-[1-({3,4-difluoro-2-[(2-fluoro-4-iodophenyl)amino]phenyl}carbonyl)azetidin-3-yl]-N3-(2-hydroxyethyl)-N3-methyl-beta-alaninamide |
| 57 | 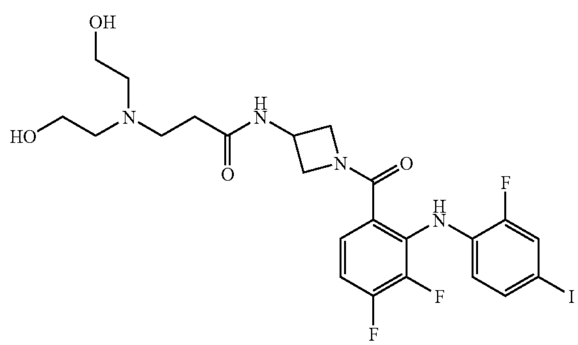 | N-[1-({3,4-difluoro-2-[(2-fluoro-4-iodophenyl)amino]phenyl}carbonyl)azetidin-3-yl]-N3,N3-bis(2-hydroxyethyl)-beta-alaninamide |
| 58 | 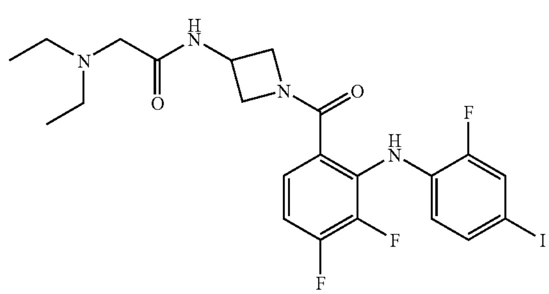 | N-[1-({3,4-difluoro-2-[(2-fluoro-4-iodophenyl)amino]phenyl}carbonyl)azetidin-3-yl]-N2,N2-diethylglycinamide |

TABLE 1-continued

| Cmpd No. | Structure | Name |
|---|---|---|
| 59 | 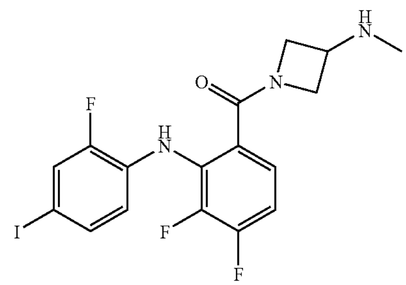 | 1-({3,4-difluoro-2-[(2-fluoro-4-iodophenyl)amino]phenyl}carbonyl)-N-methylazetidin-3-amine |
| 60 | 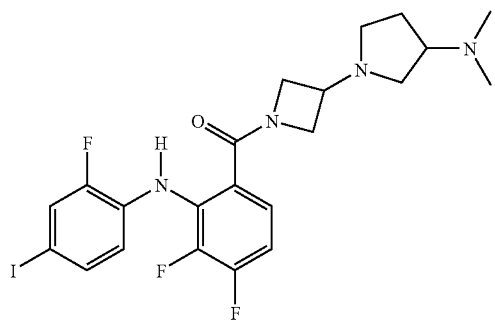 | 1-[1-({3,4-difluoro-2-[(2-fluoro-4-iodophenyl)amino]phenyl}carbonyl)azetidin-3-yl]-N,N-dimethylpyrrolidin-3-amine |
| 61 | 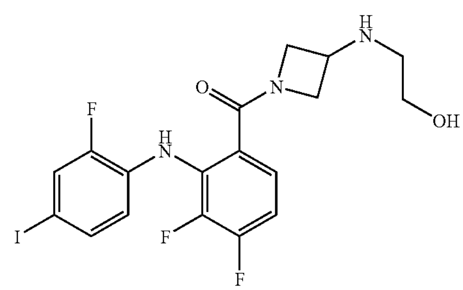 | 2-{[1-({3,4-difluoro-2-[(2-fluoro-4-iodophenyl)amino]phenyl}carbonyl)azetidin-3-yl]amino}ethanol |
| 62 | 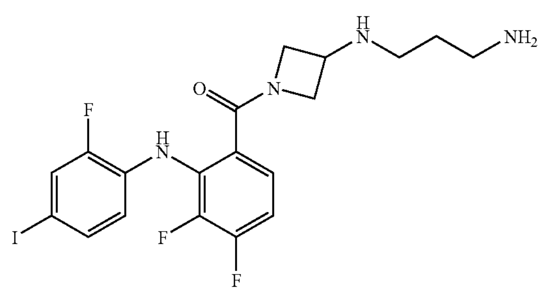 | N-[1-({3,4-difluoro-2-[(2-fluoro-4-iodophenyl)amino]phenyl}carbonyl)azetidin-3-yl]propane-1,3-diamine |
| 63 | 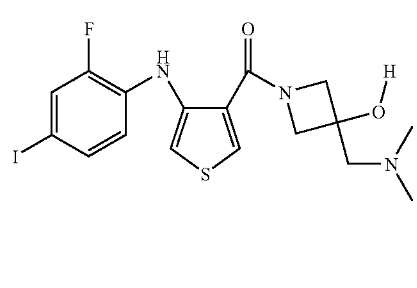 | 3-[(dimethylamino)methyl]-1-({4-[(2-fluoro-4-iodophenyl)amino]-3-thienyl}carbonyl)azetidin-3-ol |

TABLE 1-continued

| Cmpd No. | Structure | Name |
|---|---|---|
| 64 | 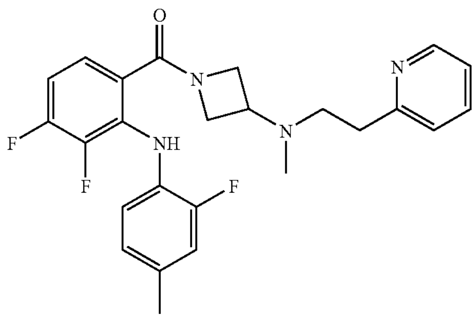 | 1-({3,4-difluoro-2-[(2-fluoro-4-iodophenyl)amino]phenyl}carbonyl)-N-methyl-N-(2-pyridin-2-ylethyl)azetidin-3-amine |
| 65 | 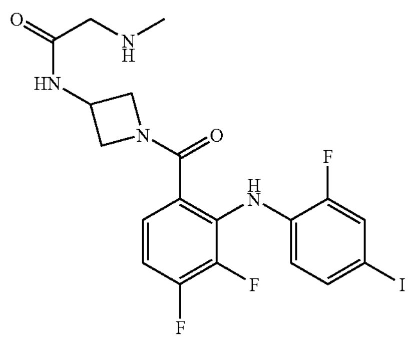 | N-[1-({3,4-difluoro-2-[(2-fluoro-4-iodophenyl)amino]phenyl}carbonyl)azetidin-3-yl]-N2-methylglycinamide |
| 66 | 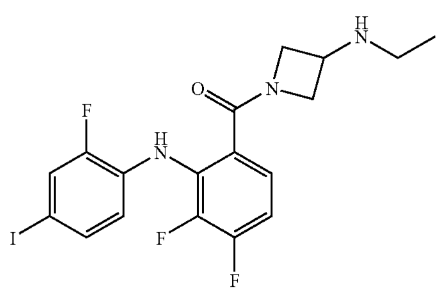 | 1-({3,4-difluoro-2-[2-fluoro-4-iodophenyl)amino]phenyl}carbonyl)-N-ethylazetidin-3-amine |
| 67 | 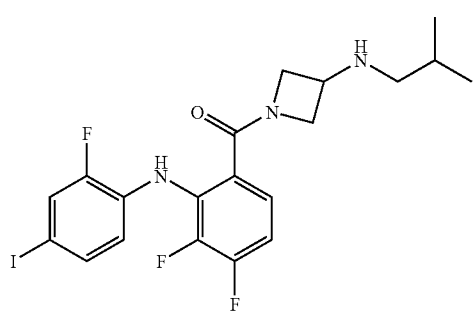 | 1-({3,4-difluoro-2-[(2-fluoro-4-iodophenyl)amino]phenyl}carbonyl)-N-(2-methylpropyl)azetidin-3-amine |
| 68 | 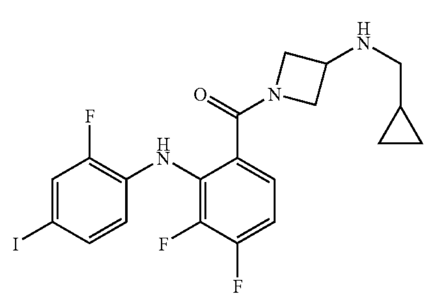 | N-(cyclopropylmethyl)-1-({3,4-difluoro-2-[(2-fluoro-4-iodophenyl)amino]phenyl}carbonyl)azetidin-3-amine |

TABLE 1-continued

| Cmpd No. | Structure | Name |
|---|---|---|
| 69 | 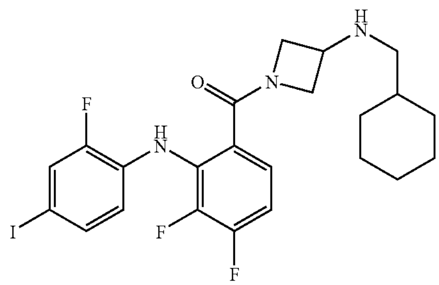 | N-(cyclohexylmethyl)-1-({3,4-difluoro-2-[(2-fluoro-4-iodophenyl)amino]phenyl}carbonyl)azetidin-3-amine |
| 70 | 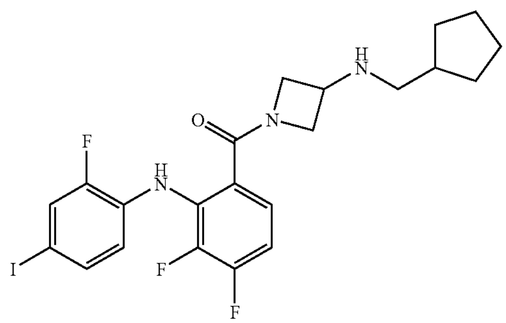 | N-(cyclopentylmethyl)-1-({3,4-difluoro-2-[(2-fluoro-4-iodophenyl)amino]phenyl}carbonyl)azetidin-3-amine |
| 71 | 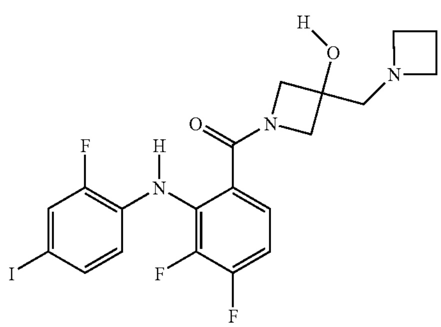 | 3-(azetidin-1-ylmethyl])-1-({3,4-difluoro-2-[(2-fluoro-4-iodophenyl)amino]phenyl}carbonyl)azetidin-3-ol |
| 72 | 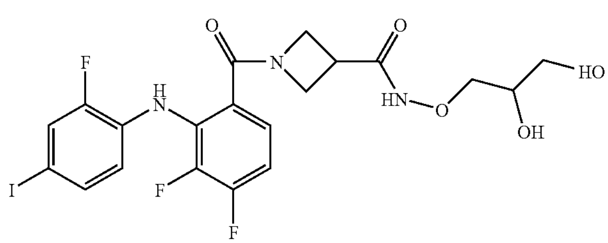 | 1-({3,4-difluoro-2-[(2-fluoro-4-iodophenyl)amino]phenyl}carbonyl)-N-[(2,3-dihydroxypropyl)oxy]azetidine-3-carboxamide |
| 73 | 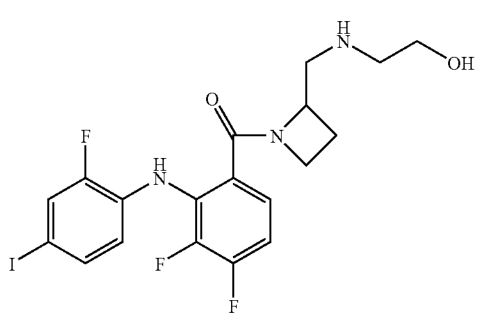 | 2-({[1-({3,4-difluoro-2-[(2-fluoro-4-iodophenyl)amino]phenyl}carbonyl)azetidin-2-yl]methyl}amino)ethanol |

TABLE 1-continued

| Cmpd No. | Structure | Name |
| --- | --- | --- |
| 74 | 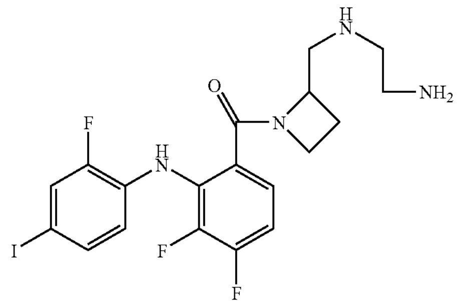 | N-{[1-({3,4-difluoro-2-[(2-fluoro-4-iodophenyl)amino]phenyl}carbonyl)azetidin-2-yl]methyl}ethane-1,2-diamine |
| 75 | 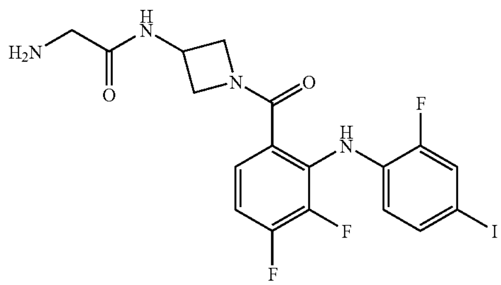 | N-[1-({3,4-difluoro-2-[(2-fluoro-4-iodophenyl)amino]phenyl}carbonyl)azetidin-3-yl]glycinamide |
| 76 | 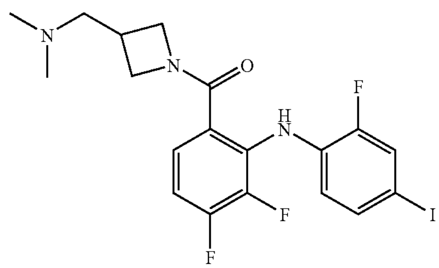 | 6-({3-[(dimethylamino)methyl]azetidin-1-yl}carbonyl)-2,3-difluoro-N-(2-fluoro-4-iodophenyl)aniline |
| 77 | 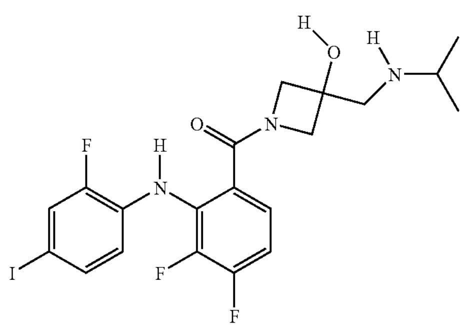 | 1-({3,4-difluoro-2-[(2-fluoro-4-iodophenyl)amino]phenyl}carbonyl)-3-{[(1-methylethyl)amino]methyl}azetidin-3-ol |
| 78 | 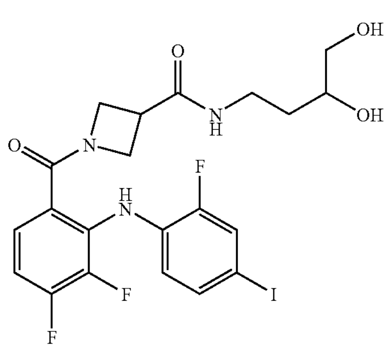 | 1-({3,4-difluoro-2-[(2-fluoro-4-iodophenyl)amino]phenyl}carbonyl)-N-(3,4-dihydroxybutyl)azetidine-3-carboxamide |

TABLE 1-continued

| Cmpd No. | Structure | Name |
|---|---|---|
| 79 | 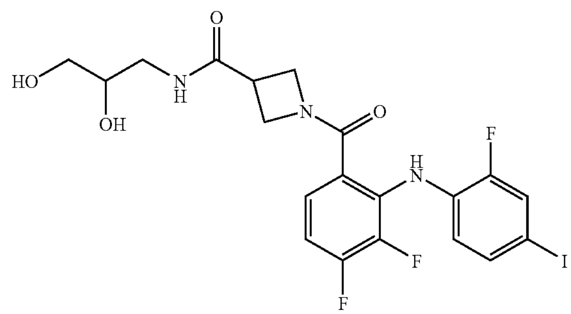 | 1-({3,4-difluoro-2-[(2-fluoro-4-iodophenyl)amino]phenyl}carbonyl)-N-(2,3-dihydroxypropyl)azetidine-3-carboxamide |
| 80 | 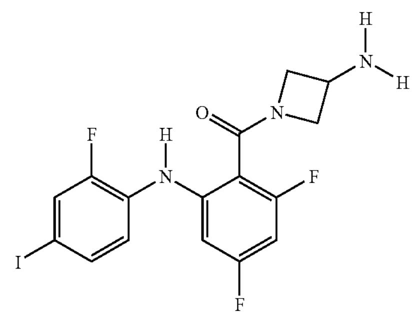 | 1-({2,4-difluoro-6-[(2-fluoro-4-iodophenyl)amino]phenyl}carbonyl)azetidin-3-amine |
| 81 | 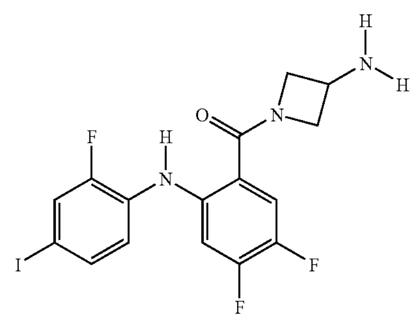 | 1-({4,5-difluoro-2-[(2-fluoro-4-iodophenyl)amino]phenyl}carbonyl)azetidin-3-amine |
| 82 | 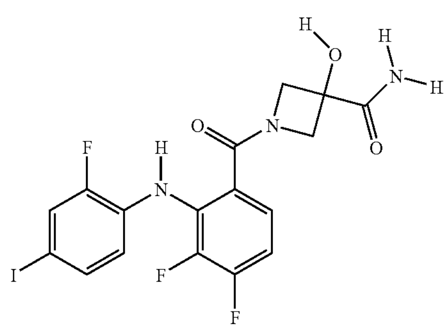 | 1-({3,4-difluoro-2-[(2-fluoro-4-iodophenyl)amino]phenyl}carbonyl)-3-hydroxyazetidine-3-carboxamide |
| 83 | 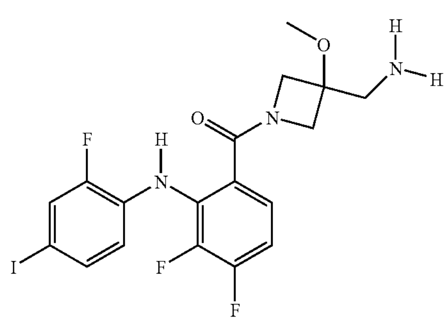 | 6-{[3-(aminomethyl)-3-(methyloxy)azetidin-1-yl]carbonyl}-2,3-difluoro-N-(2-fluoro-4-iodophenyl)aniline |

TABLE 1-continued

| Cmpd No. | Structure | Name |
|---|---|---|
| 84 | 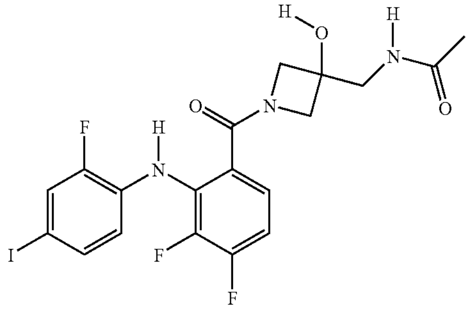 | N-{[1-({3,4-difluoro-2-[(2-fluoro-4-iodophenyl)amino]phenyl}carbonyl)-3-hydroxyazetidin-3-yl]methyl}acetamide |
| 85 | 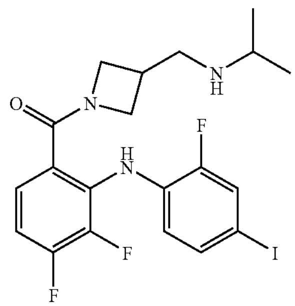 | 2,3-difluoro-N-(2-fluoro-4-iodophenyl)-6-[(3-{[(1-methylethyl)amino]methyl}azetidin-1-yl)carbonyl]aniline |
| 86 | 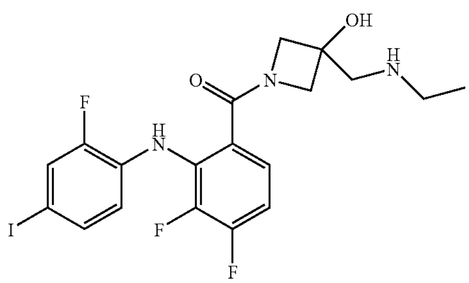 | 1-({3,4-difluoro-2-[(2-fluoro-4-iodophenyl)amino]phenyl}carbonyl)-3-[(ethylamino)methyl]azetidin-3-ol |
| 87 | 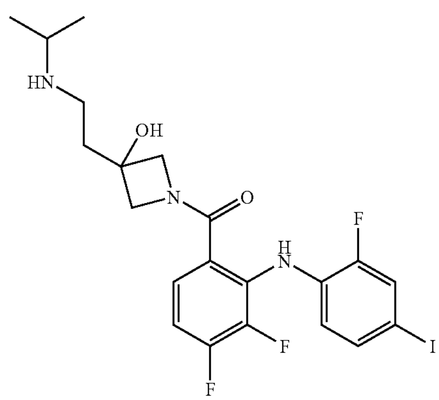 | 1-({3,4-difluoro-2-[(2-fluoro-4-iodophenyl)amino]phenyl}carbonyl)-3-{2-[(1-methylethyl)amino]ethyl}azetidin-3-ol |
| 88 | 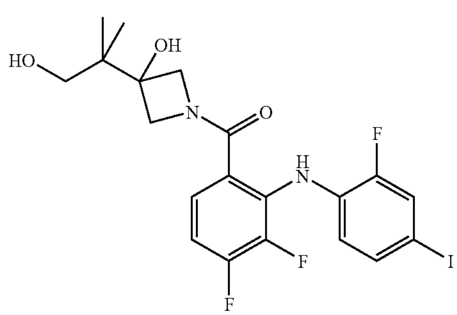 | 1-({3,4-difluoro-2-[(2-fluoro-4-iodophenyl)amino]phenyl}carbonyl)-3-(2-hydroxy-1,1-dimethylethyl)azetidin-3-ol |

TABLE 1-continued

| Cmpd No. | Structure | Name |
|---|---|---|
| 89 | 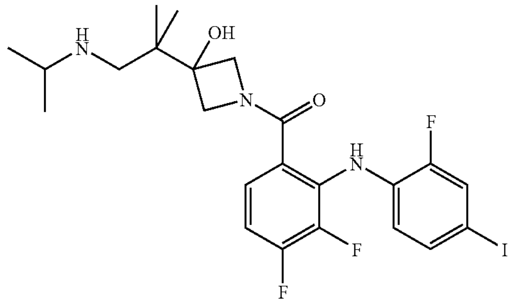 | 1-({3,4-difluoro-2-[(2-fluoro-4-iodophenyl)amino]phenyl}carbonyl)-3-{1,1-dimethyl-2-[(1-methylethyl)amino]ethyl}azetidin-3-ol |
| 90 | 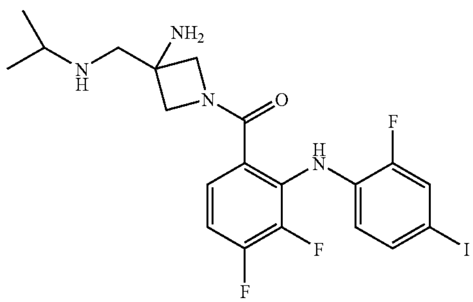 | 1-({3,4-difluoro-2-[(2-fluoro-4-iodophenyl)amino]phenyl}carbonyl)-3-{[(1-methylethyl)amino]methyl}azetidin-3-amine |
| 91 | 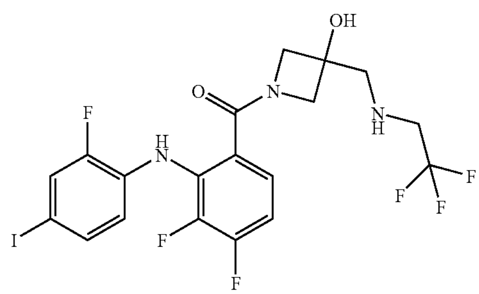 | 3-[(cyclopropylamino)methyl]-1-({3,4-difluoro-2-{(2-fluoro-4-iodophenyl)amino]phenyl}carbonyl)azetidin-3-ol |
| 92 | 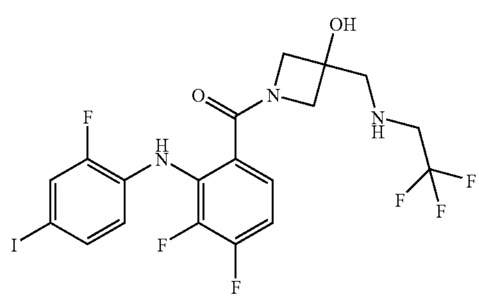 | 1-({3,4-difluoro-2-[(2-fluoro-4-iodophenyl)amino]phenyl}carbonyl)-3-{[(2,2,2-trifluoroethyl)amino]methyl}azetidin-3-ol |
| 93 | 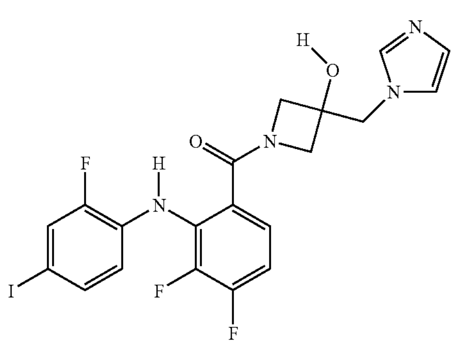 | 1-({3,4-difluoro-2-{(2-fluoro-4-iodophenyl)amino]phenyl}carbonyl)-3-(1H-imidazol-1-ylmethyl)azetidin-3-ol |

TABLE 1-continued

| Cmpd No. | Structure | Name |
|---|---|---|
| 94 | 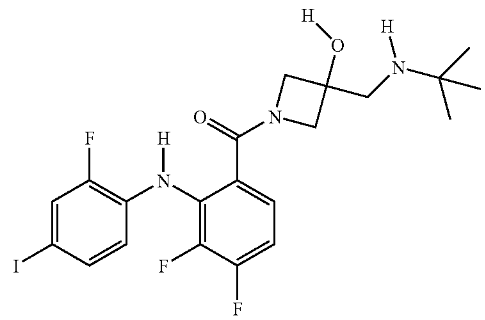 | 1-({3,4-difluoro-2-[(2-fluoro-4-iodophenyl)amino]phenyl}carbonyl)-3-{[(1,1-dimethylethyl)amino]methyl}azetidin-3-ol |
| 95 | 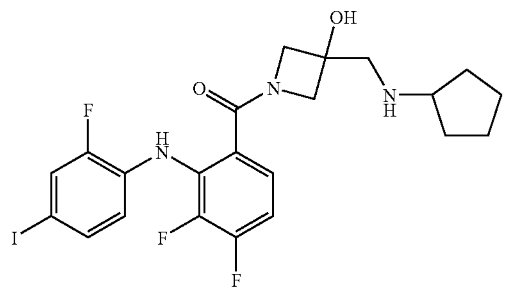 | 3-[(cyclopentylamino)methyl]-1-({3,4-difluoro-2-[(2-fluoro-4-iodophenyl)amino]phenyl}carbonyl)-azetidin-3-ol |
| 96 | 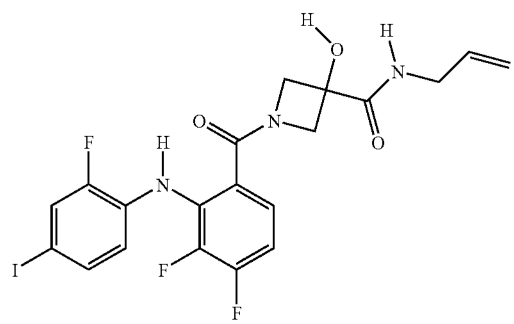 | 1-({3,4-difluoro-2-[(2-fluoro-4-iodophenyl)amino]phenyl}carbonyl)-3-hydroxy-N-prop-2-en-1-ylazetidine-3-carboxamide |
| 97 | 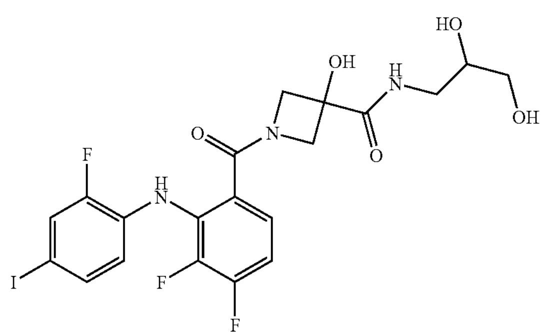 | 1-({3,4-difluoro-2-[(2-fluoro-4-iodophenyl)amino]phenyl}carbonyl)-N-(2,3-dihydroxypropyl)-3-hydroxyazetidine-3-carboxamide |
| 98 | 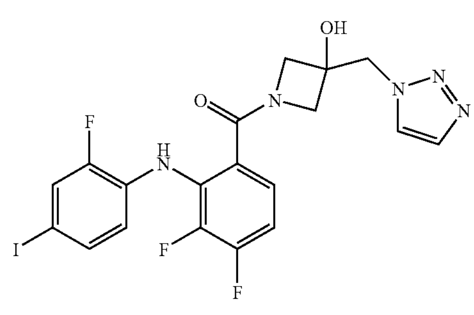 | 1-({3,4-difluoro-2-[(2-fluoro-4-iodophenyl)amino)phenyl}carbonyl)-3-(1H-1,2,3-triazol-1-ylmethyl)azetidin-3-ol |

TABLE 1-continued

| Cmpd No. | Structure | Name |
|---|---|---|
| 99 | 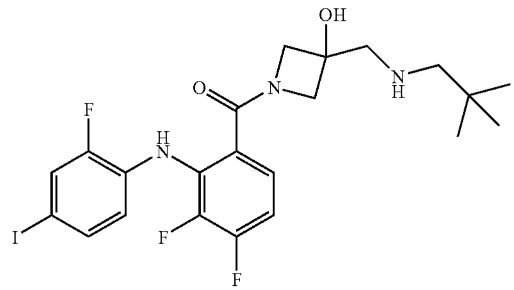 | 1-({3,4-difluoro-2-[(2-fluoro-4-iodophenyl)amino]phenyl}carbonyl)-3-{[(2,2-dimethylpropyl)amino]methyl}azetidin-3-ol |
| 100 | 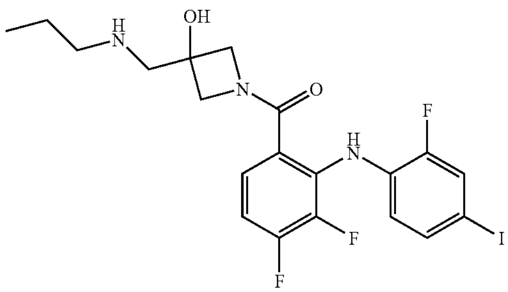 | 1-({3,4-difluoro-2-[(2-fluoro-4-iodophenyl)amino]phenyl}carbonyl)-3-[(propylamino)methyl]azetidin-3-ol |
| 101 | 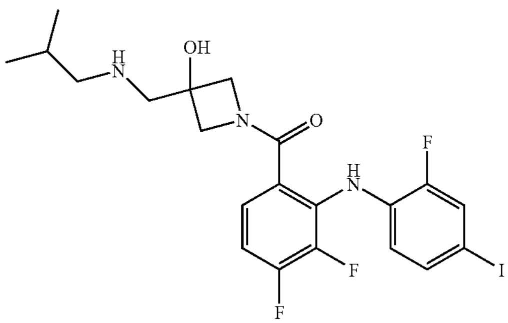 | 1-({3,4-difluoro-2-[(2-fluoro-4-iodophenyl)amino]phenyl}carbonyl)-methylpropyl)amino]methyl}azetidin-3-ol |
| 102 | 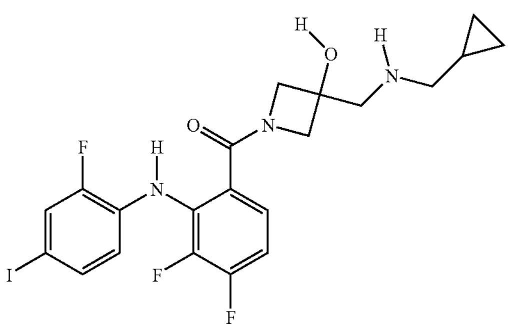 | 3-{[(cyclopropylmethyl)amino]methyl}-1-({3,4-difluoro-2-[(2-fluoro-4-iodophenyl)amino]phenyl}carbonyl)-azetidin-3-ol |
| 103 | 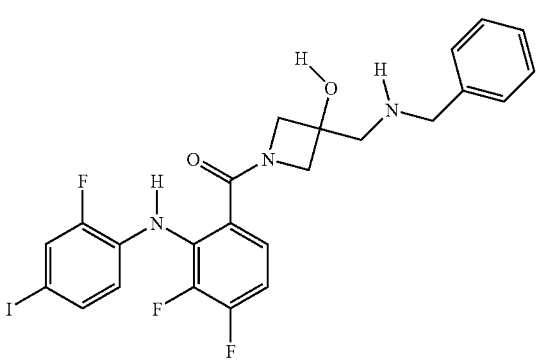 | 1-({3,4-difluoro-2-[(2-fluoro-4-iodophenyl)amino]phenyl}carbonyl)-3-{[(phenylmethyl)amino]methyl}azetidin-3-ol |

TABLE 1-continued

| Cmpd No. | Structure | Name |
| --- | --- | --- |
| 104 | 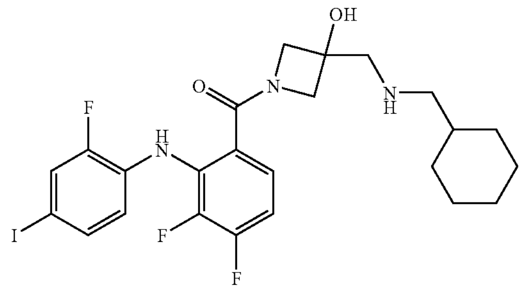 | 3-{[(cyclohexylmethyl)amino]methyl}-1-({3,4-difluoro-2-[(2-fluoro-4-iodophenyl)amino]phenyl}carbonyl)azetidin-3-ol |
| 105 | 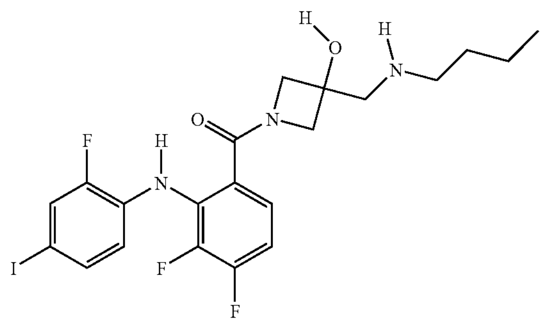 | 3-[(butylamino)methyl]-1-({3,4-difluoro-2-[(2-fluoro-4-iodophenyl)amino]phenyl}carbonyl)azetidin-3-ol |
| 106 | 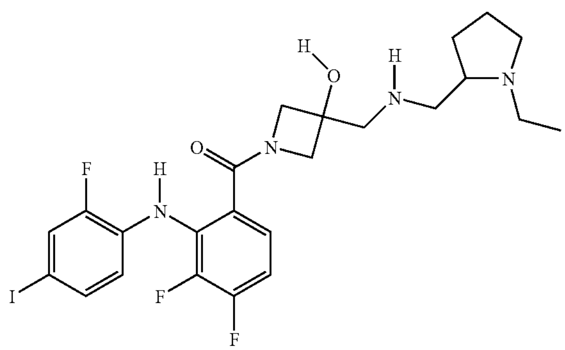 | 1-({3,4-difluoro-2-[(2-fluoro-4-iodophenyl)amino]phenyl}carbonyl)-3-({[(1-ethylpyrrolidin-2-yl)methyl]amino}methyl)azetidin-3-ol |
| 107 | 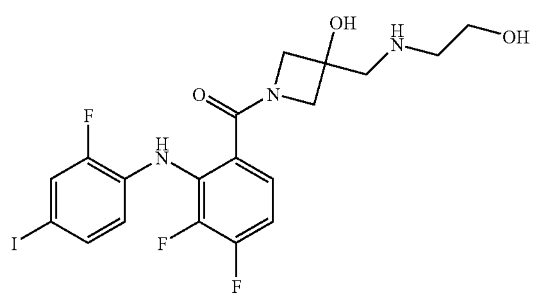 | 1-({3,4-difluoro-2-[(2-fluoro-4-iodophenyl)amino]phenyl}carbonyl)-3-{[(2-hydroxyethyl)amino]methyl}azetidin-3-ol |
| 108 | 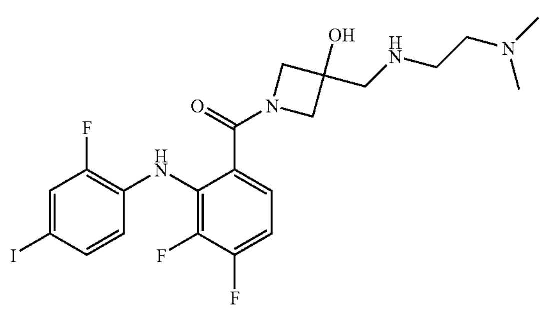 | 1-({3,4-difluoro-2-[(2-fluoro-4-iodophenyl)amino]phenyl}carbonyl)-3-({[2-(dimethylamino)ethyl]amino}methyl)azetidin-3-ol |

TABLE 1-continued

| Cmpd No. | Structure | Name |
|---|---|---|
| 109 | 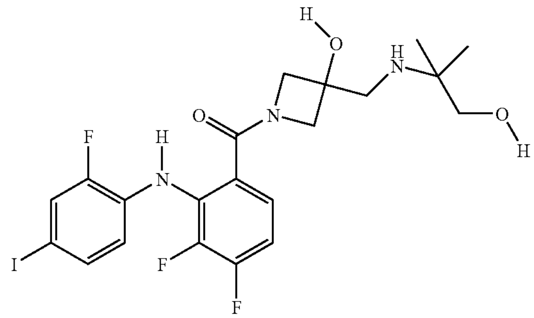 | 1-({3,4-difluoro-2-[(2-fluoro-4-iodophenyl)amino]phenyl}carbonyl)-3-{[(2-hydroxy-1,1-dimethylethyl)amino]methyl}azetidin-3-ol |
| 110 | 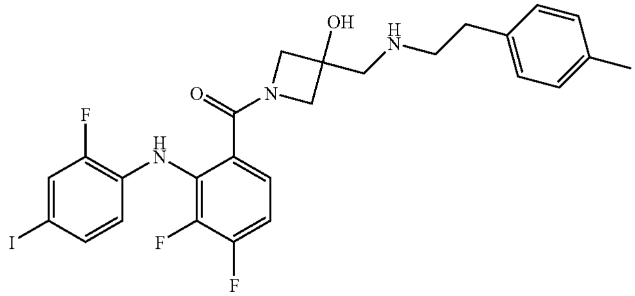 | 1-({3,4-difluoro-2-[(2-fluoro-4-iodophenyl)amino]phenyl}carbonyl)-3-({[2-(4-methylphenyl)ethyl]amino}methyl)azetidin-3-ol |
| 111 | 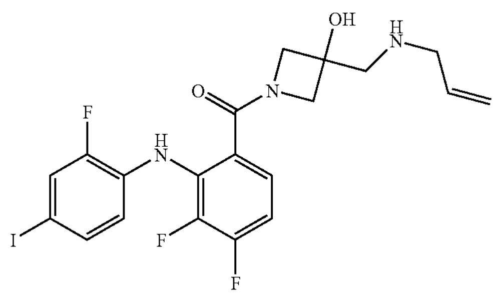 | 1-({3,4-difluoro-2-[(2-fluoro-4-iodophenyl)amino]phenyl}carbonyl)-3-[(prop-2-en-1-ylamino)methyl]azetidin-3-ol |
| 112 | 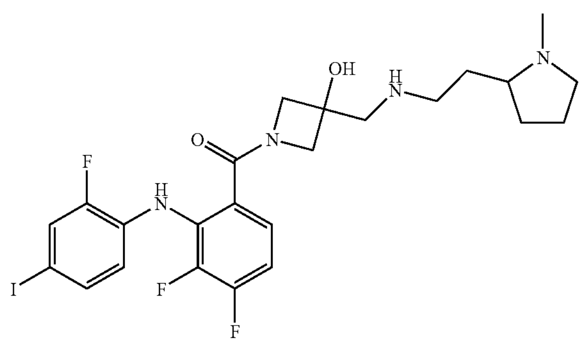 | 1-({3,4-difluoro-2-[(2-fluoro-4-iodophenyl)amino]phenyl}carbonyl)-3-({[2-(1-methylpyrrolidin-2-yl)ethyl]amino}methyl)azetidin-3-ol |
| 113 | 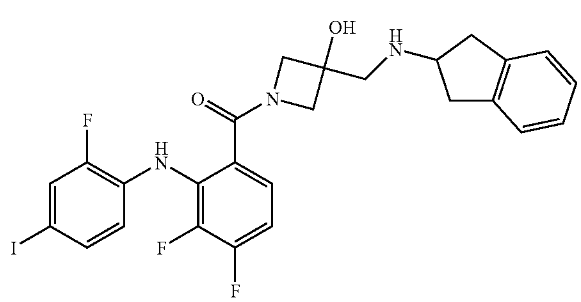 | 1-({3,4-difluoro-2-{(2-fluoro-4-iodophenyl)amino]phenyl}carbonyl)-3-[(2,3-dihydro-1H-inden-2-ylamino)methyl]azetidin-3-ol |

TABLE 1-continued

| Cmpd No. | Structure | Name |
|---|---|---|
| 114 | 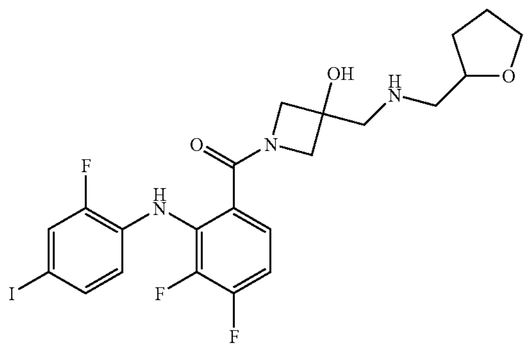 | 1-({3,4-difluoro-2-[(2-fluoro-4-iodophenyl)amino]phenyl}carbonyl)-3-{[(tetrahydrofuran-2-ylmethyl)amino]methyl}azetidin-3-ol |
| 115 | 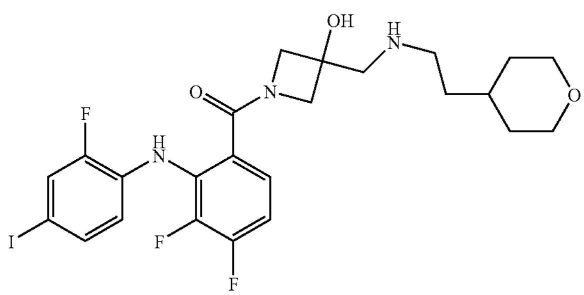 | 1-({3,4-difluoro-2-{(2-fluoro-4-iodophenyl)amino]phenyl}carbonyl)-3-({[2-(tetrahydro-2H-pyran-4-yl)ethyl]amino}methyl)azetidin-3-ol |
| 116 | 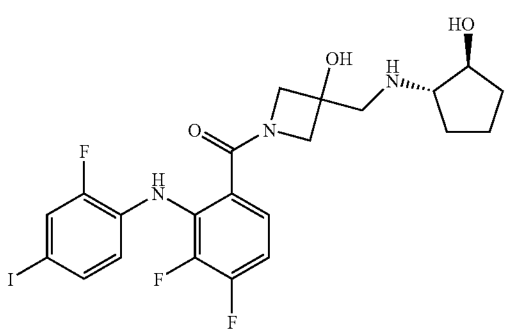 | 1-({3,4-difluoro-2-[(2-fluoro-4-iodophenyl)amino]phenyl}carbonyl)-3-({[(1S,2S)-2-hydroxycyclopentyl]amino}methyl)azetidin-3-ol |
| 117 | 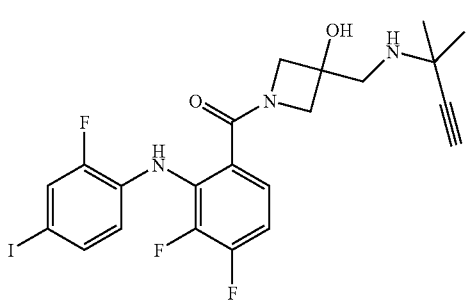 | 1-({3,4-difluoro-2-[(2-fluoro-4-iodophenyl)amino]phenyl}carbonyl)-3-{[(1,1-dimethylprop-2-yn-1-yl)amino]methyl}azetidin-3-ol |

TABLE 1-continued

| Cmpd No. | Structure | Name |
|---|---|---|
| 118 | 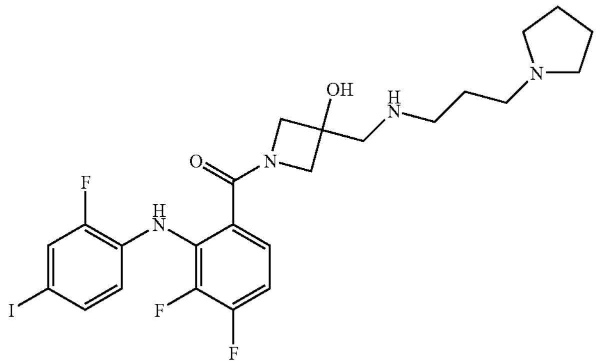 | 1-({3,4-difluoro-2-[(2-fluoro-4-iodophenyl)amino]phenyl}carbonyl)-3-{[(3-pyrrolidin-1-ylpropyl)amino]methyl}azetidin-3-ol |
| 119 | 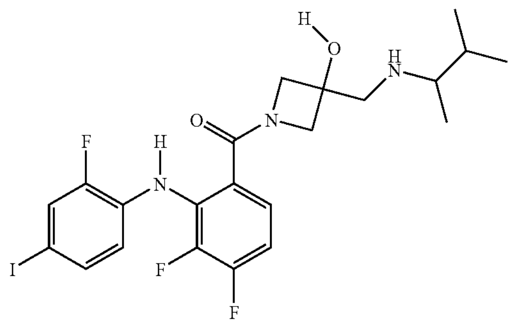 | 1-({3,4-difluoro-2-[(2-fluoro-4-iodophenyl)amino]phenyl}carbonyl)-3-{[(1,2-dimethylpropyl)amino]methyl}azetidin-3-ol |
| 120 | 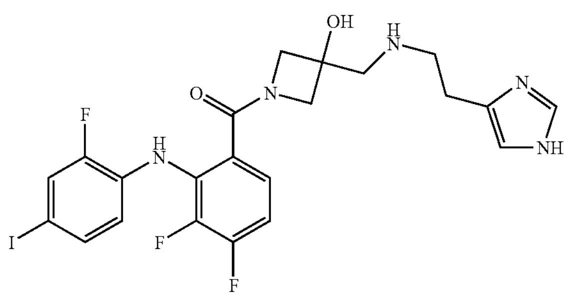 | 1-({3,4-difluoro-2-[(2-fluoro-4-iodophenyl)amino]phenyl}carbonyl)-3-({[2-(1H-imidazol-4-yl)ethyl]amino}methyl)azetidin-3-ol |
| 121 | 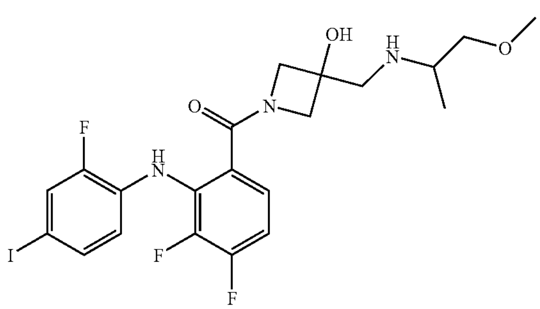 | 1-({3,4-difluoro-2-[(2-fluoro-4-iodophenyl)amino]phenyl}carbonyl)-3-({[1-methyl-2-(methyloxy)ethyl]amino}methyl)azetidin-3-ol |
| 122 | 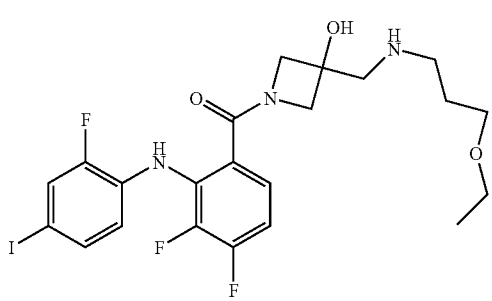 | 1-({3,4-difluoro-2-[(2-fluoro-4-iodophenyl)amino]phenyl}carbonyl)-3-({[3-(ethyloxy)propyl]amino}methyl)azetidin-3-ol |

TABLE 1-continued

| Cmpd No. | Structure | Name |
|---|---|---|
| 123 | 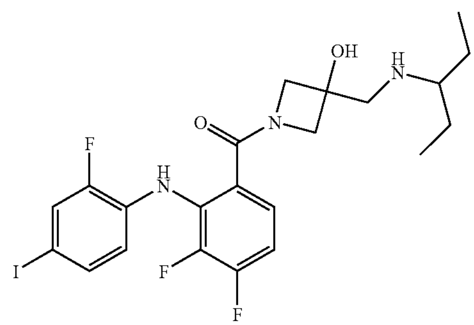 | 1-({3,4-difluoro-2-[(2-fluoro-4-iodophenyl)amino]phenyl}carbonyl)-3-{[(1-ethylpropyl)amino]methyl}azetidin-3-ol |
| 124 | 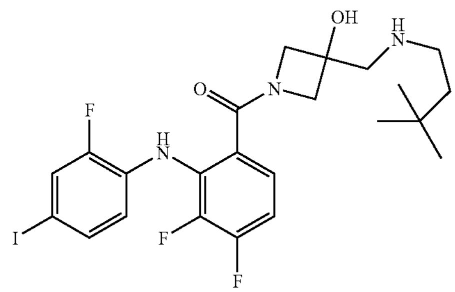 | 1-({3,4-difluoro-2-[(2-fluoro-4-iodophenyl)amino]phenyl}carbonyl)-3-{[(3,3-dimethylbutyl)amino]methyl}azetidin-3-ol |
| 125 | 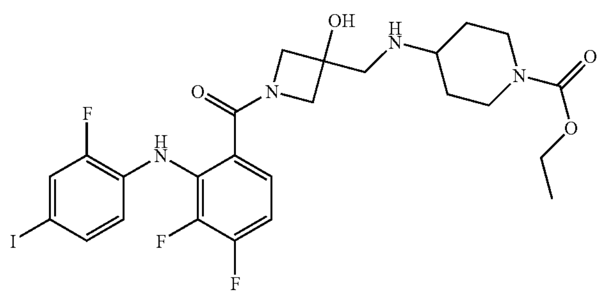 | ethyl 4-({[1-({3,4-difluoro-2-[(2-fluoro-4-iodophenyl)amino]phenyl}carbonyl)-3-hydroxyazetidin-3-yl]methyl}amino)piperidine-1-carboxylate |
| 126 | 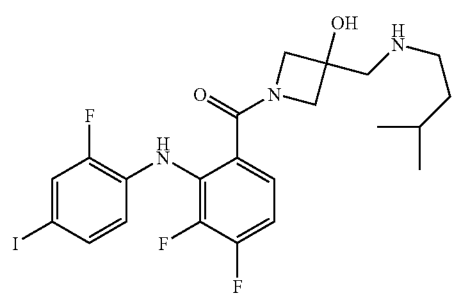 | 1-({3,4-difluoro-2-[(2-fluoro-4-iodophenyl)amino]phenyl}carbonyl)-3-{[(3-methylbutyl)amino]methyl}azetidin-3-ol |
| 127 | 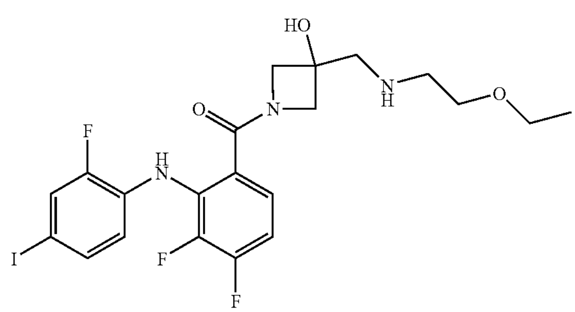 | 1-({3,4-difluoro-2-[(2-fluoro-4-iodophenyl)amino]phenyl}carbonyl)-3-({[2-(ethyloxy)ethyl]amino}methyl)azetidin-3-ol |

TABLE 1-continued

| Cmpd No. | Structure | Name |
|---|---|---|
| 128 | 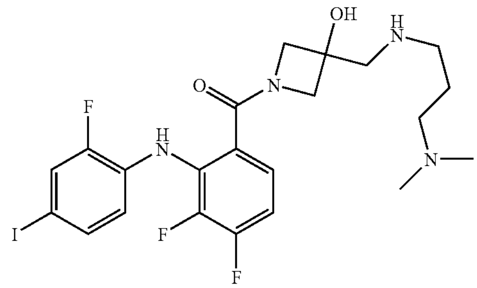 | 1-({3,4-difluoro-2-[(2-fluoro-4-iodophenyl)amino]phenyl}carbonyl)-3-({[3-(dimethylamino)propyl]amino}methyl)azetidin-3-ol |
| 129 | 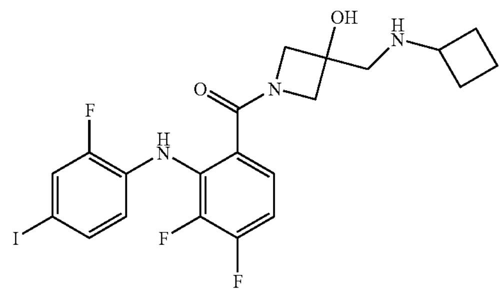 | 3-[(cyclobutylamino)methyl]-1-({3,4-difluoro-2-[(2-fluoro-4-iodophenyl)amino]phenyl}carbonyl)azetidin-3-ol |
| 130 | 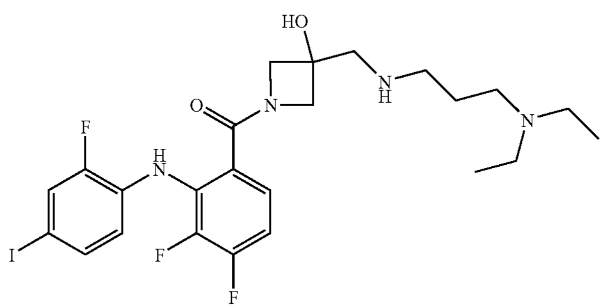 | 3-({[3-(diethylamino)propyl]amino}methyl)-1-({3,4-difluoro-2-{(2-fluoro-4-iodophenyl)amino]phenyl}carbonyl)azetidin-3-ol |
| 131 | 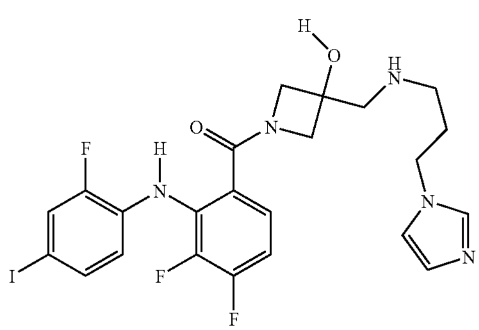 | 1-({3,4-difluoro-2-[(2-fluoro-4-iodophenyl)amino]phenyl}carbonyl)-3-({[3-(1H-imidazol-1-yl)propyl]amino}methyl)azetidin-3-ol |
| 132 | 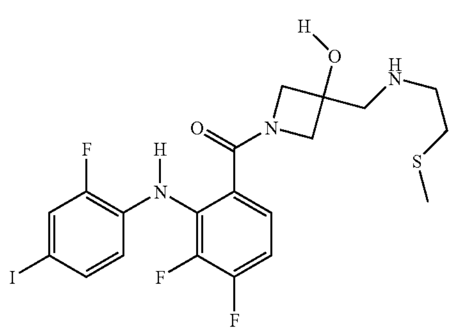 | 1-({3,4-difluoro-2-[(2-fluoro-4-iodophenyl)amino]phenyl}carbonyl)-3-({[2-(methylthio)ethyl]amino}methyl)azetidin-3-ol |

TABLE 1-continued

| Cmpd No. | Structure | Name |
|---|---|---|
| 133 | 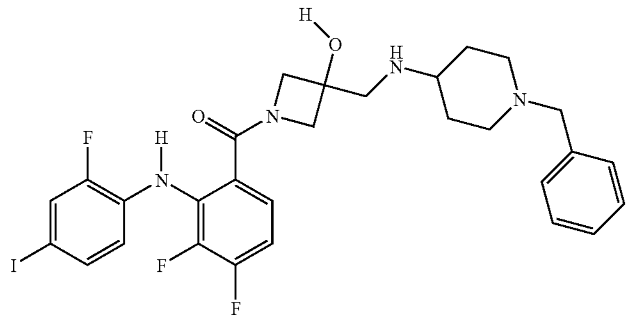 | 1-({3,4-difluoro-2-(2-fluoro-4-iodophenyl)amino]phenyl}carbonyl)-3-({[1-(phenylmethyl)piperidin-4-yl]amino}methyl)azetidin-3-ol |
| 134 | 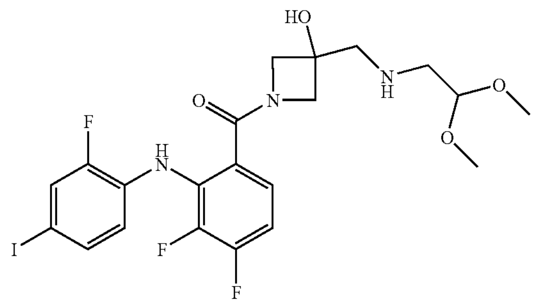 | 3-({[2,2-bis(methyloxy)ethyl]amino}methyl)-1-({3,4-difluoro-2-[(2-fluoro-4-iodophenyl)amino]phenyl}carbonyl)azetidin-3-ol |
| 135 | 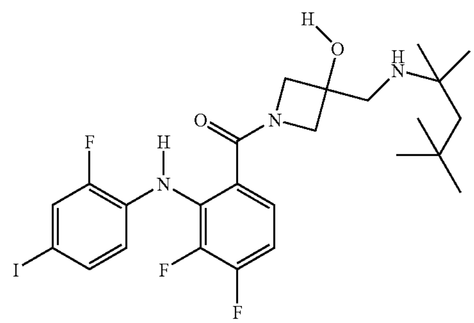 | 1-({3,4-difluoro-2-[(2-fluoro-4-iodophenyl)amino]phenyl}carbonyl)-3-{[(1,1,3,3-tetramethylbutyl)amino]methyl}azetidin-3-ol |
| 136 | 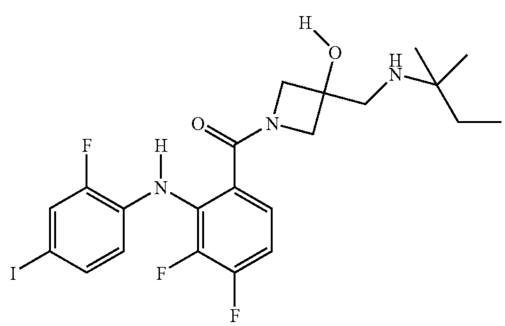 | 1-({3,4-difluoro-2-{(2-fluoro-4-iodophenyl)amino]phenyl}carbonyl)-3-{[(1,1-dimethylpropyl)amino]methyl}azetidin-3-ol |
| 137 | 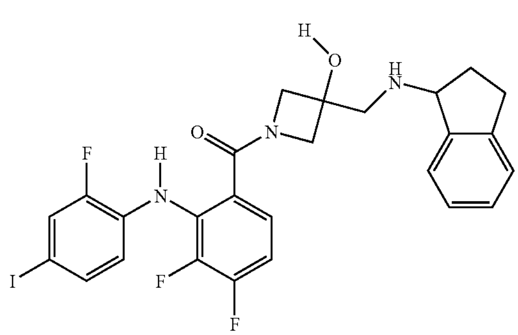 | 1-({3,4-difluoro-2-[(2-fluoro-4-iodophenyl)amino]phenyl}carbonyl)-3-[(2,3-dihydro-1H-inden-1-ylamino)methyl]azetidin-3-ol |

TABLE 1-continued

| Cmpd No. | Structure | Name |
|---|---|---|
| 138 | 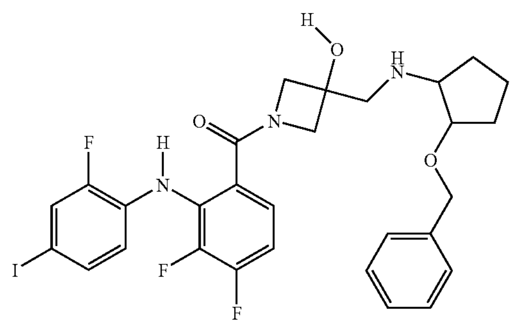 | 1-({3,4-difluoro-2-[(2-fluoro-4-iodophenyl)amino]phenyl}carbonyl)-3-[({2-[(phenylmethyl)oxy]cyclopentyl}amino)methyl]azetidin-3-ol |
| 139 | 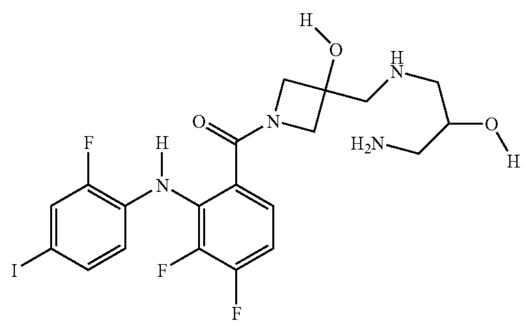 | 3-{[(3-amino-2-hydroxypropyl)amino]methyl}-1-({3,4-difluoro-2-[(2-fluoro-4-iodophenyl)amino]phenyl}carbonyl)azetidin-3-ol |
| 140 | 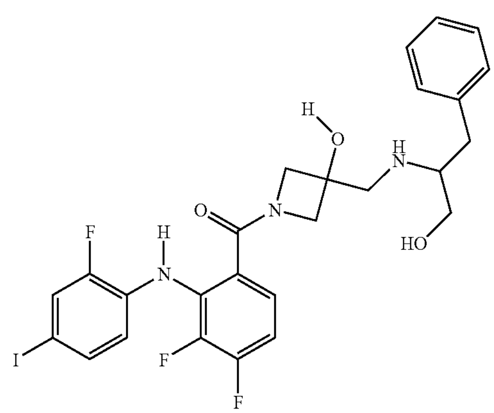 | 1-({3,4-difluoro-2-[(2-fluoro-4-iodophenyl)amino]phenyl}carbonyl)-3-({[2-hydroxy-1-(phenylmethyl)ethyl]amino}methyl)azetidin-3-ol |
| 141 | 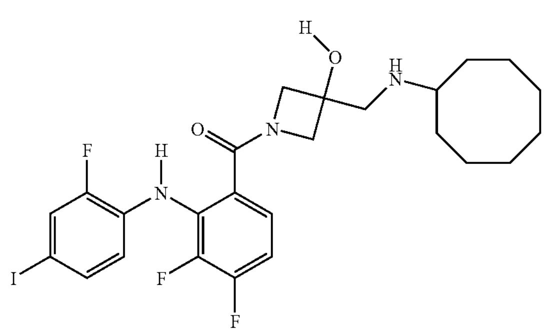 | 3-[(cyclooctylamino)methyl]-1-({3,4-difluoro-2-[(2-fluoro-4-iodophenyl)amino]phenyl}carbonyl)azetidin-3-ol |

| Cmpd No. | Structure | Name |
|---|---|---|
| 142 | 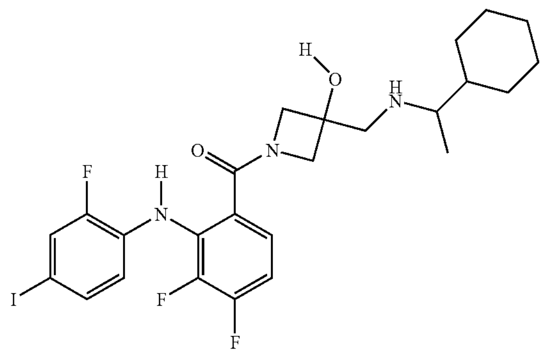 | 3-{[(1-cyclohexylethyl)amino]methyl}-1-({3,4-difluoro-2-[(2-fluoro-4-iodophenyl)amino]phenyl}carbonyl)azetidin-3-ol |
| 143 | 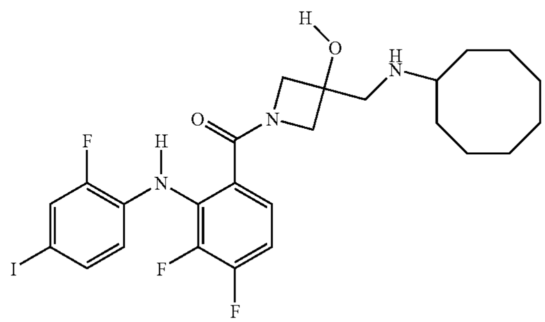 | 3-[(cycloheptylamino)methyl]-1-({3,4-difluoro-2-[(2-fluoro-4-iodophenyl)amino]phenyl}carbonyl)azetidin-3-ol |
| 144 | 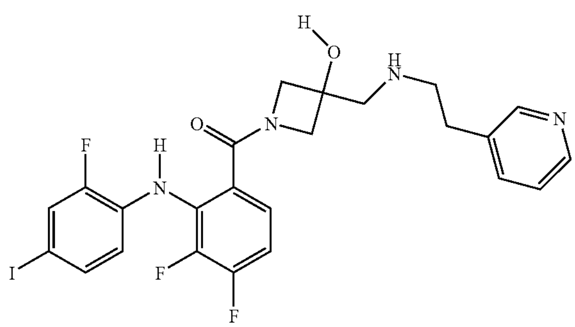 | 1-({3,4-difluoro-2-[(2-fluoro-4-iodophenyl)amino]phenyl}carbonyl)-3-{[(2-pyridin-3-ylethyl)amino]methyl}azetidin-3-ol |
| 145 | 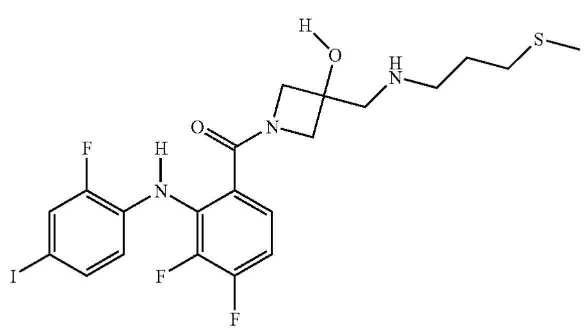 | 1-({3,4-difluoro-2-[(2-fluoro-4-iodophenyl)amino]phenyl}carbonyl)-3-({[3-(methylthio)propyl]amino}methyl)azetidin-3-ol |

| Cmpd No. | Structure | Name |
|---|---|---|
| 146 | 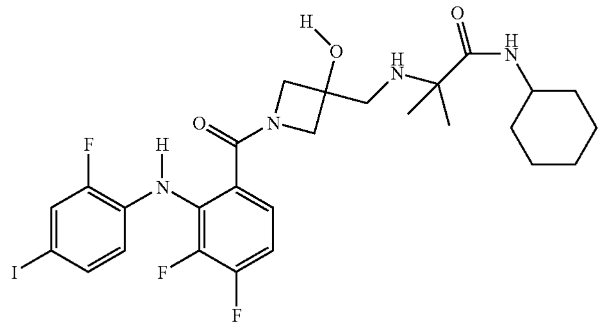 | N-cyclohexyl-N~2~-{[1-({3,4-difluoro-2-[(2-fluoro-4-iodophenyl)amino]phenyl}carbonyl)-3-hydroxyazetidin-3-yl]methyl}-2-methylalaninamide |
| 147 | 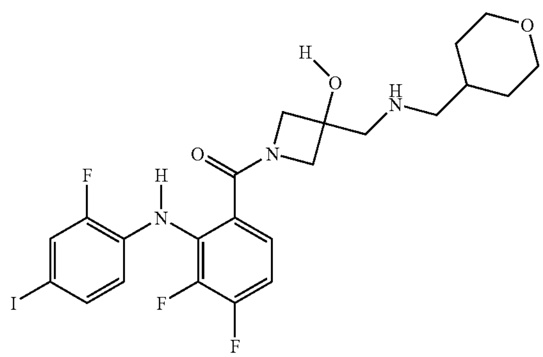 | 1-({3,4-difluoro-2-[(2-fluoro-4-iodophenyl)amino]phenyl}carbonyl)-3-{[(tetrahydro-2H-pyran-4-ylmethyl)amino]methyl}azetidin-3-ol |
| 148 | 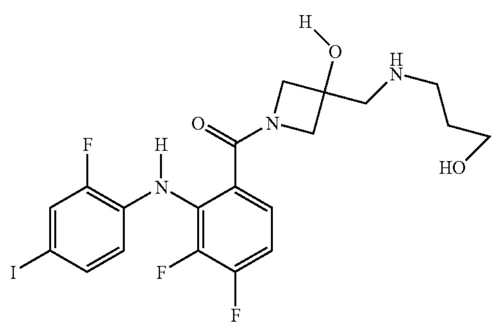 | 1-({3,4-difluoro-2-[(2-fluoro-4-iodophenyl)amino]phenyl}carbonyl)-3-{[(3-hydroxypropyl)amino]methyl}azetidin-3-ol |
| 149 | 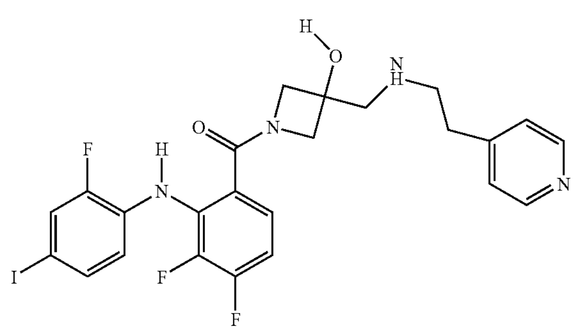 | 1-({3,4-difluoro-2-[(2-fluoro-4-iodophenyl)amino]phenyl}carbonyl)-3-{[[(2-pyridin-4-ylethyl)amino]methyl}azetidin-3-ol |

TABLE 1-continued

| Cmpd No. | Structure | Name |
|---|---|---|
| 150 | 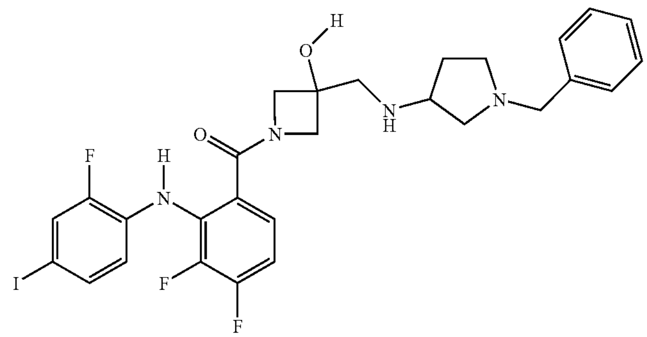 | 1-({3,4-difluoro-2-[(2-fluoro-4-iodophenyl)amino]phenyl}carbonyl)-3-({[1-(phenylmethyl)pyrrolidin-3-yl]amino}methyl)azetidin-3-ol |
| 151 | | 1-({3,4-difluoro-2-[(2-fluoro-4-iodophenyl)amino]phenyl}carbonyl)-3-({[2-(2-thienyl)ethyl]amino}methyl)azetidin-3-ol |
| 151 | | 1-({3,4-difluoro-2-[(2-fluoro-4-iodophenyl)amino]phenyl}carbonyl)-3-({[2-(2-thienyl)ethyl]amino}methyl)azetidin-3-ol |
| 152 | 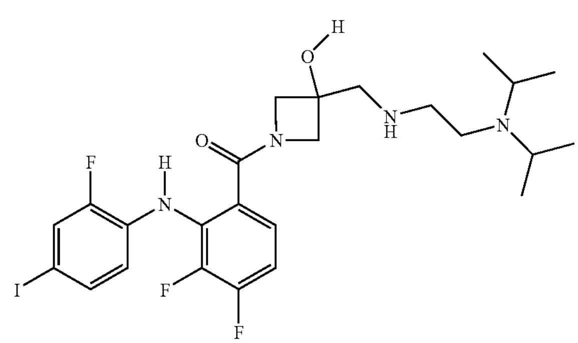 | 3-[({2-[bis(1-methylethyl)amino]ethyl}amino)methyl]-1-({3,4-difluoro-2-[(2-fluoro-4-iodophenyl)amino]phenyl}carbonyl)azetidin-3-ol |

TABLE 1-continued

| Cmpd No. | Structure | Name |
| --- | --- | --- |
| 153 | 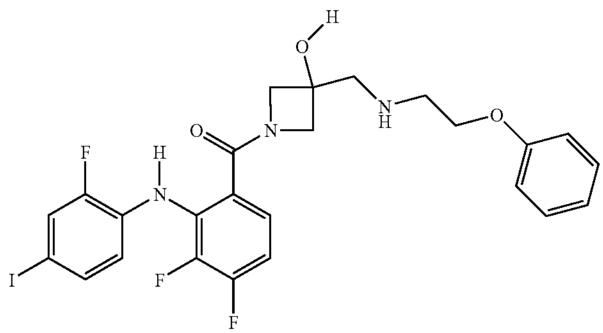 | 1-({3,4-difluoro-2-[(2-fluoro-4-iodophenyl)amino]phenyl}carbonyl)-3-({[2-(phenyloxy)ethyl]amino}methyl)azetidin-3-ol |
| 154 | 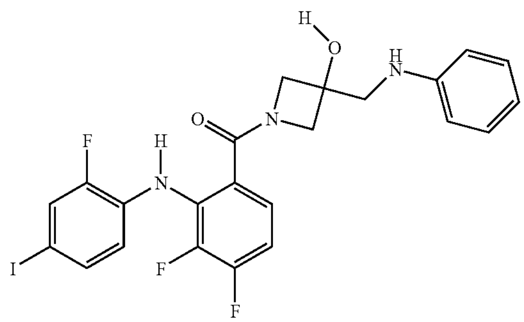 | 1-({3,4-difluoro-2-[(2-fluoro-4-iodophenyl)amino]phenyl}carbonyl)-3-[(phenylamino)methyl]azetidin-3-ol |
| 155 | 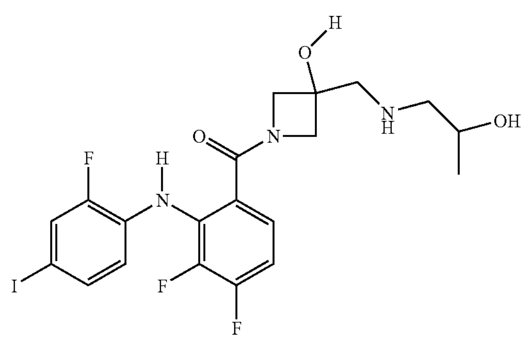 | 1-({3,4-difluoro-2-[(2-fluoro-4-iodophenyl)amino]phenyl}carbonyl)-3-{[(2-hydroxypropyl)amino]methyl}azetidin-3-ol |
| 156 | 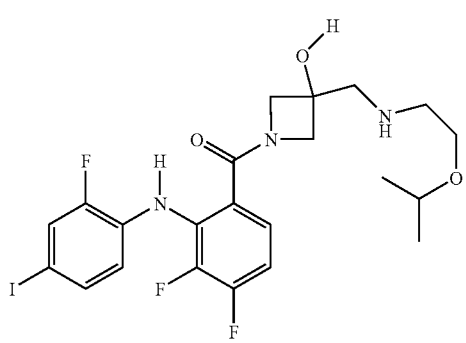 | 1-({3,4-difluoro-2-[(2-fluoro-4-iodophenyl)amino]phenyl}carbonyl)-3-[({2-[(1-methylethyl)oxy]ethyl}amino)methyl]azetidin-3-ol |

TABLE 1-continued

| Cmpd No. | Structure | Name |
| --- | --- | --- |
| 157 | 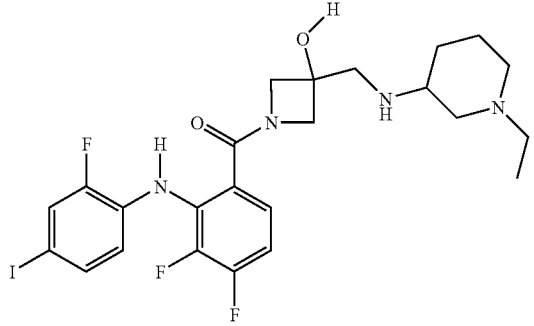 | 1-({3,4-difluoro-2-[(2-fluoro-4-iodophenyl)amino]phenyl}carbonyl)-3-{[(1-ethylpiperidin-3-yl)amino]methyl}azetidin-3-ol |
| 158 | 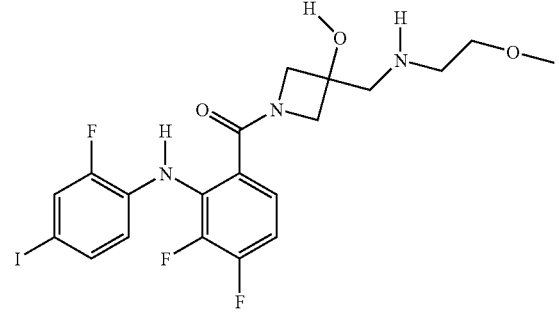 | 1-({3,4-difluoro-2-[(2-fluoro-4-iodophenyl)amino]phenyl}carbonyl)-3-({[2-(methyloxy)ethyl]amino}methyl)azetidin-3-ol |
| 159 | 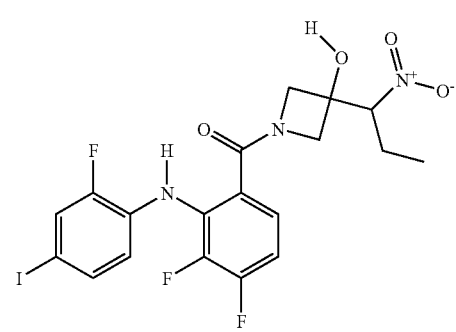 | 1-({3,4-difluoro-2-[(2-fluoro-4-iodophenyl)amino]phenyl}carbonyl)-3-(1-nitropropyl)azetidin-3-ol |
| 160 | 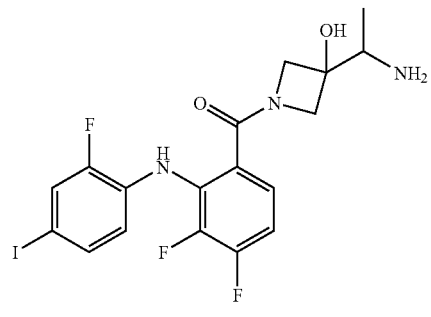 | 3-(1-aminoethyl)-1-({3,4-difluoro-2-[(2-fluoro-4-iodophenyl)amino]phenyl}carbonyl)azetidin-3-ol |

| Cmpd No. | Structure | Name |
| --- | --- | --- |
| 161 | 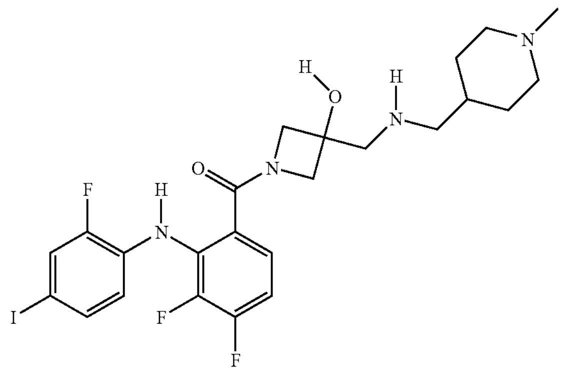 | 1-({3,4-difluoro-2-[(2-fluoro-4-iodophenyl)amino]phenyl}carbonyl)-3-({[(1-methylpiperidin-4-yl)methyl]amino}methyl)azetidin-3-ol |
| 162 | 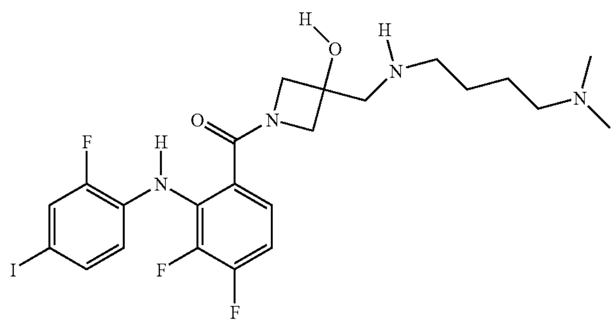 | 1-({3,4-difluoro-2-[(2-fluoro-4-iodophenyl)amino]phenyl}carbonyl)-3-({[4-(dimethylamino)butyl]amino}methyl)azetidin-3-ol |
| 163 | 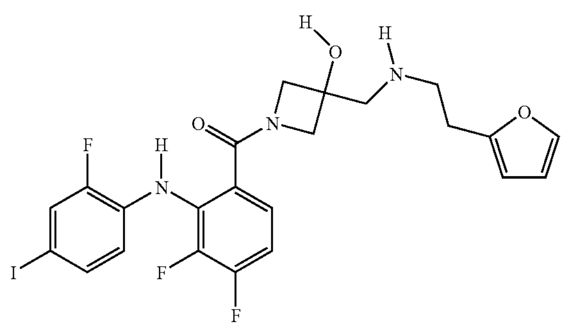 | 1-({3,4-difluoro-2-[(2-fluoro-4-iodophenyl)amino]phenyl}carbonyl)-3-{[(2-furan-2-ylethyl)amino]methyl}azetidin-3-ol |
| 164 | 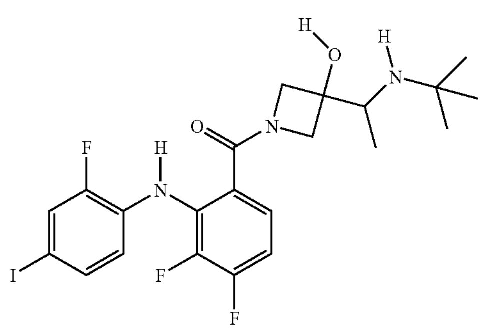 | 1-({3,4-difluoro-2-[(2-fluoro-4-iodophenyl)amino]phenyl}carbonyl)-3-{1-[(1,1-dimethylethyl)amino]ethyl}azetidin-3-ol |

TABLE 1-continued

| Cmpd No. | Structure | Name |
|---|---|---|
| 165 | 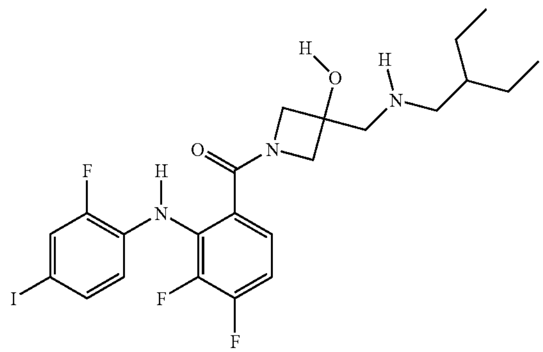 | 1-({3,4-difluoro-2-[(2-fluoro-4-iodophenyl)amino]phenyl}carbonyl)-3-{[(2-ethylbutyl)amino]methyl}azetidin-3-ol |
| 166 | 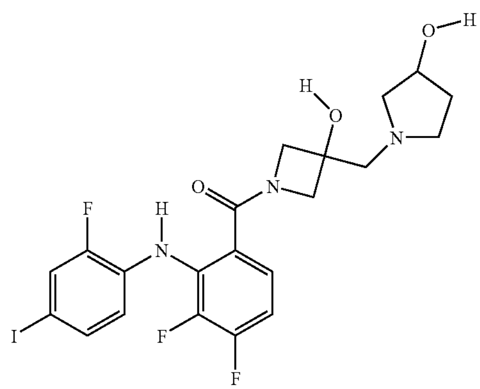 | 1-{[1-({3,4-difluoro-2-[(2-fluoro-4-iodophenyl)amino]phenyl}carbonyl)-3-hydroxyazetidin-3-yl]methyl}pyrrolidin-3-ol |
| 167 | 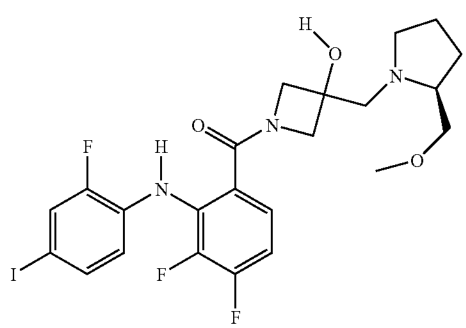 | 1-({3,4-difluoro-2-[(2-fluoro-4-iodophenyl)amino]phenyl}carbonyl)-3-({(2S)-2-[(methyloxy)methyl]pyrrolidin-1-yl}methyl)azetidin-3-ol |
| 168 | 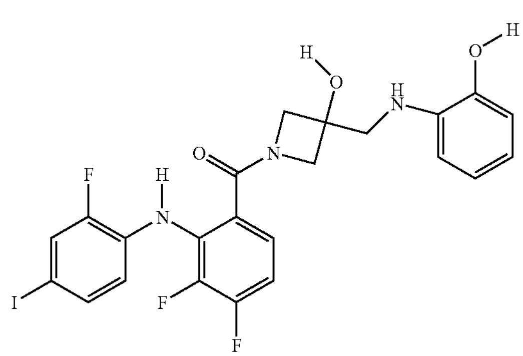 | 1-({3,4-difluoro-2-[(2-fluoro-4-iodophenyl)amino]phenyl}carbonyl)-3-{[(2-hydroxyphenyl)amino]methyl}azetidin-3-ol |

TABLE 1-continued

| Cmpd No. | Structure | Name |
|---|---|---|
| 169 | 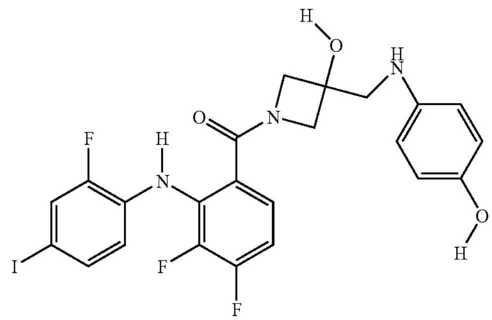 | 1-({3,4-difluoro-2-[(2-fluoro-4-iodophenyl)amino]phenyl}carbonyl)-3-{[(4-hydroxyphenyl)amino]methyl}azetidin-3-ol |
| 170 | 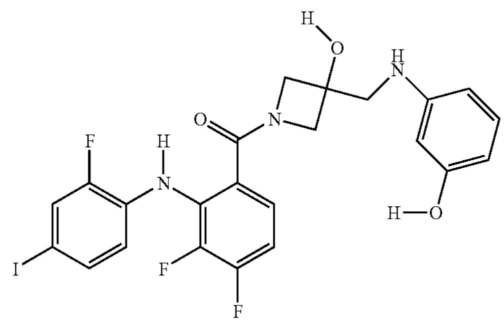 | 1-({3,4-difluoro-2-[(2-fluoro-4-iodophenyl)amino]phenyl}carbonyl)-3-{[(3-hydroxyphenyl)amino]methyl}azetidin-3-ol |
| 171 | 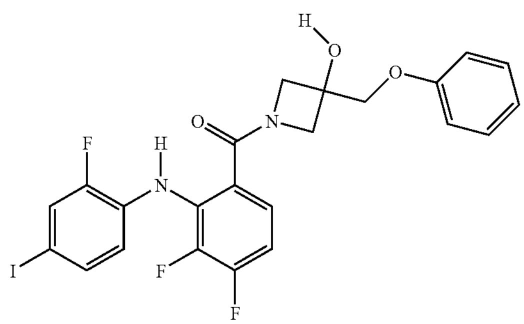 | 1-({3,4-difluoro-2-[(2-fluoro-4-iodophenyl)amino]phenyl}carbonyl)-3-[(phenyloxy)methyl]azetidin-3-ol |
| 172 | 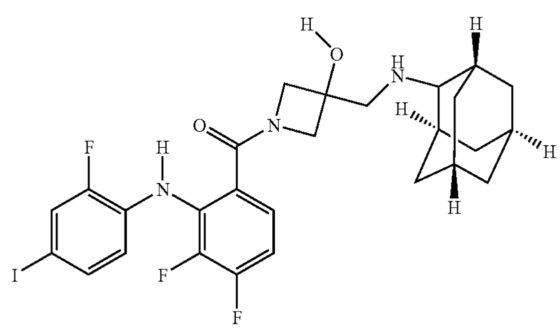 | 1-({3,4-difluoro-2-[(2-fluoro-4-iodophenyl)amino]phenyl}carbonyl)-3-{[(1r,3r,5R,7R)-tricyclo[3.3.1.1~3,7~]dec-2-ylamino]methyl}azetidin-3-ol |
| 173 | 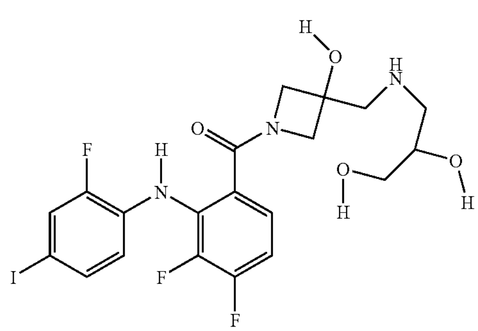 | 3-({[1-({3,4-difluoro-2-[(2-fluoro-4-iodophenyl)amino]phenyl}carbonyl)-3-hydroxyazetidin-3-yl]methyl}amino)propane-1,2-diol |

TABLE 1-continued

| Cmpd No. | Structure | Name |
|---|---|---|
| 174 | 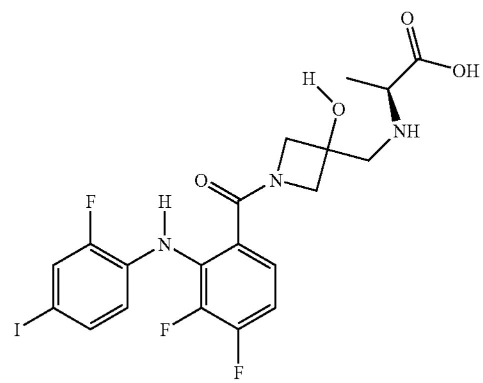 | N-{[1-({3,4-difluoro-2-[(2-fluoro-4-iodophenyl)amino]phenyl}carbonyl)-3-hydroxyazetidin-3-yl]methyl}-L-alanine |
| 175 | 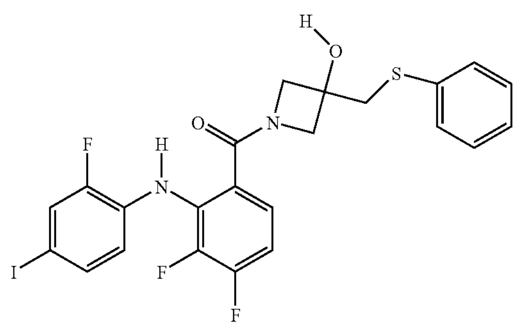 | 1-({3,4-difluoro-2-[(2-fluoro-4-iodophenyl)amino]phenyl}carbonyl)-3-[(phenylthio)methyl]azetidin-3-ol |
| 176 | 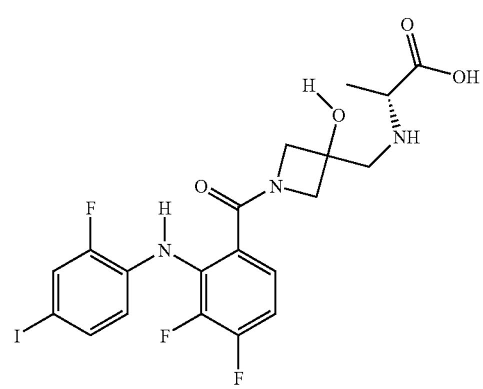 | N-{[1-({3,4-difluoro-2-[(2-fluoro-4-iodophenyl)amino]phenyl}carbonyl)-3-hydroxyazetidin-3-yl]methyl}-D-alanine |
| 177 | 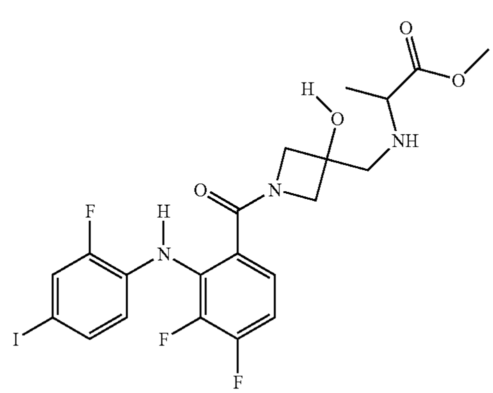 | methyl N-{[1-({3,4-difluoro-2-[(2-fluoro-4-iodophenyl)amino]phenyl}carbonyl)-3-hydroxyazetidin-3-yl]methyl}alaninate |

| Cmpd No. | Structure | Name |
|---|---|---|
| 178 | 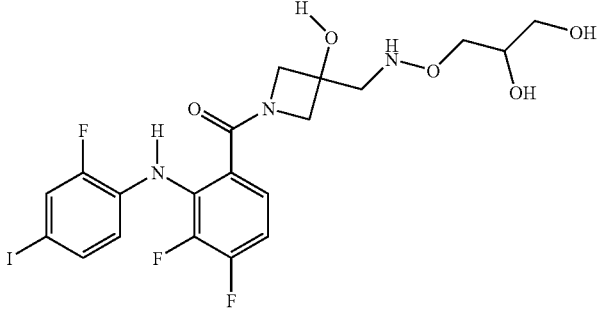 | 3-[({[1-({3,4-difluoro-2-[(2-fluoro-4-iodophenyl)amino]phenyl}carbonyl)-3-hydroxyazetidin-3-yl]methyl}amino)oxy]propane-1,2-diol |
| 179 | 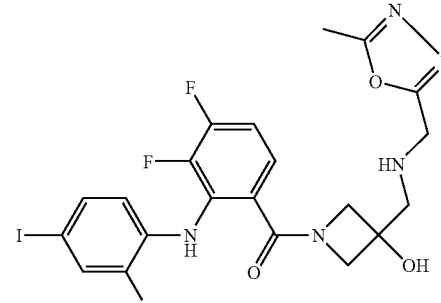 | 1-({3,4-difluoro-2-[(2-fluoro-4-iodophenyl)amino]phenyl}carbonyl)-3-({[(5-methyl-1,3,4-oxadiazol-2-yl)methyl]amino}methyl)azetidin-3-ol |
| 180 | 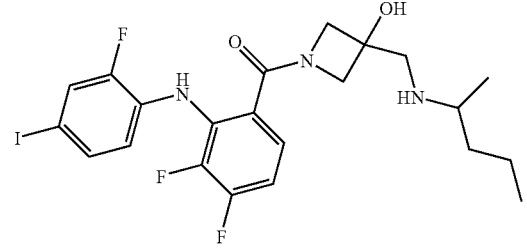 | 1-({3,4-difluoro-2-[(2-fluoro-4-iodophenyl)amino]phenyl}carbonyl)-3-{[(1-methylbutyl)amino]methyl}azetidin-3-ol |
| 181 | 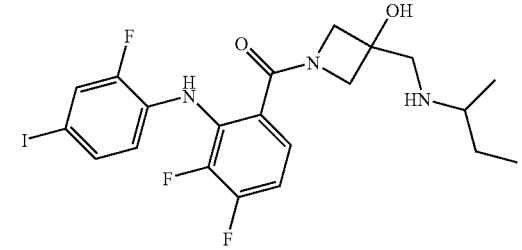 | 1-({3,4-difluoro-2-[(2-fluoro-4-iodophenyl)amino]phenyl}carbonyl)-3-{[(1-methylpropyl)amino]methyl}azetidin-3-ol |
| 182 | 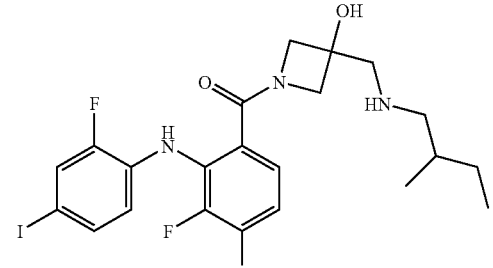 | 1-({3,4-difluoro-2-[(2-fluoro-4-iodophenyl)amino]phenyl}carbonyl)-3-{[(2-methylbutyl)amino]methyl}azetidin-3-ol |

TABLE 1-continued

| Cmpd No. | Structure | Name |
|---|---|---|
| 183 | 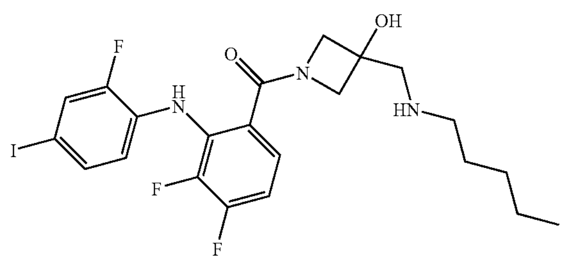 | 1-({3,4-difluoro-2-[(2-fluoro-4-iodophenyl)amino]phenyl}carbonyl)-3-[(pentylamino)methyl]azetidin-3-ol |
| 184 | 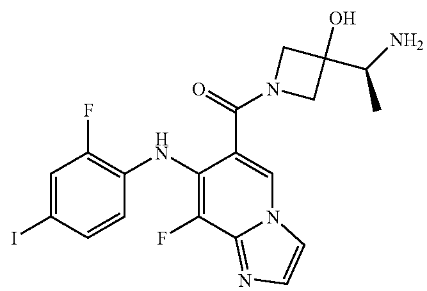 | 3-[(1S)-1-aminoethyl]-1-({8-fluoro-7-[(2-fluoro-4-iodophenyl)amino]imidazo[1,2-a]pyridin-6-yl}carbonyl)azetidin-3-ol |
| 185 | 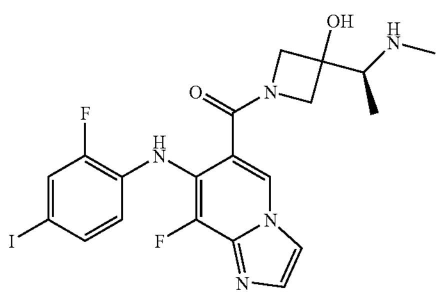 | 1-({8-fluoro-7-[(2-fluoro-4-iodophenyl)amino]imidazo[1,2-a]pyridin-6-yl}carbonyl)-3-[(1S)-1-(methylamino)ethyl]azetidin-3-ol |
| 186 | 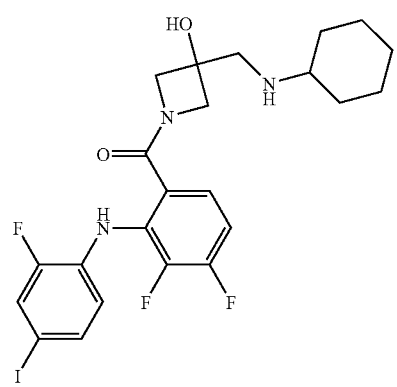 | 3-[(cyclohexylamino)methyl]-1-({3,4-difluoro-2-[(2-fluoro-4-iodophenyl)amino]phenyl}carbonyl)azetidin-3-ol |
| 187 | 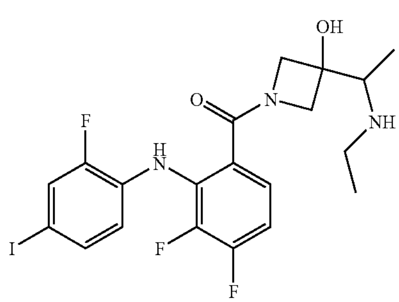 | 1-({3,4-difluoro-2-[(2-fluoro-4-iodophenyl)amino]phenyl}carbonyl)-3-[1-(ethylamino)ethyl]azetidin-3-ol |

| Cmpd No. | Structure | Name |
|---|---|---|
| 188 | 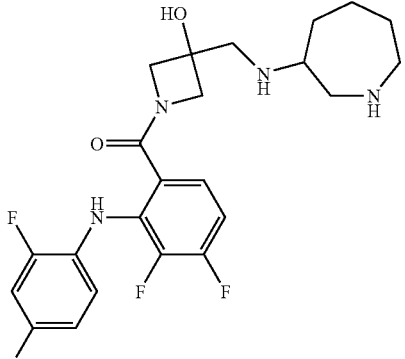 | 3-[(azepan-3-ylamino)methyl]-1-({3,4-difluoro-2-[(2-fluoro-4-iodophenyl)amino]phenyl}carbonyl)azetidin-3-ol |
| 189 | 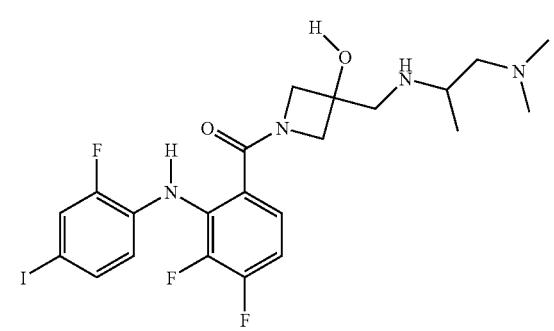 | 1-({3,4-difluoro-2-[(2-fluoro-4-iodophenyl)amino]phenyl}carbonyl)-3-({[2-(dimethylamino)-1-methylethyl]amino}methyl)azetidin-3-ol |
| 190 | 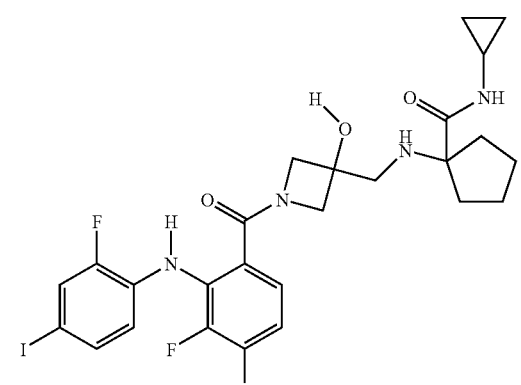 | N-cyclopropyl-1-({[1-({3,4-difluoro-2-[(2-fluoro-4-iodophenyl)amino]phenyl}carbonyl)-3-hydroxyazetidin-3-yl]methyl}amino)cyclopentanecarboxamide |
| 191 | 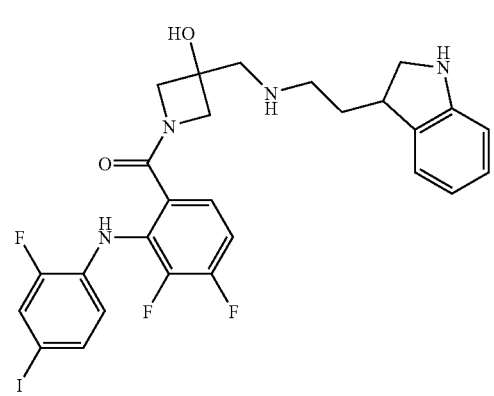 | 1-({3,4-difluoro-2-[(2-fluoro-4-iodophenyl)amino]phenyl}carbonyl)-3-({[2-(2,3-dihydro-1H-indol-3-yl)ethyl]amino}methyl)azetidin-3-ol |

TABLE 1-continued

| Cmpd No. | Structure | Name |
| --- | --- | --- |
| 192 | 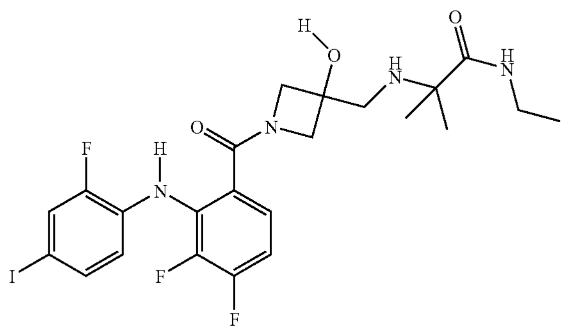 | N~2~-{[1-({3,4-difluoro-2-[(2-fluoro-4-iodophenyl)amino]phenyl}carbonyl)-3-hydroxyazetidin-3-yl]methyl}-N-ethyl-2-methylalaninamide |
| 193 | 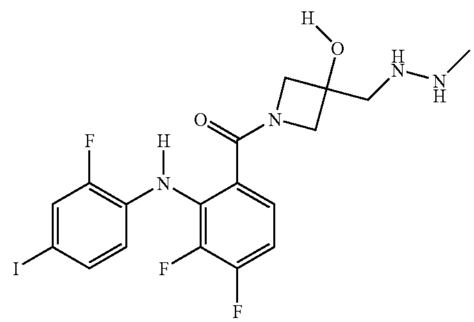 | 1-({3,4-difluoro-2-[(2-fluoro-4-iodophenyl)amino]phenyl}carbonyl)-3-[(2-methylhydrazino)methyl]azetidin-3-ol |
| 194 | 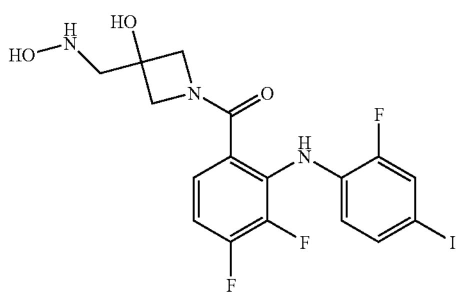 | 1-({3,4-difluoro-2-[(2-fluoro-4-iodophenyl)amino]phenyl}carbonyl)-3-[(hydroxyamino)methyl]azetidin-3-ol |
| 195 | 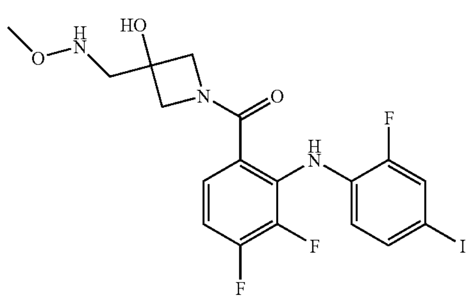 | 1-({3,4-difluoro-2-[(2-fluoro-4-iodophenyl)amino]phenyl}carbonyl)-3-{[(methyloxy)amino]methyl}azetidin-3-ol |
| 196 | 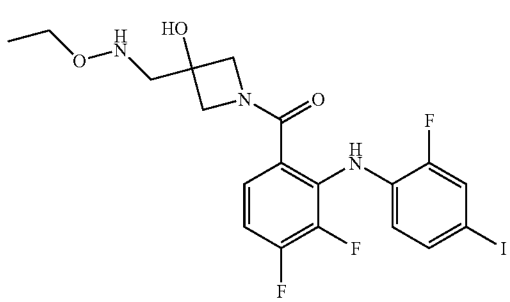 | 1-({3,4-difluoro-2-[(2-fluoro-4-iodophenyl)amino]phenyl}carbonyl)-3-{[(ethyloxy)amino]methyl}azetidin-3-ol |

TABLE 1-continued

| Cmpd No. | Structure | Name |
| --- | --- | --- |
| 197 | 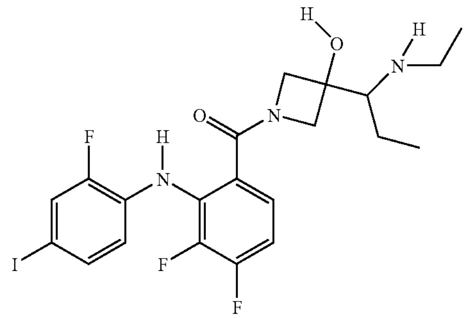 | 1-({3,4-difluoro-2-[(2-fluoro-4-iodophenyl)amino]phenyl}carbonyl)-3-[1-(ethylamino)propyl]azetidin-3-ol |
| 198 | 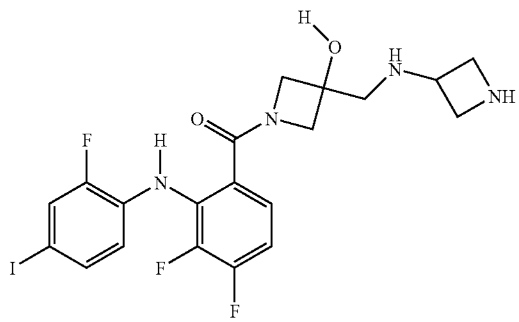 | 3-[(azetidin-3-ylamino)methyl]-1-({3,4-difluoro-2-{(2-fluoro-4-iodophenyl)amino]phenyl}carbonyl)azetidin-3-ol |
| 199 | 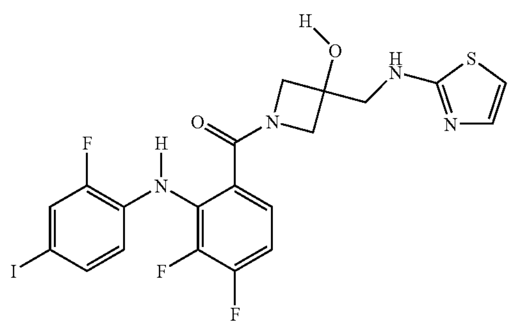 | 1-({3,4-difluoro-2-[(2-fluoro-4-iodophenyl)amino]phenyl}carbonyl)-3-[(1,3-thiazol-2-ylamino)methyl]azetidin-3-ol |
| 200 | 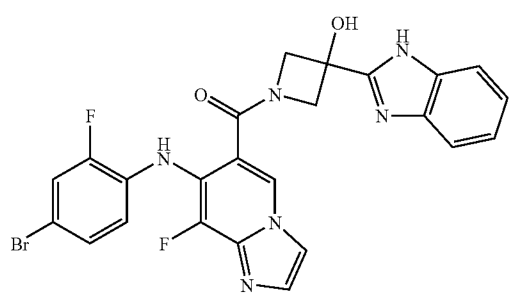 | 3-(1H-benzimidazol-2-yl)-1-({8-fluoro-7-[(2-fluoro-4-iodophenyl)amino]imidazo[1,2-a]pyridin-6-yl}carbonyl)azetidin-3-ol |
| 201 | 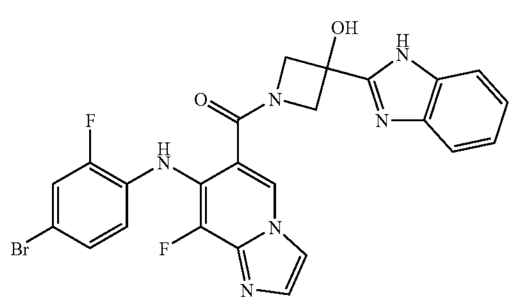 | 3-(1H-benzimidazol-2-yl)-1-({7-[(4-bromo-2-fluorophenyl)amino]-8-fluoroimidazo[1,2-a]pyridin-6-yl}carbonyl)azetidin-3-ol |

| Cmpd No. | Structure | Name |
| --- | --- | --- |
| 202 | 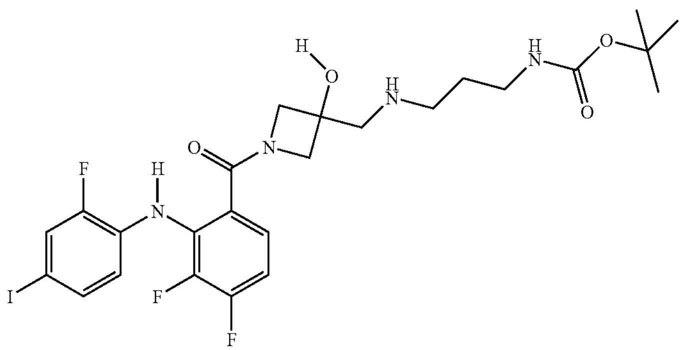 | 1,1-dimethylethyl [3-({[1-({3,4-difluoro-2-[(2-fluoro-4-iodophenyl)amino]phenyl}carbonyl)-3-hydroxyazetidin-3-yl]methyl}amino)propyl]carbamate |
| 203 | 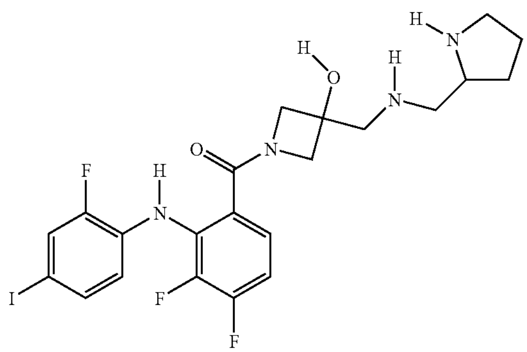 | 1-({3,4-difluoro-2-[(2-fluoro-4-iodophenyl)amino]phenyl}carbonyl)-3-{[(pyrrolidin-2-ylmethyl)amino]methyl}azetidin-3-ol |
| 204 | 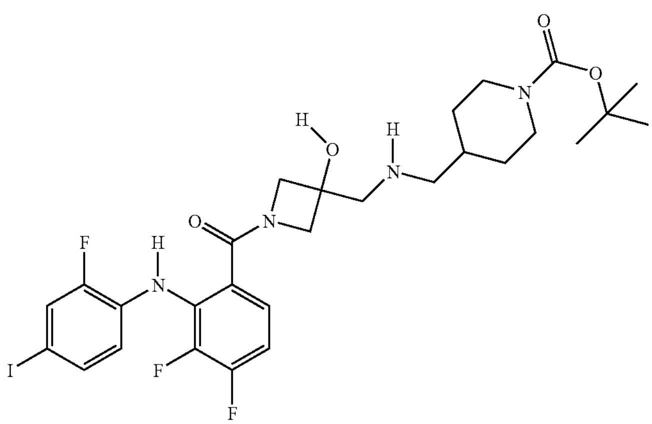 | 1,1-dimethylethyl 4-[({[1-({3,4-difluoro-2-[(2-fluoro-4-iodophenyl)amino]phenyl}carbonyl)-3-hydroxyazetidin-3-yl]methyl}amino)methyl]piperidine-1-carboxylate |
| 205 | 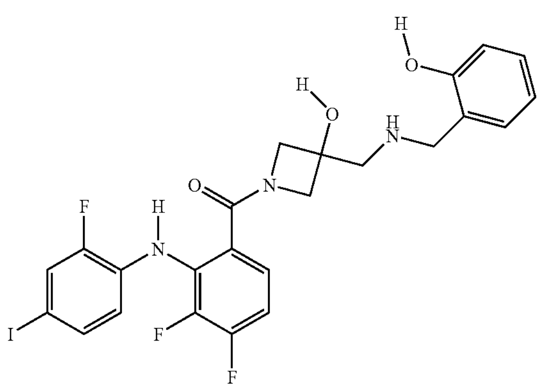 | 1-({3,4-difluoro-2-[(2-fluoro-4-iodophenyl)amino]phenyl}carbonyl)-3-({[(2-hydroxyphenyl)methyl]amino}methyl)azetidin-3-ol |

TABLE 1-continued

| Cmpd No. | Structure | Name |
|---|---|---|
| 206 | 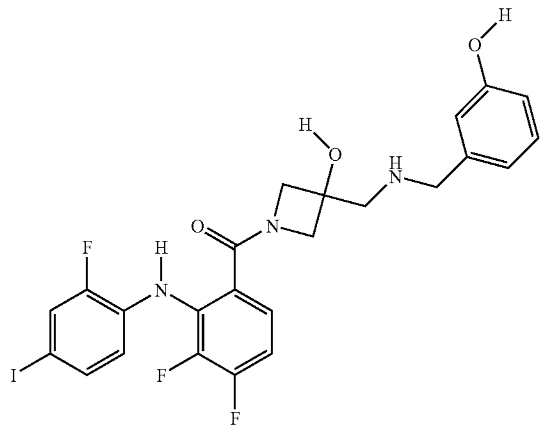 | 1-({3,4-difluoro-2-[(2-fluoro-4-iodophenyl)amino]phenyl}carbonyl)-3-({[(3-hydroxyphenyl)methyl]amino}methyl)azetidin-3-ol |
| 207 | 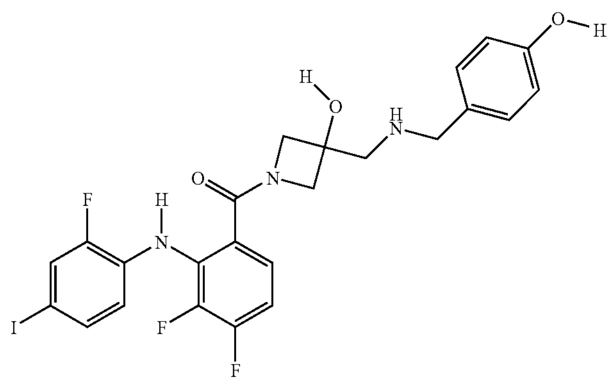 | 1-({3,4-difluoro-2-[(2-fluoro-4-iodophenyl)amino]phenyl}carbonyl)-3-({[(4-hydroxyphenyl)methyl]amino}methyl)azetidin-3-ol |
| 208 | 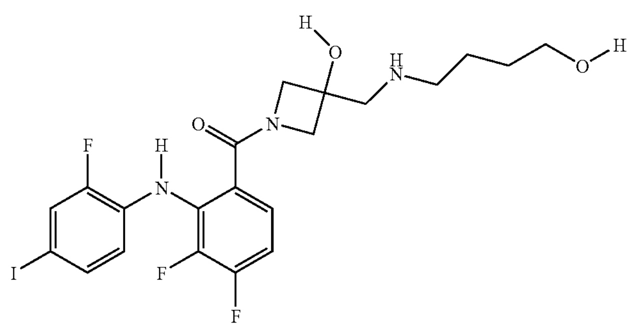 | 1-({3,4-difluoro-2-[(2-fluoro-4-iodophenyl)amino]phenyl}carbonyl)-3-{[(4-hydroxybutyl)amino]methyl}azetidin-3-ol |
| 209 | 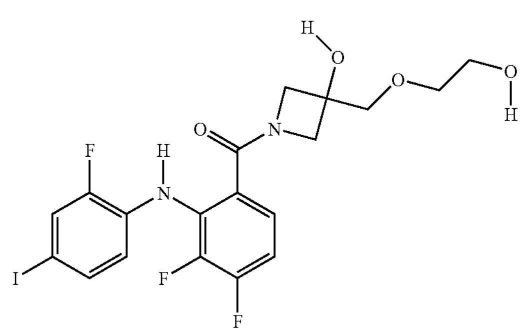 | 1-({3,4-difluoro-2-[(2-fluoro-4-iodophenyl)amino]phenyl}carbonyl)-3-{[(2-hydroxyethyl)oxy]methyl}azetidin-3-ol |

| Cmpd No. | Structure | Name |
|---|---|---|
| 210 | 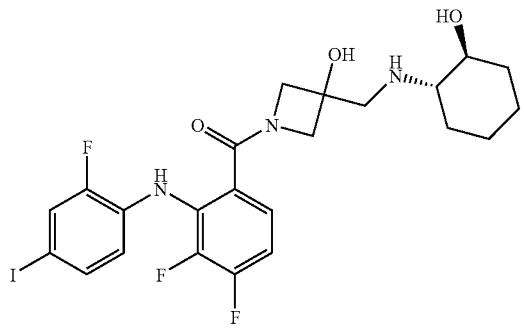 | 1-({3,4-difluoro-2-[(2-fluoro-4-iodophenyl)amino]phenyl}carbonyl)-3-({[(1S,2S)-2-hydroxycyclohexyl]amino}methyl)azetidin-3-ol |
| 211 | 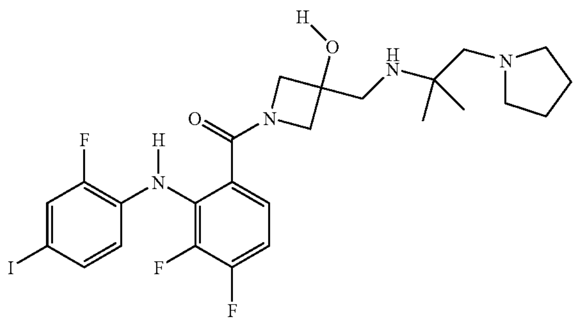 | 1-({3,4-difluoro-2-[(2-fluoro-4-iodophenyl)amino]phenyl}carbonyl)-3-{[(1,1-dimethyl-2-pyrrolidin-1-ylethyl)amino]methyl}azetidin-3-ol |
| 212 | 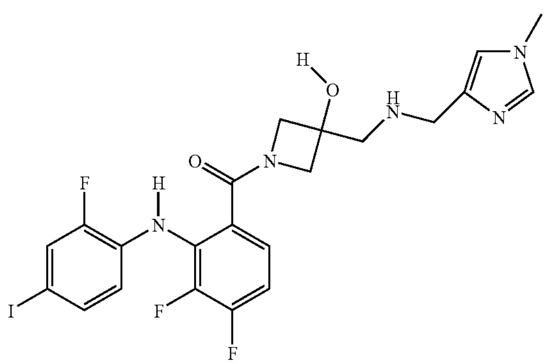 | 1-({3,4-difluoro-2-[(2-fluoro-4-iodophenyl)amino]phenyl}carbonyl)-3-({[(1-methyl-1H-imidazol-4-yl)methyl]amino}methyl)azetidin-3-ol |
| 213 | 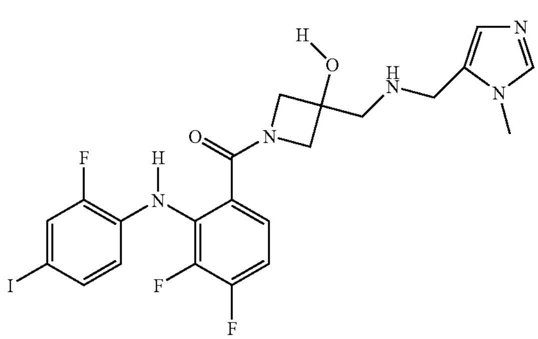 | 1-({3,4-difluoro-2-[(2-fluoro-4-iodophenyl)amino]phenyl}carbonyl)-3-({[(1-methyl-1H-imidazol-5-yl)methyl]amino}methyl)azetidin-3-ol |

TABLE 1-continued

| Cmpd No. | Structure | Name |
|---|---|---|
| 214 | 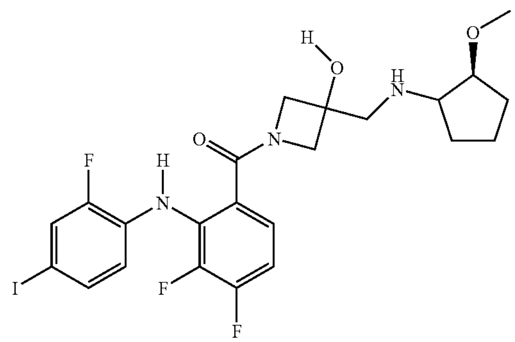 | 1-({3,4-difluoro-2-[(2-fluoro-4-iodophenyl)amino]phenyl}carbonyl)-3-({[(2S)-2-(methyloxy)cyclopentyl]amino}methyl)azetidin-3-ol |
| 215 | 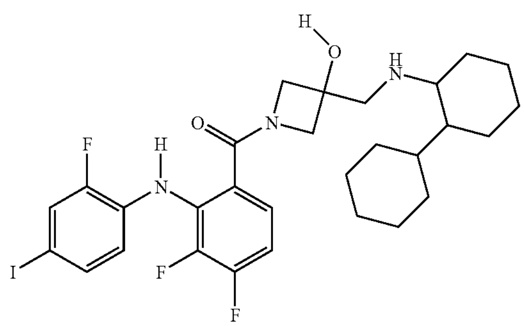 | 3-{[1,1'-bi(cyclohexyl)-2-ylamino]methyl}-1-({3,4-difluoro-2-[(2-fluoro-4-iodophenyl)amino]phenyl}carbonyl)azetidin-3-ol |
| 216 | 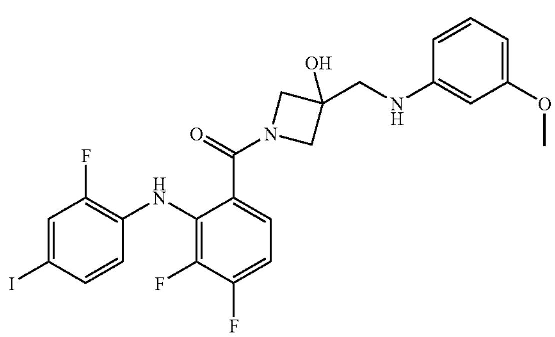 | 1-({3,4-difluoro-2-[(2-fluoro-4-iodophenyl)amino]phenyl}carbonyl)-3-({[3-(methyloxy)phenyl]amino}methyl)azetidin-3-ol |
| 217 | 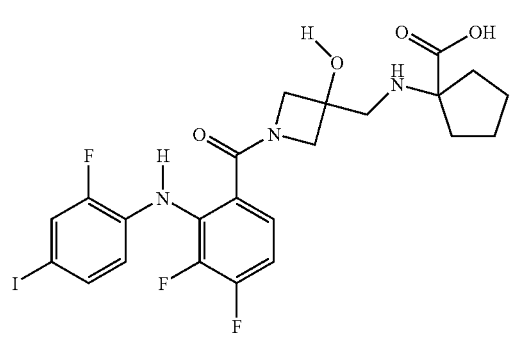 | 1-({[1-({3,4-difluoro-2-[(2-fluoro-4-iodophenyl)amino]phenyl}carbonyl)-3-hydroxyazetidin-3-yl]methyl}amino)cyclopentanecarboxylic acid |

TABLE 1-continued

| Cmpd No. | Structure | Name |
|---|---|---|
| 218 | 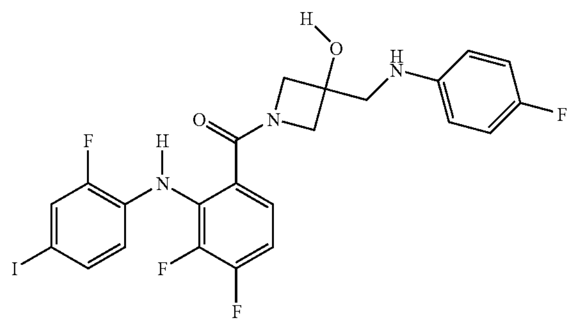 | 1-({3,4-difluoro-2-[(2-fluoro-4-iodophenyl)amino]phenyl}carbonyl)-3-{[(4-fluorophenyl)amino]methyl}azetidin-3-ol |
| 219 | 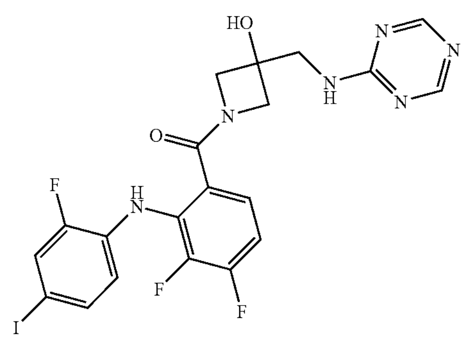 | 1-({3,4-difluoro-2-[(2-fluoro-4-iodophenyl)amino]phenyl}carbonyl)-3-[(1,3,5-triazin-2-ylamino)methyl]azetidin-3-ol |
| 220 | 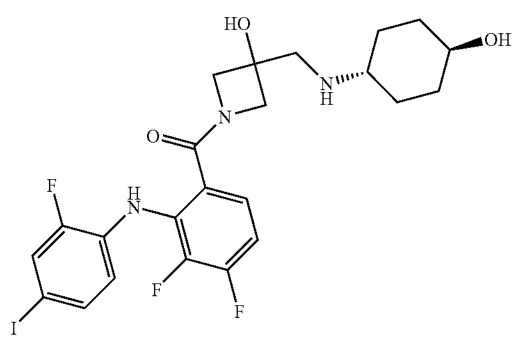 | 1-({3,4-difluoro-2-{(2-fluoro-4-iodophenyl)amino]phenyl}carbonyl)-3-{[(trans-4-hydroxycyclohexyl)amino]methyl}azetidin-3-ol |
| 221 | 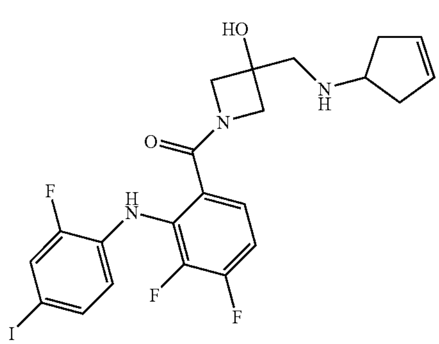 | 3-[(cyclopent-3-en-1-ylamino)methyl]-1-({3,4-difluoro-2-{(2-fluoro-4-iodophenyl)amino]phenyl}carbonyl)azetidin-3-ol |

TABLE 1-continued

| Cmpd No. | Structure | Name |
|---|---|---|
| 222 | 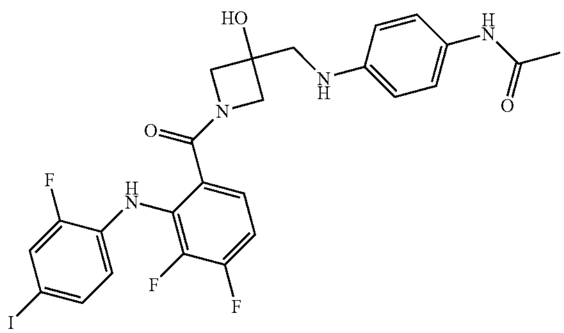 | N-[4-({[1-({3,4-difluoro-2-[(2-fluoro-4-iodophenyl)amino]phenyl}carbonyl)-3-hydroxyazetidin-3-yl]methyl}amino)phenyl]acetamide |
| 223 | 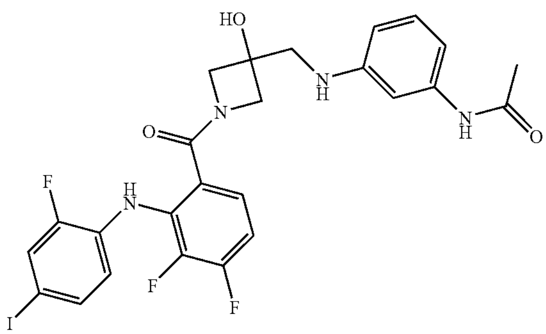 | N-[3-({[1-({3,4-difluoro-2-[(2-fluoro-4-iodophenyl)amino]phenyl}carbonyl)-3-hydroxyazetidin-3-yl]methyl}amino)phenyl]acetamide |
| 224 | 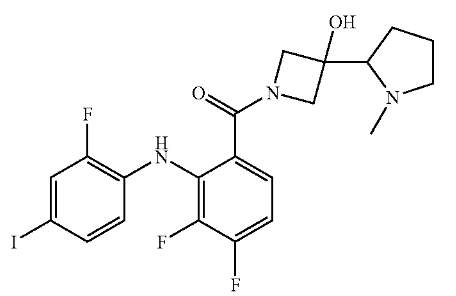 | 1-({3,4-difluoro-2-[(2-fluoro-4-iodophenyl)amino]phenyl}carbonyl)-3-(1-methylpyrrolidin-2-yl)azetidin-3-ol |
| 225 | 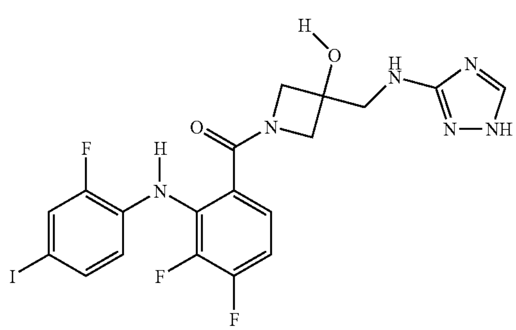 | 1-({3,4-difluoro-2-[(2-fluoro-4-iodophenyl)amino]phenyl}carbonyl)-3-[(1H-1,2,4-triazol-3-ylamino)methyl]azetidin-3-ol |

TABLE 1-continued

| Cmpd No. | Structure | Name |
|---|---|---|
| 226 | 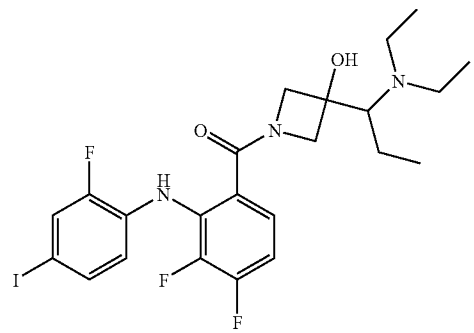 | 3-[1-(diethylamino)propyl]-1-({3,4-difluoro-2-[(2-fluoro-4-iodophenyl)amino]phenyl}carbonyl)azetidin-3-ol |
| 227 | 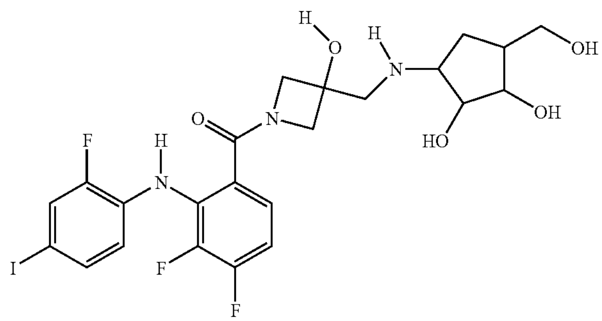 | 3-({[1-({3,4-difluoro-2-[(2-fluoro-4-iodophenyl)amino]phenyl}carbonyl)-3-hydroxyazetidin-3-yl]methyl}amino)-5-(hydroxymethyl)cyclopentane-1,2-diol |
| 228 | 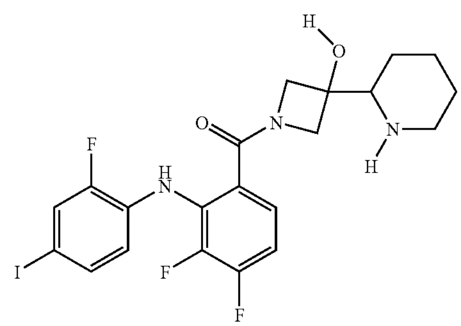 | 1-({3,4-difluoro-2-[(2-fluoro-4-iodophenyl)amino]phenyl}carbonyl)-3-piperidin-2-ylazetidin-3-ol |
| 229 | 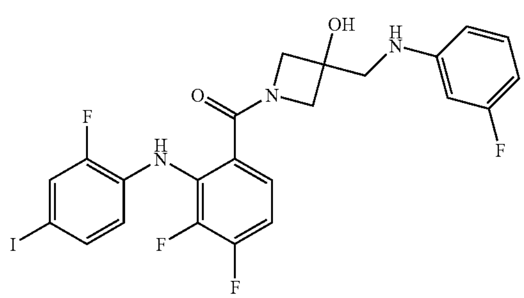 | 1-({3,4-difluoro-2-[(2-fluoro-4-iodophenyl)amino]phenyl}carbonyl)-3-{[(3-fluorophenyl)amino]methyl}azetidin-3-ol |
| 230 | 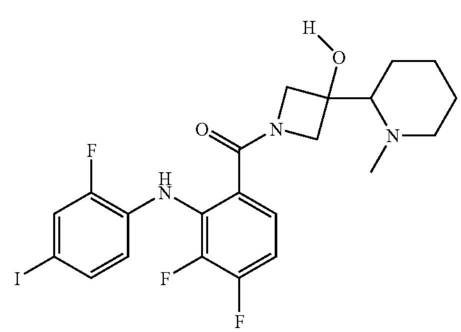 | 1-({3,4-difluoro-2-[(2-fluoro-4-iodophenyl)amino]phenyl}carbonyl)-3-(1-methylpiperidin-2-yl)azetidin-3-ol |

| Cmpd No. | Structure | Name |
| --- | --- | --- |
| 231 | 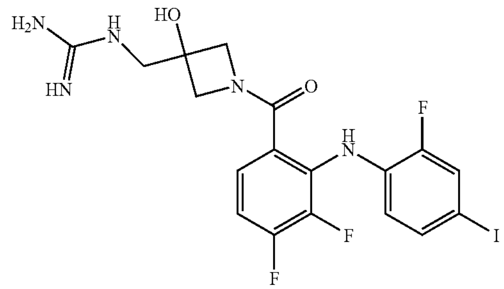 | 1-{[1-({3,4-difluoro-2-[(2-fluoro-4-iodophenyl)amino]phenyl}carbonyl)-3-hydroxyazetidin-3-yl]methyl}guanidine |
| 232 | 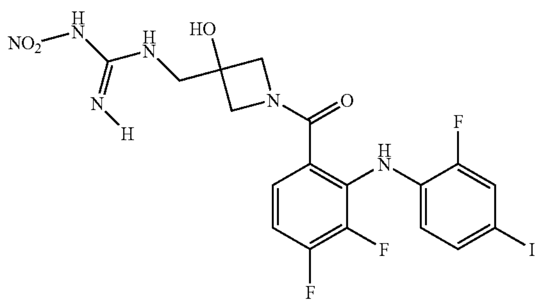 | 1-{[1-({3,4-difluoro-2-[(2-fluoro-4-iodophenyl)amino]phenyl}carbonyl)-3-hydroxyazetidin-3-yl]methyl}-3-nitroguanidine |
| 233 | 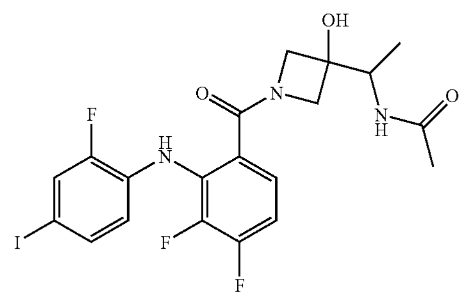 | N-{1-[1-({3,4-difluoro-2-[(2-fluoro-4-iodophenyl)amino]phenyl}carbonyl)-3-hydroxyazetidin-3-yl]ethyl}acetamide |
| 234 | 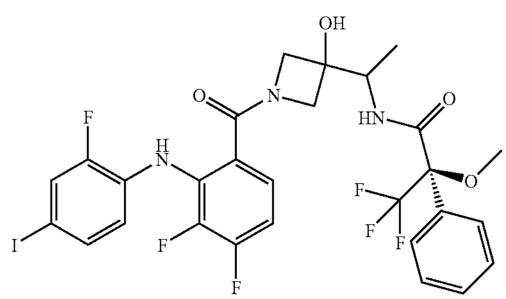 | (2R)-N-{1-[1-({3,4-difluoro-2-[(2-fluoro-4-iodophenyl)amino]phenyl}carbonyl)-3-hydroxyazetidin-3-yl]ethyl}-3,3,3-trifluoro-2-(methyloxy)-2-phenylpropanamide |
| 235 | 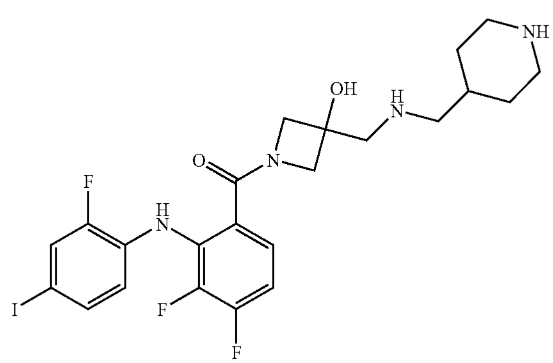 | 1-({3,4-difluoro-2-[(2-fluoro-4-iodophenyl)amino]phenyl}carbonyl)-3-{[(piperidin-4-ylmethyl)amino]methyl}azetidin-3-ol |

| Cmpd No. | Structure | Name |
| --- | --- | --- |
| 236 | 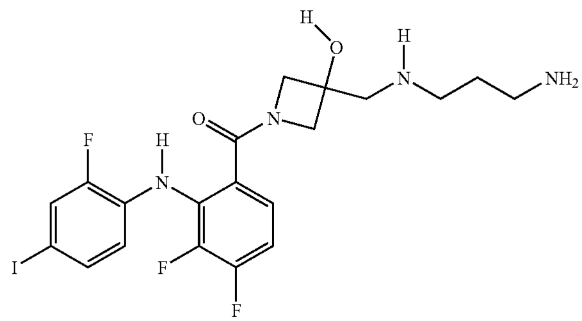 | 3-{[(3-aminopropyl)amino]methyl}-1-({3,4-difluoro-2-[(2-fluoro-4-iodophenyl)amino]phenyl}carbonyl)azetidin-3-ol |
| 237 | 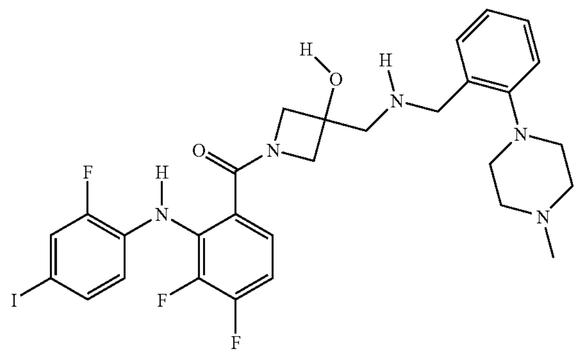 | 1-({3,4-difluoro-2-[(2-fluoro-4-iodophenyl)amino]phenyl}carbonyl)-3-[({[2-(4-methylpiperazin-1-yl)phenyl]methyl}amino)methyl]azetidin-3-ol |
| 238 | 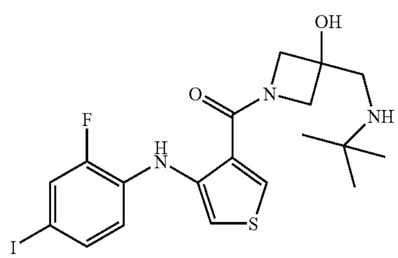 | 3-{[(1,1-dimethylethyl)amino]methyl}-1-({4-[(2-fluoro-4-iodophenyl)amino]-3-thienyl}carbonyl)azetidin-3-ol |
| 239 | 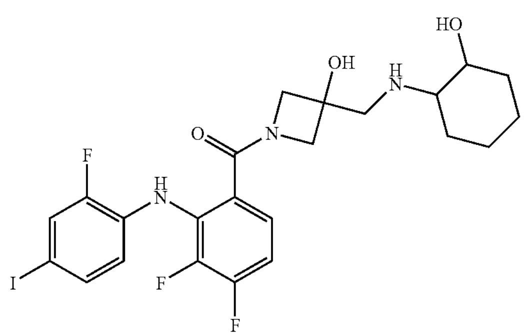 | 1-({3,4-difluoro-2-[(2-fluoro-4-iodophenyl)amino]phenyl}carbonyl)-3-{[(2-hydroxy-cyclohexyl)amino]methyl}azetidin-3-ol |
| 240 | 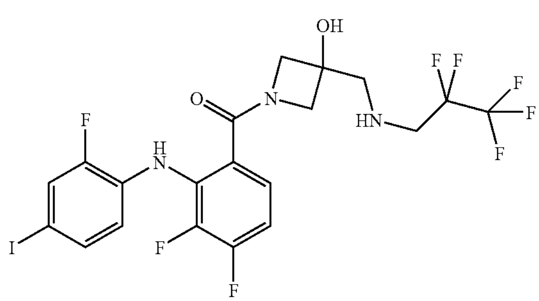 | 1-({3,4-difluoro-2-[(2-fluoro-4-iodophenyl)amino]phenyl}carbonyl)-3-{[(2,2,3,3,3-pentafluoropropyl)amino]methyl}azetidin-3-ol |

TABLE 1-continued

| Cmpd No. | Structure | Name |
|---|---|---|
| 241 | 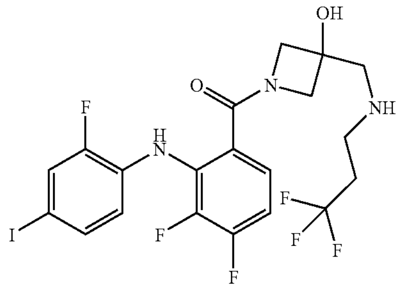 | 1-({3,4-difluoro-2-[(2-fluoro-4-iodophenyl)amino]phenyl}carbonyl)-3-{[(3,3,3-trifluoropropyl)amino]methyl}azetidin-3-ol |
| 242 | 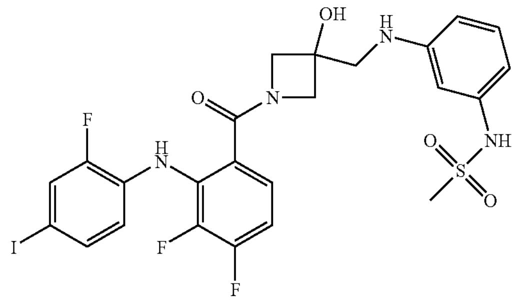 | N-[3-({[1-({3,4-difluoro-2-[(2-fluoro-4-iodophenyl)amino]phenyl}carbonyl)-3-hydroxyazetidin-3-yl]methyl}amino)phenyl]methanesulfonamide |
| 243 | 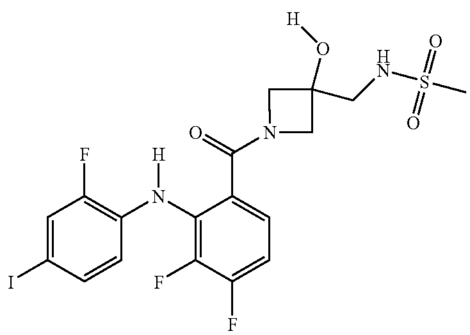 | N-{[1-({3,4-difluoro-2-[(2-fluoro-4-iodophenyl)amino]phenyl}carbonyl)-3-hydroxyazetidin-3-yl]methy}methanesulfonamide |
| 244 | 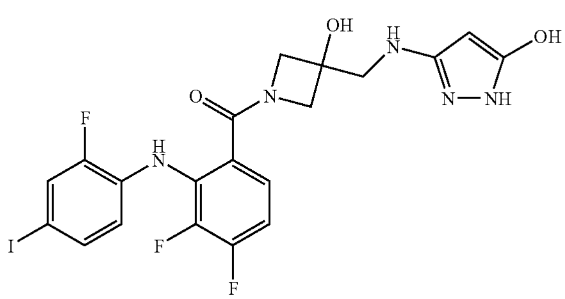 | 3-({[1-({3,4-difluoro-2-[(2-fluoro-4-iodophenyl)amino]phenyl}carbonyl)-3-hydroxyazetidin-3-yl]methyl}amino)-1H-pyrazol-5-ol |
| 245 | 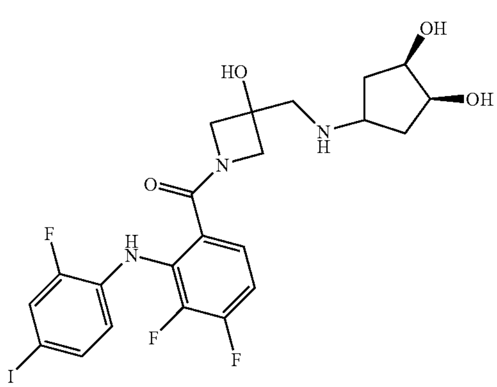 | (1R,2S)-4-({[1-({3,4-difluoro-2-[(2-fluoro-4-iodophenyl)amino]phenyl}carbonyl)-3-hydroxyazetidin-3-yl]methyl}amino)cyclopentane-1,2-diol |

TABLE 1-continued

| Cmpd No. | Structure | Name |
|---|---|---|
| 246 | 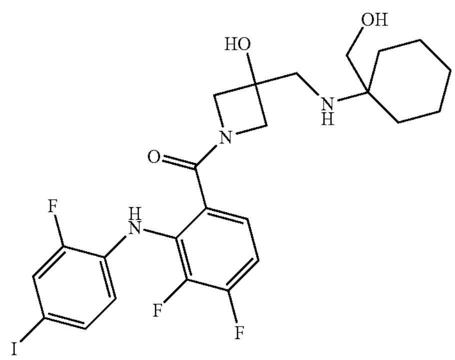 | 1-({3,4-difluoro-2-[(2-fluoro-4-iodophenyl)amino]phenyl}carbonyl)-3-({[1-(hydroxymethyl)cyclohexyl]amino}methyl)azetidin-3-ol |
| 247 | 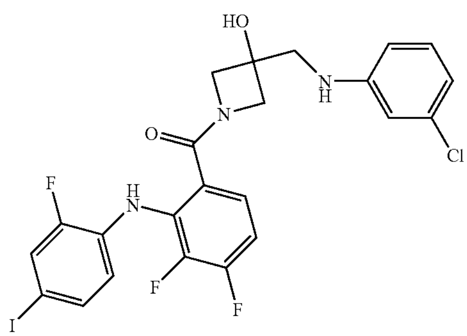 | 3-{[(3-chlorophenyl)amino]methyl}-1-({3,4-difluoro-2-[(2-fluoro-4-iodophenyl)amino]phenyl}carbonyl)azetidin-3-ol |
| 248 | 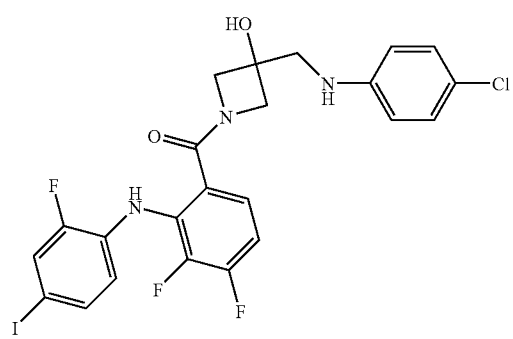 | 3-{[(4-chlorophenyl)amino]methyl}-1-({3,4-difluoro-2-[(2-fluoro-4-iodophenyl)amino]phenyl}carbonyl)azetidin-3-ol |
| 249 | 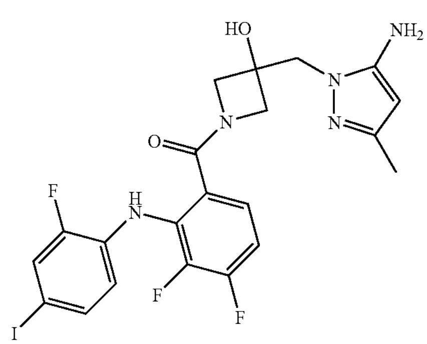 | 3-[(5-amino-3-methyl-1H-pyrazol-1-yl)methyl]-1-({3,4-difluoro-2-[(2-fluoro-4-iodophenyl)amino]phenyl}carbonyl)azetidin-3-ol |

| Cmpd No. | Structure | Name |
|---|---|---|
| 250 | 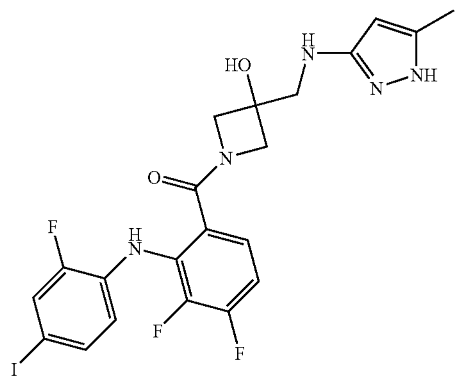 | 1-({3,4-difluoro-2-[(2-fluoro-4-iodophenyl)amino]phenyl}carbonyl)-3-{[(5-methyl-1H-pyrazol-3-yl)amino]methyl}azetidin-3-ol |
| 251 | 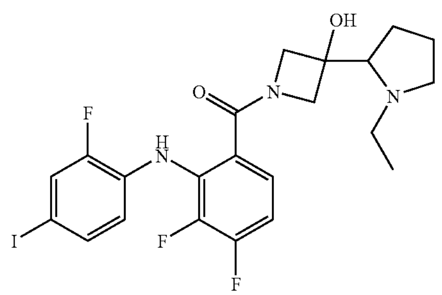 | 1-({3,4-difluoro-2-[(2-fluoro-4-iodophenyl)amino]phenyl}carbonyl)-3-(1-ethylpyrrolidin-2-yl)azetidin-3-ol |
| 252 | 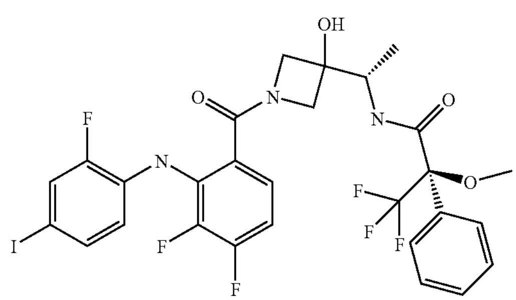 | (2R)-N-{(1S)-1-[1-({3,4-difluoro-2-[(2-fluoro-4-iodophenyl)amino]phenyl}carbonyl)-3-hydroxyazetidin-3-yl]ethyl}-3,3,3-trifluoro-2-(methyloxy)-2-phenylpropanamide |
| 253 | 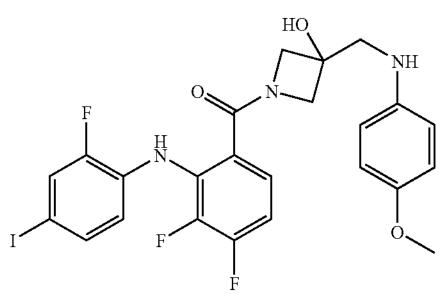 | 1-({3,4-difluoro-2-[(2-fluoro-4-iodophenyl)amino]phenyl}carbonyl)-3-({[4-(methyloxy)phenyl]amino}methyl)azetidin-3-ol |
| 254 | 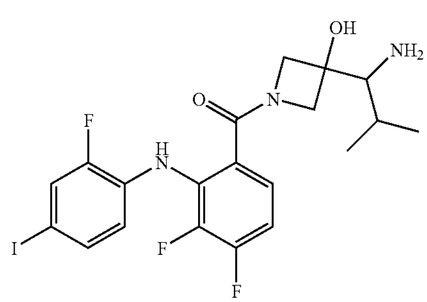 | 3-(1-amino-2-methylpropyl)-1-({3,4-difluoro-2-[(2-fluoro-4-iodophenyl)amino]phenyl}carbonyl)azetidin-3-ol |

TABLE 1-continued

| Cmpd No. | Structure | Name |
|---|---|---|
| 255 | 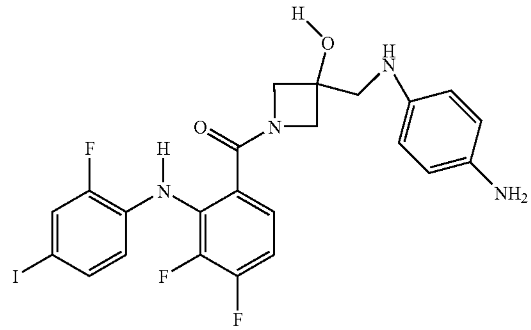 | 3-{[(4-aminophenyl)amino]methyl}-1-({3,4-difluoro-2-[(2-fluoro-4-iodophenyl)amino]phenyl}carbonyl)azetidin-3-ol |
| 256 | 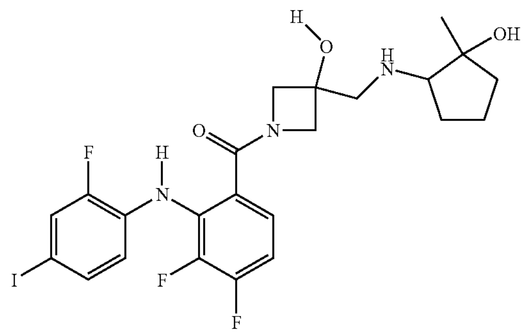 | 1-({3,4-difluoro-2-[(2-fluoro-4-iodophenyl)amino]phenyl}carbonyl)-3-{[(2-hydroxy-2-methylcyclopentyl)amino]methyl}azetidin-3-ol |
| 257 | 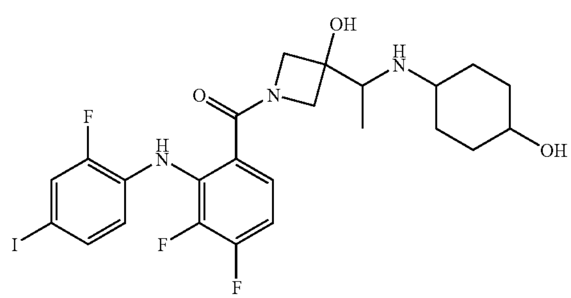 | 1-({3,4-difluoro-2-[(2-fluoro-4-iodophenyl)amino]phenyl}carbonyl)-3-{1-[(4-hydroxy-cyclohexyl)amino]ethyl}azetidin-3-ol |
| 258 | 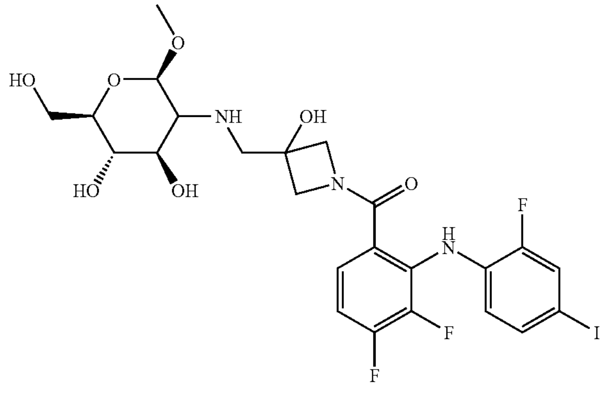 | methyl (2xi)-2-deoxy-2-({[1-({3,4-difluoro-2-[(2-fluoro-4-iodophenyl)amino]phenyl}carbonyl)-3-hydroxyazetidin-3-yl]methyl}amino)-beta-D-arabino-hexopyranoside |

TABLE 1-continued

| Cmpd No. | Structure | Name |
|---|---|---|
| 259 | 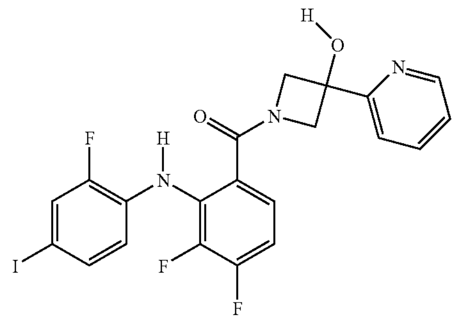 | 1-({3,4-difluoro-2-[(2-fluoro-4-iodophenyl)amino]phenyl}carbonyl)-3-pyridin-2-ylazetidin-3-ol |
| 260 | 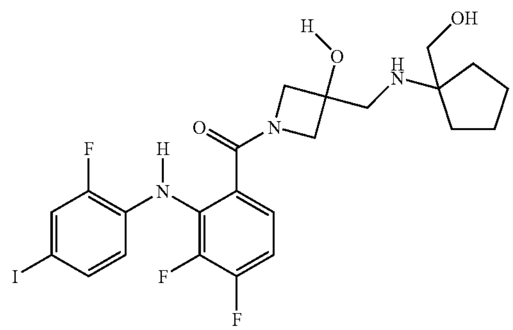 | 1-({3,4-difluoro-2-[(2-fluoro-4-iodophenyl)amino]phenyl}carbonyl)-3-({[1-(hydroxymethyl)cyclopentyl]amino}methyl)azetidin-3-ol |
| 261 | 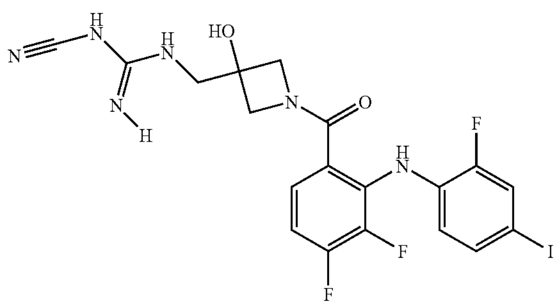 | 1-cyano-3-{[1-({3,4-difluoro-2-[(2-fluoro-4-iodophenyl)amino]phenyl}carbonyl)-3-hydroxyazetidin-3-yl]methyl}guanidine |
| 262 | 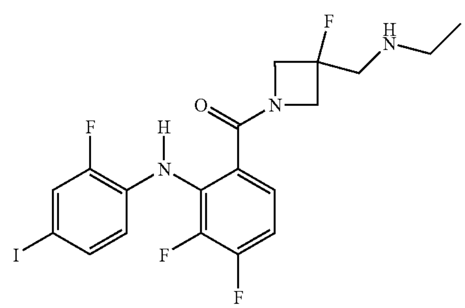 | 6-({3-[(ethylamino)methyl]-3-fluoroazetidin-1-yl}carbonyl)-2,3-difluoro-N-(2-fluoro-4-iodophenyl)aniline |
| 263 | 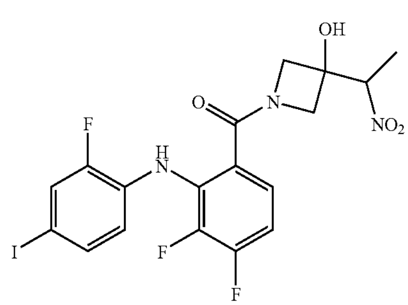 | 1-({3,4-difluoro-2-[(2-fluoro-4-iodophenyl)amino]phenyl}carbonyl)-3-(1-nitroethyl)azetidin-3-ol |

TABLE 1-continued

| Cmpd No. | Structure | Name |
| --- | --- | --- |
| 264 | 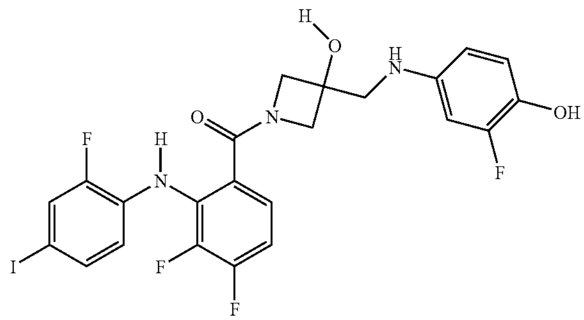 | 1-({3,4-difluoro-2-[(2-fluoro-4-iodophenyl)amino]phenyl}carbonyl)-3-{[(3-fluoro-4-hydroxyphenyl)amino]methyl}azetidin-3-ol |
| 265 | 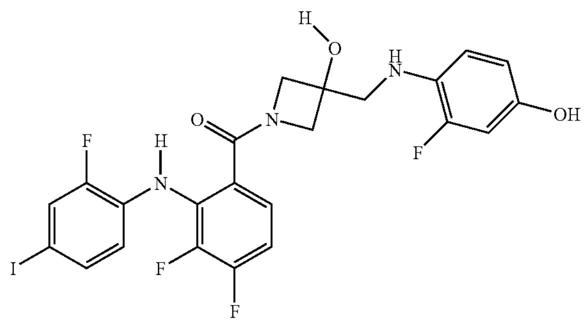 | 1-({3,4-difluoro-2-[(2-fluoro-4-iodophenyl)amino]phenyl}carbonyl)-3-{[(2-fluoro-4-hydroxyphenyl)amino]methyl}azetidin-3-ol |
| 266 | 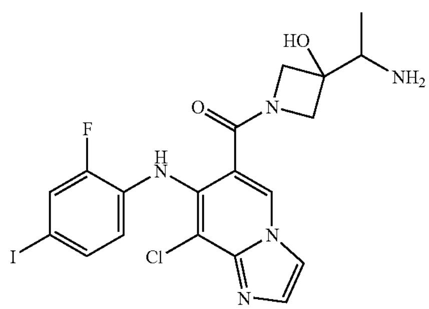 | 3-(1-aminoethyl)-1-({8-chloro-7-[(2-fluoro-4-iodophenyl)amino]imidazo[1,2-a]pyridin-6-yl}carbonyl)azetidin-3-ol |
| 267 | 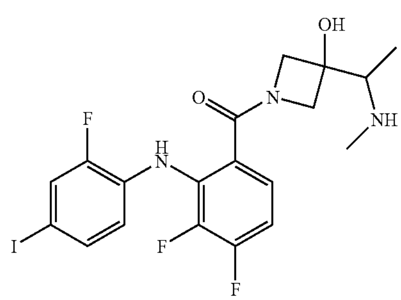 | 1-({3,4-difluoro-2-[(2-fluoro-4-iodophenyl)amino]phenyl}carbonyl)-3-[1-(methylamino)ethyl]azetidin-3-ol |
| 268 | 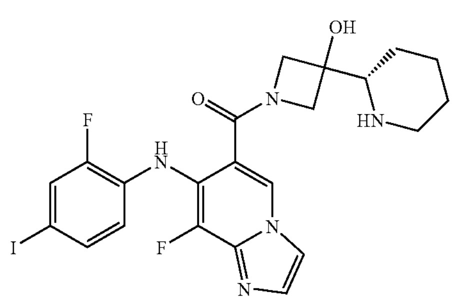 | 1-({8-fluoro-7-[(2-fluoro-4-iodophenyl)amino]imidazo[1,2-a]pyridin-6-yl}carbonyl)-3-{(2S)-piperidin-2-yl}azetidin-3-ol |

TABLE 1-continued

| Cmpd No. | Structure | Name |
|---|---|---|
| 269 | 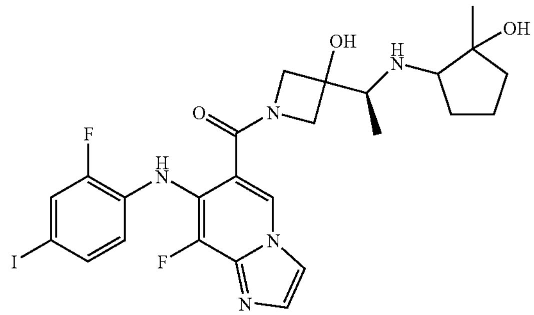 | 1-({8-fluoro-7-[(2-fluoro-4-iodophenyl)amino]imidazo[1,2-a]pyridin-6-yl}carbonyl)-3-{(1S)-1-[(2-hydroxy-2-methylcyclopentyl)amino]ethyl}azetidin-3-ol |
| 270 | 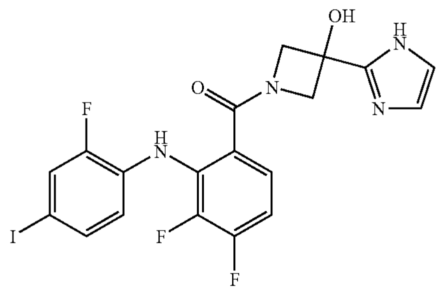 | 1-({3,4-difluoro-2-[(2-fluoro-4-iodophenyl)amino]phenyl}carbonyl)-3-(1H-imidazol-2-yl)azetidin-3-ol |
| 271 | 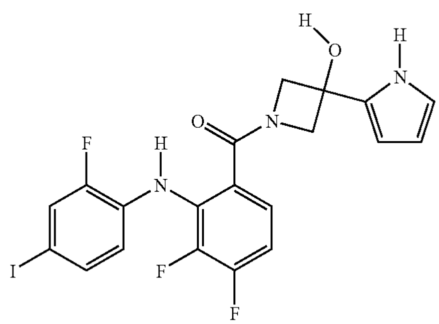 | 1-({3,4-difluoro-2-[(2-fluoro-4-iodophenyl)amino]phenyl}carbonyl)-3-(1H-pyrrol-2-yl)azetidin-3-ol |
| 272 | 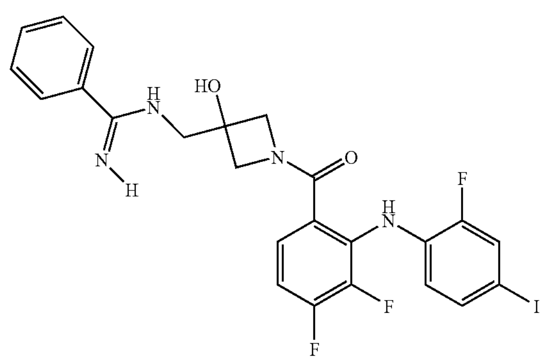 | N-{[1-({3,4-difluoro-2-[(2-fluoro-4-iodophenyl)amino]phenyl}carbonyl)-3-hydroxyazetidin-3-yl]methyl}benzenecarboximidamide |
| 273 | 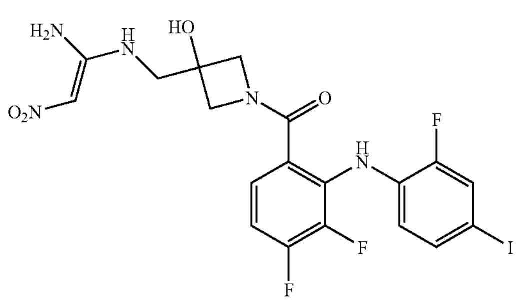 | 3-({[[(E)-1-amino-2-nitroethenyl]amino}methyl)-1-({3,4-difluoro-2-[(2-fluoro-4-iodophenyl)amino]phenyl}carbonyl)azetidin-3-ol |

TABLE 1-continued

| Cmpd No. | Structure | Name |
|---|---|---|
| 274 | 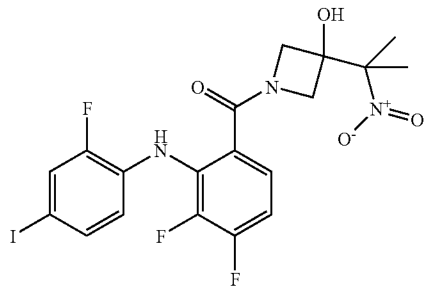 | 1-({3,4-difluoro-2-[(2-fluoro-4-iodophenyl)amino]phenyl}carbonyl)-3-(1-methyl-1-nitroethyl)azetidin-3-ol |
| 275 | 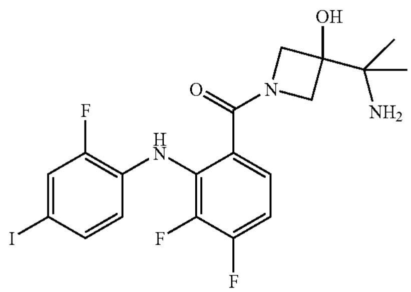 | 3-(1-amino-1-methylethyl)-1-({3-4-difluoro-2-[(2-fluoro-4-iodophenyl)amino}phenyl}carbonyl)azetidin-3-ol |
| 276 | 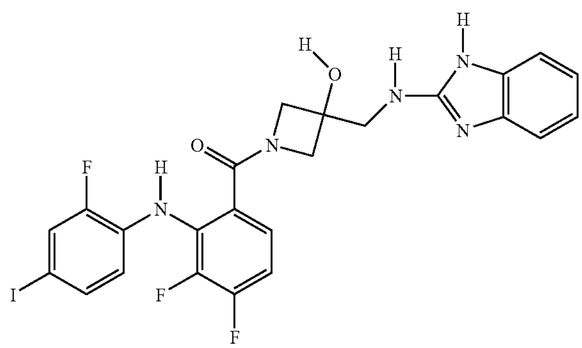 | 3-[(1H-benzimidazol-2-ylamino)methyl]-1-({3,4-difluoro-2-[(2-fluoro-4-iodophenyl)amino]phenyl}carbonyl)azetidin-3-ol |
| 277 | 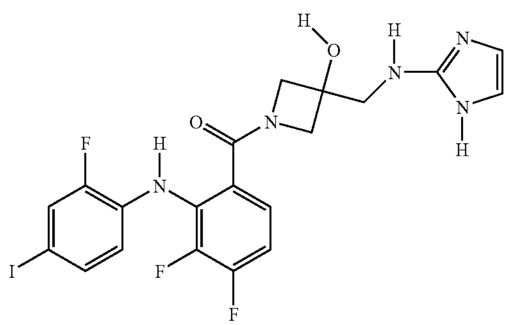 | 1-({3,4-difluoro-2-[(2-fluoro-4-iodophenyl)amino]phenyl}carbonyl)-3-[(1H-imidazol-2-ylamino)methyl]azetidin-3-ol |
| 278 | 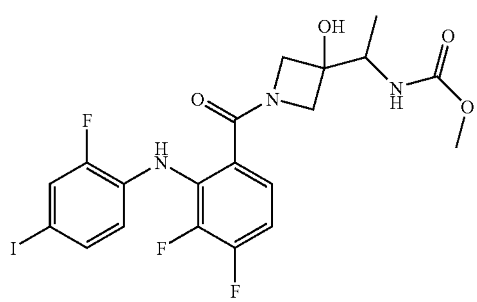 | methyl {1-[1-({3,4-difluoro-2-[(2-fluoro-4-iodophenyl)amino]phenyl}carbonyl)-3-hydroxyazetidin-3-yl]ethyl}carbamate |

| Cmpd No. | Structure | Name |
| --- | --- | --- |
| 279 | 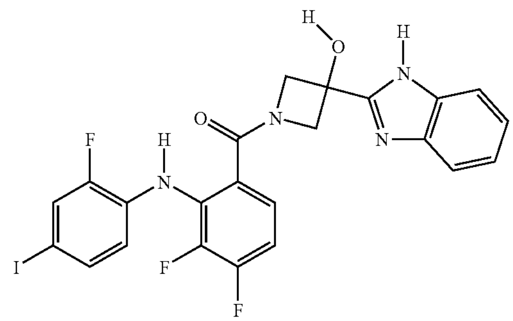 | 3-(1H-benzimidazol-2-yl)-1-({3,4-difluoro-2-[(2-fluoro-4-iodophenyl)amino]phenyl}carbonyl)azetidin-3-ol |
| 280 | 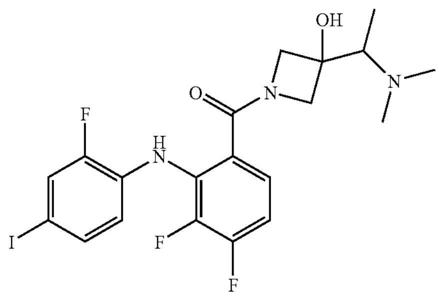 | 1-({3,4-difluoro-2-[(2-fluoro-4-iodophenyl)amino]phenyl}carbonyl)-3-[1-(dimethylamino)ethyl]azetidin-3-ol |
| 281 | 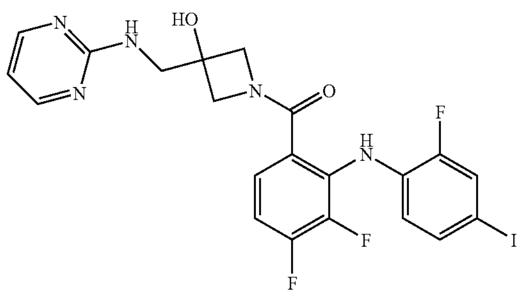 | 1-({3,4-difluoro-2-[(2-fluoro-4-iodophenyl)amino]phenyl}carbonyl)-3-[(pyrimidin-2-ylamino)methyl]azetidin-3-ol |
| 282 | 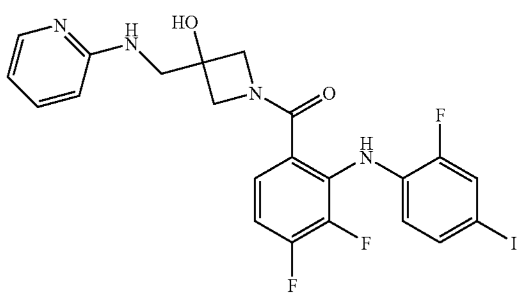 | 1-({3,4-difluoro-2-[(2-fluoro-4-iodophenyl)amino]phenyl}carbonyl)-3-[(pyridin-2-ylamino)methyl]azetidin-3-ol |
| 283 | 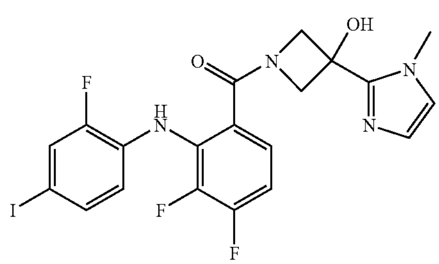 | 1-({3,4-difluoro-2-[(2-fluoro-4-iodophenyl)amino]phenyl}carbonyl)-3-(1-methyl-1H-imidazol-2-yl)azetidin-3-ol |

TABLE 1-continued

| Cmpd No. | Structure | Name |
|---|---|---|
| 284 | 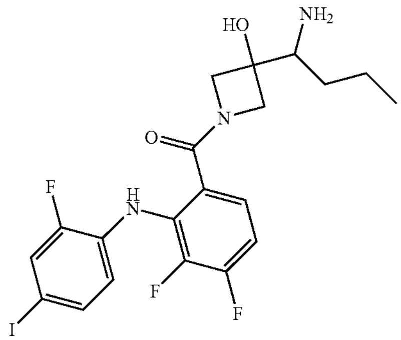 | 3-(1-aminobutyl)-1-({3,4-difluoro-2-[(2-fluoro-4-iodophenyl)amino]phenyl}carbonyl)azetidin-3-ol |
| 285 | 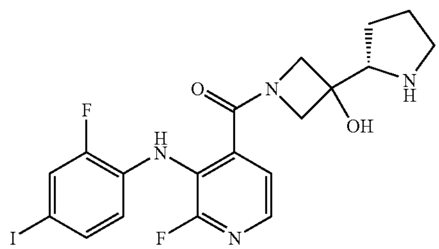 | 1-({2-fluoro-3-[(2-fluoro-4-iodophenyl)amino]pyridin-4-yl}carbonyl)-3-[(2S)-pyrrolidin-2-yl]azetidin-3-ol |
| 286 | 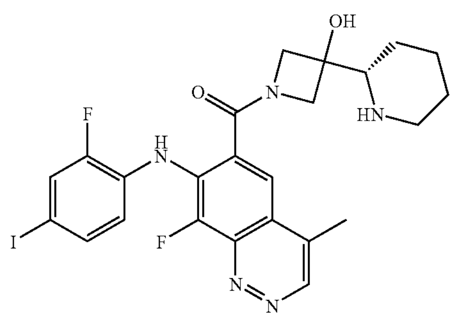 | 1-({8-fluoro-7-{(2-fluoro-4-iodophenyl)amino]-4-methylcinnolin-6-yl}carbonyl)-3-[(2S)-piperidin-2-yl]azetidin-3-ol |
| 287 | 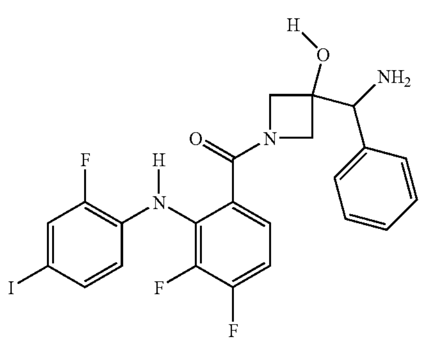 | 3-[amino(phenyl)methyl]-1-({3,4-difluoro-2-[(2-fluoro-4-iodophenyl)amino]phenyl}carbonyl)azetidin-3-ol |
| 288 | 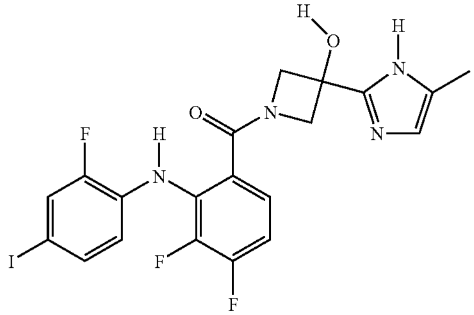 | 1-({3,4-difluoro-2-[(2-fluoro-4-iodophenyl)amino]phenyl}carbonyl)-3-(5-methyl-1H-imidazol-2-yl)azetidin-3-ol |

TABLE 1-continued

| Cmpd No. | Structure | Name |
|---|---|---|
| 289 | 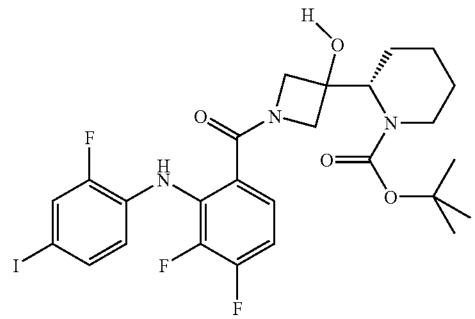 | 1,1-dimethylethyl (2S)-2-[1-({3,4-difluoro-2-[(2-fluoro-4-iodophenyl)amino]phenyl}carbonyl)-3-hydroxyazetidin-3-yl]piperidine-1-carboxylate |
| 290 | 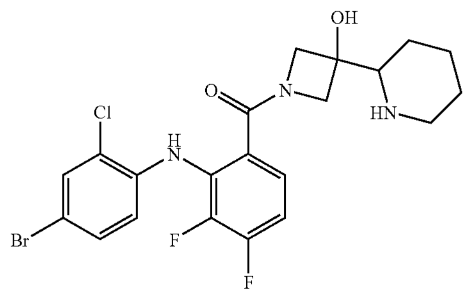 | 1-({2-[(4-bromo-2-chlorophenyl)amino]-3,4-difluorophenyl}carbonyl)-3-piperidin-2-ylazetidin-3-ol |
| 291 | 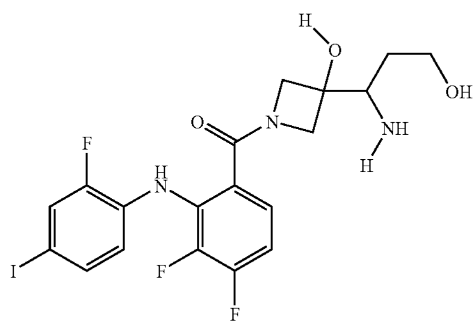 | 3-(1-amino-3-hydroxypropyl)-1-({3,4-difluoro-2-[(2-fluoro-4-iodophenyl)amino]phenyl}carbonyl)azetidin-3-ol |
| 292 | 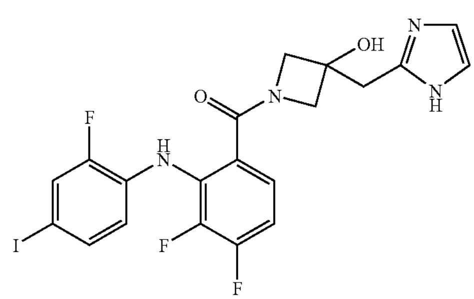 | 1-({3,4-difluoro-2-[(2-fluoro-4-iodophenyl)amino]phenyl}carbonyl)-3-(1H-imidazol-2-ylmethyl)azetidin-3-ol |
| 293 | 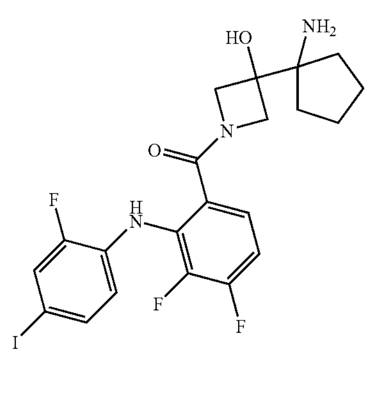 | 3-(1-aminocyclopentyl)-1-({3,4-difluoro-2-[(2-fluoro-4-iodophenyl)amino]phenyl}carbonyl)azetidin-3-ol |

TABLE 1-continued

| Cmpd No. | Structure | Name |
|---|---|---|
| 294 | 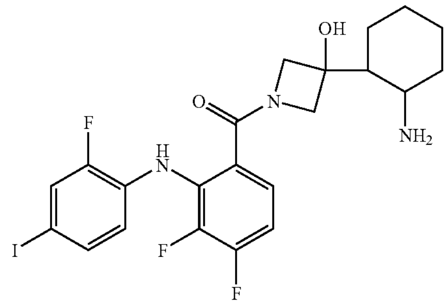 | 3-(2-aminocyclohexyl)-1-({3,4-difluoro-2-[(2-fluoro-4-iodophenyl)amino]phenyl}carbonyl)azetidin-3-ol |
| 295 | 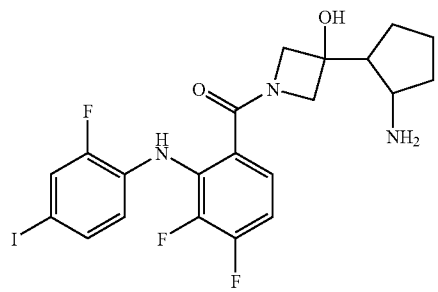 | 3-(2-aminocyclopentyl)-1-({3,4-difluoro-2-[(2-fluoro-4-iodophenyl)amino]phenyl}carbonyl)-azetidin-3-ol |
| 296 | 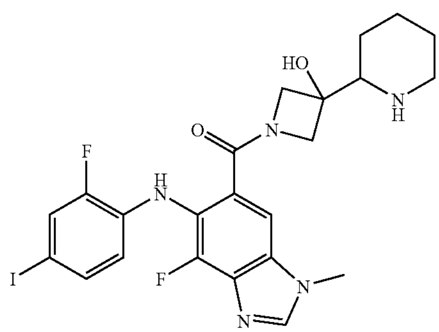 | 1-({4-fluoro-5-[(2-fluoro-4-iodophenyl)amino]-1-methyl-1H-benzimidazol-6-yl}carbonyl)-3-piperidin-2-ylazetidin-3-ol |
| 297 | 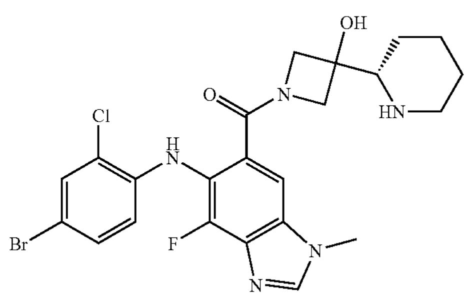 | 1-({5-[(4-bromo-2-chlorophenyl)amino]-4-fluoro-1-methyl-1H-benzimidazol-6-yl}carbonyl)-3-[(2S)-piperidin-2-yl]azetidin-3-ol |
| 298 | 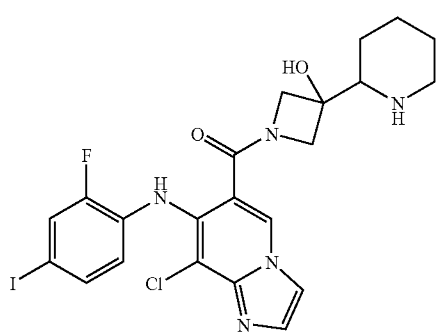 | 1-({8-chloro-7-[(2-fluoro-4-iodophenyl)amino]imidazo[1,2-a]pyridin-6-yl}carbonyl)-3-piperidin-2-ylazetidin-3-ol |

TABLE 1-continued

| Cmpd No. | Structure | Name |
|---|---|---|
| 299 | 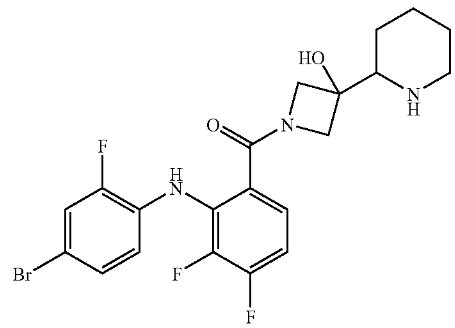 | 1-({2-[(4-bromo-2-fluorophenyl)amino]-3,4-difluorophenyl}carbonyl)-3-piperidin-2-ylazetidin-3-ol |
| 300 | 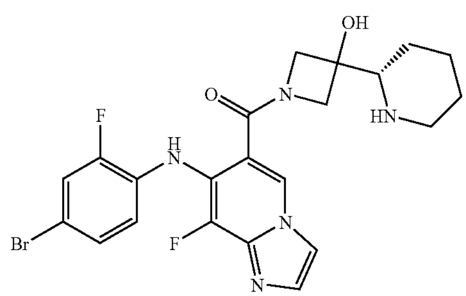 | 1-({7-[(4-bromo-2-fluorophenyl)amino]-8-fluoroimidazo[1,2-a]pyridin-6-yl}carbonyl)-3-[(2S)-piperidin-2-yl]azetidin-3-ol |
| 301 | 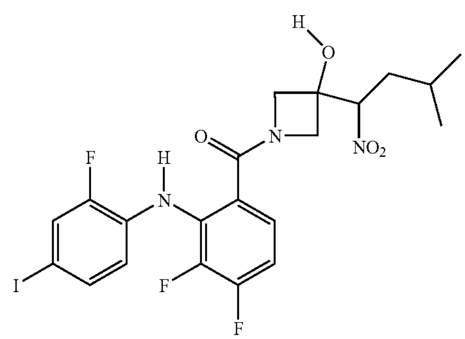 | 1-({3,4-difluoro-2-[(2-fluoro-4-iodophenyl)amino]phenyl}carbonyl)-3-(3-methyl-1-nitrobutyl)azetidin-3-ol |
| 302 | 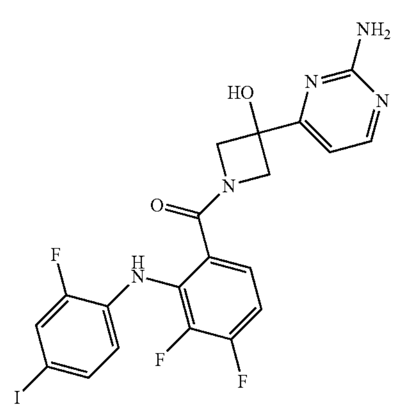 | 3-(2-aminopyrimidin-4-yl)-1-({3,4-difluoro-2-[(2-fluoro-4-iodophenyl)amino]phenyl}carbonyl)azetidin-3-ol |

| Cmpd No. | Structure | Name |
|---|---|---|
| 303 | 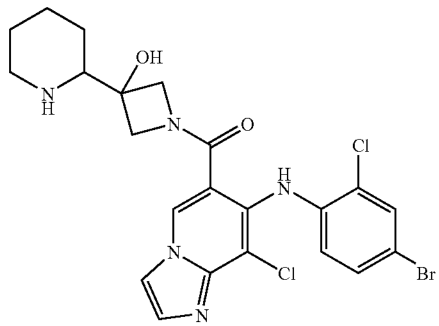 | 1-({7-[(4-bromo-2-chlorophenyl)amino]-8-chloroimidazo[1,2-a]pyridin-6-yl}carbonyl)-3-piperidin-2-ylazetidin-3-ol |
| 304 | 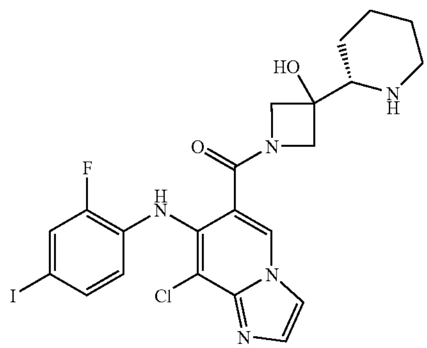 | 1-({8-chloro-7-[(2-fluoro-4-iodophenyl)amino]imidazo[1,2-a]pyridin-6-yl}carbonyl)-3-[(2S)-piperidin-2-yl]azetidin-3-ol |
| 305 | 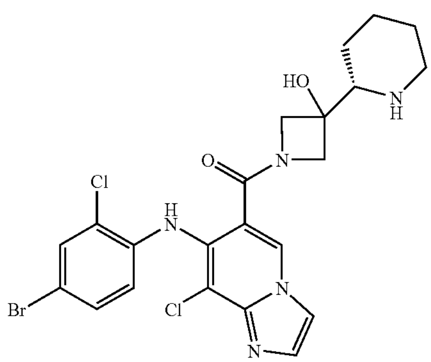 | 1-({7-[(4-bromo-2-chlorophenyl)amino]-8-chloroimidazo[1,2-a]pyridin-6-yl}carbonyl)-3-[(2S)-piperidin-2-yl]azetidin-3-ol |
| 306 | 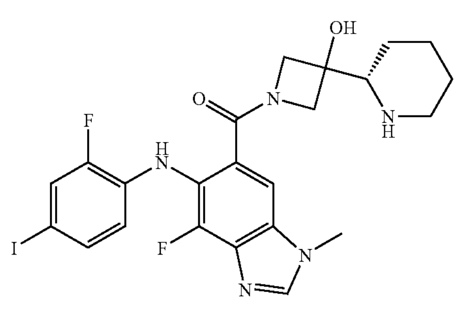 | 1-({4-fluoro-5-[(2-fluoro-4-iodophenyl)amino]-1-methyl-1H-benzimidazol-6-yl}carbonyl)-3-[(2S)-piperidin-2-yl]azetidin-3-ol |

TABLE 1-continued

| Cmpd No. | Structure | Name |
|---|---|---|
| 307 | 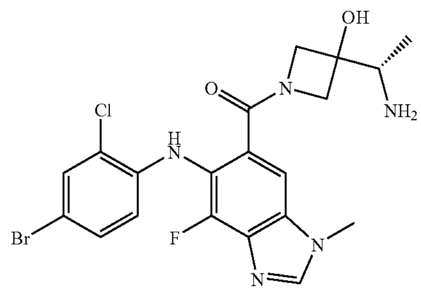 | 3-[(1S)-1-aminoethyl]-1-({5-[(4-bromo-2-chlorophenyl)amino]-4-fluoro-1-methyl-1H-benzimidazol-6-yl}carbonyl)azetidin-3-ol |
| 308 | 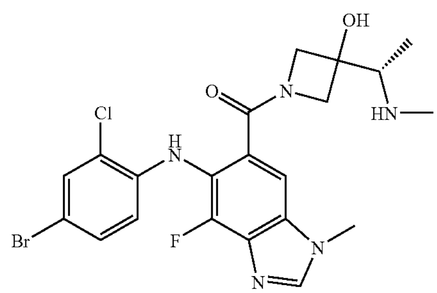 | 1-({5-[(4-bromo-2-chlorophenyl)amino]-4-fluoro-1-methyl-1H-benzimidazol-6-yl}carbonyl)-3-[(1S)-1-(methylamino)ethyl]azetidin-3-ol |
| 309 | 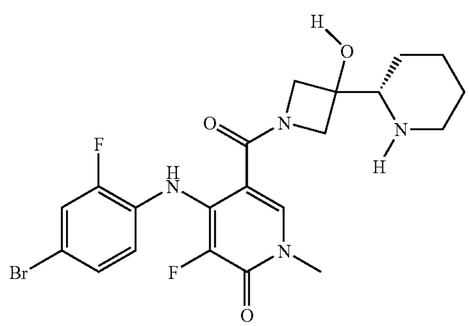 | 4-[(4-bromo-2-fluorophenyl)amino]-3-fluoro-5-({3-hydroxy-3-[(2S)-piperidin-2-yl]azetidin-1-yl}carbonyl)pyridin-2(1H)-one |
| 310 | 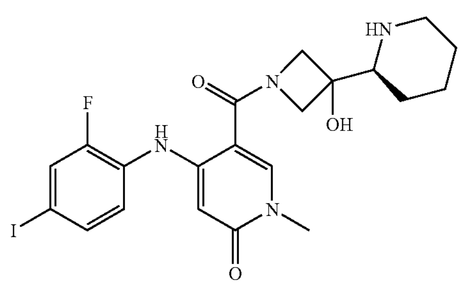 | 4-[(2-fluoro-4-iodophenyl)amino]-5-({3-hydroxy-3-[(2S)-piperidin-2-yl]azetidin-1-yl}carbonyl)-1-methylpyridin-2(1H)-one |
| 311 | 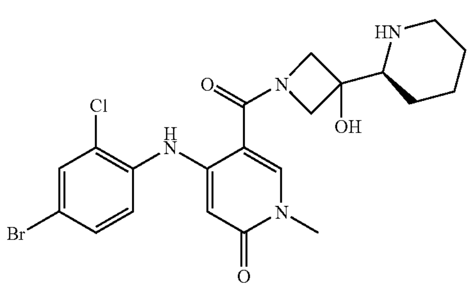 | 4-[(2-fluoro-4-iodophenyl)amino]-5-({3-hydroxy-3-[(2S)-piperidin-2-yl]azetidin-1-yl}carbonyl)-1-methylpyridin-2(1H)-one |

TABLE 1-continued

| Cmpd No. | Structure | Name |
|---|---|---|
| 312 | 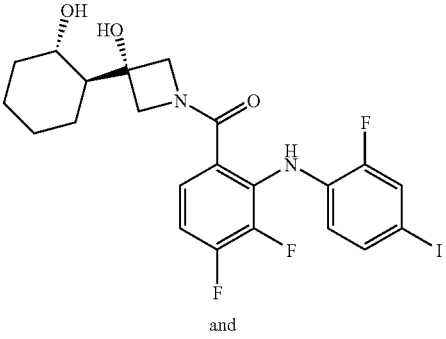 and 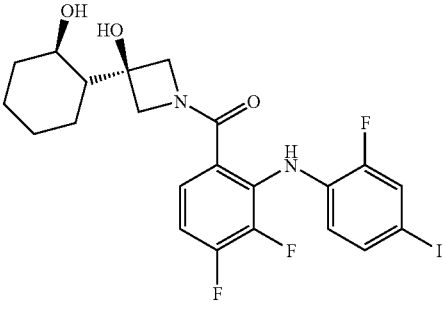 | (±)-1-({3,4-difluoro-2-[(2-fluoro-4-iodophenyl)amino]phenyl}carbonyl)-3-[(trans)-2-hydroxycyclohexyl]azetidin-3-ol |
| 313 | 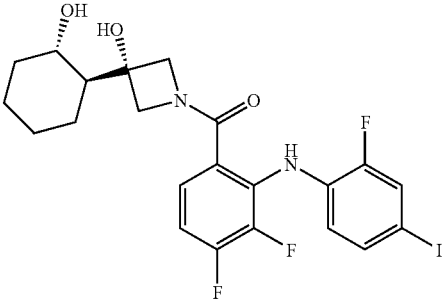 | (3,4-difluoro-2-(2-fluoro-4-iodophenylamino)phenyl)(3-hydroxy-3-[(1S,2S)-2-hydroxycyclohexyl]azetidin-1-yl)methanone |
| 314 | 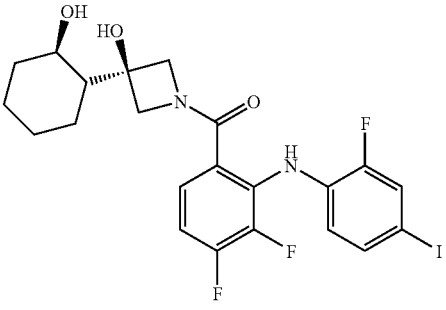 | (3,4-difluoro-2-(2-fluoro-4-iodophenyl-amino)phenyl)(3-hydroxy-3-((1S,2R)-2-hydroxycyclohexyl)azetidin-1-yl)methanone |
| 315 | 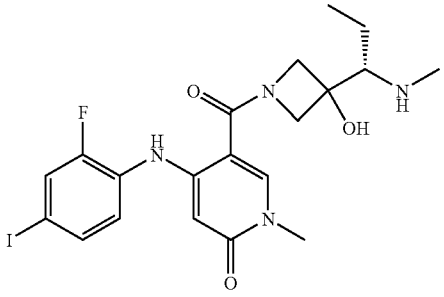 | 4-[(2-fluoro-4-iodophenyl)amino]-5-({3-hydroxy-3-](1S)-1-(methylamino)propyl]azetidin-1-yl}carbonyl)-1-methylpyridin-2(1H)-one |

TABLE 1-continued

| Cmpd No. | Structure | Name |
|---|---|---|
| 316 | 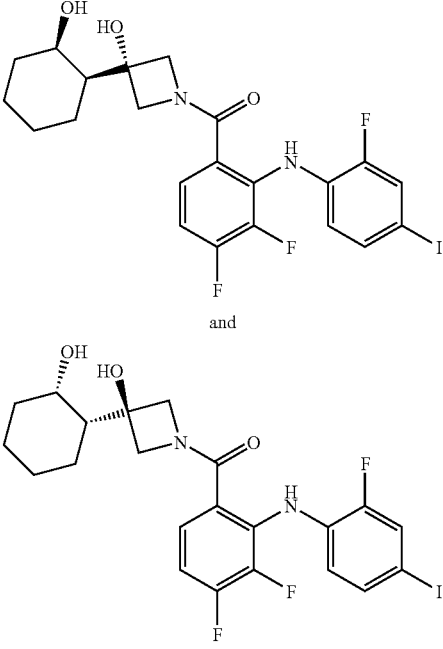 | (±)-1-({3,4-difluoro-2-{(2-fluoro-4-iodophenyl)amino]phenyl}carbonyl)-3-[(cis)-2-hydroxy-cyclohexyl]azetidin-3-ol |
| 317 | 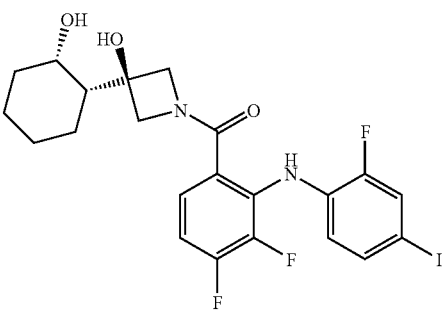 | (3,4-difluoro-2-(2-fluoro-4-iodophenylamino)phenyl)(3-hydroxy-3-((1S,2R)-2-hydroxy-cyclohexyl)azetidin-1-yl)methanone |
| 318 | 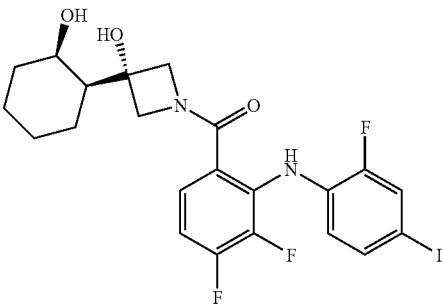 | (3,4-difluoro-2-(2-fluoro-4-iodophenylamino)phenyl)(3-hydroxy-3-((1R,2S)-2-hydroxy-cyclohexyl)azetidin-1-yl)methanone |
| 319 | 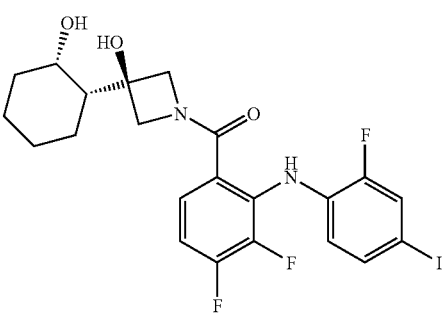 | 5-({3-[(1S)-1-(dimethylamino)ethyl]-3-hydroxy-azetidin-1-yl}carbonyl)-4-[(2-fluoro-4-iodophenyl)amino]-1-methylpyridin-2(1H)-one |

TABLE 1-continued

| Cmpd No. | Structure | Name |
| --- | --- | --- |
| 320 | 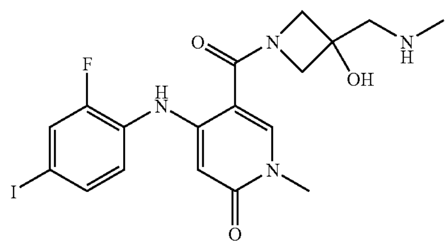 | 4-{(2-fluoro-4-iodophenyl)amino}-5-({3-hydroxy-3-[(methylamino)methyl]azetidin-1-yl}carbonyl)-1-methylpyridin-2(1H)-one |
| 321 | 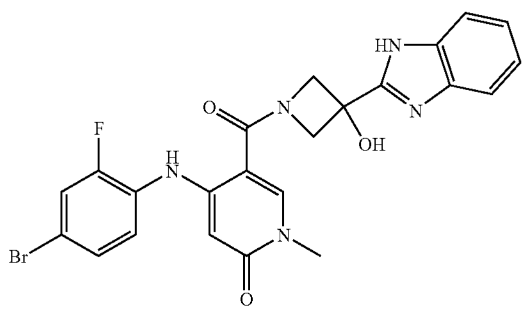 | 5-{[3-(1H-benzimidazo]-2-yl)-3-hydroxy-azetidin-1-yl]carbonyl}-4-[(4-bromo-2-fluoro-phenyl)amino-1-methylpyridin-2(1H)-one |
| 322 | 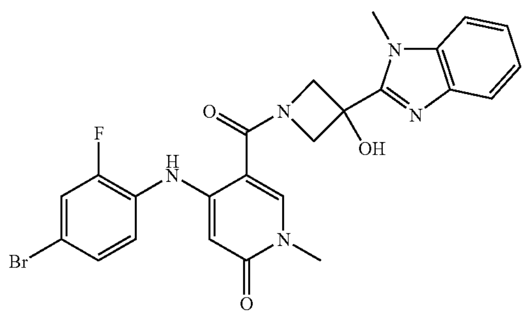 | 4-[(4-bromo-2-fluorophenyl)amino]-5-{[3-hydroxy-3-(1-methyl-1H-benzimidazol-2-yl)azetidin-1-yl]carbonyl}-1-methylpyridin-2(1H)-one |
| 323 | 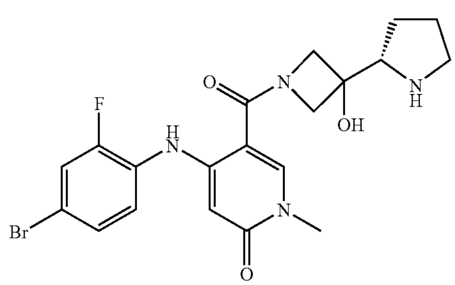 | 4-[(4-bromo-2-fluorophenyl)amino]-5-({3-hydroxy-3-[(2S)-pyrrolidin-2-yl]azetidin-1-yl}carbonyl)-1-methylpyridin-2(1H)-one |
| 324 | 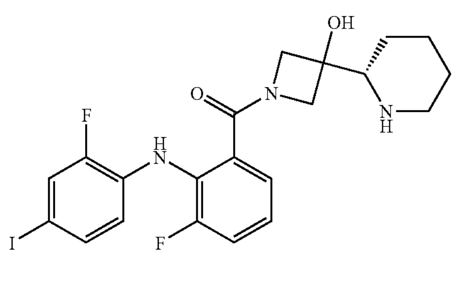 | 1-({3-fluoro-2-{(2-fluoro-4-iodophenyl)amino]phenyl}carbonyl)-3-[(2S)-piperidin-2-yl]azetidin-3-ol |

TABLE 1-continued

| Cmpd No. | Structure | Name |
|---|---|---|
| 325 | 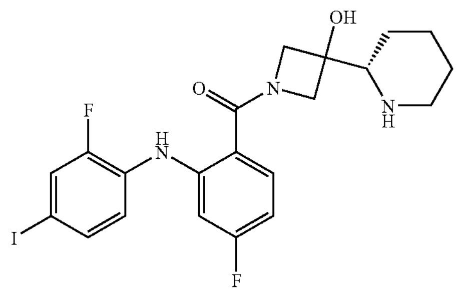 | 1-({4-fluoro-2-[(2-fluoro-4-iodophenyl)amino]phenyl}carbonyl)-3-[(2S)-piperidin-2-yl]azetidin-3-ol |
| 326 | 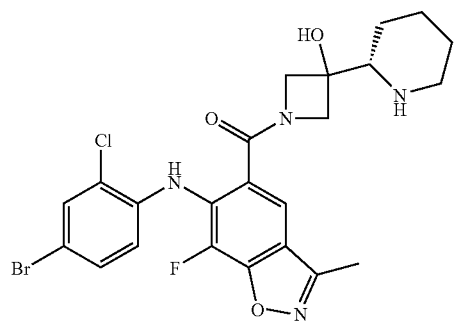 | 1-({6-[(4-bromo-2-chlorophenyl)amino]-7-fluoro-3-methyl-1,2-benzisoxazol-5-yl}carbonyl)-3-[(2S)-piperidin-2-yl]azetidin-3-ol |
| 327 | 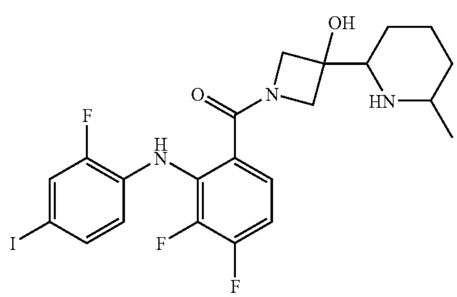 | 1-({3,4-difluoro-2-[(2-fluoro-4-iodophenyl)amino]phenyl}carbonyl)-3-(6-methylpiperidin-2-yl)azetidin-3-ol |
| 328 | 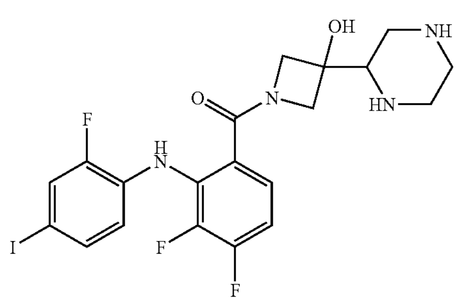 | 1-({3,4-difluoro-2-[(2-fluoro-4-iodophenyl)amino]phenyl}carbonyl)-3-piperazin-2-ylazetidin-3-ol |
| 329 | 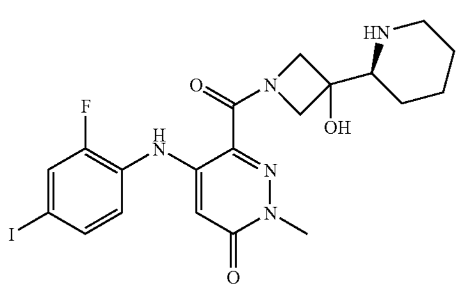 | 5-[(2-fluoro-4-iodophenyl)amino]-6-({3-hydroxy-3-[(2S)-piperidin-2-yl]azetidin-1-yl}carbonyl)-2-methylpyridazin-3(2H)-one |

TABLE 1-continued

| Cmpd No. | Structure | Name |
|---|---|---|
| 330 | 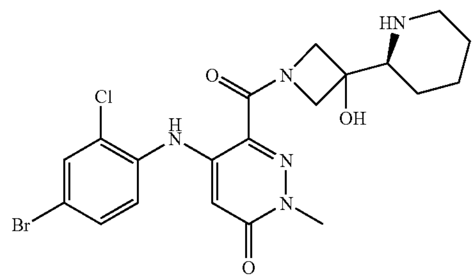 | 5-[(4-bromo-2-chlorophenyl)amino]-6-({3-hydroxy-3-[(2S)-piperidin-2-yl]azetidin-1-yl}carbonyl)-2-methylpyridazin-3(2H)-one |
| 331 | 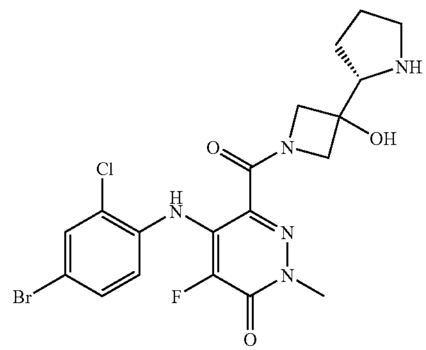 | 5-[(4-bromo-2-chlorophenyl)amino]-4-fluoro-6-({3-hydroxy-3-[(2S)-pyrrolidin-2-yl]azetidin-1-yl}carbonyl)-2-methylpyridazin-3(2H)-one |
| 332 | 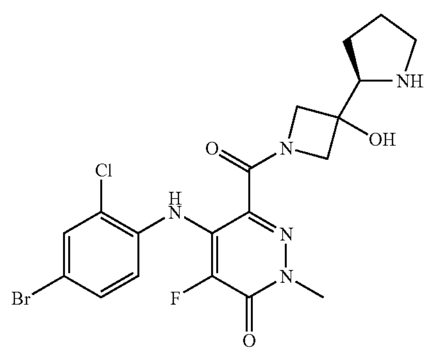 | 5-[(4-bromo-2-chlorophenyl)amino]-4-fluoro-6-({3-hydroxy-3-[(2R)-pyrrolidin-2-yl]azetidin-4-yl}carbonyl)-2-methylpyridazin-3(2H)-one |
| 333 | 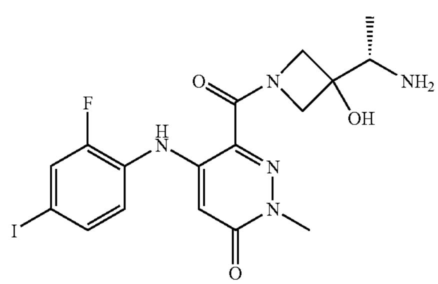 | 6-({3-[(1S)-1-aminoethyl]-3-hydroxyazetidin-1-yl}carbonyl)-5-[(2-fluoro-4-iodophenyl)amino]-2-methylpyridazin-3(2H)-one |
| 334 | 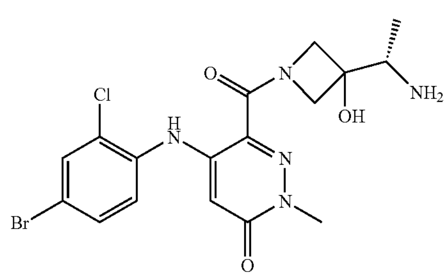 | 6-({3-[(1S)-1-aminoethyl]-3-hydroxyazetidin-1-yl}carbonyl)-5-[(4-bromo-2-chlorophenyl)amino]-2-methylpyridazin-3(2H)-one |

TABLE 1-continued

| Cmpd No. | Structure | Name |
|---|---|---|
| 335 | 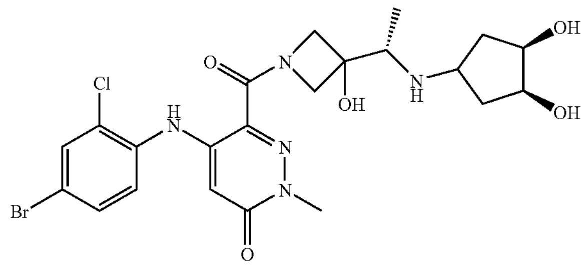 | 5-[(4-bromo-2-chlorophenyl)amino]-6-{[3-((1S)-1-{[(3R,4S)-3,4-dihydroxycyclopentyl]amino}ethyl)-3-hydroxyazetidin-1-yl]carbonyl}-2-methylpyridazin-3(2H)-one |
| 336 | 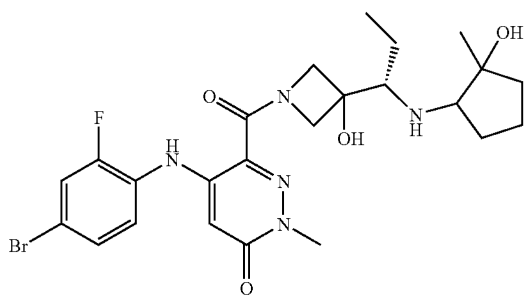 | 5-[(4-bromo-2-fluorophenyl)amino]-6-[(3-hydroxy-3-{(1S)-1-[(2-hydroxy-2-methyl-cyclopentyl)amino]propyl}azetidin-1-yl)carbonyl]-2-methylpyridazin-3(2H)-one |
| 337 | 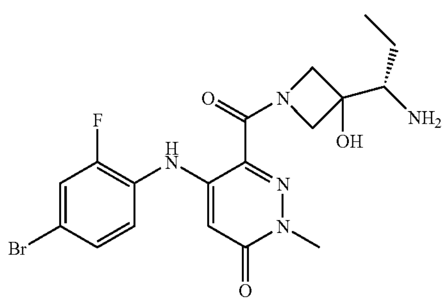 | 6-({3-[(1S)-1-aminopropyl]-3-hydroxy-azetidin-1-yl}carbonyl)-5-[(4-bromo-2-fluoro-phenyl)amino]-2-methylpyridazin-3(2H)-one |
| 338 | 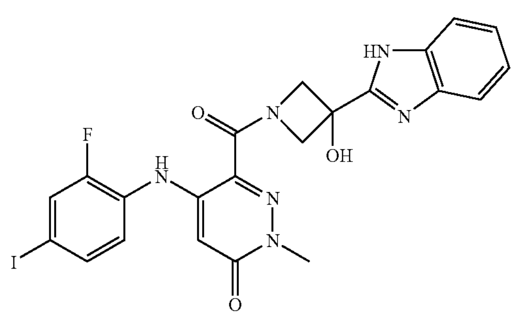 | 6-{[3-(1H-benzimidazol-2-yl)-3-hydroxy-azetidin-1-yl]carbonyl}-5-[(2-fluoro-4-iodophenyl)amino]-2-methylpyridazin-3(2H)-one |
| 339 | 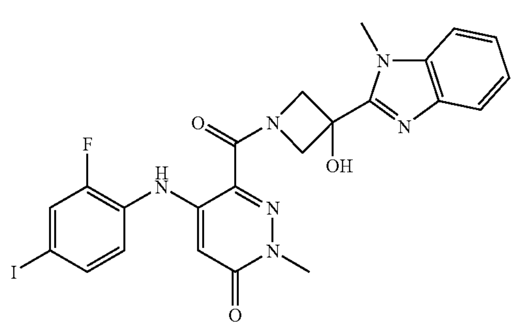 | 5-[(2-fluoro-4-iodophenyl)amino]-6-{[3-hydroxy-3-(1-methyl-1H-benzimidazol-2-yl)azetidin-1-yl]carbonyl}-2-methylpyridazin-3(2H)-one |

| Cmpd No. | Structure | Name |
|---|---|---|
| 340 | 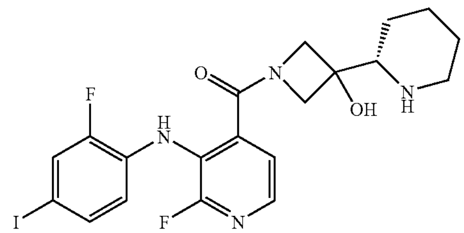 | 1-({2-fluoro-3-[(2-fluoro-4-iodophenyl)amino]pyridin-4-yl}carbonyl)-3-[(2S)-piperidin-2-yl]azetidin-3-ol |
| 341 | 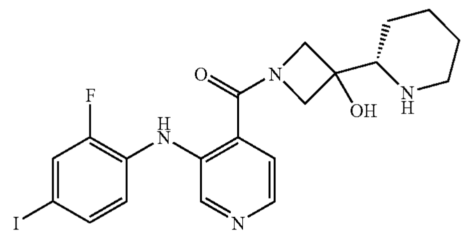 | 1-({3-[(2-fluoro-4-iodophenyl)amino]pyridin-4-yl}carbonyl)-3-[(2S)-piperidin-2-yl]azetidin-3-ol |
| 342 | 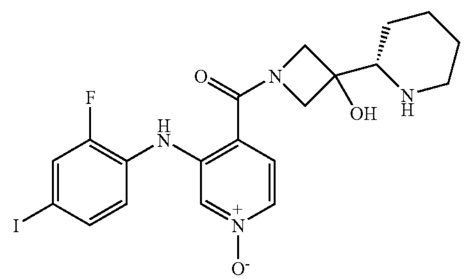 | 1-({3-[(2-fluoro-4-iodophenyl)amino]-1-oxidopyridin-4-yl}carbonyl)-3-[(2S)-piperidin-2-yl]azetidin-3-ol |
| 343 | 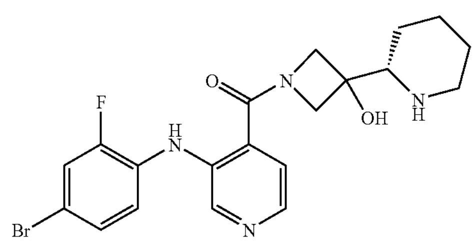 | 1-({2-fluoro-3-[(2-fluoro-4-bromophenyl)amino]pyridin-4-yl}carbonyl)-3-[(2S)-piperidin-2-yl]azetidin-3-ol |
| 344 | 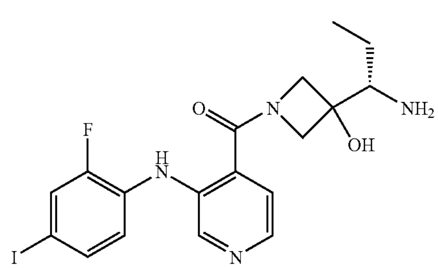 | 3-[(1S)-1-aminopropyl]-1-({3-[(2-fluoro-4-iodophenyl)amino)pyridin-4-yl}carbonyl)azetidin-3-ol |
| 345 | 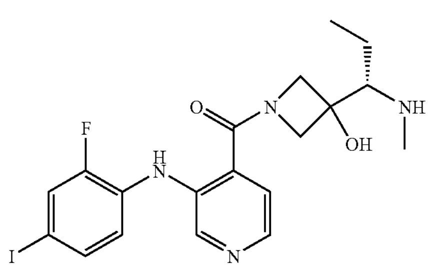 | 1-({3-[(2-fluoro-4-iodophenyl)amino]pyridin-4-yl}carbonyl)-3-[(1S)-1-(methylamino)propyl]azetidin-3-ol |

| Cmpd No. | Structure | Name |
|---|---|---|
| 346 | 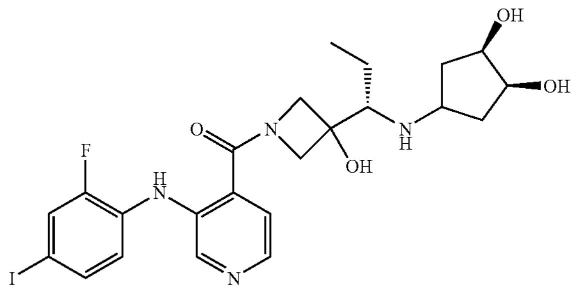 | (1R,2S)-4-({(1S)-1-[1-({2-fluoro-3-[(2-fluoro-4-iodophenyl)amino]pyridin-4-yl}carbonyl)-3-hydroxyazetidin-3-yl]propyl}amino)cyclopentane-1,2-diol |
| 347 | 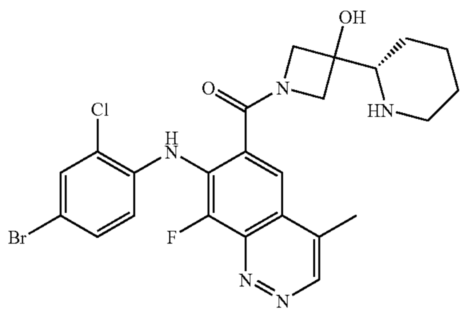 | 1-({7-[(4-bromo-2-chlorophenyl)amino]-8-fluoro-4-methylcinnolin-6-yl}carbonyl)-3-[(2S)-piperidin-2-yl]azetidin-3-ol |
| 348 | 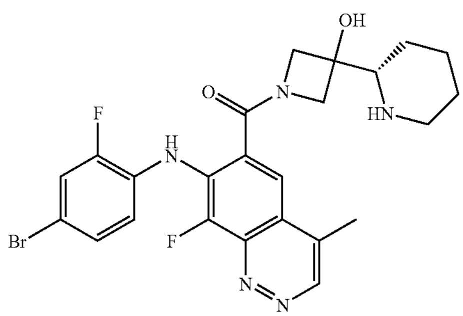 | 1-({7-[(4-bromo-2-fluorophenyl)amino]-8-fluoro-4-methylcinnolin-6-yl}carbonyl)-3-[(2S)-piperidin-2-yl]azetidin-3-ol |
| 349 | 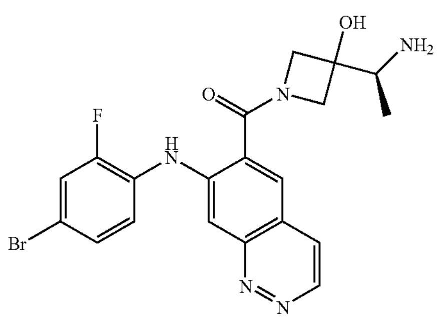 | 3-[(1S)-1-aminoethyl]-1-({7-[(4-bromo-2-fluorophenyl)amino]cinnolin-6-yl}carbonyl)azetidin-3-ol |
| 350 | 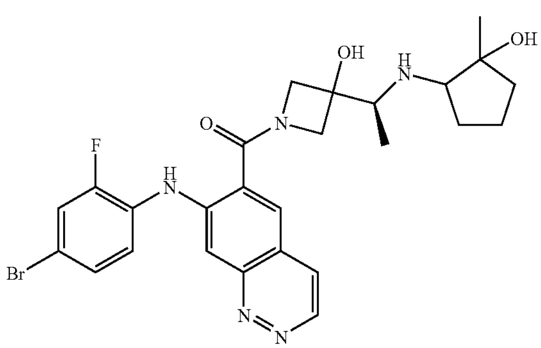 | 1-({7-[(4-bromo-2-fluorophenyl)amino]cinnolin-6-yl}carbonyl)-3-{(1S)-1-[(2-hydroxy-2-methylcyclopentyl)amino]ethyl}azetidin-3-ol |

| Cmpd No. | Structure | Name |
| --- | --- | --- |
| 351 | 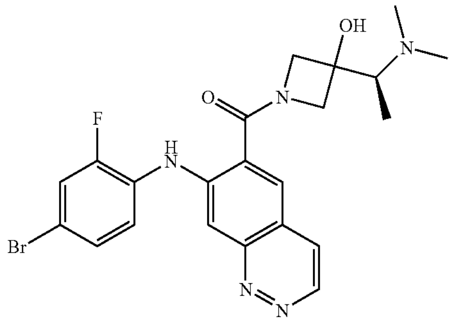 | 1-({7-[(4-bromo-2-fluorophenyl)amino]cinnolin-6-yl}carbonyl)-3-{(1S)-1-(dimethylamino)ethyl]azetidin-3-ol |
| 352 | 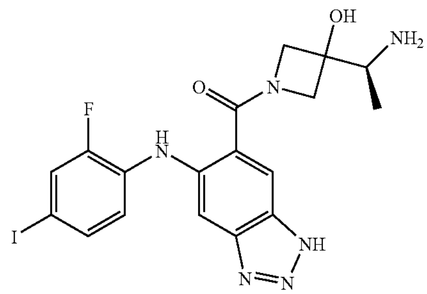 | 3-[(1S)-1-aminoethyl]-1-({5-[(2-fluoro-4-iodophenyl)amino]-1H-1,2,3-benzotriazol-6-yl}carbonyl)azetidin-3-ol |
| 353 | 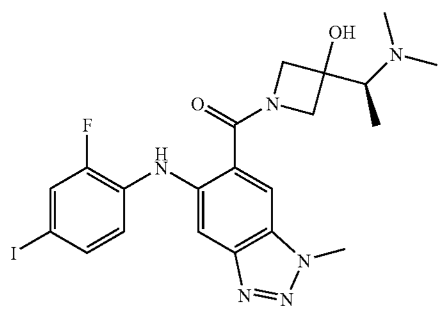 | 3-[(1S)-1-(dimethylamino)ethyl]-1-({5-[(2-fluoro-4-iodophenyl)amino]-1-methyl-1H-1,2,3-benzotriazol-6-yl}carbonyl)azetidin-3-ol |
| 354 | 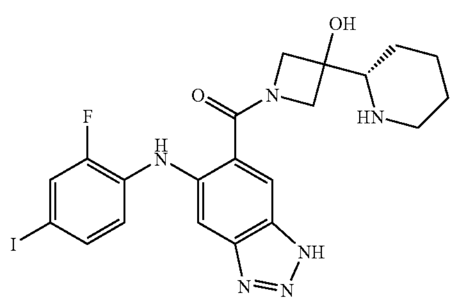 | 1-({5-[(2-fluoro-4-iodophenyl)amino]-1H-1,2,3-benzotriazol-6-yl}carbonyl)-3-[(2S)-piperidin-2-yl]azetidin-3-ol |
| 355 | 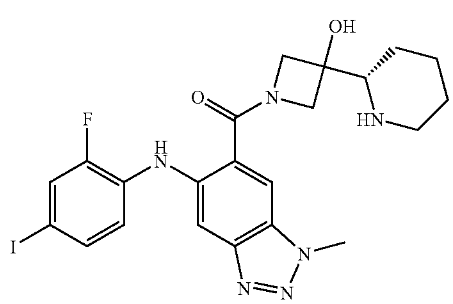 | 1-({5-[(2-fluoro-4-iodophenyl)amino]-1-methyl-1H-1,2,3-benzotriazol-6-yl}carbonyl)-3-[(2S)-piperidin-2-yl]azetidin-3-ol |

| Cmpd No. | Structure | Name |
| --- | --- | --- |
| 356 | 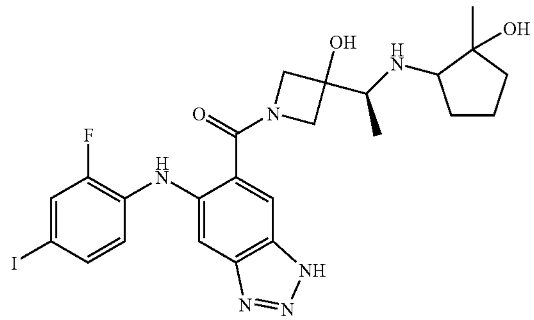 | 1-({5-[(2-fluoro-4-iodophenyl)amino]-1H-1,2,3-benzotriazol-6-yl}carbonyl)-3-{(1S)-1-[(2-hydroxy-2-methylcyclopentyl)amino]ethyl}azetidin-3-ol |
| 357 | 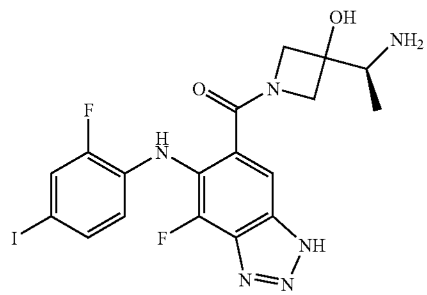 | 3-[(1S)-1-aminoethyl]-1-({4-fluoro-5-[(2-fluoro-4-iodophenyl)amino]-1H-1,2,3-benzotriazol-6-yl}carbonyl)azetidin-3-ol |
| 358 | 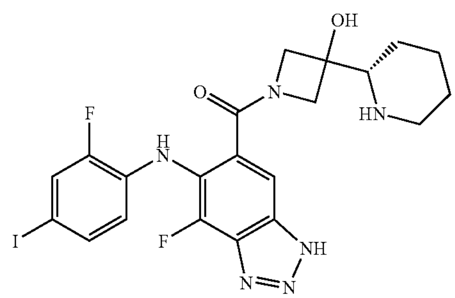 | 1-({4-fluoro-5-[(2-fluoro-4-iodophenyl)amino]-1H-1,2,3-benzotriazol-6-yl}carbonyl)-3-{(2S)-piperidin-2-yl}azetidin-3-ol |
| 359 | 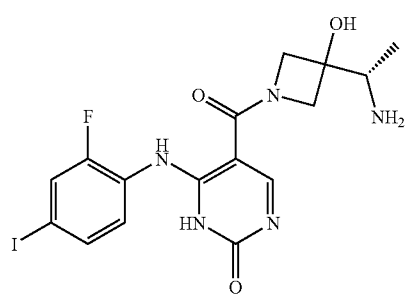 | 5-({3-[(1S)-1-aminoethyl]-3-hydroxy-azetidin-1-yl}carbonyl)-6-[(2-fluoro-4-iodophenyl)amino]pyrimidin-2(1H)-one |
| 360 | 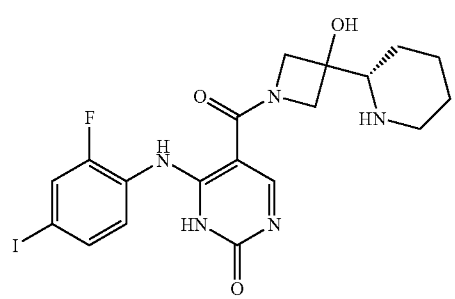 | 6-[(2-fluoro-4-iodophenyl)amino]-5-({3-hydroxy-3-[(2S)-piperidin-2-yl]azetidin-1-yl}carbonyl)pyrimidin-2(1H)-one |

TABLE 1-continued

| Cmpd No. | Structure | Name |
|---|---|---|
| 361 | 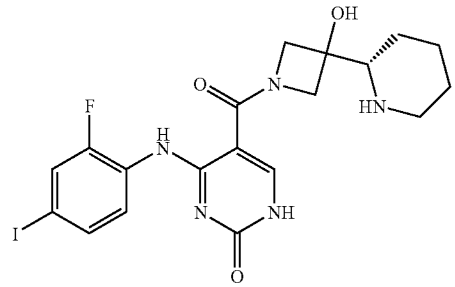 | 4-[(2-fluoro-4-iodophenyl)amino]-5-({3-hydroxy-3-[(2S)-piperidin-2-yl]azetidin-1-yl}carbonyl)pyrimidin-2(1H)-one |
| 362 | 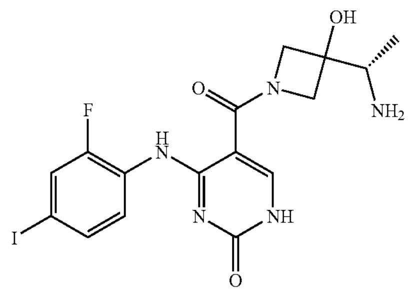 | 5-({3-[(1S)-1-aminoethyl]-3-hydroxyazetidin-1-yl}carbonyl)-4-[(2-fluoro-4-iodophenyl)amino]pyrimidin-2(1H)-one |

General Administration

In one aspect, the invention provides pharmaceutical compositions comprising an inhibitor of MEK according to the invention and a pharmaceutically acceptable carrier, excipient, or diluent. In certain other embodiments, administration may preferably be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semisolid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts or hydrates, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

Representative pharmaceutical formulations containing a compound of Formula I are described below in the Pharmaceutical Composition Examples.

Utility

Certain compounds of this invention have been tested using the assay described in Biological Example 1 and have been determined to be MEK inhibitors. As such compounds of Formula I are useful for treating diseases, particularly cancer in which MEK activity contributes to the pathology and/or symptomatology of the disease. For example, cancer in which MEK activity contributes to its pathology and/or symptomatology include malignant melanomas, colorectal cancer, pancreatic cancer, lung cancer, papillary and anaplastic thyroid cancer, and endometriod ovarian cancers, and the like.

Suitable in vitro assays for measuring MEK activity and the inhibition thereof by compounds are known in the art. For example, see WO 2006/061712 for measuring MEK1 and MEK2 in vitro. For further details of an in vitro assay for measuring MEK activity see Biological Examples, Example 1 infra. Following the examples disclosed herein, as well as that disclosed in the art, a person of ordinary skill in the art can determine the inhibitory activity of a compound of this invention.

Assays for measurement of in vitro efficacy in treatment of cancer are known in the art. For example, see WO 2006/061712, which is herein incorporated by reference, for cell-based assays for colon cancer. In addition, cell-based tumor models are described in Biological Examples, Example 2 and 3 infra.

Suitable in vivo models for cancer are known to those of ordinary skill in the art (including WO 2006/061712). For further details of in vivo models for colorectal cancer, melanoma, breast adenocarcinoma, and lung anaplastic carcinoma, see Biological Example 4, infra.

General Synthesis

Compounds of this invention can be made by the synthetic procedures described below. The starting materials and reagents used in preparing these compounds are either available from commercial suppliers such as Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4$^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure and over a temperature range from about −78° C. to about 150° C., more preferably from about 0° C. to about 125° C. and most preferably at about room (or ambient) temperature, e.g., about 20° C. Unless otherwise stated (as in the case of an hydrogenation), all reactions are performed under an atmosphere of nitrogen.

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The compounds of the invention, or their pharmaceutically acceptable salts, may have asymmetric carbon atoms or quaternized nitrogen atoms in their structure. Compounds of Formula I that may be prepared through the syntheses described herein may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention. Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. When compounds of Formula I contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of Formula I can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The chemistry for the preparation of the compounds of this invention is known to those skilled in the art.

An intermediate of Formula II:

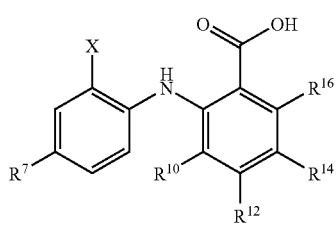

where $R^7$, X, $R^{10}$, $R^{12}$, $R^{14}$, and $R^{16}$ are as defined in the Summary of the Invention for Group A can be prepared using procedures known to one of ordinary skill in the art. In particular, see (for example) U.S. Pat. No. 7,019,033, WO 2002006213, WO 2003062191, WO 2003062189, WO 2002018319, WO2001005392, WO 2000064856, WO 2001005392, WO 9901421, WO 2004056789, Davis, E. M. et al. *Org. Process Res. & Dev.* 2005, 9, 843-6, and Shapiro, N. et al. *Synthetic Commun.* 2005, 35, 2265-9 which are incorporated by reference herein. The following intermediates were prepared using similar procedures as described in the above references: 3,4-difluoro-2-[(2-fluoro-4-iodophenyl)amino]benzoic acid; 2-[(2-chloro-4-iodophenyl)amino]-3,4-difluorobenzoic acid; 4-fluoro-2-[(2-fluoro-4-iodophenyl)amino]benzoic acid; 4,5-difluoro-2-[(2-fluoro-4-iodophenyl)amino]benzoic acid; and 2-[(4-bromo-2-fluorophenyl)amino]-3,4-difluorobenzoic acid.

An intermediate of Formula III(a) or III(b):

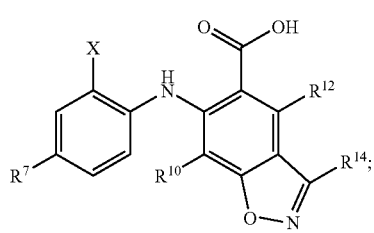

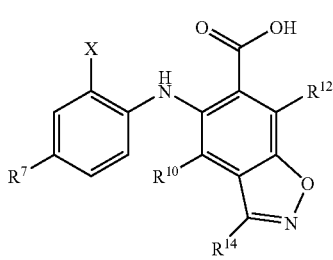

where $R^7$, X, $R^{10}$, $R^{12}$, and $R^{14}$ are as defined in the Summary of the Invention for Group B can be prepared using procedures known to one of ordinary skill in the art. In particular for formula III(a), where $R^{14}$ is amino or alkyl (particularly methyl); $R^{10}$ is halo (particularly fluoro); $R^7$ is hydrogen or halo (particularly bromo or chloro); X is halo (particularly chloro); and $R^{12}$ is hydrogen see for example WO2006030610, US2005049419, and US2005/0054701 which are incorporated by reference herein. 6-[(4-bromo-2-chlorophenyl)amino]-7-fluoro-3-methyl-1,2-benzisoxazole-5-carboxylic acid was prepared using methods similar to those disclosed in WO2006030610, US2005049419, and US2005/0054701.

An intermediate of Formula IV(a) or IV(b):

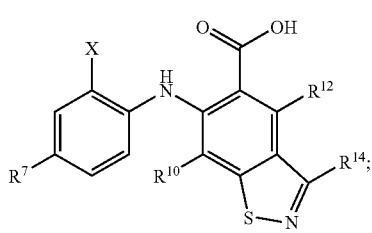

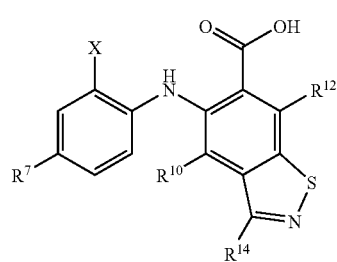

where $R^7$, X, $R^{10}$, $R^{12}$, and $R^{14}$ are as defined in the Summary of the Invention for Group B can be prepared using procedures known to one of ordinary skill in the art.

An intermediate of Formula V(a) or V(b):

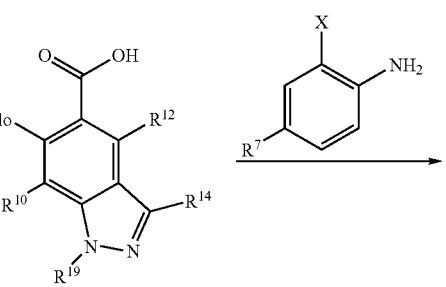

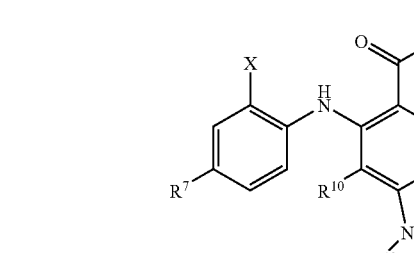

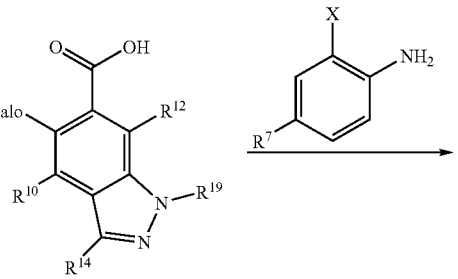

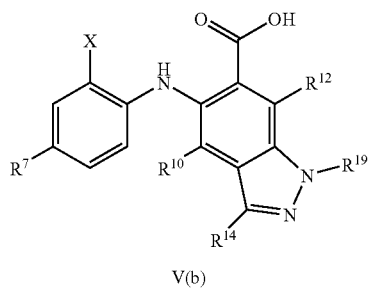

V(b)

where $R^7$, X, $R^{10}$, $R^{12}$, $R^{14}$, and $R^{19}$ are as defined in the Summary of the Invention for Group B can be prepared using procedures known to one of ordinary skill in the art. In particular the halo precursor of V(a) can be prepared using, for example, WO2003101968 and WO2002083648 which are incorporated by reference herein. In particular the halo precursor of V(b) can be prepared using, for example, US2004192653, US2004180896, US2004176325 which are incorporated by reference herein. The halo precursors are then reacted with an appropriate aniline to yield the intermediates of Formula V(a) and V(b).

An intermediate of Formula VI(a) or VI(b):

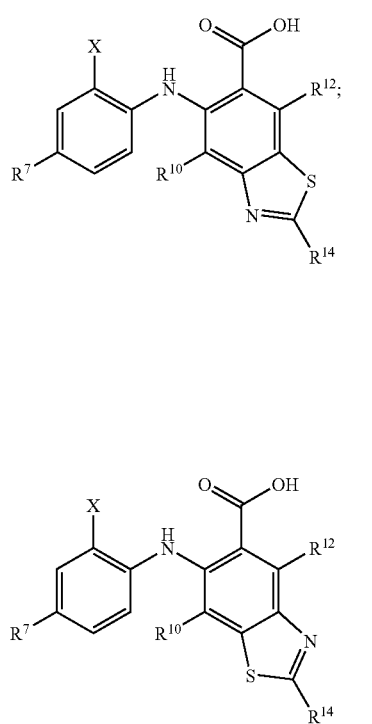

where $R^7$, X, $R^{10}$, $R^{12}$, and $R^{14}$ are as defined in the Summary of the Invention for Group B can be prepared using procedures known to one of ordinary skill in the art. In particular, for VI(b) see for example WO2000042022 and WO2001005390 which are incorporated by reference herein.

An intermediate of Formula VII(a) or VII(b):

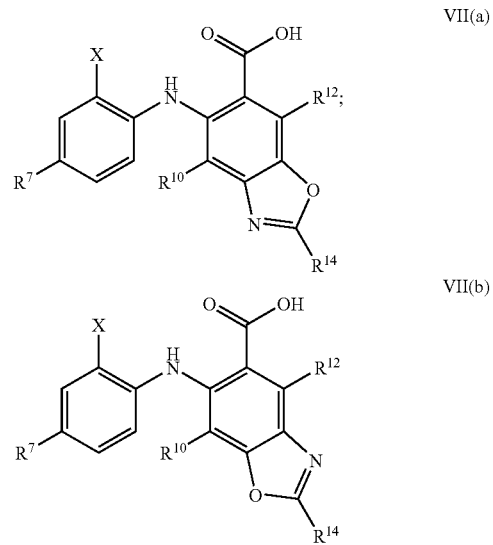

where $R^7$, X, $R^{10}$, $R^{12}$, and $R^{14}$ are as defined in the Summary of the Invention for Group B can be prepared using procedures known to one of ordinary skill in the art. For intermediate VII(b) see, for example, WO2001005390 and WO2000042022 which are incorporated by reference herein.

An intermediate of Formula VIII(a) or VIII(b):

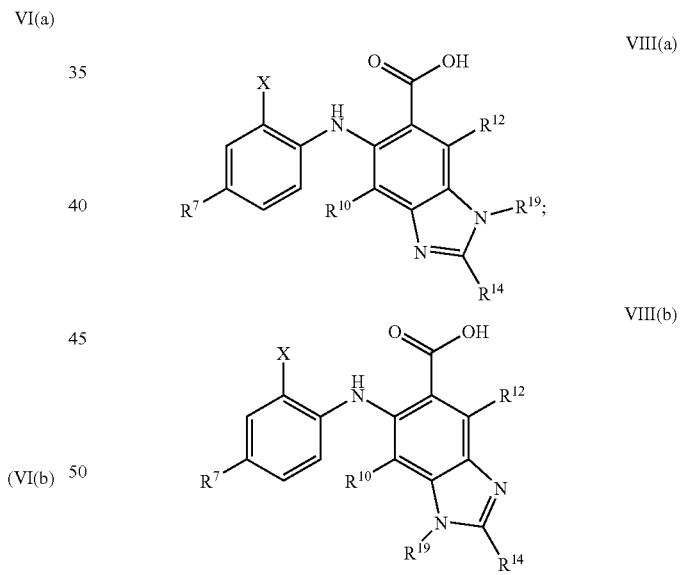

where $R^7$, X, $R^{10}$, $R^{12}$, $R^{14}$, and $R^{19}$ are as defined in the Summary of the Invention for Group B can be prepared using procedures known to one of ordinary skill in the art. In particular for formula VIII(b) where $R^{10}$ is halo (particularly fluoro), $R^{12}$ is hydrogen, $R^{14}$ is hydrogen, and $R^{19}$ is hydrogen or alkyl (particularly methyl) or alkenyl (particularly allyl), see WO 05/023251, WO2005009975, and WO2001005390 which are incorporated by reference herein. In particular for VIII(a) where X is halo (particularly chloro or fluoro) or alkyl (particularly methyl), $R^7$ is halo (particularly iodo, bromo, or chloro) or haloalkoxy (particularly trifluormethoxy), $R^{10}$ is halo (particularly fluoro or chloro), $R^{14}$ is hydrogen or alkyl (particularly methyl), and $R^{19}$ is hydrogen or alkyl (particularly methyl), see for example US 2004/0116710, WO 03/077914, WO 03/077855, WO 00/42022, WO2005009975, and WO2001005390 which are incorporated by reference herein. The following intermediates were prepared using similar procedures described in US 2004/0116710, WO 03/077914, WO 03/077855, WO 00/42022, WO2005009975, and WO2001005390: 5-[(4-bromo-2-chlorophenyl)amino]-4-fluoro-1-methyl-1H-benzimidazole-6-carboxylic acid and 4-fluoro-5-[(2-fluoro-4-iodophenyl)amino]-1-methyl-1H-benzimidazole-6-carboxylic acid.

An intermediate of Formula IX:

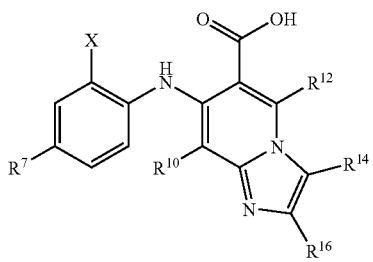

IX where $R^7$, X, $R^{10}$, $R^{12}$, $R^{14}$, and $R^{16}$ are as defined in the Summary of the Invention for Group B can be prepared using procedures known to one of ordinary skill in the art. In particular, where $R^{10}$ is hydrogen or halo (particularly chloro or fluoro); $R^{12}$ is hydrogen; $R^{14}$ is hydrogen, amino, alkylamino, or dialkylamino; $R^{16}$ is hydrogen; X is halo (particularly chloro); and $R^7$ is halo (particularly bromo) see for example WO 05/023759, US 2005/0054701, US 2006030610, US 2005049419, and US 2005049276 which are incorporated by reference herein. The following intermediates were prepared using similar procedures as those described in WO 05/023759, as well as US 2006030610 and US 2005/0054701: 7-[(4-bromo-2-chlorophenyl)amino]-8-chloroimidazo[1,2-a]pyridine-6-carboxylic acid and 8-chloro-7-[(2-fluoro-4-iodophenyl)amino]imidazo[1,2-a]pyridine-6-carboxylic acid. The following intermediates can be prepared using similar procedures described in the references given above: 8-Fluoro-7-[(2-fluoro-4-iodophenyl)amino]imidazo[1,2-a]pyridine-6-carboxylic acid and 7-[(4-Bromo-2-fluorophenyl)amino]-8-fluoroimidazo[1,2-a]pyridine-6-carboxylic acid.

An intermediate of Formula X(a) and X(b):

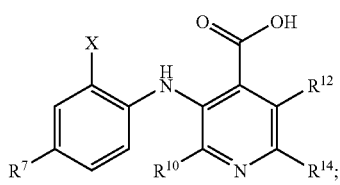

X(a)

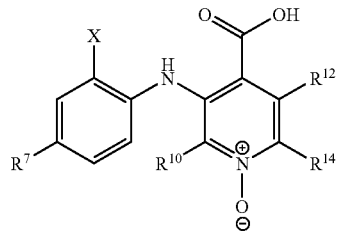

X(b)

where $R^7$, X, $R^{10}$, $R^{12}$, and $R^{14}$ are as defined in the Summary of the Invention for Group B can be prepared using procedures known to one of ordinary skill in the art. In particular, where $R^{10}$ is hydrogen, halo (specifically chloro), or alkyl (specifically methyl), $R^{12}$ is hydrogen, and $R^{14}$ is hydrogen, halo (specifically bromo), see for example WO 06/045514 which is incorporated by reference herein. To prepare the intermediate of Formula X(b), the nitrogen in the pyridine ring of X(a) can then be oxidized with an agent such as MCPBA or $H_2O_2$. The following X(a) and X(b) intermediates were prepared using similar methods as disclosed in WO 06/045514: 3-[(2-Fluoro-4-iodophenyl)amino]pyridine-4-carboxylic acid and 3-[(2-Fluoro-4-iodophenyl)amino]pyridine-4-carboxylic acid 1-oxide. The following X(a) intermediates can be prepared using similar methods as disclosed in WO 06/045514: 2-Fluoro-3-[(2-fluoro-4-iodophenyl)amino]pyridine-4-carboxylic acid and 3-[(4-Bromo-2-fluorophenyl)amino]pyridine-4-carboxylic acid.

An intermediate of Formula XI(a):

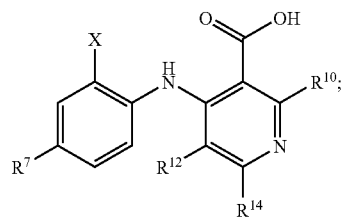

XI(a)

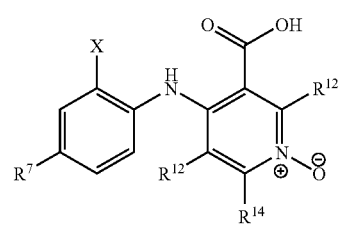

XI(b)

where $R^7$, X, $R^{10}$, $R^{12}$, and $R^{14}$ are as defined in the Summary of the Invention for Group B can be prepared using procedures known to one of ordinary skill in the art. In particular, where $R^{10}$ is hydrogen, $R^{12}$ is hydrogen or halo (particularly chloro or fluoro), $R^{14}$ is amino or halo (particularly chloro), X is halo (particularly chloro), and $R^7$ is halo (particularly bromo) see for example US 2005/0054701, US 200549419, and US 2006030610 which are incorporated by reference herein. The intermediate of Formula XI(b) can be prepared by oxidizing the nitrogen in the pyridine ring of XI(a) with an agent such as MCPBA or $H_2O_2$.

An intermediate of Formula XII:

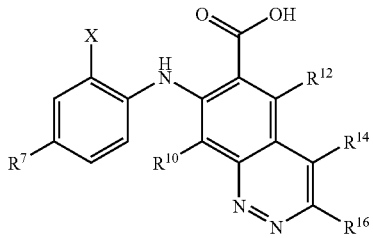

where $R^7$, X, $R^{10}$, $R^{12}$, $R^{14}$, and $R^{16}$ are as defined in the Summary of the Invention for Group B can be prepared using procedures known to one of ordinary skill in the art. In particular, see for example WO 05/051302 which is incorporated by reference herein. The following intermediates can be prepared using similar methods as disclosed in WO 05/051302: 8-Fluoro-7-[(2-fluoro-4-iodophenyl)amino]-4-methylcinnoline-6-carboxylic acid; 7-[(4-Bromo-2-chlorophenyl)amino]-8-fluoro-4-methylcinnoline-6-carboxylic acid; 7-[(4-Bromo-2-fluorophenyl)amino]-8-fluoro-4-methylcinnoline-6-carboxylic acid; and 7-[(4-Bromo-2-fluorophenyl)amino]cinnoline-6-carboxylic acid.

An intermediate of Formula XIII:

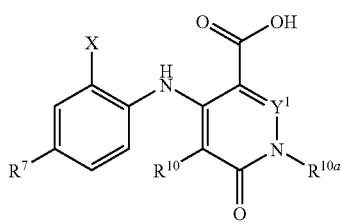

where $R^7$, X, $R^{10}$, $R^{10a}$, and $Y^1$ are as defined in the Summary of the Invention for Group C can be prepared using procedures known to one of ordinary skill in the art, including for example the procedures in US 05/0256123, Wallace, E. M. et al. J. Med. Chem. 2006, 49, 441-4, WO 2005000818, and WO 2005051301 (where $Y^1$ is carbon) which are incorporated by reference herein. 4-[(4-Bromo-2-fluorophenyl)amino]-5-fluoro-1-methyl-6-oxo-1,6-dihydropyridine-3-carboxylic acid was prepared using similar procedures to those disclosed in US 05/0256123 and WO 2005051301. 4-Chloro-1-methyl-6-oxo-1,6-dihydropyridazine-3-carboxylic acid was prepared using similar procedures to those disclosed in US 2005256123. The following intermediates can be prepared using the methods disclosed in the above references:
4-[(2-Fluoro-4-iodophenyl)amino]-1-methyl-6-oxo-1,6-dihydropyridine-3-carboxylic acid;
4-[(4-Bromo-2-chlorophenyl)amino]-1-methyl-6-oxo-1,6-dihydropyridine-3-carboxylic acid;
4-[(4-Bromo-2-fluorophenyl)amino]-1-methyl-6-oxo-1,6-dihydropyridine-3-carboxylic acid;
4-[(4-Bromo-2-chlorophenyl)amino]-1-methyl-6-oxo-1,6-dihydropyridazine-3-carboxylic acid;
4-[(4-Bromo-2-chlorophenyl)amino]-5-fluoro-1-methyl-6-oxo-1,6-dihydropyridazine-3-carboxylic acid; and
4-[(4-Bromo-2-fluorophenyl)amino]-1-methyl-6-oxo-1,6-dihydropyridazine-3-carboxylic acid.

An intermediate of Formula XIV:

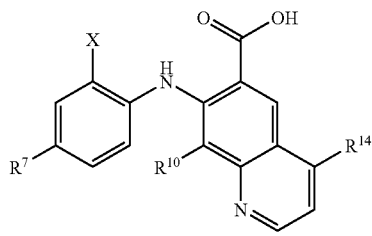

where $R^7$, X, $R^{10}$, and $R^{14}$ are as defined in the Summary of the Invention for Group B can be prepared using procedures known to one of ordinary skill in the art. In particular, see for example WO 05/051302 which is incorporated by reference herein.

An intermediate of Formula XVI

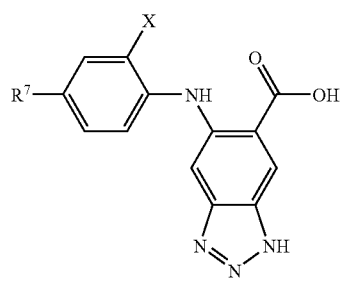

where X and $R^7$ are as defined in the Summary of the Invention for a Compound of Group B can be prepared using procedures known to one of ordinary skill in the art. In particular, see for example WO 2001005390 and WO 2000042022 for procedures that can be used to prepare the following: 5-[(2-Fluoro-4-iodophenyl)amino]-1H-benzotriazole-6-carboxylic acid; 5-[(2-Fluoro-4-iodophenyl)amino]-1-methyl-1H-benzotriazole-6-carboxylic acid; and 4-Fluoro-5-[(2-fluoro-4-iodophenyl)amino]-1H-benzotriazole-6-carboxylic acid.

An intermediate of Formula XVII

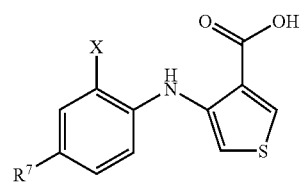

where X and $R^7$ are as defined in the Summary of the Invention for a Compound of Group B can be prepared using procedures known to one of ordinary skill in the art. In particular, see Example 29.

227
An intermediate of Formula XVIII(a) or XVIII(b)

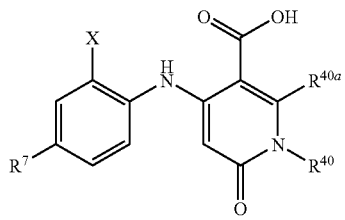

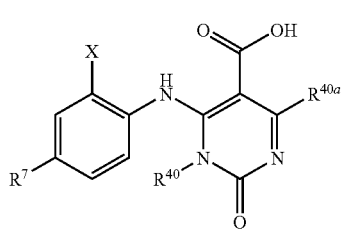

where X, R⁷, R⁴⁰, and R⁴⁰ᵃ are as defined in the Summary of the Invention for a Compound of Group D can be prepared using procedures known to one of ordinary skill in the art. In particular, the halo precursors to XVIII(a) and XVIII(b)

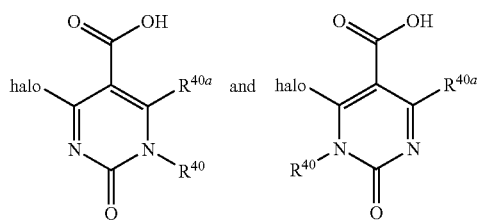

respectively can be prepared using procedures similar to those described in Machon and Dlugosz *Acta Poloniae Pharmaceutica* 1983, 40(1), 1-6 and von Angerer, *Science of Synthesis* 2004, 16, 379-572 (General Review written in English). The halo precursors are then reacted with

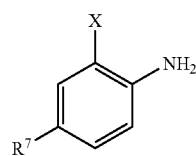

using procedures known to one of ordinary skill in the art and the synthetic methods disclosed herein. The following intermediates can be prepared as described above: 6-[(2-fluoro-4-iodophenyl)amino]-2-oxo-1,2-dihydropyrimidine-5-carboxylic acid and 4-[(2-fluoro-4-iodophenyl)amino]-2-oxo-1,2-dihydropyrimidine-5-carboxylic acid.

228
An intermediate of Formula XIX

XIX where X and R⁷ are as defined in the Summary of the Invention for a Compound of Group C can be prepared using methods known to one of ordinary skill in the art. In particular see US 2005049276.

An intermediate of Formula XX

XX where X and R⁷ are as defined in the Summary of the Invention for a Compound of Group C can be prepared using methods known to one of ordinary skill in the art. In particular see US 2005049276.

The synthesis of azetidines substituted at the 3-position can be conveniently carried out according to Scheme 1:

Scheme 1

(1)   (2)

starting from the N-diphenylmethyl protected azetidin-3-ol (1), readily prepared by reaction of epichlorohydrin and diphenylmethylamine (Chatterjee, Shym S.; Triggle, D. J. *Chemical Communications* (London) 1968, 2, 93). Protecting group exchange, from Boc to CBz, on the azetidine is carried out according to literature protocols (Greene, T. W., Wuts, P. G. Protective Groups in Organic Synthesis, Wiley-Interscience) and subsequent oxidation to the azetidinone (2) where P is CBz provides a useful intermediate for the preparation of compounds of the invention.

For example, the ketone intermediates of formula 2 can be broadly functionalized at the 3-position according to Scheme 2.

or alkyl optionally substituted as described for $R^4$ in the Summary of the Invention for a compound of Group A, Group B, Group C, or Group D. Alternatively, the intermediate 2 can be reacted with ketone or aldehyde anions of formula 19 in a Claisen-type condensation to give (5) where $R^{4''}$ is alkyl optionally substituted as described for $R^4$ in the Summary of the Invention for a compound of Group A, Group B, Group C, or Group D and $R^{4'''}$ is hydrogen or $R^{4''}$. In addition, 2 can be reacted with Wittig reagents of formula 20 (where R' and R'' are independently hydrogen, alkyl, alkenyl, aryl, or heteroaryl and the alkyl, alkenyl, aryl, and heteroaryl are optionally substituted as described for $R^4$ in the Summary of the Invention for a compound of Group A, Group B, Group C, or Group D) to prepare intermediates of formula 6, which are also useful as precursors for compounds of the invention.

According to Scheme 3, intermediates of formula (6) where (R' and R'' are hydrogen and P is a nitrogen-protecting group such as CBz or Boc)

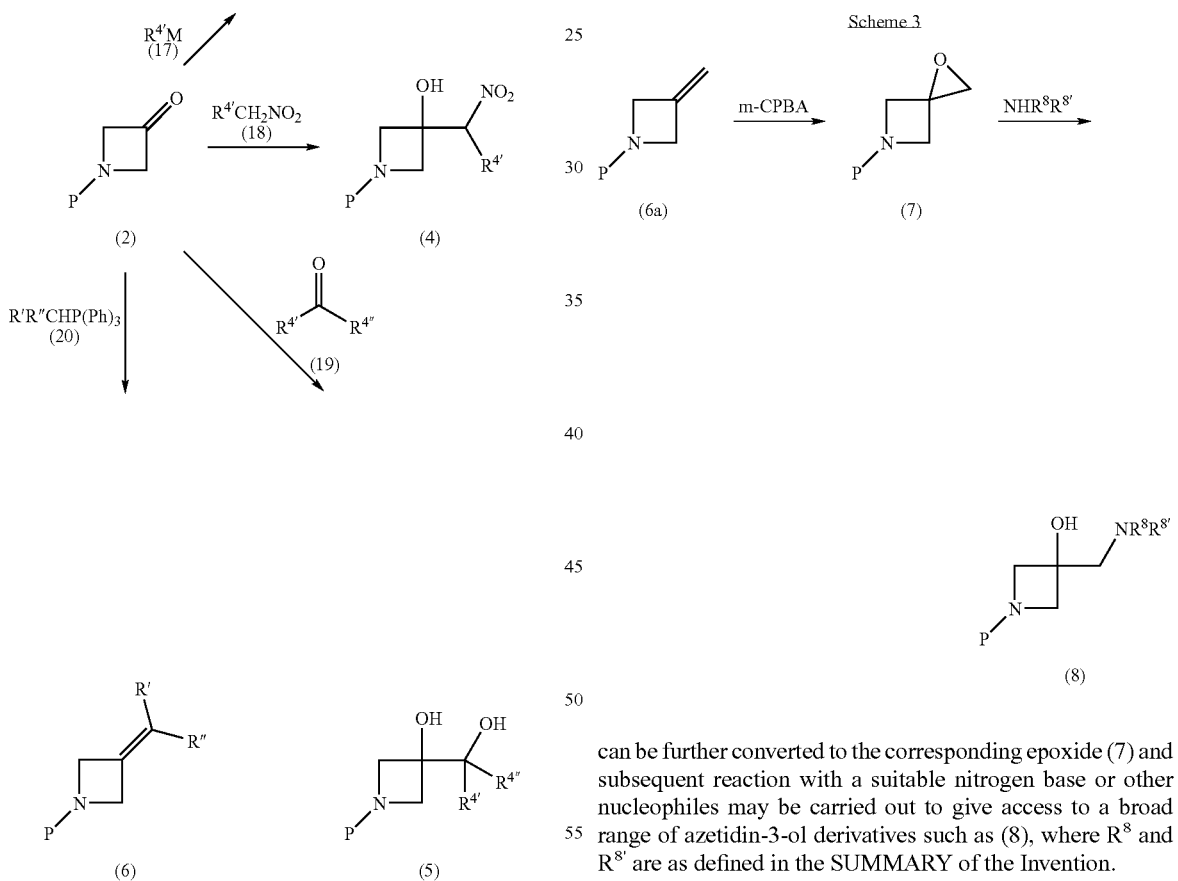

can be further converted to the corresponding epoxide (7) and subsequent reaction with a suitable nitrogen base or other nucleophiles may be carried out to give access to a broad range of azetidin-3-ol derivatives such as (8), where $R^8$ and $R^{8'}$ are as defined in the SUMMARY of the Invention.

An intermediate of formula (3), where $R^4$ is as defined in the Summary of the Invention for a compound of Group A, Group B, Group C, or Group D can be prepared by reacting the intermediate 2 with Grignard reagents or other organometallic species of formula 17, such as organolithiums. Alternatively, the intermediate 2 can be reacted with nitroalkane anions of formula 18 prepared in-situ as in the Henry reaction (The Henry reaction, recent examples: Luzzio, F. A. *Tetrahedron* 2001, 57(6), 915-945) to give (4) where $R^{4''}$ is hydrogen In some cases the preparation of optically pure compounds is desired where the azetidine contains one or more stereocenters. Numerous techniques for the preparation of optically pure compounds through both resolution techniques and asymmetric synthesis are well known in the art. In one such case, an asymmetric synthesis methodology can be employed where an azetidine precursor of formula (2) is reacted with an intermediate of formula 21 where R' is not hydrogen, as depicted in Scheme 4.

Scheme 4

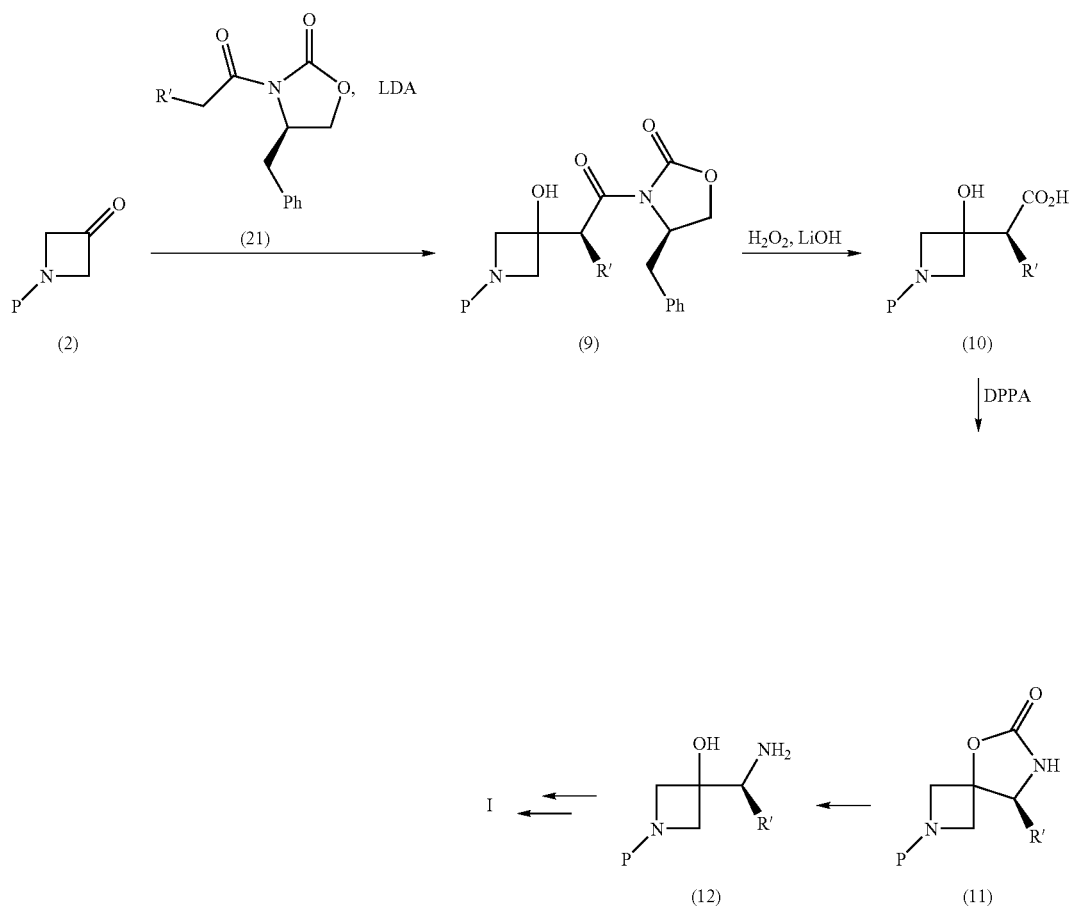

One such useful approach makes use of Evans oxazolidinone methodology (Diastereoselective aldol condensation using a chiral oxazolidinone auxiliary. Gage, James R.; Evans, David A. *Organic Syntheses* 1990, 68, 83-91). The condensation of an azetidinone (2) with the a chiral oxazolidinone in the presence of a base such as LDA affords an intermediate oxazolidinone (9), where P is a nitrogen-protecting group such as CBz or Boc, with diastereoselectivity. Treatment with lithium hydroxide in aqueous hydrogen peroxide gives carboxylic acid (10) which can be subject to Curtius rearrangement to provide the chiral oxazolidinone (11) then carried forward as required to a useful intermediate (12). Further protecting group manipulation and derivatization as required can be employed to prepare compounds of Formula I.

Alternatively, a racemic mixture of an intermediate of formula (13), useful to prepare a compound of Formula I where $R^3$ is hydroxy and $R^4$ is heterocycloalkyl (in particular, where $R^4$ is a N-protected piperidine), can be prepared according to Scheme 5.

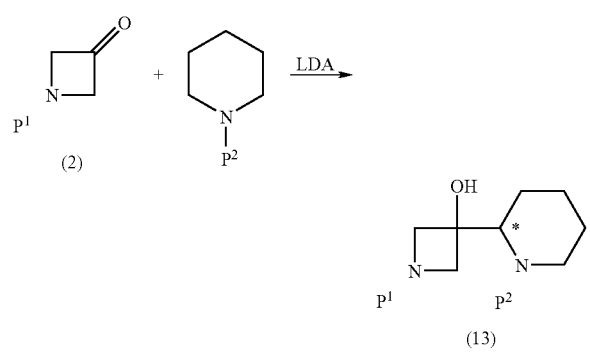

Scheme 5

In the reaction schemes $P^1$ and $P^2$ are orthogonal nitrogen-protecting groups. For example, $P^1$ is Boc and $P^2$ is CBz or $P^1$ is CBz and $P^2$ is Boc. The reaction is carried out in-situ by treating 22 to generate the lithated amine and by subsequently treating it with a ketone such as (2) according to the method of Peter Beak (Beak, Peter; Lee, Won Koo α-Lithioamine synthetic equivalents: syntheses of diastereoisomers from the Boc-piperidines. Journal of Organic Chemistry 1990, 55(9), 2578-80). The racemate (13) thus prepared can be resolved by functionalization, as depicted in Scheme 6, with a chiral acid such as the readily-available Mosher acid (14).

Scheme 6

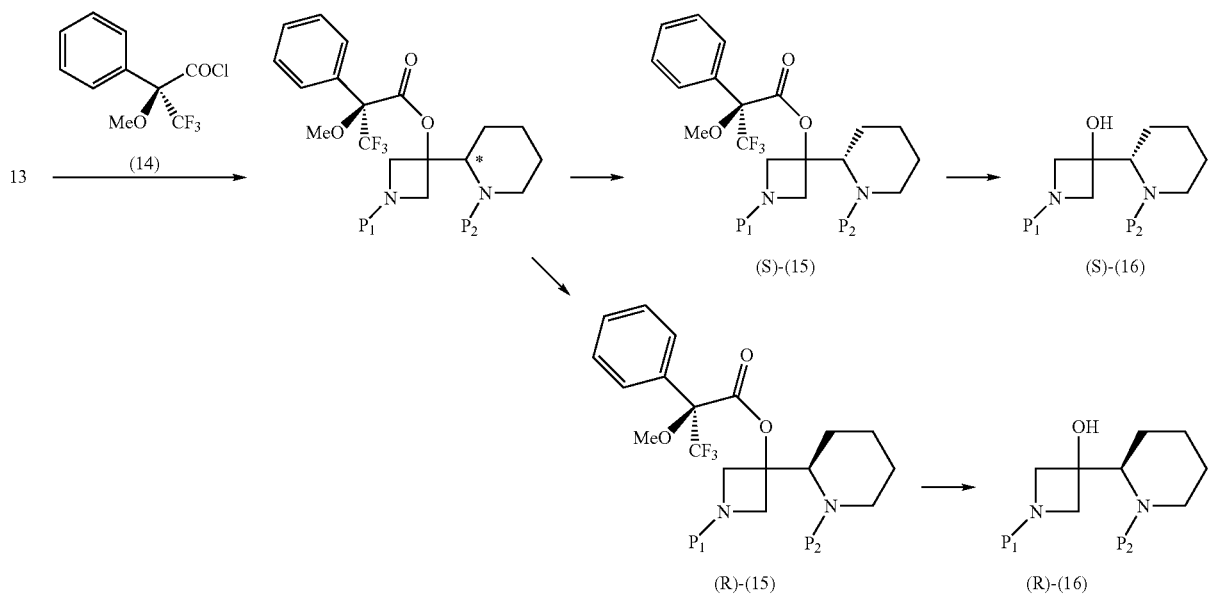

The resulting diastereomeric esters (15) can be separated by chromatographic means and then carried forward individually as the enantiomerically pure intermediates (R)-(16) and (S)-(16).

Compounds of the Invention can be prepared by reacting an intermediate of Formula II, III(a), III(b), IV(a), IV(b), V(a), V(b), VI(a), VI(b), VII(a), VII(b), VIII(a), VIII(b), IX, X(a), X(b), XI(a), XI(b), XII, XIII, XIV, XVI, XVII, XVIII (a), XVIII(b), XIX, or XX with intermediate 17 according to Scheme 7:

Scheme 7

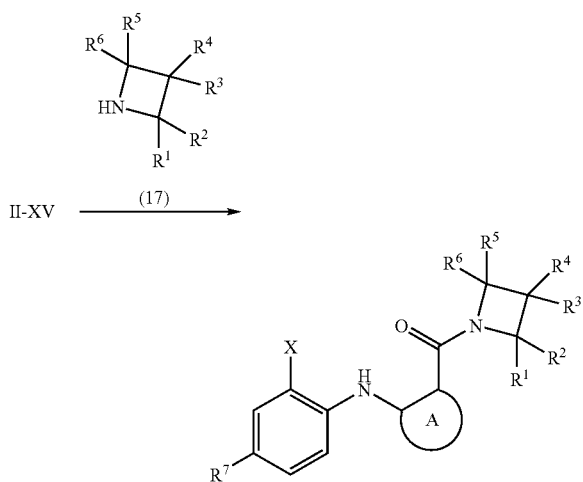

The reaction is carried out in a solvent such as DMF, THF, or DCM in the presence of a base such as DIPEA, N-methylmorpholine, DMAP, or triethylamine and optionally in the presence of a coupling agent such as PyBOP, HBTU, or EDCI.

Alternatively an intermediate of Formula II, III(a), III(b), IV(a), IV(b), V(a), V(b), VI(a), VI(b), VII(a), VII(b), VIII(a), VIII(b), IX, X(a), X(b), XI(a), XI(b), XII, XIII, XIV, XVI, XVII, XVIII(a), XVIII(b), XIX, or XX can be converted into an acid halide according to Scheme 8

Scheme 8

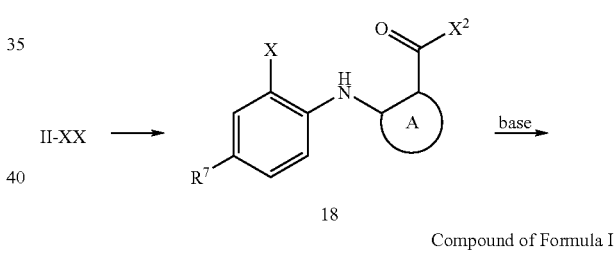

Compound of Formula I where $X^2$ is halo, such as chloro or fluoro, and all other groups are as defined in the Summary of the Invention for a compound of Group A, Group B, Group C, or Group D. The reaction is carried out in a solvent such as dioxane, THF, or DCM in the presence of a base such as DIPEA, sodium bicarbonate. The acid halide of formula 18 can then be reacted with an azetidine intermediate of formula 17 to prepare a compound of Formula I.

SYNTHETIC EXAMPLES

Generally, the compounds listed below were identified by LC-MS, and/or isolated, and characterized by $^1$H-NMR (most typically 400 MHz). Liquid chromatography-mass spectral (LC-MS) analyses were performed using at least one of: a Hewlett-Packard Series 1100 MSD, an Agilent 1100 Series LC/MSD (available from Agilent Technologies Deutschland GmbH of Waldbronn Germany), or a Waters 8-Channel MUX System (available from Waters Corporation of Milford, Mass.). Compounds were identified according to either their observed mass [MH$^+$] or [MNa$^+$] ion (positive mode) or [MH$^-$] ion (negative mode). $^1$H-NMR data for compounds was taken with a Varian AS400 Spectrometer (400 MHz, available from Varian GmbH, Darmstadt, Germany). Starting materials and intermediates used to prepare a compound of the invention are either commercially available or can be prepared by one of ordinary skill in the art.

Reference 1

3,4-difluoro-2-[(2-fluoro-4-iodophenyl)amino]benzoyl fluoride

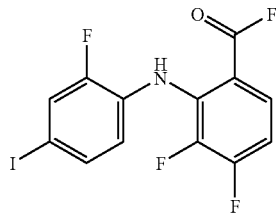

To a stirred mixture of 3,4-difluoro-2-[(2-fluoro-4-iodophenyl)amino]benzoic acid (12 g, 30.5 mmol), prepared using procedures similar to those described in U.S. Pat. No. 7,019,033, in dichloromethane (70 mL) at 0° C. was added pyridine (2.5 mL, 30.8 mmol) followed by dropwise addition of cyanuric fluoride (2.8 mL, 33.6 mmol). The reaction mixture was stirred at 0° C. for 10 minutes and then warmed to room temperature and stirred for 2 hours. The reaction mixture was diluted with water and extracted with dichloromethane (100 mL). The aqueous layer was extracted once with dichloromethane (50 mL). The combined organic layers were washed with saturated aqueous sodium bicarbonate solution, brine, dried over anhydrous sodium sulfate and concentrated in vacuo to give crude product as a brownish solid. Crude product was purified by flash chromatography (plug, 25% ethyl acetate in hexanes) to afford 3,4-difluoro-2-[(2-fluoro-4-iodophenyl)amino]benzoyl fluoride as a beige solid (11.8 g, 97% yield). $^1$H NMR (400 MHz, CD$_3$OD): 8.41 (s, 1H), 7.80-7.81 (m, 1H), 7.52 (dd, 1H), 7.43-7.47 (m, 1H), 6.96-7.03 (m, 1H), 6.85-6.92 (m, 1H).

Reference 2

2-[(4-bromo-2-chlorophenyl)amino]-3,4-difluorobenzoic acid

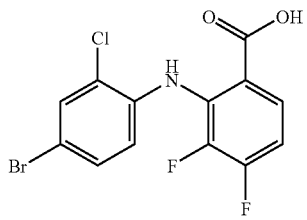

To a solution of 2,3,4-trifluorobenzoic acid (1 g, 5.68 mmol) and 4-bromo-2-chloroaniline (1.2 g, 5.68 mmol) in acetonitrile (10 mL) was added lithium amide (0.39 g, 17.04 mmol) and the reaction stirred at 60° C. for 1.5 hours. The mixture was cooled to room temperature and then to 0° C. and acidified with aq. hydrochloric acid. The obtained precipitate was collected by filtration and washed with cold water and dried in vacuo to afford 2[(4-bromo-2-chlorophenyl)amino]-3,4-difluorobenzoic acid (1.92 g, 94% yield) as a beige solid. MS (EI) for C$_{13}$H$_7$BrClF$_2$NO$_2$: 363 (MH$^+$).

Using the same or analogous synthetic techniques and substituting, as necessary, with alternative reagents, 2-[(4-iodo-2-fluorophenyl)amino]-3-fluorobenzoic acid was prepared. MS (EI) for C$_{13}$H$_8$F$_2$INO$_2$: 376 (MH$^+$).

Reference 3

Phenylmethyl 1-oxa-5-azaspiro[2.3]hexane-5-carboxylate

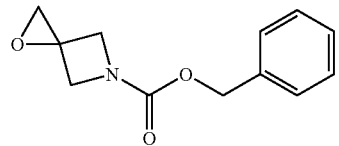

To a solution of azetidin-3-ol hydrochloride in tetrahydrofuran (90 mL) and water (10 mL) was added triethylamine (15 mL, 0.106 mol) followed by slow addition of benzyl chloroformate (8.0 mL, 0.056 mol) at room temperature. The reaction mixture was stirred at room temperature for 16 hours then partitioned with water and ethyl acetate. The organic layer was washed with brine, dried over anhydrous magnesium sulfate and concentrated. The residue was purified by flash chromatography (SiO$_2$, 25-50% ethyl acetate in hexanes) to afford phenylmethyl 3-hydroxyazetidine-1-carboxylate (3.56 g, 33% yield) as a clear and colorless oil. $^1$H NMR (400 MHz, CDCl$_3$): 7.36-7.31 (m, 5H), 5.09 (s, 2H), 4.64-4.57 (m, 1H), 4.22 (dd, 2H), 3.88 (dd, 2H), 2.61 (d, 1H, J=4.0 Hz). MS (EI) for C$_{11}$H$_{13}$NO$_3$: 208 (MH$^+$).

To a solution of phenylmethyl 3-hydroxyazetidine-1-carboxylate (3.5 g, 0.0168 mol) in dichloromethane (100 mL) was added Dess-Martin periodinane (10.7 g, 0.0.25 mol) at room temperature and stirred for 5 h. The reaction mixture was quenched with 1:1 ratio of saturated aqueous sodium bicarbonate and 1M sodium thiosulfate (200 mL) and then partitioned with dichloromethane. The organic layer was dried over anhydrous magnesium sulfate and concentrated in vacuo to afford phenylmethyl 3-oxoazetidine-1-carboxylate (3.43 g, 99% yield) as a clear and colorless oil without further purification. $^1$H NMR (400 MHz, CDCl$_3$): 7.39-7.31 (m, 5H), 5.17 (s, 2H), 4.77 (s, 4H). MS (EI) for C$_{11}$H$_{11}$NO$_3$:205 (M$^+$).

A suspension of methyltriphenylphosphonium bromide (23.0 g, 0.0649 mol) and potassium tert-butoxide (7.3 g, 0.0649 mol) in diethyl ether (140 mL) was stirred at room temperature for 20 min, and then heated to 35° C. for 1 h. To this bright yellow reaction mixture was slowly added a dilute solution of phenylmethyl 3-oxoazetidine-1-carboxylate (3.33 g, 0.0162 mol) in diethyl ether (50 mL) The reaction mixture was stirred at 35° C. for 12 hours then filtered through a bed of celite and rinsed with ethyl ether. The filtrate was washed with water and brine, dried over anhydrous magnesium sulfate and concentrated. The residue was purified by flash chromatography (SiO$_2$, 5-10% ethyl acetate in hexanes) to afford phenylmethyl 3-methylideneazetidine-1-carboxylate (2.46 g, 75% yield) as a clear and colorless oil). $^1$H NMR (400 MHz, CDCl$_3$): 7.27-7.22 (m, 5H), 5.02 (s, 2H), 4.93-4.90 (m, 2H), 4.48-4.47 (m, 4H). MS (EI) for C$_{12}$H$_{13}$NO$_2$: 203 (MH$^+$).

To a solution of phenylmethyl 3-methylideneazetidine-1-carboxylate (2.46 g, 0.0121 mol) in chloroform (100 mL) was added 3-chloroperoxybenzoic acid (12.5 g, 0.0726 mol) at 0°

C. The reaction mixture was allowed to warm up to room temperature over a period of 12 hours then quenched with 1 M sodium thiosulfate/saturated aqueous sodium bicarbonate (1:1). The layers were separated and the organic layer was dried over anhydrous magnesium sulfate then concentrated. The residue was purified by flash chromatography (5-15% ethyl acetate in hexanes) to afford phenylmethyl 1-oxa-5-azaspiro[2.3]hexane-5-carboxylate (2.2 g, 83% yield) as clear and colorless oil. $^1$H NMR (400 MHz, CDCl$_3$): 7.37-7.29 (m, 5H), 5.12 (s, 2H), 4.35-4.26 (m, 4H), 2.85 (s, 2H). MS (EI) for $C_{12}H_{13}NO_3$: 220 (MH$^+$).

Reference 4

4-(2-fluoro-4-iodophenylamino)-1-methyl-6-oxo-1, 6-dihydropyridazine-3-carboxylic acid

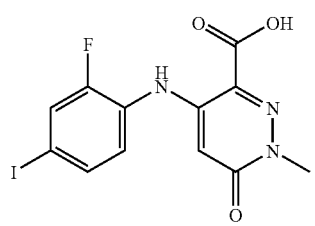

4-chloro-1-methyl-6-oxo-1,6-dihydropyridazine-3-carboxylic acid was prepared using procedures similar to those disclosed in US 2005256123.

To a solution of 4-chloro-1-methyl-6-oxo-1,6-dihydropyridazine-3-carboxylic acid (350 mg, 1.855 mmol) and 2-fluoro-4-iodoaniline (1.06 g, 4.453 mmol) in tetrahydrofuran (13.3 mL) was sparged with nitrogen for 5 minutes followed by the slow addition of lithium bis(trimethylsilyl)amide, 1.0 M in THF (7.4 mL). The reaction mixture stirred for an additional 4 hours at room temperature. The mixture was quenched with 1 N HCl and concentrated in vacuo. The residue was partitioned between ethyl acetate and 1 N aqueous HCl. The aqueous layer was extracted (3×) with ethyl acetate. The combined organic layer was washed with brine, dried over anhydrous sodium sulfate, filtered and evaporated to afford 4-(2-fluoro-4-iodophenylamino)-1-methyl-6-oxo-1,6-dihydropyridazine-3-carboxylic acid (939 mg, 100% yield). $^1$H NMR (CDCl$_3$): 7.27 (dd, 1H), 7.21 (d, 1H), 6.54 (t, 1H), 4.84 (broad s, 2H), 2.09 (s, 1H), 1.26 (t, 3H); MS (EI) for $C_{12}H_9N_3O_3FI$: 389 (MH$^+$).

A solution of 4-(2-fluoro-4-iodophenylamino)-1-methyl-6-oxo-1,6-dihydropyridazine-3-carboxylic acid (939 mg, 2.413 mmol) in dichloromethane (60 mL) in the presence of dimethylformamide (8.0 mL) was cooled to 0° C. Malonyl chloride (1.26 mL, 14.48 mmol) was added and stirred at room temperature for 1 hour. The reaction mixture was evaporated and partitioned between ethyl acetate and 1M aqueous ammonium chloride. The aqueous layer was extracted 1× with ethyl acetate. The combined organic layers were washed with brine, dried over anhydrous sodium sulfate, filtered and concentrated in vacuo to afford 4-(2-fluoro-4-iodophenylamino)-1-methyl-6-oxo-1,6-dihydropyridazine-3-carbonyl chloride. This crude material was taken into the next step without further purification. MS (EI) for $C_{12}H_8N_3O_2ClFI$: 408 (MH$^+$).

To a solution of 4-(2-fluoro-4-iodophenylamino)-1-methyl-6-oxo-1,6-dihydropyridazine-3-carbonyl chloride in methanol (15 mL) and benzene (12 mL) was added dropwise trimethylsilyl diazomethane (1 mL) and stirred at room temperature for 15 minutes. The reaction mixture was quenched with acetic acid and evaporated. The residue was partitioned between ethyl acetate and brine. The organic layer was separated, dried over anhydrous sodium sulfate, filtered and concentrated in vacuo. The residue was purified on silica gel chromatography column (7:3 hexanes/ethyl acetate) to afford methyl 4-(2-fluoro-4-iodophenylamino)-1-methyl-6-oxo-1,6-dihydropyridazine-3-carboxylate (84.9 mg, 8.7% yield), $^1$H NMR (CDCl$_3$): 7.49-7.56 (m, 3H), 7.12 (t, 1H), 6.13 (d, 1H), 4.00 (s, 3H), 3.83 (s, 3H); MS (EI) for $C_{13}H_{11}N_3O_3FI$: 404 (MH$^+$).

Methyl 4-(2-fluoro-4-iodophenylamino)-1-methyl-6-oxo-1,6-dihydropyridazine-3-carboxylate (84.9 mg, 0.211 mmol) was dissolved in tetrahydrofuran (5 mL), methanol (2.5 mL) and water (2.5 mL). Aqueous 2 M lithium hydroxide (200 μL) was added at room temperature. After 10 minutes, the reaction mixture was heated to 50° C. for 30 minutes and continued to stir at room temperature for 16 hours at which time the solvents were evaporated. The residue was made acidic with 2 M aqueous hydrochloric acid to pH 2 and extracted with ethyl acetate. The organic layer separated, dried over anhydrous sodium sulfate, filtered and concentrated in vacuo to provide 4-(2-fluoro-4-iodophenylamino)-1-methyl-6-oxo-1,6-dihydropyridazine-3-carboxylic acid (54.0 mg, 66% yield). MS (EI) for $C_{12}H_9N_3O_3FI$: 390 (MH$^+$).

Reference 5

1,1-dimethylethyl 2-(3-hydroxy-1-{[(phenylmethyl)oxy]carbonyl}azetidin-3-yl)piperidine-1-carboxylate

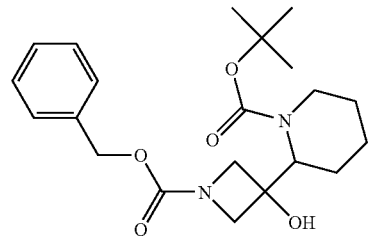

To a solution of 1,1-dimethylethyl piperidine-1-carboxylate (0.50 g, 2.7 mmol) in anhydrous diethyl ether (9.0 mL) under anhydrous nitrogen gas was added N,N,N',N'-tetramethylethane-1,2-diamine (0.41 mL, 2.7 mmol), and the solution was cooled to −78° C. To this solution was added (2-methylpropyl)lithium (2.1 mL, 1.4 M in cyclohexane, 3.0 mmol) in small portions. To this anion solution was added phenylmethyl 3-oxoazetidine-1-carboxylate (1.0 g, 5.4 mmol), prepared using procedures as described in Reference 3, in anhydrous ether (2.0 mL), while maintaining the internal temperature at less than −60° C. The solution was allowed to warm to room temperature and stirred overnight. The reaction was quenched with water, and partitioned between water and diethyl ether. The layers were separated and the aqueous layer was extracted with diethyl ether twice. The combined organic layers were dried (magnesium sulfate), filtered and concentrated in vacuo. Chromatography (silica gel, 3:1 hexanes/ethyl acetate) gave 0.13 g (13%) of 1,1-dimethylethyl 2-(3-hydroxy-1-{[(phenylmethyl)oxy]carbonyl}azetidin-3-yl)piperidine-1-carboxylate. $^1$H NMR (400 MHz, CDCl$_3$): 7.31 (m, 5H), 5.08 (s, 2H), 4.05 (d, 1H), 4.00 (d, 1H), 3.84 (d, 2H), 3.80 (broad s, 1H), 3.55 (broad s, 1H), 3.10 (broad s, 1H), 1.92

(m, 1H), 1.45-1.62 (m, 6H), 1.43 (s, 9H). MS (EI) for $C_{21}H_{30}N_2O_5$: 335 (M-tBu), 315 (M-OtBu).

Example 1

1-({3,4-difluoro-2-[(2-fluoro-4-iodophenyl)amino]phenyl}carbonyl)azetidin-3-ol

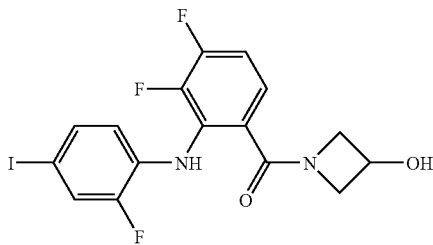

3,4-Difluoro-2-[(2-fluoro-4-iodophenyl)amino]benzoic acid (2.1 g, 5.3 mmol), prepared using procedures similar to those in U.S. Pat. No. 7,019,033, was taken into DMF (10 mL) followed by addition of PyBOP (2.6 g, 5.3 mmol) and the mixture was allowed to stir at room temperature over 15 minutes. Azetidin-3-ol hydrochloride (870 mg, 8.0 mmol) and DIPEA (1.85 mL, 11.2 mmol) was then added and the mixture was allowed to stir an additional hour at room temperature. The mixture was then partitioned with ethyl acetate and 0.5 M aqueous sodium hydroxide solution. The organic layer was then washed with water (3×) then brine and dried over anhydrous sodium sulfate. Filtration and concentration followed by silica gel flash chromatography using ethyl acetate: hexanes (5:1) eluent afforded 1-({3,4-difluoro-2-[(2-fluoro-4-iodophenyl)amino]phenyl}carbonyl)azetidin-3-ol (2.09 g, 87% yield) as a colorless amorphous solid. $^1$H NMR (400 MHz, CDCl$_3$): 8.47 (s, 1H), 7.39 (dd, 1H), 7.32 (d, 1H), 7.13-7.09 (m, 1H), 6.84-6.78 (m, 1H), 6.63-6.57 (m, 1H), 4.74-4.67 (m, 1H), 4.43-4.39 (m, 2H), 4.20-3.96 (br d, 2H), 2.50 (d, 1H).

Using the same or analogous synthetic techniques and substituting, as necessary, with alternative reagents, the compounds in Examples 1(a)-(e) were prepared.

Example 1(a)

1-[1-({3,4-difluoro-2-[(2-fluoro-4-iodophenyl)amino]phenyl}-carbonyl)azetidin-3-yl]-N,N-dimethylpyrrolidin-3-amine. The title compound was prepared by reacting 3,4-difluoro-2-[(2-fluoro-4-iodophenyl)amino]benzoic acid with N-methyl-N-(2-(pyridin-2-yl)ethyl)azetidin-3-amine. The azetidine intermediate was prepared using procedures similar to those described in Abdel-Magid, et. al., *Tetrahedron Letters* 1990, 31(39), 5595 starting with tert-butyl 3-oxoazetidine-1-carboxylate, which itself was prepared as described in Example 3. The title compound: $^1$H NMR (400 MHz, d$_6$-DMSO): 8.56 (s, 1H), 7.58 (m, 1H), 7.38 (d, 1H), 7.31 (m, 1H), 7.16 (m, 1H), 6.67 (m, 1H), 4.16 (m, 1H), 3.97 (m, 2H), 3.77 (m, 1H), 3.26 (br s, 4H), 2.63 (m, 1H), 2.42 (br s, 6H), 1.99 (br s, 1H), 1.74 (br s, 1H). MS (EI) for $C_{22}H_{24}F_3IN_4O$: 545 (MH$^+$).

Example 1(b)

1-({3,4-difluoro-2-[(2-fluoro-4-iodophenyl)amino]phenyl}carbonyl)-N-methyl-N-(2-pyridin-2-ylethyl)azetidin-3-amine. The title compound was prepared by reacting 3,4-difluoro-2-[(2-fluoro-4-iodophenyl)amino]benzoic acid with 1-(azetidin-3-yl)-N,N-dimethylpyrrolidin-3-amine. The azetidine intermediate was prepared using procedures similar to those described in Abdel-Magid, et. al., *Tetrahedron Letters* 1990, 31(39), 5595 starting with tert-butyl 3-oxoazetidine-1-carboxylate, which itself was prepared as described in Example 3. The title compound: $^1$H NMR (400 MHz, CD$_3$OD): 8.50 (d, 1H), 7.94 (t, 1H), 7.50-7.30 (m, 5H), 7.07 (q, 1H), 6.66-6.61 (m, 1H), 4.52-4.48 (m, 2H), 4.31 (s, 2H), 4.23-4.18 (m, 1H), 3.48-3.46 (m, 2H), 3.17-3.13 (m, 2H), 2.88 (s, 3H); MS (EI) for $C_{24}H_{22}F_3IN_4O$: 567 (MH$^+$).

Example 1(c)

6-(Azetidin-1-ylcarbonyl)-2,3-difluoro-N-(2-fluoro-4-iodophenyl)aniline:
$^1$H NMR (400 MHz, CDCl$_3$): 8.57 (s, 1H), 7.41-7.38 (dd, 1H), 7.34-7.31 (dt, 1H), 7.13-7.09 (m, 1H), 6.83-6.77 (m, 1H), 6.64-6.58 (m, 1H), 4.27 (b, 2H), 4.18 (b, 2H), 2.38-2.30 (p, 2H); MS (EI) for $C_{16}H_{12}F_3IN_3O$: 433 (MH$^+$).

Example 1(d)

[1-({3,4-Difluoro-2-[(2-fluoro-4-iodophenyl)amino]phenyl}carbonyl)azetidin-3-yl]methanol: $^1$H NMR (400 MHz, CDCl$_3$): 8.52 (s, 1H), 7.41-7.38 (dd, 1H), 7.34-7.31 (dt, 1H), 7.15-7.11 (m, 1H), 6.83-6.77 (m, 1H), 6.64-6.58 (m, 1H), 4.29-4.20 (m, 2H), 4.09 (b, 1H), 3.93 (b, 1H), 3.82-3.81 (d, 2H), 2.89-2.75 (m, 1H); MS (EI) for $C_{17}H_{14}F_3IN_2O_2$: 463 (MH$^+$).

Example 1(e)

1-({3,4-Difluoro-2-[(2-fluoro-4-iodophenyl)amino]phenyl}carbonyl)azetidine-3-carboxylic acid: $^1$H NMR (400 MHz, CDCl$_3$): 7.79 (b, 2H), 7.42-7.38 (dd, 1H), 7.34-7.32 (dt, 1H), 7.15-7.11 (m, 1H), 6.89-6.83 (m, 1H), 6.65-6.60 (m, 1H), 4.46-4.29 (m, 4H), 3.55-3.47 (m, 1H); MS (EI) for $C_{17}H_{12}F_3IN_2O_3$: 477 (MH$^+$).

Example 2

N-[1-({3,4-Difluoro-2-[(2-fluoro-4-iodophenyl)amino]phenyl}carbonyl)azetidin-3-yl]-N2,N2-diethylglycinamide

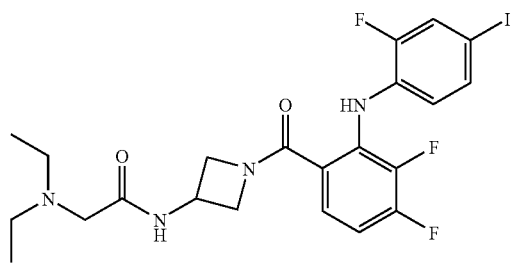

A solution of 3,4-difluoro-2-[(2-fluoro-4-iodophenyl)amino]benzoic acid (200 mg, 0.51 mmol), prepared using procedures similar to those in U.S. Pat. No. 7,019,033, PyBOP (256 mg, 0.51 mmol), commercially available tert-butyl azetidin-3-ylcarbamate (131 mg, 0.77 mmol) and N,N-diisopropylethylamine (180 μL, 1.02 mmol) in dimethylformamide (3 mL) was stirred at room temperature for 15 hours. The reaction mixture was partitioned between 5% aqueous lithium chloride and ethyl acetate. The organic portion was washed with 20% aqueous citric acid, saturated aqueous sodium bicarbonate, brine, dried over sodium sulfate, filtered and concentrated in vacuo to afford a brown residue which was purified by silica gel column chromatography eluting with 30% ethyl acetate in hexanes to afford 1,1-dimethylethyl [1-({3,4-difluoro-2-[(2-fluoro-4-iodophenyl)amino]phenyl}carbonyl)azetidin-3-yl]carbamate (225 mg, 80% yield) as a colorless oil. $^1$H NMR (400 MHz, DMSO): 8.56 (s, 1H), 7.60-7.55 (m, 2H), 7.38 (d, 1H), 7.30-7.26 (m, 1H), 7.20-7.13 (m, 1H), 6.71-6.66 (m, 1H), 4.37-4.20 (m, 2H), 4.18-4.06 (m, 1H), 3.98-3.93 (m, 1H), 3.82-3.75 (m, 1H), 1.37 (s, 9H). MS (EI) $C_{21}H_{21}N_3O_3F_3I$: 548 (MH$^+$).

A solution of 1,1-dimethylethyl [1-({3,4-difluoro-2-[(2-fluoro-4-iodophenyl)amino]phenyl}carbonyl)azetidin-3-yl]carbamate (113 mg, 0.20 mmol) and trifluoroacetic acid (500 μL) in dichloromethane (2 mL) was added stirred at room temperature for one hour then was partitioned between saturated aqueous sodium bicarbonate, and dichloromethane. The organic portion was washed with brine, dried over anhydrous sodium sulfate, filtered and concentrated to afford a colorless residue which was purified by column chromatography eluting with 10% methanol in dichloromethane to afford 1-({3,4-difluoro-2-[(2-fluoro-4-iodophenyl)amino]phenyl}carbonyl)azetidin-3-amine (85 mg, 95% yield) as a white foam. $^1$H NMR (400 MHz, CDCl$_3$): 8.53 (s, 1H), 7.39 (d, 1H), 7.32 (d, 1H), 7.13-7.09 (m, 1H), 6.84-6.77 (m, 1H), 6.63-6.57 (m, 1H), 4.46-4.39 (m, 2H), 3.98-3.75 (br m, 4H); MS (EI) for $C_{16}H_{13}F_3IN_3O$: 448 (MH$^+$).

A solution of 1-({3,4-difluoro-2-[(2-fluoro-4-iodophenyl)amino]phenyl}carbonyl)azetidin-3-amine (100 mg, 0.22 mmol), PyBOP (131 mg, 0.25 mmol), N,N-diisopropylethylamine (80 μL, 0.44 mol) and bromoacetic acid (35 mg, 0.25 mmol) in dimethylformamide (1 mL) was stirred at room temperature for 15 hours. The reaction mixture was concentrated in vacuo and the resultant residue was purified by column chromatography eluting with 80% ethyl acetate in hexanes to afford 2-bromo-N-[1-({3,4-difluoro-2-[(2-fluoro-4-iodophenyl)amino]phenyl}carbonyl)azetidin-3-yl]acetamide (102 mg, 82% yield) as a white foam. MS (EI) for $C_{18}H_{14}BrF_3IN_3O_2$: 568.

A solution of 2-bromo-N-[1-({3,4-difluoro-2-[(2-fluoro-4-iodophenyl)amino]phenyl}carbonyl)azetidin-3-yl]acetamide (30 mg, 0.05 mmol) and N,N-diethylamine (100 μL, excess) in dichloromethane (2 mL) was stirred at room temperature for 15 hours. The reaction mixture was concentrated in vacuo and purified by preparative reverse phase HPLC (CH$_3$CN/H$_2$O with 0.1% TFA). Isolated product was concentrated in vacuo to afford N-[1-({3,4-difluoro-2-[(2-fluoro-4-iodophenyl)amino]phenyl}carbonyl)azetidin-3-yl]-N2,N2-diethylglycinamide trifluoroacetate salt (13.0 mg, 38% yield) as a white solid. $^1$H NMR (400 MHz, CDCl$_3$): 9.36 (br s, 1H), 9.25 (d, 1H), 8.60 (s, 1H), 7.60 (d, 1H), 7.40 (d, 1H), 7.33-7.27 (m, 1H), 7.22-7.15 (m, 1H), 6.73-6.66 (m, 1H), 4.54-4.40 (m, 2H), 4.25-4.20 (m, 1H), 4.04-3.82 (m, 4H), 3.17-3.12 (m, 4H), 1.18-1.15 (m, 6H); MS (EI) $C_{22}H_{24}F_3IN_4O_2$: 561 (MH$^+$).

Using the same or analogous synthetic techniques and/or substituting with alternative reagents, the compounds in Examples 2(a)-(n) were prepared.

Example 2(a)

1,1-Dimethylethyl[1-({3,4-difluoro-2-[(2-fluoro-4-iodophenyl)amino]phenyl}carbonyl)azetidin-3-yl]carbamate: $^1$H NMR (400 MHz, CDCl$_3$): 8.52 (br s, 1H), 7.40 (dd, 1H), 7.33 (dt, 1H), 7.13-7.07 (m, 1H), 6.80 (ddd, 1H), 6.61 (ddd, 1H), 5.01-4.88 (br, 1H), 4.55-4.37 (br, 4H), 4.05 (br d, 1H), 1.43 (s, 9H); MS (EI) for $C_{21}H_{21}F_3IN_3O_3S$: 548 (MH$^+$).

Example 2(b)

1-({3,4-difluoro-2-[(2-fluoro-4-iodophenyl)amino]phenyl}carbonyl)azetidin-3-amine trifluoroacetate salt: $^1$H NMR (400 MHz, CDCl$_3$): 8.53 (s, 1H), 7.39 (d, 1H), 7.32 (d, 1H), 7.13-7.09 (m, 1H), 6.84-6.77 (m, 1H), 6.63-6.57 (m, 1H), 4.46-4.39 (m, 2H), 3.98-3.75 (br m, 4H); MS (EI) for $C_{16}H_{13}F_3IN_3O$: 448 (MH$^+$).

Example 2(c)

N-[1-({3,4-difluoro-2-[(2-fluoro-4-iodophenyl)amino]phenyl}carbonyl)azetidin-3-yl]-2-methylpropanamide: $^1$H NMR (400 MHz, DMSO): 8.60 (s, 1H), 8.38 (d, 1H), 7.59 (d, 1H), 7.38 (d, 1H), 7.32-7.28 (m, 1H), 7.18-7.13 (m, 1H), 6.72-6.66 (m, 1H), 4.45-4.35 (m, 1H), 4.18-3.77 (m, 4H), 2.36-2.28 (m, 1H), 0.99 (d, 6H); MS (EI) $C_{20}H_{19}F_3IN_3O_2$: 518 (MH$^+$).

Example 2(d)

N-[1-({3,4-difluoro-2-[(2-fluoro-4-iodophenyl)amino]phenyl}carbonyl)azetidin-3-yl]formamide: $^1$H NMR (400 MHz, DMSO): 8.69 (d, 1H), 8.58 (s, 1H), 8.02 (s, 1H), 7.59 (d, 1H), 7.39 (d, 1H), 7.31-7.27 (m, 1H), 7.19-7.13 (m, 1H), 6.70-6.66 (m, 1H), 4.55-4.46 (m, 1H), 4.42-4.36 (m, 1H), 4.20-4.16 (m, 1H), 4.01-3.97 (m, 1H), 3.82-3.79 (m, 1H); MS (EI) $C_{17}H_{13}F_3IN_3O_2$: 476 (MH$^+$).

Example 2(e)

N-[1-({3,4-difluoro-2-[(2-fluoro-4-iodophenyl)amino]phenyl}carbonyl)azetidin-3-yl]-3,4-dihydroxybutanamide: $^1$H NMR (400 MHz, DMSO): 8.60 (s, 1H), 8.47 (d, 1H), 7.59 (d, 1H), 7.39 (d, 1H), 7.31-7.28 (m, 1H), 7.20-7.14 (m, 1H), 6.72-6.66 (m, 1H), 4.45-4.35 (m, 2H), 4.18-4.14 (m, 1H), 4.00-3.92 (m, 1H), 3.84-3.78 (m, 2H), 3.31-3.18 (m, 2H), 2.38-2.18 (m, 1H), 2.09-2.03 (m, 1H); MS (EI) $C_{20}H_{19}F_3IN_3O_4$: 550 (MH$^+$).

Example 2(f)

methyl[1-({3,4-difluoro-2-[(2-fluoro-4-iodophenyl)amino]phenyl}carbonyl)azetidin-3-yl]carbamate: $^1$H NMR (400 MHz, DMSO): 8.58 (s, 1H), 7.84 (d, 1H), 7.59 (d, 1H), 7.39 (d, 1H), 7.35-7.27 (m, 1H), 7.20-7.13 (m, 1H), 6.71-6.66 (m, 1H), 4.38-4.25 (m, 2H), 4.17-4.12 (m, 1H), 4.00-3.97 (m, 1H), 3.83-3.78 (m, 1H), 3.53 (s, 3H); MS (EI) $C_{18}H_{15}F_3IN_3O_3$: 506 (MH$^+$).

Example 2(g)

N-[1-({3,4-difluoro-2-[(2-fluoro-4-iodophenyl)amino]phenyl}carbonyl)azetidin-3-yl]-2-(4-methylpiperazin-1-yl)acetamide trifluoroacetate salt: $^1$H NMR (400 MHz, DMSO): 8.64 (s, 1H), 8.54 (d, 1H), 7.60 (d, 1H), 7.39 (d, 1H), 7.32-7.29 (m, 1H), 7.21-7.15 (m, 1H), 6.72-6.66 (m, 1H), 4.54-4.28 (m, 2H), 4.19-4.15 (m, 1H), 4.06-4.00 (m, 1H), 3.91-3.84 (m, 1H), 3.44-3.24 (m, 2H), 3.16-2.92 (m, 6H), 2.78 (s, 3H), 2.62-2.50 (m, 2H); MS (EI) $C_{23}H_{25}F_3IN_5O_2$: 588 (MH$^+$).

Example 2(h)

N-[1-({3,4-difluoro-2-[(2-fluoro-4-iodophenyl)amino]phenyl}carbonyl)azetidin-3-yl]-N,N-bis(2-hydroxyethyl)glycinamide trifluoroacetate salt: $^1$H NMR (400 MHz, DMSO): 9.19 (d, 1H), 7.60 (d, 1H), 7.41 (d, 1H), 7.31-7.27 (m, 1H), 7.21-7.15 (m, 1H), 6.73-6.66 (m, 1H), 4.51-4.40 (m, 2H), 4.23-4.18 (m, 1H), 4.05-3.98 (m, 3H), 3.86-3.82 (m, 1H), 3.75-3.69 (m, 3H), 3.32 (br s, 4H) $C_{22}H_{24}F_3IN_4O_4$: 593 (MH$^+$).

Example 2(i)

N-[1-({3,4-difluoro-2-[(2-fluoro-4-iodophenyl)amino]phenyl}carbonyl)azetidin-3-yl]-2-piperidin-1-ylacetamide trifluoroacetate salt: $^1$H NMR (400 MHz, DMSO): 9.20 (d, 1H), 7.60 (d, 1H), 7.41 (d, 1H), 7.31-7.27 (m, 1H), 7.21-7.15 (m, 1H), 6.73-6.66 (m, 1H), 4.52-4.40 (m, 2H), 4.24-4.18 (m, 1H), 4.05-4.00 (m, 1H), 3.87-3.80 (m, 3H), 3.40-3.32 (m, 2H), 3.00-2.91 (m, 2H), 1.82-1.66 (m, 6H); MS (EI) $C_{23}H_{24}F_3IN_4O_2$: 573 (MH$^+$).

Example 2(j)

N-[1-({3,4-difluoro-2-[(2-fluoro-4-iodophenyl)amino]phenyl}carbonyl)azetidin-3-yl]-N3-(2-hydroxyethyl)-N3-methyl-beta-alaninamide hydrochloride: $^1$H NMR (400 MHz, DMSO): 9.36 (br s, 1H), 8.86 (d, 1H), 8.60 (s, 1H), 7.59 (d, 1H), 7.39 (d, 1H), 7.32-7.26 (m, 1H), 7.21-7.14 (m, 1H), 6.72-6.66 (m, 1H), 5.35-5.33 (m, 1H), 4.48-4.37 (m, 2H), 4.20-4.15 (m, 1H), 4.02-3.96 (m, 1H), 3.84-3.79 (m, 1H), 3.74-3.68 (m, 2H), 3.42-3.06 (m, 4H), 2.75 (s, 3H), 2.65-2.60 (m, 2H); MS (EI) $C_{22}H_{24}F_3IN_4O_3$: 577 (MH$^+$).

Example 2(k)

N-[1-({3,4-difluoro-2-[(2-fluoro-4-iodophenyl)amino]phenyl}carbonyl)azetidin-3-yl]-N3,N3-bis(2-hydroxyethyl)-beta-alaninamide hydrochloride: $^1$H NMR (400 MHz, DMSO): 9.39 (br s, 1H), 8.91 (d, 1H), 8.61 (s, 1H), 7.59 (d, 1H), 7.39 (d, 1H), 7.31-7.27 (m, 1H), 7.21-7.14 (m, 1H), 6.72-6.66 (m, 1H), 5.31 (br s, 2H), 4.46-4.36 (m, 2H), 4.20-4.15 (m, 1H), 4.02-3.97 (m, 1H), 3.85-3.72 (m, 5H), 3.30-3.17 (m, 4H), 2.68-2.63 (m, 2H); MS (EI) $C_{23}H_{26}F_3IN_4O_4$: 607 (MH$^+$).

Example 2(m)

N-[1-({3,4-difluoro-2-[(2-fluoro-4-iodophenyl)amino]phenyl}carbonyl)azetidin-3-yl]-N2-methylglycinamide trifluoroacetate salt: $^1$H NMR (400 MHz, DMSO): 9.09 (d, 1H), 8.69 (br s, 2H), 8.60 (s, 1H), 7.60 (d, 1H), 7.39 (d, 1H), 7.31-7.27 (m, 1H), 7.22-7.15 (m, 1H), 6.73-6.66 (m, 1H), 4.54-4.41 (m, 2H), 4.25-4.19 (m, 1H), 3.99-3.96 (m, 1H), 3.84-3.78 (m, 1H), 3.72-3.67 (m, 2H), 2.58-2.54 (m, 3H); MS (EI) $C_{19}H_{18}F_3IN_4O_2$: 519 (MH$^+$).

Example 2(n)

N-[1-({3,4-difluoro-2-[(2-fluoro-4-iodophenyl)amino]phenyl}carbonyl)azetidin-3-yl]glycinamide trifluoroacetate salt: $^1$H NMR (400 MHz, DMSO): 8.59 (s, 1H), 8.46 (br s, 1H), 7.59 (d, 1H), 7.39 (d, 1H), 7.32-7.28 (m, 1H), 7.20-7.13 (m, 1H), 6.72-6.66 (m, 1H), 4.49 (br s, 1H), 4.40-4.35 (m, 1H), 4.18-4.13 (m, 1H), 4.05-4.01 (m, 1H), 3.86-3.81 (m, 1H), 3.07 (s, 2H); MS (EI) $C_{18}H_{16}F_3IN_4O_2$: 505 (MH$^+$).

Example 3

1-({3,4-difluoro-2-[(2-fluoro-4-iodophenyl)amino]phenyl}carbonyl)-3-(morpholin-4-ylmethyl)azetidin-3-ol

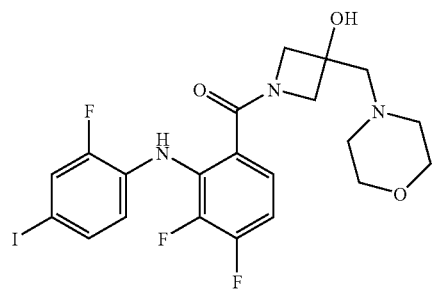

A mixture of 3-azetidinol hydrochloride (10 g, 91 mmol), di-tert-butyl dicarbonate (18.8 g, 86.3 mmol) and sodium bicarbonate (15.3 g, 182 mmol) in dioxane:water (400 mL, 1:1) was stirred at room temperature for 15 hours. The organic portion was removed in vacuo and the aqueous portion was extracted with ethyl acetate three times. The combined organic portion was washed with 5% aqueous HCl, water, brine, dried over sodium sulfate, filtered and concentrated in-vacuo to afford 12.8 g, 74 mmol (81%) of 1,1-dimethylethyl 3-hydroxyazetidine-1-carboxylate as a colorless oil without further purification. $^1$H NMR (400 MHz, DMSO): 5.62 (d, 1H), 4.40-4.33 (m, 1H), 4.02-3.95 (m, 2H), 3.62-3.54 (m, 2H), 1.37 (s, 9H). GC/MS for $C_8H_{15}NO_3$: 173.

A solution of oxalyl chloride (545 μL, 6.36 mmol) in dichloromethane (25 mL) was cooled to −78° C. While maintaining an internal temperature of −78° C., the dropwise addition of DMSO (903 μL, 12.7 mmol) followed by 1,1-dimethylethyl 3-hydroxyazetidine-1-carboxylate (1 g, 5.78 mmol in 30 mL of dichloromethane) and finally triethylamine (3.25 mL, 23.1 mmol in 20 mL of dichloromethane) was performed. The mixture was allowed to warm to room temperature and was stirred for 15 hours. The reaction mixture was diluted with water and partitioned and the organic portion was washed twice with water. The combined aqueous portion was extracted once with dichloromethane. The combined organic portion was washed with brine, dried over sodium sulfate, filtered and concentrated in vacuo to afford a yellow oil which was purified by column chromatography. Eluting with 30% ethyl acetate in hexanes, isolated product was concentrated in vacuo to afford 893 mg, 5.20 mmol (90%) of 1,1-dimethylethyl 3-oxoazetidine-1-carboxylate as a colorless oil, which solidified upon standing. $^1$H NMR (400 MHz, DMSO): 4.67 (s, 4H), 1.42 (s, 9H). GC/MS for $C_8H_{13}NO_3$: 171.

A mixture of potassium tert-butoxide (15.5 g, 137 mmol) and methyltriphenylphosphine bromide (49 g, 137 mmol) in diethyl ether (300 mL) was stirred at room temperature for 1 hour, followed by the addition of 1,1-dimethylethyl 3-oxoazetidine-1-carboxylate (10 g, 58 mmol in 100 mL diethyl ether). The mixture was stirred at 35° C. for 2 hours and then allowed to cool to room temperature. The mixture was filtered through a pad of celite, washing with diethyl ether. The filtrate was partitioned with water and washed twice with water, brine, dried over sodium sulfate, filtered and concentrated in vacuo to give an orange oil which was purified by column chromatography. Eluting with 10% ethyl acetate in hexanes, isolated product was concentrated in vacuo to afford 9.80 g, 58 mmol (100%) of 1,1-dimethylethyl 3-methylideneazetidine-1-carboxylate as a colorless oil. $^1$H NMR (400 MHz, DMSO): 5.05-4.85 (m, 2H), 4.95-4.63 (m, 4H), 1.45 (s, 9H). GC-MS for $C_9H_{15}NO_2$: 169.

To a solution of 1,1-dimethylethyl 3-methylideneazetidine-1-carboxylate (2.96 g, 17.5 mmol) in chloroform (180 mL) was added 3-chloroperoxybenzoic acid (77%, 13.9 g, 62.0 mmol), and the resulting mixture was stirred at room temperature for 2 days. The reaction mixture was quenched with a 1:1 mixture (150 mL) of 10% sodium thiosulfate and saturated sodium bicarbonate solutions. The organic portion was isolated, dried over sodium sulfate, filtered and concentrated to give an oily residue which was then purified by flash chromatography (15-50% ethyl acetate-hexanes) to give 1,1-dimethylethyl 1-oxa-5-azaspiro[2.3]hexane-5-carboxylate (1.65 g, 51%), GC-MS for $C_9H_{15}NO_3$: 185.

1,1-Dimethylethyl 1-oxa-5-azaspiro[2.3]hexane-5-carboxylate (51 mg, 0.28 mmol) was taken into THF (1 mL) followed by addition of morpholine (123 μL, 1.4 mmol) and the mixture was stirred for one hour at room temperature. The solution was then concentrated and the residue partitioned with ethyl acetate and water. The organic layer was washed once with water then brine and the organic layer dried over anhydrous sodium sulfate. Filtration and concentration gave a colorless oil that was purified by silica gel flash chromatography using ethyl acetate to 10% methanol in dichloromethane as eluents. The combined pure fractions were concentrated and the residue treated with neat TFA (1 mL) for 5 minutes then concentrated. The residue was taken into methanol (2 mL) and basified to pH >10 by addition of Biorad AG-1X hydroxide form resin. Filtration and concentration afforded 3-(morpholin-4-ylmethyl)azetidin-3-ol (11.6 mg, 24% yield) as a colorless oil. $^1$H NMR (400 MHz, $CD_3OD$): 3.69-3.66 (m, 4H), 3.55 (d, 2H), 3.49 (d, 2H), 2.66 (s, 2H), 2.57-2.55 (m, 4H).

3-(Morpholin-4-ylmethyl)azetidin-3-ol (11.6 mg, 0.07 mmol) was taken into DMF (1 mL) followed by addition of DIPEA (35 μL, 0.21 mmol) and 3,4-difluoro-2-[(2-fluoro-4-iodophenyl)amino]benzoyl fluoride (28 mg, 0.07 mmol), prepared using procedures similar to those described in Reference 1, and the mixture was stirred for 30 minutes at room temperature. The solution was then concentrated in vacuo and the residue purified by preparative reverse phase HPLC. Lyophillization of the combined fractions gave 1-({3,4-difluoro-2-[(2-fluoro-4-iodophenyl)amino]phenyl}carbonyl)-3-(morpholin-4-ylmethyl)azetidin-3-ol trifluoroacetate salt (6.3 mg) as a colorless amorphous solid. $^1$H NMR (400 MHz, $CD_3OD$): 7.48 (d, 1H), 7.36 (d, 1H), 7.33-7.29 (m, 1H), 7.08-7.02 (m, 1H), 6.65-6.60 (m, 1H), 4.39 (br d, 1H), 4.24-4.18 (br, 2H), 4.08-3.96 (br m, 3H), 3.80 (br s, 2H), 3.51 (d, 2H), 3.40 (br s, 2H), 3.24 (br s, 2H).

Using the same or analogous synthetic techniques and substituting, as necessary, with alternative reagents, the following compounds were prepared.

Example 3(a)

1-({3,4-difluoro-2-[(2-fluoro-4-iodophenyl)amino]phenyl}carbonyl)-3-(pyrrolidin-1-ylmethyl)azetidin-3-ol: MS (EI) for $C_{21}H_{21}F_3IN_3O_2$: 532 (MH$^+$).

Example 3(b)

1-{[1-({3,4-difluoro-2-[(2-fluoro-4-iodophenyl)amino]phenyl}carbonyl)-3-hydroxyazetidin-3-yl]methyl}piperidin-4-ol: MS (EI) for $C_{22}H_{23}F_3IN_3O_3$: 562 (MH$^+$).

Example 3(c)

3-{[bis(2-hydroxyethyl)amino]methyl}-1-({3,4-difluoro-2-[(2-fluoro-4-iodophenyl)amino]phenyl}carbonyl)azetidin-3-ol: MS (EI) for $C_{21}H_{23}F_3IN_3O_4$: 566 (MH$^+$).

Example 3(d)

1-({3,4-difluoro-2-[(2-fluoro-4-iodophenyl)amino]phenyl}carbonyl)-3-[(4-methylpiperazin-1-yl)methyl]azetidin-3-ol: MS (EI) for $C_{22}H_{24}F_3IN_4O_2$: 561 (MH$^+$).

Example 3(e)

1-({3,4-difluoro-2-[(2-fluoro-4-iodophenyl)amino]phenyl}carbonyl)-3-[(4-methyl-1,4-diazepan-1-yl)methyl]azetidin-3-ol: MS (EI) for $C_{23}H_{26}F_3IN_4O_2$: 575 (MH$^+$).

Example 3(f)

1-({3,4-difluoro-2-[(2-fluoro-4-iodophenyl)amino]phenyl}carbonyl)-3-{[methyl(1-methylpyrrolidin-3-yl)amino]methyl}azetidin-3-ol: MS (EI) for $C_{23}H_{26}F_3IN_4O_2$: 575 (MH$^+$).

Example 3(g)

3-(1,4'-bipiperidin-1'-ylmethyl)-1-({3,4-difluoro-2-[(2-fluoro-4-iodophenyl)amino]phenyl}carbonyl)azetidin-3-ol: MS (EI) for $C_{27}H_{32}F_3IN_3O_2$: 629 (MH$^+$).

Example 3(h)

3-({4-[2-(diethylamino)ethyl]piperazin-1-yl}methyl)-1-({3,4-difluoro-2-[(2-fluoro-4-iodophenyl)amino]phenyl}carbonyl)azetidin-3-ol: MS (EI) for $C_{27}H_{35}F_3IN_3O_2$: 647 (MH$^+$).

Example 3(i)

1-({3,4-difluoro-2-[(2-fluoro-4-iodophenyl)amino]phenyl}carbonyl)-3-{[(2-hydroxyethyl)(methyl)amino]methyl}azetidin-3-ol: MS (EI) for $C_{20}H_{21}F_3IN_3O_3$: 536 (MH$^+$).

Example 3(j)

3-(azetidin-1-ylmethyl)-1-({3,4-difluoro-2-[(2-fluoro-4-iodophenyl)amino]phenyl}carbonyl)azetidin-3-ol: MS (EI) for $C_{20}H_{19}F_3IN_3O_2$: 518 (MH$^+$).

Example 3(k)

1-({3,4-difluoro-2-[(2-fluoro-4-iodophenyl)amino]phenyl}carbonyl)-3-{[(1-methylethyl)amino]methyl}azetidin-3-ol: MS (EI) for $C_{20}H_{21}F_3IN_3O_2$: 520 (MH$^+$).

Example 3(m)

3-(aminomethyl)-1-({3,4-difluoro-2-[(2-fluoro-4-iodophenyl)amino]phenyl}carbonyl)azetidin-3-ol: MS (EI) for $C_{17}H_{15}F_3IN_3O_2$: 478 (MH$^+$).

Example 3(n)

N-{[1-({3,4-difluoro-2-[(2-fluoro-4-iodophenyl)amino]phenyl}carbonyl)-3-hydroxyazetidin-3-yl]methyl}acetamide: MS (EI) for $C_{19}H_{17}F_3IN_3O_3$: 520 (MH$^+$).

Example 3(o)

1-({3,4-difluoro-2-[(2-fluoro-4-iodophenyl)amino]phenyl}carbonyl)-3-{[(1,1-dimethylethyl)amino]methyl}azetidin-3-ol: MS (EI) for $C_{21}H_{23}F_3IN_3O_4$: 534 (MH$^+$).

Example 3(q)

1-({3,4-difluoro-2-[(2-fluoro-4-iodophenyl)amino]phenyl}carbonyl)-3-[(hydroxyamino)methyl]azetidin-3-ol: $^1$H NMR (400 MHz, d$_4$-MeOH): 7.45 (2d, 1H), 7.35 (m, 1H), 7.28 (m, 1H), 7.03 (m, 1H), 6.63 (m, 1H), 4.32 (d, 1H), 4.05 (dd, 2H), 3.85 (d, 1H), 3.00 (s, 2H); MS (EI) for $C_{17}H_{15}F_3IN_3O_3$: 494 (MH$^+$).

Example 3(r)

1-({3,4-difluoro-2-[(2-fluoro-4-iodophenyl)amino]phenyl}carbonyl)-3-{[(methyloxy)amino]methyl}azetidin-3-ol: $^1$H NMR (400 MHz, d$_4$-MeOH): 7.45 (2d, 1H), 7.35 (m, 1H), 7.27 (m, 1H), 7.04 (m, 1H), 6.62 (m, 1H), 4.26 (d, 1H), 4.08 (d, 1H), 4.00 (d, 1H), 3.84 (d, 1H), 3.30 (s, 3H), 3.00 (d, 2H); MS (EI) for $C_{18}H_{17}F_3IN_3O_3$: 508 (MH$^+$).

Example 3(s)

1-({3,4-difluoro-2-[(2-fluoro-4-iodophenyl)amino]phenyl}carbonyl)-3-{[(ethyloxy)amino]methyl}azetidin-3-ol: $^1$H NMR (400 MHz, d$_4$-MeOH): 7.45 (2d, 1H), 7.34 (m, 1H), 7.26 (m, 1H), 7.03 (m, 1H), 6.63 (m, 1H), 4.26 (d, 1H), 4.12 (d, 1H), 4.00 (d, 1H), 3.84 (d, 1H), 3.61 (dd, 2H), 3.00 (s, 2H), 1.06 (t, 3H); MS (EI) for $C_{19}H_{19}F_3IN_3)_3$: 522 (MH$^+$).

Example 3(t)

1-{[(1-({3,4-difluoro-2-[(2-fluoro-4-iodophenyl)amino]phenyl}carbonyl)-3-hydroxyazetidin-3-yl]methyl}guanidine acetate salt: $^1$H NMR (400 MHz, d$_4$-MeOH): 7.46 (2d, 1H), 7.36 (m, 1H), 7.30 (m, 1H), 7.04 (m, 1H), 6.62 (m, 1H), 4.18 (d, 1H), 4.08 (d, 1H), 4.02 (d, 1H), 3.88 (1H), 3.40 (s, 2H); MS (EI) for $C_{18}H_{17}F_3IN_5O_2$: 520 (MH$^+$).

Example 3(u)

N-{[1-({3,4-difluoro-2-[(2-fluoro-4-iodophenyl)amino]phenyl}carbonyl)-3-hydroxyazetidin-3-yl]methyl}benzenecarboximidamide hydrochloride: $^1$H NMR (400 MHz, d$_4$-MeOH): 7.70 (d, 3H), 7.58 (m, 2H), 7.46 (dd, 1H), 7.36 (m, 1H), 7.31 (m, 1H), 7.04 (m, 1H), 6.62 (m, 1H), 4.28 (m, 1H), 4.15 (m, 2H), 3.96 (m, 1H), 3.78 (s, 2H); MS (EI) for $C_{24}H_{20}F_3IN_4O_2$: 581 (MH$^+$).

Example 3(v)

1-({3,4-difluoro-2-[(2-fluoro-4-iodophenyl)amino]phenyl}carbonyl)-3-[(pyrimidin-2-ylamino)methyl]azetidin-3-ol hydrochloride: $^1$H NMR (400 MHz, d$_4$-MeOH): 8.48 (s, 2H), 7.46 (2d, 1H), 7.36 (m, 1H), 7.28 (m, 1H), 7.04 (m, 1H), 6.85 (t, 1H), 6.61 (m, 1H), 4.24 (d, 1H), 4.06 (t, 2H), 3.87 (d, 1H), 3.75 (d, 2H); MS (EI) for $C_{21}H_{17}F_3IN_5O_2$: 556 (MH$^+$).

Example 3(w)

1-({3,4-difluoro-2-[(2-fluoro-4-iodophenyl)amino]phenyl}carbonyl)-3-[(pyridin-2-ylamino)methyl]azetidin-3-ol hydrochloride: $^1$H NMR (400 MHz, d$_4$-MeOH): 7.87 (dd, 1H), 7.85 (dd, 1H), 7.46 (2d, 1H), 7.36 (m, 2H), 7.06 (m, 2H), 6.89 (m, 1H), 6.61 (m, 1H), 4.53 (d, 2H), 4.46 (m, 1H), 4.28 (m, 1H), 4.16 (m, 1H), 3.96 (m, 1H); MS (EI) for $C_{22}H_{18}F_3IN_4O_2$: 555 (MH$^+$).

Example 3(x)

1-({3,4-difluoro-2-[(2-fluoro-4-iodophenyl)amino]phenyl}carbonyl)-3-[(ethylamino)methyl]azetidin-3-ol: $^1$H NMR (400 MHz, d$_6$-DMSO): 8.61 (s, 2H), 7.59 (d, 1H), 7.40 (d, 1H), 7.36-7.33 (m, 1H), 7.23-7.18 (m, 1H), 6.71 (s, 2H); 4.31-4.26 (m, 1H), 4.13-4.05 (m, 2H), 3.88-3.84 (m, 1H), 3.21 (br m, 2H), 2.97-2.90 (m, 2H), 1.19 (t, 3H). MS (EI) for $C_{19}H_{19}F_3IN_3O_2$: 506 (MH$^+$).

Example 3(y)

3-[(cyclopropylamino)methyl]-1-({3,4-difluoro-2-[(2-fluoro-4-iodophenyl)amino]phenyl}carbonyl)azetidin-3-ol: $^1$H NMR (400 MHz, d$_6$-DMSO): 8.99 (br s, 2H), 8.60 (s, 1H), 7.58 (d, 1H), 7.39 (d, 1H), 7.36-7.33 (m, 1H), 7.23-7.16 (m, 1H), 6.72 (s, 2H), 4.34-4.29 (m, 1H), 4.14-4.04 (m, 2H), 3.88-3.84 (m, 1H), 2.70-2.64 (m, 1H), 0.89 (br s, 2H), 0.74-0.69 (br s, 2H). MS (EI) for $C_{20}H_{19}F_3IN_3O_2$: 518 (MH$^+$).

Example 3(z)

1-({3,4-difluoro-2-[(2-fluoro-4-iodophenyl)amino]phenyl}carbonyl)-3-{[(2,2,2-trifluoroethyl)amino]methyl}azetidin-3-ol: $^1$H NMR (400 MHz, d$_6$-DMSO): 8.60 (s, 1H), 7.58 (d, 1H), 7.38 (d, 1H), 7.35-7.30 (m, 1H), 7.22-7.17 (m, 1H), 6.72-6.67 (m, 1H), 4.25-4.19 (m, 1H), 4.07-3.98 (m, 2H), 3.86-3.77 (m, 2H), 3.19-3.09 (m, 2H), MS (EI) for $C_{19}H_{16}F_6IN_3O_2$: 560 (MH$^+$).

Example 3(aa)

1-({3,4-difluoro-2-[(2-fluoro-4-iodophenyl)amino]phenyl}carbonyl)-3-(1H-1,2,3-triazol-1-ylmethyl)azetidin-3-ol: $^1$H NMR (400 MHz, d$_6$-DMSO): 8.55 (s, 1H), 8.04 (s, 1H), 7.66 (s, 1H), 7.58 (d, 1H), 7.39 (d, 1H), 7.34-7.29 (m, 1H), 7.22-7.15 (m, 1H), 6.72-6.66 (m, 1H), 6.29 (s, 1H), 4.64 (s, 211), 4.29-4.25 (m, 1H), 4.13-4.09 (m, 1H), 4.00-3.96 (m, 1H), 3.77-3.73 (m, 1H), 3.16 (d, 1H). MS (EI) for $C_{19}H_{15}F_3IN_5O_2$: 530 (MH$^+$).

Example 3(bb)

1-({3,4-difluoro-2-[(2-fluoro-4-iodophenyl)amino]phenyl}carbonyl)-3-{[(2,2-dimethylpropyl)amino]methyl}azetidin-3-ol: $^1$H NMR (400 MHz, d$_6$-DMSO): 8.61 (s, 1H), 8.30 (s, 2H), 7.59 (d, 1H), 7.39 (d, 1H), 7.36-7.17 (m, 4H), 6.77-6.66 (m, 4H), 4.35-4.30 (m, 1H), 4.16-4.08 (m, 2H), 3.92-3.87 (m, 1H), 3.31-3.27 (m, 2H), 2.78-2.74 (m, 2H), 1.76 (s, 4H), 0.99 (s, 9H). MS (EI) for $C_{22}H_{25}F_3IN_3O_2$: 548 (MH$^+$).

Example 3(cc)

1-({3,4-difluoro-2-[(2-fluoro-4-iodophenyl)amino]phenyl}carbonyl)-3-({[2-(4-methylphenyl)ethyl]amino}methyl)azetidin-3-ol acetate salt: $^1$H NMR (400 MHz, CDCl$_3$): 8.48 (s, 1H), 7.39 (dd, 1H), 7.31-7.34 (m, 1H), 7.08 (dd, 5H), 6.77-6.83 (m, 1H), 6.58-6.63 (m, 1H), 4.20 (br s, 1H), 4.01 (d, 1H), 2.87 (t, 4H), 2.75 (t, 4H), 2.5 (br s, 2H), 2.33 (s, 3H), 2.08 (s, 2H). MS (EI) for C$_{26}$H$_{25}$F$_3$IN$_3$O$_2$: 594 (M-H).

Example 3(dd)

1-({3,4-difluoro-2-[(2-fluoro-4-iodophenyl)amino]phenyl}carbonyl)-3-[(2,3-dihydro-1H-inden-2-ylamino)methyl]azetidin-3-ol acetate salt: $^1$H NMR (400 MHz, CDCl$_3$): 8.48 (s, 1H), 7.40 (dd, 1H), 7.32-7.34 (m, 1H), 7.15-7.22 (m, 4H), 7.10-7.14 (m, 1H), 6.77-6.83 (m, 1H), 6.58-6.64 (m, 1H), 4.22 (br s, 1H), 4.04 (d, 1H), 3.57-3.63 (m, 1H), 3.17 (dd, 2H), 2.94 (s, 2H), 2.75 (dd, 2H), 2.48 (br s, 4H), 2.08 (s, 2H). MS (EI) for C$_{26}$H$_{23}$F$_3$IN$_3$O$_2$: 592 (M-H).

Example 3(ee)

1-({3,4-difluoro-2-[(2-fluoro-4-iodophenyl)amino]phenyl}carbonyl)-3-({[(1S,2S)-2-hydroxycyclopentyl]amino}methyl)azetidin-3-ol acetate salt: $^1$H NMR (400 MHz, CD$_3$OD): 7.46 (dd, 1H), 7.33-7.37 (m, 1H), 7.26-7.31 (m, 1H), 7.00-7.08 (m, 1H), 6.58-6.65 (m, 1H), 4.2 (t, 1H), 3.86-4.06 (m, 4H), 2.92-3.10 (m, 3H), 2.00-2.10 (m, 1H), 1.91-1.97 (m, 3H), 1.66-1.78 (m, 2H), 1.52-1.61 (m, 1H), 1.32-1.44 (m, 1H). MS (EI) for C$_{22}$H$_{23}$F$_3$IN$_3$O$_3$: 560 (M-H).

Example 3(ff)

1-({3,4-difluoro-2-[(2-fluoro-4-iodophenyl)amino]phenyl}carbonyl)-3-{[(1,2-dimethylpropyl)amino]methyl}azetidin-3-ol acetate salt: $^1$H NMR (400 MHz, CD$_3$OD): 7.45 (dd, 1H), 7.33-7.37 (m, 1H), 7.26-7.31 (m, 1H), 7.01-7.08 (m, 1H), 6.59-6.64 (m, 1H), 4.14-4.22 (m, 1H), 3.98-4.06 (m, 2H), 3.84-3.90 (m, 1H), 2.86-3.20 (m, 2H), 2.65 (br s, 1H), 1.92 (s, 2H), 1.76-1.86 (m, 1H), 1.06 (d, 3H), 0.91 (dd, 6H). MS (EI) for C$_{22}$H$_{25}$F$_3$IN$_3$O$_2$: 546 (M-H).

Example 3(gg)

1-({3,4-difluoro-2-[(2-fluoro-4-iodophenyl)amino]phenyl}carbonyl)-3-({[1-methyl-2-(methyloxy)ethyl]amino}methyl)azetidin-3-ol acetate salt: $^1$H NMR (400 MHz, CD$_3$OD): 7.55 (dd, 1H), 7.33-7.36 (m, 1H), 7.26-7.31 (m, 1H), 7.01-7.09 (m, 1H), 6.59-6.65 (m, 1H), 4.14-4.22 (m, 1H), 3.96-4.06 (m, 2H), 3.85-3.92 (m, 1H), 3.40-3.48 (m, 1H), 3.34 (s, 3H), 2.90-3.15 (m, 3H), 1.94 (s, 3H), 1.11 (d, 3H). MS (EI) for C$_{21}$H$_{23}$F$_3$IN$_3$O$_3$: 548 (M-H).

Example 3(hh)

1-({3,4-difluoro-2-[(2-fluoro-4-iodophenyl)amino]phenyl}carbonyl)-3-{[(1-ethylpropyl)amino]methyl}azetidin-3-ol acetate salt: $^1$H NMR (400 MHz, CD$_3$OD): 7.45 (dd, 1H), 7.33-7.36 (m, 1H), 7.26-7.31 (m, 1H), 7.01-7.09 (m, 1H), 6.58-6.65 (m, 1H), 4.15-4.20 (m, 1H), 3.99-4.06 (m, 2H), 3.86-3.91 (m, 1H), 2.94 (s, 2H), 2.55-2.63 (m, 1H), 1.92 (s, 2H), 1.48-1.58 (m, 4H), 0.92 (t, 6H). MS (EI) for C$_{22}$H$_{25}$F$_3$IN$_3$O$_2$: 546 (M-H).

Example 3(ii)

1-({3,4-difluoro-2-[(2-fluoro-4-iodophenyl)amino]phenyl}carbonyl)-3-(1H-imidazol-1-ylmethyl)azetidin-3-ol: $^1$H NMR (400 MHz, CD$_3$OD): 7.67 (br s, 1H), 7.67 (br s, 1H), 7.48 (m, 1H), 7.36 (m, 1H), 6.91 (br s, 1H), 6.63 (m, 1H), 4.25 (s, 2H), 4.22 (m, 1H), 4.02 (m, 2H), 3.82 (m, 1H). MS (EI) for C$_{20}$H$_{16}$F$_3$IN$_4$O$_2$: 529 (MH$^+$).

Example 3(jj)

3-{[(cyclopropylmethyl)amino]methyl}-1-({3,4-difluoro-2-[(2-fluoro-4-iodophenyl)amino]phenyl}carbonyl)azetidin-3-ol: $^1$H NMR (400 MHz, CD$_3$OD): 7.47 (m, 1H), 7.36 (m, 1H), 7.31 (m, 1H), 7.05 (m, 1H), 6.62 (m, 1H), 4.30 (m, 1H), 4.24 (m, 2H), 3.99 (m, 1H), 3.66 (m, 2H), 2.91 (d, 2H), 1.08 (m, 1H), 0.71 (m, 2H), 0.40 (m, 2H). MS (EI) for C$_{21}$H$_{21}$F$_3$IN$_3$O$_2$: 532 (MH$^+$).

Example 3(kk)

1-({3,4-difluoro-2-[(2-fluoro-4-iodophenyl)amino]phenyl}carbonyl)-3-{[(phenylmethyl)amino]methyl}azetidin-3-ol hydrochloride: $^1$H NMR (400 MHz, CD$_3$OD): 7.47 (m, 5H), 7.43 (m, 1H), 7.35 (m, 1H), 7.27 (m, 1H), 7.04 (m, 1H), 6.61 (m, 1H), 4.24 (m, 3H), 4.08 (m, 2H), 3.96 (m, 1H). MS (EI) for C$_{24}$H$_{21}$F$_3$IN$_3$O$_2$: 568 (MH$^+$).

Example 3(mm)

3-[(butylamino)methyl]-1-({3,4-difluoro-2-[(2-fluoro-4-iodophenyl)amino]phenyl}carbonyl)azetidin-3-ol: $^1$H NMR (400 MHz, d$_6$-DMSO): 8.56 (s, 1H), 7.57 (dd, 1H), 7.36 (d, 1H), 7.31 (t, 1H), 7.17 (q, 1H), 6.67 (dt, 1H), 4.04 (d, 1H), 3.88 (q, 2H), 3.69 (d, 1H), 2.59 (s, 2H), 1.90 (s, 2H), 1.22-1.33 (m, 4H), 0.84 (t, 3H); MS (EI) for C$_{21}$H$_{23}$F$_3$IN$_3$O$_2$: 534 (MH$^+$).

Example 3(nn)

1-({3,4-difluoro-2-[(2-fluoro-4-iodophenyl)amino]phenyl}carbonyl)-3-({[(1-ethylpyrrolidin-2-yl)methyl]amino}methyl)azetidin-3-ol: $^1$H NMR (400 MHz, d$_6$-DMSO): 8.59 (s, 1H), 7.57 (dd, 1H), 7.36 (d, 1H), 7.31 (t, 1H), 7.17 (q, 1H), 6.68 (dt, 1H), 4.02 (t, 1H), 3.89 (q, 2H), 3.69 (d, 1H), 2.98 (s, 1H), 2.67-2.76 (m, 1H), 2.62 (s, 1H), 2.39-2.45 (m, 1H), 2.29 (s, 1H), 1.97-2.13 (m, 2H), 1.69 (s, 1H), 1.54 (s, 3H), 0.97 (t, 3H); MS (EI) for C$_{24}$H$_{28}$F$_3$IN$_4$O$_2$: 589 (MH$^+$).

Example 3(oo)

1-({3,4-difluoro-2-[(2-fluoro-4-iodophenyl)amino]phenyl}carbonyl)-3-{[(2-hydroxyethyl)amino]methyl}azetidin-3-ol: $^1$H NMR (400 MHz, d$_6$-DMSO): 8.57 (s, 1H), 7.57 (dd, 1H), 7.37 (d, 1H), 7.32 (t, 1H), 7.18 (q, 1H), 6.68 (dt, 1H), 4.06 (d, 1H), 3.87 (d, 2H), 3.70 (d, 1H), 3.42 (t, 2H), 2.65 (s, 2H), 2.56 (dt, 2H). 1.91 (s, 2H); MS (EI) for C$_{19}$H$_{19}$F$_3$IN$_3$O$_3$: 522 (MH$^+$).

Example 3(pp)

1-({3,4-difluoro-2-[(2-fluoro-4-iodophenyl)amino]phenyl}carbonyl)-3-({[2-(dimethylamino)ethyl]amino}methyl)azetidin-3-ol: $^1$H NMR (400 MHz, d$_6$-DMSO): 8.58 (s, 1H), 7.57 (dd, 1H), 7.36 (d, 1H), 7.31 (t, 1H), 7.17 (q, 1H), 6.68 (dt, 1H), 4.02 (d, 1H), 3.87 (t, 2H), 3.70 (d, 1H), 2.62 (s, 1H), 2.54 (t, 1H), 2.23 (t, 1H), 2.09 (s, 4H), 7.85 (s, 6H); MS (EI) for $C_{21}H_{24}F_3IN_4O_2$: 549 (MH$^+$).

Example 3(qq)

1-({3,4-difluoro-2-[(2-fluoro-4-iodophenyl)amino]phenyl}carbonyl)-3-({[2-(1-methylpyrrolidin-2-yl)ethyl]amino}methyl)azetidin-3-ol: $^1$H NMR (400 MHz, d$_6$-DMSO): 8.58 (s, 1H), 7.57 (dt, 1H), 7.36 (d, 1H), 7.31 (t, 1H), 7.17 (q, 1H), 6.68 (dt, 1H), 4.04 (d, 1H), 3.89 (d, 2H), 3.79 (d, 1H), 2.88-2.92 (m, 1H), 2.61 (s, 2H), 2.15 (s, 3H), 1.93-2.04 (m, 2H), 1.75-1.83 (m, 3H), 1.54-1.70 (m, 3H), 1.20-1.37 (m, 2H); MS (EI) for $C_{24}H_{28}F_3IN_4O_2$: 589 (MH$^+$).

Example 3(rr)

1-({3,4-difluoro-2-[(2-fluoro-4-iodophenyl)amino]phenyl}carbonyl)-3-{[(tetrahydrofuran-2-ylmethyl)amino]methyl}azetidin-3-ol: $^1$H NMR (400 MHz, d$_6$-DMSO): 8.58 (s, 1H), 7.57 (dd, 1H), 7.37 (d, 1H), 7.31 (t, 1H), 7.14 (q, 1H), 6.68 (dt, 1H), 5.75 (s, 1H), 4.03 (t, 1H), 3.87 (t, 2H), 3.76 (q, 1H), 3.68 (q, 2H), 3.54-3.58 (m, 1H), 2.63 (s, 2H), 1.91 (s, 2H), 1.71-1.87 (m, 3H), 1.40-1.48 (m, 1H); MS (EI) for $C_{22}H_{23}F_3IN_3O_3$: 562 (MH$^+$).

Example 3(ss)

1-({3,4-difluoro-2-[(2-fluoro-4-iodophenyl)amino]phenyl}carbonyl)-3-{[(3-pyrrolidin-1-ylpropyl)amino]methyl}azetidin-3-ol: $^1$H NMR (400 MHz, d$_6$-DMSO): 8.58 (s, 1H), 7.57 (dd, 1H), 7.36 (d, 1H), 7.31 (t, 1H), 7.17 (q, 1H), 6.68 (dt, 1H), 4.04 (d, 1H), 3.89 (d, 2H), 3.69 (d, 1H), 2.60 (s, 1H), 2.34-2.37 (m, 4H), 1.86 (s, 8H), 1.64 (s, 2H), 1.46-1.53 (m, 1H); MS (EI) for $C_{24}H_{28}F_3IN_4O_2$: 589 (MH$^+$).

Example 3(tt)

1-({3,4-difluoro-2-[(2-fluoro-4-iodophenyl)amino]phenyl}carbonyl)-3-({[2-(methyloxy)ethyl]amino}methyl)azetidin-3-ol: $^1$H NMR (400 MHz, d$_6$-DMSO): $^1$H NMR (400 MHz, d$_6$-DMSO): 8.57 (s, 1H), 7.57 (dd, 1H), 7.37 (d, 1H), 7.31 (t, 1H), 7.17 (q, 1H), 6.68 (dt, 1H), 4.03 (d, 1H), 3.86 (d, 2H), 3.70 (d, 1H), 3.21 (s, 3H), 2.63 (s, 4H), 1.88 (s, 2H); MS (EI) for $C_{20}H_{21}F_3IN_3O_3$: 536 (MH$^+$).

Example 3(uu)

1-({3,4-difluoro-2-[(2-fluoro-4-iodophenyl)amino]phenyl}carbonyl)-3-({[(1-methylpiperidin-4-yl)methyl]amino}methyl)azetidin-3-ol: $^1$H NMR (400 MHz, d$_6$-DMSO): 8.58 (s, 1H), 7.57 (d, 1H), 7.37 (d, 1H), 7.31 (t, 1H), 7.17 (q, 1H), 6.68 (t, 1H), 4.03 (d, 1H), 3.89 (t, 2H), 3.69 (d, 1H), 2.68 (d, 2H), 2.57 (s, 1H), 2.34 (d, 2H), 1.88 (s, 4H), 1.73 (t, 2H), 1.57 (d, 2H), 1.23 (s, 1H), 1.05 (q, 2H); MS (EI) for $C_{24}H_{28}F_3IN_4O_3$: 589 (MH$^+$).

Example 3(vv)

1-({3,4-difluoro-2-[(2-fluoro-4-iodophenyl)amino]phenyl}carbonyl)-3-({[4-(dimethylamino)butyl]amino}methyl)azetidin-3-ol: $^1$H NMR (400 MHz, d$_6$-DMSO): 7.57 (dd, 1H), 7.36 (d, 1H), 7.31 (t, 1H), 7.18 (q, 1H), 6.68 (dt, 1H), 4.03 (d, 1H), 3.88 (t, 2H), 3.70 (d, 1H), 3.08 (s, 1H), 2.60 (s, 1H), 2.44-2.47 (m, 2H), 2.28-2.33 (m, 1H), 2.07-2.16 (m, 6H), 1.29-1.35 (m, 4H); MS (EI) for $C_{23}H_{28}F_3IN_4O_2$: 577 (MH$^+$).

Example 3(ww)

1-({3,4-difluoro-2-[(2-fluoro-4-iodophenyl)amino]phenyl}carbonyl)-3-{[(2-furan-2-ylethyl)amino]methyl}azetidin-3-ol: $^1$H NMR (400 MHz, d$_6$-DMSO): 8.58 (s, 1H), 7.57 (d, 1H), 7.49 (s, 1H), 7.36 (d, 1H), 7.31 (t, 1H), 7.17 (q, 1H), 6.68 (t, 1H), 6.33 (s, 1H), 6.08 (s, 1H), 5.72 (s, 1H), 4.04 (d, 1H), 3.87 (d, 2H), 3.70 (d, 1H), 2.74 (d, 2H), 2.69 (d, 2H), 2.64 (s, 2H); MS (EI) for $C_{23}H_{21}F_3IN_3O_3$: 572 (MH$^+$).

Example 3(xx)

1-({3,4-difluoro-2-[(2-fluoro-4-iodophenyl)amino]phenyl}carbonyl)-3-{[(2-ethylbutyl)amino]methyl}azetidin-3-ol: $^1$H NMR (400 MHz, d$_6$-DMSO): 8.58 (s, 1H), 7.56 (dd, 1H), 7.36 (d, 1H), 7.31 (t, 1H), 7.17 (q, 1H), 6.67 (dt, 1H), 4.03 (d, 1H), 3.90 (d, 2H), 3.69 (d, 1H), 2.58 (s, 2H), 2.37 (d, 2H), 1.17-1.27 (m, 5H), 0.78 (t, 6H); MS (EI) for $C_{23}H_{27}F_3IN_3O_2$: 562 (MH$^+$).

Example 3(yy)

1,1-dimethylethyl [3-({[1-({3,4-difluoro-2-[(2-fluoro-4-iodophenyl)amino]phenyl}carbonyl)-3-hydroxyazetidin-3-yl]methyl}amino)propyl]carbamate: $^1$H NMR (400 MHz, d$_6$-DMSO): 8.58 (s, 1H), 7.57 (d, 1H), 7.30-7.38 (m, 3H), 7.17 (q, 1H), 6.82 (t, 1H), 6.68 (dt, 1H), 4.07 (d, 1H), 3.89 (d, 2H), 3.70 (d, 1H), 3.36 (s, 2H), 2.93 (q, 2H), 2.61 (s, 2H), 1.46 (t, 2H), 1.36 (s, 9H); MS (EI) for $C_{25}H_{30}F_3IN_4O_4$: 635 (MH$^+$).

Example 3(zz)

1-({3,4-difluoro-2-[(2-fluoro-4-iodophenyl)amino]phenyl}carbonyl)-3-{[(pyrrolidin-2-ylmethyl)amino]methyl}azetidin-3-ol: $^1$H NMR (400 MHz, d$_6$-DMSO): 8.53 (s, 1H), 7.58 (dd, 1H), 7.37 (d, 1H), 7.33 (d, 1H), 7.18 (q, 1H), 6.67 (dt, 1H), 6.25 (s, 1H), 4.07 (d, 1H), 3.96 (q, 2H), 3.78 (s, 3H), 3.34 (s, 6H), 1.73 (s, 1H), 1.35-1.39 (m, 1H); MS (EI) for $C_{22}H_{24}F_3IN_4O_2$: 561 (MH$^+$).

Example 3(aaa)

1,1-dimethylethyl 4-[({[1-({3,4-difluoro-2-[(2-fluoro-4-iodophenyl)amino]phenyl}carbonyl)-3-hydroxyazetidin-3-yl]methyl}amino)methyl]piperidine-1-carboxylate: $^1$H NMR (400 MHz, d$_6$-DMSO): 8.56 (s, 1H), 7.56 (dd, 1H), 7.36 (d, 1H), 7.30 (t, 1H), 7.17 (q, 1H), 6.68 (dt, 1H), 4.03 (d, 1H), 3.88 (t, 4H), 3.69 (d, 1H), 2.58 (s, 2H), 2.35 (d, 2H), 1.60 (d, 2H), 1.47 (s, 1H), 1.39 (s, 10H), 0.90 (q, 2H); MS (EI) for $C_{28}H_{34}F_3IN_4O_4$: 675 (MH$^+$).

Example 3(bbb)

1-({3,4-difluoro-2-[(2-fluoro-4-iodophenyl)amino]phenyl}carbonyl)-3-({[(2-hydroxyphenyl)methyl]amino}methyl)azetidin-3-ol: $^1$H NMR (400 MHz, d$_6$-DMSO): 8.56 (s, 1H), 7.54 (dd, 1H), 7.35 (d, 1H), 7.30 (t, 1H), 7.17 (q, 1H), 7.05 (t, 2H), 6.64-6.72 (m, 3H), 4.07 (d, 1H), 3.90 (t, 2H), 3.78 (s, 2H), 3.72 (d, 1H), 2.65 (s, 2H); MS (EI) for $C_{24}H_{21}F_3IN_3O_3$: 584 (MH$^+$).

Example 3(ccc)

1-({3,4-difluoro-2-[(2-fluoro-4-iodophenyl)amino]phenyl}carbonyl)-3-({[(3-hydroxyphenyl)methyl]amino}methyl)azetidin-3-ol: $^1$H NMR (400 MHz, $d_6$-DMSO): 8.58 (s, 1H), 7.56 (d, 1H), 7.35 (d, 1H), 7.29 (t, 1H), 7.16 (q, 1H), 7.06 (t, 1H), 6.64-6.72 (m, 3H), 6.60 (dd, 1H), 4.07 (d, 1H), 3.88 (t, 2H), 3.69 (d, 1H), 3.60 (s, 2H), 2.58 (d, 2H); MS (EI) for $C_{24}H_{21}F_3IN_3O_3$: 584 (MH$^+$).

Example 3(ddd)

1-({3,4-difluoro-2-[(2-fluoro-4-iodophenyl)amino]phenyl}carbonyl)-3-({[(4-hydroxyphenyl)methyl]amino}methyl)azetidin-3-ol: $^1$H NMR (400 MHz, $d_6$-DMSO): 8.57 (s, 1H), 7.55 (dd, 1H), 7.35 (d, 1H), 7.27 (t, 1H), 7.16 (q, 1H), 7.06 (d, 2H), 6.64-6.70 (m, 3H), 4.04 (d, 1H), 3.85 (t, 2H), 3.68 (d, 1H), 3.55 (s, 2H), 2.56 (d, 2H); MS (EI) for $C_{24}H_{21}F_3IN_3O_3$: 584 (MH$^+$).

Example 3(eee)

3-({[1-({3,4-difluoro-2-[(2-fluoro-4-iodophenyl)amino]phenyl}carbonyl)-3-hydroxyazetidin-3-yl]methyl}amino)-5-(hydroxymethyl)cyclopentane-1,2-diol: $^1$H NMR (400 MHz, $d_6$-DMSO): 8.60 (broad s, 1H), 7.57 (dd, 1H), 7.37 (d, 1H), 7.32 (t, 1H), 7.16 (q, 1H), 6.68 (t, 1H), 4.06 (q, 2H), 3.86 (t, 3H), 3.72 (dd, 1H), 3.60 (t, 1H), 3.36-3.43 (m, 2H), 3.30 (dd, 1H), 2.80 (q, 1H), 2.62-2.72 (m, 2H), 1.88-1.95 (m, 1H), 0.82-0.90 (m, 1H); MS (EI) for $C_{23}H_{25}F_3IN_3O_5$: 608 (MH$^+$).

Example 3(fff)

1-({3,4-difluoro-2-[(2-fluoro-4-iodophenyl)amino]phenyl}carbonyl)-3-{[(piperidin-4-ylmethyl)amino]methyl}azetidin-3-ol: $^1$H NMR (400 MHz, $d_o$-DMSO): 8.59 (broad s, 1H), 7.57 (dd, 1H), 7.37 (d, 1H), 7.30 (t, 1H), 7.17 (q, 1H), 6.68 (dt, 1H), 4.03 (d, 1H), 3.87 (d, 2H), 3.69 (d, 1H), 3.01 (d, 2H), 2.59 (s, 2H), 2.43-2.56 (m, 1H), 2.35 (d, 2H), 1.65 (d, 2H), 1.47 (s, 1H), 1.07 (q, 2H); MS (EI) for $C_{23}H_{26}F_3IN_4O_2$: 575 (MH$^+$).

Example 3(ggg)

3-{[(3-aminopropyl)amino]methyl}-1-({3,4-difluoro-2-[(2-fluoro-4-iodophenyl)amino]phenyl}carbonyl)azetidin-3-ol: $^1$H NMR (400 MHz, $d_6$-DMSO): 7.57 (dd, 1H), 7.37 (d, 1H), 7.31 (t, 1H), 7.17 (q, 1H), 6.68 (dt, 1H), 4.05 (d, 1H), 3.88 (d, 2H), 3.69 (d, 1H), 2.61 (t, 3H), 2.53-2.56 (m, 1H), 1.49 (t, 1.49); MS (EI) for $C_{23}H_{26}F_3IN_4O_2$: 535 (MH$^+$).

Example 3(hhh)

1-({3,4-difluoro-2-[(2-fluoro-4-iodophenyl)amino]phenyl}carbonyl)-3-[({[2-(4-methylpiperazin-1-yl)phenyl]methyl}amino)methyl]azetidin-3-ol: $^1$H NMR (400 MHz, $d_6$-DMSO): 8.59 (broad s, 1H), 7.55 (dd, 1H), 7.34 (t, 2H), 7.28 (d, 1H), 7.13-7.20 (m, 1H), 7.05 (d, 1H), 6.99 (t, 1H), 6.66 (dt, 1H), 4.03 (d, 1H), 3.90 (t, 2H), 3.71 (d, 3H), 2.83 (s, 5H), 2.60 (s, 2H), 2.42 (s, 3H), 2.20 (s, 3H); MS (EI) for $C_{29}H_{31}F_3IN_5O_2$: 666 (MH$^+$).

Example 3(iii)

3-[(1H-benzimidazol-2-ylamino)methyl]-1-({3,4-difluoro-2-[(2-fluoro-4-iodophenyl)amino]phenyl}carbonyl)azetidin-3-ol: $^1$H NMR (400 MHz, CDCl$_3$): 8.04 (s, 2H), 7.28-7.35 (m, 2H), 7.23-7.26 (m, 2H), 7.09-7.12 (m, 2H), 6.80 (q, 1H), 6.57-6.63 (m, 1H), 5.28 (broad s, 2H), 4.38 (s, 3H), 4.25 (s, 1H), 4.21 (d, 2H); MS (EI) for $C_{24}H_{19}F_3IN_5O_2$: 594 (MH$^+$).

Example 3(jjj)

1-({3,4-difluoro-2-[(2-fluoro-4-iodophenyl)amino]phenyl}carbonyl)-3-[(1H-imidazol-2-ylamino)methyl]azetidin-3-ol: $^1$H NMR (400 MHz, $d_6$-DMSO): 12.12 (s, 1H), 8.68 (s, 1H), 7.57-7.61 (m, 3H), 7.36-7.41 (m, 2H), 7.19 (q, 1H), 6.99 (s, 1H), 6.91 (s, 1H), 6.71 (dt, 1H), 6.45 (s, 1H), 4.28 (d, 1H), 4.06 (d, 1H), 4.03 (d, 1H), 3.82 (d, 2H); MS (EI) for $C_{24}H_{17}F_3IN_5O_2$: 544 (MH$^+$).

Example 3(kkk)

1-({3,4-difluoro-2-[(2-fluoro-4-iodophenyl)amino]phenyl}carbonyl)-3-{2-[(2,2,3,3,3-pentafluoropropyl)amino]ethyl}azetidin-3-ol: $^1$H NMR (400 MHz, $d_6$-DMSO): 8.58 (br s, 1H), 7.56 (dd, 1H), 7.37 (dd, 1H), 7.34-7.28 (m, 1H), 7.22-7.13 (m, 1H), 6.68 (ddd, 1H), 5.82 (br s, 1H), 4.06 (d, 1H), 3.91 (t, 2H), 3.70 (d, 1H), 3.40-3.25 (m, 2H), 2.76 (d, 2H), 2.40-2.31 (m, 1H); MS (EI) for $C_{20}H_{16}F_8IN_3O_2$: 610 (MH$^+$).

Example 3(mmm)

1-({3,4-difluoro-2-[(2-fluoro-4-iodophenyl)amino]phenyl}carbonyl)-3-{2-[(3,3,3-trifluoropropyl)amino]ethyl}azetidin-3-ol: $^1$H NMR (400 MHz, $d_6$-DMSO): 8.58 (br s, 1H), 7.57 (dd, 1H), 7.37 (dd, 1H), 7.34-7.28 (m, 1H), 7.22-7.13 (m, 1H), 6.68 (ddd, 1H), 5.76 (br s, 1H), 4.05 (d, 1H), 3.88 (d, 2H), 3.70 (d, 1H), 2.71 (t, 2H), 2.63 (s, 2H), 2.41-2.26 (m, 2H); MS (EI) for $C_{20}H_{18}F_6IN_3O_2$: 574 (MH$^+$).

Example 3(nnn)

1-({3,4-difluoro-2-[(2-fluoro-4-iodophenyl)amino]phenyl}carbonyl)-3-[(2,3-dihydro-1H-inden-1-ylamino)methyl]azetidin-3-ol acetate salt: $^1$H NMR (400 MHz, DMSO): 8.61-8.56 (m, 1H), 7.55 (d, 1H), 7.37-7.07 (m, 8H), 6.71-6.64 (m, 1H), 4.16-4.05 (m, 2H), 3.98-3.85 (m, 2H), 3.72-3.68 (m, 1H), 2.90-2.82 (m, 1H), 2.74-2.64 (m, 2H), 1.91 (s, 3H), 1.73-1.63 (m, 1H); MS (EI) for $C_{26}H_{23}F_3IN_3O_2$: 594 (MH$^+$).

Example 3(ooo)

3-[(cyclooctylamino)methyl]-1-({3,4-difluoro-2-[(2-fluoro-4-iodophenyl)amino]phenyl}carbonyl)azetidin-3-ol acetate salt: $^1$H NMR (400 MHz, DMSO): 8.56 (s, 1H), 7.55 (d, 1H), 7.20-7.14 (m, 2H), 6.70-6.66 (m, 1H), 4.03-3.98 (m, 1H), 3.92-3.86 (m, 2H), 3.72-3.67 (m, 1H), 2.60 (s, 2H), 1.90 (s, 3H), 1.64-1.22 (m, 15H); MS (EI) for $C_{25}H_{29}F_3IN_3O_2$: 588 (MH$^+$).

Example 3(ppp)

3-[(cycloheptylamino)methyl]-1-({3,4-difluoro-2-[(2-fluoro-4-iodophenyl)amino]phenyl}carbonyl)azetidin-3-ol acetate salt: $^1$H NMR (400 MHz, DMSO): 8.55 (s, 1H), 7.55 (d, 1H), 7.36-7.28 (m, 1H), 7.21-7.14 (m, 1H), 6.70-6.66 (m, 1H), 4.04-4.00 (m, 1H), 3.92-3.85 (m, 2H), 3.71-3.66 (m, 1H), 2.60 (s, 2H), 1.90 (s, 3H), 1.70-1.13 (m, 13H); MS (EI) for $C_{24}H_{27}F_3IN_3O_2$: 574 (MH$^+$).

Example 3(qqq)

1-({3,4-difluoro-2-[(2-fluoro-4-iodophenyl)amino]phenyl}carbonyl)-3-{[(2-pyridin-3-ylethyl)amino]methyl}azetidin-3-ol acetate salt: $^1$H NMR (400 MHz, DMSO): 8.58 (s, 1H), 8.42-8.37 (m, 2H), 7.62-7.54 (m, 2H), 7.38-7.27 (m, 3H), 7.21-7.14 (m, 1H), 6.71-6.66 (m, 1H), 4.06-4.02 (m, 1H), 3.90-3.86 (m, 2H), 3.72-3.68 (m, 1H), 2.80-2.64 (m, 6H), 1.90 (s, 3H); MS (EI) for $C_{24}H_{22}F_3IN_4O_2$: 583 (MH$^+$).

Example 3(rrr)

N-cyclohexyl-N2-{[1-({3,4-difluoro-2-[(2-fluoro-4-iodophenyl)amino]phenyl}carbonyl)-3-hydroxyazetidin-3-yl]methyl}-2-methylalaninamide acetate salt: $^1$H NMR (400 MHz, DMSO): 8.66 (br s 1H), 8.55 (s, 1H), 7.93-7.90 (m, 1H), 7.58 (d, 1H), 7.40-7.31 (m, 2H), 7.24-7.17 (m, 1H), 6.71-6.66 (m, 1H), 6.60 (br s, 1H), 4.28-4.23 (m, 1H), 4.14-4.02 (m, 2H), 3.89-3.83 (m, 1H), 3.12 (br s, 2H), 1.90 (s, 3H), 1.74-1.42 (m, 11H), 1.31-1.02 (m, 6H); MS (EI) for $C_{27}H_{32}F_3IN_4O_3$: 645 (MH$^+$).

Example 3(sss)

1-({3,4-difluoro-2-[(2-fluoro-4-iodophenyl)amino]phenyl}carbonyl)-3-{[(tetrahydro-2H-pyran-4-ylmethyl)amino]methyl}azetidin-3-ol acetate salt: $^1$H NMR (400 MHz, DMSO): 8.56 (s, 1H), 7.56 (d, 1H), 7.38-7.27 (m, 2H), 7.20-7.14 (m, 1H), 6.71-6.66 (m, 1H), 4.05-4.01 (m, 1H), 3.91-3.78 (m, 4H), 3.71-3.67 (m, 1H), 3.25-3.18 (m, 2H), 2.60 (s, 2H), 2.36 (d, 2H), 1.90 (s, 3H), 1.57-1.50 (m, 3H), 1.13-1.02 (m, 2H); MS (EI) for $C_{23}H_{25}F_3IN_3O_3$: 576 (MH$^+$).

Example 3(ttt)

1-({3,4-difluoro-2-[(2-fluoro-4-iodophenyl)amino]phenyl}carbonyl)-3-({[2-(dimethylamino)-1-methylethyl]amino}methyl)azetidin-3-ol trifluoroacetate salt: $^1$H NMR (400 MHz, DMSO): 8.59-8.54 (m, 1H), 7.56 (d, 1H), 7.38-7.28 (m, 2H), 7.21-7.13 (m, 1H), 6.71-6.63 (m, 1H), 4.04-3.95 (m, 1H), 3.88-3.78 (m, 2H), 3.73-3.68 (m, 1H), 2.70-2.50 (m, 3H), 2.08 (s, 6H), 1.88 (s, 2H), 0.85-0.82 (m, 3H); MS (EI) for $C_{22}H_{26}F_3IN_4O_2$: 563 (MH$^+$).

Example 3(uuu)

N-cyclopropyl-1-({[1-({3,4-difluoro-2-[(2-fluoro-4-iodophenyl)amino]phenyl}carbonyl)-3-hydroxyazetidin-3-yl]methyl}amino)cyclopentanecarboxamide trifluoroacetate salt: $^1$H NMR (400 MHz, DMSO): 8.80 (br s, 1H), 8.58 (s, 1H), 8.04 (s, 1H), 7.59 (d, 1H), 7.40-7.31 (m, 2H), 7.25-7.16 (m, 1H), 6.74-6.58 (m, 2H), 4.26-3.82 (m, 4H), 3.10 (br s, 2H), 2.69-2.64 (m, 1H), 2.11-1.88 (m, 4H), 1.82-1.61 (m, 4H), 0.67-0.62 (m, 2H), 0.52-0.48 (m, 2H); MS (EI) for $C_{26}H_{28}F_3IN_4O_3$: 629 (MH$^+$).

Example 3(vvv)

N2-{[1-({3,4-difluoro-2-[(2-fluoro-4-iodophenyl)amino]phenyl}carbonyl)-3-hydroxyazetidin-3-yl]methyl}-N-ethyl-2-methylalaninamide acetate salt: $^1$H NMR (400 MHz, DMSO): 8.60 (s, 1H), 7.60-7.72 (m, 1H), 7.56 (d, 1H), 7.38-7.30 (m, 2H), 7.22-7.14 (m, 1H), 6.69-6.63 (m, 1H), 4.07-4.04 (m, 1H), 3.95-3.90 (m, 2H), 3.72-3.68 (m, 1H), 3.05-3.01 (m, 2H), 2.47 (br s, 2H), 1.90 (s, 3H), 1.09 (s, 6H), 0.94 (t, 3H); MS (EI) for $C_{23}H_{26}F_3IN_4O_3$: 591 (MH$^+$).

Example 3(www)

1-({3,4-difluoro-2-[(2-fluoro-4-iodophenyl)amino]phenyl}carbonyl)-3-[(2-methylhydrazino)methyl]azetidin-3-ol acetate salt: $^1$H NMR (400 MHz, DMSO): 8.54 (s, 1H), 7.57 (d, 1H), 7.38-7.30 (m, 2H), 7.19-7.12 (m, 1H), 6.69-6.63 (m, 1H), 4.04-4.01 (m, 1H), 3.92-3.84 (m, 2H), 3.68-3.63 (m, 1H), 2.55 (s, 2H), 2.39 (s, 3H), 1.90 (s, 3H); MS (EI) for $C_{18}H_{18}F_3IN_4O_2$: 507 (MH$^+$).

Example 3(xxx)

3-[(azetidin-3-ylamino)methyl]-1-({3,4-difluoro-2-[(2-fluoro-4-iodophenyl)amino]phenyl}carbonyl)azetidin-3-ol acetate salt: $^1$H NMR (400 MHz, DMSO): 7.57 (d, 1H), 7.39-7.30 (m, 2H), 7.20-7.13 (m, 1H), 6.70-6.65 (m, 1H), 4.10-4.04 (m, 1H), 3.90-3.83 (m, 2H), 3.78-3.67 (m, 3H), 3.61-3.53 (m, 1H), 3.48-3.42 (m, 2H), 2.61-2.54 (m, 2H), 1.90 (s, 3H); MS (EI) for $C_{20}H_{20}F_3IN_4O_2$: 533 (MH$^+$).

Example 3(yyy)

1-({3,4-difluoro-2-[(2-fluoro-4-iodophenyl)amino]phenyl}carbonyl)-3-[(1,3-thiazol-2-ylamino)methyl]azetidin-3-ol acetate salt: $^1$H NMR (400 MHz, DMSO): 8.60 (s, 1H), 7.57 (d, 1H), 7.38-7.28 (m, 2H), 7.20-7.13 (m, 1H), 6.75 (d, 1H), 6.70-6.64 (m, 1H), 5.93 (d, 1H), 4.26-4.22 (m, 1H), 4.11-4.08 (m, 1H), 4.00-3.88 (m, 3H), 3.74-3.70 (m, 1H), 1.90 (s, 3H); MS (EI) for $C_{20}H_{16}F_3IN_4O_2S$: 561 (MH$^+$).

Example 3(zzz)

1-({3,4-difluoro-2-[(2-fluoro-4-iodophenyl)amino]phenyl}carbonyl)-3-({[3-(methyloxy)phenyl]amino}methyl)azetidin-3-ol: $^1$H NMR (400 MHz, DMSO): 8.57 (s, 1H), 7.56 (d, 1H), 7.38-7.30 (m, 2H), 7.20-7.12 (m, 1H), 6.95-6.91 (m, 1H), 6.70-6.66 (m, 1H), 6.21-6.17 (m, 2H), 6.14-6.10 (m, 1H), 5.94 (s, 1H), 5.49-5.44 (m, 1H), 4.14-4.10 (m, 1H), 3.98-3.93 (m, 2H), 3.78-3.75 (m, 1H), 3.65 (s, 3H), 3.21 (d, 2H); MS (EI) for $C_{24}H_{21}F_3IN_3O_3$: 584 (MH$^+$).

Example 3(ab)

1-({3,4-difluoro-2-[(2-fluoro-4-iodophenyl)amino]phenyl}carbonyl)-3-({[4-(methyloxy)phenyl]amino}methyl)azetidin-3-ol: $^1$H NMR (400 MHz, DMSO): 8.56 (s, 1H), 7.58 (d, 1H), 7.39-7.30 (d, 2H); 7.20-7.13 (m, 1H), 6.71-6.66 (m, 3H), 6.55 (d, 2H), 5.93 (s, 1H), 5.00-4.95 (m, 1H), 4.14-4.08 (m, 1H), 3.98-3.92 (m, 2H), 3.79-3.74 (m, 1H), 3.63 (s, 3H), 3.13 (d, 2H); MS (EI) for $C_{24}H_{21}F_3IN_3O_3$: 584 (MH$^+$).

Example 3(ac)

1-({3,4-difluoro-2-[(2-fluoro-4-iodophenyl)amino]phenyl}carbonyl)-3-({[2-(ethyloxy)ethyl]amino}methyl)azetidin-3-ol: $^1$H NMR (400 MHz, CD$_3$OD): 7.48-7.43 (d, 1H), 7.36-7.33 (d, 1H), 7.31-7.26 (m, 1H), 7.08-7.00 (q, 1H), 6.65-6.58 (t, 1H), 4.24-4.16 (d, 1H), 4.08-3.98 (t, 2H), 3.92-3.85 (d, 1H), 3.60-3.55 (t, 2H), 3.54-3.47 (q, 2H), 3.01-2.96 (s, 2H), 2.94-2.89 (t, 2H), 1.20-1.15 (t, 3H); MS (EI) for $C_{21}H_{23}F_3IN_3O_3$: 550 (MH$^+$).

Example 3(ad)

3-({[2,2-bis(methyloxy)ethyl]amino}methyl)-1-({3,4-difluoro-2-[(2-fluoro-4-iodophenyl)amino]phenyl}carbonyl)azetidin-3-ol acetate salt: $^1$H NMR (400 MHz, CD$_3$OD): 7.48-7.43 (d, 1H), 7.37-7.32 (d, 1H), 7.30-7.24 (m, 1H), 7.08-7.00 (q, 1H), 6.65-6.57 (t, 1H), 4.48-4.42 (t, 1H), 4.20-4.11 (d, 1H), 4.02-3.93 (t, 2H), 3.86-3.80 (d, 1H), 3.38-3.34 (s, 6H), 2.84-2.80 (s, 2H), 2.75-2.70 (d, 2H), 1.93-1.87 (s, 3H); MS (EI) for C$_{21}$H$_{23}$F$_3$IN$_3$O$_4$: 566 (MH$^+$).

Example 3(ae)

1-({3,4-difluoro-2-[(2-fluoro-4-iodophenyl)amino]phenyl}carbonyl)-3-{[(3-hydroxypropyl)amino]methyl}azetidin-3-ol acetate salt: $^1$H NMR (400 MHz, CD$_3$OD): 7.48-7.43 (d, 1H), 7.38-7.33 (d, 1H), 7.32-7.26 (m, 1H), 7.09-7.00 (q, 1H), 6.66-6.58 (t, 1H). 4.31-4.23 (d, 1H), 4.16-4.05 (t, 2H), 3.99-3.89 (d, 1H), 3.70-3.64 (t, 2H), 3.26-3.22 (s, 2H), 3.11-3.04 (t, 2H), 1.93-1.89 (s, 3H), 1.89-1.82 (t, 3H); MS (EI) for C$_{20}$H$_{21}$F$_3$IN$_3$O$_3$: 536 (MH$^+$).

Example 3(af)

1-({3,4-difluoro-2-[(2-fluoro-4-iodophenyl)amino]phenyl}carbonyl)-3-{[(2-pyridin-4-ylethyl)amino]methyl}azetidin-3-ol acetate salt: $^1$H NMR (400 MHz, CD$_3$OD): 8.36-8.32 (d, 2H), 7.38-7.33 (d, 1H), 7.26-7.14 (m, 3H), 7.00-6.91 (q, 1H), 4.12-4.04 (d, 1H), 3.96-3.88 (t, 2H), 3.80-3.73 (d, 2H), 2.92-2.74 (m, 6H), 1.87-1.84 (s, 3H); MS (EI) for C$_{24}$H$_{22}$F$_3$IN$_4$O$_2$: 583 (MH$^+$).

Example 3(ag)

1-({3,4-difluoro-2-[(2-fluoro-4-iodophenyl)amino]phenyl}carbonyl)-3-({[1-(phenylmethyl)pyrrolidin-3-yl]amino}methyl)azetidin-3-ol acetate salt: $^1$H NMR (400 MHz, CD$_3$OD): 7.47-7.24 (m, 8H), 7.08-7.00 (q, 1H), 6.64-6.57 (t, 1H), 4.19-4.11 (d, 1H), 4.05-3.81 (m, 5H), 3.52-3.44 (m, 1H), 3.09-2.99 (m, 2H), 2.91-2.76 (m, 3H), 1.93-1.91 (s, 3H), 1.82-1.71 (m, 1H); MS (EI) for C$_{28}$H$_{25}$F$_3$IN$_4$O$_2$: 637 (MH$^+$).

Example 3(ah)

1-({3,4-difluoro-2-[(2-fluoro-4-iodophenyl)amino]phenyl}carbonyl)-3-({[2-(2-thienyl)ethyl]amino}methyl)azetidin-3-ol acetate salt: $^1$H NMR (400 MHz, CD$_3$OD): 7.47-7.42 (d, 1H), 7.36-7.31 (d, 1H), 7.30-7.24 (m, 1H), 7.21-7.17 (d, 1H), 7.08-7.00 (q, 1H), 6.93-6.89 (t, 1H), 6.86-6.83 (d, 1H), 6.64-6.57 (t, 1H), 4.18-4.11 (d, 1H), 4.01-3.93 (t, 2H), 3.85-3.78 (d, 1H), 3.04-2.97 (t, 2H), 2.92-2.87 (t, 2H), 2.82-2.78 (s, 2H), 1.92-1.87 (s, 3H); MS (EI) for C$_{23}$H$_{21}$F$_3$IN$_3$O$_2$S: 588 (MH$^+$).

Example 3(ai)

3-[({2-[bis(1-methylethyl)amino]ethyl}amino)methyl]-1-({3,4-difluoro-2-[(2-fluoro-4-iodophenyl)amino]phenyl}carbonyl)azetidin-3-ol acetate salt: $^1$H NMR (400 MHz, CD$_3$OD): 7.48-7.43 (d, 1H), 7.36-7.33 (d, 1H), 7.31-7.26 (m, 1H), 7.08-7.00 (q, 1H), 6.65-6.58 (t, 1H), 4.18-4.13 (d, 1H), 4.06-3.98 (t, 2H), 3.88-3.82 (d, 2H), 3.57-3.47 (q, 2H), 3.05-2.99 (t, 2H), 2.92-2.85 (t, 4H), 1.92-1.88 (s, 3H), 1.28-1.22 (d, 12H); MS (EI) for C$_{25}$H$_{32}$F$_3$IN$_4$O$_2$: 605 (MH$^+$).

Example 3(aj)

1-({3,4-difluoro-2-[(2-fluoro-4-iodophenyl)amino]phenyl}carbonyl)-3-({[2-(phenyloxy)ethyl]amino}methyl)azetidin-3-ol acetate salt: $^1$H NMR (400 MHz, CD$_3$OD): 7.36-7.31 (d, 1H), 7.26-7.22 (d, 1H), 7.20-7.13 (m, 3H), 6.97-6.89 (t, 1H), 6.86-6.80 (m, 3H), 6.54-6.47 (t, 1H), 4.13-4.07 (d, 1H), 4.01-3.96 (t, 2H), 3.79-3.74 (d, 1H), 2.97-2.91 (t, 2H), 2.84-2.79 (s, 2H), 1.84-1.81 (s, 3H); MS (EI) for C$_{25}$H$_{23}$F$_3$IN$_3$O$_3$: 598 (MH$^+$).

Example 3(ak)

1-({3,4-difluoro-2-[(2-fluoro-4-iodophenyl)amino]phenyl}carbonyl)-3-{[(2-hydroxypropyl)amino]methyl}azetidin-3-ol acetate salt: $^1$H NMR (400 MHz, CD$_3$OD): 7.48-7.43 (d, 1H), 7.36-7.33 (d, 1H), 7.31-7.26 (m, 1H), 7.08-7.00 (q, 1H), 6.65-6.58 (t, 1H), 4.27-4.19 (d, 1H), 4.10-4.00 (m, 2H), 3.15-3.00 (t, 2H), 3.57-3.47 (q, 2H), 3.15-3.00 (t, 2H), 2.87-2.81 (d, 1H), 2.72-2.64 (t, 1H), 1.94-1.91 (s, 3H), 1.19-1.15 (d, 3H); MS (EI) for C$_{20}$H$_{21}$F$_3$IN$_3$O$_3$: 536 (MH$^+$).

Example 3(am)

1-({3,4-difluoro-2-[(2-fluoro-4-iodophenyl)amino]phenyl}carbonyl)-3-[({2-[(1-methylethyl)oxy]ethyl}amino)methyl]azetidin-3-01 acetate salt: $^1$H NMR (400 MHz, CD$_3$OD): 7.48-7.43 (d, 1H), 7.36-7.33 (d, 1H), 7.31-7.26 (m, 1H), 7.08-7.00 (q, 1H), 6.65-6.58 (t, 1H), 4.21-4.13 (d, 1H), 4.04-3.95 (t, 2H), 3.88-3.82 (d, 1H), 3.64-3.51 (m, 3H), 2.89-2.84 (s, 2H), 2.83-2.77 (t, 2H), 1.91-1.89 (s, 3H), 1.15-1.12 (d, 6H); MS (EI) for C$_{22}$H$_{25}$F$_3$IN$_3$O$_3$: 564 (MH$^+$).

Example 3(an)

1-({3,4-difluoro-2-[(2-fluoro-4-iodophenyl)amino]phenyl}carbonyl)-3-{[(1-ethylpiperidin-3-yl)amino]methyl}azetidin-3-ol acetate salt: $^1$H NMR (400 MHz, CD$_3$OD): 7.48-7.43 (d, 1H), 7.36-7.33 (d, 1H), 7.31-7.26 (m, 1H), 7.08-7.00 (q, 1H), 6.65-6.58 (t, 1H), 4.17-4.10 (d, 1H), 4.04-3.95 (t, 2H), 3.88-3.82 (d, 1H), 3.24-3.06 (m, 2H), 2.95-2.75 (m, 6H), 2.76-2.46 (m, 2H), 1.93-1.90 (s, 3H), 1.74-1.62 (m, 1H), 1.44-1.31 (m, 1H), 1.28-1.20 (t, 3H); MS (EI) for C$_{24}$H$_{28}$F$_3$IN$_4$O$_2$: 589 (MH$^+$).

Example 3(ao)

1-({3,4-difluoro-2-[(2-fluoro-4-iodophenyl)amino]phenyl}carbonyl)-3-({[(5-methyl-1,3,4-oxadiazol-2-yl)methyl]amino}methyl)azetidin-3-ol acetate salt: $^1$H NMR (400 MHz, CD$_3$OD): 7.48-7.43 (d, 1H), 7.36-7.33 (d, 1H), 7.31-7.26 (m, 1H), 7.08-7.00 (q, 1H), 6.65-6.58 (t, 1H), 4.20-4.13 (d, 1H), 4.00-3.90 (t, 2H), 3.83-3.75 (d, 1H), 2.84-2.78 (s, 2H), 2.53-2.48 (s, 2H), 1.93-1.87 (s, 3H); MS (EI) for C$_{21}$H$_{19}$F$_3$IN$_5$O$_3$: 574 (MH$^+$).

Example 3(ap)

1-({3,4-difluoro-2-[(2-fluoro-4-iodophenyl)amino]phenyl}carbonyl)-3-{[(1-methylbutyl)amino]methyl}azetidin-3-ol acetate salt: $^1$H NMR (400 MHz, CD$_3$OD): 7.48-7.43 (d, 1H), 7.38-7.33 (d, 1H), 7.32-7.27 (m, 1H), 7.09-7.01 (q, 1H), 6.65-6.58 (t, 1H), 4.25-4.19 (d, 1H), 4.12-4.02 (t, 2H), 3.96-3.90 (d, 1H), 3.16-2.96 (m, 3H), 1.91-

1.89 (s, 3H), 1.68-1.57 (m, 1H), 1.49-1.29 (m, 3H), 1.23-1.18 (d, 3H), 0.99-0.92 (t, 3H); MS (EI) for $C_{22}H_{25}F_3IN_3O_2$: 548 (MH$^+$).

Example 3(aq)

1-({3,4-difluoro-2-[(2-fluoro-4-iodophenyl)amino]phenyl}carbonyl)-3-{[(1-methylpropyl)amino]methyl}azetidin-3-ol acetate salt: $^1$H NMR (400 MHz, CD$_3$OD): 7.48-7.43 (d, 1H), 7.37-7.33 (d, 1H), 7.32-7.26 (m, 1H), 7.09-7.01 (q, 1H), 6.65-6.58 (t, 1H), 4.27-4.20 (d, 1H), 4.14-4.03 (t, 2H), 3.98-3.92 (d, 1H), 3.20-3.16 (s, 2H), 3.07-2.97 (m, 1H), 1.91-1.89 (s, 3H), 1.80-1.70 (m, 1H), 1.54-1.41 (m, 1H), 1.26-1.22 (d, 3H), 1.00-0.94 (t, 3H); MS (EI) for $C_{21}H_{23}F_3IN_3O_2$: 534 (MH$^+$).

Example 3(ar)

1-({3,4-difluoro-2-[(2-fluoro-4-iodophenyl)amino]phenyl}carbonyl)-3-{[(2-methylbutyl)amino]methyl}azetidin-3-ol acetate salt: $^1$H NMR (400 MHz, CD$_3$OD): 7.48-7.43 (d, 1H), 7.37-7.33 (d, 1H), 7.32-7.26 (m, 1H), 7.09-7.01 (q, 1H), 6.65-6.58 (t, 1H), 4.26-4.19 (d, 1H), 4.10-4.01 (t, 2H), 3.94-3.87 (d, 1H), 3.05-2.99 (s, 2H), 2.77-2.70 (m, 1H), 2.61-2.54 (m, 1H), 1.91-1.89 (s, 3H), 1.73-1.61 (m, 1H), 1.49-1.39 (m, 1H), 1.24-1.12 (m, 1H), 0.94-0.84 (m, 6H); MS (EI) for $C_{22}H_{25}F_3IN_3O2$: 548 (MH$^+$).

Example 3(as)

1-({3,4-difluoro-2-[(2-fluoro-4-iodophenyl)amino]phenyl}carbonyl)-3-[(pentylamino)methyl]azetidin-3-ol acetate salt: $^1$H NMR (400 MHz, CD$_3$OD): 7.48-7.43 (d, 1H), 7.37-7.33 (d, 1H), 7.32-7.26 (m, 1H), 7.09-7.01 (q, 1H), 6.65-6.58 (t, 1H), 4.29-4.23 (d, 1H), 4.15-4.05 (t, 2H), 3.98-3.90 (d, 1H), 3.21-3.18 (s, 2H), 2.93-2.86 (m, 2H), 1.91-1.89 (s, 3H), 1.70-1.60 (m, 2H), 1.42-1.29 (m, 4H), 0.97-0.90 (t, 3H); MS (EI) for $C_{22}H_{25}F_3IN_3O_2$: 548 (MH$^+$).

Example 3(at)

3-[(cyclohexylamino)methyl]-1-({3,4-difluoro-2-[(2-fluoro-4-iodophenyl)amino]phenyl}carbonyl)azetidin-3-ol acetate salt: $^1$H NMR (400 MHz, CD$_3$OD): 7.48-7.43 (d, 1H), 7.38-7.34 (d, 1H), 7.33-7.27 (m, 1H), 7.09-7.01 (q, 1H), 6.65-6.58 (t, 1H), 4.25-4.19 (d, 1H), 4.14-4.03 (t, 2H), 3.98-3.90 (d, 1H), 3.21-3.18 (s, 2H), 2.93-2.86 (m, 1H), 2.07-2.00 (d, 2H), 1.92-1.90 (s, 3H), 1.89-1.82 (d, 2H), 1.73-1.66 (d, 1H), 1.42-1.14 (m, 5H); MS (EI) for $C_{23}H_{25}F_3IN_3O_2$: 560 (MH$^+$).

Example 3(au)

3-[(azepan-3-ylamino)methyl]-1-({3,4-difluoro-2-[(2-fluoro-4-iodophenyl)amino]phenyl}carbonyl)azetidin-3-ol acetate salt: $^1$H NMR (400 MHz, CD$_3$OD): 7.48-7.43 (d, 1H), 7.37-7.33 (d, 1H), 7.32-7.26 (m, 1H), 7.09-7.01 (q, 1H), 6.65-6.58 (t, 1H), 4.19-4.13 (d, 1H), 4.05-3.95 (t, 2H), 3.90-3.81 (d, 1H), 3.37-3.34 (s, 2H), 3.22-3.03 (m, 2H), 2.91-2.64 (m, 3H), 1.93-1.89 (s, 3H), 1.88-1.52 (m, 6H); MS (EI) for $C_{23}H_{26}F_3IN_4O_2$: 575 (MH$^+$).

Example 3(av)

1-({3,4-difluoro-2-[(2-fluoro-4-iodophenyl)amino]phenyl}carbonyl)-3-({[2-(2,3-dihydro-1H-indol-3-yl)ethyl]amino}methyl)azetidin-3-ol acetate salt: $^1$H NMR (400 MHz, CD$_3$OD): 7.58-7.54 (d, 1H), 7.48-7.43 (d, 1H), 7.36-7.33 (d, 1H), 7.31-7.26 (m, 1H), 7.14-6.99 (m, 4H), 6.65-6.58 (t, 1H), 4.25-4.19 (d, 1H), 4.10-4.02 (t, 2H). 3.95-3.88 (d, 1H), 3.23-3.03 (m, 9H), 1.94-1.92 (s, 3H); MS (EI) for $C_{27}H_{26}F_3IN_4O_2$: 623 (MH$^+$).

Example 3(aw)

1-({3,4-difluoro-2-[(2-fluoro-4-iodophenyl)amino]phenyl}carbonyl)-3-[(1,3,5-triazin-2-ylamino)methyl]azetidin-3-ol acetate salt: $^1$H NMR (400 MHz, CD$_3$OD): 8.48-8.46 (s, 1H), 8.36-8.34 (s, 1H), 7.48-7.43 (d, 1H), 7.37-7.33 (d, 1H), 7.28-7.22 (m, 1H), 7.06-6.98 (q, 1H), 6.65-6.58 (t, 1H), 4.24-4.18 (d, 1H), 4.10-3.96 (t, 2H), 3.84-3.78 (d, 1H), 3.69-3.67 (s, 2H), 1.99-1.97 (s, 3H); MS (EI) for $C_{20}H_{16}F_3IN_6O_2$: 557 (MH$^+$).

Example 3(ax)

1-({3,4-difluoro-2-[(2-fluoro-4-iodophenyl)amino]phenyl}carbonyl)-3-{[(4-hydroxycyclohexyl)amino]methyl}azetidin-3-ol acetate salt: $^1$H NMR (400 MHz, CD$_3$OD): 7.48-7.43 (d, 1H), 7.37-7.33 (d, 1H), 7.32-7.26 (m, 1H), 7.09-7.01 (q, 1H), 6.65-6.58 (t, 1H), 4.22-4.15 (d, 1H), 4.08-3.99 (t, 2H), 3.93-3.87 (d, 1H), 3.56-3.47 (m, 1H), 3.05-3.02 (s, 2H), 2.76-2.68 (m, 1H), 2.03-1.96 (m, 4H), 1.93-1.89 (s, 3H), 1.35-1.23 (m, 4H); MS (EI) for $C_{23}H_{25}F_3IN_3O_3$: 576 (MH$^+$).

Example 3(ay)

3-[(cyclopent-3-en-1-ylamino)methyl]-1-({3,4-difluoro-2-[(2-fluoro-4-iodophenyl)amino]phenyl}carbonyl)azetidin-3-ol acetate salt: $^1$H NMR (400 MHz, CD$_3$OD): 7.48-7.43 (d, 1H), 7.37-7.33 (d, 1H), 7.32-7.26 (m, 1H), 7.09-7.01 (q, 1H), 6.65-6.58 (t, 1H), 5.70-5.65 (s, 2H), 4.20-4.14 (d, 1H), 4.03-3.95 (t, 2H), 3.90-3.81 (d, 1H), 3.58-3.50 (m, 1H), 2.90-2.86 (s, 2H), 2.68-2.58 (m, 2H), 2.26-2.16 (m, 2H), 1.93-1.89 (s, 3H); MS (EI) for $C_{22}H_{21}F_3IN_3O_2$: 544 (MH$^+$).

Example 3(az)

N-[4-({[1-({3,4-difluoro-2-[(2-fluoro-4-iodophenyl)amino]phenyl}carbonyl)-3-hydroxyazetidin-3-yl]methyl}amino)phenyl]acetamide acetate salt: $^1$H NMR (400 MHz, CD$_3$OD): 7.48-7.43 (d, 1H), 7.37-7.33 (d, 1H), 7.27-7.20 (m, 3H), 7.09-7.01 (q, 1H), 6.65-6.55 (m, 3H), 4.22-4.16 (d, 1H), 4.08-3.98 (t, 2H), 3.88-3.82 (d, 1H), 3.28-3.24 (s, 2H), 2.08-2.05 (s, 3H), 2.91-2.64 (m, 3H), 1.93-1.89 (s, 3H); MS (EI) for $C_{25}H_{22}F_3IN_4O_3$: 611 (MH$^+$).

Example 3(ba)

N-[3-({[1-({3,4-difluoro-2-[(2-fluoro-4-iodophenyl)amino]phenyl}carbonyl)-3-hydroxyazetidin-3-yl]methyl}amino)phenyl]acetamide acetate salt: $^1$H NMR (400 MHz, CD$_3$OD): 7.48-7.43 (d, 1H), 7.36-7.33 (d, 1H), 7.27-7.20 (m, 1H), 7.04-6.96 (m, 3H), 6.72-6.68 (d, 1H), 6.65-6.58 (t, 1H), 6.40-6.35 (d, 1H), 4.24-4.18 (d, 1H), 4.08-3.98 (t, 2H), 3.87-3.81 (d, 1H), 3.28-3.25 (s, 2H), 2.10-2.07 (s, 3H), 1.97-1.95 (s, 3H); MS (EI) for $C_{25}H_{22}F_3IN_4O_3$: 611 (MH$^+$).

Example 3(bc)

(1R,2S)-4-({[1-({3,4-difluoro-2-[(2-fluoro-4-iodophenyl)amino]phenyl}carbonyl)-3-hydroxyazetidin-3-yl]methyl}amino)cyclopentane-1,2-diol acetate salt: $^1$H NMR (400 MHz, DMSO): 8.58-8.54 (s, 1H), 7.61-7.53 (d, 1H), 7.39-7.28 (m, 2H), 7.21-7.13 (m, 1H), 6.71-6.63 (t, 1H), 5.58-5.64 (s, 1H), 5.63-5.58 (s, 1H), 4.06-4.01 (d, 1H), 3.90-3.84 (t, 2H), 3.72-3.66 (d, 1H), 3.31-3.26 (m, 3H), 2.61-2.57 (s, 2H), 2.46-2.36 (m, 2H), 2.02-1.93 (dd, 2H), 1.91-1.88 (s, 3H); MS (EI) for $C_{22}H_{23}F_3IN_3O_4$: 578 (MH$^+$).

Example 3(bd)

1-({3,4-difluoro-2-[(2-fluoro-4-iodophenyl)amino]phenyl}carbonyl)-3-({[1-(hydroxymethyl)cyclohexyl]amino}methyl)azetidin-3-ol acetate salt: $^1$H NMR (400 MHz, CD$_3$OD): 7.48-7.43 (d, 1H), 7.37-7.33 (d, 1H), 7.32-7.26 (m, 1H), 7.09-7.01 (q, 1H), 6.65-6.58 (t, 1H), 4.22-4.15 (d, 1H), 4.08-3.99 (t, 2H), 3.89-3.83 (d, 1H), 3.49-3.45 (s, 2H), 2.86-2.80 (s, 2H), 1.91-1.89 (s, 3H), 1.67-1.34 (m, 10H); MS (EI) for $C_{24}H_{27}F_3IN_3O_3$: 590 (MH$^+$).

Example 3(be)

3-{[(3-chlorophenyl)amino]methyl}-1-({3,4-difluoro-2-[(2-fluoro-4-iodophenyl)amino]phenyl}carbonyl)azetidin-3-ol acetate salt: $^1$H NMR (400 MHz, CD$_3$OD): 7.48-7.43 (d, 1H), 7.37-7.33 (d, 1H), 7.32-7.26 (m, 1H), 7.08-6.98 (m, 2H), 6.65-6.55 (m, 3H), 6.53-6.44 (d, 1H), 4.22-4.15 (d, 1H), 4.06-3.98 (t, 2H), 3.88-3.82 (d, 1H), 3.27-3.24 (s, 2H), 1.91-1.89 (s, 3H); MS (EI) for $C_{23}H_{18}ClF_3IN_3O_2$: 588 (MH$^+$).

Example 3(bf)

3-{[(4-chlorophenyl)amino]methyl}-1-({3,4-difluoro-2-[(2-fluoro-4-iodophenyl)amino]phenyl}carbonyl)azetidin-3-ol acetate salt: $^1$H NMR (400 MHz, CD$_3$OD): 7.45-7.40 (d, 1H), 7.35-7.30 (d, 1H), 7.28-7.22 (m, 1H), 7.06-6.97 (m, 3H), 6.62-6.54 (m, 3H), 6.53-6.44 (d, 1H), 4.22-4.15 (d, 1H), 4.06-3.98 (t, 2H), 3.88-3.82 (d, 1H), 3.26-3.22 (s, 2H), 1.96-1.94 (s, 3H); MS (EI) for $C_{23}H_{18}ClF_3IN_3O_2$: 588 (MH$^+$).

Example 3(bg)

3-[(5-amino-3-methyl-1H-pyrazol-1-yl)methyl]-1-({3,4-difluoro-2-[(2-fluoro-4-iodophenyl)amino]phenyl}carbonyl)azetidin-3-ol acetate salt: $^1$H NMR (400 MHz, CD$_3$OD): 7.38-7.33 (d, 1H), 7.28-7.24 (d, 1H), 7.21-7.15 (m, 1H), 6.98-6.90 (q, 1H), 6.56-6.49 (t, 1H), 5.16-5.14 (s, 1H), 4.36-4.30 (d, 1H), 4.22-4.16 (d, 1H), 3.99-3.97 (s, 1H), 3.95-3.90 (d, 1H), 3.77-3.71 (d, 1H), 1.96-1.92 (s, 3H), 1.85-1.82 (s, 3H); MS (EI) for $C_{21}H_{19}F_3IN_5O_2$: 558 (MH$^+$).

Example 3(bh)

1-({3,4-difluoro-2-[(2-fluoro-4-iodophenyl)amino]phenyl}carbonyl)-3-{[(5-methyl-1H-pyrazol-3-yl)amino]methyl}azetidin-3-ol acetate salt: $^1$H NMR (400 MHz, CD$_3$OD): 7.38-7.33 (d, 1H), 7.28-7.24 (d, 1H), 7.21-7.15 (m, 1H), 6.98-6.90 (q, 1H), 6.56-6.49 (t, 1H), 5.22-5.19 (s, 1H), 4.15-4.08 (d, 1H), 4.02-3.88 (m, 2H), 3.75-3.68 (d, 1H), 3.20-3.18 (s, 2H), 2.07-2.05 (s, 3H), 1.85-1.82 (s, 3H); MS (EI) for $C_{21}H_{19}F_3IN_5O_2$: 558 (MH$^+$).

Example 3(bi)

3-[(diethylamino)methyl]-1-({3,4-difluoro-2-[(2-fluoro-4-iodophenyl)amino]phenyl}carbonyl)azetidin-3-ol: $^1$H NMR (400 MHz, d$_6$-DMSO): 8.54 (s, 1H), 7.58-7.55 (dd, 1H), 7.38-7.35 (dt, 1H), 7.33-7.31 (m, 1H), 7.22-7.15 (m, 1H), 6.69-6.64 (m, 1H), 5.56 (b, 1H), 4.06-4.04 (d, 1H), 3.90-3.88 (m, 2H), 3.72-3.69 (d, 1H), 2.51-2.49 (m, 6H), 0.86-0.83 (t, 6H); MS (EI) for $C_{21}H_{23}F_3IN_3O_2$: 534 (MH$^+$).

Example 3(bj)

1-({3,4-difluoro-2-[(2-fluoro-4-iodophenyl)amino]phenyl}carbonyl)-3-[(dimethylamino)methyl]azetidin-3-ol: $^1$H NMR (400 MHz, d$_6$-DMSO): 8.56 (s, 1H), 7.59-7.56 (dd, 1H), 7.38-7.36 (dt, 1H), 7.34-7.33 (m, 1H), 7.21-7.14 (m, 1H), 6.71-6.65 (m, 1H), 5.55 (b, 1H), 4.07-4.05 (d, 1H), 3.89-3.84 (t, 2H), 3.74-3.719 (d, 1H), 2.46 (m, 2H), 2.19 (br s, 6H); MS (EI) for $C_{19}H_{19}F_3IN_3O_2$: 506 (MH$^+$).

Example 3(bk)

1-({3,4-difluoro-2-[(2-fluoro-4-iodophenyl)amino]phenyl}carbonyl)-3-{[(2-hydroxy-1,1-dimethylethyl)amino]methyl}azetidin-3-ol: $^1$H NMR (400 MHz, CDCl$_3$): 8.40 (s, 1H), 7.38 (dd, 1H), 7.33-7.30 (m, 1H), 7.12 (m, 1H), 6.85-6.79 (m, 1H), 6.63-6.57 (m, 1H), 4.22-4.11 (br m, 4H), 3.55 (s, 2H), 3.15 (s, 2H), 1.32 (s, 6H); MS (EI) for $C_{21}H_{23}F_3IN_3O_3$: 550 (MH$^+$).

Example 3(bm)

1-({3,4-difluoro-2-[(2-fluoro-4-iodophenyl)amino]phenyl}carbonyl)-3-[(prop-2-en-1-ylamino)methyl]azetidin-3-ol: $^1$H NMR (400 MHz, CDCl$_3$): 8.47 (s, 1H), 7.40 (dd, 1H), 7.34-7.31 (m, 1H), 7.12 (m, 1H), 6.83-6.77 (m, 1H), 6.64-6.59 (m, 1H), 6.64-6.59 (m, 1H), 5.88-5.78 (m, 1H), 5.00-5.12 (m, 2H), 4.13 (br m, 4H), 3.26 (d, 2H), 2.88 (d, 2H), 2.02 (s, 1H); MS (EI) for $C_{21}H_{19}F_3IN_3O_2$: 518 (MH$^+$).

Example 3(bn)

1-({3,4-difluoro-2-[(2-fluoro-4-iodophenyl)amino]phenyl}carbonyl)-3-({[2-(tetrahydro-2H-pyran-4-yl)ethyl]amino}methyl)azetidin-3-ol: $^1$H NMR (400 MHz, CDCl$_3$): 8.45 (s, 1H), 7.39 (dd, 1H), 7.34-7.31 (m, 1H), 7.14-7.10 (m, 1H), 6.84-6.77 (m, 1H), 6.63-6.58 (m, 1H), 4.26-4.04 (m, 4H), 3.95 (dd, 2H), 3.35 (t, 2H), 2.92 (d, 2H), 2.67 (m, 2H), 1.40-1.25 (m, 8H); MS (EI) for $C_{24}H_{27}F_3IN_3O_3$: 590 (MH$^+$).

Example 3(bo)

1-({3,4-difluoro-2-[(2-fluoro-4-iodophenyl)amino]phenyl}carbonyl)-3-{[(1,1-dimethylprop-2-yn-1-yl)amino]methyl}azetidin-3-ol): $^1$H NMR (400 MHz, CDCl$_3$): 8.46 (s, 1H), 7.39 (dd, 1H), 7.33-7.30 (m, 1H), 7.15-7.11 (m, 1H), 6.84-6.77 (m, 1H), 6.64-6.58 (m, 1H), 4.20 (br, 1H), 4.07 (br, 1H), 2.92 (s, 2H), 1.58 (m, 4H), 0.92 (dd, 6h); MS (EI) for $C_{22}H_{21}F_3IN_3O_2$: 572 (MH$^+$).

Example 3(bp)

1-({3,4-difluoro-2-[(2-fluoro-4-iodophenyl)amino]phenyl}carbonyl)-3-({[2-(1H-imidazol-4-yl)ethyl]amino}methyl)azetidin-3-ol): $^1$H NMR (400 MHz, CDCl$_3$): 8.44 (s, 1H), 7.33-7.14 (m, 3H), 7.00 (m, 1H), 6.67 (dd, 1H), 6.59 (m, 1H), 6.44 (m, 1H), 3.93 (d, 2H), 2.75 (m, 2H), 2.60 (m, 1H), 2.42 (m, 1H) 2.02 (AcOH; s, 3H), 1.86 (m, 4H); MS (EI) for $C_{22}H_{21}F_3IN_5O_2$: 572 (MH$^+$).

Example 3(bq)

1-({3,4-difluoro-2-[(2-fluoro-4-iodophenyl)amino]phenyl}carbonyl)-3-({[3-(ethyloxy)propyl]amino}methyl)azetidin-3-ol: $^1$H NMR (400 MHz, CDCl$_3$): 8.49 (s, 1H), 7.39 (dd, 1H), 7.34-7.31 (m, 1H), 7.14-7.10 (m, 1H), 6.83-6.76 (m, 1H), 6.64-6.58 (m, 1H), 4.26-4.03 (br m, 4H), 3.53-3.44 (m, 4H), 2.92-2.73 (m, 4H), 1.72 (m, 2H) 1.18 (t, 3H); MS (EI) for C$_{22}$H$_{23}$F$_3$IN$_3$O$_3$: 564 (MH$^+$).

Example 3(br)

1-({3,4-difluoro-2-[(2-fluoro-4-iodophenyl)amino]phenyl}carbonyl)-3-{[(3,3-dimethylbutyl)amino]methyl}azetidin-3-ol: $^1$H NMR (400 MHz, CDCl$_3$): 8.46 (s, 1H), 7.39 (dd, 1H), 7.34-7.31 (m, 1H), 7.14-7.10 (m, 1H), 6.84-6.77 (m, 1H), 6.63-6.58 (m, 1H), 4.18 (br, 3H), 3.15 (s, 2H), 2.71 (m, 2H) 2.05 (AcOH; s, 3H), 1.43 (m, 2H), 0.90 (s, 9H); MS (EI) for C$_{23}$H$_{27}$F$_3$IN$_3$O$_2$: 562 (MH$^+$).

Example 3(bs)

1-({3,4-difluoro-2-[(2-fluoro-4-iodophenyl)amino]phenyl}carbonyl)-3-{[(3-methylbutyl)amino]methyl}azetidin-3-ol: $^1$H NMR (400 MHz, CDCl$_3$): 8.46 (s, 1H), 7.39 (dd, 1H), 7.34-7.30 (m, 1H), 7.14-7.11 (m, 1H), 6.84-6.77 (m, 1H), 6.63-6.59 (m, 1H), 4.27-3.61 (br m, 6H), 2.98 (m, 2H), 2.72 (t, 2H) 2.05 (AcOH; s, 3H), 1.61 (m, 1H), 1.43 (m, 2H), 0.90 (d, 6H); MS (EI) for C$_{22}$H$_{25}$F$_3$IN$_3$O$_2$: 547 (MH$^+$).

Example 3(bt)

1-({3,4-difluoro-2-[(2-fluoro-4-iodophenyl)amino]phenyl}carbonyl)-3-({[3-(dimethylamino)propyl]amino}methyl)azetidin-3-ol: MS (EI) for C$_{22}$H$_{26}$F$_3$IN$_4$O$_2$: 563 (MH$^+$).

Example 3(bu)

1-({3,4-difluoro-2-[(2-fluoro-4-iodophenyl)amino]phenyl}carbonyl)-3-({[3-(1H-imidazol-1-yl)propyl]amino}methyl)azetidin-3-ol: $^1$H NMR (400 MHz, CDCl$_3$): 8.46 (s, 1H), 7.53 (s, 1H), 7.40 (dd, 1H), 7.34-7.30 (m, 1H), 7.14-7.09 (m, 1H), 7.05 (s, 1H), 6.89 (s, 1H), 6.84-6.77 (m, 1H), 6.63-6.59 (m, 1H), 4.24-4.00 (br m, 6H), 2.84 (m, 2H), 2.61 (m, 2H), 1.94 (m, 2H); MS (EI) for C$_{23}$H$_{21}$F$_3$IN$_5$O$_2$: 586 (MH$^+$).

Example 3(bv)

1-({3,4-difluoro-2-[(2-fluoro-4-iodophenyl)amino]phenyl}carbonyl)-3-({[2-(methylthio)ethyl]amino}methyl)azetidin-3-ol: $^1$H NMR (400 MHz, CDCl$_3$): 8.49 (s, 1H), 7.39 (dd, 1H), 7.34-7.31 (m, 1H), 7.14-7.11 (m, 1H), 6.83-6.77 (m, 1H), 6.63-6.59 (m, 1H), 4.26-4.03 (br m, 4H), 2.88 (s, 2H), 2.82 (t, 2H), 2.62 (t, 2H), 2.08 (s, 3H); MS (EI) for C$_{23}$H$_{21}$F$_3$IN$_3$O$_2$S: 552 (MH$^+$).

Example 3(bw)

1-({3,4-difluoro-2-[(2-fluoro-4-iodophenyl)amino]phenyl}carbonyl)-3-{[(1,1,3,3-tetramethylbutyl)amino]methyl}azetidin-3-ol: $^1$H NMR (400 MHz, CDCl$_3$): 8.49 (s, 1H), 7.38 (dd, 1H), 7.34-7.30 (m, 1H), 7.14-7.11 (m, 1H), 6.83-6.77 (m, 1H), 6.64-6.59 (m, 1H), 4.25-4.01 (br m, 4H), 2.82 (s, 2H), 1.45 (s, 2H), 1.15 (s, 6H), 0.90 (s, 9H); MS (EI) for C$_{25}$H$_{31}$F$_3$IN$_3$O$_2$: 590 (MH$^+$).

Example 3(bx)

1-({3,4-difluoro-2-[(2-fluoro-4-iodophenyl)amino]phenyl}carbonyl)-3-{[(1,1-dimethylpropyl)amino]methyl}azetidin-3-ol: $^1$H NMR (400 MHz, CDCl$_3$): 8.50 (s, 1H), 7.39 (dd, 1H), 7.35-7.30 (m, 1H), 7.15-7.11 (m, 1H), 6.83-6.77 (m, 1H), 6.65-6.59 (m, 1H), 4.27-4.01 (br m, 4H), 2.82 (s, 2H), 1.46 (s, 2H), 1.08 (s, 6H), 0.89 (s, 3H); MS (EI) for C$_{22}$H$_{21}$F$_3$IN$_4$O$_3$: 548 (MH$^+$).

Example 3(by)

3-{[(3-amino-2-hydroxypropyl)amino]methyl}-1-({3,4-difluoro-2-[(2-fluoro-4-iodophenyl)amino]phenyl}carbonyl)azetidin-3-ol: MS (EI) for C$_{23}$H$_{22}$F$_3$IN$_4$O$_3$: 551 (MH$^+$).

Example 3(bz)

1-{[1-({3,4-difluoro-2-[(2-fluoro-4-iodophenyl)amino]phenyl}carbonyl)-3-hydroxyazetidin-3-yl]methyl}pyrrolidin-3-ol: MS (EI) for C$_{21}$H$_{21}$F$_3$IN$_3$O$_3$: 548 (MH$^+$).

Example 3(ca)

1-({3,4-difluoro-2-[(2-fluoro-4-iodophenyl)amino]phenyl}carbonyl)-3-({(2S)-2-[(methyloxy)methyl]pyrrolidin-1-yl}methyl)azetidin-3-ol: MS (EI) for C$_{23}$H$_{25}$F$_3$IN$_3$O$_3$: 576 (MH$^+$).

Example 3(cb)

1-({3,4-difluoro-2-[(2-fluoro-4-iodophenyl)amino]phenyl}carbonyl)-3-{[(2-hydroxyphenyl)amino]methyl}azetidin-3-ol: $^1$H NMR (400 MHz, CDCl$_3$): 8.46 (s, 1H), 7.41 (dd, 1H), 7.35-7.30 (m, 1H), 7.15-7.11 (m, 1H), 6.89-5.98 (m, 6H), 4.92 (s, 1H), 4.28-4.05 (br m, 4H), 3.44 (s, 2H); MS (EI) for C$_{23}$H$_{19}$F$_3$IN$_3$O$_3$: 570 (MH$^+$).

Example 3(cd)

1-({3,4-difluoro-2-[(2-fluoro-4-iodophenyl)amino]phenyl}carbonyl)-3-{[(4-hydroxyphenyl)amino]methyl}azetidin-3-ol: $^1$H NMR (400 MHz, CDCl$_3$): 8.46 (s, 1H), 7.78 (s, 1H), 7.40-7.05 (m, 4H), 6.72 (m, 1H), 6.62 (d, 1H), 6.50 (m, 1H), 6.42 (d, 1H) 4.04-3.98 (m, 4H), 3.18 (s, 2H); MS (EI) for C$_{23}$H$_{19}$F$_3$IN$_3$O$_3$: 570 (MH$^+$).

Example 3(ce)

1-({3,4-difluoro-2-[(2-fluoro-4-iodophenyl)amino]phenyl}carbonyl)-3-{[(3-hydroxyphenyl)amino]methyl}azetidin-3-ol: $^1$H NMR (400 MHz, CDCl$_3$): 8.52 (s, 1H), 8.22 (s, 1H), 7.39 (dd, 1H), 7.34-7.31 (m, 1H), 7.14-7.11 (m, 1H), 6.85 (dd, 1H), 6.84-6.77 (m, 1H), 6.63-6.59 (m, 1H), 6.15 (d, 1H) 6.09-6.01 (m, 3H), 4.16-3.95 (br m, 4H), 3.22 (d, 2H) 2.15 (AcOH; s, 3H); MS (EI) for C$_{23}$H$_{19}$F$_3$IN$_3$O$_3$: 570 (MH$^+$).

Example 3(d)

1-({3,4-difluoro-2-[(2-fluoro-4-iodophenyl)amino]phenyl}carbonyl)-3-[(phenyloxy)methyl]azetidin-3-ol: MS (EI) for $C_{23}H_{18}F_3IN_2O_3$: 555 (MH$^+$).

Example 3(cg)

3-({[1-({3,4-difluoro-2-[(2-fluoro-4-iodophenyl)amino]phenyl}carbonyl)-3-hydroxyazetidin-3-yl]methyl}amino)propane-1,2-diol: MS (EI) for $C_{20}H_{21}F_3IN_3O_4$: 552 (MH$^+$).

Example 3(ch)

1-({3,4-difluoro-2-[(2-fluoro-4-iodophenyl)amino]phenyl}carbonyl)-3-[(phenylthio)methyl]azetidin-3-ol: $^1$H NMR (400 MHz, CDCl$_3$): 8.46 (s, 1H), 7.45-7.23 (m, 5H), 7.14-7.05 (m, 1H), 6.78 (dd, 1H), 6.60 (m, 1H), 4.14-3.92 (br m, 4H), 3.33 (s, 2H); MS (EI) for $C_{23}H_{18}F_3IN_2O_2$: 571 (MH$^+$).

Example 3(ci)

1-({3,4-difluoro-2-[(2-fluoro-4-iodophenyl)amino]phenyl}carbonyl)-3-{[(4-hydroxybutyl)amino]methyl}azetidin-3-ol: $^1$H NMR (400 MHz, CDCl$_3$): 8.43 (s, 1H), 7.38 (dd, 1H), 7.34-7.30 (m, 1H), 7.14-7.10 (m, 1H), 6.84-6.77 (m, 1H), 6.63-6.58 (m, 1H), 4.26-4.04 (m, 4H), 3.61 (m, 2H), 2.96 (s, 2H), 2.73 (s, 2H); MS (EI) for $C_{21}H_{23}F_3IN_3O_3$: 550 (MH$^+$).

Example 3(cj)

1-({3,4-difluoro-2-[(2-fluoro-4-iodophenyl)amino]phenyl}carbonyl)-3-{[(2-hydroxyethyl)oxy]methyl}azetidin-3-ol: $^1$H NMR (400 MHz, CDCl$_3$): 8.51 (s, 1H), 7.39 (dd, 1H), 7.35-7.31 (m, 1H), 7.14-7.11 (m, 1H), 6.84-6.77 (m, 1H), 6.63-6.59 (m, 1H), 4.21-4.05 (br m, 4H), 3.77 (m, 2H), 3.66 (m, 2H); MS (EI) for $C_{19}H_{18}F_3IN_2O_4$: 523 (MH$^+$).

Example 3(ck)

1-({3,4-difluoro-2-[(2-fluoro-4-iodophenyl)amino]phenyl}carbonyl)-3-({[(1S,2S)-2-hydroxycyclohexyl]amino}methyl)azetidin-3-ol: MS (EI) for $C_{23}H_{25}F_3IN_3O_3$: 576 (MH$^+$).

Example 3(cm)

1-({3,4-difluoro-2-[(2-fluoro-4-iodophenyl)amino]phenyl}carbonyl)-3-{[(1,1-dimethyl-2-pyrrolidin-1-ylethyl)amino]methyl}azetidin-3-ol: $^1$H NMR (400 MHz, CDCl$_3$): 8.49 (s, 1H), 7.39 (dd, 1H), 7.34-7.29 (m, 1H), 7.14-7.11 (m, 1H), 6.83-6.77 (m, 1H), 6.64-6.59 (m, 1H), 4.25-4.07 (br m, 4H), 2.88 (d, 2H), 2.62 (m, 4H), 2.58 (m, 2H), 1.78 (m, 4H), 2.05 (AcOH; s, 3H); MS (EI) for $C_{25}H_{30}F_3IN_4O_2$: 603 (MH$^+$).

Example 3(cn)

1-({3,4-difluoro-2-[(2-fluoro-4-iodophenyl)amino]phenyl}carbonyl)-3-({[(1-methyl-1H-imidazol-4-yl)methyl]amino}methyl)azetidin-3-ol: $^1$H NMR (400 MHz, CDCl$_3$): 8.50 (s, 1H), 7.41-7.11 (m, 3H), 7.12 (m, 1H), 6.85-6.79 (m, 2H), 4.12-3.98 (br m, 4H), 3.78 (s, 2H), 3.66 (s, 3H), 2.95 (s, 2H), 2.08 (AcOH; s, 4H), 2.05 (AcOH; s, 3H); MS (EI) for $C_{22}H_{21}F_3IN_5O_2$: 572 (MH$^+$).

Example 3(co)

1-({3,4-difluoro-2-[(2-fluoro-4-iodophenyl)amino]phenyl}carbonyl)-3-({[(1-methyl-1H-imidazol-5-yl)methyl]amino}methyl)azetidin-3-ol: $^1$H NMR (400 MHz, CDCl$_3$): 8.45 (s, 1H), 7.47 (s, 1H), 7.39 (dd, 1H), 7.33-7.30 (m, 1H), 7.15-7.10 (m, 1H), 6.91 (s, 1H), 6.87-6.77 (m, 1H), 6.63-6.58 (m, 1H), 4.18-4.02 (m, 4H), 3.3.80 (s, 2H), 3.62 (s, 3H), 2.90 (s, 1H), 2.05 (AcOH; s, 3H); MS (EI) for $C_{22}H_{21}F_3IN_5O_2$: 572 (MH$^+$).

Example 3(cp)

1-({3,4-difluoro-2-[(2-fluoro-4-iodophenyl)amino]phenyl}carbonyl)-3-({[(2S)-2-(methyloxy)cyclopentyl]amino}methyl)azetidin-3-ol: MS (EI) for $C_{23}H_{25}F_3IN_3O_3$: 576 (MH$^+$).

Example 3(cq)

1-({3,4-difluoro-2-[(2-fluoro-4-iodophenyl)amino]phenyl}carbonyl)-3-({[(1R)-2-hydroxycyclohexyl]amino}methyl)azetidin-3-ol: MS (EI) for $C_{23}H_{25}F_3IN_3O_3$: 576 (MH$^+$).

Example 3(cr)

N-[3-({[1-({3,4-difluoro-2-[(2-fluoro-4-iodophenyl)amino]phenyl}carbonyl)-3-hydroxyazetidin-3-yl]methyl}amino)phenyl]methanesulfonamide: $^1$H NMR (400 MHz, CDCl$_3$): 7.33 (dd, 1H), 7.22 (m, 1H), 7.08 (dd, 1H), 6.83-6.77 (m, 1H), 6.03-5.98 (m, 2H), 6.64-6.59 (m, 1H), 4.08-3.77 (br m, 5H), 2.88 (s, 3H); MS (EI) for $C_{24}H_{22}F_3IN_4O_4S$: 647 (MH$^+$).

Example 3(cs)

3-{[(4-aminophenyl)amino]methyl}-1-({3,4-difluoro-2-[(2-fluoro-4-iodophenyl)amino]phenyl}carbonyl)azetidin-3-ol: $^1$H NMR (400 MHz, CDCl$_3$): 8.44 (s, 1H), 7.39 (dd, 1H), 7.34-7.30 (m, 1H), 7.14-7.10 (m, 1H), 6.84-6.77 (m, 1H), 6.64-6.53 (m, 5H), 4.22-4.04 (br m, 4H), 3.34 (s, 2H); MS (EI) for $C_{23}H_{20}F_3IN_4O_2$: 569 (MH$^+$).

Example 3(ct)

1-({3,4-difluoro-2-[(2-fluoro-4-iodophenyl)amino]phenyl}carbonyl)-3-{[(2-hydroxy-2-methylcyclopentyl)amino]methyl}azetidin-3-ol: MS (EI) for $C_{23}H_{25}F_3IN_3O_3$: 576 (MH$^+$).

Example 3(cu)

3-[(cyclopentylamino)methyl]-1-({3,4-difluoro-2-[(2-fluoro-4-iodophenyl)amino]phenyl}carbonyl)azetidin-3-ol: $^1$H NMR (400 MHz, CD$_3$OD): 7.44 (dd, 1H), 7.36-7.31 (m, 1H), 7.30-7.24 (m, 1H), 7.09-6.99 (m, 1H), 6.64-6.57 (m, 1H), 4.17-4.10 (m, 1H), 4.01-3.91 (m, 2H), 3.87-3.79 (m, 1H), 3.07-2.97 (m, 1H), 2.75 (s, 2H), 1.92-1.79 (m, 2H), 1.75-1.62 (m, 2H), 1.61-1.47 (m, 2H), 1.37-1.22 (m, 2H). MS (EI) for $C_{22}H_{23}F_3IN_3O_2$: 546 (MH$^+$).

Example 3(cv)

3-{[(cyclohexylmethyl)amino]methyl}-1-({3,4-difluoro-2-[(2-fluoro-4-iodophenyl)amino]phenyl}carbonyl)azetidin-3-ol acetate (salt): $^1$H NMR (400 MHz, CD$_3$OD): 7.46 (dd, 1H), 7.39-7.32 (m, 1H), 7.31-7.25 (m, 1H), 7.11-6.99 (m, 1H), 6.67-6.57 (m, 1H), 4.27-4.15 (m, 1H), 4.12-3.97 (m, 2H), 3.96-3.85 (m, 1H), 3 (s, 2H), 2.62 (d, 2H), 1.90 (s, 3H), 1.82-1.45 (m, 6H), 1.40-1.07 (m, 3H), 1.04-0.80 (m, 2H). MS (EI) for C$_{24}$H$_{27}$F$_3$IN$_3$O$_2$: 574 (MH$^+$).

Example 3(cw)

1-({3,4-difluoro-2-[(2-fluoro-4-iodophenyl)amino]phenyl}carbonyl)-3-[(propylamino)methyl]azetidin-3-ol: $^1$H NMR (400 MHz, d$_6$-DMSO): δ 8.56 (s, 1H), 7.57 (dd, 1H), 7.37 (dd, 1H), 7.32 (m, 1H), 7.18 (m, 1H), 6.67 (m, 1H), 4.03 (d, 1H), 3.89 (m, 2H), 3.69 (d, 1H), 2.59 (s, 2H), 2.42 (t, 2H), 1.90 (s, 3H), 1.32 (m, 2H), 0.81 (t, 3H); MS (EI) for C$_{20}$H$_{21}$F$_3$IN$_3$O$_2$: 520 (MH$^+$).

Example 3(cx)

1-({3,4-difluoro-2-[(2-fluoro-4-iodophenyl)amino]phenyl}carbonyl)-3-{[(2-methylpropyl)amino]methyl}azetidin-3-ol: $^1$H NMR (400 MHz, d$_6$-DMSO): δ 8.56 (s, 1H), 7.56 (dd, 1H), 7.36 (dd, 1H), 7.31 (m, 1H), 7.18 (m, 1H), 6.67 (m, 1H), 4.02 (d, 1H), 3.89 (m, 2H), 3.70 (d, 1H), 2.57 (s, 2H), 2.27 (d, 2H), 1.91 (s, 3H), 1.55 (m, 1H), 0.79 (d, 6H); MS (EI) for C$_{21}$H$_{23}$F$_3$IN$_3$O$_2$: 534 (MH$^+$).

Example 3(cy)

methyl (2xi)-2-deoxy-2-({[1-({3,4-difluoro-2-[(2-fluoro-4-iodophenyl)amino]phenyl}carbonyl)-3-hydroxyazetidin-3-yl]methyl}amino)-beta-D-amino-hexopyranoside: $^1$H NMR (400 MHz, d$_4$-methanol, ~3:1 mixture of anomers): δ 7.46 (d, 1H), 7.34 (d, 1H), 7.28 (m, 1H), 7.04 (q, 1H), 6.62 (m, 1H), 4.19-5.92 (m, 4H), 3.87-3.78 (m, 2H), 3.68 (m, 1H), 3.56-3.18 (m, 5H), 2.99-2.82 (m, 3H), 2.56 (m, 0.25H), 2.29 (m, 0.75H) MS (EI) for C$_{24}$H$_{27}$F$_3$IN$_3$O$_7$: 652 (M-H).

Example 3(cz)

3-({[3-(diethylamino)propyl]amino}methyl)-1-({3,4-difluoro-2-[(2-fluoro-4-iodophenyl)amino]phenyl}carbonyl)azetidin-3-ol acetate salt: $^1$H NMR (400 MHz, CD$_3$OD): 7.48-7.43 (d, 1H), 7.38-7.33 (d, 1H), 7.32-7.26 (m, 1H), 7.09-7.00 (q, 1H), 6.66-6.58 (t, 1H), 4.24-4.16 (d, 1H), 4.11-3.99 (t, 2H), 3.92-3.85 (d, 1H), 3.10-3.02 (m, 8H), 2.99-2.96 (s, 2H), 2.92-2.87 (t, 2H), 1.93-1.87 (s, 3H), 1.27-1.20 (t, 6H); MS (EI) for C$_{24}$H$_{30}$F$_3$IN$_4$O$_2$: 591 (MH$^+$).

Example 4

1-({3,4-difluoro-2-[(2-fluoro-4-iodophenyl)amino]phenyl}carbonyl)-N-(2-hydroxyethyl)azetidine-3-carboxamide

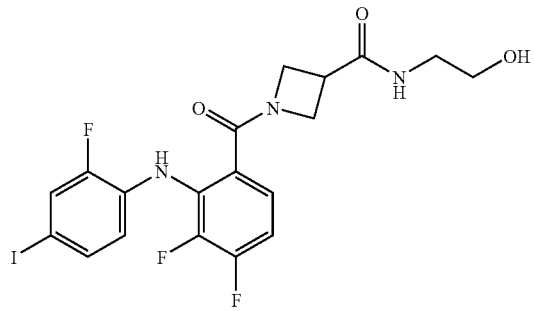

To a solution of 1-({3,4-difluoro-2-[(2-fluoro-4-iodophenyl)amino]phenyl}carbonyl)azetidine-3-carboxylic acid (15 mg, 0.03 mmol), prepared using procedures similar to those in Example 1, in N,N-dimethylformamide (2.00 mL) was added HBTU (38 mg, 0.10 mmol). The mixture was stirred for 15 minutes at room temperature followed by the addition of 2-aminoethanol (3.6 µL, 0.06 mmol) and N-methylmorpholine (110 µL, 1.00 mmol). The mixture was allowed to stir at room temperature for 3 d, then diluted the mixture with chloroform (20 mL), and washed with water (30 mL). The aqueous phase was back extracted with chloroform (10 mL). The combined organic phases were dried over sodium sulfate, filtered and the filtrate concentrated in vacuo. The residue was purified by high pressure liquid chromatography to afford the title compound (9.20 mg, 58%) as the trifluoroacetic acid salt: $^1$H NMR (400 MHz, CDCl$_3$): 8.54 (s, 1H), 7.41-7.37 (m, 1H), 7.34-7.31 (m, 1H), 7.18-7.14 (m, 1H), 6.85-6.77 (m, 1H), 6.64-6.58 (m, 1H), 4.66 (br, 1H), 4.40-4.24 (br, 3H), 3.83-3.23 (br m, 7H), 1.18 (t, 3H); MS (EI) for C$_{19}$H$_{17}$F$_3$IN$_3$O$_3$: 542 (MNa$^+$).

Using the same or analogous synthetic techniques and substituting, as necessary, with alternative reagents, the following compounds of the invention were prepared:

Example 4(a)

1-({3,4-difluoro-2-[(2-fluoro-4-iodophenyl)amino]phenyl}carbonyl)-N-(3,4-dihydroxybutyl)azetidine-3-carboxamide: $^1$H NMR (400 MHz, CDCl$_3$): 8.55 (s, 1H), 7.40 (dd, 1H), 7.31-7.35 (m, 1H), 7.14-7.18 (m, 1H), 6.78-6.84 (m, 1H), 6.59-6.65 (m, 1H), 6.14 (br s, 1H), 4.50-4.60 (m, 1H), 4.20-4.40 (m, 3H), 3.60-3.80 (m, 3H), 3.40-3.52 (m, 2H), 3.20-3.32 (m, 2H), 1.96 (br s, 1H), 1.18-1.28 (m, 2H). MS (EI) for C$_{21}$H$_{21}$F$_3$IN$_3$O$_4$: 562 (M-H).

Example 4(b)

N-butyl-1-({3,4-difluoro-2-[(2-fluoro-4-iodophenyl)amino]phenyl}carbonyl)azetidine-3-carboxamide: $^1$H NMR (400 MHz, CDCl$_3$): 8.53 (s, 1H), 7.39 (dd, 1H), 7.33-7.31 (m, 1H), 7.17-7.13 (m, 1H), 6.83-6.77 (m, 1H), 6.64-6.58 (m, 1H), 5.50 (m, 1H), 4.57 (br, 1H), 4.29 (br m, 3H), 3.27 (m, 3H), 1.49 (m, 1H), 1.33 (m, 2H), 0.92 (t, 3H); MS (EI) for $C_{21}H_{21}F_3IN_3O_2$: 532 (MH$^+$), 554 (MNa$^+$). 1-({3,4-difluoro-2-[(2-fluoro-4-iodophenyl)amino]phenyl}carbonyl)-N-prop-2-en-1-ylazetidine-3-carboxamide: $^1$H NMR (400 MHz, CDCl$_3$): 8.54 (s, 1H), 7.39 (dd, 1H), 7.34-7.31 (m, 1H), 7.17.7.12 (m, 1H), 6.83-6.77 (m, 1H), 6.64-6.58 (m, 1H), 5.88-5.77 (m, 1H), 5.57 (br, 1H), 5.21-5.16 (m, 2H), 4.59 (br, 1H), 4.30 (br m, 3H), 3.9 (tt, 2H), 3.32-3.25 (m, 1H)); MS (EI) for $C_{20}H_{17}F_3IN_3O_2$: 516 (MH$^+$), 538 (MNa$^+$).

Example 4(c)

1-({3,4-difluoro-2-[(2-fluoro-4-iodophenyl)amino]phenyl}carbonyl)-N-ethylazetidine-3-carboxamide: $^1$H NMR (400 MHz, CDCl$_3$): 8.54 (s, 1H), 7.38 (dd, 1H), 7.33-7.30 (m, 1H), 7.17-7.12 (m, 1H), 6.83-6.77 (m, 1H), 6.63-6.57 (m, 1H), 5.55 (br s, 1H), 4.57 (br s, 1H), 4.28 (br m, 1H), 3.36-3.29 (m, 2H), 3.27-3.20 (m, 1H), 1.15 (t, 3H); MS (EI) for $C_{19}H_{17}F_3IN_3O_2$: 504 (MH$^+$), 526 (MNa$^+$).

Example 4(d)

1-({3,4-difluoro-2-[(2-fluoro-4-iodophenyl)amino]phenyl}carbonyl)-N-(2-hydroxyethyl)azetidine-3-carboxamide: $^1$H NMR (400 MHz, CDCl$_3$): 8.50 (s, 1H), 7.39 (dd, 1H), 7.33-7.30 (m, 1H), 7.16-7.12 (m, 1H), 6.84-6.77 (m, 1H), 6.63-6.57 (m, 1H), 4.57 (br, 1H), 4.28 (br, 3H), 3.73 (t, 2H), 3.49-3.44 (m, 2H), 3.33-3.27 (m, 1H), 2.18 (br, 1H); MS (EI) for $C_{19}H_{17}F_3IN_3O_3$: 542 (MNa$^+$).

Example 4(e)

1-({3,4-difluoro-2-[(2-fluoro-4-iodophenyl)amino]phenyl}carbonyl)-N-(2-piperidin-1-ylethyl)azetidine-3-carboxamide: $^1$H NMR (400 MHz, CDCl$_3$): 11.28 (s, 1H), 8.55 (s, 1H), 7.38 (dd, 1H), 7.33-7.30 (m, 1H), 7.15-7.10 (m, 1H), 6.82-6.76 (m, 1H), 6.63-6.58 (m, 1H), 4.42 (b, 1H), 4.26 (br m, 3H), 3.68 (br s, 2H), 3.58 (br d, 2H), 3.36 (br m, 1H) 3.17 (br s, 1H), 2.63 (m, 4H), 1.92 (m, 5H); MS (EI) for $C_{24}H_{26}F_3IN_4O_2$: 587 (MH$^+$).

Example 4(f)

1-({3,4-difluoro-2-[(2-fluoro-4-iodophenyl)amino]phenyl}carbonyl)-N-phenylazetidine-3-carboxamide: $^1$H NMR (400 MHz, CDCl$_3$): 8.52 (s, 1H), 7.50 (d, 1H), 7.41-7.27 (m, 4H), 7.16 (m, 2H), 6.85-6.78 (m, 1H), 6.65-6.59 (m, 1H), 4.37 (br, 3H), 3.43 (m, 1H); MS (EI) for $C_{23}H_{17}F_3IN_3O_2$: 574 (MNa$^+$).

Example 4(g)

N-[2-(diethylamino)ethyl]-1-({3,4-difluoro-2-[(2-fluoro-4-iodophenyl)amino]phenyl}carbonyl)azetidine-3-carboxamide: $^1$H NMR (400 MHz, CDCl$_3$): 11.43 (s, 1H), 8.90 (s, 1H), 8.55 (s, 1H), 7.39 (dd, 1H), 7.33-7.30 (m, 1H), 7.15-7.10 (m, 1H), 6.87-6.77 (m, 1H), 6.63-6.58 (m, 1H), 4.44-4.22 (m, 4H), 3.65 (m, 2H), 3.38 (m, 1H), 3.19-3.13 (m, 5H), 1.33 (t, 6H); MS (EI) for $C_{21}H_{21}F_3IN_3O_2$: 575 (MH$^+$).

Example 4(h)

1-({3,4-difluoro-2-[(2-fluoro-4-iodophenyl)amino]phenyl}carbonyl)-N-[(2,3-dihydroxypropyl)oxy]azetidine-3-carboxamide: MS (EI) for $C_{20}H_{19}F_3IN_3O_5$: 566 (MH$^+$).

Example 4(i)

1-({3,4-Difluoro-2-[(2-fluoro-4-iodophenyl)amino]phenyl}carbonyl)-N-(2,3-dihydroxypropyl)azetidine-3-carboxamide: $^1$H NMR (400 MHz, CDCl$_3$): 8.40 (br s, 1H), 7.35 (dd, 1H), 7.30 (br d, 1H), 7.16-7.09 (m, 1H), 6.89-6.76 (m, 2H), 6.58 (ddd, 1H), 4.58-4.40 (br, 1H), 4.27 (br t, 2H), 4.22-4.14 (br, 1H), 4.08-3.12 (m, 5H), 2.18-1.82 (br, 2H); MS (EI) for $C_{20}H_{19}F_3IN_3O_4$: 550 (MH$^+$).

Example 4(j)

1-({3,4-Difluoro-2-[(2-fluoro-4-iodophenyl)amino]phenyl}carbonyl)-N-hydroxyazetidine-3-carboxamide: $^1$H NMR (400 MHz, CDCl$_3$): 8.23-8.10 (b, 1H), 7.35-7.28 (m, 2H), 7.14-7.07 (m, 1H), 6.86-6.80 (m, 1H), 6.60-6.54 (m, 1H), 4.52-4.38 (b, 1H), 4.32-4.08 (m, 3H), 3.30-3.21 (m, 1H); MS (EI) for $C_{17}H_{13}F_3IN_3O_3$: 492 (MH$^+$).

Example 5

6-({3-[dimethylamino)methyl]azetidin-1-yl}carbonyl)-2,3-difluoro-N-(2-fluoro-4-iodophenyl)aniline

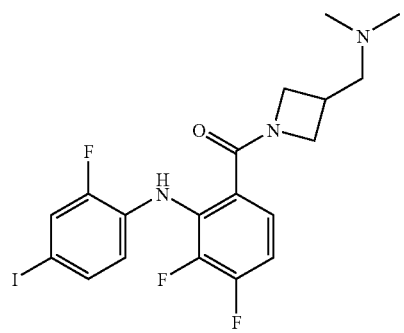

A mixture of 1-({3,4-difluoro-2-[(2-fluoro-4-iodophenyl)amino]phenyl}carbonyl)azetidine-3-carboxylic acid (196 mg, 0.41 mmol), prepared using procedures similar to those in Example 1, triethylamine (58 μL, 0.41 mmol), PyBOP (213 mg, 0.41 mmol) and sodium borohydride (48 mg, 1.24 mmol) in tetrahydrofuran (2 mL) was stirred at room temperature for 15 hours. The reaction mixture was concentrated in vacuo and the resultant residue was partitioned between 20% aqueous citric acid and ethyl acetate. The organic portion was washed with brine, dried over sodium sulfate, filtered and concentrated in vacuo to afford a colorless residue that was purified by column chromatography. Eluting with 60% ethyl acetate in hexanes, isolated product was concentrated in vacuo to afford 48 mg, 0.11 mmol (25%) of [1-({3,4-difluoro-2-[(2-fluoro-4-iodophenyl)amino]phenyl}carbonyl)azetidin-3-yl]methanol as a white solid. $^1$H NMR (400 MHz, CDCl$_3$): 7.44 (d, 1H), 7.34 (d, 1H), 7.28-7.23 (m, 1H), 7.04-6.97 (m, 1H), 4.26-4.18 (m, 1H), 4.02-3.94 (m, 2H), 3.78-3.72 (m, 1H), 3.03 (d, 2H), 3.34 (s, 1H), 2.80-2.71 (m, 1H). MS (EI) for $C_{17}H_{14}F_3IN_2O$: 463 (MH$^+$).

A solution of 1-({3,4-difluoro-2-[(2-fluoro-4-iodophenyl)amino]phenyl}carbonyl)azetidin-3-yl]methanol (48 mg, 0.11 mmol), 1,4-diazabicyclo[2.2.2]octane (18 mg, 0.16 mmol) and methanesulfonyl chloride (10 μL, 0.13 mmol) in tetrahydrofuran (2 mL) was stirred at room temperature for 15 minutes. The mixture was then partitioned between water and ethyl acetate. The organic portion was washed with brine, dried over sodium sulfate, filtered and concentrated in vacuo to afford a colorless residue which was purified by column chromatography. Eluting with 70% ethyl acetate in hexanes, isolated product was concentrated in vacuo to afford 28 mg, 0.05 mmol (47%) of [1-({3,4-difluoro-2-[(2-fluoro-4-iodophenyl)amino]phenyl}carbonyl)azetidin-3-yl]methyl methanesulfonate as a colorless residue which was immediately dissolved in ethylene glycol dimethyl ether (2 mL). To the solution was added dimethylamine (excess) and the solution was stirred in a seal tube at 50° C. for 15 hours. The reaction mixture was concentrated in vacuo, and the resultant residue was purified by preparative reverse phase HPLC. Isolated product was concentrated in vacuo to afford 12 mg, 0.02 mmol (40%) of 6-({3-[dimethylamino)methyl]azetidin-1-yl}carbonyl)-2,3-difluoro-N-(2-fluoro-4-iodophenyl)aniline acetate salt as a white solid. $^1$H NMR (400 MHz, DMSO): 8.54 (br s, 1H), 7.58 (d, 1H), 7.37 (d, 1H), 7.33-7.28 (m, 1H), 7.18-7.12 (m, 1H), 6.70-6.64 (m, 1H), 4.18-4.12 (m, 1H), 3.99-3.76 (m, 1H), 3.52-3.47 (m, 1H), 2.52-2.48 (m, 1H), 2.39 (d, 2H), 1.85 (s, 6H); MS (EI) for $C_{19}H_{19}F_3IN_3O$: 490 (MH$^+$).

Using the same or analogous synthetic techniques and/or substituting with alternative reagents, the following compounds of the invention were prepared:

Example 5(a)

2,3-difluoro-N-(2-fluoro-4-iodophenyl)-6-[(3-{[(1-methylethyl)amino]methyl}azetidin-1-yl)carbonyl]aniline: $^1$H NMR (400 MHz, CDCl$_3$): 8.54 (s, 1H), 7.40 (dd, 1H), 7.31-7.33 (m, 1H), 7.11-7.15 (m, 1H), 6.76-6.82 (m, 1H), 6.58-6.64 (m, 1H), 4.23-4.30 (m, 2H), 3.90-4.00 (m, 1H), 3.76-3.84 (m, 1H), 2.69-2.85 (m, 4H), 1.05 (d, 6H). MS (EI) for $C_{20}H_{21}F_3IN_3O$: 502 (M-H).

Example 5(b)

2-({[1-({3,4-difluoro-2-[(2-fluoro-4-iodophenyl)amino]phenyl}carbonyl)azetidin-2-yl]methyl}amino)ethanol: MS (EI) for $C_{19}H_{19}F_3IN_3O_2$: 506 (MH$^+$).

Example 5(c)

N-{[1-({3,4-difluoro-2-[(2-fluoro-4-iodophenyl)amino]phenyl}carbonyl)azetidin-2-yl]methyl}ethane-1,2-diamine: MS (EI) for $C_{19}H_{20}F_3IN_4O$: 505 (MH$^+$).

Example 5(d)

6-({3-[dimethylamino)methyl]azetidin-1-yl}carbonyl)-2,3-difluoro-N-(2-fluoro-4-iodophenyl)aniline acetate salt: $^1$H NMR (400 MHz, DMSO): 8.54 (br s, 1H), 7.58 (d, 1H), 7.37 (d, 1H), 7.33-7.28 (m, 1H), 7.18-7.12 (m, 1H), 6.70-6.64 (m, 1H), 4.18-4.12 (m, 1H), 3.99-3.76 (m, 1H), 3.52-3.47 (m, 1H), 2.52-2.48 (m, 1H), 2.39 (d, 2H), 1.85 (s, 6H); MS (EI) for $C_{19}H_{19}F_3IN_3O$: 490 (MH$^+$).

Example 6

1-({3,4-Difluoro-2-[(2-fluoro-4-iodophenyl)amino]phenyl}carbonyl)azetidin-3-one

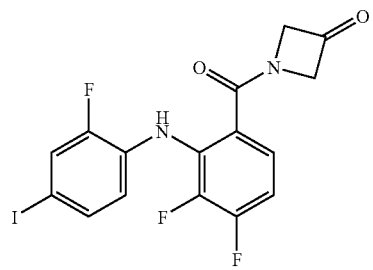

1-({3,4-Difluoro-2-[(2-fluoro-4-iodophenyl)amino]phenyl}carbonyl)azetidin-3-ol (132 mg, 0.295 mmol) ures similar to those in Example 1, was dissolved in dichloromethane (8 mL) and cooled to 0° C. Dess-Martin periodinane (187 mg, 0.441 mmol) was added and the mixture was stirred at ambient for 2 h. The mixture was quenched with saturated sodium bicarbonate solution: 10% sodium thiosulfate solution (1:1; 6 mL) and diluted with ethyl acetate. The organic portion was washed with brine, dried over anhydrous sodium sulfate, filtered and concentrated in vacuo. Column chromatography (silica gel, 40-50% ethyl acetate in hexanes) gave 1-({3,4-difluoro-2-[(2-fluoro-4-iodophenyl)amino]phenyl}carbonyl)azetidin-3-one (122 mg, 0.273 mmol, 93% yield): $^1$H NMR (400 MHz, CDCl$_3$): 8.43 (br s, 1H), 7.44-7.38 (m, 1H), 7.36-7.32 (m, 1H), 7.27-7.20 (m, 1H), 6.86 (ddd, 1H), 6.64 (ddd, 1H), 4.94-4.93 (m, 4H); MS (EI) for $C_{16}H_{10}F_3IN_2O_2$: 447 (MH$^+$).

Example 7

1-({3,4-Difluoro-2-[(2-fluoro-4-iodophenyl)amino]phenyl}carbonyl)-3-(hydroxymethyl)azetidin-3-ol

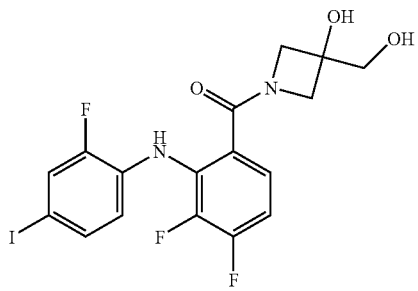

Methyl triphenylphosphonium bromide (508 mg, 1.42 mmol) was treated with potassium tert-butoxide (159 mg, 1.42 mmol) in tetrahydrofuran (5 mL) at 0° C. for 10 minutes. 1-({3,4-Difluoro-2-[(2-fluoro-4-iodophenyl)amino]phenyl}carbonyl)azetidin-3-one (270 mg, 0.605 mmol), prepared using procedures similar to those described in Example 6, was dissolved in tetrahydrofuran (2 mL) and was added to the mixture. The mixture was stirred at ambient for 15 h and then the mixture was filtered and the filtrate was partitioned between ethyl acetate and water. The aqueous portion was extracted with ethyl acetate. The combined organic portion was washed with brine, dried over anhydrous sodium sulfate, filtered and concentrated in vacuo. Column chromatography (silica gel, 20% ethyl acetate in hexanes) gave 2,3-difluoro-N-(2-fluoro-4-iodophenyl)-6-[(3-methylideneazetidin-1-yl)carbonyl]aniline (57 mg, 0.128 mmol, 21% yield): $^1$H NMR (400 MHz, CDCl$_3$): 8.56 (br s, 1H), 7.39 (dd, 1H), 7.35-7.30 (m, 1H), 7.18-7.12 (m, 1H), 6.86-6.76 (m, 1H), 6.62 (ddd, 1H), 5.14-5.00 (br, 2H), 4.74 (br d, 4H); MS (EI) for $C_{17}H_{12}F_3IN_2O$: 445 (MH$^+$).

2,3-Difluoro-N-(2-fluoro-4-iodophenyl)-6-[(3-methylidene azetidin-1-yl)carbonyl]aniline (56 mg, 0.126 mmol) and 4-methylmorpholine N-oxide (44 mg, 0.376 mmol) were dissolved in acetone/water (4:1; 10 mL) and osmium tetroxide (4 wt. % in water; 0.7 mL) was added. The solution was stirred at ambient for 4 h, then was quenched with saturated sodium bisulfate (2 mL) and concentrated in vacuo. The residue was partitioned between ethyl acetate and water. The organic portion was washed with brine, dried over anhydrous sodium sulfate, filtered and concentrated in vacuo. Column chromatography (silica gel, 80% ethyl acetate in hexanes) and then reverse phase HPLC gave 1-({3,4-difluoro-2-[(2-fluoro-4-iodophenyl)amino]phenyl}carbonyl)-3-(hydroxymethyl)azetidin-3-ol (17 mg, 0.036 mmol, 28% yield): $^1$H NMR (400 MHz, CDCl$_3$): 8.43 (br s, 1H), 7.40 (dd, 1H), 7.35-7.31 (m, 1H), 7.16-7.10 (m, 1H), 6.81 (ddd, 1H), 6.61 (ddd, 1H), 4.25-4.00 (m, 4H), 3.78 (s, 2H); MS (EI) for $C_{17}H_{14}F_3IN_2O_3$: 479 (MH$^+$).

Example 8

3-(2-aminopyrimidin-4-yl)-1-({3,4-difluoro-2-[(2-fluoro-4-iodophenyl)amino]phenyl}carbonyl)azetidin-3-ol

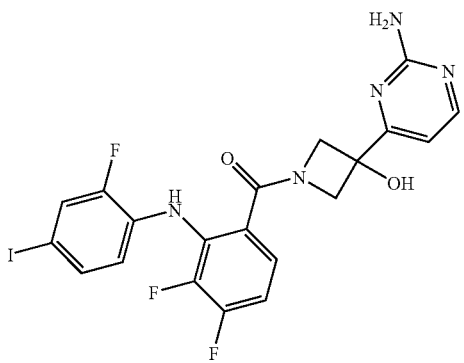

To a solution of 4-iodo-2-(methylthio)pyrimidine (2.00 g, 7.92 mmol) in tetrahydrofuran (4.00 ml) was added isopropylmagnesium chloride (815 mg, 7.92 mmol). The mixture was allowed to stir for 1 h at 0° C., followed by the addition of 1,1-dimethylethyl 3-oxoazetidiene-1-carboxylate (1.64 g, 9.60 mmol), prepared using procedures similar to those described in Example 3. The reaction mixture was then allowed to warm to room temperature and stirred for 6 h. The mixture was quenched with 1 N hydrochloric acid (10 mL) and extracted with ethyl acetate. The organic layer was separated, dried over anhydrous sodium sulfate, filtered and the filtrate concentrated in vacuo. The residue was purified by column chromatography (SiO$_2$, hexanes/ethyl acetate) to afford 1,1-dimethylethyl 3-hydroxy-3-[2-(methylthio)pyrimidin-4-yl]azetidine-1-carboxylate (380 mg, 16%) as a yellow oil. $^1$H NMR (400 MHz, CDCl$_3$): 8.62-8.59 (d, 1H), 7.36-7.33 (d, 1H), 5.14-5.11 (s, 1H), 4.29-4.24 (d, 2H), 4.13-4.08 (d, 2H), 2.61-2.58 (s, 3H), 1.50-1.47 (s, 9H); MS (EI) for $C_{13}H_{19}N_3O_3S$: 298 (MH$^+$).

A solution of 1,1-dimethylethyl 3-hydroxy-3-[2-(m ethylthio)pyrimidin-4-yl]azetidine-1-carboxylate (480 mg, 1.62 mmol), and 3-chloroperoxybenzoic (558 mg, 3.23 mmol) acid in dichloromethane (25 mL) was stirred at room temperature for 22 h. The reaction mixture was quenched with a saturated solution of sodium thiosulfate and the pH adjusted to 7 with sodium carbonate. The organic layer was separated, dried over anhydrous sodium sulfate, filtered and the filtrate concentrated in vacuo. The resulting crude 1,1-dimethylethyl 3-hydroxy-3-[2-(methylsulfonyl)pyrimidin-4-yl]azetidine-1-carboxylate (524 mg, 98%) was used without further purification. $^1$H NMR (400 MHz, CDCl$_3$): 9.01-8.97 (d, 1H), 7.96-7.93 (d, 1H), 4.57-4.53 (s, 1H), 4.31-4.27 (d, 2H), 4.23-4.18 (d, 2H), 3.42-3.39 (s, 3H), 1.50-1.47 (s, 9H); MS (EI) for $C_{13}H_{19}N_3O_5S$: 330 (MH$^+$).

A solution of 1,1-dimethylethyl 3-hydroxy-3-[2-(methylsulfonyl)pyrimidin-4-yl]azetidine-1-carboxylate (215 mg, 0.652 mmol), and aqueous ammonia (7 mL, 28% solution) in dioxane (15 mL) within a sealed steel bomb cylinder was heated at 80° C. for 4 h. The mixture was cooled to room temperature and the solvent was evaporated. The residue was dissolved in dichloromethane and a solution of saturated sodium carbonate. The organic layer was separated, dried over anhydrous sodium sulfate, filtered and the filtrate concentrated in vacuo. The resulting crude 1,1-dimethylethyl 3-(2-aminopyrimidin-4-yl)-3-hydroxyazetidine-1-carboxylate (140 mg, 100%) was used without further purification. $^1$H NMR (400 MHz, CDCl$_3$): 8.38-8.35 (d, 1H), 6.97-6.94 (d, 1H), 5.30-5.28 (s, 2H), 4.23-4.18 (d, 2H), 4.08-4.04 (d, 2H), 1.48-1.45 (s, 9H).

To a solution of 1,1-dimethylethyl 3-(2-aminopyrimidin-4-yl)-3-hydroxyazetidine-1-carboxylate (140 mg, 0.524 mmol) in dichloromethane (10 ml) was added trifluoroacetic acid (3 ml). The reaction mixture was stirred for 2 h at room temperature. The mixture was concentrated in vacuo. The resulting crude 3-(2-aminopyrimidin-4-yl)azetidin-3-ol (87 mg, 100%) was used without further purification.

A solution of 3,4-difluoro-2-[(2-fluoro-4-iodophenyl)amino]benzoic acid (201 mg, 0.512 mmol), prepared using procedures similar to those described in U.S. Pat. No. 7,019,033, 3-(2-aminopyrimidin-4-yl)azetidin-3-ol (87 mg, 0.52 mmol), benzotriazol-1-yl-oxy-tris(pyrrolidino)phosphonium hexafluorophosphate (293 mg, 0.563 mmol) and N,N-diisopropylethylamine (270 uL, 2.82 mmol) in N,N-dimethylformamide (2 mL) was stirred at room temperature for 20 h. The mixture was partitioned between ethyl acetate and saturated sodium bicarbonate. The organic layer was separated and washed with brine, dried over sodium sulfate, filtered and the filtrate concentrated in vacuo. The residue was purified by reverse phase HPLC to afford the title compound 3-(2-aminopyrimidin-4-yl)-1-({3,4-difluoro-2-[(2-fluoro-4-iodophenyl)amino]phenyl}carbonyl)azetidin-3-ol (22 mg, 7%). $^1$H NMR (400 MHz, CD$_3$OD): 8.23-8.20 (d, 1H), 7.48-7.43 (d, 1H), 7.35-7.32 (m, 2H), 7.09-7.00 (m, 1H), 6.88-6.84 (d, 1H), 6.70-6.63 (t, 1H), 4.59-4.54 (d, 1H), 4.45-4.40 (d, 1H), 4.23-4.18 (d, 1H), 3.04-3.99 (t, 1H); MS (EI) for $C_{20}H_{15}F_3IN_5O_2$: 542 (MH$^+$).

Using the same or analogous synthetic techniques and substituting, as necessary, with alternative reagents, the following compounds of the invention were prepared:

Example 8(a)

1-({3,4-difluoro-2-[(2-fluoro-4-iodophenyl)amino]phenyl}carbonyl)-3-pyridin-2-ylazetidin-3-ol: $^1$H NMR (400 MHz, CD$_3$OD): 8.47 (m, 1H), 7.80 (m, 1H), 7.65 (d, 1H), 7.44 (m, 1H), 7.33 (m, 3H), 7.04 (m, 1H), 6.65 (m, 1H), 4.61 (d, 1H), 4.44 (d, 1H), 4.29 (d, 1H), 4.12 (d, 1H). MS (EI) for C$_{21}$H$_{15}$F$_3$IN$_3$O$_2$: 526 (MH$^+$).

Example 8(b)

1-({3,4-difluoro-2-[(2-fluoro-4-iodophenyl)amino]phenyl}carbonyl)-3-(1H-imidazol-2-yl)azetidin-3-ol: $^1$H NMR (400 MHz, CD$_3$OD): 7.42 (m, 1H), 7.37 (m, 1H), 7.32 (m, 1H), 7.02 (m, 3H), 6.63 (m, 1H), 4.65 (d, 1H), 4.42 (d, 1H), 4.33 (d, 1H), 4.16 (d, 1H). MS (EI) for C$_{19}$H$_{14}$F$_3$IN$_4$O$_2$: 515 (MH$^+$).

Example 8(c)

3-(1H-benzimidazol-2-yl)-1-({3,4-difluoro-2-[(2-fluoro-4-iodophenyl)amino]phenyl}carbonyl)azetidin-3-ol: $^1$H NMR (400 MHz, CD$_3$OD): 7.55 (br s, 2H), 7.42 (m, 2H), 7.33 (m, 1H), 7.23 (m, 2H), 7.04 (m, 1H), 6.65 (m, 1H), 4.76 (d, 1H), 4.57 (d, 1H), 4.43 (d, 1H), 4.25 (d, 1H). MS (EI) for C$_{23}$H$_{16}$F$_3$IN$_4$O$_2$: 565 (MH$^+$).

Example 8(d)

1-({3,4-difluoro-2-[(2-fluoro-4-iodophenyl)amino]phenyl}carbonyl)-3-methyl-1H-imidazol-2-yl)azetidin-3-ol: $^1$H NMR (400 MHz, CD$_3$OD): 7.41 (m, 1H), 7.36 (m, 1H), 7.31 (m, 1H), 7.02 (m, 1H), 6.67 (br s, 1H), 6.63 (m, 1H), 4.63 (d, 1H), 4.39 (d, 1H), 4.30 (d, 1H), 4.13 (d, 1H), 2.18 (s, 3H). MS (EI) for C$_{20}$H$_{16}$F$_3$IN$_4$O$_2$: 529 (MH$^+$).

Example 8(e)

1-({3,4-difluoro-2-[(2-fluoro-4-iodophenyl)amino]phenyl}carbonyl)-3-prop-2-en-1-ylazetidin-3-ol: $^1$H NMR (400 MHz, CDCl$_3$): 8.47 (br s, 1H), 7.40 (dd, 1H), 7.35-7.31 (m, 1H), 7.15-7.10 (m, 1H), 6.81 (ddd, 1H), 6.62 (ddd, 1H), 5.84-5.72 (m, 1H), 5.27-5.20 (m, 2H), 4.22-3.94 (m, 4H), 2.52 (d, 2H), 2.25 (s, 1H); MS (EI) for C$_{19}$H$_{16}$F$_3$IN$_2$O$_2$: 489 (MH$^+$).

Example 8(f)

3-[1-({3,4-difluoro-2-[(2-fluoro-4-iodophenyl)amino]phenyl}carbonyl)-3-hydroxyazetidin-3-yl]propane-1,2-diol: $^1$H NMR (400 MHz, CDCl$_3$): 8.43 (br s, 1H), 7.39 (dd, 1H), 7.35-7.30 (m, 1H), 7.16-7.10 (m, 1H), 6.82 (ddd, 1H), 6.61 (ddd, 1H), 4.31-3.91 (M, 5H), 3.68 (br d, 1H), 3.54-3.49 (m, 1H), 2.01-1.80 (m, 2H); MS (EI) for C$_{19}$H$_{18}$F$_3$IN$_2$O$_4$: 523 (MH$^+$).

Example 8(g)

1-({3,4-difluoro-2-[(2-fluoro-4-iodophenyl)amino]phenyl}carbonyl)-3-ethenylazetidin-3-ol: $^1$H NMR (400 MHz, CDCl$_3$): 8.48 (br s, 1H), 7.40 (dd, 1H), 7.35-7.31 (m, 1H), 7.17-7.11 (m, 1H), 6.81 (ddd, 1H), 6.62 (ddd, 1H), 6.15 (dd, 1H), 5.39 (d, 1H), 5.28 (d, 1H), 4.30-4.10 (m, 4H); MS (EI) for C$_{18}$H$_{14}$F$_3$IN$_2$O$_2$: 475 (MH$^+$).

Example 8(h)

1-[1-({3,4-difluoro-2-[(2-fluoro-4-iodophenyl)amino]phenyl}carbonyl)-3-hydroxyazetidin-3-yl]ethane-1,2-diol hydrochloride: $^1$H NMR (400 MHz, d$_6$-DMSO): 8.66 (d, 1H), 7.58 (dd, 1H), 7.38 (d, 1H), 7.33-7.27 (m, 1H), 7.17 (q, 1H), 6.74-6.65 (m, 1H), 4.50-3.58 (br, 3H), 4.29 (dd, 1H), 4.14 (dd, 1H), 3.87 (t, 1H), 3.66 (t, 1H), 3.56-3.32 (m, 3H); MS (EI) for C$_{18}$H$_{16}$F$_3$IN$_2$O$_4$: 509 (MH$^+$).

Example 8(i)

1-({3,4-difluoro-2-[(2-fluoro-4-iodophenyl)amino]phenyl}carbonyl)-3-ethylazetidin-3-ol: $^1$H NMR (400 MHz, CDCl$_3$): 8.23 (br s, 1H), 7.40 (d, 1H), 7.33 (d, 1H), 7.15-7.10 (m, 1H), 6.85-6.79 (m, 1H), 6.64-6.58 (m, 1H), 4.14-3.94 (m, 4H), 1.78 (q, 2H), 0.96 (t, 3H); MS (EI) for C$_{18}$H$_{16}$F$_3$IN$_2$O$_2$: 477 (MH$^+$).

Example 8(j)

1-({3,4-difluoro-2-[(2-fluoro-4-iodophenyl)amino]phenyl}carbonyl)-3-methylazetidin-3-ol: $^1$H NMR (400 MHz, CDCl$_3$): 8.31 (br s, 1H), 7.40 (d, 1H), 7.33 (d, 1H), 7.15-7.11 (m, 1H), 6.85-6.78 (m, 1H), 6.65-6.59 (m, 1H), 4.24-4.04 (m, 4H), 1.55 (s, 3H); MS (EI) for C$_{17}$H$_{14}$F$_3$IN$_2$O$_2$: 463 (MH$^+$).

Example 8(k)

3-(2-aminopyrimidin-4-yl)-1-({3,4-difluoro-2-[(2-fluoro-4-iodophenyl)amino]phenyl}carbonyl)azetidin-3-ol acetate salt: $^1$H NMR (400 MHz, CD$_3$OD): 8.22-8.20 (d, 1H), 7.48-7.43 (d, 1H), 7.38-7.30 (m, 1H), 7.09-7.01 (q, 1H), 6.88-6.84 (d, 1H), 6.70-6.61 (t, 1H), 4.59-4.54 (d, 1H), 4.44-4.39 (d, 1H), 4.23-4.19 (d, 1H), 4.05-3.99 (d, 1H), 3.90-3.81 (d, 1H), 1.99-1.97 (s, 3H); MS (EI) for C$_{20}$H$_{15}$F$_3$IN$_5$O$_2$: 542 (MH$^+$).

Example 8(m)

1-({3,4-difluoro-2-[(2-fluoro-4-iodophenyl)amino]phenyl}carbonyl)-3-(1H-pyrrol-2-yl)azetidin-3-ol: $^1$H NMR (400 MHz, CD$_3$OD): 7.37 (dd, 1H), 7.31-7.23 (m, 2H), 7.07-6.97 (m, 1H), 6.73-6.68 (m, 1H), 6.65-6.56 (m, 1H), 6.06-5.98 (m, 2H), 4.49-4.40 (m, 1H), 4.32-4.18 (m, 2H), 4.15-88-4.07 (m, 1H). MS (EI) for C$_{20}$H$_{15}$F$_3$IN$_3$O$_2$: 514 (MH$^+$)

Example 8(n)

1-({3,4-difluoro-2-[(2-fluoro-4-iodophenyl)amino]phenyl}carbonyl)-3-(1-methyl-1H-imidazol-2-yl)azetidin-3-ol: $^1$H NMR (400 MHz, CD$_3$OD): 7.34 (dd, 1H), 7.31-7.25 (m, 1H), 7.23-7.18 (m, 1H), 7.11-7.09 (m, 1H), 7.06-6.97 (m, 1H), 6.89-6.86 (m, 1H), 6.62-6.55 (m, 1H), 4.88-4.80 (m, 1H), 4.52-4.44 (m, 1H), 4.38-4.30 (m, 1H), 4.21-4.12 (m, 1H), 3.68 (s, 3H). MS (EI) for C$_{20}$H$_{16}$F$_3$IN$_4$O$_2$: 529 (MH$^+$).

Example 9

1-({3,4-difluoro-2-[(2-fluoro-4-iodophenyl)amino]phenyl}carbonyl)-3-(trifluoromethyl)azetidin-3-ol

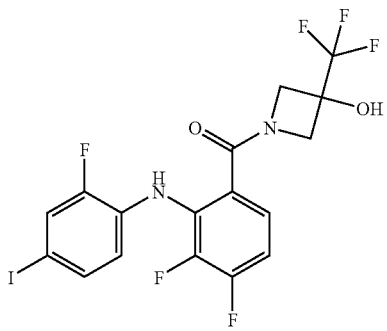

1-({3,4-difluoro-2-[(2-fluoro-4-iodophenyl)amino]phenyl}carbonyl)azetidin-3-one (25 mg, 0.056 mmol), prepared using procedures described in Example 6, was taken into DMF (0.5 mL) followed by addition of (trifluoromethyl)trimethylsilane (40 µL, 0.28 mmol) and cesium carbonate (22 mg, 0.067 mmol) and the mixture was stirred for one hour at room temperature. The mixture was partitioned with ethyl ether and water and the organic phase washed three times with additional water then brine and dried over anhydrous sodium sulfate. Filtration and concentration followed by silica gel flash chromatography of the residue using hexanes:ethyl acetate 3:2 as eluent afforded 1-({3,4-difluoro-2-[(2-fluoro-4-iodophenyl)amino]phenyl}carbonyl)-3-(trifluoromethyl)azetidin-3-ol (19.8 mg, 69% yield) as a colorless crystalline solid. $^1$H-NMR (400 MHz, CDCl$_3$): 8.31-8.26 (br, 1H), 7.40 (d, 1H), 7.33 (d, 1H), 7.13-7.10 (m, 1H), 6.86-6.80 (m, 1H), 6.65-6.60 (m, 1H), 4.42 (br s, 2H), 4.18 (br s, 2H). MS (EI) for $C_{17}H_{11}F_6IN_2O_2$: 517 (MH$^+$).

Example 10

1-({3,4-difluoro-2-[(2-fluoro-4-iodophenyl)amino]phenyl}carbonyl)azetidin-3-one oxime

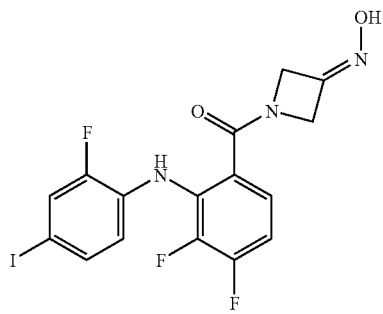

To a solution of 1-({3,4-difluoro-2-[(2-fluoro-4-iodophenyl)amino]phenyl}carbonyl)azetidin-3-one (100 mg, 0.22 mmol), prepared using procedures similar to those described in Example 6, in dioxane (1.0 mL) was added hydroxylamine (0.10 mL, 50% solution in water, 1.5 mmol), and the resulting solution was heated at 60° C. for 18 h. The mixture was cooled to room temperature and the crude product was purified by reverse phase HPLC to afford 1-({3,4-difluoro-2-[(2-fluoro-4-iodophenyl)amino]phenyl}carbonyl)azetidin-3-one oxime (56 mg, 54% yield): $^1$HNMR (400 MHz, CDCl$_3$), 8.43 (br s), 7.43-7.39 (m, 2H), 7.35-7.32 (dd, 1H), 7.19-7.15 (m, 1H), 6.87-6.81 (m, 1H), 6.65-6.59 (m, 1H), 4.89 (br s, 2H), 4.85 (br s, 2H); MS (EI) for $C_{16}H_{11}F_3IN_3O_2$: 462 (MH$^+$).

Example 11

N-butyl-1-({3,4-difluoro-2-[(2-fluoro-4-iodophenyl)amino]phenyl}carbonyl)azetidin-3-amine

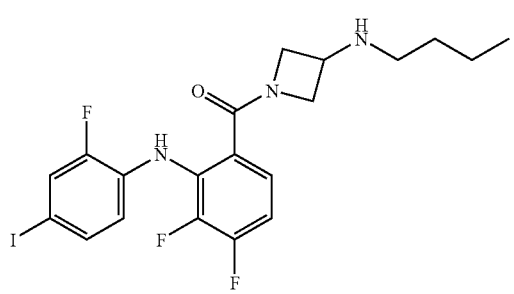

To a solution of 1-({3,4-difluoro-2-[(2-fluoro-4-iodophenyl)amino]phenyl}carbonyl)azetidin-3-amine (0.09 M in acetonitrile, 500 µL, 0.045 mmol), prepared using procedures similar to those described in Example 2, was added triethylamine (20 µL, 0.135 mmol) and n-butylbromide (6.14 µL, 0.054 mmol) followed by additional acetonitrile (1.0 mL). The reaction mixture was stirred at room temperature for 16 h, at which time it was purified directly by reverse phase HPLC to afford the title compound (8.4 mg). $^1$H NMR (400 MHz, CDCl$_3$): 8.50 (s, 1H), 7.39 (dd, 1H), 7.32 (dd, 1H), 7.13-7.09 (m, 1H), 6.84-6.77 (m, 1H), 6.63-6.57 (m, 1H), 4.35 (br s, 2H), 4.00 (br s, 1H), 3.87 (br s, 1H), 3.74-3.68 (m, 1H), 3.20 (br s, 3.5H), 2.56 (t, 2H), 2.03 (s, 2H), 1.50-1.42 (m, 2H), 1.39-1.29 (m, 2H), 0.91 (t, 3H). MS (EI) for $C_{20}H_{21}F_3IN_3O$: 504 (MH$^+$).

Example 12

1-({3,4-difluoro-2-[(2-fluoro-4-iodophenyl)amino]phenyl}carbonyl)-N-methylazetidin-3-amine

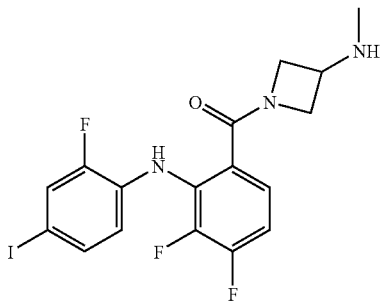

To a solution of 1-({3,4-difluoro-2-[(2-fluoro-4-iodophenyl)amino]phenyl}carbonyl)azetidin-3-amine (0.10 M in acetonitrile, 1.0 mL, 0.09 mmol), prepared using procedures similar to those described in Example 2, in 1:1 ratio of methanol and tetrahydrofuran (2.0 mL) was added formaldehyde (37% wt, 6.7 µL, 0.09 mmol) followed by sodium cyanoborohydride (11.0 mg, 0.18 mmol). The reaction mixture was stirred at room temperature for 16 h, at which time it was quenched with saturated aqueous ammonium chloride. The solution was then purified directly by reverse phase HPLC to afford the title compound (14.9 mg). $^1$H NMR (400 MHz, CDCl$_3$): 8.13 (br s, 1H), 7.35 (d, 1H), 7.30 (d, 1H), 7.09-7.04 (m, 1H), 6.84-6.78 (m, 1H), 6.60-6.54 (m, 1H), 4.46-4.33 (br m, 4H), 3.93 (br m, 1H), 2.64 (s, 3H). MS (EI) for $C_{17}H_{15}F_3IN_3O$: 462 (MH$^+$).

Using the same or analogous synthetic techniques and substituting, as necessary, with alternative reagents, the following compounds of the invention were prepared:

Example 12(a)

1-({3,4-difluoro-2-[(2-fluoro-4-iodophenyl)amino]phenyl}carbonyl)-N-methylazetidin-3-amine: $^1$H NMR (400 MHz, CDCl$_3$): 8.13 (br s, 1H), 7.35 (d, 1H), 7.30 (d, 1H), 7.09-7.04 (m, 1H), 6.84-6.78 (m, 1H), 6.60-6.54 (m, 1H), 4.46-4.33 (br m, 4H), 3.93 (br m, 1H), 2.64 (s, 3H). MS (EI) for $C_{17}H_{15}F_3IN_3O$: 462 (MH$^+$).

Example 12(b)

2-{[1-({3,4-difluoro-2-[(2-fluoro-4-iodophenyl)amino]phenyl}carbonyl)azetidin-3-yl]amino}ethanol: $^1$H NMR (400 MHz, CDCl$_3$): 8.20 (s, 1H), 7.36 (d, 1H), 7.30 (d, 1H), 7.13-7.09 (m, 1H), 6.85-6.79 (m, 1H), 6.61-6.55 (m, 1H), 4.43 (br m, 3H), 3.98 (br m, 1H), 3.87 (br m, 1H), 3.02 (br m, 1H), 1.24-1.20 (m, 1H). MS (EI) for $C_{18}H_{17}F_3IN_3O_2$: 492 (MH$^+$).

Example 12(c)

N-[1-({3,4-difluoro-2-[(2-fluoro-4-iodophenyl)amino]phenyl}carbonyl)azetidin-3-yl]propane-1,3-diamine: $^1$H NMR (400 MHz, CDCl$_3$): 8.51 (s, 1H), 7.39 (d, 1H), 7.32 (d, 1H), 7.14-7.10 (m, 1H), 6.84-6.77 (m, 1H), 6.63-6.57 (m, 1H), 4.33 (br s, 2H), 3.99 (br s, 1H), 3.84 (br s, 1H), 3.71-3.64 (m, 1H), 2.91 (t, 2H), 2.70-2.66 (m, 2H), 2.01 (s, 4H), 1.76-1.69 (m, 2H). MS (EI) for $C_{19}H_{20}F_3IN_4O$: 505 (MH$^+$).

Example 12(d)

1-({3,4-difluoro-2-[(2-fluoro-4-iodophenyl)amino]phenyl}carbonyl)-N-ethylazetidin-3-amine: $^1$H NMR (400 MHz, CDCl$_3$): 8.47 (s, 1H), 7.38 (d, 1H), 7.31 (d, 1H), 7.13-7.09 (m, 1H), 6.83-6.77 (m, 1H), 6.62-6.57 (m, 1H), 4.49 (br s, 3H), 4.36 (br s, 2H), 4.08 (br s, 1H), 3.94 (br s, 1H), 3.77-3.72 (m, 1H), 2.69-2.63 (m, 2H), 1.99 (s, 2H), 1.14 (t, 3H). MS (EI) for $C_{18}H_{17}F_3IN_3O$: 476 (MH$^+$).

Example 12(e)

1-({3,4-difluoro-2-[(2-fluoro-4-iodophenyl)amino]phenyl}carbonyl)-N-(2-methylpropyl)azetidin-3-amine: $^1$H NMR (400 MHz, CDCl$_3$): 8.50 (s, 1H), 7.38 (d, 1H), 7.31 (d, 1H), 7.14-7.09 (m, 1H), 6.83-6.76 (m, 1H), 6.63-6.57 (m, 1H), 4.34 (br s, 2H), 4.00 (br s, 1H), 3.86 (br s, 1H), 3.71-3.66 (m, 1H), 3.42 (br s, 1H), 2.36 (d, 2H), 2.00 (s, 1H), 1.75-1.65 (m, 1H), 0.91 (d, 6H). MS (EI) for $C_{20}H_{21}F_3IN_3O$: 504 (MH$^+$).

Example 12(f)

N-(cyclopropylmethyl)-1-({3,4-difluoro-2-[(2-fluoro-4-iodophenyl)amino]phenyl}carbonyl)azetidin-3-amine: $^1$H NMR (400 MHz, CDCl$_3$): 8.48 (s, 1H), 7.39 (d, 1H), 7.32 (d, 1H), 7.13-7.09 (m, 1H), 6.84-6.77 (m, 1H), 6.63-6.57 (m, 1H), 5.78 (s, 3H), 4.36 (br s, 2H), 4.10 (br s, 1H), 3.94 (br s, 1H), 3.81-3.75 (m, 1H), 2.49 (d, 2H), 2.01 (s, 4H), 0.94-0.86 (m, 1H), 0.53 (d, 2H), 0.13 (d, 2H). MS (EI) for $C_{20}H_{19}F_3IN_3O$: 502 (MH$^+$).

Example 12(g)

N-(cyclohexylmethyl)-1-({3,4-difluoro-2-[(2-fluoro-4-iodophenyl)amino]phenyl}carbonyl)azetidin-3-amine: $^1$H NMR (400 MHz, CDCl$_3$): 8.48 (s, 1H), 7.38 (dd, 1H), 7.31 (d, 1H), 7.13-7.08 (m, 1H), 6.83-6.77 (m, 1H), 6.63-6.57 (m, 1H), 4.55 (br s, 2H), 4.33 (br m, 2H), 4.02 (br s, 1H) 3.87 (br s, 114), 3.71-3.65 (m, 1H), 2.38 (d, 2H), 1.74-1.68 (m, 4H), 1.46-1.36 (m, 1H), 1.27-1.12 (m, 3H), 0.94-0.84 (m, 2H). MS (EI) for $C_{23}H_{25}F_3IN_3O$: 544 (MH$^+$).

Example 12(h)

N-(cyclopentylmethyl)-1-({3,4-difluoro-2-[(2-fluoro-4-iodophenyl)amino]phenyl}carbonyl)azetidin-3-amine: $^1$H NMR (400 MHz, CDCl$_3$): 8.32 (s, 1H), 7.37 (d, 1H), 7.31 (d, 1H), 7.11-7.07 (m, 1H), 6.84-6.77 (m, 1H), 6.63-6.57 (m, 1H), 4.44-4.37 (m, 3H), 4.02-3.96 (m, 1H), 2.84 (d, 2H), 2.54 (br s, 5H), 2.20-2.12 (m, 1H), 1.88-1.81 (m, 2H), 1.68-1.54 (m, 4H), 1.24-1.15 (m, 2H). MS (EI) for $C_{22}H_{23}F_3IN_3O$: 530 (MH$^+$).

Example 13

1-({2,4-difluoro-6-[(2-fluoro-4-iodophenyl)amino]phenyl}carbonyl)azetidin-3-amine

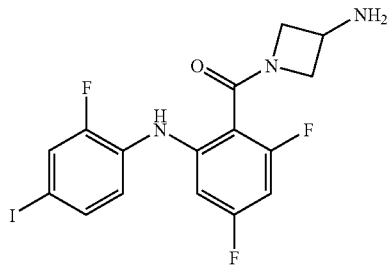

2,4,6-Trifluorobenzoic acid (643 mg, 3.65 mmol) and 2-fluoro-4-iodoaniline (1.0 g, 4.22 mmol) were taken into acetonitrile (30 mL) followed by addition of lithium amide (290 mg, 12.7 mmol) and the mixture was heated to 60° C. under a nitrogen atmosphere for one hour. On cooling to room temperature the mixture was added to 1 N aqueous hydrochloric acid (100 mL) and the precipitate formed was collected by filtration and washed once with water then hexanes and dried in vacuo to give 2,4-difluoro-6-[(2-fluoro-4-iodophenyl)amino]benzoic acid (849 mg, 59% yield) as a tan solid. $^1$H-NMR (400 MHz, D$_6$-DMSO): 13.72 (br s, 1H), 9.46 (s, 1H), 7.75 (d, 1H), 7.56 (d, 1H) 7.28 (tr, 1H), 6.73-6.67 (m, 1H), 6.53 (d, 1H).

2,4-Difluoro-6-[(2-fluoro-4-iodophenyl)amino]benzoic acid (100 mg, 0.25 mmol) was taken into DMF (1 mL) followed by addition of PyBOP (137 mg, 0.26 mmol) and the mixture was stirred for 15 minutes then NMM (60 µL, 0.5 mmol) and commercially available 1,1-dimethylethyl azetidin-3-ylcarbamate (43 mg, 0.25 mmol) were subsequently added. The mixture was allowed to stir for 12 hours at room temperature then partitioned with ethyl acetate and water. The organic phase was washed three times with additional water then brine and dried over anhydrous sodium sulfate. Filtration and concentration followed by silica gel flash chromatography of the residue using hexanes:ethyl acetate 3:1 as eluent afforded 1,1-dimethylethyl [1-({2,4-difluoro-6-[(2-fluoro-4-iodophenyl)amino]phenyl}carbonyl)azetidin-3-yl]carbamate (125 mg) as a colorless oil.

The oil was taken into trifluoroacetic acid (1 mL) and allowed to stand at room temperature for 5 minutes then concentrated in vacuo. The residue was portioned with ethyl acetate and saturated aqueous sodium bicarbonate and the organic phase washed with brine then dried over anhydrous sodium sulfate. The organic solution was filtered and concentrated then the residue taken into methanol (1 mL) followed by addition of 4 N HCl in dioxane until the solution was acidic. The solution was concentrated and the residue triturated with ethyl ether to give a thick precipitate. The solid was collected by filtration and dried in vacuo to give 1-({2,4-difluoro-6-[(2-fluoro-4-iodophenyl)amino] phenyl}carbonyl)azetidin-3-amine hydrochloride (58 mg, 48% overall yield). $^1$H-NMR (400 MHz, D$_6$-DMSO): 8.67 (br s, 3H), 8.45 (s, 1H), 7.71 (d, 1H), 7.54 (d, 1H), 7.25 (tr, 1H), 6.77 (tr, 1H), 6.48 (d, 1H), 4.28-4.23 (m, 2H), 4.13-4.06 (m, 3H). MS (EI) for C$_{16}$H$_{13}$F$_3$IN$_3$O: 448 (MH$^+$).

Example 14

1-({4,5-difluoro-2-[(2-fluoro-4-iodophenyl)amino] phenyl}carbonyl)azetidin-3-amine

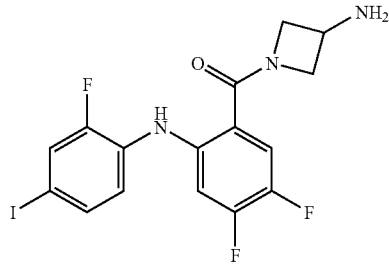

2,4,5-Trifluorobenzoic acid (643 mg, 3.65 mmol) and 2-fluoro-4-iodoaniline (1.0 g, 4.22 mmol) were taken into acetonitrile (30 mL) followed by addition of lithium amide (290 mg, 12.7 mmol) and the mixture was heated to 60° C. under a nitrogen atmosphere for one hour. On cooling to room temperature the mixture was added to 1 N aqueous hydrochloric acid (100 mL) and the precipitate formed was collected by filtration and washed once with water then hexanes and dried in vacuo to give 4,5-difluoro-2-[(2-fluoro-4-iodophenyl)amino]benzoic acid (624 mg, 43% yield) as a tan solid. $^1$H-NMR (400 MHz, D$_6$-DMSO): 13.65 (br s, 1H), 9.63 (s, 1H), 7.84 (tr, 1H), 7.71 (d, 1H), 7.52 (d, 1H), 7.32 (tr, 1H), 7.03-6.98 (dd, 1H).

4,5-difluoro-2-[(2-fluoro-4-iodophenyl)amino]benzoic acid (100 mg, 0.25 mmol) was taken into DMF (1 mL) followed by addition of PyBOP (137 mg, 0.26 mmol) and the mixture was stirred for 15 minutes then NMM (60 µL, 0.5 mmol) and commercially available 1,1-dimethylethyl azetidin-3-ylcarbamate (43 mg, 0.25 mmol) were subsequently added. The mixture was allowed to stir for 12 hours at room temperature then partitioned with ethyl acetate and water. The organic phase was washed three times with additional water then brine and dried over anhydrous sodium sulfate. Filtration and concentration followed by silica gel flash chromatography of the residue using hexanes:ethyl acetate 3:1 as eluent afforded 1,1-dimethylethyl [1-({4,5-difluoro-2-[(2-fluoro-4-iodophenyl)amino]phenyl}carbonyl)azetidin-3-yl]carbamate (131 mg) as a colorless oil. The oil was taken into trifluoroacetic acid (1 mL) and allowed to stand at room temperature for 5 minutes then concentrated in vacuo. The residue was portioned with ethyl acetate and saturated aqueous sodium bicarbonate and the organic phase washed with brine then dried over anhydrous sodium sulfate. The organic solution was filtered and concentrated then the residue taken into methanol (1 mL) followed by addition of 4 N HCl in dioxane until the solution was acidic. The solution was concentrated and the residue triturated with ethyl ether to give a thick precipitate. The solid was collected by filtration and dried in vacuo to give 1-({4,5-difluoro-2-[(2-fluoro-4-iodophenyl) amino]phenyl}carbonyl)azetidin-3-amine hydrochloride (67 mg, 55% overall yield). $^1$H-NMR (400 MHz, D$_6$-DMSO): 9.02 (s, 1H), 8.54 (br s, 3H), 7.68 (dd, 1H), 7.53-7.47 (m, 2H), 7.22 (tr, 1H), 7.16 (dd, 1H), 4.60 (br s, 1H), 4.23 (br s, 2H), 4.03 (br m, 2H). MS (EI) for C$_{16}$H$_{13}$F$_3$IN$_3$O: 448 (MH$^+$).

Example 15

1-({3,4-Difluoro-2-[(2-fluoro-4-iodophenyl)amino] phenyl}carbonyl)-N-(2,3-dihydroxypropyl)-3-hydroxyazetidine-3-carboxamide

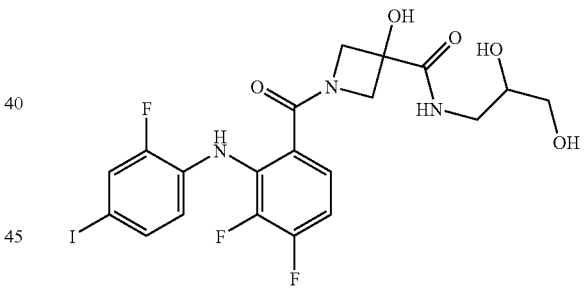

1-(Diphenylmethyl)azetidin-3-ol hydrochloride (2.75 g, 9.98 mmol), prepared using procedures similar to those described for Scheme 1 of the General Synthetic Section, 3 Å molecular sieves and 4-methylmorpholine (1.1 mL, 10.0 mmol) were suspended in dichloromethane (20 mL) at 0° C. 4-Methylmorpholine N-oxide (2.93 g, 25.0 mmol) and tetrapropylammonium perruthenate (140 mg, 0.399 mmol) were added and the mixture was stirred at ambient for 24 h. The mixture was filtered through a plug of silica using 5% triethylamine in ethyl acetate as eluent. The filtrate was concentrated in vacuo and the residue was partitioned between ethyl acetate and saturated sodium bicarbonate solution. The organic portion was washed with brine, dried over anhydrous sodium sulfate, filtered and concentrated in vacuo. Column chromatography (silica gel, 8:1 hexanes:ethyl acetate) gave 1-(diphenylmethyl)azetidin-3-one (871 mg, 3.68 mmol, 37% yield): $^1$H NMR (400 MHz, CDCl$_3$): 7.50-7.46 (m, 4H), 7.33-7.27 (m, 4H), 7.27-7.19 (m, 2H), 4.59 (s, 1H), 4.01 (s, 4H); MS (EI) for C$_{16}$H$_{15}$NO: 238 (MH$^+$).

1-(Diphenylmethyl)azetidin-3-one (600 mg, 2.53 mmol), was dissolved in dichloromethane (1 mL) and treated with triethylamine (0.5 mL, 3.59 mmol) and trimethylsilylcyanide (0.8 mL, 6.01 mmol) at ambient for 2 h and then the mixture was concentrated in vacuo to afford 1-(diphenylmethyl)-3-[(trimethylsilyl)oxy]azetidine-3-carbonitrile (774 mg, 2.30 mmol, 91% yield) as a yellow solid. 1-(diphenylmethyl)-3-[(trimethylsilyl)oxy]azetidine-3-carbonitrile (250 mg, 0.744 mmol) was dissolved in dichloromethane (2 mL) at 0° C. and concentrated sulfuric acid (0.2 mL) was added dropwise. The mixture was stirred at ambient for 2 h and then was cooled to 0° C. and 25% ammonium hydroxide solution was added carefully dropwise to pH ~10-11. The mixture was extracted twice with dichloromethane. The combined organic portion was washed with brine, dried over anhydrous sodium sulfate, filtered and concentrated in vacuo to afford a residue which was triturated with hexanes/ether to afford 1-(diphenylmethyl)-3-hydroxyazetidine-3-carboxamide (160 mg, 0.567 mmol, 76% yield) as an off-white solid: $^1$H NMR (400 MHz, CDCl$_3$): 7.92 (br s, 1H), 7.39-7.34 (m, 4H), 7.33-7.27 (m, 4H), 7.27-7.19 (m, 2H), 5.61 (br s, 1H), 4.45 (s, 1H), 4.34 (s, 1H), 3.50 (dd, 2H), 3.20 (dd, 2H); MS (EI) for $C_{17}H_{18}N_2O_2$: 283 (MH$^+$).

1-(Diphenylmethyl)-3-hydroxyazetidine-3-carboxamide (1.1 g, 3.90 mmol) was treated with 10% sodium hydroxide in ethanol (15 mL) and water (2 mL) at reflux for 2 h and then was concentrated in vacuo. The residue was neutralized with 1 N hydrochloric acid (pH ~7) and the precipitate was collected by filtration and lyophilized to afford 1-(diphenylmethyl)-3-hydroxyazetidine-3-carboxylic acid (assume 3.90 mmol) which was used without further purification: $^1$H NMR (400 MHz, d$_6$-DMSO): 7.45-7.40 (m, 4H), 7.31-7.25 (m, 4H), 7.21-7.15 (m, 2H), 4.52 (s, 1H), 3.46 (dd, 2H), 3.02 (dd, 2H); MS (EI) for $C_{17}H_{17}NO_3$: 284 (MH$^+$).

1-(Diphenylmethyl)-3-hydroxyazetidine-3-carboxylic acid (assume 3.90 mmol) was suspended in methanol (40 mL) and 4 N hydrochloric acid in dioxane (1 mL, 4 mmol) was added. 20 wt % Palladium hydroxide on carbon (100 mg) was added to the solution and the mixture was treated with hydrogen at 40 psi for 2 h. The mixture was filtered and the filtrate was concentrated in vacuo to afford 3-hydroxyazetidine-3-carboxylic acid hydrochloride which was dissolved in tetrahydrofuran (5 mL) and water (5 mL) and treated with potassium carbonate (1.615 g, 11.7 mmol) and di-tert-butyl dicarbonate (935 mg, 4.29 mmol) were added. The mixture was stirred at ambient for 17 h and then the mixture was partitioned between ethyl acetate and water. The aqueous portion was extracted with ethyl acetate and then was acidified to pH ~3-4 and extracted twice more with ethyl acetate. The combined organic portion was washed with brine, dried over anhydrous sodium sulfate, filtered and concentrated in vacuo to afford 1-{[(1,1-dimethylethyl)oxy]carbonyl}-3-hydroxyazetidine-3-carboxylic acid which was dissolved in DMF (3 mL). Benzotriazol-1-yloxytris(pyrrolidino)phosphonium hexafluorophosphate (2.028 g, 3.90 mmol) and N,N-diisopropylethylamine (0.7 mL, 4.03 mmol) were added. The mixture was stirred at ambient for 5 minutes and then allylamine (0.6 mL, 8.03 mmol) was added and the mixture was stirred for 17 h. The mixture was partitioned between ethyl acetate and 5% lithium chloride. The organic portion was washed with 20% citric acid, saturated sodium bicarbonate and brine, then was dried over anhydrous sodium sulfate, filtered and concentrated in vacuo. Column chromatography (silica gel, ethyl acetate) gave 1,1-dimethylethyl 3-hydroxy-3-[(prop-2-en-1-ylamino)carbonyl]azetidine-1-carboxylate (782 mg, 3.05 mmol, 78% yield from 1-(diphenylmethyl)-3-hydroxyazetidine-3-carboxamide). 1,1-Dimethylethyl 3-hydroxy-3-[(prop-2-en-1-ylamino)carbonyl]azetidine-1-carboxylate (782 mg, 3.05 mmol) was dissolved in methanol (10 mL) and 4 N hydrochloric acid in dioxane (2 mL, 8 mmol) was added. The mixture was refluxed for 15 minutes and then was concentrated in vacuo to afford 3-hydroxy-N-prop-2-en-1-ylazetidine-3-carboxamide hydrochloride (3.05 mmol).

3,4-Difluoro-2-[(2-fluoro-4-iodophenyl)amino]benzoic acid (1.20 g, 3.05 mmol), prepared using procedures similar to those described in U.S. Pat. No. 7,019,033, 4-(dimethylamino)pyridine (1.20 g, 9.86 mmol) and 1-(3-dimethylaminopropyl)-3-ethylcarbodiimide hydrochloride (701 mg, 3.66 mmol) were dissolved in DMF (10 mL). The mixture was stirred at ambient for 5 minutes and then 3-hydroxy-N-prop-2-en-1-ylazetidine-3-carboxamide hydrochloride (3.05 mmol) in DMF (5 mL) was added and the mixture was stirred for 15 h. The mixture was partitioned between ethyl acetate and 5% lithium chloride. The organic portion was washed with 20% citric acid, saturated sodium bicarbonate and brine, then was dried over anhydrous sodium sulfate, filtered and concentrated in vacuo. Column chromatography (silica gel, 60-85% ethyl acetate in hexanes) and then reverse phase HPLC gave 1-({3,4-difluoro-2-[(2-fluoro-4-iodophenyl)amino]phenyl}carbonyl)-3-hydroxy-N-prop-2-en-1-ylazetidine-3-carboxamide (150 mg, 0.282 mmol, 9% yield): $^1$H NMR (400 MHz, d$_6$-DMSO): 8.64 (br s, 1H), 8.13 (t, 1H), 7.58 (dd, 1H), 7.38 (dd, 1H), 7.34-7.28 (m, 1H), 7.21-7.12 (m, 1H), 6.84 (br s, 1H), 6.72 (ddd, 1H), 5.83-5.72 (m, 1H), 5.10-4.99 (m, 2H), 4.38 (d, 1H), 4.20 (d, 1H), 4.02 (d, 1H), 3.86 (d, 1H), 3.73-3.68 (m, 2H); MS (EI) for $C_{20}H_{17}F_3IN_3O_3$: 532 (MH$^+$).

1-({3,4-Difluoro-2-[(2-fluoro-4-iodophenyl)amino]phenyl}carbonyl)-3-hydroxy-N-prop-2-en-1-ylazetidine-3-carboxamide (88 mg, 0.166 mmol) and 4-methylmorpholine N-oxide (58 mg, 0.496 mmol) were dissolved in acetone/water (4:1; 10 mL) and osmium tetroxide (2.5 wt. % in water; 0.1 mL) was added. The solution was stirred at ambient for 15 h, then was quenched with saturated sodium bisulfite (2 mL) and concentrated in vacuo. The residue was partitioned between ethyl acetate and brine. The aqueous portion was extracted with ethyl acetate. The combined organic portion was washed with brine, dried over anhydrous sodium sulfate, filtered and concentrated in vacuo. Purification by reverse phase HPLC gave 1-({3,4-difluoro-2-[(2-fluoro-4-iodophenyl)amino]phenyl}carbonyl)-N-(2,3-dihydroxypropyl)-3-hydroxyazetidine-3-carboxamide (68 mg, 0.120 mmol, 72% yield): $^1$H NMR (400 MHz, d$_6$-DMSO): 8.65 (br s, 1H), 7.72 (t, 1H), 7.58 (dd, 1H), 7.41-7.36 (m, 1H), 7.34-7.28 (m, 1H), 7.21-7.12 (m, 1H), 6.92 (br s, 1H), 6.72 (ddd, 1H), 5.00-4.10 (br, 2H), 5.10-4.99 (m, 2H), 4.39 (d, 1H), 4.20 (d, 1H), 4.02 (d, 1H), 3.54-3.45 (m, 1H), 3.34-3.21 (m, 2H), 3.06-2.96 (m, 1H); MS (EI) for $C_{20}H_{19}F_3IN_3O_5$: 566 (MH$^+$).

Example 15(a)

Using the same or analogous synthetic techniques and substituting, as necessary, with alternative reagents, the following compounds of the invention were prepared: 1-({3,4-Difluoro-2-[(2-fluoro-4-iodophenyl)amino]phenyl}carbonyl)-3-hydroxyazetidine-3-carboxamide: $^1$H NMR (400 MHz, d$_6$-DMSO): 8.63 (br s, 1H), 7.58 (dd, 1H), 7.42-7.36 (m, 3H), 7.34-7.28 (m, 1H), 7.22-7.12 (m, 1H), 6.76-6.68 (m, 2H), 4.39 (d, 1H), 4.19 (d, 1H), 4.00 (d, 1H), 3.83 (d, 1H); MS (EI) for $C_{17}H_{13}F_3IN_3O_3$: 492 (MH+).

Example 16

6-{[3-(aminomethyl)-3-(methyloxy)azetidin-1-yl]carbonyl}-2,3-difluoro-N-(2-fluoro-4-iodophenyl)aniline

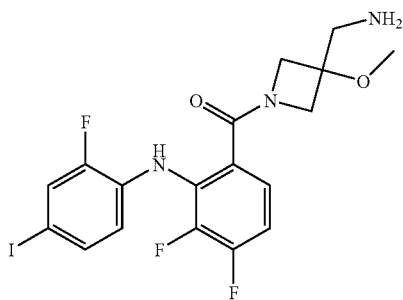

Phenylmethyl 1-oxa-5-azaspiro[2.3]hexane-5-carboxylate (165 mg, 0.75 mmol), prepared using procedures similar to those described in Reference 3, in THF (1 mL) was added to anhydrous ammonia saturated in THF (10 mL) and the mixture was allowed to stir in a sealed vessel at room temperature over 24 hours. The solution was then concentrated and taken back into THF (1 mL) followed by addition of di-tert-butyldicarbonate (164 mg, 0.75 mmol) and stirred for one hour at room temperature. The mixture was then concentrated and the residue purified by silica gel flash chromatography using hexanes:ethyl acetate (1:1) as eluent to give phenylmethyl 3-[({[(1,1-dimethylethyl)oxy]carbonyl}amino)methyl]-3-hydroxyazetidine-1-carboxylate (16.5 mg, 7% yield) and unreacted epoxide (120 mg, 73% recovery). $^1$H-NMR (400 MHz, CDCl$_3$): 7.34 (m, 5H), 5.10 (br, 1H), 5.09 (s, 2H), 4.68 (s, 1H), 3.90 (dd AB, 4H), 3.41 (d, 2H), 1.44 (s, 9H).

Phenylmethyl 3-[({[(1,1-dimethylethyl)oxy]carbonyl}amino)methyl]-3-hydroxyazetidine-1-carboxylate (16.5 mg, 0.05 mmol) and 10% Pd/C (8 mg) were taken into methanol (2 mL) and hydrogenated at ambient pressure over 12 hours. The catalyst was removed by filtration and the filtrate concentrated and dried in vacuo. The residue was taken into THF (1 mL) followed by addition of DIPEA (10 µL, 0.06 mmol) and 3,4-difluoro-2-[(2-fluoro-4-iodophenyl)amino]benzoyl fluoride (19.8 mg, 0.05 mmol), prepared using procedures similar to those described in Reference 1, and the solution was stirred at room temperature for 30 minutes. Concentration and purification of the residue by silica gel flash chromatography using hexanes:ethyl acetate (1:1.5) afforded 1,1-dimethylethyl{[1-({3,4-difluoro-2[(2-fluoro-4-iodophenyl)amino]phenyl}carbonyl)-3-hydroxyazetidine-3-yl]methyl}carbamate (19 mg, 66% yield).

1,1-Dimethylethyl{[1-({3,4-difluoro-2[(2-fluoro-4-iodophenyl)amino]phenyl}carbonyl)-3-hydroxyazetidine-3-yl]methyl}carbamate (8.0 mg, 0.014 mmol) and silver (I) oxide (12 mg, 0.05 mmol) were taken into methyl iodide (0.5 mL) and the mixture was brought to reflux for 4 hours. The suspension was then cooled to room temperature and diluted with an excess of ethyl ether then filtered. The filtrate was concentrated and purified by silica gel flash chromatography using hexanes:ethyl acetate (1:1) as eluent to give 1,1-dimethylethyl{[1-({3,4-difluoro-2[(2-fluoro-4-iodophenyl)amino]phenyl}carbonyl)-3-(methyloxy)azetidine-3-yl]methyl}carbamate (2 mg). The material was taken into TFA (0.5 mL) and allowed to stand for 5 minutes then concentrated in vacuo. The residue was azetroped twice from methanol (2 mL) and the residue dried in vacuo to afford 6-{[3-(aminomethyl)-3-(methyloxy)azetidin-1-yl]carbonyl}-2,3-difluoro-N-(2-fluoro-4-iodophenyl)aniline trifluoroacetate salt (2.3 mg, 27% yield) as an amorphous solid. MS (EI) for $C_{18}H_{17}F_3IN_3O$: 492 (MH+).

Example 17

1-({3,4-difluoro-2-[(2-fluoro-4-iodophenyl)amino]phenyl}carbonyl)-3-{2-[(1-methylethyl)amino]ethyl}azetidin-3-ol

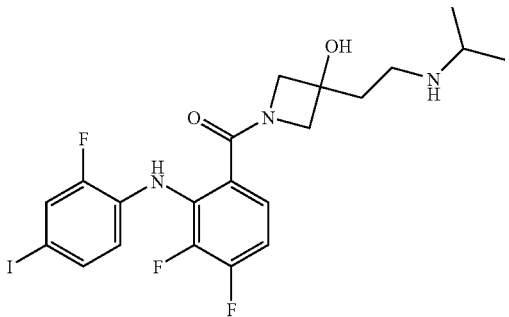

A solution of tert-butyl acetate (566 µL, 4.2 mmol) in THF (10 mL) was cooled to −78° C. To the solution was added LHMDS (5.25 mL of a 1.0 M solution in hexanes, 5.25 mmol), and the resulting mixture was stirred for 20 min at −78° C. To the solution was added 1-(diphenylmethyl)azetidin-3-one (500 mg, 2.1 mmol), prepared using procedures similar to those described in Example 15. After stirring for 1 h, saturated aqueous ammonium chloride was added, and the mixture was warmed to rt. Water and ether were added, and the resulting biphasic mixture was partitioned. The aqueous phase was extracted once with ether. The combined organic extracts were dried over magnesium sulfate, filtered, and concentrated in vacuo. The residue was purified by flash chromatography (80% hexanes:20% ethyl acetate) to provide 1,1-dimethylethyl [1-(diphenylmethyl)-3-hydroxyazetidin-3-yl]acetate as a pale yellow solid (644 mg, 1.8 mmol, 87% yield). $^1$H NMR (400 MHz, CDCl$_3$): δ 7.40 (m, 4H), 7.26 (m, 4H), 7.19 (m, 2H), 4.40 (s, 1H), 4.02 (s, 1H), 3.15 (m, 2H), 3.05 (m, 2H), 2.83 (s, 2H), 1.45 (s, 9H).

To a solution of 1,1-dimethylethyl [1-(diphenylmethyl)-3-hydroxyazetidin-3-yl]acetate (333 mg, 0.94 mmol) in THF (3 mL) at 0° C. was added lithium aluminum hydride (940 µL of a 1.0 M solution in THF, 0.94 mmol). The mixture was stirred for 3 h 20 min while warming to rt. Water (36 µL) was added carefully to the solution, followed by 15% sodium hydroxide (36 µL) and more water (108 µL). The resulting precipitate was removed by filtration through celite, and the filtrate was concentrated to dryness yielding 1-(diphenylmethyl)-3-(2-hydroxyethyl)azetidin-3-ol (228 mg, 0.80 mmol, 85% yield) as a colorless syrup. $^1$H NMR (400 MHz, CDCl$_3$): δ 7.38 (m, 4H), 7.26 (m, 4H), 7.19 (m, 2H), 4.37 (s, 1H), 3.92 (m, 2H), 3.32 (m, 2H), 2.96 (m, 2H), 2.07 (m, 2H).

Palladium hydroxide (100 mg) was suspended in a solution of 1-(diphenylmethyl)-3-(2-hydroxyethyl)azetidin-3-ol (228 mg, 0.80 mmol) in methanol (15 mL), and the mixture was subjected to an atmosphere of hydrogen at 50 psi for 4 h. The catalyst was then removed by filtration through celite, and the filtrate was concentrated in vacuo to provide 3-(2-hydroxyethyl)azetidin-3-ol. This material was used in the subsequent reaction without purification. To a solution of 3,4-difluoro-2-[(2-fluoro-4-iodophenyl)amino]benzoic acid (314 mg, 0.80 mmol), prepared using procedures similar to those described in U.S. Pat. No. 7,019,033, in DMF (4 mL) was added PyBOP (416 mg, 0.80 mmol) and triethylamine (223 µL, 1.6 mmol). Finally, the unpurified 3-(2-hydroxyethyl)azetidin-3-ol was added, and the resulting mixture was stirred at rt for 16 h. Water and ethyl acetate were added, and the layers were separated. The aqueous phase was extracted with once more with ethyl acetate. The combined organic extracts were washed with brine, dried over magnesium sulfate, filtered, and concentrated in vacuo. The residue was purified by flash chromatography, eluting with ethyl acetate, to provide 1-({3,4-difluoro-2-[(2-fluoro-4-iodophenyl)amino]phenyl}carbonyl)-3-(2-hydroxyethyl)azetidin-3-ol as a colorless oil (303 mg, 0.62 mmol, 78% yield). $^1$H NMR (400 MHz, CDCl$_3$): δ 8.46 (s, 1H), 7.39 (dd, 1H), 7.32 (m, 1H), 7.13 (m, 1H), 6.81 (m, 1H), 6.60 (m, 1H), 4.37 (br s, 1H), 4.28 (br m, 4H), 3.94 (br s, 2H), 2.19 (br s, 1H), 2.02 (m, 2H); MS (EI) for C$_{18}$H$_{16}$F$_3$IN$_2$O$_3$: 491 (M-H).

A solution of oxalyl chloride (13 µL, 0.15 mmol) in dichloromethane (1 mL) was cooled to −78° C., and DMSO (22 µL, 0.31 mmol) was then added. To this mixture was added 1-({3,4-difluoro-2-[(2-fluoro-4-iodophenyl)amino]phenyl}carbonyl)-3-(2-hydroxyethyl)azetidin-3-ol (67.8 mg, 0.14 mmol) as a suspension in dichloromethane (1 mL). After stirring at −78° C. for 10 min, triethylamine (78 µL, 0.56 mmol) was added and the mixture was allowed to warm to rt. The solution was diluted with dichloromethane, and washed with 0.5 N HCl. The aqueous phase wash then extracted with dichloromethane. The organic extracts were combined, dried over magnesium sulfate, filtered, and concentrated. The residue was purified by flash chromatography to provide [1-({3,4-difluoro-2-[(2-fluoro-4-iodophenyl)amino]phenyl}carbonyl)-3-hydroxyazetidin-3-yl]acetaldehyde as a white solid (22.1 mg, 0.045 mmol, 32% yield). $^1$H NMR (400 MHz, CDCl$_3$): δ 9.82 (s, 1H), 8.46 (s, 1H), 7.39 (m, 1H), 7.33 (m, 1H), 7.11 (m, 1H), 6.81 (m, 1H), 6.61 (m, 1H), 4.32-3.96 (br m, 4H), 3.41 (t, 2H), 3.07 (s, 1H); MS (EI) for C$_{18}$H$_{14}$F$_3$IN$_2$O$_3$: 491 (MH$^+$).

To a solution of [1-({3,4-difluoro-2-[(2-fluoro-4-iodophenyl)amino]phenyl}carbonyl)-3-hydroxyazetidin-3-yl]acetaldehyde (38.0 mg, 0.078 mmol) in 1,2-dichloroethane (1 mL) was added isopropylamine (27 µL, 0.31 mmol) followed by sodium triacetoxyborohydride (26 mg, 0.12 mmol). The mixture was stirred for 3 h before quenching with 1 drop of concentrated HCl. The quenched mixture was concentrated to dryness, and then purified by preparative HPLC to provide 1-({3,4-difluoro-2-[(2-fluoro-4-iodophenyl)amino]phenyl}carbonyl)-3-{2-[(1-methylethyl)amino]ethyl}azetidin-3-ol (21.5 mg) as a pale yellow solid. $^1$H NMR (400 MHz, d$_6$-DMSO): δ 8.54 (s, 1H), 7.57 (dd, 1H), 7.38 (dd, 1H), 7.31 (m, 1H), 7.17 (m, 1H), 6.67 (m, 1H), 4.02 (m, 1H), 3.89 (m, 2H), 3.71 (m, 1H), 2.70 (m, 1H), 2.63 (m, 2H), 1.86 (s, 3H), 1.75 (m, 2H), 0.97 (d, 6H); MS (EI) for C$_{21}$H$_{23}$F$_3$IN$_3$O$_2$: 534 (MH$^+$).

Example 18

1-({3,4-difluoro-2-[(2-fluoro-4-iodophenyl)amino]phenyl}carbonyl)-3-{1,1-dimethyl-2-[(1-methylethyl)amino]ethyl}azetidin-3-ol

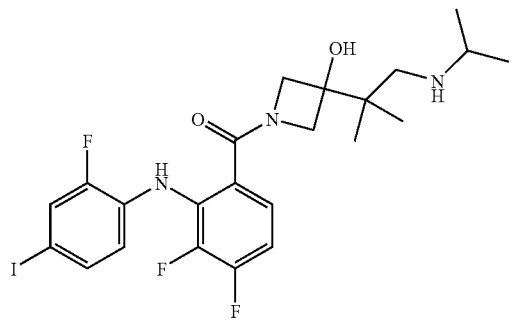

To a solution of 1-({3,4-difluoro-2-[(2-fluoro-4-iodophenyl)amine]phenyl}carbonyl)azetidin-3-one (500 mg, 1.12 mmol), prepared using procedures similar to those described in Example 6, in dichloromethane (5 mL) cooled to 0° C. was added titanium tetrachloride (125 µL, 1.12 mmol). The dark brown solution was stirred at 0° C. for 45 minutes, followed by the addition of methyltrimethylsilyl dimethylketene acetal (550 µL, 2.24 mmol) at 0° C. Upon addition the solution was allowed to warm to room temperature, and was stirred for 1 hour. The reaction mixture was then partitioned between saturated aqueous sodium bicarbonate and ethyl acetate. The aqueous portion was extracted twice using ethyl acetate. The combined organic portion was washed with water, brine, dried over sodium sulfate, filtered and concentrated in vacuo to afford a brown oil which was purified by column chromatography. Eluting with 10% diethyl ether in dichloromethane, the isolated product was concentrated in vacuo to afford 520 mg, 0.95 mmol (85%) of methyl 2-[1-({3,4-difluoro-2-[(2-fluoro-4-iodophenyl)amino]phenyl}carbonyl)-3-hydroxyazetidin-3-yl]-2-methylpropanoate as a white foam. $^1$H NMR (400 MHz, CDCl$_3$): 8.34 (s, 1H), 7.38 (d, 1H), 7.31 (d, 1H), 7.13-7.08 (m, 1H), 6.85-6.77 (m, 1H), 6.63-6.56 (m, 1H), 4.26-4.20 (m, 2H), 4.13-4.09 (m, 1H), 4.00-3.93 (m, 1H), 3.70 (s, 3H), 1.23 (s, 6H). MS (EI) for C$_{21}$H$_{20}$F$_3$IN$_2$O$_4$: 547 (MH$^-$).

A solution of methyl 2-[1-({3,4-difluoro-2-[(2-fluoro-4-iodophenyl)amine]phenyl}carbonyl)-3-hydroxyazetidin-3-yl]-2-methylpropanoate (520 mg, 0.95 mmol) in 4N aqueous potassium hydroxide (5 mL) was stirred at 50° C. for 1 hour. Using concentrated aqueous hydrochloric acid, the reaction mixture was acidified to pH 5, and then partitioned with ethyl acetate. The aqueous portion was extracted twice using ethyl acetate, and the combined organic portion was washed with brine, dried over sodium sulfate, filtered and concentrated in vacuo to afford 300 mg, 0.56 mmol (59%) of 2-[1-({3,4-difluoro-2-[(2-fluoro-4-iodophenyl)amino]phenyl}carbonyl)-3-hydroxyazetidin-3-yl]-2-methylpropanoic acid as a white solid. $^1$H NMR (400 MHz, DMSO): 8.49 (s, 1H), 7.57-7.52 (m, 1H), 7.37-7.25 (m, 2H), 7.17-7.13 (m, 1H), 6.68-6.58 (m, 1H), 3.98-3.94 (m, 2H), 3.80-3.77 (m, 1H), 3.55-3.52 (m, 1H), 0.88 (s, 6H). MS (EI) for C$_{20}$H$_{18}$F$_3$IN$_2$O$_4$: 535 (MH$^+$).

To solution of 2-[1-({3,4-difluoro-2-[(2-fluoro-4-iodophenyl)amino]phenyl}carbonyl)-3-hydroxyazetidin-3-yl]-2-methylpropanoic acid (300 mg, 0.56 mmol) in tetrahydrofuran (5 mL) was added triethylamine (80 μL, 0.56 mmol), followed by PyBOP (295 mg, 0.56 mmol) and finally sodium borohydride (64 mg, 1.68 mmol). The mixture was stirred at room temperature for 1 hour. The reaction mixture was quenched by adding 20% aqueous citric acid, and then partitioned with ethyl acetate. The organic portion was washed with saturated aqueous sodium bicarbonate, brine, dried over sodium sulfate, filtered and concentrated in vacuo to afford a white solid which was purified by column chromatography. Eluting with 60% ethyl acetate in hexanes, the isolated product was concentrated in vacuo to afford 238 mg, 0.46 mmol (82%) of 1-({3,4-difluoro-2-[(2-fluoro-4-iodophenyl)amino]phenyl}carbonyl)-3-(2-hydroxy-1,1-dimethylethyl)azetidin-3-ol as a white solid. $^1$H NMR (400 MHz, DMSO): 8.53 (s, 1H), 7.57 (d, 1H), 7.38-7.28 (m, 2H), 7.22-7.15 (m, 1H), 6.70-6.64 (m, 1H), 5.61 (s, 1H), 4.57 (br s, 1H), 4.30-4.27 (m, 1H), 4.18-4.15 (m, 1H), 3.80-3.77 (m, 1H), 3.68-3.64 (m, 1H), 3.25 (s, 2H), 0.76 (d, 6H); MS (EI) for $C_{20}H_{20}F_3IN_2O_3$: 521 (MH$^+$).

A mixture of 1-({3,4-difluoro-2-[(2-fluoro-4-iodophenyl)amino]phenyl}carbonyl)-3-(2-hydroxy-1,1-dimethylethyl)azetidin-3-ol (200 mg, 0.38 mmol) and Dess-Martin periodinane (240 mg, 0.57 mmol) in dichloromethane (2 mL) was stirred at room temperature for 2 hours. 10% aqueous sodium thiosulfate (2 mL), and saturated aqueous sodium bicarbonate (2 mL) was added and the mixture was stirred at room temperature for 15 minute. The mixture was partitioned and the aqueous layer was extracted twice using dichloromethane. The combined organic portion was washed with brine, dried over sodium sulfate, filtered and concentrated in vacuo, to afford a white solid which was purified by column chromatography. Eluting with 30% ethyl acetate in hexanes, the isolated product was concentrated in vacuo to afford 100 mg, 0.20 mmol (53%) of 2-[1-({3,4-difluoro-2-[(2-fluoro-4-iodophenyl)amino]phenyl}carbonyl)-3-hydroxyazetidin-3-yl]-2-methylpropanal as a white solid, which was immediately dissolved in tetrahydrofuran (2 mL). To the solution was added isopropylamine (34 μL, 0.40 mmol), followed by triacetoxyborohydride (212 mg, 1.0 mmol). The solution was stirred at room temperature for 15 hours. The reaction mixture was concentrated in vacuo and partitioned between 20% aqueous citric acid and ethyl acetate. The aqueous portion was extracted twice using ethyl acetate, and the combined organic portion was washed with saturated aqueous sodium bicarbonate, brine, dried over sodium sulfate, filtered and concentrated in vacuo to afford a yellow oil which was purified by preparative reverse phase HPLC. The isolated product was concentrated in vacuo to afford 50 mg, 0.07 mmol (36%) of 1-({3,4-difluoro-2-[(2-fluoro-4-iodophenyl)amino]phenyl}carbonyl)-3-{1,1-dimethyl-2-[(1-methylethyl)amino]ethyl}azetidin-3-ol acetate salt as a white solid. $^1$H NMR (400 MHz, DMSO): 8.47 (br s, 1H), 7.55 (d, 1H), 7.36-7.29 (m, 2H), 7.22-7.15 (m, 1H), 6.68-6.63 (m, 1H), 4.17-4.08 (m, 2H), 3.76-3.73 (m, 1H), 3.56-3.52 (m, 1H), 2.58-2.51 (m, 1H), 2.45-2.37 (m, 2H), 0.92 (t, 6H), 0.78 (d, 6H); MS (EI) for $C_{23}H_{27}F_3IN_3O_2$: 562 (MH$^+$).

Example 19

1-({3,4-difluoro-2-[(2-fluoro-4-iodophenyl)amino]phenyl}carbonyl)-3-{[(1-methylethyl)amino]methyl}azetidin-3-amine

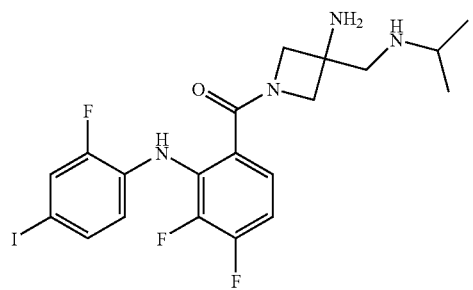

To a solution of the 1-(diphenylmethyl)-3-[(phenylmethyl)amino]azetidine-3-carbonitrile (0.80 g, 2.2 mmol), prepared using procedures similar to those described in Kozikowski and Fauq *Synlett* 1991, 11, 783-4, in ethanol (30 mL) was added solid sodium hydroxide (7.5 mmol), and the resulting mixture was stirred at room temperature for 3 days. Water (6 mL) was added to the reaction mixture and stirring was continued at 90° C. for 2 h. The pH of the reaction mixture was adjusted to 5 with concentrated hydrochloric acid and a white solid precipitated. The mixture was cooled, diluted with water (50 mL) and the solid was collected, washed with water then dried in vacuo to give the 1-(diphenylmethyl)-3-[(phenylmethyl)amino]azetidine-3-carboxylic acid (0.75 g, 88% yield), MS (EI) for $C_{24}H_{24}N_2O_2$: 373 (MH$^+$).

To a mixture of 1-(diphenylmethyl)-3-[(phenylmethyl)amino]azetidine-3-carboxylic acid (0.50 g, 1.34 mmol), N,N-diisopropylethylamine (0.47 mL, 2.68 mmol) in DMF (3 mL) was added 1-benzotriazolyloxytripyrrolidinylphosphonium hexafluorophosphate (1.34 g, 2.68 mol) and the resulting mixture was stirred at room temperature for 10 minutes. To this mixture was added 2-propylamine (0.22 mL, 2.68 mmol) and stirring was continued for 18 h. The reaction mixture was diluted with ethyl acetate (100 mL) and washed with 2% aqueous citric acid, 5% lithium chloride, and brine solutions (50 mL each), dried over sodium sulfate, filtered and concentrated to give an oily residue which was purified by flash chromatography (silica gel, eluting with 15-25% ethyl acetate-hexane) to give 1-(diphenylmethyl)-N-(1-methylethyl)-3-[(phenylmethyl)amino]azetidine-3-carboxamide (0.51 g, 92% yield), MS (EI) for $C_{27}H_{31}N_3O$: 414 (MH$^+$).

To a solution of the 1-(diphenylmethyl)-N-(1-methylethyl)-3-[(phenylmethyl)amino]azetidine-3-carboxamide (0.40 g, 0.97 mmol) in tetrahydrofuran (10 mL) at room was added a solution of lithium aluminum hydride in tetrahydrofuran (1M, 2.90 mL, 2.90 mmol), and the resulting mixture was stirred at 50° C. for 3 h. The reaction mixture was cooled to room temperature, quenched with 20% aqueous hydroxide solution (1 mL), diluted with ether (50 mL) and filtered. The filtrate was washed with brine solution (20 mL each), dried over sodium sulfate, filtered and concentrated to give an oily residue which was purified by flash chromatography (silica gel, eluting with 5% methanol-dichloromethane) to give 1-(diphenylmethyl)-3-{[(1-methylethyl)amino]methyl}-N-(phenylmethyl)azetidin-3-amine (0.35 g, 90% yield), $^1$H NMR (400 MHz, CDCl₃): 7.42-7.14 (m, 15H), 4.34 (s, 1H), 3.66 (s, 2H), 3.22-3.18 (d, 2H), 2.97 (s, 2H), 2.90-2.86 (d, 2H), 2.68-2.62 (p, 1H), 1.09-1.07 (d, 6H); MS (EI) for $C_{27}H_{33}N_3$: 400 (MH⁺).

To a solution of the 1-(diphenylmethyl)-3-{[(1-methylethyl)amino]methyl}-N-(phenylmethyl)azetidin-3-amine (0.35 g, 0.88 mmol) in methanol was added a solution of hydrogen chloride in dioxane (4 molar solution, 0.96 mL, 4.40 mmol) and the resulting mixture was concentrated to give a white solid which was taken back into methanol. To this solution were added palladium hydroxide (20% on carbon, 0.50 g, 0.19 mmol) and the resulting mixture shaken at 50 psi in a Parr apparatus for 3 h. The reaction mixture was filtered and concentrated to give a solid, which was washed with ether and dried in vacuo to give 3-{[(1-methylethyl)amino]methyl}azetidin-3-amine hydrochloride as a white solid (0.18 g, 81% yield). MS (EI) for $C_7H_{17}N_3$: 144 (MH⁺).

To a mixture of the 3-{[(1-methylethyl)amino]methyl}azetidin-3-amine hydrochloride (20 mg, 0.079 mmol) in saturated sodium bicarbonate solution (1.0 mL) and dioxane (1.0 mL) was added 3,4-difluoro-2-[(2-fluoro-4-iodophenyl)amino]benzoyl fluoride (31 mg, 0.079 mmol), prepared using procedures similar to those described in Reference 1, and the resulting mixture was stirred at room temperature for 18 h. The reaction mixture was diluted with water (5 mL) and extracted with ethyl acetate (3×5 mL). The combined extract was washed with water then brine solution (5 mL each), dried over sodium sulfate, filtered and concentrated to give an oily residue which was purified by reverse phase HPLC to afford 1-({3,4-difluoro-2-[(2-fluoro-4-iodophenyl)amino]phenyl}carbonyl)-3-{[(1-methylethyl)amino]methyl}azetidin-3-amine (15 mg, 37% yield). ¹H NMR (400 MHz, d₄-Methanol): 7.46-7.43 (dd, 1H), 7.35-7.33 (dd, 1H), 7.31-7.27 (m, 1H), 7.08-7.01 (dd, 1H), 6.63, 6.58 (td, 1H), 4.09-4.07 (d, 1H), 3.91-3.85 (dd, 2H), 3.76-3.73 (d, 1H). 2.80-2.74 (m, 1H), 2.73 (s, 2H), 1.07-1.05 (d, 6H); MS (EI) for $C_{20}H_{22}F_3IN_4O$: 519 (MH⁺).

Example 20

3-(1-amino-2-methylpropyl)-1-({3,4-difluoro-2-[(2-fluoro-4-iodophenyl)amino]phenyl}carbonyl)azetidin-3-ol

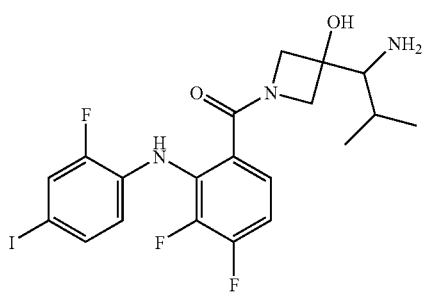

1,1-Dimethylethyl 3-oxoazetidine-1-carboxylate (677.2 mg, 3.96 mmol), prepared using procedures similar to those described in Example 3, was taken into 2-methyl-1-ntropropane (5 mL) then cooled to 0° C. followed by addition of potassium tert-butoxide (444 mg, 3.96 mmol) and the resulting mixture was allowed to warm to room temperature over 30 minutes. The mixture was partitioned with ethyl acetate and 0.5 N aqueous hydrochloric acid then once with water and brine then dried over anhydrous magnesium sulfate. Filtration and concentration afforded a residue (1.5 g) that was further purified by silica gel flash chromatography using 3:1 hexanes:ethyl acetate as eluent to give 1,1-dimethylethyl 3-hydroxy-3-(2-methyl-1-nitropropyl)azetidine-1-carboxylate (730 mg, 67% yield) as a colorless crystalline solid. ¹H-NMR (400 MHz, CDCl₃): 4.50 (d, 1H), 3.93 (dd AB, 2H), 3.85 (s, 2H), 3.58 (s, 1H), 2.54-2.48 (m, 1H), 1.44 (s, 9H), 1.04 (d, 6H).

1,1-Dimethylethyl 3-hydroxy-3-(2-methyl-1-nitropropyl)azetidine-1-carboxylate (105 mg, 0.38 mmol) was taken into methanol (1 mL) followed by addition of 4 N anhydrous hydrogen chloride in dioxane (1 mL) and the acidic solution was allowed to stand for 15 minutes at room temperature then concentrated and dried in vacuo to an amorphous residue. 3,4-Difluoro-2-[(2-fluoro-4-iodophenyl)amino]benzoic acid (150 mg, 0.38 mmol), prepared using procedures similar to those described in U.S. Pat. No. 7,019,033, was taken into DMF (0.7 mL) followed by addition of PyBOP (198 mg, 0.38 mmol) and the solution was allowed to stir for 10 minutes at room temperature. The above amine hydrochloride salt and DIPEA (190 μL, 1.1 mmol) in DMF solution (0.7 mL) was added and the mixture was allowed to stir for one hour at room temperature. The mixture was partitioned with ethyl acetate and 0.5 N aqueous hydrochloric acid and the organic phase washed three times with water then brine and dried over anhydrous magnesium sulfate. Filtration and concentration afforded a residue that was further purified by silica gel flash chromatography using 1.5:1 hexanes:ethyl acetate as eluent to give 1-({3,4-difluoro-2-[(2-fluoro-4-iodophenyl)amino]phenyl}carbonyl)-3-(2-methyl-1-nitropropyl)azetidin-3-ol (189 mg, 90% yield) as an amorphous solid. ¹H-NMR (400 MHz, CDCl₃): 8.41 (br s, 1H), 7.41 (dd, 1H), 7.34 (d, 1H), 7.09 (br m, 1H), 6.81 (q, 1H), 6.65-6.60 (m, 1H), 4.49 (d, 1H), 4.15-4.09 (m, 4H), 3.66 (s, 1H), 2.56-2.46 (m, 1H) 1.03 (d, 6H).

1-({3,4-Difluoro-2-[(2-fluoro-4-iodophenyl)amino]phenyl}carbonyl)-3-(2-methyl-1-nitropropyl)azetidin-3-ol (189 mg, 0.34 mmol) was taken into 4:1 THF:water (5 mL) followed by addition of iron powder (192 mg, 3.4 mmol) and ammonium formate (429 mg, 6.8 mmol) and the mixture was heated to reflux. After four hours additional aliquots of iron powder (192 mg, 3.4 mmol) and ammonium formate (429 mg, 6.8 mmol) were added and the mixture was allowed to reflux an additional 12 hours. The mixture was cooled to room temperature and diluted with ethyl acetate then filtered. The filtrate was partitioned with ethyl acetate and saturated aqueous sodium bicarbonate then the organic layer washed with brine and dried over anhydrous sodium sulfate. Filtration and concentration afforded a residue that was further purified by silica gel flash chromatography using ethyl acetate to 10% methanol in dichloromethane as eluents to give a residue (36.5 mg) that was further purified by preparative reverse phase HPLC to give 3-(1-amino-2-methylpropyl)-1-({3,4-difluoro-2-[(2-fluoro-4-iodophenyl)amino]phenyl}carbonyl)azetidin-3-ol trifluoroacetate salt (7.9 mg) as a colorless amorphous solid after lyophillization of the combined pure fractions. ¹H-NMR (400 MHz, D₆-DMSO): 8.63 (s, 1H), 7.58 (dd, 1H), 7.37 (d, 1H), 7.35-7.31 (m, 1H), 7.17 (q, 1H), 6.71-6.66 (m, 1H), 4.23 (dd, 1H), 4.03 (dd, 1H), 3.80 (dd, 1H), 3.66 (dd, 1H), 2.34 (dd, 1H), 1.79-1.70 (m, 1H), 0.84-0.77 (m, 6H). MS (EI) for $C_{20}H_{21}F_3IN_3O_2$: 520 (MH⁺).

Using the same or analogous synthetic techniques and substituting, as necessary, with alternative reagents, the following compounds of the invention were prepared:

Example 20(a)

3-(1-aminoethyl)-1-({3,4-difluoro-2-[(2-fluoro-4-iodophenyl)amino]phenyl}carbonyl)azetidin-3-ol: ¹H NMR (400 MHz, d$_6$-DMSO): 8.56 (s, 1H), 7.91 (br s, 2H), 7.58 (d, 1H), 7.39 (d, 1H), 7.36-7.32 (m, 1H), 7.24-7.17 (m, 1H), 6.72-6.65 (m, 2H), 4.33-4.29 (m, 1H), 4.23-4.19 (m, 1H), 4.16-4.14 (m, 1H), 4.07-3.94 (m, 1H), 3.82-3.77 (m, 1H), 3.51-3.45 (m, 1H), 1.15-1.12 (m, 1H), 1.10-1.08 (m, 1H). MS (EI) for C$_{18}$H$_{17}$F$_3$IN$_3$O$_2$: 492 (MH$^+$).

Example 20(b)

1-({3,4-difluoro-2-[(2-fluoro-4-iodophenyl)amino]phenyl}carbonyl)-3-[1-(ethylamino)ethyl]azetidin-3-ol: $^1$H NMR (400 MHz, d$_6$-DMSO): 8.61 (d, 1H), 8.50 (s, 1H), 8.20 (s, 1H), 7.59 (d, 1H), 7.39 (d, 1H), 7.36-7.32 (m, 1H), 7.24-7.17 (m, 1H), 6.82 (s, 1H), 6.74-6.67 (m, 1H), 4.38 (d, 1H), 4.27 (d, 1H), 4.18 (d, 1H), 4.06 (d, 2H), 3.99 (d, 1H), 3.89 (d, 1H), 3.82 (d, 1H), 3.49-3.43 (m, 1H), 3.04-2.80 (m, 4H), 1.21-1.12 (m, 6H). MS (EI) for C$_{26}$H$_{21}$F$_3$IN$_3$O$_2$: 520 (MH$^+$).

Example 20(c)

1-({3,4-difluoro-2-[(2-fluoro-4-iodophenyl)amino]phenyl}carbonyl)-3-(1-nitroethyl)azetidin-3-ol: $^1$H NMR (400 MHz, d$_6$-DMSO): 8.57 (d, 1H), 7.58 (d, 1H), 7.38 (d, 1H), 7.37-7.33 (m, 1H), 7.22-7.17 (m, 1H), 6.73-6.66 (m, 1H), 6.57 (s, 1H), 5.06-4.97 (m, 1H), 4.54 (d, 0.5H), 4.37 (d, 0.5H), 4.29 (d, 0.5H), 4.14 (d, 0.5 H), 4.05 (d, 0.5 H), 3.95 (d, 0.5H), 3.86 (d, 0.5H), 3.80 (d, 0.5H), 1.44-1.38 (m, 3H). MS (EI) for C$_{18}$H$_{16}$F$_3$IN$_3$O$_4$: 523 (MH$^+$).

Example 20(d)

1-({3,4-difluoro-2-[(2-fluoro-4-iodophenyl)amino]phenyl}carbonyl)-3-[1-(methylamino)ethyl]azetidin-3-ol: $^1$H NMR (400 MHz, d$_6$-DMSO): 8.63-8.55 (m, 1H), 8.44-8.23 (m, 1H), 7.79 (br s, 1H), 7.60 (d, 1H), 7.39 (d, 1H), 7.36-7.31 (m, 1H), 7.24-7.17 (m, 1H), 6.82 (br s, 0.5H), 6.73-6.65 (m, 1H), 4.38-3.77 (m, 4H), 1.18-1.07 (m, 3H). MS (EI) for C$_{19}$H$_{19}$F$_3$IN$_3$O$_2$: 505 (M$^+$).

Example 20(e)

methyl{1-[1-({3,4-difluoro-2-[(2-fluoro-4-iodophenyl)amino]phenyl}carbonyl)-3-hydroxyazetidin-3-yl]ethyl}carbamate: $^1$H NMR (400 MHz, d$_6$-DMSO): 8.59 (d, 1H), 7.58 (d, 1H), 7.41-7.05 (m, 4H), 6.72-6.64 (m, 1H), 5.84 (d, 1H), 4.20 (d, 0.5H), 4.08-4.04 (m, 1H), 3.92-3.85 (m, 1.5H), 3.76-3.71 (m, 1H), 3.69-3.63 (m, 1H), 3.46 (d, 2H), 0.99-0.95 (m, 3H). MS (EI) for C$_{20}$H$_{19}$F$_3$IN$_3$O$_4$: 550 (MH$^+$).

Example 20(f)

1-({3,4-difluoro-2-[(2-fluoro-4-iodophenyl)amino]phenyl}carbonyl)-3-[1-(dimethylamino)ethyl]azetidin-3-ol: $^1$H NMR (400 MHz, d$_6$-DMSO): 9.45 (s, 1H), 8.61 (d, 1H), 7.60 (d, 1H), 7.39 (d, 1H), 7.38-7.33 (m, 1H), 7.24-7.18 (m, 1H), 7.05 (s, 1H), 6.73-6.66 (m, 1H), 4.48 (d, 0.5H), 4.36 (d, 0.5 H), 4.26 (d, 0.5H), 4.16-4.11 (m, 1H), 4.00-3.94 (m, 1H), 3.86 (d, 0.5H), 3.60-3.54 (m, 1H), 2.75-2.70 (m, 3H), 2.66-2.62 (br s, 3H), 1.22 (dd, 3H). MS (EI) for C$_{20}$H$_{21}$F$_3$IN$_3$O$_2$: 520 (MH$^+$).

Example 20(g)

1-({3,4-difluoro-2-[(2-fluoro-4-iodophenyl)amino]phenyl}carbonyl)-3-(1-nitropropyl)azetidin-3-ol: $^1$H NMR (400 MHz, CD$_3$OD): 7.46 (m, 1H), 7.35 (m, 1H), 7.28 (m, 1H), 7.07 (m, 1H), 6.61 (m, 1H), 4.65 (m, 1H), 4.44 (m, 1H), 4.25 (m, 1H), 4.02 (m, 1H), 3.86 (m, 1H), 2.04 (m, 1H), 1.76 (m, 1H), 0.94 (m, 3H). MS (EI) for C$_{19}$H$_{17}$F$_3$IN$_3$O$_4$: 536 (MH$^+$).

Example 20(h)

3-(1-aminopropyl)-1-({3,4-difluoro-2-[(2-fluoro-4-iodophenyl)amino]phenyl}carbonyl)azetidin-3-ol: $^1$H NMR (400 MHz, CD$_3$OD): 7.45 (m, 1H), 7.34 (m, 1H), 7.28 (m, 1H), 7.05 (m, 1H), 6.61 (m, 1H), 4.21 (m, 1H), 4.09-3.86 (m, 2H), 3.78 (m, 1H), 2.63 (m, 1H), 1.50 (m, 1H), 1.24 (m, 1H), 0.98 (m, 3H). MS (EI) for C$_{19}$H$_{19}$F$_3$IN$_3$O$_2$: 506 (MH$^+$).

Example 20(i)

1-({3,4-difluoro-2-[(2-fluoro-4-iodophenyl)amino]phenyl}carbonyl)-3-[1-(ethylamino)propyl]azetidin-3-ol: $^1$H NMR (400 MHz, CD$_3$OD): 7.45 (m, 1H), 7.34 (m, 1H), 7.28 (m, 1H), 7.05 (m, 1H), 6.61 (m, 1H), 4.23 (m, 1H), 4.02 (m, 1H), 3.90 (m, 1H), 3.79 (m, 1H), 2.70 (m, 1H), 2.54 (m, 1H), 1.53 (m, 1H), 1.40 (m, 1H), 1.05 (m, 3H), 0.95 (m, 3H). MS (EI) for C$_{21}$H$_{23}$F$_3$IN$_3$O$_2$: 534 (MH$^+$).

Example 20(j)

3-[1-(diethylamino)propyl]-1-({3,4-difluoro-2-[(2-fluoro-4-iodophenyl)amino]phenyl}carbonyl)azetidin-3-ol: $^1$H NMR (400 MHz, CD$_3$OD): 7.44 (m, 1H), 7.33 (m, 1H), 7.27 (m, 1H), 7.07 (m, 1H), 6.60 (m, 1H), 4.21 (m, 1H), 4.10 (m, 1H), 4.03-3.70 (m, 2H), 2.71-2.45 (m, 5H), 1.67 (m, 1H), 1.49 (m, 1H), 0.94 (m, 9H). MS (EI) for C$_{23}$H$_{27}$F$_3$IN$_3$O$_2$: 562 (MH$^+$).

Example 20(k)

3-[amino(phenyl)methyl]-1-({3,4-difluoro-2-[(2-fluoro-4-iodophenyl)amino]phenyl}carbonyl)azetidin-3-ol): MS (EI) for C$_{23}$H$_{19}$F$_3$IN$_3$O$_2$: 554 (MH$^+$).

Example 20(m)

1-({3,4-difluoro-2-[(2-fluoro-4-iodophenyl)amino]phenyl}carbonyl)-3-(3-methyl-1-nitrobutyl)azetidin-3-ol): $^1$H NMR (400 MHz, CDCl$_3$): 8.38 (s, 1H), 7.39 (dd, 1H), 7.34-7.31 (m, 1H), 7.14-7.10 (m, 1H), 6.84-6.77 (m, 1H), 6.63-6.58 (m, 1H), 4.68 (dd, 1H), 4.23-4.04 (br m, 4H), 2.13 (t, 2H), 1.64-1.44 (br m, 3H), 0.93 (d, 6H); MS (EI) for C$_{21}$H$_{21}$F$_3$IN$_3$O$_4$: 564 (MH$^+$).

Example 20(n)

3-(1-aminobutyl)-1-({3,4-difluoro-2-[(2-fluoro-4-iodophenyl)amino]phenyl}carbonyl)azetidin-3-ol acetate salt: $^1$H NMR (400 MHz, CD$_3$OD): 7.48-7.43 (d, 1H), 7.38-7.33 (d, 1H), 7.32-7.26 (m, 1H), 7.09-7.00 (q, 1H), 6.66-6.58 (t, 1H), 4.33-4.22 (d, 1H), 4.13-3.81 (m, 3H), 3.17-3.09 (t, 1H), 1.93-1.89 (s, 3H), 1.89-1.82 (t, 3H), 1.56-1.24 (m, 4H), 0.97-0.88 (t, 3H); MS (EI) for C$_{20}$H$_{21}$F$_3$IN$_3$O$_2$: 520 (MH$^+$).

Example 20(o)

3-(1-aminocyclopentyl)-1-({3,4-difluoro-2-[(2-fluoro-4-iodophenyl)amino]phenyl}carbonyl)azetidin-3-ol acetate salt: $^1$H NMR (400 MHz, CDCl$_3$): 8.27-8.21 (s, 1H), 7.42-7.36 (d, 1H), 7.34-7.29 (d, 1H), 7.15-7.09 (t, 1H), 7.09-7.01 (q, 1H), 6.88-6.79 (q, 1H), 6.63-6.53 (m, 1H), 4.18-3.92 (m, 4H), 2.12-2.08 (s, 3H), 2.06-1.70 (m, 7H), 0.92-0.68 (m, 4H); MS (EI) for C$_{21}$H$_{21}$F$_3$IN$_3$O$_2$: 532 (MH$^+$).

Example 20(p)

N-{1-[1-({3,4-difluoro-2-[(2-fluoro-4-iodophenyl)amino]phenyl}carbonyl)-3-hydroxyazetidin-3-yl]ethyl}acetamide: $^1$H NMR (400 MHz, CDCl3): 8.42 (s, 1H), 7.41-7.38 (dd, 1H), 7.34-7.32 (dt, 1H), 7.12-7.09 (m, 1H), 6.85-6.78 (m, 1H), 6.63-6.57 (m, 1H), 5.76 (b, 1H), 4.28-3.98 (m, 5H), 2.00 (s, 3H), 1.20-1.19 (d, 3H); MS (EI) for C$_{20}$H$_{19}$F$_3$IN$_3$O$_3$: 534 (MH$^+$).

Example 20(q)

(2R)-N-{1-[1-({3,4-difluoro-2-[(2-fluoro-4-iodophenyl)amino]phenyl}carbonyl)-3-hydroxyazetidin-3-yl]ethyl}-3,3,3-trifluoro-2-(methyloxy)-2-phenylpropanamide: $^1$H NMR (400 MHz, CDCl3): 8.47 (s, 1H), 7.45-7.40 (m, 5H), 7.33-7.31 (m, 1H), 7.21-7.19 (m, 1H), 7.12-7.05 (m, 1H), 6.85-6.76 (m, 1H), 6.63-6.58 (m, 1H), 4.20-3.99 (m, 5H), 3.36 (s, 1.5H), 3.34 (s, 1.5H), 1.27-1.25 (d, 1.5H), 1.24-1.22 (d, 1.5H); MS (EI) for C$_{28}$H$_{24}$F$_6$IN$_3$O$_4$: 708 (MH$^+$).

Example 20(r)

(2R)-N-{(1R)-1-[1-({3,4-difluoro-2-[(2-fluoro-4-iodophenyl)amino]phenyl}carbonyl)-3-hydroxyazetidin-3-yl]ethyl}-3,3,3-trifluoro-2-(methyloxy)-2-phenylpropanamide: $^1$H NMR (400 MHz, CDCl3): 8.49 (s, 1H), 7.46-7.391 (m, 5H), 7.33-7.31 (m, 1H), 7.21-7.16 (m, 1H), 7.14-7.10 (m, 1H), 6.85-6.79 (m, 1H), 6.64-6.58 (m, 1H), 4.24-4.00 (m, 5H), 3.35 (s, 3H), 1.25-1.23 (d, 3H); MS (EI) for C$_{28}$H$_{24}$F$_6$IN$_3$O$_4$: 708 (MH$^+$).

Example 20(s)

1-({3,4-difluoro-2-[(2-fluoro-4-iodophenyl)amino]phenyl}carbonyl)-3-(1-methyl-1-nitroethyl)azetidin-3-ol: $^1$H NMR (400 MHz, CDCl3): 8.28 (s, 1H), 7.41-7.38 (dd, 1H), 7.34-7.32 (dt, 1H), 7.14-7.10 (m, 1H), 6.87-6.81 (m, 1H), 6.64-6.59 (m, 1H), 4.33-4.15 (m, 4H), 1.64 (s, 6H); MS (EI) for C$_{19}$H$_{17}$F$_3$IN$_3$O$_4$: 536 (MH$^+$).

Example 20(t)

3-(1-amino-1-methylethyl)-1-({3,4-difluoro-2-[(2-fluoro-4-iodophenyl)amino]phenyl}carbonyl)azetidin-3-ol: $^1$H NMR (400 MHz, CDCl3): 8.30 (s, 1H), 7.39-7.36 (dd, 1H), 7.32-7.30 (dt, 1H), 7.13-7.09 (m, 1H), 6.85-6.79 (m, 1H), 6.62-6.56 (m, 1H), 4.25-3.97 (m, 4H), 1.14 (s, 6H); MS (EI) for C$_{19}$H$_{19}$F$_3$IN$_3$O$_2$: 506 (MH$^+$).

Example 21

1-({3,4-Difluoro-2-[(2-fluoro-4-iodophenyl)amino]phenyl}carbonyl)-3-{1-[(trans-4-hydroxycyclohexyl)amino]ethyl}azetidin-3-ol hydrochloride

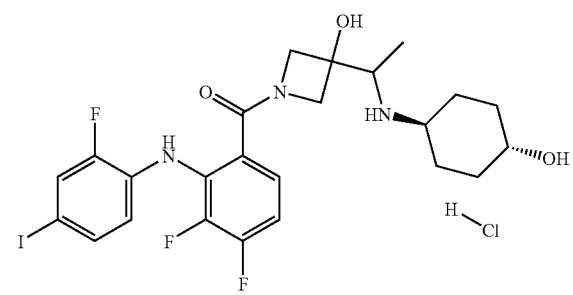

Potassium tert-butoxide (1.672 g, 14.9 mmol) and ethyltriphenylphosphonium bromide (5.538 g, 14.9 mmol) were stirred in ether (30 mL) at ambient for 1 h. 1,1-Dimethylethyl 3-oxoazetidine-1-carboxylate (954 mg, 6.0 mmol), prepared using procedures similar to those described in Example 3, was added and the mixture was 35° C. for 4.5 h. Mixture was filtered through celite and the solid was washed with ether. The filtrate was washed with water, brine, dried over anhydrous sodium sulfate, filtered and concentrated in vacuo. Column chromatography (silica gel, 20% ether in hexanes) gave 1,1-dimethylethyl 3-ethylideneazetidine-1-carboxylate (506 mg, 2.76 mmol, 49% yield): $^1$H NMR (400 MHz, CDCl$_3$): 5.37-5.28 (m, 1H), 4.47-4.39 (m, 4H), 1.56-1.51 (m, 3H), 1.45 (s, 9H).

1,1-Dimethylethyl 3-ethylideneazetidine-1-carboxylate (506 mg, 2.76 mmol), and 4-methylmorpholine N-oxide (1.04 g, 8.89 mmol) were dissolved in acetone/water (4:1; 30 mL) and osmium tetroxide (2.5 wt. % in t-butanol; 0.2 mL) was added. The solution was stirred at ambient for 5 days, then was quenched with saturated sodium bisulfate (2 mL) and concentrated in vacuo. The residue was partitioned between ethyl acetate and brine. The aqueous portion was extracted with ethyl acetate. The combined organic portion was washed with brine, dried over anhydrous sodium sulfate, filtered and concentrated in vacuo. Column chromatography (silica gel, ethyl acetate) gave 1,1-dimethylethyl 3-hydroxy-3-(1-hydroxyethyl)azetidine-1-carboxylate (375 mg, 1.73 mmol, 63% yield): $^1$H NMR (400 MHz, CDCl$_3$): 4.00-3.77 (m, 5H), 2.65 (br s, 1H), 1.86, (br s, 1H), 1.44 (s, 9H), 1.25 (d, 3H).

1,1-Dimethylethyl 3-hydroxy-3-(1-hydroxyethyl)azetidine-1-carboxylate (200 mg, 0.922 mmol) was dissolved in methanol (5 mL) and 4 N hydrochloric acid in dioxane (1 mL, 4 mmol) was added. The mixture was refluxed for 15 minutes and then was concentrated in vacuo to afford 3-(1-hydroxyethyl)azetidin-3-ol hydrochloride (0.922 mmol).

3,4-Difluoro-2-[(2-fluoro-4-iodophenyl)amino]benzoic acid (362 mg, 0.921 mmol), prepared using procedures similar to those described in U.S. Pat. No. 7,019,033, 4-(dimethylamino)pyridine (337 mg, 2.76 mmol) and 1-(3-dimethylaminopropyl)-3-ethylcarbodiimide hydrochloride (212 mg, 1.11 mmol) were dissolved in DMF (3 mL). The mixture was stirred at ambient for 5 minutes and then 3-(1-hydroxyethyl)azetidin-3-ol hydrochloride (0.922 mmol) in DMF (2 mL)

was added and the mixture was stirred for 15 h. The mixture was partitioned between ethyl acetate and 5% lithium chloride. The organic portion was washed with 20% citric acid, saturated sodium bicarbonate and brine, then was dried over anhydrous sodium sulfate, filtered and concentrated in vacuo. Column chromatography (silica gel, 80% ethyl acetate in hexanes) gave 1-({3,4-difluoro-2-[(2-fluoro-4-iodophenyl)amino]phenyl}carbonyl)-3-(1-hydroxyethyl)azetidin-3-ol (296 mg, 0.602 mmol, 65% yield): MS (EI) for $C_{18}H_{16}F_3IN_2O_3$: 493 (MH$^+$).

1-({3,4-Difluoro-2-[(2-fluoro-4-iodophenyl)amino]phenyl}carbonyl)-3-(1-hydroxyethyl)azetidin-3-ol (267 mg, 0.543 mmol), was dissolved in dichloromethane (10 mL) and treated with 4-(dimethylamino)pyridine (80 mg, 0.661 mmol) and 2,4,6-triisopropylbenzenesulfonyl chloride (183 mg, 0.604 mmol) at ambient for 15 h. Triethylamine (0.076 mL, 0.545 mmol) was added and the mixture was stirred at ambient for 3 h and then at 35° C. for 4 h and then at ambient for a further 15 h. 2,4,6-Triisopropylbenzenesulfonyl chloride (110 mg, 0.363 mmol) was added and the mixture was stirred at 35° C. for 3 h and then 4-(dimethylamino)pyridine (80 mg, 0.661 mmol) was added and the mixture was stirred at 35° C. for 2 h. 2,4,6-Triisopropylbenzenesulfonyl chloride (303 mg, 1.0 mmol) was added and the mixture was stirred at 35° C. for a further 18 h. The mixture was adsorbed on to silica and purified by column chromatography (silica gel, 30-50% ethyl acetate in hexanes) to give 1-[1-({3,4-difluoro-2-[(2-fluoro-4-iodophenyl)amino]phenyl}carbonyl)-3-hydroxyazetidin-3-yl]ethyl 2,4,6-tris(1-methylethyl)benzenesulfonate (201 mg, 0.265 mmol, 49% yield): MS (EI) for $C_{33}H_{38}F_3IN_2O_5S$: 759 (MH$^+$).

1-[1-({3,4-Difluoro-2-[(2-fluoro-4-iodophenyl)amino]phenyl}carbonyl)-3-hydroxyazetidin-3-yl]ethyl 2,4,6-tris(1-methylethyl)benzenesulfonate (194 mg, 0.256 mmol) was dissolved in tetrahydrofuran (2 mL) and was cooled to 0° C. Sodium hydride (60 wt % dispersion in oil; 31 mg, 0.775 mmol) was added and the mixture was stirred at 0° C. for 15 minutes. The mixture was quenched with saturated sodium bicarbonate solution and partitioned with ethyl acetate. The aqueous portion was extracted with ethyl acetate. The combined organic portion was washed with brine, dried over anhydrous sodium sulfate, filtered and concentrated in vacuo. Column chromatography (silica gel, 50% ethyl acetate in hexanes) gave 2,3-difluoro-N-(2-fluoro-4-iodophenyl)-6-[(2-methyl-1-oxa-5-azaspiro[2.3]hex-5-yl)carbonyl]aniline (120 mg, 0.253 mmol, 99% yield): MS (EI) for $C_{18}H_{14}F_3IN_2O_2$: 475 (MH$^+$).

2,3-Difluoro-N-(2-fluoro-4-iodophenyl)-6-[(2-methyl-1-oxa-5-azaspiro[2.3]hex-5-yl)carbonyl]aniline (50 mg, 0.105 mmol) was dissolved in dimethylsulfoxide (0.8 mL) and treated with trans-4-cyclohexanolamine (70 mg, 0.609 mmol) with 100 W microwave power at 100° C. for 45 minutes. The mixture was purified by reverse phase HPLC and the clean fractions were combined, neutralized with saturated sodium bicarbonate solution and the organic solvent was removed in vacuo. The remaining aqueous residue was extracted twice with ethyl acetate. The combined organic portion was washed with brine, dried over anhydrous sodium sulfate, filtered and concentrated in vacuo to give a residue which was treated with aqueous hydrochloric acid and then was lyophilized to afford 1-({3,4-difluoro-2-[(2-fluoro-4-iodophenyl)amino]phenyl}carbonyl)-3-{1-[(trans-4-hydroxycyclohexyl)amino]ethyl}azetidin-3-ol hydrochloride (36 mg, 0.058 mmol, 55% yield): $^1$H NMR (400 MHz, d$_6$-DMSO): 8.61 (br s, 0.5H), 8.55 (br s, 0.5H), 8.49-8.33 (m, 1H), 8.08-7.90 (m, 1H), 7.59 (dd, 1H), 7.39 (br d, 1H), 7.37-7.30 (m, 1H), 7.21 (br q, 1H), 6.81 (br d, 1H), 6.77-6.65 (m, 1H), 4.20 (br d, 1H), 4.09-4.02 (m, 1H), 3.97 (br d, 1H), 3.93-3.80 (m, 1H), 3.62-3.47 (m, 1H), 3.03-2.90 (m, 1H), 2.07-1.93 (m, 2H), 1.93-1.77 (m, 2H), 1.54-1.06 (m, 8H); MS (EI) for $C_{24}H_{27}F_3IN_3O_3$: 590 (MH$^+$).

Example 21(a)

Using the same or analogous synthetic techniques and substituting, as necessary, with alternative reagents, the following compound of the invention was prepared: 1-({3,4-Difluoro-2-[(2-fluoro-4-iodophenyl)amino]phenyl}carbonyl)-3-{1-[(1,1-dimethylethyl)amino]ethyl}azetidin-3-ol: $^1$H NMR (400 MHz, d$_6$-DMSO): 8.63 (br s, 0.4H), 8.53 (br s, 0.6H), 7.56 (dt, 1H), 7.40-7.34 (m, 1H), 7.32-7.26 (m, 1H), 7.25-7.13 (m, 1H), 6.72-6.62 (m, 1H), 5.43 (br s, 1H), 4.14-3.56 (m, 4H), 2.69-2.53 (m, 1H), 1.00-0.85 (br, 12H); MS (EI) for $C_{22}H_{25}F_3IN_3O_2$: 548 (MH$^+$).

Example 22(a) and 22(b)

1-({3,4-difluoro-2-[(2-fluoro-4-iodophenyl)amino]phenyl}carbonyl)-3-[(2R)-piperidin-2-yl]azetidin-3-ol

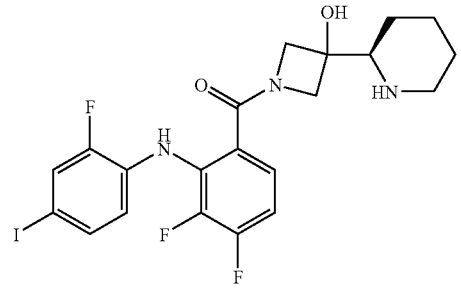

and 1-({3,4-difluoro-2-[(2-fluoro-4-iodophenyl)amino]phenyl}carbonyl)-3-[(2S)-piperidin-2-yl]azetidin-3-ol

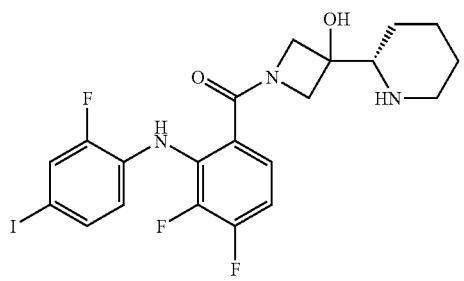

To a solution of 1,1-dimethylethyl 2-(3-hydroxy-1-{[(phenylmethyl)oxy]carbonyl}azetidin-3-yl)piperidine-1-carboxylate (368 mg, 0.94 mmol), prepared using procedures similar to those described in Reference 5, in dichloromethane (5 mL) was added DMAP (115 mg, 0.94 mmol) and the resulting solution was cooled to 0° C. (R)-(−)-α-Methoxy-α-trifluoromethylphenylacetyl chloride (105 μL, 0.56 mmol)

was added to the solution by syringe and the mixture was allowed to warm to room temperature then stirred an additional 12 hours. The solution was then partitioned with saturated aqueous sodium bicarbonate and the organic phase dried over anhydrous magnesium sulfate then filtered and concentrated to an oily residue. Silica gel flash chromatography using hexanes:ethyl acetate 3:1 as eluent afforded the less polar 1,1-dimethylethyl(2R)-2-(1-{[(phenylmethyl)oxy]carbonyl}-3-{[(2R)-3,3,3-trifluoro-2-(methyloxy)-2-phenylpropanoyl]oxy}azetidin-3-yl)piperidine-1-carboxylate (27.5 mg, 5% yield), the more polar 1,1-dimethylethyl(2S)-2-(1-{[(phenylmethyl)oxy]carbonyl}-3-{[(2R)-3,3,3-trifluoro-2-(methyloxy)-2-phenylpropanoyl]oxy}azetidin-3-yl)piperidine-1-carboxylate (105 mg, 19% yield) and starting material (253 mg, 69% recovery).

The starting material thus recovered was taken into dichloromethane (3 mL) followed by addition of DMAP (115 mg, 0.94 mmol) and (R)-(−)-α-methoxy-α-trifluoromethylphenylacetyl chloride (105 µL, 0.56 mmol) and the mixture was allowed to stir at room temperature over 12 hours. Proceeding as before afforded combined 1,1-dimethylethyl(2R)-2-(1-{[(phenylmethyl)oxy]carbonyl}-3-{[(2R)-3,3,3-trifluoro-2-(methyloxy)-2-phenylpropanoyl]oxy}azetidin-3-yl)piperidine-1-carboxylate (46.6 mg, 8% yield), the more polar 1,1-dimethylethyl(2S)-2-(1-{[(phenylmethyl)oxy]carbonyl}-3-{[(2R)-3,3,3-trifluoro-2-(methyloxy)-2-phenylpropanoyl]oxy}azetidin-3-yl)piperidine-1-carboxylate (228 mg, 41% yield) and starting material (100.8 mg, 27% recovery).

The starting material thus recovered was taken into tetrahydrofuran:dichloromethane (1:1, 2 mL) followed by addition of DMAP (47 mg, 0.39 mmol) and (R)-(−)-α-methoxy-α-trifluoromethylphenylacetyl chloride (80 µL, 0.43 mmol) and the mixture was heated to 60° C. over 12 hours. Proceeding as before afforded combined less polar 1,1-dimethylethyl(2R)-2-(1-{[(phenylmethyl)oxy]carbonyl}-3-{[(2R)-3,3,3-trifluoro-2-(methyloxy)-2-phenylpropanoyl]oxy}azetidin-3-yl)piperidine-1-carboxylate (144 mg, 26% yield). The chiral ester derivatives thus obtained were again subject to silica gel flash chromatography using hexanes:ethyl acetate 3:1 as eluent to give the pure less polar 1,1-dimethylethyl(2R)-2-(1-{[(phenylmethyl)oxy]carbonyl}-3-{[(2R)-3,3,3-trifluoro-2-(methyloxy)-2-phenylpropanoyl]oxy}azetidin-3-yl)piperidine-1-carboxylate (122.8 mg, 22% yield) and the more polar 1,1-dimethylethyl(2S)-2-(1-{[(phenylmethyl)oxy]carbonyl}-3-{[(2R)-3,3,3-trifluoro-2-(methyloxy)-2-phenylpropanoyl]oxy}azetidin-3-yl)piperidine-1-carboxylate (177.6 mg, 32% yield) both as colorless amorphous residues.

1,1-Dimethylethyl(2R)-2-(1-{[(phenylmethyl)oxy]carbonyl}-3-{[(2R)-3,3,3-trifluoro-2-(methyloxy)-2-phenylpropanoyl]oxy}azetidin-3-yl)piperidine-1-carboxylate (122.8 mg, 0.21 mmol) was taken into methanol (4 mL) followed by addition of 1M aqueous sodium hydroxide (1 mL) and the resulting solution was stirred for one hour at room temperature. The solution was then partitioned with ethyl acetate and 1N aqueous hydrochloric acid. The organic layer was washed with brine, dried over anhydrous magnesium sulfate then filtered and concentrated. The residue was purified by silica gel flash chromatography using hexanes:ethyl acetate 2:1 to give 1,1-dimethylethyl(2R)-2-(3-hydroxy-1-{[(phenylmethyl)oxy]carbonyl}azetidin-3-yl)piperidine-1-carboxylate (60.8 mg, 81% yield) a colorless amorphous solid. 1,1-dimethylethyl(2S)-2-(3-hydroxy-1-{[(phenylmethyl)oxy]carbonyl}azetidin-3-yl)piperidine-1-carboxylate (87.4 mg, 75% yield) was prepared analogously.

1,1-Dimethylethyl(2R)-2-(3-hydroxy-1-{[(phenylmethyl)oxy]carbonyl}azetidin-3-yl)piperidine-1-carboxylate (60.8 mg, 0.16 mmol) and 10% Pd/C (30 mg) were taken into methanol (2 mL) and the mixture hydrogenated at ambient pressure for one hour. The suspension was then filtered through a celite pad and concentrated then dried in vacuo to a colorless solid. The solid amine was taken into THF (1 mL) followed by addition of DIPEA (42 µL, 0.24 mmol) and 3,4-difluoro-2-[(2-fluoro-4-iodophenyl)amino]benzoyl fluoride (63 mg, 0.16 mmol), prepared using procedures similar to those described in Reference 1, and the mixture stirred at room temperature for 30 minutes. The reaction mixture was partitioned with ethyl acetate and 1 N aqueous hydrochloric acid and the organic layer washed with brine, dried over anhydrous magnesium sulfate then filtered and concentrated. Purification of the residue by silica gel flash chromatography using hexanes:ethyl acetate 3:2 as eluent afforded 1,1-dimethylethyl(2R)-2-[1-({3,4-difluoro-2-[(2-fluoro-4-iodophenyl)amino]phenyl}carbonyl)-3-hydroxyazetidin-3-yl]piperidine-1-carboxylate (74.9 mg, 74% yield) as an amorphous solid. 1,1-Dimethylethyl(2R)-2-[1-({3,4-difluoro-2-[(2-fluoro-4-iodophenyl)amino]phenyl}carbonyl)-3-hydroxyazetidin-3-yl]piperidine-1-carboxylate $^1$H NMR (400 MHz, CDCl$_3$): 8.53 (br s, 0.5H), 8.40 (br s, 0.5H), 7.41-7.38 (dd, 1H), 7.34-7.31 (dt, 1H), 7.17-7.14 (m, 1H), 6.86-6.79 (m, 1H), 6.63-6.587 (m, 1H), 4.24-3.90 (m, 4H), 3.37-3.23 (m, 1H), 2.90-2.80 (m, 1H), 1.85-1.54 (m, 7H), 1.43 (s, 9H); MS (EI) for C$_{26}$H$_{29}$F$_3$IN$_3$O$_4$: 576 (M-C$_4$H$_9$$^+$).

1,1-dimethylethyl(2R)-2-[1-({3,4-difluoro-2-[(2-fluoro-4-iodophenyl)amino]phenyl}carbonyl)-3-hydroxyazetidin-3-yl]piperidine-1-carboxylate (74.9 mg, 0.12 mmol) was taken into methanol (1 mL) followed by addition of 4 N HCl in dioxane (1 mL) and the solution was stirred at room temperature for one hour. The solution was then concentrated and the residue partitioned with chloroform and saturated aqueous sodium bicarbonate. The organic layer was washed with brine, dried over anhydrous sodium sulfate then filtered and concentrated. Purification of the residue by silica gel flash chromatography using ethyl acetate then concentrated aqueous ammonia in chloroform and methanol (0.1:10:1) as eluents afforded 1-({3,4-difluoro-2-[(2-fluoro-4-iodophenyl)amino]phenyl}carbonyl)-3-[(2R)-piperidin-2-yl]azetidin-3-ol (57.3 mg) as a colorless amorphous solid. The free base was taken into methanol (1 mL) then brought to about pH 1 by addition of 4 N HCl in dioxane and the solution concentrated. The residue was triturated with ethyl ether to afford a suspension. The solid was collected by filtration to afford 1-({3,4-difluoro-2-[(2-fluoro-4-iodophenyl)amino]phenyl}carbonyl)-3-[(2R)-piperidin-2-yl]azetidin-3-ol hydrochloride salt (49 mg, 72% yield) as a colorless solid. $^1$H NMR (400 MHz, CDCl$_3$): 8.43-8.39 (d, 1H), 7.41-7.38 (dd, 1H), 7.33-7.31 (dt, 1H), 7.14-7.10 (m, 1H), 6.84-6.80 (m, 1H), 6.63-6.57 (m, 1H), 4.12-3.99 (m, 4H), 3.10-3.08 (d, 1H), 2.72-2.69 (d, 1H), 2.64-2.62 (m, 1H), 1.61-1.58 (m, 2H), 1.36-1.16 (m, 4H); MS (EI) for C$_{21}$H$_{21}$F$_3$IN$_3$O$_2$: 532 (MH$^+$).

Using the same or analogous synthetic techniques and substituting, as necessary, with alternative reagents, the following compounds of the invention were prepared:

Example 22(c)

1,1-dimethylethyl(2 S)-2-[1-({3,4-difluoro-2-[(2-fluoro-4-iodophenyl)amino]phenyl}carbonyl)-3-hydroxyazetidin-3-yl]piperidine-1-carboxylate: $^1$H NMR (400 MHz, CDCl$_3$): 8.52 (br s, 0.5H), 8.39 (br s, 0.5H), 7.41-7.38 (dd, 1H), 7.34-7.31 (dt, 1H), 7.17-7.12 (m, 1H), 6.85-6.79 (m, 1H), 6.63-6.57 (m, 1H), 4.25-3.88 (m, 4H), 3.34-3.26 (m, 1H), 2.80-

2.90 (m, 1H), 1.85-1.54 (m, 7H), 1.43 (s, 9H); MS (EI) for $C_{26}H_{29}F_3IN_3O_4$: 576 (M-$C_4H_9^+$).

Example 22(d)

1-({3,4-difluoro-2-[(2-fluoro-4-iodophenyl)amino]phenyl}carbonyl)-3-[(2S)-piperidin-2-yl]azetidin-3-ol hydrochloride: $^1$H NMR (400 MHz, d$_4$-Methanol): 7.49-7.46 (dd, 1H), 7.37-7.35 (dt, 1H), 7.35-7.30 (m, 1H), 7.10-7.04 (m, 1H), 6.64-6.59 (m, 1H), 4.39-4.32 (dd, 1H), 4.21-4.18 (dd, 1H), 4.13-4.07 (m, 1H), 3.97-3.88 (dd, 1H), 3.57-3.32 (m, 1H), 3.02-2.96 (dd, 1H), 1.90-1.50 (m, 7H); MS (EI) for $C_{21}H_{21}F_3IN_3O_2$: 532 (MH$^+$).

Example 22(e)

1-({2-[(4-bromo-2-chlorophenyl)amino]-3,4-difluorophenyl}carbonyl)-3-piperidin-2-ylazetidin-3-ol acetate salt: $^1$H NMR (400 MHz, CD$_3$OD): 7.56 (d, 1H), 7.29-7.38 (m, 2H), 7.08-7.16 (m, 1H), 6.64-6.70 (m, 1H), 4.30-4.40 (m, 1H), 4.18-4.26 (m, 1H), 4.04-4.14 (m, 1H), 3.90-4.00 (m, 1H), 3.16-3.26 (m, 2H), 2.86-2.96 (m, 1H), 1.91 (s, 3H), 1.76-1.88 (m, 3H), 1.44-1.64 (m, 3H). MS (EI) for $C_{21}H_{21}BrClF_2N_3O_2$: 500 (M-H).

Example 22(f)

1-({2-[(4-bromo-2-fluorophenyl)amino]-3,4-difluorophenyl}carbonyl)-3-piperidin-2-ylazetidin-3-ol acetate salt: $^1$H NMR (400 MHz, DMSO): 8.52 (br s, 1H), 7.50 (d, 1H), 7.35-7.15 (m, 3H), 6.88-6.79 (m, 1H), 4.15-3.96 (m, 1H), 3.84-3.78 (m, 1H), 3.68-3.63 (m, 1H), 2.95-2.88 (m, 1H), 2.48-2.40 (m, 2H), 1.71-1.42 (m, 3H), 1.25-1.14 (m, 2H), 1.03-0.90 (m, 1H); MS (EI) for $C_{21}H_{21}BrF_3N_3O_2$: 485 (MH$^+$).

Example 22(g)

1-({3,4-difluoro-2-[(2-fluoro-4-iodophenyl)amino]phenyl}carbonyl)-3-pyrrolidin-2-ylazetidin-3-ol: $^1$H NMR (400 MHz, CD$_3$OD): 7.45 (dd, 1H), 7.37-7.31 (m, 1H), 7.30-7.25 (m, 1H), 7.13-6.99 (m, 1H), 6.67-6.54 (m, 1H), 4.20-4.09 (m, 1H), 4.08-3.91 (m, 2H), 3.88-3.79 (m, 1H), 3.27 (t, 1H), 2.99-2.89 (m, 1H), 2.88-2.81 (m, 1H), 1.93-1.67 (m, 3H), 1.55-1.42 (m, 1H). MS (EI) for $C_{20}H_{19}F_3IN_3O_2$: 518 (MH$^+$).

Example 22(h)

1-({3,4-difluoro-2-[(2-fluoro-4-iodophenyl)amino]phenyl}carbonyl)-3-(1-methylpyrrolidin-2-yl)azetidin-3-ol acetate (salt): $^1$H NMR (400 MHz, CD$_3$OD): 7.46 (dd, 1H), 7.38-7.26 (m, 2H), 7.12-6.99 (m, 1H), 6.66-6.56 (m, 1H), 4.37-3.87 (m, 4H), 2.94-2.82 (m, 1H), 2.75-2.63 (m, 3H), 2.20-2.06 (m, 1H), 2.00-1.67 (m, 8H). MS (EI) for $C_{21}H_{21}F_3IN_3O_2$: 532 (MH$^+$).

Example 22(i)

1-({3,4-difluoro-2-[(2-fluoro-4-iodophenyl)amino]phenyl}carbonyl)-3-(1-ethylpyrrolidin-2-yl)azetidin-3-ol acetate (salt): $^1$H NMR (400 MHz, CD$_3$OD): 7.46 (d, 1H), 7.38-7.33 (m, 1H), 7.32-7.27 (m, 1H), 7.12-7.01 (m, 1H), 6.66-6.57 (m, 1H), 4.34-3.89 (m, 4H), 3.57 (t, 1H), 3.51-3.40 (m, 1H), 3.28-2.81 (m, 3H), 2.25-1.72 (m, 8H), 1.31-1.18 (m, 3H). MS (EI) for $C_{22}H_{23}F_3IN_3O_2$: 546 (MH$^+$).

Example 22(j)

1-({4-fluoro-5-[(2-fluoro-4-iodophenyl)amino]-1-methyl-1H-benzimidazol-6-yl}carbonyl)-3-[(2S)-piperidin-2-yl]azetidin-3-ol acetate salt: $^1$H NMR (400 MHz, d$_4$-MeOH): 8.30 (s, 1H), 7.56 (s, 1H), 7.42 (d, 1H), 7.24 (d, 1H), 6.34 (m, 1H), 4.20 (d, 2H), 3.92 (s, 3H), 3.38-3.24 (m, 3H), 3.08 (bs, 1H), 2.88 (bs (1H), 1.90-1.70 (m, 3H), 1.66-1.32 (m, 3H); MS (EI) for $C_{23}H_{24}F_2IN_5O_2$: 568 (MH$^+$).

Example 22(k)

1-({7-fluoro-6-[(2-fluoro-4-iodophenyl)amino]-1-methyl-1H-benzimidazol-5-yl}carbonyl)-3-[(2S)-piperidin-2-yl]azetidin-3-ol acetate salt: $^1$H NMR (400 MHz, d$_4$-MeOH): 8.22 (s, 1H), 7.60 (s, 1H), 7.42 (d, 1H), 7.26 (d, 1H), 6.46 (m, 1H), 4.21 (d, 2H), 4.06 (s, 3H), 3.88 (m, 1H), 3.38-3.24 (m, 3H), 3.10 (bs, 1H), 2.88 (bs (1H), 1.88-1.70 (m, 3H), 1.64-1.28 (m, 3H); MS (EI) for $C_{23}H_{24}F_2IN_5O_2$: 568 (MH$^+$).

Example 22(m)

4-[(4-bromo-2-fluorophenyl)amino]-3-fluoro-5-({3-hydroxy-3-[(2S)-piperidin-2-yl]azetidin-1-yl}carbonyl)-1-methylpyridin-2(1H)-one: MS (EI) for $C_{21}H_{23}BrF_2N_4O_3$: 498 (MH$^+$).

Example 22(n)

1-({8-chloro-7-[(2-fluoro-4-iodophenyl)amino]imidazo[1,2-a]pyridin-6-yl}carbonyl)-3-[(2S)-piperidin-2-yl]azetidin-3-ol: $^1$H NMR (400 MHz, d$_6$-DMSO): 8.79 (s, 1H), 8.04 (d, 1H), 7.91 (d, 1H), 7.64 (dd, 1H), 7.55 (d, 1H), 6.95-7.02 (m, 1H), 4.38 (d, 1H), 4.15 (dd, 1H), 3.99 (dd, 1H), 3.72 (q, 1H), 3.32-3.39 (m, 1H), 3.00-3.12 (m, 1H), 1.93 (t, 3H), 1.51-1.70 (m, 3H); MS (EI) for $C_{22}H_{22}ClFIN_5O_2$: 532 (MH$^+$).

Example 22(o)

1-({7-[(4-bromo-2-chlorophenyl)amino]-8-chloroimidazo[1,2-a]pyridin-6-yl}carbonyl)-3-[(2S)-piperidin-2-yl]azetidin-3-ol: $^1$H NMR (400 MHz, d$_4$-MeOH): 8.85 (s, 1H), 8.06 (d, 1H), 7.91 (d, 1H), 7.71 (d, 1H), 7.45 (d, 1H), 7.01 (d, 1H), 4.48 (d, 1H), 4.10-4.27 (m, 2H), 3.87 (q, 1H), 3.37 (d, 2H), 3.02 (s, 1H), 1.88-1.94 (m, 3H), 1.58-1.69 (m, 3H); $C_{22}H_{22}BrCl_2N_5O_2$: 540 (MH$^+$).

Example 22(p)

1-({6-[(4-bromo-2-chlorophenyl)amino]-7-fluoro-3-methyl-1,2-benzisoxazol-5-yl}carbonyl)-3-[(2S)-piperidin-2-yl]azetidin-3-ol: $^1$H NMR (400 MHz, CDCl$_3$): 8.50 (m, 1H), 7.51 (d, 1H), 7.42 (s, 1H), 7.26 (dd, 1H), 6.79 (dd, 1H), 4.20-3.98 (br m, 4H), 3.11 (d, 1H), 2.77-2.50 (br m, 5H), 1.80-1.15 (br m, 6H); MS (EI) for $C_{23}H_{23}BrClFN_4O_3$: 537 (MH$^+$).

Example 22(q)

1-({3-fluoro-2-[(2-fluoro-4-iodophenyl)amino]phenyl}carbonyl)-3-[(2S)-piperidin-2-yl]azetidin-3-ol: $^1$H NMR (400 MHz, d$_4$-MeOH): 7.53 (2d, 1H), 7.46 (m, 2H), 7.16 (t, 1H), 6.86 (m, 1H), 6.63 (m, 1H), 4.36 (m, 1H), 4.22 (m, 1H), 4.02 (m, 1H), 3.88 (m, 1H), 3.08 (d, 1H), 2.66 (dd, 1H), 2.56 (m, 1H), 1.82 (bs, 1H), 1.66 (d, 1H), 1.58 (d, 1H), 1.38 (m, 2H), 1.22 (m, 1H); MS (EI) for $C_{21}H_{22}F_2IN_3O_2$: 514 (MH$^+$).

Example 22(r)

1-({4-fluoro-2-[(2-fluoro-4-iodophenyl)amino]phenyl}carbonyl)-3-[(2S)-piperidin-2-yl]azetidin-3-ol: $^1$H NMR (400 MHz, d$_4$-MeOH): 7.42 (2d, 1H), 7.34-7.18 (m, 4H), 6.46 (m, 1H), 4.10 (m, 2H), 3.84 (m, 2H), 3.04 (d, 1H), 2.52 (dd, 2H), 1.76 (bs, 0.5H), 1.58 (m, 2.5H), 1.32 (m, 2H), 1.18 (m, 0.5H), 1.04 (m, 0.5H); MS (EI) for $C_{21}H_{22}F_2IN_3O_2$: 514 (MH$^+$).

Example 22(s)

5-[(2-fluoro-4-iodophenyl)amino]-6-({3-hydroxy-3-[(2S)-piperidin-2-yl]azetidin-1-yl}carbonyl)-2-methylpyridazin-3(2H)-one: $^1$H NMR (400 MHz, d$_6$-DMSO): 10.19 (s, 1H), 7.78 (dd, 1H), 7.59 (d, 1H), 7.32 (t, 1H), 5.95 (s, 1H), 4.59 (q, 1H), 4.13-4.27 (m, 2H), 3.77 (d, 1H), 3.62 (s, 3H), 3.02 (d, 2H), 2.71 (d, 1H), 1.78 (s, 1H), 1.68 (d, 1H), 1.53 (d, 1H), 1.32 (s, 2H), 1.17 (t, 1H); MS (EI) for $C_{20}H_{23}FIN_5O_3$: 528 (MH+).

Example 23

1-{[1-({3,4-difluoro-2-[(2-fluoro-4-iodophenyl)amino]phenyl}carbonyl)-3-hydroxyazetidin-3-yl]methyl}-3-nitroguanidine hydrochloride

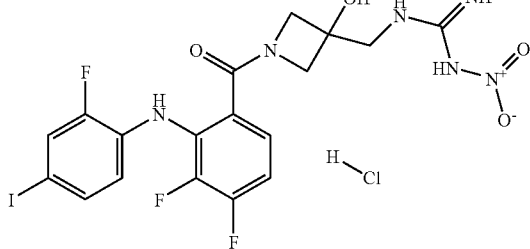

To a mixture of 2,3-difluoro-N-(2-fluoro-4-iodophenyl)-6-(1-oxa-5-azaspiro[2,3]hex-5-ylcarbonyl)aniline (0.15 g, 0.33 mmol), prepared using procedures similar to those described in Example 21, and nitroguanidine (0.1 g, 1.00 mmol) in tetrahydrofuran (3.00 mL) an aqueous solution of sodium hydroxide (1.0 mL, 2.0 mmol) was added and the reaction mixture was stirred at 70° C. for 16 hours. The reaction mixture was concentrated in vacuo. The crude product was purified by reverse phase preparative HPLC. The fractions were collected, and the solvent was concentrated. The residue was partitioned with ethyl acetate. The organic layer was washed with saturated aqueous sodium bicarbonate, brine and dried over anhydrous sodium sulfate. Filtration and concentration resulted in an amorphous residue, which was dissolved in methanol, and 4 N HCl in dioxane (80 μL, 0.33 mmol) was added to the solution. A white precipitate formed and was collected by filtration. The solid was washed with hexane, and dried to afford 76 mg (38%) 1-{[1-({3,4-difluoro-2-[(2-fluoro-4-iodophenyl)amino]phenyl}carbonyl)-3-hydroxyazetidin-3-yl]methyl}-3-nitroguanidine hydrochloride. $^1$H NMR (400 MHz, d$_4$-MeOH): 7.46 (2d, 1H), 7.36 (m, 1H), 7.29 (m, 1H), 7.02 (m, 1H), 6.63 (m, 1H), 4.22 (m, 1H), 4.01 (m, 2H), 3.86 (m, 1H), 3.51 (d, 2H); MS (EI) for $C_{18}H_{16}F_3IN_6O_4$: 565 (MH$^+$).

Example 23(a)

Using the same or analogous synthetic techniques and substituting, as necessary, with alternative reagents, the following compounds of the invention were prepared: 1-cyano-3-{[1-({3,4-difluoro-2-[(2-fluoro-4-iodophenyl)amino]phenyl}carbonyl)-3-hydroxyazetidin-3-yl]methyl}guanidine hydrochloride. $^1$H NMR (400 MHz, d$_4$-MeOH): 7.47 (2d, 1H), 7.36 (m, 1H), 7.27 (m, 1H), 7.03 (m, 1H), 6.63 (m, 1H), 4.18 (m, 1H), 3.98 (m, 2H), 3.80 (m, 1H), 3.43 (s, 2H); MS (EI) for $C_{19}H_{16}F_3IN_6O_2$: 545 (MH$^+$).

Example 24

6-({3-[(ethylamino)methyl]-3-fluoroazetidin-1-yl}carbonyl)-2,3-difluoro-N-(2-fluoro-4-iodophenyl)aniline

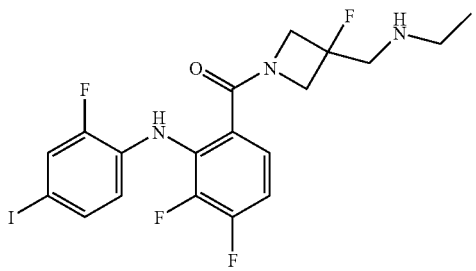

To 1,1-dimethylethyl [{1-({3,4-difluoro-2-[(2-fluoro-4-iodophenyl)amino]phenyl}carbonyl)-3-hydroxyazetidin-3-yl]methyl}ethylcarbamate (27 mg, 0.044 mmol), prepared using procedures similar to those in Example 3 and followed by Boc-protection, in chloroform (2.5 mL) added DAST (11.8 μL, 0.089 mmol) and stirred for 3.5 hr at room temperature. Quenched with water (15 mL), partitioned phases and extracted aqueous phase with chloroform (2×15 mL). The combined chloroform extracts were dried over sodium sulfate, filtered and the filtrate concentrated in vacuo. The residue was purified on a silica gel column to afford 1,1-dimethylethyl [{1-({3,4-difluoro-2-[(2-fluoro-4-iodophenyl)amino]phenyl}carbonyl)-3-fluoroazetidin-3-yl]methyl}ethyl carbamate (19.0 mg, 70%).

To the 1,1-dimethylethyl [{1-({3,4-difluoro-2-[(2-fluoro-4-iodophenyl)amino]phenyl}carbonyl)-3-fluoroazetidin-3-yl]methyl}ethylcarbamate (19.0 mg, 0.031 mmol) in acetonitrile (1.0 mL) added a solution 4.0N hydrogen chloride in dioxane (1.0 mL). After 1.5 hr the solution was concentrated in vacuo. The residue was purified by preparative reverse phase HPLC to afford the title compound (4.30 mg, 27%). $^1$H NMR (400 MHz, CDCl$_3$): 8.25 (s, 1H), 7.33 (dd, 1H), 7.33-7.25 (m, 1H), 7.18-7.14 (m, 1H), 6.84-6.77 (m, 1H), 6.63-

6.58 (m, 1H), 4.33-4.05 (br m, 4H), 3.07-2.95 (br m, 2H), 2.65 (q, 2H), 1.08 (t, 3H); MS (EI) for $C_{19}H_{18}F_4IN_3O$: 508 (MH$^+$).

Example 25

3-(2-aminocyclohexyl)-1-({3,4-difluoro-2-[(2-fluoro-4-iodophenyl)amino]phenyl}carbonyl)azetidin-3-ol

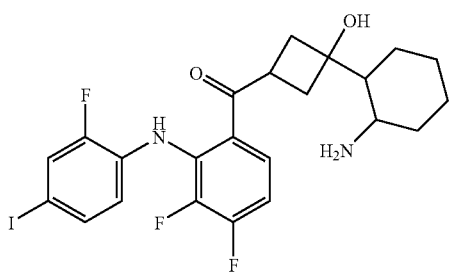

A solution of 1-(trimethylsiloxy)cyclohexene (200 mg, 1.17 mmol) and benzyl 3-oxoazetidine-1-carboxylate (289 mg, 1.41 mmol), prepared using procedures similar to those described in Reference 3, in tetrahydrofuran (3.90 mL) was cooled to −78° C. for 10 minutes followed by the addition of titanium tetrachloride (0.13 mL, 1.17 mmol). The reaction mixture stirred for an additional 5 hours at −78° C. The mixture was quenched with aqueous sodium bicarbonate and the aqueous layer was extracted with ether (2×). The organic layer was separated, dried over anhydrous sodium sulfate, filtered and the filtrate was concentrated in vacuo. The residue was purified on silica gel chromatography column (3:2 hexanes/ethyl acetate) to afford benzyl 3-hydroxy-3-(2-oxocyclohexyl)azetidine-1-carboxylate (328 mg, 37%). $^1$H NMR (CDCl$_3$): 7.28-7.34 (m, 5H), 5.08 (s, 2H), 4.02 (d, 1H), 3.89 (d, 1H), 3.87 (s, 1H), 3.55 (s, 1H), 2.71 (q, 1H), 2.29-2.43 (m, 2H), 2.11 (s, 2H), 1.95 (s, 1H), 1.66 (d, 3H); MS (EI) for $C_{17}H_{21}NO_4$: 303 (MH+).

A solution of benzyl 3-hydroxy-3-(2-oxocyclohexyl)azetidine-1-carboxylate (100 mg, 330 mmol) in methanol (1.60 mL) in the presence of ammonium acetate (191 mg, 2.48 mmol) was cooled to 0° C. for 1 hour. Sodium cyanoborohydride (81.5 mg, 1.30 mmol) was added and the mixture was stirred at room temperature for 16 hours. To the reaction mixture was added 6 N hydrogen chloride (800 µL) and extracted with ethyl acetate. The aqueous layer was basified with aqueous sodium bicarbonate (pH 9) and extracted with dichloromethane. The combined organic portion was dried over anhydrous sodium sulfate, filtered and concentrated in vacuo to afford benzyl-3-(2-aminocyclohexyl)-3-hydroxyazetidine-1-carboxylate (73.7 mg, 73%). MS (EI) for $C_{17}H_{24}N_2O_3$: 305 (MH+).

To a solution of benzyl-3-(2-aminocyclohexyl)-3-hydroxyazetidine-1-carboxylate (202 mg, 0.663 mmol) in dioxane-water (1:1, 2.5 mL) was added di-tert-butyl dicarbonate (138 mg, 0.630 mmol) and solid sodium bicarbonate (112 mg, 1.33 mmol). The reaction mixture was stirred at room temperature for 2 hours and evaporated. The residue was partitioned between ethyl acetate and water. The organic layer was washed with brine, dried over anhydrous sodium sulfate, filtered and concentrated in vacuo to afford benzyl 3-(2-tert-butoxycarbonylamino)cyclohexyl)-3-hydroxyazetidine-1-carboxylate (237 mg, 100%). $^1$H NMR (CH$_3$OH): 7.15-7.21 (m, 5H), 5.45 (s, 0.5H), 5.20 (d, 0.5H), 4.95 (s, 2H), 4.81 (s, 1H), 3.81 (d, 2H), 1.43-1.74 (m, 5H), 1.39 (s, 1H), 1.31 (s, 11H), 1.20 (s, 1H). MS (EI) for $C_{22}H_{32}N_2O_5$: 405 (MH+).

A solution of benzyl 3-(2-tert-butoxycarbonylamino)cyclohexyl)-3-hydroxyazetidine-1-carboxylate (237 mg, 0.586 mmol) in ethyl acetate (2 mL) was hydrogenated over 10% palladium-carbon (200 mg, 0.586 mmol) at 40 psi for 16 hours. The reaction mixture was filtered and concentrated in vacuo to provide tert-butyl 2-(3-hydroxyazetidin-3-yl)cyclohexylcarbamate (181 mg, 100%). $^1$H NMR (CDCl$_3$): 5.10 (s, 1H), 4.80 ((s, 1H), 3.78-3.86 (m, 1H), 3.61 (d, 1H), 3.57 (s, 1H), 3.36 (d, 1H), 1.77 (s, 2H). 1.40-1.53 (m, 1H), 1.36 (d, 9H), 1.25 (s, 2H). MS (EI) for $C_{14}H_{26}N_2O_3$: 271 (MH+).

To a solution of tert-butyl 2-(3-hydroxyazetidin-3-yl)cyclohexylcarbamate (181 mg, 0.669 mmol) and 3,4-difluoro-2-(2-fluoro-4-iodophenylamino)benzoyl fluoride (265 mg, 0.669 mmol), prepared using procedures similar to those described in Reference 1, in tetrahydrofuran (2.2 mL) was added N,N-diisopropylethylamine (110 µL) at room temperature. After an hour, the reaction mixture was heated to 50° C. and stirred for 45 minutes, at which time it was cooled to room temperature and evaporated. The residue was partitioned between ethyl acetate and 10% citric acid. The organic layer was washed with aqueous sodium chloride, dried over anhydrous sodium sulfate, filtered and concentrated in vacuo to afford tert-butyl-2-(1-(3,4-difluoro-2-(2-fluoro-4-iodophenylamino)benzoyl)-3-hydroxyazetidin-3-yl)cyclohexylcarbamate. This crude material was taken into the next step without further purification.

Tert-butyl-2-(1-(3,4-difluoro-2-(2-fluoro-4-iodophenylamino)benzoyl)-3-hydroxyazetidin-3-yl)cyclohexylcarbamate was dissolved in a mixture of methanol (4 mL) and hydrogen chloride (4 M in dioxane) (3 mL). The solution was heated to reflux then cooled to room temperature and stirred for 16 hours. The reaction mixture was concentrated and purified by reverse phase HPLC. The purified fractions were evaporated to dryness and partitioned between ethyl acetate and aqueous sodium bicarbonate. The organic layer was dried over sodium sulfate, filtered and concentrated in vacuo to afford an oil. The residue was taken up in methanol (2 mL) and was added hydrogen chloride (4M in dioxane) (700 µL) and evaporated to dryness to afford the title compound 3-(2-aminocyclohexyl)-1-({3,4-difluoro-2-[(2-fluoro-4-iodophenyl)amino]phenyl}carbonyl)azetidin-3-ol hydrochloride (44.7 mg, 12%).

$^1$H NMR (400 MHz, d$_6$-DMSO): 8.58 (d, 1H), 7.59 (dd, 1H), 7.54 (s, 2H), 7.38 (d, 1H), 7.33 (t, 1H), 7.16-7.25 (m, 1H), 6.69 (dt, 1H), 6.41 (s, 1H), 4.26 (d, 0.5H), 4.17 (d, 0.5H), 4.04 (t, 1H), 3.90 (t, 1H), 3.79 (d, 0.5H), 3.65-3.73 (m, 0.5H), 3.45-3.51 (m, 1H), 1.88 (s, 1H), 1.65-1.88 (m, 2H), 1.47 (s, 4H), 1.16-1.37 (m, 2H); MS (EI) for $C_{22}H_{23}F_3IN_3O_2$: 546 (MH$^+$).

Using the same or analogous synthetic techniques and substituting, as necessary, with alternative reagents, the following compounds of the invention were prepared:

Example 25(c)

3-(2-aminocyclopentyl)-1-({3,4-difluoro-2-[(2-fluoro-4-iodophenyl)amino]phenyl}carbonyl)azetidin-3-ol; $^1$H NMR (400 MHz, d$_6$-DMSO): 8.56 (d, 1H), 7.82 (d, 1H), 7.59 (td, 1H), 7.45 (s, 1H), 7.38 (d, 1H), 7.30-7.35 (m, 1H), 7.18-7.24 (m, 1H), 6.68-6.72 (m, 1H0, 6.41 (s, 0.5H), 6.17 (s, 0.5H), 3.91-4.27 (m, 2.5H), 3.78-3.86 (m, 1H), 3.65-3.73 (m, 1H), 3.44-3.52 (m, 0.5H), 2.19-2.26 (m, 1H), 1.54-1.94 (m, 5H), 1.30-1.39 (m, 1H); MS (EI) for $C_{21}H_{21}F_3IN_3O_2$: 532 (MH$^+$).

Example 25(a) and Example 25(b)

(±)-1-({3,4-difluoro-2-[(2-fluoro-4-iodophenyl)amino]phenyl}carbonyl)-3-[(trans)-2-hydroxycyclohexyl]azetidin-3-ol and (±)-1-({3,4-difluoro-2-[(2-fluoro-4-iodophenyl)amino]phenyl}carbonyl)-3-[(cis)-2-hydroxycyclohexyl]azetidin-3-ol The compounds of examples 25a and 25b were synthesized starting from benzyl 3-hydroxy-3-(2-oxycyclohenyl)azetidine-1-carboxylate prepared according to the procedure given in example 25. The ketone was reduced to give benzyl 3-hydroxy-3-(2-hydroxycyclohexyl)azetidine-1-carboxylate as a mixture of racemic diastereomers which were subjected to hydrogenation to afford 3-(2-hydroxycyclohexyl)azetidin-3-ol. 3-(2-hydroxycyclohexyl)azetidin-3-ol was then carried forward in a coupling step with 3,4-difluoro-2-(2-fluoro-4-iodophenylamino)benzoyl fluoride in the usual manner. The coupled material thus obtained was purified by preparative reverse phase HPLC where fraction 1 was tentatively assigned as (±)-1-({3,4-difluoro-2-[(2-fluoro-4-iodophenyl)amino]phenyl}carbonyl)-3-[(trans)-2-hydroxycyclohexyl]azetidin-3-ol (Example 25a) and fraction 2 was tentatively assigned as (±)-1-({3,4-difluoro-2-[(2-fluoro-4-iodophenyl)amino]phenyl}carbonyl)-3-[(cis)-2-hydroxycyclohexyl]azetidin-3-ol.

Example 25(a)

First eluting fraction: $^1$H NMR. (400 MHz, $d_4$-MeOH): 7.44 (2d, 1H), 7.34 (t, 1H), 7.25 (m, 1H), 7.03 (m, 1H), 6.60 (m, 1H), 4.46 (d, 0.5H), 4.28 (d, 0.5H), 4.22 (d, 0.5H), 3.98 (dd, 1H), 3.89 (d, 0.5H), 3.85 (s, 0.5H), 3.77 (d, 0.5H), 3.56 (m, 1H), 1.90 (m, 1H), 1.46-1.74 (m, 4H), 0.98-1.32 (m, 4H); MS (EI) for $C_{22}H_{22}F_3IN_2O_3$: 547 (MH$^+$).

Example 25(b)

Second eluting fraction: $^1$H NMR (400 MHz, $d_4$-MeOH): 7.44 (2d, 1H), 7.33 (d, 1H), 7.26 (m, 1H), 7.04 (m, 1H), 6.59 (dd, 1H), 4.20 (m, 1.5H), 4.19 (s, 0.5H), 4.00 (m, 1.5H), 3.86 (dd, 1H), 3.74 (d, 0.5H), 1.76 (m, 2H), 1.50-1.68 (m, 5H), 1.18-1.46 (m, 4H); MS (EI) for $C_{22}H_{22}F_3IN_2O_3$: 547 (MH$^+$).

Example 26

3-({[(E)-1-amino-2-nitroethenyl]amino}methyl)-1-({3,4-difluoro-2-[(2-fluoro-4-iodophenyl)amino]phenyl}carbonyl)azetidin-3-ol

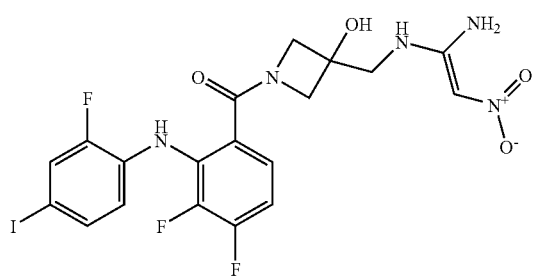

A solution of 3-(aminomethyl)-1-({3,4-difluoro-2-[(2-fluoro-4-iodophenyl)amino]phenyl}carbonyl)azetidin-3-ol (0.24 g, 0.5 mmol), prepared using procedures similar to those described in Example 3, and commercially available 1,1-bis(methylthio)-2-nitroethylene (0.083 g, 0.5 mmol) in ethanol (5 mL) was stirred at 70° C. for 16 hours. The reaction mixture was concentrated in vacuo. The residue was partitioned between ethyl acetate and water. The organic layer was washed with brine, dried over sodium sulfate, filtered and concentrated to afford 0.10 g, (39%) 1-({3,4-difluoro-2-[(2-fluoro-4-iodophenyl)amino]phenyl}carbonyl)-3-({[(Z)-1-(methylthio)-2-nitroethenyl]amino}methyl)azetidin-3-ol. MS (EI) for $C_{20}H_{18}F_3IN_4O_4S$: 595 (MH$^+$).

To a solution of (0.05 g 0.08 mmol) 1-({3,4-difluoro-2-[(2-fluoro-4-iodophenyl)amino]phenyl}carbonyl)-3-({[(Z)-1-(methylthio)-2-nitroethenyl]amino}methyl)azetidin-3-ol in ethanol (2 mL) was added ammonium hydroxide (0.1 mL, 0.8 mmol) and the reaction mixture was stirred at 70° C. for 16 hours. The reaction mixture was concentrated in vacuo. The crude product was purified by reverse phase preparative HPLC. The fractions were collected and the solvent was concentrated. The residue was partitioned with ethyl acetate. The organic layer was washed with saturated aqueous sodium bicarbonate, brine and dried over anhydrous sodium sulfate. Filtration and concentration resulted in an amorphous residue, which was dissolved in methanol, and 4 N HCl in dioxane (40 µL, 0.16 mmol) was added to the solution. A white precipitate formed and was collected by vacuum filtration. The solid was washed with hexane, and dried to afford 42 mg (87%) 3-({[(E)-1-amino-2-nitroethenyl]amino}methyl)-1-({3,4-difluoro-2-[(2-fluoro-4-iodophenyl)amino]phenyl}carbonyl)azetidin-3-ol hydrochloride. $^1$H NMR (400 MHz, $d_4$-MeOH): 7.58 (t, 0.5H), 7.44 (t, 0.5H), 7.36 (m, 1H), 7.31 (m, 1H), 7.04 (m, 1H), 6.63 (m, 1H), 3.90-4.30 (m, 4H) 3.72 (s, 2H); MS (EI) for $C_{19}H_{17}F_3IN_5O_4$: 564 (MH$^+$).

Example 27

1-({3,4-difluoro-2-[(2-fluoro-4-iodophenyl)amino]phenyl}carbonyl)-3-(1H-imidazol-2-ylmethyl)azetidin-3-ol

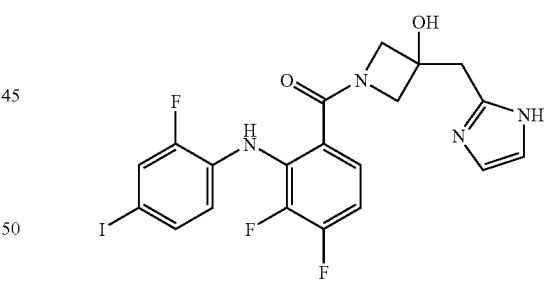

A solution of 2-methyl-1-({[2-(trimethylsilyl)ethyl]oxy}methyl)-1H-imidazole (0.5 g, 2.3 mmol) (prepared using procedures similar to those described in Clader et. al. *J. of Med. Chem.* 1995, 38(10), 1600-7) in tetrahydrofuran (5 mL) was cooled to −78° C., and n-butyllithium was added (2.5 M in hexanes, 0.990 mL, 2.5 mmol). After 2 hours, 1,1-dimethylethyl 3-oxoazetidine-1-carboxylate (0.60 g, 3.5 mmol), prepared using procedures similar to those described in Example 3, in 2.0 mL tetrahydrofuran was added and the solution was allowed to warm to room temperature and stirred overnight. The reaction mixture was quenched with an excess of saturated aqueous ammonium chloride solution and partitioned between water and ethyl acetate. The layers were separated and the aqueous layer was extracted with ethyl acetate (2×10 mL). The combined organic layers were dried over sodium sulfate, filtered and concentrated in vacuo. Column chromatography (silica gel, 3:1 hexanes/ethyl acetate) gave 0.37 g (41%) of 3-{[1-({[2-(trimethylsilyl)ethyl]oxy}methyl)-1H-imidazol-2-yl]methyl}azetidin-3-ol: $^1$H NMR (400 MHz, CDCl$_3$): 6.96-6.92 (m, 1H), 5.23 (s, 2H), 3.98 (d, 2H), 3.79 (d, 2H), 3.52-3.47 (m, 2H), 3.13 (s, 2H), 1.43 (s, 9H), 0.94-0.88 (m, 2H), 0.00 (s, 9H).

3-{[1-({[2-(trimethylsilyl)ethyl]oxy}methyl)-1H-imidazol-2-yl]methyl}azetidin-3-ol (0.19 g, 0.49 mmol) was dissolved in dichloromethane (1.5 mL) and trifluroacetic acid (1.5 mL) was added. The reaction mixture was stirred at room temperature overnight and the solvent was removed under vacuum to give 0.16 g of 3-(1H-imidazol-2-ylmethyl)azetidin-3-ol trifluoroacetate salt (87%). The crude residue was used without further purification for the next step.

To a solution of 3-(1H-imidazol-2-ylmethyl)azetidin-3-ol trifluoroacetate salt (0.16 g, 0.42 mmol) and N,N-diisopropylethylamine (0.370 mL, 2.13 mmol) in tetrahydrofuran (2.0 mL) 3,4-difluoro-2-[(2-fluoro-4-iodophenyl)amino]benzoyl fluoride (0.17 g, 0.42 mmol), prepared using procedures similar to those described in Reference 1, was added and the reaction mixture was stirred for 3 hours at room temperature. The solution was partitioned between ethyl acetate and saturated aqueous sodium bicarbonate and the organic layer was dried over sodium sulfate and concentrated in vacuo. Purification by reverse-phase HPLC followed by lyophilization of the pure fractions gave 0.032 g (13%) of 1-({3,4-difluoro-2-[(2-fluoro-4-iodophenyl)amino]phenyl}carbonyl)-3-(1H-imidazol-2-ylmethyl)azetidin-3-ol acetate salt: $^1$H NMR (400 MHz, CD$_3$OD): 7.45 (dd, 1H), 7.38-7.33 (m, 1H), 7.25-7.18 (m, 1H), 7.08-6.96 (m, 1H), 6.89 (s, 2H), 6.65-6.56 (m, 1H), 4.33-4.22 (m, 1H), 4.17-4.00 (m, 2H), 3.91-3.80 (m, 1H), 3.08 (s, 2H), 1.96 (s, 3H). MS (EI) for C$_{20}$H$_{16}$F$_3$IN$_4$O$_2$: 529 (MH$^+$).

Example 28

3-[(1R)-1-aminoethyl]-1-({3,4-difluoro-2-[(2-fluoro-4-iodophenyl)amino]phenyl}carbonyl)azetidin-3-ol

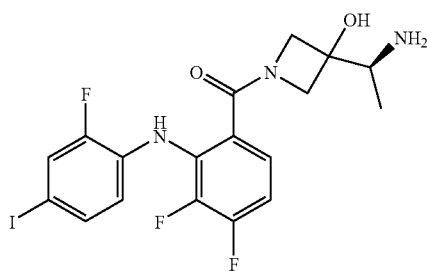

To a solution of diisopropylamine (6.5 mL, 46.3 mmol) in THF (200 mL) at −78° C. was added butyllithium (17 mL of a 2.5 M solution in hexanes, 42.5 mmol) over 5 min. The solution of lithium diisopropylamide was stirred for 15 min at −78° C. A solution of (S)-4-benzyl-3-propionyl-2-oxazolidinone (9.0 g, 38.6 mmol) in THF (100 mL) was added to the lithium diisopropylamide by addition funnel over 26 min. The reaction temperature was kept below −70° C. during the course of the addition. After the addition, the mixture was stirred for a further 30 min at −78° C. Then phenylmethyl 3-oxoazetidine-1-carboxylate (9.5 g, 46.3 mmol) was added by addition funnel over 25 minutes as a solution in THF (100 mL). Again, the reaction mixture was kept below −70° C. during the reagent addition. After stirring for an additional 1 hour at −78° C., the reaction mixture was quenched with saturated ammonium chloride solution and was then allowed to warm to rt. Water was added to dissolve any precipitated ammonium chloride, and ethyl acetate was added. The layers were partitioned, and the aqueous phase was extracted twice with ethyl acetate. The combined organic extracts were washed with 5% aqueous sodium bicarbonate, dried over sodium sulfate, filtered, and concentrated. The residue was purified by column chromatography (50% ethyl acetate:50% hexanes) to provide phenylmethyl 3-hydroxy-3-{(1R)-1-methyl-2-oxo-2-[(4S)-2-oxo-4-(phenylmethyl)-1,3-oxazolidin-3-yl]ethyl}azetidine-1-carboxylate as a white crystalline solid (6.03 g, 13.8 mmol, 36% yield). $^1$H NMR (400 MHz, CDCl$_3$) δ 7.37 (m, 8H), 7.20 (d, 2H), 5.12 (s, 2H), 4.66 (m, 1H), 4.27-4.20 (m, 2H), 4.10 (q, 1H), 4.03-3.93 (m, 3H), 3.28 (dd, 1H), 2.77 (dd, 1H), 1.29 (d, 3H).

A solution of lithium hydroxide monohydrate (1.16 g, 27.6 mmol) in 30% hydrogen peroxide (13.2 mL, 138 mmol) was prepared and was subsequently added slowly to a solution of phenylmethyl 3-hydroxy-3-{(1R)-1-methyl-2-oxo-2-[(4S)-2-oxo-4-(phenylmethyl)-1,3-oxazolidin-3-yl]ethyl}azetidine-1-carboxylate (6.03 g, 13.8 mmol) in THF (80 mL) and water (20 mL) at 0° C. After the mixture was stirred for 1 h at rt, the hydrogen peroxide was quenched carefully with 1 M sodium sulfite (150 mL, 150 mmol). The THF was removed in vacuo, and the mixture was then acidified to pH=2 with concentrated hydrochloric acid. The aqueous mixture was extracted twice with ethyl acetate. The combined organic extracts were dried over magnesium sulfate, filtered, and concentrated in vacuo. The resulting residue was purified by column chromatography (gradient, 5% methanol:95% dichloromethane to 10% methanol:90% dichloromethane) to provide (2R)-2-(3-hydroxy-1-{[(phenylmethyl)oxy]carbonyl}azetidin-3-yl)propanoic acid as a colorless oil (2.77 g, 9.9 mmol, 72% yield). $^1$H NMR (400 MHz, CDCl$_3$) δ 7.37-7.31 (m, 5H), 5.10 (s, 2H), 3.99 (s, 2H), 3.93 (s, 2H), 2.88 (q, 1H), 1.28 (d, 3H); MS (EI) for C$_{14}$H$_{17}$NO$_5$: 280 (MH$^+$).

To a solution of (2R)-2-(3-hydroxy-1-{[(phenylmethyl)oxy]carbonyl}azetidin-3-yl)propanoic acid (2.77 g, 9.9 mmol) in toluene (100 mL) was added triethylamine (1.52 mL, 10.9 mmol) followed by diphenyl phosphoryl azide (2.24 mL, 10.4 mmol). The mixture was heated to 80° C. for 2 h and was then cooled to rt. The volatile materials were removed in vacuo, and the residue was purified by column chromatography (gradient: 50% hexanes:50% ethyl acetate up to 100% ethyl acetate). The desired product, (8R)-8-methyl-6-oxo-5-oxa-2,7-diazaspiro[3.4]octane-2-carboxylic acid phenylmethyl ester, was isolated as a viscous, colorless syrup (1.84 g, 6.6 mmol, 67% yield). $^1$H NMR (400 MHz, CDCl$_3$) δ 7.39-7.32 (m, 5H), 5.66 (br s, 1H), 5.12 (s, 2H), 4.34 (dd, 1H), 4.30 (dd, 1H), 4.17 (dd, 1H), 4.05 (dd, 1H), 3.98 (q, 1H), 1.34 (d, 3H).

To a solution of (8R)-8-methyl-6-oxo-5-oxa-2,7-diazaspiro[3.4]octane-2-carboxylic acid phenylmethyl ester (1.84 g, 6.6 mmol) in methanol (66 mL) was added wet 10% palladium on carbon (50% by mass, 500 mg). The resulting suspension was stirred under 1 atm of hydrogen for 1 h. The catalyst was then removed by filtration through celite. The filtrate was concentrated in vacuo to provide (8R)-8-methyl-5-oxa-2,7-diazaspiro[3.4]octan-6-one as a white solid (0.99 g, quantitative yield). $^1$H NMR (400 MHz, CDCl$_3$) δ 5.23 (br s, 1H), 4.07 (d, 1H), 4.02 (d, 1H), 3.92 (d, 1H), 3.79 (d, 1H), 3.58 (d, 1H), 1.38 (d, 3H); MS (EI) for C$_6$H$_{10}$N$_2$O$_2$: 143 (MH$^+$).

A solution of (8R)-8-methyl-5-oxa-2,7-diazaspiro[3.4]octan-6-one (937 mg, 6.6 mmol), acetic acid (0.756 mL, 13.2 mmol), and benzaldehyde (1.0 mL, 9.9 mmol) in methanol (65 mL) was treated with sodium cyanoborohydride (829 mg, 13.2 mmol) at rt for 30 min. The mixture was then cooled to 0° C., and 3 N hydrochloric acid (100 mL) was added. The methanol was then removed in vacuo. The resulting aqueous solution was washed with ethyl acetate. The ethyl acetate wash was back extracted with 1 N hydrochloric acid, and the aqueous acidic phases were combined and basified with potassium carbonate. The organic phase was discarded. The aqueous mixture was then extracted three times with ethyl acetate. The combined organic extracts were dried over magnesium sulfate, filtered, and concentrated in vacuo. The desired (8R)-8-methyl-2-(phenylmethyl)-5-oxa-2,7-diazaspiro[3.4]octan-6-one was obtained in 93% purity as a milky colorless liquid (1.33 g, 5.73 mmol, 87% yield). MS (EI) for $C_{13}H_{16}N_2O_2$: 233 (MH⁺).

To a solution of (8R)-8-methyl-2-(phenylmethyl)-5-oxa-2,7-diazaspiro[3.4]octan-6-one (1.33 g, 5.7 mmol) in dioxane (40 mL) and water (20 mL) was added barium hydroxide octahydrate (9.0 g, 28.5 mmol), and the mixture was heated to reflux for 2 h. After cooling to rt, the mixture was acidified with 3 N hydrochloric acid (10 mL) and dichloromethane (50 mL) was added. The biphasic mixture was treated with potassium carbonate (1.6 g, 11.4 mmol) and di-tert-butyl dicarbonate (2.11 g, 9.7 mmol). After stirring vigorously at rt for 17 h, solids were removed by filtration, and the layers were partitioned. The aqueous phase was extracted with dichloromethane, and the organic extracts were combined and dried over magnesium sulfate, filtered, and concentrated. The residue was taken up in methanol (60 mL) and was treated with potassium carbonate (3.0 g, 22 mmol) added in two portions over 4 h at reflux. After cooling, the methanol was removed in vacuo, and the residual solids were loaded directly on to a silica column. After purification (5% methanol:95% dichloromethane), 1,1-dimethylethyl{(1R)-1-[3-hydroxy-1-(phenylmethyl)azetidin-3-yl]ethyl}carbamate was obtained as a colorless syrup (1.07 g, 3.5 mmol, 62% yield). MS (EI) for $C_{17}H_{26}N_2O_3$: 307 (MH⁺).

To a solution of 1,1-dimethylethyl{(1R)-1-[3-hydroxy-1-(phenylmethyl)azetidin-3-yl]ethyl}carbamate (1.07 g, 3.5 mmol) in methanol was added wet 10% palladium on carbon (50% by mass, 250 mg). The resulting suspension was subjected to 1 atmosphere of hydrogen for 7 h, and an additional 250 mg of catalyst was added over the course of the reaction. The catalyst was then removed by filtration through celite. The filtrate was then concentrated in vacuo to provide 1,1-dimethylethyl [(1R)-1-(3-hydroxyazetidin-3-yl)ethyl]carbamate as a colorless syrup (800 mg, quantitative yield). MS (EI) for $C_{10}H_{20}N_2O_3$: 161 (M-tert-butyl+H).

To a solution of 1,1-dimethylethyl [(1R)-1-(3-hydroxyazetidin-3-yl)ethyl]carbamate (200 mg, 0.92 mmol) in dichloromethane (5 mL) was added diisopropylethylamine (228 µL, 1.38 mmol) and 3,4-difluoro-2-[(2-fluoro-4-iodophenyl)amino]benzoyl fluoride (prepared according to the procedures described in Reference 1) (363 mg, 0.92 mmol). The mixture was stirred at rt for 16 h, after which the volatile materials were removed in vacuo. The residue was purified by column chromatography (50% hexanes:50% ethyl acetate) to provide 1,1-dimethylethyl{(1R)-1-[1-({3,4-difluoro-2-[(2-fluoro-4-iodophenyl)amino]phenyl}carbonyl)-3-hydroxyazetidin-3-yl]ethyl}carbamate as a colorless film (333 mg, 0.56 mmol, 61% yield). ¹H NMR (400 MHz, CDCl₃) δ 8.47 (br s, 1H), 7.40 (dd, 1H), 7.32 (d, 1H), 7.12 (m, 1H), 6.81 (m, 1H), 6.61 (m, 1H), 4.74 (br d, 1H), 4.22 (d, 1H), 4.15-4.07 (m, 2H), 3.96 (br s, 1H), 3.77 (m, 1H), 1.43 (s, 9H), 1.18 (d, 3H); MS (EI) for $C_{23}H_{25}F_3IN_3O_4$: 536 (M-tert-butyl+H).

A solution of 1,1-dimethylethyl{(1R)-1-[1-({3,4-difluoro-2-[(2-fluoro-4-iodophenyl)amino]phenyl}carbonyl)-3-hydroxyazetidin-3-yl]ethyl}carbamate (333 mg, 0.56 mmol) in methanol (10 mL) was treated with hydrochloric acid (4 N in dioxane, 1.4 mL, 5.6 mmol) at 60° C. for 30 min. After cooling, the volatile materials were removed in vacuo to provide 3-[(1R)-1-aminoethyl]-1-({3,4-difluoro-2-[(2-fluoro-4-iodophenyl)amino]phenyl}carbonyl)azetidin-3-ol hydrochloride as a white solid (285 mg, 0.54 mmol, 97% yield). ¹H NMR (400 MHz, DMSO-d₆) δ 8.56 (s, 1H), 7.83 (br s, 3H), 7.59 (dd, 1H), 7.39 (d, 1H), 7.34 (m, 1H), 7.21 (q, 1H), 6.69 (m, 1H), 6.65 (s, 1H), 4.25 (dd, 1H), 4.10 (dd, 1H), 3.98 (dd, 1H), 3.80 (m, 1H), 3.48 (m, 1H), 1.11 (dd, 3H); MS (EI) for $C_{18}H_{17}F_3IN_3O_2$: 492 (MH⁺)

To establish the enantiomeric excess (ee) of this material, 3-[(1R)-1-aminoethyl]-1-({3,4-difluoro-2-[(2-fluoro-4-iodophenyl)amino]phenyl}carbonyl)azetidin-3-ol hydrochloride (21 mg, 0.040 mmol) was dissolved in dichloromethane (400 µL) and was treated with diisopropylethylamine (20 µL, 0.12 mmol) and (R)-(−)-α-methoxy-α-(trifluoromethyl)phenylacetyl chloride at rt for 15 min. An aliquot was removed and was analyzed by chiral HPLC. The diastereomeric excess of (2S)-N-{(1R)-1-[1-({3,4-difluoro-2-[(2-fluoro-4-iodophenyl)amino]phenyl}carbonyl)-3-hydroxyazetidin-3-yl]ethyl}-3,3,3-trifluoro-2-(methyloxy)-2-phenylpropanamide was found to be 91%, and by extrapolation the ee of 3-[(1R)-1-aminoethyl]-1-({3,4-difluoro-2-[(2-fluoro-4-iodophenyl)amino]phenyl}carbonyl)azetidin-3-ol was also assigned to be 91%.

Example 28a

Using the sequence described above, beginning with (R)-4-benzyl-3-propionyl-2-oxazolidinone, 3-[(1S)-1-aminoethyl]-1-({3,4-difluoro-2-[(2-fluoro-4-iodophenyl)amino]phenyl}carbonyl)azetidin-3-ol was prepared using similar procedures except that the phenylmethyl 3-hydroxy-3-{(1S)-1-methyl-2-oxo-2-[(4R)-2-oxo-4-(phenylmethyl)-1,3-oxazolidin-3-yl]ethyl}azetidine-1-carboxylate required additional recrystallizations from isopropanol. Using the same method described above in Example 28, 3-[(1S)-1-aminoethyl]-1-({3,4-difluoro-2-[(2-fluoro-4-iodophenyl)amino]phenyl}carbonyl)azetidin-3-ol was determined to have 98.4% ee. ¹H NMR (400 MHz, DMSO-d₆) δ 8.56 (s, 1H), 7.84 (br s, 3H), 7.59 (dd, 1H), 7.39 (d, 1H), 7.34 (m, 1H), 7.21 (q, 1H), 6.69 (m, 1H), 6.65 (s, 1H), 4.25 (dd, 1H), 4.10 (dd, 1H), 3.98 (dd, 1H), 3.80 (m, 1H), 3.48 (m, 1H), 1.11 (dd, 3H); MS (EI) for $C_{18}H_{17}F_3IN_3O_2$: 492 (MH⁺).

Example 28b

To 3-[(1S)-1-aminoethyl]-1-({3,4-difluoro-2-[(2-fluoro-4-iodophenyl)amino]phenyl}carbonyl)azetidin-3-ol (87.4 mg, 0.18 mmol), prepared using procedures similar to those described in Example 28, was added formaldehyde (37% aqueous, 14 mg, 0.18 mmol) in methanol (2 mL) and sodium borohydride (7 mg, 0.18 mmol). The mixture was stirred for 3 h at rt, after which sodium borohydride (16 mg, 0.42 mmol) was added. Upon stirring an additional 1.25 h, more formaldehyde (37% aqueous, 1 drop) was added, and the mixture was stirred 3 days at rt. A further small spatula (~50 mg) of sodium borohydride was then added, and the mixture was stirred at rt for 30 min. After quenching with 1 N HCl, the reaction mixture was purified directly by preparative HPLC. The clean material was converted to its hydrochloride salt to provide 1-({3,4-difluoro-2-[(2-fluoro-4-iodophenyl)amino]phenyl}carbonyl)-3-[(1S)-1-(methylamino)ethyl]azetidin-3-ol as a yellow solid (21.7 mg, 0.040 mmol, 22% yield). $^1$H NMR (400 MHz, CD$_3$OD) δ 7.47 (dd, 1H), 7.36 (d, 1H), 7.31 (m, 1H), 7.06 (q, 1H), 6.62 (dt, 1H), 4.36 (dd, 1H), 4.21-3.91 (m, 3H), 3.44 (q, 1H), 2.66 (s, 3H), 1.29 (br m, 3H); MS (EI) for C$_{19}$H$_{19}$F$_3$IN$_3$O$_2$: 506 (MH$^+$).

Example 29

3-{[(1,1-Dimethylethyl)amino]methyl}-1-({4-[(2-fluoro-4-iodophenyl)amino]-3-thienyl}carbonyl)azetidin-3-ol

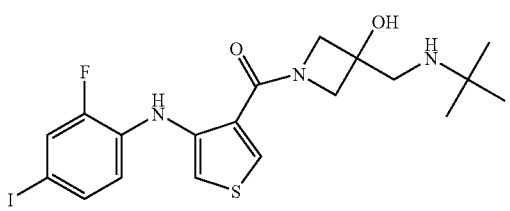

To a mixture of methyl 4-oxotetrahydrothiophene-3-carboxylate (1.75 g, 11 mmol) (commercially available or prepared using procedures similar to those described in Rossy et. al. *J. Org. Chem.* 1980, 45(4), 617-2) in 15 mL of ethanol was added 2-fluoro-4-iodoaniline (2.6 g, 11 mmol) followed by addition of several drops of acetic acid. The mixture was refluxed for 3 hrs. The mixture was cooled to room temperature and the product precipitated. This product was filtered off, washed with ethyl acetate, ether, dried in vacuo to afford the methyl 4-[(2-fluoro-4-iodophenyl)amino]-2,5-dihydrothiophene-3-carboxylate (1.7 g, 42%). $^1$HNMR (d$_6$-DMSO): 9.80 (s, 1H), 7.71 (d, 1H), 7.49 (dd, 1H), 7.24 (t, 1H), 4.10 (t, 2H), 3.79 (t, 2H), 3.69 (s, 3H); MS (EI) for C$_{12}$H$_{11}$FINO$_2$S: 380 (MH$^+$).

To a mixture of methyl 4-[(2-fluoro-4-iodophenyl)amino]-2,5-dihydrothiophene-3-carboxylate (1.2 g, 3.16 mmol) in 10 ml of anhydrous toluene was added 2,3,5,6-tetrachlorocyclohexa-2,5-diene-1,4-dione (0.78 g, 3.16 mmol). The mixture was refluxed for 2 h. The mixture was cooled to 50° C. and concentrated in vacuo to dryness and cooled to room temperature. To the residue was added ethanol and the mixture was refluxed for several minutes, cooled to room temperature and light blue crystalline product was filtered off and dried in vacuo to afford methyl 4-[(2-fluoro-4-iodophenyl)amino]thiophene-3-carboxylate (0.74 g, 62%). $^1$HNMR (d$_6$-DMSO): 8.78 (s, 1H), 8.42 (d, 1H), 7.64 (d, 1H), 7.46 (d, 1H), 7.37 (t, 1H), 7.14 (s, 1H), 3.85 (s, 3H); MS (EI) for C$_{12}$H$_9$FINO$_2$S: 378 (MH$^+$).

A mixture of methyl 4-[(2-fluoro-4-iodophenyl)amino]thiophene-3-carboxylate (0.74 g, 1.96 mmol) in the solution of potassium hydroxide (0.3 g) in ethanol/water (4 ml/4 ml) was heated up to 60° C. and stirred at this temperature for 30 min. The mixture was cooled to room temperature, diluted with 4 ml of water and extracted with ether. The water layer was acidified with 1 N HCl to pH 2, the product precipitated and was filtered off, washed several times with water and dried in vacuo to afford 4-[(2-fluoro-4-iodophenyl)amino]thiophene-3-carboxylic acid (0.59 g, 83%). $^1$H NMR (d$_6$-DMSO): 13.20 (s, 1H), 9.13 (s, 1H), 8.35 (d, 1H), 7.62 (dd, 1H), 7.48-7.38 (m, 2H), 7.11 (s, 1H); MS (EI) for C$_{11}$H$_7$FINO$_2$S: 362 (MH$^-$).

4-[(2-fluoro-4-iodophenyl)amino]thiophene-3-carboxylic acid (200 mg, 0.551 mmol), 4-(dimethylamino)pyridine (202 mg, 1.65 mmol) and 1-(3-dimethylaminopropyl)-3-ethylcarbodiimide hydrochloride (127 mg, 0.662 mmol) were dissolved in DMF (3 mL). The mixture was stirred at ambient for 5 minutes and then 3-(hydroxymethyl)azetidin-3-ol hydrochloride (72 mg, 0.516 mmol) was added and the mixture was stirred for 15 h. The mixture was partitioned between ethyl acetate and 20% citric acid. The aqueous portion was extracted with ethyl acetate. The combined organic portion was washed with 5% lithium chloride, saturated sodium bicarbonate and brine, then was dried over anhydrous sodium sulfate, filtered and concentrated in vacuo. The residue was crystallized from dichloromethane to afford 1-({4-[(2-fluoro-4-iodophenyl)amino]-3-thienyl}carbonyl)-3-(hydroxymethyl)azetidin-3-ol (247 mg, 0.551 mmol, quantitative yield) as off-white crystals: MS (EI) for C$_{15}$H$_{14}$FIN$_2$O$_3$S: 449 (MH$^+$).

1-({4-[(2-Fluoro-4-iodophenyl)amino]-3-thienyl}carbonyl)-3-(hydroxymethyl)azetidin-3-ol (247 mg, 0.551 mmol), was suspended in dichloromethane (10 mL) and treated with 4-(dimethylamino)pyridine (80 mg, 0.661 mmol), and 2,4,6-triisopropylbenzenesulfonyl chloride (183 mg, 0.604 mmol) at ambient for 15 h. The mixture was adsorbed on to silica and purified by column chromatography (silica gel, 30% ethyl acetate in hexanes) to give [1-({4-[(2-fluoro-4-iodophenyl)amino]-3-thienyl}carbonyl)-3-hydroxyazetidin-3-yl]methyl 2,4,6-tris(1-methylethyl)benzenesulfonate (101 mg, 0.141 mmol, 26% yield): MS (EI) for C$_{30}$H$_{36}$FIN$_2$O$_5$S$_2$: 715 (MH$^+$).

[1-({4-[(2-Fluoro-4-iodophenyl)amino]-3-thienyl}carbonyl)-3-hydroxyazetidin-3-yl]methyl 2,4,6-tris(1-methylethyl)benzenesulfonate (101 mg, 0.141 mmol) was dissolved in tetrahydrofuran (2 mL) and was treated with sodium hydride (60 wt % dispersion in oil; 17 mg, 0.425 mmol) at ambient for 20 minutes. Tetrahydrofuran (2 mL) and tert-butylamine (0.1 mL) were added and the mixture was stirred at ambient for 16 h. The mixture was concentrated in vacuo and partitioned between ethyl acetate and water. The organic portion was washed with brine, dried over anhydrous sodium sulfate, filtered and concentrated in vacuo. The residue was purified by reverse phase HPLC and the clean fractions were combined, neutralized with saturated sodium bicarbonate solution and the organic solvent was removed in vacuo. The remaining aqueous residue was extracted twice with ethyl acetate. The combined organic portion was washed with brine, dried over anhydrous sodium sulfate, filtered and concentrated in vacuo to afford 3-{[(1,1-dimethylethyl)amino]methyl}-1-({4-[(2-fluoro-4-iodophenyl)amino]-3-thienyl}carbonyl)azetidin-3-ol (8 mg, 0.016 mmol, 11% yield): $^1$H NMR (400 MHz, d$_6$-DMSO): 9.64 (br, 1H), 8.08 (d, 1H), 7.59 (dd, 1H), 7.44 (dd, 1H), 7.36 (t, 1H), 7.12 (d, 1H), 4.39 (d, 1H), 4.22 (d, 1H), 4.03 (d, 1H), 3.80 (d, 1H), 2.68 (br, 2H) 1.04 (s, 9H); MS (EI) for C$_{19}$H$_{23}$FIN$_3$O$_2$S: 504 (MH$^+$).

Using the same or analogous synthetic techniques and substituting, as necessary, with alternative reagents, the following compounds of the invention were prepared:

Example 29(a)

3-[(dimethylamino)methyl]-1-({4-[(2-fluoro-4-iodophenyl)amino]-3-thienyl}carbonyl)azetidin-3-ol: $^1$H NMR (400 MHz, CD$_3$OD): 7.91 (d, 1H), 7.46-7.41 (m, 2H), 7.33 (t, 1H), 7.00 (d, 1H), 4.66 (s, 1H), 4.49 (s, 1H), 4.30 (s, 1H), 4.15 (s, 1H), 3.54 (s, 1H), 3.17-3.13 (m, 3H), 2.90 (s, 2H), 1.87-1.83 (m, 3H); MS (EI) for $C_{17}H_{19}FIN_3O_2S$: 476 (MH$^+$).

Example 29(b)

1-({4-[(2-fluoro-4-iodophenyl)amino]-3-thienyl}carbonyl)azetidin-3-amine: $^1$H NMR (400 MHz, CD$_3$OD): 7.90 (d, 1H), 7.46-7.41 (m, 2H), 7.31 (t, 1H), 6.99 (d, 1H), 4.47 (br.s, 2H), 4.22-4.16 (m, 2H); MS (EI) for $C_{14}H_{13}FIN_3OS$: 418 (MH$^+$).

Example 30

3-(1-aminoethyl)-1-({8-chloro-7-[(2-fluoro-4-iodophenyl)amino]imidazo[1,2-a]pyridin-6-yl}carbonyl)azetidin-3-ol

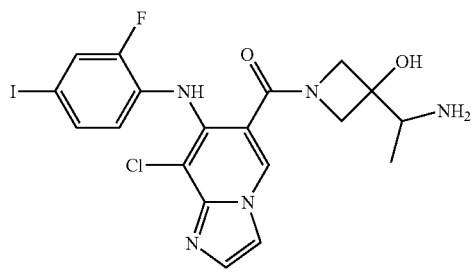

To a suspension of sodium hydride (72 mg, 1.75 mmol, 60% wt) in tetrahydrofuran (1 mL) cooled to 0° C. was added nitroethane (125 μL, 1.75 mmol). The suspension was allowed to warm to room temperature and was stirred for 15 minutes, then cooled back to 0° C. To the suspension was added dropwise a solution of 1,1-dimethylethyl 3-oxoazetidine-1-carboxylate (300 mg, 1.75 mmol, in 2 mL of tetrahydrofuran), prepared using procedures similar to those described in Reference 3. The suspension was stirred at room temperature for 1 hour. The reaction mixture was quenched by adding 20% aqueous citric acid, and then was partitioned with ethyl acetate. The aqueous portion was extracted twice using ethyl acetate and the combined organic portion was washed with saturated sodium bicarbonate, brine, dried over sodium sulfate, filtered and concentrated in vacuo to afford a colorless oil that was purified by column chromatography. Eluting with 30% ethyl acetate in hexanes, the isolated product was concentrated in vacuo to afford 250 mg, 1.02 mmol (58%) of 1,1-dimethylethyl 3-hydroxy-3-(1-nitroethyl)azetidine-1-carboxylate as a colorless oil. $^1$H NMR (400 MHz, DMSO): 6.46 (s, 1H), 5.01 (q, 1H), 4.24-3.97 (m, 2H), 3.77-3.60 (m, 2H), 1.41 (d, 3H), 1.39 (s, 9H).

1,1-Dimethylethyl 3-hydroxy-3-(1-nitroethyl)azetidine-1-carboxylate was dissolved in methanol (5 mL) and treated with 4 N HCl in dioxane. The solution was briefly heated to reflux and then was concentrated in vacuo to afford 178 mg, 0.98 mmol (96%) of 3-(1-nitroethyl)azetidin-3-ol hydrochloride as a white solid. $^1$H NMR (400 MHz, DMSO): 9.30 (br s, 1H), 8.96 (br s, 1H), 5.12 (q, 1H), 4.44-4.38 (m, 1H), 4.22-4.17 (m, 1H), 3.94-3.87 (m, 1H), 3.85-3.77 (m, 1H), 1.44 (d, 3H).

A solution of 8-chloro-7-[(2-fluoro-4-iodophenyl)amino]imidazo[1,2-a]pyridine-6-carboxylic acid (150 mg, 0.35 mmol) (prepared using procedures similar to those described in US 2006030610 and US 2005054701), N,N-diisopropylethylamine (300 μL, 1.74 mmol), PyBOP (180 mg, 0.35 mmol) and 3-(1-nitroethyl)azetidin-3-ol hydrochloride (76 mg, 0.42 mmol) in dimethylformamide (3 mL) was stirred at room temperature for 15 hours. The reaction mixture was then partitioned between 5% aqueous lithium chloride, and ethyl acetate. The aqueous portion was extracted twice using ethyl acetate. The combined organic portion was washed with 20% aqueous citric acid, brine, dried over sodium sulfate, filtered and concentrated in vacuo to afford a brown residue which was purified by column chromatography. Eluting with 5% methanol in dichloromethane, the isolated product was concentrated in vacuo to afford 195 mg, 0.35 mmol (100%) of 1-({8-chloro-7-[(2-fluoro-4-iodophenyl)amino]imidazo[1,2-a]pyridin-6-yl}carbonyl)-3-(1-nitro ethyl)azetidin-3-ol as a yellow foam. $^1$H NMR (400 MHz, CDCl$_3$): 8.28 (s, 1H), 7.68 (s, 1H), 7.59 (s, 1H), 7.43 (d, 1H), 7.31 (d, 1H), 7.23 (br s, 1H), 6.55-6.51 (m, 1H), 6.02 (br s, 1H), 4.79 (q, 1H), 4.45-3.96 (4H), 1.56 (d, 3H). MS (EI) for $C_{20}H_{19}ClFI_6O_4$: 560 (MH$^+$).

To a solution of 1-({8-chloro-7-[(2-fluoro-4-iodophenyl)amino]imidazo[1,2-a]pyridin-6-yl}carbonyl)-3-(1-nitroethyl)azetidin-3-ol (195 mg 0.35 mmol) in tetrahydrofuran/water (5 mL, 4:1) was added iron powder (193 mg, 3.5 mmol) and ammonium formate (438 mg, 7.0 mmol). The mixture was stirred at 80° C. for 1 hour, then cooled to room temperature and filtered through a pad of celite. The celite was washed three times with boiling ethanol (20 mL). The filtrate was concentrated in vacuo and the residue was diluted with ethyl acetate. The precipitate which formed was filtered through a pad a celite and the filtrate was partitioned with water. The aqueous portion was extracted twice with ethyl acetate. The combined organic portion was washed with brine, dried over sodium sulfate, filtered and concentrated in vacuo to afford a yellow residue which was purified by preparative reverse phase HPLC. The isolated product was concentrated in vacuo to afford 35 mg, 0.05 mmol (15%) of 3-(1-aminoethyl)-1-({8-chloro-7-[(2-fluoro-4-iodophenyl)amino]imidazo[1,2-a]pyridin-6-yl}carbonyl)azetidin-3-ol acetate salt as a white solid. $^1$H NMR (400 MHz, DMSO): 8.79 (s, 1H), 8.00 (s, 1H), 7.61 (s, 1H), 7.54 (d, 1H), 7.32 (d, 1H), 6.54-6.48 (m, 1H), 4.24-4.13 (m, 1H), 3.98-3.84 (m, 2H), 3.61-3.56 (m, 1H), 2.83 (q, 1H), 0.92-0.88 (m, 3H); MS (EI) for $C_{19}H_{18}ClFI_5O_2$: 530 (MH$^+$).

Example 31

1-({8-chloro-7-[(2-fluoro-4-iodophenyl)amino]imidazo[1,2-a]pyridin-6-yl}carbonyl)-3-piperidin-2-ylazetidin-3-ol

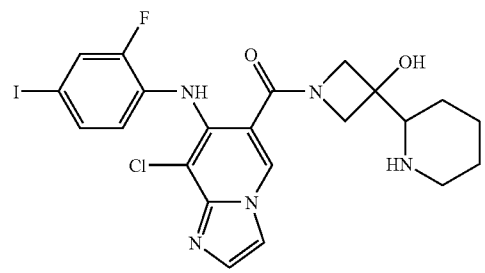

To a solution of 1,1-dimethylethyl 2-(3-hydroxy-1-{[(phenylmethyl)oxy]carbonyl}azetidin-3-yl)piperidine-1-carboxylate (595 mg, 1.52 mmol), prepared using procedures similar to those described in Reference 5, in methanol (5 mL)

was added catalytic palladium on carbon (5% wt). The heterogeneous mixture was stirred under a hydrogen gas atmosphere for 15 hours at ambient pressure and then was filtered. The filtrate was concentrated in vacuo to afford 385 mg, 1.50 mmol (98%) of 1,1-dimethylethyl 2-(3-hydroxyazetidin-3-yl)piperidine-1-carboxylate as a colorless film without further purification.

A solution of 8-chloro-7-[(2-fluoro-4-iodophenyl)amino] imidazo[1,2-a]pyridine-6-carboxylic acid (78 mg, 0.18 mmol) (prepared using procedures similar to those described in US 2006030610 and US 2005054701), 1,1-dimethylethyl 2-(3-hydroxyazetidin-3-yl)piperidine-1-carboxylate (46.7 mg, 0.18 mmol), 4-(dimethylamino)pyridine (66 mg, 0.55 mmol), and finally 1-(3-dimethylaminopropyl)-3-ethylcarbodiimide hydrochloride (42 mg, 0.21 mmol) in dimethylformamide (2 mL) was stirred at room temperature for 15 hours. The reaction mixture was partition between 5% aqueous lithium chloride and ethyl acetate and the aqueous portion was extracted twice using ethyl acetate. The combined organic portion was washed with 1 N HCl, brine, dried over sodium sulfate, filtered and concentrated in vacuo to afford a brown residue which was purified by column chromatography. Eluting with ethyl acetate, the isolated product was concentrated in vacuo to afford 101 mg, 0.15 mmol (83%) of 1,1-dimethylethyl 2-[1-({8-chloro-7-[(2-fluoro-4-iodophenyl)amino]imidazo[1,2-a]pyridin-6-yl}carbonyl)-3-hydroxyazetidin-3-yl]piperidine-1-carboxylate as a white solid. The solid was immediately dissolved in methanol (5 mL) and 4 N HCl in dioxane was added. The solution was briefly heated to reflux and then was concentrated in vacuo. The resultant residue was purified by preparative reverse phase HPLC. Isolated product was concentrated in vacuo to afford 36 mg, 0.06 mmol (40%) of 1-({8-chloro-7-[(2-fluoro-4-iodophenyl)amino]imidazo[1,2-a]pyridin-6-yl}carbonyl)-3-piperidin-2-ylazetidin-3-ol acetate as a white solid. $^1$H NMR (400 MHz, DMSO): 8.78 (s, 1H), 8.19 (s, 0.5H), 8.15 (s, 0.5H), 8.00 (s, 1H), 7.62 (s, 1H), 7.55 (d, 1H), 7.31 (d, 1H), 6.54-6.49 (m, 1H), 4.24-4.12 (m, 1H), 3.97-3.86 (m, 2H), 3.63-3.56 (m, 1H), 2.98-2.90 (m, 1H), 2.50-2.40 (m, 1H), 1.72-1.61 (m, 1H), 1.56-1.43 (m, 2H), 1.32-1.14 (m, 2H), 1.07-0.94 (m, 1H); MS (EI) for $C_{22}H_{22}ClIF_5O_2$: 570 (MH$^+$).

Using the same or analogous synthetic techniques and/or substituting with alternative reagents, the following compounds of the invention were prepared:

Example 31(a)

1-({4-fluoro-5-[(2-fluoro-4-iodophenyl)amino]-1-methyl-1H-benzimidazol-6-yl}carbonyl)-3-piperidin-2-ylazetidin-3-ol acetate salt: $^1$H NMR (400 MHz, DMSO): 8.35 (s, 1H), 7.84-7.77 (m, 1H), 7.54-7.49 (m, 2H), 7.25 (d, 1H), 6.31-6.25 (m, 1H), 4.04-3.92 (m, 2H), 3.90 (s, 3H), 3.86-3.78 (m, 1H), 3.70-3.62 (m, 1H), 2.94-2.85 (m, 1H), 2.45-2.32 (m, 2H), 1.66-1.36 (m, 3H), 1.26-1.08 (m, 2H), 1.01-0.80 (m, 1H); MS (EI) for $C_{23}H_{24}F_2IN_5O_2$: 568 (MH$^+$).

Example 31(a)

1-({7-[(4-bromo-2-chlorophenyl)amino]-8-chloroimidazo[1,2-a]pyridin-6-yl}carbonyl)-3-piperidin-2-ylazetidin-3-ol acetate salt: $^1$H NMR (400 MHz, DMSO): 8.87 (s, 1H), 8.29 (s, 0.5H), 8.21 (s, 0.5H), 8.04 (s, 1H), 7.67-7.63 (m, 2H), 7.32 (d, 1H), 6.59 (d, 1H), 4.35-4.22 (m, 1H), 4.08-3.98 (m, 2H), 3.72-3.67 (m, 1H), 2.96-2.88 (m, 1H), 2.50-2.44 (m, 2H), 1.66-1.42 (m, 3H), 1.26-1.17 (m, 2H), 1.04-0.94 (m, 1H); MS (EI) for $C_{22}H_{22}BrCl_2N_5O_2$: 540 (MH$^+$).

Example 32

3-(1-Amino-3-hydroxypropyl)-1-({3,4-difluoro-2-[(2-fluoro-4-iodophenyl)amino]phenyl}carbonyl) azetidin-3-ol trifluoroacetate salt

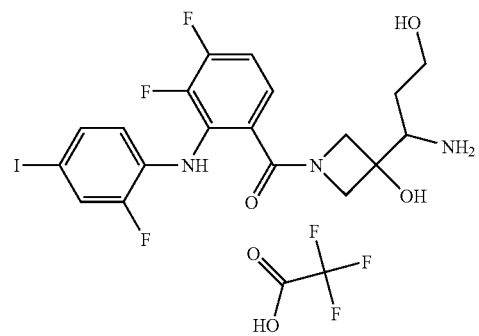

Potassium tert-butoxide (1.393 g, 12.4 mmol) and [2-(1,3-dioxolan-2-yl)ethyl]-triphenylphosphonium bromide (5.51 g, 12.4 mmol) were stirred in ether (30 mL) at amibient for 1 h. Phenylmethyl 3-oxoazetidine-1-carboxylate (1.025 g, 5.0 mmol), prepared using procedures similar to those described in Reference 3, was added and the mixture was stirred at 35° C. for 6 h and then at ambient for 4 days. Mixture was filtered through celite and the solid was washed with ether. The filtrate was washed with water, brine, dried over anhydrous sodium sulfate, filtered and concentrated in vacuo. Column chromatography (silica gel, 20% ether in hexanes) gave phenylmethyl 3-[2-(1,3-dioxolan-2-yl)ethylidene]azetidine-1-carboxylate (220 mg, 0.761 mmol, 15% yield): $^1$H NMR (400 MHz, CDCl$_3$): 7.39-7.28 (m, 5H), 5.43-5.35 (m, 1H), 5.11 (s, 2H), 4.89 (t, 1H), 4.56 (br d, 4H), 4.00-3.92 (m, 2H), 3.91-3.83 (m, 2H), 2.27 (br t, 2H).

Phenylmethyl 3-[2-(1,3-dioxolan-2-yl)ethylidene]azetidine-1-carboxylate (220 mg, 0.761 mmol), and 4-methylmorpholine N-oxide (287 mg, 2.45 mmol) were dissolved in acetone/water (4:1; 10 mL) and osmium tetroxide (4 wt. % in water; 0.05 mL) was added. The solution was stirred at ambient for 20 h, then was quenched with saturated sodium bisulfite (2 mL) and concentrated in vacuo. The residue was partitioned between ethyl acetate and brine. The aqueous portion was extracted with ethyl acetate. The combined organic portion was washed with brine, dried over anhydrous sodium sulfate, filtered and concentrated in vacuo. Column chromatography (silica gel, ethyl acetate) gave phenylmethyl 3-[2-(1,3-dioxolan-2-yl)-1-hydroxyethyl]-3-hydroxyazetidine-1-carboxylate (244 mg, 0.755 mmol, 99% yield): $^1$H NMR (400 MHz, CDCl$_3$): 7.38-7.28 (m, 5H), 5.11-5.07 (m, 3H), 4.14-4.01 (m, 4H), 3.96-3.86 (m, 5H), 3.47 (d, 1H), 2.97-2.94 (m, 1H), 1.98-1.84 (m, 2H).

Phenylmethyl 3-[2-(1,3-dioxolan-2-yl)-1-hydroxyethyl]-3-hydroxyazetidine-1-carboxylate (235 mg, 0.728 mmol) was dissolved in methanol (5 mL) and treated with 5 wt % palladium on carbon (50 mg) under hydrogen at ambient for 1.5 h. The mixture was filtered and the filtrate was concentrated in vacuo to afford 3-[2-(1,3-dioxolan-2-yl)-1-hydroxyethyl]azetidin-3-ol (0.729 mmol): MS (EI) for $C_8H_{15}NO_4$: 190 (MH$^+$).

3,4-Difluoro-2-[(2-fluoro-4-iodophenyl)amino]benzoic acid (287 mg, 0.730 mmol), prepared using procedures similar to those described in U.S. Pat. No. 7,019,033, 4-(dimethylamino)pyridine (178 mg, 1.46 mmol) and 1-(3-dimethylaminopropyl)-3-ethylcarbodiimide hydrochloride (168 mg, 0.88 mmol) were dissolved in DMF (3 mL). The mixture was stirred at ambient for 10 minutes and then 3-[2-(1,3-dioxolan-2-yl)-1-hydroxyethyl]azetidin-3-ol (0.729 mmol) in DMF (2 mL) was added and the mixture was stirred for 15 h. The mixture was partitioned between ethyl acetate and 5% lithium chloride. The organic portion was washed with 20% citric acid, saturated sodium bicarbonate and brine, then was dried over anhydrous sodium sulfate, filtered and concentrated in vacuo. Column chromatography (silica gel, gradient 90% ethyl acetate in hexanes to 100% ethyl acetate) gave 1-({3,4-difluoro-2-[(2-fluoro-4-iodophenyl)amino]phenyl}carbonyl)-3-[2-(1,3-dioxolan-2-yl)-1-hydroxyethyl]azetidin-3-ol (148 mg, 0.262 mmol, 36% yield): MS (EI) for $C_{21}H_{20}F_3IN_2O_5$: 565 (MH$^+$).

1-({3,4-Difluoro-2-[(2-fluoro-4-iodophenyl)amino]phenyl}carbonyl)-3-[2-(1,3-dioxolan-2-yl)-1-hydroxyethyl]azetidin-3-ol (148 mg, 0.262 mmol), was dissolved in dichloromethane (10 mL) and treated with 4-(dimethylamino)pyridine (38 mg, 0.31 mmol), triethylamine (0.036 mL, 0.262 mmol) and 2,4,6-triisopropylbenzenesulfonyl chloride (303 mg, 1.0 mmol) at 35° C. for 15 h. 2,4,6-Triisopropylbenzenesulfonyl chloride (100 mg, 0.33 mmol) was added and the mixture was stirred at 35° C. for 3.5 h. The mixture was adsorbed on to silica and purified by column chromatography (silica gel, 40-50% ethyl acetate in hexanes and then 100% ethyl acetate) to give 1-[1-({3,4-difluoro-2-[(2-fluoro-4-iodophenyl)amino]phenyl}carbonyl)-3-hydroxyazetidin-3-yl]-dioxolan-2-yl)ethyl 2,4,6-tris(1-methylethyl)benzenesulfonate (30 mg, 0.0361 mmol, 14% yield): MS (EI) for $C_{36}H_{42}F_3IN_2O_7S$: 831 (MH$^+$).

1-[1-({3,4-Difluoro-2-[(2-fluoro-4-iodophenyl)amino]phenyl}carbonyl)-3-hydroxyazetidin-3-yl]-2-(1,3-dioxolan-2-yl)ethyl 2,4,6-tris(1-methylethyl)benzenesulfonate (50 mg, 0.060 mmol) was dissolved in tetrahydrofuran (1 mL) and was cooled to 0° C. Sodium hydride (60 wt % dispersion in oil; 7 mg, 0.18 mmol) was added and the mixture was stirred at 0° C. for 45 minutes. The mixture was quenched with saturated sodium bicarbonate solution and partitioned with ethyl acetate. The aqueous portion was extracted with ethyl acetate. The combined organic portion was washed with brine, dried over anhydrous sodium sulfate, filtered and concentrated in vacuo. Column chromatography (silica gel, 50% ethyl acetate in hexanes) gave 6-{[2-(1,3-dioxolan-2-ylmethyl)-1-oxa-5-azaspiro[2.3]hex-5-yl]carbonyl}-2,3-difluoro-N-(2-fluoro-4-iodophenyl)aniline (31 mg, 0.057 mmol, 94% yield): MS (EI) for $C_{21}H_{18}F_3IN_2O_4$: 547 (MH$^+$).

6-{[2-(1,3-Dioxolan-2-ylmethyl)-1-oxa-5-azaspiro [2.3]hex-5-yl]carbonyl}-2,3-difluoro-N-(2-fluoro-4-iodophenyl)aniline (31 mg, 0.057 mmol) was dissolved in dimethylformamide (0.5 mL) and sodium azide (20 mg, 0.308 mmol) was added. The mixture was stirred at ambient for 22 h. The mixture was partitioned between ethyl acetate and 5% lithium chloride. The aqueous portion was extracted with ethyl acetate. The combined organic portion was washed with water, brine, then was dried over anhydrous sodium sulfate, filtered and concentrated in vacuo. Column chromatography (silica gel, 50% ethyl acetate in hexanes) gave 3-[1-azido-2-(1,3-dioxolan-2-yl)ethyl]-1-({3,4-difluoro-2-[(2-fluoro-4-iodophenyl)amino]phenyl}carbonyl)azetidin-3-ol (25 mg, 0.042 mmol, 74% yield): MS (EI) for $C_{21}H_{19}F_3IN_5O_4$: 590 (MH$^+$).

3-[1-Azido-2-(1,3-dioxolan-2-yl)ethyl]-1-({3,4-difluoro-2-[(2-fluoro-4-iodophenyl)amino]phenyl}carbonyl)azetidin-3-ol (24 mg, 0.041 mmol) was dissolved in tetrahydrofuran (0.5 mL) and treated with 5% aqueous hydrochloric acid (0.5 mL) at ambient for 15 h. The mixture was neutralised with saturated sodium bicarbonate solution and was extracted twice with ethyl acetate. The combined organic portion was washed with brine, dried over anhydrous sodium sulfate, filtered and concentrated in vacuo to afford 3-azido-3-[1-({3,4-difluoro-2-[(2-fluoro-4-iodophenyl)amino]phenyl}carbonyl)-3-hydroxyazetidin-3-yl]propanal (21 mg, 0.0385 mmol) which was suspended in ethanol (2 mL) and treated with sodium borohydride (5 mg, 0.132 mmol) at ambient for 2 h. The mixture was quenched with acetic acid (4 drops) and concentrated in vacuo. The residue was partitioned between saturated sodium bicarbonate solution and ethyl acetate. The aqueous portion was extracted with ethyl acetate. The combined organic portion was washed with brine, dried over anhydrous sodium sulfate, filtered and concentrated in vacuo. Column chromatography (silica gel, 70-80% ethyl acetate in hexanes) gave 3-(1-azido-3-hydroxypropyl)-1-({3,4-difluoro-2-[(2-fluoro-4-iodophenyl)amino]phenyl}carbonyl)azetidin-3-ol (14 mg, 0.0255 mmol, 62% yield from 3-[1-azido-2-(1,3-dioxolan-2-yl)ethyl]-1-({3,4-difluoro-2-[(2-fluoro-4-iodophenyl)amino]phenyl}carbonyl)azetidin-3-ol): $^1$H NMR (400 MHz, CDCl$_3$): 8.33 (br s, 1H), 7.40 (dd, 1H), 7.32 (br d, 1H), 7.13 (br t, 1H), 6.83 (br q, 1H), 6.61 (ddd, 1H), 4.32-3.94 (m, 4H), 3.92-3.84 (m, 1H), 3.82-3.71 (m, 2H), 2.56 (br, 1H), 1.94 (br, 2H), 1.26 (br, 1H); MS (EI) for $C_{19}H_{17}F_3IN_5O_3$: 548 (MH$^+$).

3-(1-Azido-3-hydroxypropyl)-1-({3,4-difluoro-2-[(2-fluoro-4-iodophenyl)amino]phenyl}carbonyl)azetidin-3-ol (14 mg, 0.0255 mmol) was dissolved in tetrahydrofuran and water (1:1, 0.5 mL) and polymer supported triphenylphosphine (~3 mmol/g; 20 mg, 0.06 mmol) was added. The mixture was stirred at 55° C. for 1 h. Triphenylphosphine (10 mg, 0.038 mmol) was added and the mixture was stirred at 55° C. for 1.5 h. The mixture was filtered and the filtrate was purified by reverse phase HPLC to afford 3-(1-amino-3-hydroxypropyl)-1-({3,4-difluoro-2-[(2-fluoro-4-iodophenyl)amino]phenyl}carbonyl)azetidin-3-ol trifluoroacetate salt (1.7 mg, 0.003 mmol, 10% yield): $^1$H NMR (400 MHz, CD$_3$OD): 7.47 (dd, 1H), 7.36 (br d, 1H), 7.33-7.28 (m, 1H), 7.05 (br q, 1H), 6.62 (ddd, 1H), 4.38-4.26 (m, 1H), 4.18-4.00 (m, 2H), 3.98-3.88 (m, 1H), 3.78-3.67 (m, 2H), 3.61-3.56 (m, 1H), 1.87-1.70 (m, 2H); MS (EI) for $C_{19}H_{19}F_3IN_3O_3$: 522 (MH$^+$).

Example 33

1-({3,4-difluoro-2-[(2-fluoro-4-iodophenyl)amino]phenyl}carbonyl)-3-(6-methylpiperidin-2-yl)azetidin-3-ol

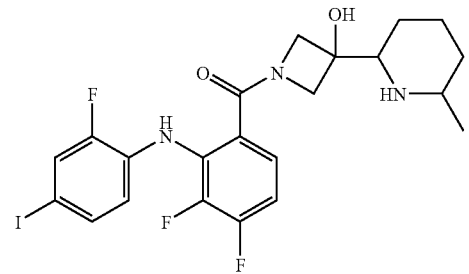

To a solution of N,N-diisopropylamine (1.6 mL, 11.2 mmol) cooled to −78° C. in THF (15 mL) was added a 2.5 M solution of n-BuLi in hexane (4.5 mL, 11.2 mmol) dropwise over 5 minutes and the mixture was stirred at this temperature for an addition 15 minutes. 6-methyl-1-(phenylmethyl)piperidine-2-carbonitrile (2.4 g, 11.2 mmol) (prepared using procedures similar to those in Bonin et. al. *Tet. Lett.* 1982, 23(33), 3369-72) in THF (10 mL) was then added dropwise over 20 minutes and the reaction mixture was stirred for a further 30 minutes. Next a solution of 1,1-dimethylethyl 3-oxoazetidine-1-carboxylate (1.3 g, 7.5 mmoL), prepared using procedures similar to those in Example 3, in THF (10 mL) was added dropwise over 30 minutes. The reaction mixture was gradually warmed to room temperature and allowed to stir overnight. The reaction mixture was quenched with 10% citric acid and extracted with ethyl acetate (3×50 mL). The combined organic layers were washed with water, brine, dried over anhydrous sodium sulfate then filtered and concentrated in vacuo to give crude product as yellow oil. Further purification by flash chromatography (30% ethyl acetate in hexanes) afforded 1,1-dimethylethyl 3-[2-cyano-6-methyl-1-(phenylmethlyl)piperidin-2-yl]-3-hydroxyazetidine-1-carboxylate as a pale yellow oil (0.2 g, 7% yield). $^1$H NMR (400 MHz, CDCl$_3$): 7.17-7.40 (m, 5H), 4.42 (d, 1H), 4.04-4.18 (m, 1H), 3.83-4.00 (m, 1H), 3.70-3.75 (m, 2H), 1.70-1.87 (m, 4H), 1.45 (s, 3H), 1.41 (s, 9H), 1.22-1.26 (m, 1H), 1.13-1.18 (m, 2H); MS (EI) for C$_{22}$H$_{31}$N$_3$O$_3$: 386 (MH$^+$).

To a stirred solution of 1,1-dimethylethyl 3-[2-cyano-6-methyl-1-(phenylmethyl)piperidin-2-yl]-3-hydroxyazetidine-1-carboxylate (180 mg, 0.47 mmol) in ethanol (1 mL) was added acetic acid (53.5 µL, 0.94 mmol) followed by sodium cyanoborohydride (58.7 mg, 0.94 mmol) and the reaction mixture stirred at 70° C. overnight. After cooling to room temperature the suspension was filtered through celite and the solid washed with additional ethanol. The filtrate was concentrated in vacuo and taken up in ethyl acetate (30 mL). The organic layer was washed with 2 M sodium hydroxide solution. The sodium hydroxide layer was separated and washed with ethyl acetate (10 mL). The combined organic layers were washed with brine, dried over anhydrous magnesium sulfate and concentrated in vacuo to give crude1,1-dimethylethyl 3-hydroxy-3-[6-methyl-1-(phenylmethyl)piperidin-2-yl]azetidine-1-carboxylate as yellow oil (60 mg, 36% yield). Crude product was used further without purification. $^1$H NMR (400 MHz, CDCl$_3$): 7.22-7.35 (m, 5H), 4.08 (d, 1H), 3.85-3.96 (m, 3H), 3.57 (d, 1H), 3.33-3.36 (m, 1H), 2.91-3.06 (m, 2H), 1.63-1.70 (m, 4H), 1.44 (s, 9H), 1.23 (d, 3H), 1.05 (d, 2H); MS (EI) for C$_{21}$H$_{32}$N$_2$O$_3$: 361 (MH$^+$).

To a solution of 1,1-dimethylethyl 3-hydroxy-3-[6-methyl-1-(phenylmethyl)piperidin-2-yl]azetidine-1-carboxylate (60 mg, 0.16 mmol) in methanol (0.5 mL) was added hydrogen chloride (4N in dioxane, 0.5 mL) and the reaction mixture stirred at 60° C. for one hour. The reaction mixture was cooled to room temperature and concentrated in vacuo and aezotroped 3 times from methanol and diethyl ether. On drying the hydrochloride salt of 3-[6-methyl-1-(phenylmethyl)piperidin-2-yl]azetidin-3-ol was obtained as a dark brown residue (40 mg, 81% yield), which was used further without purification. $^1$H NMR (400 MHz, CD$_3$OD): 7.58-7.63 (m, 2H), 7.47-7.49 (m, 3H), 4.78 (d, 1H), 4.44-4.62 (m, 2H), 4.29 (s, 2H), 4.22-4.26 (m, 1H), 4.12-4.18 (m, 1H), 4.08 (s, 1H); 1.60-2.00 (m, 8H), 1.48 (d, 3H); MS (EI) for C$_{16}$H$_{25}$ClN$_2$O: 261 (MH$^+$).

To a solution of 3-[6-methyl-1-(phenylmethyl)piperidin-2-yl]azetidin-3-ol hydrochloride (40 mg, 0.13 mmol) in ethyl acetate (3 mL) was added acetic acid (0.5 mL) and Pd/C (50 mg) and the mixture was hydrogenated at 35 psi for 3 hours. The reaction mixture was filtered through celite. The filtrate was concentrated in vacuo. The obtained residue was dissolved in a small amount of ethyl acetate and concentrated hydrochloric acid was added and the mixture was concentrated in vacuo to give the crude dihydrochloride salt of 3-[6-methylpiperidin-2-yl]azetidin-3-ol (20 mg, 54%). The crude product was used further without purification. $^1$H NMR (400 MHz, CD$_3$OD): 4.20-4.40 (m, 1H), 4.00-4.10 (m, 1H), 3.60-3.90 (m, 2H), 1.50-2.00 (m, 6H), 1.45 (d, 3H), 1.26-1.30 (m, 1H); MS (EI) for C$_9$H$_{20}$Cl$_2$N$_2$O: 171 (MH$^+$).

To a 0° C. solution of 3-[6-methylpiperidin-2-yl]azetidin-3-ol dihydrochloride (20 mg, 0.08 mmol) in DMF (1 mL) was added N,N-diisopropylethylamine (42 µL, 0.26 mmol) followed by 3,4-difluoro-2-[(2-fluoro-4-iodophenyl)amino] benzoyl fluoride (32 mg, 0.08 mmol), prepared using procedures similar to those described in Reference 1, and the reaction mixture stirred at 0° C. for 30 min. The mixture was diluted with acetonitrile and purified by preparative reverse phase HPLC (CH$_3$CN/H$_2$O with 0.1% TFA). Fractions were collected and lyophilized to give 1-({3,4-difluoro-2-[(2-fluoro-4-iodophenyl)amino]phenyl}carbonyl)-3-(6-methylpiperidin-2-yl)azetidin-3-ol acetate salt (7 mg, 16% yield) as a white solid. $^1$H NMR (400 MHz, CD$_3$OD): 7.44-7.50 (m, 1H), 7.34-7.37 (m, 1H), 7.28-7.32 (m, 1H), 7.02-7.12 (m, 1H), 6.60-6.63 (m, 1H), 4.10-4.30 (m, 2H), 3.95-4.09 (m, 2H), 3.80-3.95 (m, 1H), 3.55-3.65 (m, 1H), 3.34-3.36 (m, 1H), 1.90 (s, 3H), 1.62-1.84 (m, 6H), 1.40-1.52 (m, 1H), 1.33 (d, 3H); MS (EI) for C$_{22}$H$_{23}$F$_3$IN$_3$O$_2$: 546 (MH$^+$).

Example 34

1-({3,4-difluoro-2-[(2-fluoro-4-iodophenyl)amino] phenyl}carbonyl)-3-piperazin-2-ylazetidin-3-ol

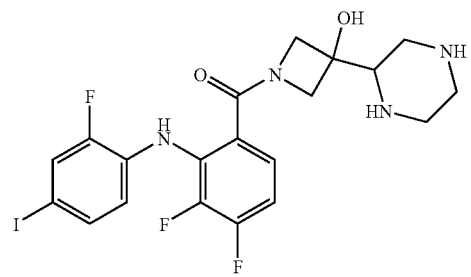

To a solution of commercially available 1,4-bis(phenylmethyl)piperazine-2,5-dione (2.0 g, 6.8 mmol) in dry THF (50 mL) at −78° C. was added lithium diisopropylamide (2.0 M solution in heptane/THF/ethylbenzene, 3.4 mL, 6.8 mmol). The resulting reddish brown suspension was stirred for 23 min at −78° C., and then a solution of 1,1-dimethylethyl 3-oxoazetidine-1-carboxylate (770 mg, 4.5 mmol) in THF (10 mL) was added over 30 min by syringe pump. The mixture became a bright yellow solution as it was allowed to warm to room temperature over 3 hours. The mixture was quenched with saturated aqueous ammonium chloride. Water was added to dissolve precipitated salts, and the resulting mixture was extracted twice with ethyl acetate. The combined organic extracts were dried over magnesium sulfate, filtered, and concentrated. The residue was purified by column chromatography (60% ethyl acetate:40% hexanes) to provide 1,1-dimethylethyl 3-[3,6-dioxo-1,4-bis(phenylmethyl)piperazin-2-yl]-3-hydroxyazetidine-1-carboxylate as a colorless foam (1.04 g, 2.23 mmol, 50% yield). $^1$H NMR. (400 MHz, CDCl₃): 7.39-7.29 (m, 7H), 7.23-7.19 (m, 3H), 5.34 (d, 1H), 4.82 (d, 1H), 4.58 (d, 1H), 4.37 (d, 1H), 4.37 (d, 1H), 4.22 (d, 1H), 4.15 (s, 1H), 4.08 (d, 1H), 3.97 (d, 1H), 3.75 (d, 1H), 3.74 (d, 1H), 3.67 (d, 1H), 3.64 (br s, 1H), 1.43 (s, 9H).

A solution of 1,1-dimethylethyl 3-[3,6-dioxo-1,4-bis(phenylmethyl)piperazin-2-yl]-3-hydroxyazetidine-1-carboxylate (1.04 g, 2.2 mmol) in methanol (10 mL) was treated with hydrogen chloride in dioxane (4 N, 5.5 mL, 22 mmol) at 60° C. for 25 min. After cooling to room temperature the solution was concentrated. Ethyl acetate and 2 N hydrochloric acid were added to the residue and the phases were separated. The organic phase was discarded. The aqueous phase was basified with 5 M sodium hydroxide and the resulting solution was extracted 4 times with ethyl acetate. The combined organic extracts were dried over magnesium sulfate, filtered, and concentrated. The residue was purified by column chromatography (85% dichloromethane:14% methanol:1% aqueous ammonium hydroxide) to provide 3-(3-hydroxyazetidin-3-yl)-1,4-bis(phenylmethyl)piperazine-2,5-dione as a colorless film (493 mg, 1.35 mmol, 61% yield). $^1$H NMR (400 MHz, CDCl₃): 7.39-7.28 (m, 6H), 7.25-7.20 (m, 4H), 5.39 (d, 1H), 4.80 (d, 1H), 4.44 (d, 1H), 4.36 (d, 1H), 4.26 (d, 1H), 4.11 (s, 1H), 3.97 (d, 1H), 3.83 (d, 1H), 3.71 (d, 1H), 3.27 (m, 2H); MS (EI) for $C_{21}H_{23}N_3O_3$: 366 (MH⁺).

A solution 3-(3-hydroxyazetidin-3-yl)-1,4-bis(phenylmethyl)piperazine-2,5-dione (493 mg, 1.35 mmol) in ethyleneglycol dimethylether (12 mL) was treated with sodium borohydride (511 mg, 13.5 mmol) followed by slow addition of boron trifluoride-diethyl etherate. The reaction mixture was then heated to reflux for 3 hours. After cooling to 0° C., methanol (17 mL) was added followed by careful addition of concentrated hydrochloric acid (7 mL). The resulting mixture was heated to reflux for 70 minutes. After cooling to room temperature, insoluble residue was removed by filtration. The filtrate was concentrated to an aqueous mixture of about 10 mL in volume. This mixture was cooled to 0° C. and was then basified to pH 10 with 5 M sodium hydroxide (approximately 17 mL). Dichloromethane (10 mL) was then added followed by di-tert-butyl dicarbonate (442 mg, 2.03 mmol). The mixture was warmed to room temperature and stirred for 15 minutes. The layers were separated and the aqueous phase was extracted twice with dichloromethane. The organic extracts were combined, dried over magnesium sulfate, filtered, and concentrated. The residue was purified by column chromatography (70% hexanes:30% ethyl acetate) to provide 1,1-dimethylethyl 3-[1,4-bis(phenylmethyl)piperazin-2-yl]-3-hydroxyazetidine-1-carboxylate as a white foam (408 mg, 0.93 mmol, 69% yield). $^1$H NMR, (400 MHz, CDCl₃): 7.35-7.24 (m, 10H), 4.12 (br s, 1H), 3.88 (d, 1H), 3.78-3.65 (m, 4H), 3.53 (d, 1H), 3.43 (d, 1H), 3.21 (m, 1H), 2.80 (br s, 1H), 2.66 (m, 1H), 2.57-2.37 (m, 4H), 1.41 (s, 9H); MS (EI) for $C_{26}H_{35}N_3O_3$: 438 (MH⁺).

To a solution of 1,1-dimethylethyl 3-[1,4-bis(phenylmethyl)piperazin-2-yl]-3-hydroxyazetidine-1-carboxylate (408 mg, 0.93 mmol) in methanol (15 mL) was added 10% palladium on carbon (wet), and the resulting suspension was subjected to an atmosphere of hydrogen for 21 hours. The catalyst was removed by filtration through celite, and the filter cake was rinsed with methanol. The combined filtrate was concentrated to provide 1,1-dimethylethyl 3-hydroxy-3-piperazin-2-ylazetidine-1-carboxylate as a brown syrup (227 mg, 0.88 mmol, 95% yield). $^1$H NMR, (400 MHz, CDCl₃): 3.94-3.76 (m, 5H), 3.12 (m, 1H), 3.01 (m, 1H), 2.94-2.81 (m, 3H), 2.78-2.70 (m, 2H); MS (EI) for $C_{12}H_{23}N_3O_3$: 258 (MH⁺).

To a solution of 1,1-dimethylethyl 3-hydroxy-3-piperazin-2-ylazetidine-1-carboxylate (227 mg, 0.88 mmol) and N,N-diisopropylethylamine (436 μL, 2.64 mmol) in THF (5 mL) was added 2-nitrobenzenesulfonyl chloride (195 mg, 0.88 mmol). The mixture was stirred at room temperature for 2 hours. The solution was concentrated and the residue was purified by column chromatography (95% dichloromethane: 5% methanol) to provide 1,1-dimethylethyl 3-hydroxy-3-{4-[(2-nitrophenyl)sulfonyl]piperazin-2-yl}azetidine-1-carboxylate as a white foam (308 mg, 0.70 mmol, 79% yield). $^1$H NMR, (400 MHz, CDCl₃): 7.98 (m, 1H), 7.72 (m, 2H), 7.64 (m, 1H), 3.96 (d, 1H), 3.94 (d, 1H), 3.85 (d, 1H), 3.79 (d, 1H), 3.79-3.73 (m, 2H), 3.11 (m, 1H), 3.05 (dd, 1H), 3.00 (br s, 1H), 2.94 (dt, 1H), 2.78 (dt, 1H), 2.68 (dd, 1H), 1.45 (s, 9H).

To a solution of 1,1-dimethylethyl 3-hydroxy-3-{4-[(2-nitrophenyl)sulfonyl]piperazin-2-yl}azetidine-1-carboxylate (308 mg, 0.70 mmol) in methanol (10 mL) was added HCl in dioxane (4 N, 1.75 mL, 7.0 mmol), and the mixture was heated to 60° C. for 30 minutes. The solution was concentrated to provide 3-{4-[(2-nitrophenyl)sulfonyl]piperazin-2-yl}azetidin-3-ol as a sticky white solid. This material was dissolved in dichloromethane (7 mL). To the solution was added N,N-diisopropylethylamine (1.16 mL, 7.0 mmol) followed by 3,4-difluoro-2-[(2-fluoro-4-iodophenyl)amino]benzoyl fluoride (277 mg, 0.7 mmol), prepared using procedures similar to those described in Reference 1, and the resulting mixture was stirred at room temperature for 16 hours. The solution was concentrated and the residue was purified by column chromatography (95% dichloromethane: 5% methanol) to provide 1-({3,4-difluoro-2-[(2-fluoro-4-iodophenyl)amino]phenyl}carbonyl)-3-{4-[(2-nitrophenyl)sulfonyl]piperazin-2-yl}azetidin-3-ol as a pale yellow foam (453 mg, 0.63 mmol, 90% yield). $^1$H NMR. (400 MHz, CDCl₃): 8.49 (s, 1H), 7.96 (dd, 1H), 7.71 (m, 2H), 7.53 (dd, 1H), 7.39 (dd, 1H), 7.33 (d, 1H), 7.15 (m, 1H), 6.84 (br s, 1H), 6.62 (m, 1H), 4.29-3.97 (br m, 4H), 3.79-3.62 (m, 3H), 3.26-2.99 (br m, 3H), 2.92-2.62 (br m, 3H); MS (EI) for $C_{26}H_{23}F_3IN_5O_6S$: 718 (MH⁺).

To a solution of 1-({3,4-difluoro-2-[(2-fluoro-4-iodophenyl)amino]phenyl}carbonyl)-3-{4-[(2-nitrophenyl)sulfonyl]piperazin-2-yl}azetidin-3-ol (139.4 mg, 0.19 mmol) in DMF (1 mL) was added potassium carbonate (79 mg, 0.57 mmol) and thiophenol (21 μL, 0.21 mmol). The mixture was stirred for 45 min at room temperature then quenched with water. The aqueous mixture was extracted twice with ethyl acetate, and the combined organic extracts were dried over magnesium sulfate, filtered, and concentrated. The residue was purified by preparative reverse phase HPLC to provide 1-({3,4-difluoro-2-[(2-fluoro-4-iodophenyl)amino]phenyl}carbonyl)-3-piperazin-2-ylazetidin-3-ol as a white solid (26.8 mg, 0.05 mmol). $^1$H NMR (400 MHz, CD₃OD): 7.45 (dd, 1H), 7.36 (m, 1H), 7.32 (m, 1H), 7.03 (m, 1H), 6.62 (ddd, 1H), 4.51 (br dd, 1H), 4.31 (br dd, 1H), 4.17-3.92 (m, 4H), 3.73-3.56 (m, 3H), 3.46 (br m, 1H), 3.26 (m, 1H); MS (EI) for $C_{20}H_{20}F_3IN_4O_2$: 533 (MH+).

Example 36

1,1-Dimethylethyl{(1S)-1-[1-({4-[(2-fluoro-4-iodophenyl)amino]-1-methyl-6-oxo-1,6-dihydropyridazin-3-yl}carbonyl)-3-hydroxyazetidin-3-yl]ethyl}carbamate

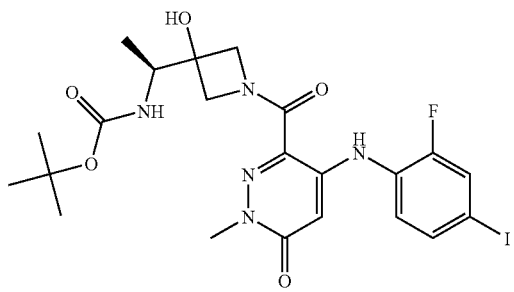

To a suspension of 4-[(2-fluoro-4-iodophenyl)amino]-1-methyl-6-oxo-1,6-dihydropyridazine-3-carboxylic acid (50 mg, 0.13 mmol) in DMF (2 mL), prepared using similar procedures to those described in Reference 4, at room temperature was added 1-hydroxybenzotriazole (36.3 mg, 0.27 mmol) and 1-(3-dimethylaminopropyl)-3-ethylcarbodiimide hydrochloride (52 mg, 0.27 mmol) and the reaction was stirred for 2 hours. 1,1-Dimethylethyl[(1S)-1-(3-hydroxyazetidin-3-yl)ethyl]carbamate (30 mg, 0.13 mmol), prepared using procedures similar to those in Example 28, and triethylamine (0.04 mL) were added and the mixture was stirred for 15 hours. The reaction mixture was partitioned between saturated sodium chloride and ethyl acetate. The organic layer was washed with 5% lithium chloride solution, saturated sodium bicarbonate, dried over anhydrous sodium sulfate, filtered and concentrated in vacuo to give crude product as yellow oil. The oil was purified by column chromatography (silica gel, ethyl acetate) to afford 1,1-dimethylethyl{(1S)-1-[1-({4-[(2-fluoro-4-iodophenyl)amino]-1-methyl-6-oxo-1,6-dihydropyridazin-3-yl}carbonyl)-3-hydroxyazetidin-3-yl]ethyl}carbamate as a yellow oil (55 mg, 73% yield): $^1$H NMR (400 MHz, CDCl$_3$): 10.24-10.23 (m, 1H), 7.52-7.50 (m, 2H), 7.12-7.07 (m, 1H), 6.10-6.09 (m, 1H), 5.13-5.09 (m, 1H), 4.91-4.82 (m, 1H), 4.60-4.39 (m, 2H), 4.10-4.08 (m, 1H), 4.00-3.87 (m, 2H), 3.70 (d, 3H), 1.43 (s, 9H), 1.24-1.20 (m, 3H); MS (EI) for $C_{22}H_{27}FIN_5O_5$: 588 (MH+).

Using the same or analogous synthetic techniques and substituting, as necessary, with alternative reagents, the following compounds of the invention were prepared:

Example 36(a)

1,1-Dimethylethyl{(1S)-1-[1-({5-[(4-bromo-2-chlorophenyl)amino]-4-fluoro-1-methyl-1H-benzimidazol-6-yl}carbonyl)-3-hydroxyazetidin-3-yl]ethyl}carbamate: $^1$H NMR (400 MHz, CDCl$_3$): 7.95 (s, 1H), 7.45-7.44 (m, 1H), 7.33-7.27 (m, 2H), 7.15-7.12 (m, 1H), 6.50-6.47 (m, 1H), 4.82-4.74 (m, 1H), 4.17-3.92 (m, 4H), 3.86 (s, 3H), 3.74-3.60 (m, 1H), 1.40 (s, 9H), 1.11-1.06 (m, 3H). MS (EI) for $C_{25}H_{28}BrClFN_5O_4$: 598 (MH+) with a chloro, bromo isotope pattern.

Example 36(b)

1,1-Dimethylethyl(2S)-2-[1-({5-[(4-bromo-2-chlorophenyl)amino]-4-fluoro-1-methyl-1H-benzimidazol-6-yl}carbonyl)-3-hydroxyazetidin-3-yl]piperidine-1-carboxylate: MS (EI) for $C_{28}H_{32}BrClFN_5O_4$: 638 (MH+) with a chloro, bromo isotope pattern.

Example 37

6-({3-[(1S)-1-aminoethyl]-3-hydroxyazetidin-1-yl}carbonyl)-5-[(2-fluoro-4-iodophenyl)amino]-2-methylpyridazin-3(2H)-one acetate salt

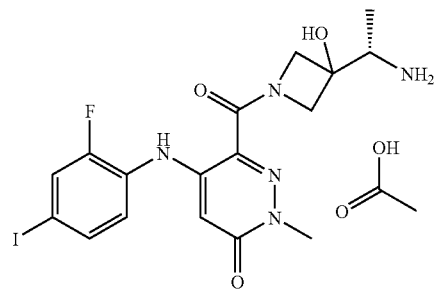

1,1-Dimethylethyl{(1S)-1-[1-({4-[(2-fluoro-4-iodophenyl)amino]-1-methyl-6-oxo-1,6-dihydropyridazin-3-yl}carbonyl)-3-hydroxyazetidin-3-yl]ethyl}carbamate (55 mg, 0.09 mmol), prepared using procedures similar to those described in Example 36, was taken up in methanol (2 mL) and hydrochloric acid (4N in dioxane, 1 mL, 4 mmol) was added and the reaction was stirred at 60° C. for 2 hours. The reaction mixture was concentrated in vacuo and was purified by reverse-phase HPLC followed by lyophilization of the pure fractions to afford 6-({3-[(1S)-1-aminoethyl]-3-hydroxyazetidin-1-yl}carbonyl)-5-[(2-fluoro-4-iodophenyl)amino]-2-methylpyridazin-3(213)-one acetate as yellow solid (40 mg, 87%). $^1$H NMR (400 MHz, CDCl$_3$): 10.17 (d, 1H), 7.52-7.46 (m, 2H), 7.09 (t, 1H), 6.13-6.12 (m, 1H), 4.51-4.48 (m, 2H), 4.18-4.03 (m, 2H), 3.73 (d, 3H), 3.35-3.28 (m, 1H), 3.22-2.80 (br, 3H), 1.21-1.19 (m, 3H); MS (EI) for $C_{17}H_{19}FIN_5O_3$: 488 (MH+).

Using the same or analogous synthetic techniques and/or substituting with alternative reagents, the following compounds of the invention were prepared:

Example 37(a)

3-[(1S)-1-Aminoethyl]-1-({5-[(4-bromo-2-chlorophenyl)amino]-4-fluoro-1-methyl-1H-benzimidazol-6-yl}carbonyl)azetidin-3-ol hydrochloride. MS (EI) for $C_{20}H_{20}BrClFN_5O_2$: 498 (MIT) with a chloro, bromo isotope pattern

Example 37(b)

1-({5-[(4-Bromo-2-chlorophenyl)amino]-4-fluoro-1-methyl-1H-benzimidazol-6-yl}carbonyl)-3-[(2S)-piperidin-2-yl]azetidin-3-ol hydrochloride. $^1$H NMR (400 MHz, CD$_3$OD): 9.42 (s, 1H), 7.97-7.96 (m, 1H), 7.57 (s, 1H), 7.30-7.27 (m, 1H), 6.70-6.66 (m, 1H), 4.60-4.55 (m, 1H), 4.28 (t, 1H), 4.19 (s, 3H), 4.13-3.98 (m, 2H), 3.38-3.32 (m, 2H), 3.00

(t, 1H), 1.86-1.30 (m, 6H). MS (EI) for $C_{23}H_{24}BrClFN_5O_2$. HCl: 538 (MH$^+$) with a chloro, bromo isotope pattern

Example 38

1-({3-[(2-fluoro-4-iodophenyl)amino]pyridin-4-yl}carbonyl)-3-[(2S)-piperidin-2-yl]azetidin-3-ol

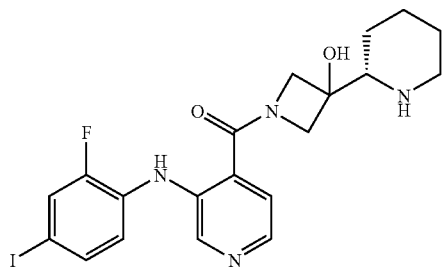

3-[(2-Fluoro-4-iodophenyl)amino]pyridine-4-carboxylic acid (200 mg, 0.559 mmol), prepared using procedures similar to those described in WO 2006/045514, was suspended in DMF (7 mL) and 1-hydroxybenzotriazole (151 mg, 1.12 mmol) and 1-(3-dimethylaminopropyl)-3-ethylcarbodiimide hydrochloride (214 mg, 1.12 mmol) were added. The mixture was stirred at ambient for 10 minutes and then triethylamine (0.078 mL, 0.559 mmol) was added. After a further 20 minutes, 1,1-dimethylethyl(2S)-2-(3-hydroxyazetidin-3-yl)piperidine-1-carboxylate (143 mg, 0.559 mmol), prepared using similar procedures to those described in Example 22(a) and 22(b), and triethylamine (0.16 mL, 1.15 mmol) were added and the mixture was stirred for 15 hours. The mixture was partitioned between ethyl acetate and saturated ammonium chloride. The organic portion was washed with 5% lithium chloride and twice with saturated sodium bicarbonate, then was dried over anhydrous sodium sulfate, filtered and concentrated in vacuo. The residue was purified by column chromatography (silica gel, 60-80% ethyl acetate in hexanes) to give 1,1-dimethylethyl(2S)-2-[1-({3-[(2-fluoro-4-iodophenyl)amino]pyridin-4-yl}carbonyl)-3-hydroxyazetidin-3-yl]piperidine-1-carboxylate (368 mg, 0.587 mmol, 74% yield): $^1$H NMR (400 MHz, CDCl$_3$): 8.73 (br m, 1H), 8.62 (br s, 1H), 8.14 (d, 1H), 7.47 (dd, 1H), 7.43-7.39 (m, 1H), 7.20-7.12 (m, 2H), 4.38-4.21 (m, 2H), 4.16-4.01 (m, 2H), 4.01-3.88 (m, 1H), 3.44-3.30 (m, 1H), 2.98-2.83 (m, 1H), 2.00-1.88 (m, 1H), 1.71-1.50 (m, 6H), 1.44 (s, 9H); MS (EI) for $C_{25}H_{30}FIN_4O_4$: 597 (MH$^+$).

1,1-Dimethylethyl(2S)-2-[1-({3-[(2-fluoro-4-iodophenyl)amino]pyridin-4-yl}carbonyl)-3-hydroxyazetidin-3-yl]piperidine-1-carboxylate (24 mg, 0.040 mmol) was dissolved in methanol (2 mL) and treated with 4 N hydrochloric acid in dioxane (0.25 mL, 1 mmol) at reflux for 20 minutes. The mixture was concentrated in vacuo and was purified by reverse-phase HPLC followed by lyophilization of the pure fractions to afford 1-({3-[(2-fluoro-4-iodophenyl)amino]pyridin-4-yl}carbonyl)-3-[(2S)-piperidin-2-yl]azetidin-3-ol acetate (14 mg, 0.025 mmol, 63% yield): $^1$H NMR (400 MHz, d$_6$-DMSO): 8.62 (br s, 1H), 8.46 (s, 1H), 8.18 (dd, 1H), 7.65 (dd, 1H), 7.45 (d, 1H), 7.37 (t, 1H), 7.16-7.08 (m, 1H), 4.25 (dd, 1H), 4.04 (dd, 1H), 3.90 (t, 1H), 3.70 (d, 1H), 2.95 (br d, 1H), 2.52-2.42 (m, 2H), 1.78-1.68 (m, 1H), 1.57 (br t, 1H), 1.47 (br d, 1H), 1.35-1.13 (m, 2H), 1.10-0.96 (m, 1H); MS (EI) for $C_{20}H_{22}FIN_4O_2$: 497 (MH$^+$).

Example 39

1-({3-[(2-fluoro-4-iodophenyl)amino]-1-oxidopyridin-4-yl}carbonyl)-3-[(2S)-piperidin-2-yl]azetidin-3-ol

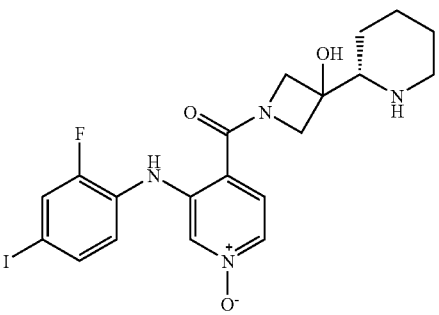

1,1-Dimethylethyl(2S)-2-[1-({3-[(2-fluoro-4-iodophenyl)amino]pyridin-4-yl}carbonyl)-3-hydroxyazetidin-3-yl]piperidine-1-carboxylate (80 mg, 0.134 mmol), prepared using procedures similar to those described in Example 38, was dissolved in dichloromethane (3 mL) and treated with 3-chloroperoxybenzoic acid (73% pure; 32 mg, 0.135 mmol) at ambient for 7 hours. 3-chloroperoxybenzoic acid (73% pure; 32 mg, 0.135 mmol) was added and the mixture was stirred for 15 hours. The mixture was purified by column chromatography (silica gel, 0-10% ethanol in ethyl acetate) to give 1,1-dimethylethyl(2S)-2-[1-({3-[(2-fluoro-4-iodophenyl)amino]-1-oxidopyridin-4-yl}carbonyl)-3-hydroxyazetidin-3-yl]piperidine-1-carboxylate (57 mg, 0.093 mmol, 69% yield): $^1$H NMR (400 MHz, CDCl$_3$): 9.38 (s, 1H), 8.00 (s, 1H), 7.68 (dd, 1H), 7.51 (dd, 1H), 7.46 (d, 1H), 7.19 (br d, 1H), 7.09 (t, 1H), 5.78 (br, 1H), 4.44-3.98 (m, 3H), 3.98-3.87 (m, 1H), 3.49-3.39 (m, 1H), 3.07-2.88 (m, 1H), 2.01-1.91 (m, 1H), 1.70-1.47 (m, 6H), 1.45 (s, 9H); MS (ET) for $C_{25}H_{30}FIN_4O_5$: 613 (MH$^+$).

1,1-Dimethylethyl(2S)-2-[1-({3-[(2-fluoro-4-iodophenyl)amino]-1-oxidopyridin-4-yl}carbonyl)-3-hydroxyazetidin-3-yl]piperidine-1-carboxylate (57 mg, 0.093 mmol) was dissolved in methanol (2 mL) and treated with 4N hydrochloric acid in dioxane (0.25 mL, 1 mmol) at 50° C. for 2.25 hours. The mixture was concentrated in vacuo and was purified by reverse-phase HPLC followed by lyophilization of the pure fractions to afford 1-({3-[(2-fluoro-4-iodophenyl)amino]-1-oxidopyridin-4-yl}carbonyl)-3-[(2S)-piperidin-2-yl]azetidin-3-ol acetate (35 mg, 0.061 mmol, 66% yield): $^1$H NMR (400 MHz, d$_6$-DMSO): 7.83 (s, 1H), 7.72 (dt, 2H), 7.55-7.51 (m, 1H), 7.47-7.41 (m, 1H), 7.24 (t, 1H), 4.45-4.32 (m, 1H), 4.14-3.95 (m, 2H), 3.72 (d, 1H), 2.97 (d, 1H), 2.58-2.43 (m, 2H), 1.80-1.73 (m, 1H), 1.67-1.55 (m, 1H), 1.49 (br d, 1H), 1.38-1.16 (m, 2H), 1.16-1.01 (m, 1H); MS (EI) for $C_{20}H_{22}FIN_4O_3$: 513 (MH$^+$).

Example 40

1-({3,4-difluoro-2-[(2-fluoro-4-iodophenyl)amino]phenyl}carbonyl)-3-[(1S)-1-(methylamino)ethyl]azetidin-3-ol

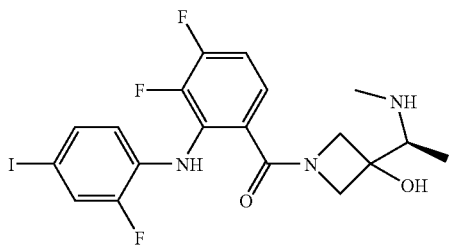

To 3-[(1S)-1-aminoethyl]-1-({3,4-difluoro-2-[(2-fluoro-4-iodophenyl)amino]phenyl}carbonyl)azetidin-3-ol (87.4 mg, 0.18 mmol), prepared using similar procedures to those described in Example 28, was added formaldehyde (37% aqueous, 14 mg, 0.18 mmol) in methanol (2 mL) and sodium borohydride (7 mg, 0.18 mmol). The mixture was stirred for 3 h at rt, after which sodium borohydride (16 mg, 0.42 mmol) was added. Upon stirring an additional 1.25 h, more formaldehyde (37% aqueous, 1 drop) was added, and the mixture was stirred 3 days at rt. A further small spatula (~50 mg) of sodium borohydride was then added, and the mixture was stirred at rt for 30 min. After quenching with 1 N HCl, the reaction mixture was purified directly by preparative HPLC. The clean material was converted to its hydrochloride salt to provide 1-({3,4-difluoro-2-[(2-fluoro-4-iodophenyl)amino]phenyl}carbonyl)-3-[(1S)-1-(methylamino)ethyl]azetidin-3-ol as a yellow solid (21.7 mg, 0.040 mmol, 22% yield). $^1$H NMR (400 MHz, CD$_3$OD) δ 7.47 (dd, 1H), 7.36 (d, 1H), 7.31 (m, 1H), 7.06 (q, 1H), 6.62 (dt, 1H), 4.36 (dd, 1H), 4.21-3.91 (m, 3H), 3.44 (q, 1H), 2.66 (s, 3H), 1.29 (br m, 3H); MS (EI) for $C_{19}H_{19}F_3IN_3O_2$: 506 (MH$^+$).

Biological Example 1

Biochemical Assay

For a biochemical measurement of MEK1 inhibitory activity, compounds of the invention were screened in a triple coupled cRaf-MEK-ERK2 assay using ALPHASCREEN (Registered Trademark of Perkin Elmer) technology (Perkin Elmer). The compound of the invention, 0.5 µL of 100% DMSO stock solution, is diluted into an assay buffer composed of 20 mM Tris (pH=7.5), 10 mM magnesium chloride, 0.03% CHAPS and 1 mM DTT. Subsequently, 10 µL of substrate mixture is added composed of unactive MEK1 (3 nM), ATP (50 µM), unactive ERK2 (4 nM), biotinylated MBP peptide (b-FFKNIVTPRTPPPSQGK, 1 µM) and antiphospho MBP peptide (0.5 nM). The mixture is then gently shaken for 30 minutes at room temperature followed by addition of active cRaf (5 µL at 0.5 nM) to initiate reaction. The mixture is then shaken for 100 minutes at room temperature then quenched by addition of 10 µL of a mixture of 5 µg/mL streptavidin donor beads and 5 µg/mL protein A acceptor beads in detection buffer (75 mM Hepes pH=7.5, 300 mM sodium chloride, 120 mM EDTA, 0.3% BSA and 0.03% Tween), followed by incubation overnight and signal detection on an ALPHAQuest® (Registered Trademark of Perkin Elmer) plate reader (Perkin Elmer).

Compounds of the invention are inhibitors of MEK. The extent to which these compounds are MEK inhibitors can be determined by one of ordinary skill in the art. In particular, the compounds can be tested in the assay described in Biological Example 1. When tested in that assay, certain compounds of the invention demonstrated the ability to bind to MEK. In one embodiment of the invention, the MEK inhibitor is selected from the compounds in Table 1 having a MEK-binding affinity of about 4 µM or less. In another embodiment, the MEK inhibitor is selected from the compounds in Table 1 having a MEK-binding affinity of about 3 µM or less. In another embodiment, the MEK inhibitor is selected from the compounds in Table 1 having a MEK-binding affinity of about 2 µM or less. In another embodiment, the MEK inhibitor is selected from the compounds in Table 1 having a MEK-binding affinity of about 1.6 µM or less. In another embodiment, the MEK inhibitor is selected from the compounds in Table 1 having a MEK-binding affinity of about 1 µM or less. In another embodiment, the MEK inhibitor is selected from the compounds in Table 1 having a MEK-binding affinity of about 0.7 µM or less. In another embodiment, the MEK inhibitor is selected from the compounds in Table 1 having a MEK-binding affinity of about 0.3 µM or less. In another embodiment, the MEK inhibitor is selected from the compounds in Table 1 having a MEK-binding affinity of about 0.2 µM or less. In another embodiment, the MEK inhibitor is selected from the compounds in Table 1 having a MEK-binding affinity of about 0.1 µM or less. In another embodiment, the MEK inhibitor is selected from the compounds in Table 1 having a MEK-binding affinity of about 0.05 µM or less.

Biological Example 2

Endogenous ERK Phosphorylation ELISA Assay

MDA-MB-231T (ATCC), Calu-6 (ATCC), HCT 116 (ATCC), A2058 (ATCC), and A375 (ATCC) cells were seeded at 20000, 30000, 30000, 20000, and 30000 cells/well, respectively, onto black 96-well microtiter plates (Costar 3904), in DMEM (Cellgro) containing 10% FBS (Heat-Inactivated, Cellgro), 1% NEAA (Cellgro), and 1% Pen/Strep (Cellgro). SK-MEL-28 (ATCC) cells were seeded at 20000 cells/well in MEM (ATCC) containing 10% FBS (Heat-Inactivated, Cellgro), and 1% Pen/Strep (Cellgro). The cells were then incubated at 37° C., 5% CO$_2$ for 24 h. Serum starvation was performed by replacing the medium with serum-free DMEM or MEM for an additional 24 h. Serial dilutions of test compounds in fresh serum-free medium in a final concentration of 0.3% DMSO (vehicle) were added to the cells and incubated for 1 h. Negative control wells were in serum-free medium+0.3% DMSO only. After treatment, the medium was removed and cells were fixed with 4% formaldehyde, followed by quenching of endogenous peroxidases with 0.6% H$_2$O$_2$. Plates were then blocked (10% FBS, Cellgro) and incubated with mouse monoclonal anti-phospho-p44/42 MAPK, E10 (1:2000, Cell Signaling), followed by secondary antibody (HRP-conjugated, goat anti-mouse IgG, 1:3000 from Jackson ImmunoResearch Laboratories, Inc). Washing of the plates was performed with PBS-T (0.1% Triton X-100) in between all incubation steps. A luminol-based substrate solution was then added and plates read using the Victor Wallac machine. IC$_{50}$ values were determined based on total ERK phosphorylation with compound treatment versus total ERK phosphorylation with 0.3% DMSO treatment alone.

Biological Example 3

BrdU Cell Proliferation Assay

MDA-MB-231T (ATCC), Calu-6 (ATCC), HCT 116 (ATCC), A2058 (ATCC), A375 (ATCC), and Colo-205 (ATCC) cells were plated at densities of 2500, 3500, 3500, 2500, 3500, and 15000 cells/well onto 96-well microtiter plates (Cat#3904, Costar), in DMEM (Cellgro) containing 10% FBS (Heat Inactivated, Cellgro), 1% Pen/Strep (Cellgro), and 1% NEAA (Cellgro). SK MEL-28 (ATCC) and WM-266-4 (ATCC) were plated at densities of 2000 and 6000 cells/well in MEM (ATCC) containing 10% FBS (Heat-Inactivated, Cellgro), and 1% Pen/Strep (Cellgro). The cells were incubated overnight at 37° C., 5% $CO_2$ for 18 h. The next day, cells were treated with a serial dilution of compound in medium (containing a final concentration of 0.3% DMSO). Triplicate wells were used for each compound concentration. The control wells received 0.3% DMSO media. The cultures were incubated at 37° C., 5% $CO_2$ for an additional 48 h. The cells were assayed for proliferation according to the "Cell Proliferation ELISA, Bromo Deoxyuridine (BrdU) (chemiluminescence) kit" from Roche. The cells were treated with the BrdU labeling solution and then fixed with FixDenat solution. Anti-BrdU-POD (PerOxiDase) conjugate was added to the cells, after which the plates were washed 3× with 1× PBS. Substrate solution was added, and the plates were read for luminescence using the Victor Wallac machine. $IC_{50}$ values were calculated based on the cell proliferation with compound treatment compared to the vehicle control.

Biological Example 4

In Vivo Mouse Models

Female athymic nude mice (NCr) 5-8 weeks of age and weighing approximately 20 g were purchased from Taconic (Germantown, N.Y.). Prior to initiation of a study, the animals were allowed to acclimate for a minimum of 48 h. During these studies, animals were provided food and water ad libitum and housed in a room conditioned at 70-75° F. and 60% relative humidity. A 12 h light and 12 h dark cycle was maintained with automatic timers.

Colo-205 human colorectal carcinoma cells were cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells were harvested by trypsinization, and $3 \times 10^6$ cells (passage #3, 92% viability) in 0.1 ml ice-cold Hank's balanced salt solution were implanted intradermally in the hind-flank of 5-8 week old female athymic nude mice.

A375 human melanoma cells were cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells were harvested by trypsinization, and $5 \times 10^6$ cells (passage #8, >99% viability) in 0.1 mL ice-cold Hank's balanced salt solution were implanted intradermally in the hind-flank of 5-8 week old female athymic nude mice.

A2058 human melanoma cells were cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells were harvested by trypsinization, and $3 \times 10^6$ cells (passage #5, 80% viability) in 0.1 mL ice-cold Hank's balanced salt solution were implanted intradermally in the hind-flank of 5-8 week old female athymic nude mice.

MDA-MB-231 human breast adenocarcinoma cells were cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells were harvested by trypsinization, and $1 \times 10^6$ cells (passage #6, >99% viability) in 0.1 mL ice-cold Hank's balanced salt solution were implanted subcutaneously into the mammary fat pad of 5-8 week old female athymic nude mice.

Calu-6 human lung anaplastic carcinoma cells were cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells were harvested by trypsinization, and $5 \times 10^6$ cells (passage #8, 96% viability) in 0.1 mL ice-cold Hank's balanced salt solution were implanted intradermally in the hind-flank of 5-8 week old female athymic nude mice.

For subcutaneous or intradermal tumors, the mean tumor weight of each animal in the respective control and treatment groups was determined twice weekly during the study. Tumor weight (TW) was determined by measuring perpendicular diameters with a caliper, using the following formula: tumor weight (mg)=[tumor volume=length (mm)×width$^2$ (mm$^2$)]/2.

Percent inhibition of tumor growth (TGI) is determined with the following formula:

$$\left(1 - \left(\frac{(X_f - X_0)}{(Y_f - X_0)}\right)\right) * 100$$

where $X_0$=average TW of all tumors on group day; $X_f$=TW of treated group on Day f; $Y_f$=TW of vehicle control group on Day f If tumors regress below their starting sizes, then the percent tumor regression is determined with the following formula:

$$\left(\frac{(X_0 - Xf)}{X_0}\right) * 100$$

TGI is calculated individually for each tumor to obtain a mean±SEM value for each experimental group. Statistical significance is determined using the 2-tailed Student's t-test (significance defined as P<0.05).

Pharmaceutical Composition Examples

The following are representative pharmaceutical formulations containing a compound of Formula I.

Tablet Formulation

The following ingredients are mixed intimately and pressed into single scored tablets.

| Ingredient | Quantity per tablet, mg |
| --- | --- |
| compound of this invention | 400 |
| Cornstarch | 50 |
| croscarmellose sodium | 25 |

| Ingredient | Quantity per tablet, mg |
|---|---|
| Lactose | 120 |
| magnesium stearate | 5 |

Capsule Formulation

The following ingredients are mixed intimately and loaded into a hard-shell gelatin capsule.

| Ingredient | Quantity per tablet, mg |
|---|---|
| compound of this invention | 200 |
| lactose, spray-dried | 148 |
| magnesium stearate | 2 |

Suspension Formulation

The following ingredients are mixed to form a suspension for oral administration

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| Flavoring | 0.035 mL |
| Colorings | 0.5 mg |
| distilled water | q.s. to 100 mL |

Injectable Formulation

The following ingredients are mixed to form an injectable formulation.

| Ingredient | Amount |
|---|---|
| compound of this invention | 1.2 g |
| sodium acetate buffer solution | 0.4 M 2.0 mL |
| HCl (1 N) or NaOH (1 M) | q.s. to suitable pH |
| water (distilled, sterile) | q.s. to 20 mL |

All of the above ingredients, except water, are combined and heated to 60-70.degree. C. with stirring. A sufficient quantity of water at 60.degree. C. is then added with vigorous stirring to emulsify the ingredients, and water then added q.s. to 100 g.

Suppository Formulation

A suppository of total weight 2.5 g is prepared by mixing the compound of the invention with Witepsol™ H-15 (triglycerides of saturated vegetable fatty acid; Riches-Nelson, Inc., New York), and has the following composition:

| Ingredient | Quantity per tablet, mg |
|---|---|
| compound of this invention | 500 |
| Witepsol ® H-15 | balance |

The foregoing invention has been described in some detail by way of illustration and example, for purposes of clarity and understanding. The invention has been described with reference to various specific embodiments and techniques. However, it should be understood that many variations and modifications may be made while remaining within the spirit and scope of the invention. It will be obvious to one of skill in the art that changes and modifications may be practiced within the scope of the appended claims. Therefore, it is to be understood that the above description is intended to be illustrative and not restrictive. All patents, patent applications and publications cited in this application are hereby incorporated by reference in their entirety for all purposes to the same extent as if each individual patent, patent application or publication were so individually denoted.

We claim:

1. A compound of formula I:

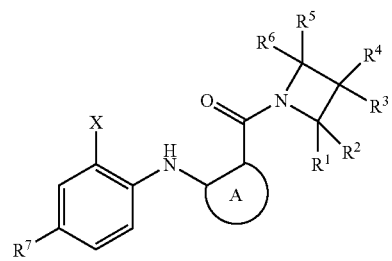

or a pharmaceutically acceptable salt thereof, wherein A, X, $R^1$, $R^2$, $R^3$, $R^4$, $R^5$, $R^6$, and $R^7$ are as defined in Group B, Group C, or Group D:

Group B:

A is heteroarylene optionally substituted with one, two, three, or four groups selected from $R^{10}$, $R^{12}$, $R^{14}$, $R^{16}$ and $R^{19}$ where $R^{10}$, $R^{12}$, $R^{14}$ and $R^{16}$ are independently hydrogen, alkyl, alkenyl, alkynyl, halo, haloalkoxy, hydroxy, alkoxy, cyano, amino, alkylamino, dialkylamino, haloalkyl, alkylsulfonylamino, alkylcarbonyl, alkenylcarbonyl, alkoxycarbonyl, alkenyloxycarbonyl, aminocarbonyl, alkylaminocarbonyl, dialkylaminocarbonyl, or alkylcarbonylamino; where $R^{19}$ is hydrogen, alkyl, or alkenyl; and where each alkyl and alkenyl, either alone or as part of another group within $R^{10}$, $R^{12}$, $R^{14}$, $R^{16}$, and $R^{19}$, is independently optionally substituted with halo, hydroxy, or alkoxy;

X is alkyl, halo, haloalkyl, or haloalkoxy;

$R^1$, $R^2$, $R^3$, $R^4$, $R^5$ and $R^6$ are independently hydrogen, halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^{8'}R^{8''}$, —$NR^8C(O)OR^{8'}$, —$NR^8C(O)R^{8'}$, —$CH_2N(R^{25})$ $(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C$ $(=NH)(N(R^{25a})(CN))$, —$CH_2NR^{25}C(=NH)(R^{25})$, —$CH_2NR^{25}C(NR^{25a}R^{25b})$=$CH(NO_2)$, alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —OR$^8$, —NR$^8$R$^{8'}$, —NR$^8$S(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^{8'}$R$^{8''}$, —NR$^8$C(O)OR$^{8'}$ and —NR$^8$C(O)R$^{8'}$; or one of R$^1$ and R$^2$ together with the carbon to which they are attached, R$^3$ and R$^4$ together with the carbon to which they are attached, and R$^5$ and R$^6$ together with the carbon to which they are attached form C(O) or C(=NOH);

m is 1 or 2;

R$^7$ is hydrogen, halo or alkyl; and

R$^8$, R$^{8'}$ and R$^{8''}$ are independently selected from hydrogen, hydroxy, optionally substituted alkoxy, alkyl, haloalkyl, alkenyl, alkynyl, aryl, cycloalkyl, heteroaryl, and heterocycloalkyl, where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, carboxy ester, nitro, cyano, —S(O)$_n$R$^{31}$ (where n is 0, 1, or 2 and R$^{31}$ is optionally substituted alkyl, optionally substituted aryl, optionally substituted cycloalkyl, optionally substituted heterocycloalkyl, or optionally substituted heteroaryl), —NR$^{36}$S(O)$_2$R$^{36a}$ (where R$^{36}$ is hydrogen, alkyl, or alkenyl and R$^{36a}$ is alkyl, alkenyl, optionally substituted aryl, optionally substituted cycloalkyl, optionally substituted heterocycloalkyl, or optionally substituted heteroaryl), —S(O)$_2$NR$^{37}$R$^{37a}$ (where R$^{37}$ is hydrogen, alkyl, or alkenyl and R$^{37a}$ is alkyl, alkenyl, optionally substituted aryl, optionally substituted cycloalkyl, optionally substituted heterocycloalkyl, or optionally substituted heteroaryl), optionally substituted cycloalkyl, optionally substituted heterocycloalkyl, optionally substituted aryl, optionally substituted arylalkyl, optionally substituted aryloxy, optionally substituted arylalkyloxy, optionally substituted heteroaryl, —NHC(O)R$^{32}$ (where R$^{32}$ is alkyl, alkenyl, alkoxy, or cycloalkyl) and —NR$^{30}$R$^{30'}$ (where R$^{30}$ and R$^{30'}$ are independently hydrogen, alkyl, or hydroxyalkyl), and —C(O)NHR$^{33}$ (where R$^{33}$ is alkyl, alkenyl, alkynyl, or cycloalkyl);

R$^{25}$ and R$^{25b}$ are independently hydrogen, alkyl, alkenyl, optionally substituted cycloalkyl, or optionally substituted aryl; and R$^{25a}$ is hydrogen, alkyl, or alkenyl;

Group C:

A is

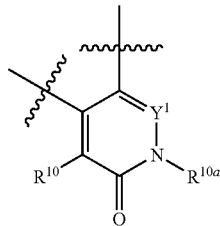

where R$^{10}$ is hydrogen, alkyl, alkenyl, alkynyl, halo, haloalkoxy, hydroxy, alkoxy, amino, alkylamino, dialkylamino, haloalkyl, —NHS(O)$_2$R$^8$, —CN, —C(O)R$^8$, —C(O)OR$^8$, —C(O)NR$^8$R$^{8'}$ and —NR$^8$C(O)R$^{8'}$;

R$^{10a}$ is hydrogen, alkyl, or alkenyl;

Y$^1$ is =CH— or =N—;

X is alkyl, halo, haloalkyl, or haloalkoxy;

R$^1$, R$^2$, R$^3$, R$^4$, R$^5$ and R$^6$ are independently hydrogen, halo, nitro, —NR$^8$R$^{8'}$, —OR$^8$, —NHS(O)$_2$R$^8$, —CN, —S(O)$_m$R$^8$, —S(O)$_2$NR$^8$R$^{8'}$, —C(O)R$^8$, —C(O)OR$^8$, —C(O)NR$^8$R$^{8'}$, —NR$^8$C(O)OR$^{8'}$, —NR$^8$C(O)NR$^{8'}$R$^{8''}$, —NR$^8$C(O)OR$^{8'}$, —NR$^8$C(O)R$^{8'}$, —CH$_2$N(R$^{25}$)(NR$^{25a}$R$^{25b}$), —CH$_2$NR$^{25}$C(=NH)(NR$^{25a}$R$^{25b}$), —CH$_2$NR$^{25}$C(=NH)(N(R$^{25a}$)(NO$_2$)), —CH$_2$NR$^{25}$C(=NH)(N(R$^{25a}$)(CN)), —CH$_2$NR$^{25}$C(=NH)(R$^{25}$), —CH$_2$NR$^{25}$C(NR$^{25a}$R$^{25b}$)=CH(NO$_2$), alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —OR$^8$, —NR$^8$R$^{8'}$, —NR$^8$S(O)$_2$R$^9$, —CN, —S(O)$_m$R$^9$, —C(O)R$^8$, —C(O)OR$^8$, —C(O)NR$^8$R$^{8'}$, —NR$^8$C(O)NR$^{8'}$R$^{8''}$, —NR$^8$C(O)OR$^{8'}$ and —NR$^8$C(O)R$^{8'}$; or one of R$^1$ and R$^2$ together with the carbon to which they are attached, R$^3$ and R$^4$ together with the carbon to which they are attached, and R$^5$ and R$^6$ together with the carbon to which they are attached form C(O) or C(=NOH);

m is 1 or 2;

R$^7$ is hydrogen, halo or alkyl; and

R$^8$, R$^{8'}$ and R$_{8''}$ are independently selected from hydrogen, hydroxy, optionally substituted alkoxy, alkyl, haloalkyl, alkenyl, alkynyl, aryl, cycloalkyl, heteroaryl, and heterocycloalkyl, where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, haloalkyl, carboxy, carboxy ester, nitro, cyano, —S(O)$_n$R$^{31}$ (where n is 0, 1, or 2 and R$^{31}$ is optionally substituted alkyl, optionally substituted aryl, optionally substituted cycloalkyl, optionally substituted heterocycloalkyl, or optionally substituted heteroaryl), —NR$^{36}$S(O)$_2$R$^{36a}$ (where R$^{36}$ is hydrogen, alkyl, or alkenyl and R$^{36a}$ is alkyl, alkenyl, optionally substituted aryl, optionally substituted cycloalkyl, optionally substituted heterocycloalkyl, or optionally substituted heteroaryl), —S(O)$_2$NR$^{37}$R$^{37a}$ (where R$^{37}$ is hydrogen, alkyl, or alkenyl and R$^{37a}$ is alkyl, alkenyl, optionally substituted aryl, optionally substituted cycloalkyl, optionally substituted heterocycloalkyl, or optionally substituted heteroaryl), optionally substituted cycloalkyl, optionally substituted heterocycloalkyl, optionally substituted aryl, optionally substituted arylalkyl, optionally substituted aryloxy, optionally substituted arylalkyloxy, optionally substituted heteroaryl, —NHC(O)R$^{32}$ (where R$^{32}$ is alkyl, alkenyl, alkoxy, or cycloalkyl) and —NR$^{30}$R$^{30'}$ (where R$^{30}$ and R$^{30'}$ are independently hydrogen, alkyl, or hydroxyalkyl), and —C(O)NHR$^{33}$ (where R$^{33}$ is alkyl, alkenyl, alkynyl, or cycloalkyl);

R$^{25}$ and R$^{25b}$ are independently hydrogen, alkyl, alkenyl, optionally substituted cycloalkyl, or optionally substituted aryl; and $R^{25a}$ is hydrogen, alkyl, or alkenyl; or Group D:

A is

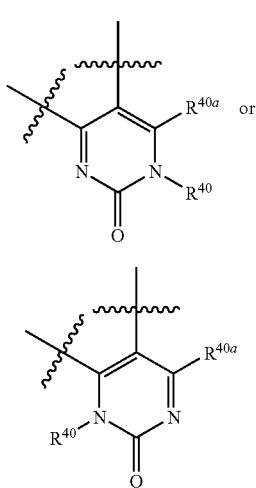

$R^{40}$ and $R^{40a}$ are independently hydrogen or alkyl;

X is alkyl, halo, haloalkyl, or haloalkoxy;

$R^1$, $R^2$, $R^3$, $R^4$, $R^5$ and $R^6$ are independently hydrogen, halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^8R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl, where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^8R^{8''}$, —$NR^8C(O)OR^{8'}$ and —$NR^8C(O)R^{8'}$; or one of $R^1$ and $R^2$ together with the carbon to which they are attached, $R^3$ and $R^4$ together with the carbon to which they are attached, and $R^5$ and $R^6$ together with the carbon to which they are attached form C(O) or C(=NOH);

m is 1 or 2;

$R^7$ is hydrogen, halo or alkyl; and $R^8$, $R^{8'}$ and $R^{8''}$ are independently selected from hydrogen, hydroxy, optionally substituted alkoxy, alkyl, haloalkyl, alkenyl, alkynyl, aryl, cycloalkyl, heteroaryl, and heterocycloalkyl, where the alkyl, alkenyl, alkynyl, aryl, cycloalkyl, heteroaryl, and heterocycloalkyl are independently optionally substituted with one, two three, four, or five groups independently selected from alkyl, halo, hydroxy, hydroxyalkyl, optionally substituted alkoxy, alkoxyalkyl, carboxy, carboxy ester, nitro, cyano, —$S(O)_nR^{31}$ (where n is 0, 1, or 2 and $R^{31}$ is optionally substituted alkyl, optionally substituted aryl, optionally substituted cycloalkyl, optionally substituted heterocycloalkyl, or optionally substituted heteroaryl), —$NR^{36}S(O)_2R^{36a}$ (where $R^{36}$ is hydrogen, alkyl, or alkenyl and $R^{36a}$ is alkyl, alkenyl, optionally substituted aryl, optionally substituted cycloalkyl, optionally substituted heterocycloalkyl, or optionally substituted heteroaryl), —$S(O)_2NR^{37}R^{37a}$ (where $R^{37}$ is hydrogen, alkyl, or alkenyl and $R^{37a}$ is alkyl, alkenyl, optionally substituted aryl, optionally substituted cycloalkyl, optionally substituted heterocycloalkyl, or optionally substituted heteroaryl), optionally substituted cycloalkyl, optionally substituted heterocycloalkyl, optionally substituted aryl, optionally substituted arylalkyl, optionally substituted aryloxy, optionally substituted arylalkyloxy, optionally substituted heteroaryl, —$NHC(O)R^{32}$ (where $R^{32}$ is alkyl, alkenyl, alkoxy, or cycloalkyl) and —$NR^{30}R^{30'}$ (where $R^{30}$ and $R^{30'}$ are independently hydrogen, alkyl, or hydroxyalkyl), and —$C(O)NHR^{33}$ (where $R^{33}$ is alkyl, alkenyl, alkynyl, or cycloalkyl);

$R^{25}$ and $R^{25b}$ are independently hydrogen, alkyl, alkenyl, optionally substituted cycloalkyl, or optionally substituted aryl; and $R^{25a}$ is hydrogen, alkyl, or alkenyl.

2. The Compound of claim 1 selected from Group B, and Group C where

Group B

A is thien-3,4-diyl, benzo[d]isoxazol-5,6-diyl, 1H-indazol-5,6-diyl (optionally substituted at the N1 position with $R^{19}$ where $R^{19}$ is alkyl or alkenyl), benzo[d]oxazol-5,6-diyl, 1H-benzo[d]imidazol-5,6-diyl (optionally substituted at the N1 position with $R^{19}$ where $R^{19}$ is alkyl or alkenyl), 1H-benzo[d][1,2,3]triazol-5,6-diyl (optionally substituted at the N1 position with $R^{19}$ where $R^{19}$ is alkyl or alkenyl), imidazo[1,2-a]pyridin-6,7-diyl, cinnolin-6,7-diyl, quinolin-6,7-diyl, pyridin-3,4-diyl, 1-oxido-pyridin-3,4-diyl, [1,2,4]triazolo[4,3-a]pyridin-6,7-diyl, or 2,3-dihydroimidazo[1,2-a]pyridin-6,7-diyl; where A is optionally substituted with one, two, or three groups independently selected from $R^{10}$, $R^{12}$, $R^{14}$, $R^{16}$ and $R^{19}$ where $R^{10}$, $R^{12}$, $R^{14}$ and $R^{16}$ are independently hydrogen, alkyl, halo, or amino; and $R^{19}$ is hydrogen or alkyl;

X is halo;

$R^1$, $R^2$, $R^5$ and $R^6$ are hydrogen;

$R^3$ is hydrogen or hydroxy;

$R^4$ is —$NR^8R^{8'}$, heterocycloalkyl, heteroaryl, or alkyl; where the alkyl is optionally substituted with —$NR^8R^{8'}$ and where the heteroaryl is optionally substituted with alkyl;

$R^7$ is halo;

$R^8$ is hydrogen or alkyl; and $R^{8'}$ is hydrogen, alkyl, or cycloalkyl; where the cycloalkyl is optionally substituted with one or two groups independently selected from hydroxy and alkyl;

Group C

A is

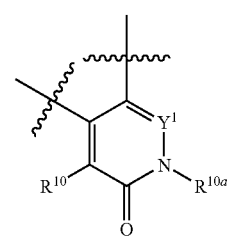

$R^{10}$ is hydrogen or halo;

$R^{10a}$ is hydrogen or alkyl;

$Y^1$ is =CH— or =N—;

X is halo;

$R^1$, $R^2$, $R^5$ and $R^6$ are hydrogen;

$R^3$ is hydrogen or hydroxy;

$R^4$ is —$NR^8R^{8'}$, heterocycloalkyl, heteroaryl, or alkyl; where the alkyl is optionally substituted with —$NR^8R^{8'}$ and where the heteroaryl is optionally substituted with alkyl;

$R^7$ is halo;

$R^8$ is hydrogen or alkyl; and $R^{8'}$ is hydrogen, alkyl, or cycloalkyl; where the cycloalkyl is optionally substituted with one or two groups independently selected from hydroxy and alkyl.

3. The compound of claim 1 where $R^3$ is halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^{8'}R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^{8'}R^{8''}$, —$NR^8C(O)OR^{8'}$ and —$NR^8C(O)R^{8'}$; and $R^4$ is as defined in claim 1; or $R^3$ and $R^4$ together with the carbon to which they are attached form C(O) or C(=NOH);

$R^{25}$ and $R^{25b}$ are independently hydrogen, alkyl, alkenyl, optionally substituted cycloalkyl, or optionally substituted aryl; and $R^{25a}$ is hydrogen, alkyl, or alkenyl.

4. The compound of claim 1 where $R^3$ and $R^4$ are independently halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^{8'}R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, alkynyl, cycloalkyl, heteroaryl, or heterocycloalkyl; where the alkyl, alkenyl, alkynyl, cycloalkyl, heteroaryl, and heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, optionally substituted heteroarylalkyl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^{8'}R^{8''}$, —$NR^8C(O)OR^{8'}$ and —$NR^8C(O)R^{8'}$; or $R^3$ and $R^4$ together with the carbon to which they are attached form C(O) or C(=NOH);

$R^{25}$ and $R^{25b}$ are independently hydrogen, alkyl, alkenyl, optionally substituted cycloalkyl, or optionally substituted aryl; and $R^{25a}$ is hydrogen, alkyl, or alkenyl.

5. The compound according to claim 1 wherein $R^7$ is halo.

6. The compound according to claim 1 wherein X is halo.

7. The compound according to claim 1 wherein $R^1$, $R^2$, $R^5$, and $R^6$ are hydrogen.

8. The compound of claim 1 where $R^3$ is hydrogen, halo, hydroxy, amino, or alkoxy.

9. The compound of claim 1 where $R^4$ is hydrogen, —$NR^8R^{8'}$, —$C(O)NR^8R^{8'}$, —$NR^8C(O)OR^{8'}$, —$NR^8C(O)R^8$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)(N(R^{25a})(CN))$, —$CH_2NR^{25}C(=NH)(R^{25})$, —$CH_2NR^{25}C(NR^{25a}R^{25b})=CH(NO_2)$, alkyl, alkenyl, cycloalkyl, heterocycloalkyl, or heteroaryl; where the alkyl is optionally substituted with one, two, or three —$OR^8$, halo, nitro, —$S(O)_mR^9$, optionally substituted heterocycloalkyl, —$NR^8R^{8'}$, —$NR^8C(O)R^{8'}$, —$NR^8S(O)_2R^9$, —$NR^8C(O)OR^{8'}$, aryl; where the cycloalkyl is optionally substituted with one or two —$NR^8R^{8'}$; where the heterocycloalkyl is optionally substituted with one or two groups independently selected from alkyl and —$C(O)OR^8$; and where the heteroaryl is optionally substituted with —$NR^8R^{8'}$;

$R^{25}$ and $R^{25b}$ are independently hydrogen, alkyl, alkenyl, optionally substituted cycloalkyl, or optionally substituted aryl; and $R^{25a}$ is hydrogen, alkyl, or alkenyl.

10. The Compound of claim 1 where $R^1$ is halo, nitro, —$NR^8R^{8'}$, —$OR^8$, —$NHS(O)_2R^8$, —CN, —$S(O)_mR^8$, —$S(O)_2NR^8R^{8'}$, —$C(O)R^8$, —$C(O)OR^8$, —$C(O)NR^8R^{8'}$, —$NR^8C(O)OR^{8'}$, —$NR^8C(O)NR^{8'}R^{8''}$, —$NR^8C(O)OR^{8'}$, —$NR^8C(O)R^{8'}$, —$CH_2N(R^{25})(NR^{25a}R^{25b})$, —$CH_2NR^{25}C(=NH)(NR^{25a}R^{25b})$, —$CH_2NR^{25}C(=NH)(N(R^{25a})(NO_2))$, —$CH_2NR^{25}C(=NH)(N(R^{25a})(CN))$, —$CH_2NR^{25}C(=NH)(R^{25})$, or —$CH_2NR^{25}C(NR^{25a}R^{25b})=CH(NO_2)$, alkyl, alkenyl, alkynyl, cycloalkyl, heteroaryl, or heterocycloalkyl; where the alkyl, alkenyl, alkynyl, cycloalkyl, heteroaryl, or heterocycloalkyl are independently optionally substituted with one, two, three, four, five, six or seven groups independently selected from halo, alkyl, haloalkyl, nitro, optionally substituted cycloalkyl, optionally substituted heterocycloalkyl, optionally substituted aryl, optionally substituted arylalkyl, optionally substituted heteroaryl, —$OR^8$, —$NR^8R^{8'}$, —$NR^8S(O)_2R^9$, —CN, —$S(O)_mR^9$, —$C(O)R^8$, —$C(O)OR^8$, —$C(O)NR^8R^{8'}$, —$NR^8C(O)NR^{8'}R^{8''}$, —$NR^8C(O)OR^{8'}$ and —$NR^8C(O)R^{8'}$;

$R^3$ is hydroxy; and $R^4$ is heterocycloalkyl, alkyl, or heteroaryl, where the alkyl is optionally substituted with —$NR^8R^{8'}$ and where the heteroaryl is optionally substituted with alkyl;

$R^{25}$ and $R^{25b}$ are independently hydrogen, alkyl, alkenyl, optionally substituted cycloalkyl, or optionally substituted aryl; and $R^{25a}$ is hydrogen, alkyl, or alkenyl.

11. The Compound of claim 1 selected from Group B where A is thien-3,4-diyl, benzo[d]isoxazol-5,6-diyl, 1H-indazol-5,6-diyl (optionally substituted at the N1 position with $R^{19}$ where $R^{19}$ is alkyl or alkenyl), benzo[d]oxazol-5,6-diyl, 1H-benzo[d]imidazol-5,6-diyl (optionally substituted at the N1 position with $R^{19}$ where $R^{19}$ is alkyl or alkenyl), 1H-benzo[d][1,2,3]triazol-5,6-diyl (optionally substituted at the N1 position with $R^{19}$ where $R^{19}$ is alkyl or alkenyl), imidazo[1,2-a]pyridin-6,7-diyl, cinnolin-6,7-diyl, quinolin-6,7-diyl, pyridin-3,4-diyl, 1-oxido-pyridin-3,4-diyl, [1,2,4]triazolo[4,3-a]pyridin-6,7-diyl, or 2,3-dihydroimidazo[1,2-a]pyridin-6,7-diyl.

12. The Compound of claim 1 where A is thien-3,4-diyl; $R^{10}$ and $R^{12}$ are hydrogen; X and $R^7$ are halo; and $R^1$, $R^2$, $R^5$, and $R^6$ are hydrogen.

13. The Compound of claim 12 where $R^3$ is hydrogen or hydroxy; and $R^4$ is —$NR^8R^{8'}$, heterocycloalkyl, heteroaryl, or alkyl, where the alkyl is optionally substituted with —$NR^8R^{8'}$.

14. The Compound of claim 1 selected from Group B where A is benzo[d]isoxazol-5,6-diyl; $R^{10}$, $R^{12}$, and $R^{14}$ are independently hydrogen, halo, or alkyl; $R^1$, $R^2$, $R^5$, and $R^6$ are hydrogen; X and $R^7$ are halo; $R^3$ is hydroxy; and $R^4$ is heterocycloalkyl, alkyl, or heteroaryl, where the alkyl is optionally substituted with —$NR^8R^{8'}$ and where the heteroaryl is optionally substituted with alkyl.

15. The Compound of claim 11 according to Formula I(g) or I(h):

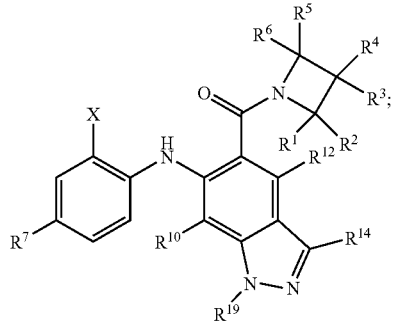

I(g)

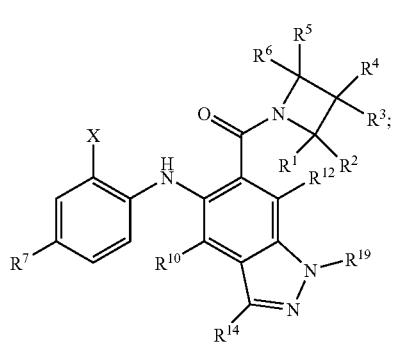

I(h)

where $R^{10}$, $R^{12}$, and $R^{14}$ are independently hydrogen, halo, or alkyl; $R^{19}$ is alkyl or alkenyl; $R^1$, $R^2$, $R^5$, and $R^6$ are hydrogen; X and $R^7$ are halo; $R^3$ is hydroxy; and $R^4$ is heterocycloalkyl, alkyl, or heteroaryl, where the alkyl is optionally substituted with —$NR^8R^{8'}$ and where the heteroaryl is optionally substituted with alkyl.

16. The Compound of claim 11 according to Formula I(i) or I(j):

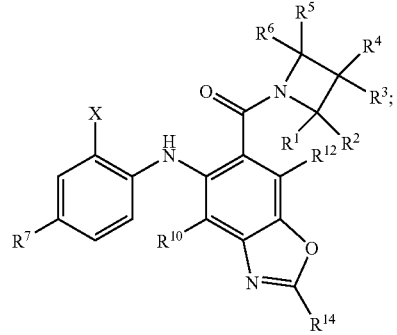

I(i)

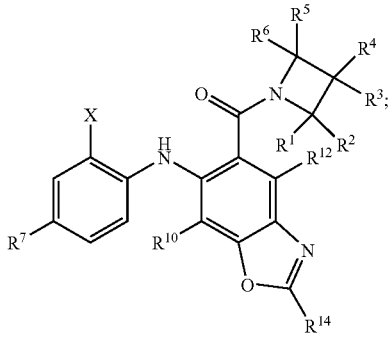

I(j)

where $R^{10}$, $R^{12}$, and $R^{14}$ are independently hydrogen, halo, or alkyl; $R^1$, $R^2$, $R^5$, and $R^6$ are hydrogen; X and $R^7$ are halo; $R^3$ is hydroxy; and $R^4$ is heterocycloalkyl, alkyl, or heteroaryl, where the alkyl is optionally substituted with —$NR^8R^{8'}$ and where the heteroaryl is optionally substituted with alkyl.

17. The Compound of 11 according to Formula I(n) or I(o):

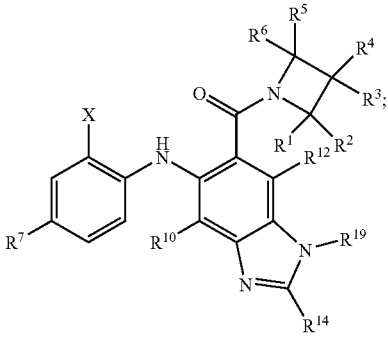

I(n)

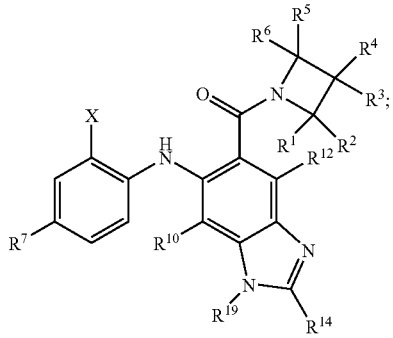

Io)

where $R^7$ is halo or alkyl; X is halo; $R^{19}$ is alkyl; $R^1$, $R^2$, $R^5$, and $R^6$ are hydrogen; $R^{10}$, $R^{12}$, and $R^{14}$ are independently hydrogen or halo; $R^3$ is hydroxy; and $R^4$ is heterocycloalkyl, alkyl, or heteroaryl, where the alkyl is optionally substituted with —$NR^8R^{8'}$ and where the heteroaryl is optionally substituted with alkyl.

18. The Compound of 11 according to Formula I(p):

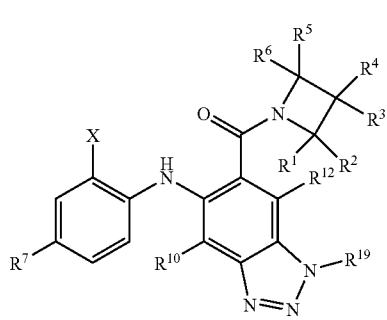

I(p)

where $R^1$, $R^2$, $R^5$, and $R^6$ are hydrogen; X and $R^7$ are halo; $R^{10}$ and $R^{12}$ are independently hydrogen, halo, or alkyl; $R^{19}$ is hydrogen or alkyl; $R^3$ is hydroxy; and $R^4$ is heterocycloalkyl, alkyl, or heteroaryl, where the alkyl is optionally substituted with —$NR^8R^{8'}$ and where the heteroaryl is optionally substituted with alkyl.

19. The Compound of 11 according to Formula I(q):

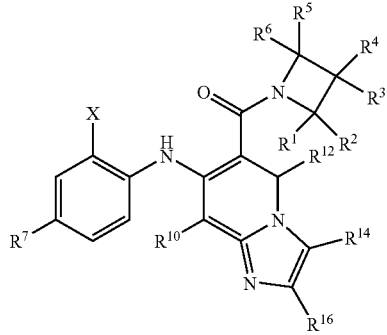

I(q)

where $R^1$, $R^2$, $R^5$, and $R^6$ are hydrogen; X and $R^7$ are halo; $R^{10}$, $R^{12}$, $R^{14}$, and $R^{16}$ are independently hydrogen or halo; $R^3$ is hydroxy; and $R^4$ is heterocycloalkyl, alkyl, or heteroaryl, where the alkyl is optionally substituted with —$NR^8R^{8'}$ and where the heteroaryl is optionally substituted with alkyl.

20. The Compound of 11 according to Formula I(r):

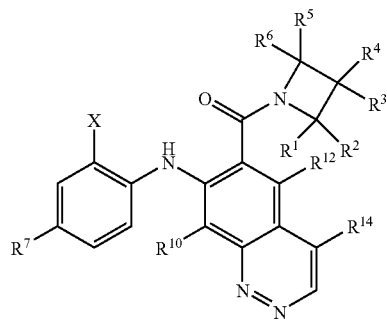

I(r)

where $R^1$, $R^2$, $R^5$, and $R^6$ are hydrogen; X and $R^7$ are halo; $R^{10}$ and $R^{12}$ are independently hydrogen, halo, or alkyl; $R^{14}$ is hydrogen, halo, alkyl, or amino; $R^3$ is hydroxy;

and $R^4$ is heterocycloalkyl, alkyl, or heteroaryl, where the alkyl is optionally substituted with —$NR^8R^{8'}$ and where the heteroaryl is optionally substituted with alkyl.

21. The Compound of 11 according to Formula I(s):

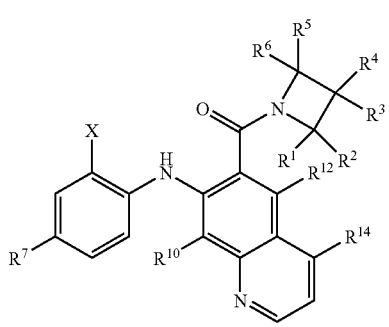

I(s)

$R^1$, $R^2$, $R^5$, and $R^6$ are hydrogen; X and $R^7$ are halo; $R^{10}$ and $R^{12}$ are independently hydrogen, halo, or alkyl; $R^{14}$ is hydrogen, halo, alkyl, or amino; $R^3$ is hydroxy; and $R^4$ is heterocycloalkyl, alkyl, or heteroaryl, where the alkyl is optionally substituted with —$NR^8R^{8'}$ and where the heteroaryl is optionally substituted with alkyl.

22. The Compound of 11 according to Formula I(u), I(v), I(w), or I(x):

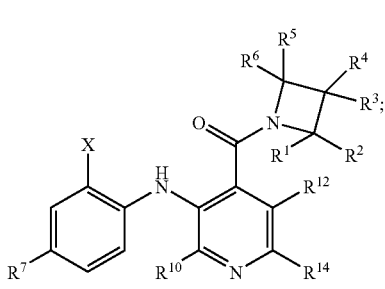

I(u)

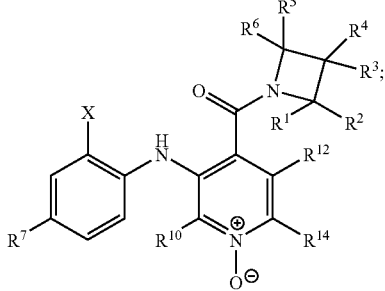

I(v)

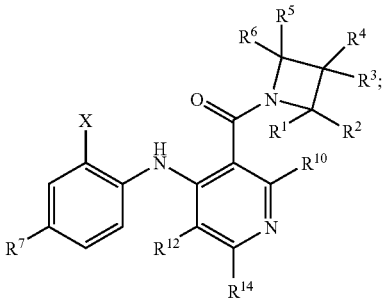

I(w)

345
-continued

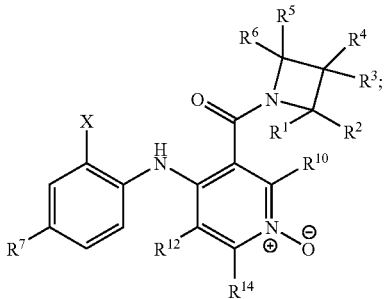

I(x)

where R¹, R², R⁵, and R⁶ are hydrogen; X and R⁷ are halo; R¹⁰, R¹², and R¹⁴ are independently hydrogen, halo, or alkyl; R³ is hydroxy; and R⁴ is heterocycloalkyl, alkyl, or heteroaryl, where the alkyl is optionally substituted with —NR⁸R⁸' and where the heteroaryl is optionally substituted with alkyl.

23. The Compound of claim 1 selected from Group C and according to Formula I(y) or I(z):

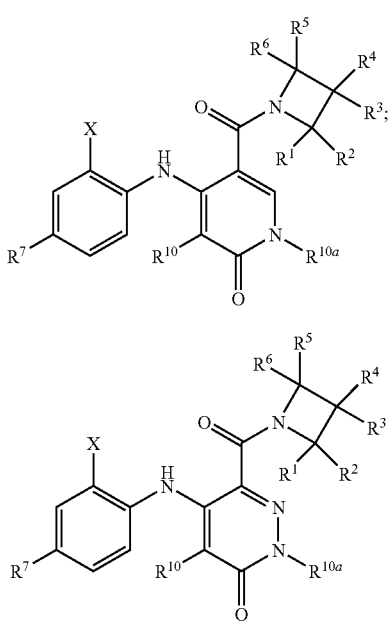

I(y)

I(z)

346 where R¹, R², R⁵, and R⁶ are hydrogen; X and R⁷ are halo; R¹⁰ is hydrogen, halo, or alkyl; R¹⁰ᵃ is alkyl; R³ is hydroxy; and R⁴ is heterocycloalkyl, alkyl, or heteroaryl, where the alkyl is optionally substituted with —NR⁸R⁸' and where the heteroaryl is optionally substituted with alkyl.

24. The Compound of claim 1 selected from Group D and according to Formula I(aa) or I(bb):

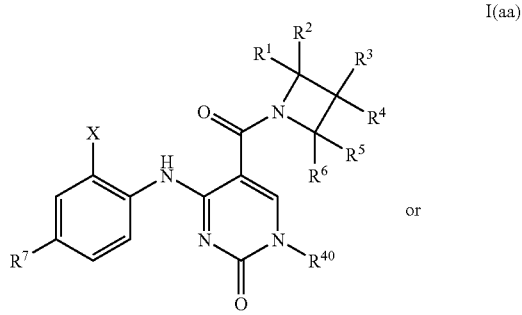

I(aa)

or

I(bb)

where R¹, R², R⁵, and R⁶ are hydrogen; X and R⁷ are halo; R³ is hydroxy; and R⁴ is heterocycloalkyl, alkyl, or heteroaryl, where the alkyl is optionally substituted with —NR⁸R⁸' and where the heteroaryl is optionally substituted with alkyl.

25. The compound according to claim 1 selected from the group consisting of:

1-({4-[(2-fluoro-4-iodophenyl)amino]-3-thienyl}carbonyl)azetidin-3-amine;
3-[(dimethylamino)methyl]-1-({4-[(2-fluoro-4-iodophenyl)amino]-3-thienyl}carbonyl)azetidin-3-ol;
3-[(1S)-1-aminoethyl]-1-({8-fluoro-7-[(2-fluoro-4-iodophenyl)amino]imidazo[1,2-a]pyridin-6-yl}carbonyl)azetidin-3-ol;
1-({8-fluoro-7-[(2-fluoro-4-iodophenyl)amino]imidazo[1,2-a]pyridin-6-yl}carbonyl)-3-[(1S)-1-(methylamino)ethyl]azetidin-3-ol;
3-(1H-benzimidazol-2-yl)-1-({8-fluoro-7-[(2-fluoro-4-iodophenyl)amino]imidazo[1,2-a]pyridin-6-yl}carbonyl)azetidin-3-ol;
3-(1H-benzimidazol-2-yl)-1-({7-[(4-bromo-2-fluorophenyl)amino]-8-fluoroimidazo[1,2-a]pyridin-6-yl}carbonyl)azetidin-3-ol;
3-{[(1,1-dimethylethyl)amino]methyl}-1-({4-[(2-fluoro-4-iodophenyl)amino]-3-thienyl}carbonyl)azetidin-3-ol;
3-(1-aminoethyl)-1-({8-chloro-7-[(2-fluoro-4-iodophenyl)amino]imidazo[1,2-a]pyridin-6-yl}carbonyl)azetidin-3-ol;
1-({8-fluoro-7-[(2-fluoro-4-iodophenyl)amino]imidazo[1,2-a]pyridin-6-yl}carbonyl)-3-[(2S)-piperidin-2-yl]azetidin-3-ol;

-continued 1-({8-fluoro-7-[(2-fluoro-4-iodophenyl)amino]imidazo[1,2-a]pyridin-6-yl}carbonyl)-3-{(1S)-1-[(2-hydroxy-2-methylcyclopentyl)amino]ethyl}azetidin-3-ol;
1-({3,4-difluoro-2-[(2-fluoro-4-iodophenyl)amino]phenyl}carbonyl)-3-(1H-imidazol-2-yl)azetidin-3-ol;
1-({2-fluoro-3-[(2-fluoro-4-iodophenyl)amino]pyridin-4-yl}carbonyl)-3-[(2S)-pyrrolidin-2-yl]azetidin-3-ol;
1-({8-fluoro-7-[(2-fluoro-4-iodophenyl)amino]-4-methylcinnolin-6-yl}carbonyl)-3-[(2S)-piperidin-2-yl]azetidin-3-ol;
1-({4-fluoro-5-[(2-fluoro-4-iodophenyl)amino]-1-methyl-1H-benzimidazol-6-yl}carbonyl)-3-piperidin-2-ylazetidin-3-ol;
1-({5-[(4-bromo-2-chlorophenyl)amino]-4-fluoro-1-methyl-1H-benzimidazol-6-yl}carbonyl)-3-[(2S)-piperidin-2-yl]azetidin-3-ol;
1-({8-chloro-7-[(2-fluoro-4-iodophenyl)amino]imidazo[1,2-a]pyridin-6-yl}carbonyl)-3-piperidin-2-ylazetidin-3-ol;
1-({7-[(4-bromo-2-fluorophenyl)amino]-8-fluoroimidazo[1,2-a]pyridin-6-yl}carbonyl)-3-[(2S)-piperidin-2-yl]azetidin-3-ol;
1-({7-[(4-bromo-2-chlorophenyl)amino]-8-chloroimidazo[1,2-a]pyridin-6-yl}carbonyl)-3-piperidin-2-ylazetidin-3-ol;
1-({8-chloro-7-[(2-fluoro-4-iodophenyl)amino]imidazo[1,2-a]pyridin-6-yl}carbonyl)-3-[(2S)-piperidin-2-yl]azetidin-3-ol;
1-({7-[(4-bromo-2-chlorophenyl)amino]-8-chloroimidazo[1,2-a]pyridin-6-yl}carbonyl)-3-[(2S)-piperidin-2-yl]azetidin-3-ol;
1--({4-fluoro-5-[(2-fluoro-4-iodophenyl)amino]-1-methyl-1H-benzimidazol-6-yl}carbonyl)-3-[(2S)-piperidin-2-yl]azetidin-3-ol;
3-[(1S)-1-aminoethyl]-1-({5-[(4-bromo-2-chlorophenyl)amino]-4-fluoro-1-methyl-1H-benzimidazol-6-yl}carbonyl)azetidin-3-ol;
1-({5-[(4-bromo-2-chlorophenyl)amino]-4-fluoro-1-methyl-1H-benzimidazol-6-yl}carbonyl)-3-[(1S)-1-(methylamino)ethyl]azetidin-3-ol;
4-[(4-bromo-2-fluorophenyl)amino]-3-fluoro-5-({3-hydroxy-3-[(2S)-piperidin-2-yl]azetidin-1-yl}carbonyl)pyridin-2(1H)-one;
4-[(2-fluoro-4-iodophenyl)amino]-5-({3-hydroxy-3-[(2S)-piperidin-2-yl]azetidin-1-yl}carbonyl)-1-methylpyridin-2(1H)-one;
4-[(2-fluoro-4-iodophenyl)amino]-5-({3-hydroxy-3-[(2S)-piperidin-2-yl]azetidin-1-yl}carbonyl)-1-methylpyridin-2(1H)-one;
4-[(2-fluoro-4-iodophenyl)amino]-5-({3-hydroxy-3-[(1S)-1-(methylamino)propyl]azetidin-1-yl}carbonyl)-1-methylpyridin-2(1H)-one;
5-({3-[(1S)-1-(dimethylamino)ethyl]-3-hydroxyazetidin-1-yl}carbonyl)-4-[(2-fluoro-4-iodophenyl)amino]-1-methylpyridin-2(1H)-one;
4-[(2-fluoro-4-iodophenyl)amino]-5-({3-hydroxy-3-[(methylamino)methyl]azetidin-1-yl}carbonyl)-1-methylpyridin-2(1H)-one;
5-{[3-(1H-benzimidazol-2-yl)-3-hydroxyazetidin-1-yl]carbonyl}-4-[(4-bromo-2-fluorophenyl)amino]-1-methylpyridin-2(1H)-one;
4-[(4-bromo-2-fluorophenyl)amino]-5-{[3-hydroxy-3-(1-methyl-1H-benzimidazol-2-yl)azetidin-1-yl]carbonyl}-1-methylpyridin-2(1H)-one;
4-[(4-bromo-2-fluorophenyl)amino]-5-({3-hydroxy-3-[(2S)-pyrrolidin-2-yl]azetidin-1-yl}carbonyl)-1-methylpyridin-2(1H)-one;
1-({6-[(4-bromo-2-chlorophenyl)amino]-7-fluoro-3-methyl-1,2-benzisoxazol-5-yl}carbonyl)-3-[(2S)-piperidin-2-yl]azetidin-3-ol;
5-[(2-fluoro-4-iodophenyl)amino]-6-({3-hydroxy-3-[(2S)-piperidin-2-yl]azetidin-1-yl}carbonyl)-2-methylpyridazin-3(2H)-one;
5-[(4-bromo-2-chlorophenyl)amino]-6-({3-hydroxy-3-[(2S)-piperidin-2-yl]azetidin-1-yl}carbonyl)-2-methylpyridazin-3(2H)-one;
5-[(4-bromo-2-chlorophenyl)amino]-4-fluoro-6-({3-hydroxy-3-[(2S)-pyrrolidin-2-yl]azetidin-1-yl}carbonyl)-2-methylpyridazin-3(2H)-one;
5-[(4-bromo-2-chlorophenyl)amino]-4-fluoro-6-({3-hydroxy-3-[(2R)-pyrrolidin-2-yl]azetidin-1-yl}carbonyl)-2-methylpyridazin-3(2H)-one;
6-({3-[(1S)-1-aminoethyl]-3-hydroxyazetidin-1-yl}carbonyl)-5-[(2-fluoro-4-iodophenyl)amino]-2-methylpyridazin-3(2H)-one;
6-({3-[(1S)-1-aminoethyl]-3-hydroxyazetidin-1-yl}carbonyl)-5-[(4-bromo-2-chlorophenyl)amino]-2-methylpyridazin-3(2H)-one;
5-[(4-bromo-2-chlorophenyl)amino]-6-{[3-((1S)-1-{[(3R,4S)-3,4-dihydroxycyclopentyl]amino}ethyl)-3-hydroxyazetidin-1-yl]carbonyl}-2-methylpyridazin-3(2H)-one;
5-[(4-bromo-2-fluorophenyl)amino]-6-[(3-hydroxy-3-{(1S)-1-[(2-hydroxy-2-methylcyclopentyl)amino]propyl}azetidin-1-yl)carbonyl]-2-methylpyridazin-3(2H)-one;
6-({3-[(1S)-1-aminopropyl]-3-hydroxyazetidin-1-yl}carbonyl)-5-[(4-bromo-2-fluorophenyl)amino]-2-methylpyridazin-3(2H)-one;
6-{[3-(1H-benzimidazol-2-yl)-3-hydroxyazetidin-1-yl]carbonyl}-5-[(2-fluoro-4-iodophenyl)amino]-2-methylpyridazin-3(2H)-one;
5-[(2-fluoro-4-iodophenyl)amino]-6-{[3-hydroxy-3-(1-methyl-1H-benzimidazol-2-yl)azetidin-1-yl]carbonyl}-2-methylpyridazin-3(2H)-one;
1-({2-fluoro-3-[(2-fluoro-4-iodophenyl)amino]pyridin-4-yl}carbonyl)-3-[(2S)-piperidin-2-yl]azetidin-3-ol;
1-({3-[(2-fluoro-4-iodophenyl)amino]pyridin-4-yl}carbonyl)-3-[(2S)-piperidin-2-yl]azetidin-3-ol;
1-({3-[(2-fluoro-4-iodophenyl)amino]-1-oxidopyridin-4-yl}carbonyl)-3-[(2S)-piperidin-2-yl]azetidin-3-ol;
1-({2-fluoro-3-[(2-fluoro-4-bromophenyl)amino]pyridin-4-yl}carbonyl)-3-[(2S)-piperidin-2-yl]azetidin-3-ol;

-continued

3-[(1S)-1-aminopropyl]-1-({3-[(2-fluoro-4-iodophenyl)amino]pyridin-4-yl}carbonyl)azetidin-3-ol;
1-({3-[(2-fluoro-4-iodophenyl)amino]pyridin-4-yl}carbonyl)-3-[(1S)-1-(methylamino)propyl]azetidin-3-ol;
(1R,2S)-4-({(1S)-1-[1-({2-fluoro-3-[(2-fluoro-4-iodophenyl)amino]pyridin-4-yl}carbonyl)-3-hydroxyazetidin-3-yl]propyl}amino)cyclopentane-1,2-diol;
1-({7-[(4-bromo-2-chlorophenyl)amino]-8-fluoro-4-methylcinnolin-6-yl}carbonyl)-3-[(2S)-piperidin-2-yl]azetidin-3-ol;
1-({7-[(4-bromo-2-fluorophenyl)amino]-8-fluoro-4-methylcinnolin-6-yl}carbonyl)-3-[(2S)-piperidin-2-yl]azetidin-3-ol;
3-[(1S)-1-aminoethyl]-1-({7-[(4-bromo-2-fluorophenyl)amino]cinnolin-6-yl}carbonyl)azetidin-3-ol;
1-({7-[(4-bromo-2-fluorophenyl)amino]cinnolin-6-yl}carbonyl)-3-{(1S)-1-[(2-hydroxy-2-methylcyclopentyl)amino]ethyl}azetidin-3-ol;
1-({7-[(4-bromo-2-fluorophenyl)amino]cinnolin-6-yl}carbonyl)-3-[(1S)-1-(dimethylamino)ethyl]azetidin-3-ol;
3-[(1S)-1-aminoethyl]-1-({5-[(2-fluoro-4-iodophenyl)amino]-1H-1,2,3-benzotriazol-6-yl}carbonyl)azetidin-3-ol;
3-[(1S)-1-(dimethylamino)ethyl]-1-({5-[(2-fluoro-4-iodophenyl)amino]-1-methyl-1H-1,2,3-benzotriazol-6-yl}carbonyl)azetidin-3-ol;
1-({5-[(2-fluoro-4-iodophenyl)amino]-1H-1,2,3-benzotriazol-6-yl}carbonyl)-3-[(2S)-piperidin-2-yl]azetidin-3-ol;
1-({5-[(2-fluoro-4-iodophenyl)amino]-1-methyl-1H-1,2,3-benzotriazol-6-yl}carbonyl)-3-[(2S)-piperidin-2-yl]azetidin-3-ol;
1-({5-[(2-fluoro-4-iodophenyl)amino]-1H-1,2,3-benzotriazol-6-yl}carbonyl)-3-{(1S)-1-[(2-hydroxy-2-methylcyclopentyl)amino]ethyl}azetidin-3-ol;
3-[(1S)-1-aminoethyl]-1-({4-fluoro-5-[(2-fluoro-4-iodophenyl)amino]-1H-1,2,3-benzotriazol-6-yl}carbonyl)azetidin-3-ol;
1-({4-fluoro-5-[(2-fluoro-4-iodophenyl)amino]-1H-1,2,3-benzotriazol-6-yl}carbonyl)-3-[(2S)-piperidin-2-yl]azetidin-3-ol;
5-({3-[(1S)-1-aminoethyl]-3-hydroxyazetidin-1-yl}carbonyl)-6-[(2-fluoro-4-iodophenyl)amino]pyrimidin-2(1H)-one;
6-[(2-fluoro-4-iodophenyl)amino]-5-({3-hydroxy-3-[(2S)-piperidin-2-yl]azetidin-1-yl}carbonyl)pyrimidin-2(1H)-one;
4-[(2-fluoro-4-iodophenyl)amino]-5-({3-hydroxy-3-[(2S)-piperidin-2-yl]azetidin-1-yl}carbonyl)pyrimidin-2(1H)-one; and
5-({3-[(1S)-1-aminoethyl]-3-hydroxyazetidin-1-yl}carbonyl)-4-[(2-fluoro-4-iodophenyl)amino]pyrimidin-2(1H)-one;
and pharmaceutically acceptable salts thereof.

26. A pharmaceutical composition comprising a compound according to claim 1, or a pharmaceutically acceptable salt thereof, and a pharmaceutically acceptable carrier, excipient, or diluent.

* * * * *